United States Patent
Masse et al.

(10) Patent No.: US 10,196,390 B2
(45) Date of Patent: Feb. 5, 2019

(54) TYK2 INHIBITORS AND USES THEREOF

(71) Applicant: Nimbus Lakshmi, Inc., Cambridge, MA (US)

(72) Inventors: Craig E. Masse, Cambridge, MA (US); Jeremy Robert Greenwood, Brooklyn, NY (US); Donna L. Romero, Chesterfield, MO (US); Geraldine C. Harriman, Charlestown, RI (US); Ronald T. Wester, Ledyard, CT (US); Mee Shelley, Tigard, OR (US); Joshua Jahmil Kennedy-Smith, New York, NY (US); Markus Dahlgren, Stratford, CT (US)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

(21) Appl. No.: 15/457,657

(22) Filed: Mar. 13, 2017

(65) Prior Publication Data

US 2017/0247373 A1    Aug. 31, 2017

Related U.S. Application Data

(63) Continuation of application No. 15/097,402, filed on Apr. 13, 2016, now Pat. No. 9,630,970, which is a continuation of application No. 14/634,041, filed on Feb. 27, 2015, now Pat. No. 9,340,540.

(60) Provisional application No. 62/096,231, filed on Dec. 23, 2014, provisional application No. 61/971,376, filed on Mar. 27, 2014, provisional application No. 61/946,358, filed on Feb. 28, 2014.

(51) Int. Cl.
| | |
|---|---|
| C07D 401/14 | (2006.01) |
| C07D 471/04 | (2006.01) |
| C07D 487/04 | (2006.01) |
| A61K 31/437 | (2006.01) |
| A61K 31/519 | (2006.01) |
| C07D 519/00 | (2006.01) |

(52) U.S. Cl.
CPC ......... *C07D 471/04* (2013.01); *C07D 487/04* (2013.01); *C07D 519/00* (2013.01)

(58) Field of Classification Search
CPC .. C07D 401/14; C07D 471/04; C07D 487/04; A61K 31/437; A61K 31/519
USPC ......... 546/119, 113; 514/265.1, 210.18, 300, 514/303; 544/280
See application file for complete search history.

(56) References Cited

U.S. PATENT DOCUMENTS

| | | | |
|---|---|---|---|
| 8,440,689 B2 * | 5/2013 | Arikawa | C07D 471/04 514/265.1 |
| 2004/0235867 A1 | 11/2004 | Bilodeau et al. | |
| 2007/0112038 A1 | 5/2007 | Marlow et al. | |
| 2010/0210623 A1 | 8/2010 | Guerin et al. | |
| 2011/0152273 A1 | 6/2011 | Arikawa et al. | |
| 2013/0034616 A1 | 2/2013 | Storck et al. | |
| 2013/0090336 A1 | 4/2013 | Bourke et al. | |
| 2013/0096104 A1 | 4/2013 | Lai et al. | |
| 2013/0116260 A1 | 5/2013 | Arikawa et al. | |
| 2013/0245031 A1 | 9/2013 | Arikawa et al. | |

FOREIGN PATENT DOCUMENTS

| | | |
|---|---|---|
| WO | WO-2005051300 A2 | 6/2005 |
| WO | WO-2011079051 | 6/2011 |

OTHER PUBLICATIONS

International Search Report and Written Opinion issued by the United States Patent and Trademark Office as International Searching Authority for International Application No. PCT/US2015/018071 dated Jun. 3, 2015 (7 pages).

Nagafuchi et al., "TYK2 Promoter Variant and Diabetes Mellitus in the Japanese," EBioMedicine 2, No Month Listed 2015 (pp. 744-749).

Watford and O'Shea, "Human Tyk2 Kinase Deficiency: Another Primary Immunodeficiency Syndrome," Immunity, vol. 25, Nov. 2006 (3 pages).

* cited by examiner

*Primary Examiner* — Niloofar Rahmani
(74) *Attorney, Agent, or Firm* — Andrea L. C. Reid; Dechert LLP

(57) ABSTRACT

The present invention provides compounds, compositions thereof, and methods of using the same for the inhibition of TYK2, and the treatment of TYK2-mediated disorders.

14 Claims, 2 Drawing Sheets

TYK2 INHIBITORS AND USES THEREOF

CROSS-REFERENCE TO RELATED APPLICATIONS

This application is a continuation of U.S. patent application Ser. No. 15/097,402, filed Apr. 13, 2013, now issued as U.S. Pat. No. 9,630,970, which is a continuation of U.S. patent application Ser. No. 14/634,041, filed Feb. 27, 2015, now issued as U.S. Pat. No. 9,340,540 which claims the benefit of U.S. Provisional Application No. 62/096,231, filed Dec. 23, 2014, U.S. Provisional Application No. 61/971,376, filed Mar. 27, 2014, and U.S. Provisional Application No. 61/946,358, filed Feb. 28, 2014, the entirety of each of which is hereby incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase. Such compounds have the general formula I:

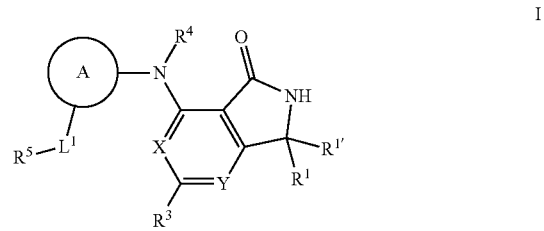

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

Figure 1:
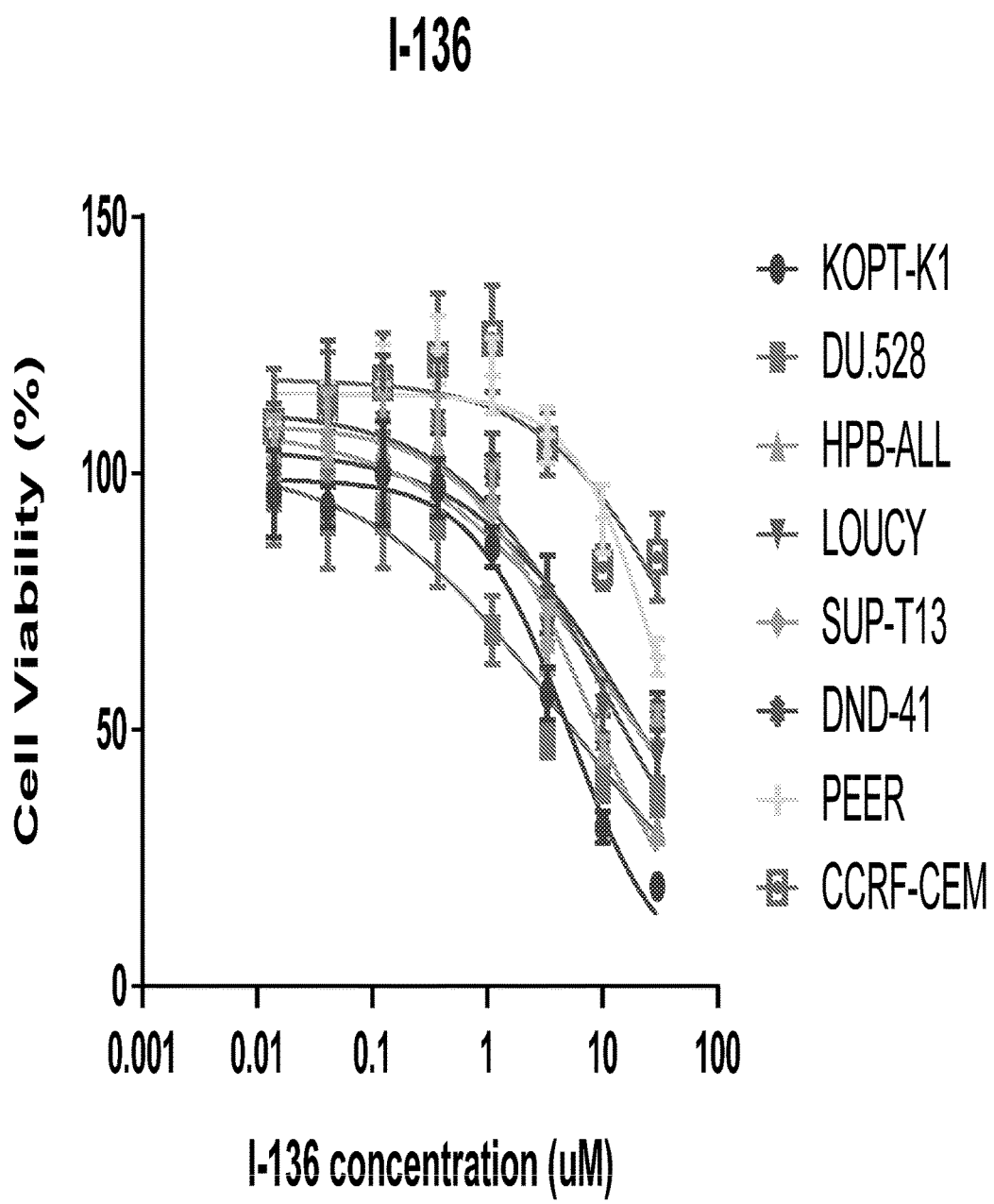
FIG. 1 depicts results of a T-ALL cell proliferation inhibition assay using compound I-136.

1. General Description of Certain Embodiments of the Invention

Compounds of the present invention, and compositions thereof, are useful as inhibitors of TYK2 protein kinase.

The binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

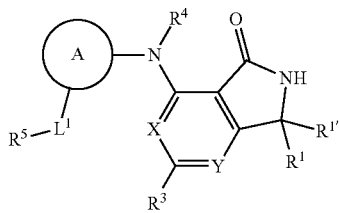

I or a pharmaceutically acceptable salt thereof, wherein:
each of X and Y is independently =C($R^6$)— or =N—, provided that X and Y are not simultaneously =C($R^6$)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R; or
$R^1$ and $R^{1'}$ are taken together with their intervening atoms to form an optionally substituted 3-7 membered spiro-fused ring having 0-2 heteroatoms independently selected from nitrogen, oxygen, and sulfur;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic;
$R^5$ is a group selected from halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S(O)$_2$R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;
each instance of $R^6$, $R^7$, and $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—, provided that when $L^1$ is a covalent bond, $R^5$ is not unsubstituted alkyl;
m is 0-4;
n is 0-4;
p is 0-3; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

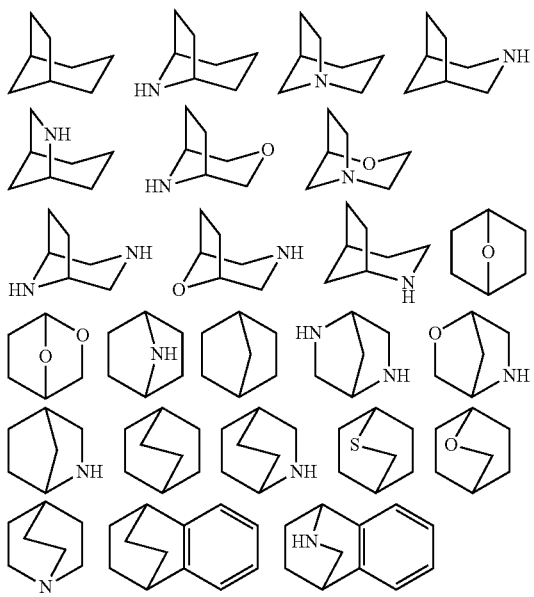
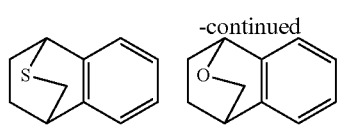

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

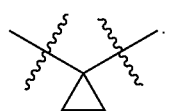 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R; —N(R°)S(O)$_2$NR°$_2$; —N(R°)S(O)$_2$R; —N(OR°) R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an IC$_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

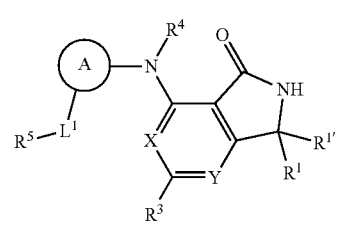

I or a pharmaceutically acceptable salt thereof, wherein:
each of X and Y is independently =C(R$^6$)— or =N—, provided that X and Y are not simultaneously =C(R$^6$)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of R$^7$;
each of R$^1$ and R$^{1'}$ is independently hydrogen, —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R; or
R$^1$ and R$^{1'}$ are taken together with their intervening atoms to form an optionally substituted 3-7 membered spiro-fused ring having 0-2 heteroatoms independently selected from nitrogen, oxygen, and sulfur;
each R$^2$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic;

$R^5$ is a group selected from halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;

each instance of $R^6$, $R^7$, and $R^8$ is independently —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each instance of $R^9$ is independently oxo, $C_{1-6}$ hydroxyaliphatic, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—, provided that when $L^1$ is a covalent bond, $R^5$ is not unsubstituted alkyl;

m is 0-4;

n is 0-4;

p is 0-3; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As defined generally above, each of X and Y is =C(R$^6$)— or =N—, provided that X and Y are not simultaneously =C(R$^6$)—. In some embodiments, both X and Y are =N—. In some embodiments, X is =N—, and Y is =C(R$^6$)—. In some embodiments, X is =C(R$^6$)—, and Y is =N—.

As defined generally above, Ring A is phenyl; a 5-6 membered heteroaryl ring having 1-4 heteroatoms independently selected from nitrogen, oxygen, and sulfur; or a 3-6 membered saturated or partially unsaturated heterocyclic ring having 1-2 heteroatoms independently selected from nitrogen, oxygen, and sulfur; wherein Ring A is substituted with m instances of $R^7$.

In some embodiments, Ring A is phenyl. In some embodiments, Ring A is a 5-6 membered heteroaryl having 1-4 heteroatoms independently selected from nitrogen, oxygen, and sulfur. Ring A is a 5-membered heteroaryl having 1-4 heteroatoms independently selected from nitrogen, oxygen, and sulfur. In some embodiments, Ring A is a 6-membered heteroaryl having 1-4 nitrogens. In some embodiments, Ring A is pyridyl. In some embodiments, Ring A is pyrazolyl.

One of skill in the art will appreciate that a when Ring A is a 5-6 membered heteroaryl ring, multiple regioisomers are possible. Unless otherwise stated, all regioisomers are intended to be encompassed. In some embodiments, Ring A is 2-pyridyl. In some embodiments, Ring A is 3-pyridyl. In some embodiments, Ring A is 3-pyrazolyl. In some embodiments, Ring A is 4-pyrazolyl.

Likewise, when Ring A is phenyl, multiple attachment points are possible. In some embodiments, when Ring A is phenyl, $L^1$ is para to the point of attachment to the rest of the molecule. In some embodiments, $L^1$ is meta to the point of attachment to the rest of the molecule. In some embodiments, $L^1$ is ortho to the point of attachment to the rest of the molecule. In some embodiments, when Ring A is phenyl, and -$L^1R^5$ taken together is $C_{1-6}$ aliphatic, said -$L^1R^5$ group is para to the point of attachment to the rest of the molecule.

As defined generally above, the n group of formula I is 0-4. In some embodiments, n is 0. In some embodiments, n is 1-4. In certain embodiments, n is 1. In some embodiments, n is 2. In certain embodiments, n is 3. In certain embodiments, n is 4.

As defined generally above, each of $R^1$ and $R^{1'}$ is independently hydrogen, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R; or $R^1$ and $R^{1'}$ are taken together with their intervening atoms to form an optionally substituted 4-7 membered spiro-fused ring having 0-2 heteroatoms independently selected from nitrogen, oxygen, and sulfur.

In certain embodiments, each of $R^1$ and $R^{1'}$ are hydrogen. In some embodiments, each of $R^1$ and $R^{1'}$ is independently —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R. In certain embodiments, each of $R^1$ and $R^{1'}$ are methyl. In some embodiments, one of $R^1$ and $R^{1'}$ is methyl, and the other is hydrogen. In some embodiments, $R^1$ and $R^{1'}$ are taken together with their intervening atoms to form an optionally substituted 3-7 membered spiro-fused ring having 0-2 heteroatoms independently selected from nitrogen, oxygen, and sulfur. In some embodiments, $R^1$ and $R^{1'}$ are taken together with their intervening atoms to form an optionally substituted 3-7 membered spiro-fused carbocyclic ring. In some embodiments, $R^1$ and $R^{1'}$ are taken together with their intervening atoms to form an optionally substituted spirocyclopropyl ring. In some embodiments, $R^1$ and $R^{1'}$ are taken together with their intervening atoms to form an optionally substituted 3-7 membered spiro-fused heterocyclic ring having 1-2 heteroatoms independently selected from nitrogen, oxygen, and sulfur.

As defined generally above, $R^3$ is a group selected from $C_{1-6}$ alkyl, phenyl, a 3-7 membered saturated or partially saturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$.

In some embodiments, $R^3$ is a group selected from phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is phenyl. In some embodiments, when X is =N—, $R^3$ is phenyl.

In some embodiments, $R^3$ is a 3-7 membered saturated or partially unsaturated carbocyclic ring. In some embodiments, $R^3$ is a 3-7 membered saturated or partially unsaturated heterocyclic ring having 1-2 heteroatoms independently selected from nitrogen, oxygen, and sulfur. In some embodiments, $R^3$ is a 5-6 membered saturated heterocyclic ring having 1-2 heteroatoms independently selected from nitrogen, oxygen, and sulfur. In some embodiments $R^3$ is pyrrolidinyl. In some embodiments, $R^3$ is piperidinyl.

In some embodiments, $R^3$ is a 5-6 membered heteroaryl ring having 1-4 heteroatoms independently selected from nitrogen, oxygen, and sulfur. In some embodiments, $R^3$ is pyridinyl. In some embodiments, $R^3$ is a $C_{3-6}$ saturated or partially unsaturated carbocyclic ring. Exemplary $R^3$ groups include those depicted in Table 1.

As defined generally above, $R^4$ is hydrogen or optionally substituted $C_{1-6}$ aliphatic. In some embodiments, $R^4$ is hydrogen. In some embodiments, $R^4$ is optionally substituted $C_{1-6}$ aliphatic. In some embodiments, $R^4$ is unsubstituted $C_{1-6}$ aliphatic. In some embodiments, $R^4$ is optionally substituted $C_{1-6}$ alkyl. In some embodiments, $R^4$ is optionally substituted $C_{3-6}$ cycloalkyl.

As defined generally above, $L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, when $L^1$ is a covalent bond, $R^5$ is not unsubstituted alkyl. In some embodiments, $L^1$ is a covalent bond. In other embodiments, $L^1$ is a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is a $C_{2-6}$ bivalent branched hydrocarbon chain. In some embodiments, $L^1$ is a $C_{3-6}$ bivalent branched alkylene chain.

In some embodiments, $L^1$ is a $C_2$ bivalent hydrocarbon chain wherein one methylene unit of the chain is replaced by —C(O)—. In some embodiments, $L^1$ is —CH$_2$C(O)— (wherein the carbonyl is adjacent to $R^5$). In some embodiments, $L^1$ is —C(O)—. In some embodiments, $L^1$ is a covalent bond or —C(O)—. Exemplary $L^1$ groups include those depicted in Table 1.

As defined generally above, $R^5$ is a group selected from halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O) OR, —N(R)C(O)R, —N(R)C(O)NR$_2$, —N(R)S(O)$_2$R, phenyl, 3-7 membered saturated or partially unsaturated heterocyclic ring having 1-2 heteroatoms independently selected from nitrogen, oxygen, and sulfur, and 5-6 membered heteroaryl ring having 1-4 heteroatoms independently selected from nitrogen, oxygen, and sulfur; wherein $R^5$ is substituted with p instances of $R^9$.

In some embodiments, $R^5$ is selected from —OR, —NR$_2$, and a 3-7 membered saturated or partially unsaturated heterocyclic ring having 1-2 heteroatoms independently selected from nitrogen, oxygen, and sulfur. In some embodiments, $R^5$ is selected from —OH, —OEt, —NH$_2$, NHEt, aziridinyl, azetidinyl, pyrrolidinyl, piperidinyl, morpholinyl, thiomorpholinyl, oxetanyl, tetrahydrothiopyranyl, and tetrahydrofuranyl. In some embodiments, $R^5$ is —OR. In some embodiments, $R^5$ is —NR$_2$. In some embodiments, $R^5$ is —NHEt or —NHiPr. Exemplary $R^5$ groups include those depicted in Table 1.

As defined generally above each instance of $R^6$ is independently —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R. In some embodiments $R^6$ is halogen or —CN. In some embodiments $R^6$ is halogen. In some embodiments, $R^6$ is fluoro. In some embodiments, $R^6$ is —CN.

As defined generally above, each instance of $R^8$ is independently —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R. In some embodiments, $R^8$ is a halogen. In some embodiments, $R^8$ is fluorine. In some embodiments, $R^8$ is chlorine. In some embodiments, $R^8$ is optionally substituted $C_{1-6}$ aliphatic. In some embodiments, $R^8$ is $C_{1-6}$ alkyl. In some embodiments, $R^8$ is methyl. In some embodiments, $R^8$ is alkyl substituted by one or more halogens. In some embodiments, $R^8$ is CF$_3$. In some embodiments, each $R^8$ is a halogen. In some embodiments, each $R^8$ is fluorine, chlorine, methyl, or CF$_3$.

One of ordinary skill in the art will appreciate that an $R^8$ substituent on a saturated carbon of $R^3$ forms a chiral center. In some embodiments, that chiral center is in the (R) configuration. In other embodiments, that chiral center is in the (S) configuration.

As defined generally above, each instance of $R^9$ is independently oxo, $C_{1-6}$ hydroxyaliphatic, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R) OR, —OC(O)R, —OC(O)NR$_2$, —N(R)C(O)OR, —N(R)C (O)R, —N(R)C(O)NR$_2$, or —N(R)S(O)$_2$R.

In some embodiments, $R^9$ is OXO. In some embodiments, $R^9$ is —$R^2$. In some embodiments, $R^9$ is optionally substituted $C_{1-6}$ aliphatic. In some embodiments, $R^9$ is $C_{1-6}$ hydroxyaliphatic. In some embodiments, $R^9$ is hydroxymethyl. In some embodiments, $R^9$ is hydroxyethyl. In some embodiments, $R^9$ is hydroxycyclobutyl. In some embodiments, $R^9$ is hydroxycyclobutyl. In some embodiments, $R^9$ is N,N-dimethylaminoethyl. In some embodiments, $R^9$ is a 3-7 membered saturated or partially unsaturated heterocyclic ring having 1-2 heteroatoms independently selected from nitrogen, oxygen, and sulfur. In some embodiments, $R^9$ is selected from —OH, —OEt, —NH$_2$, NHEt, aziridinyl, azetidinyl, pyrrolidinyl, piperidinyl, morpholinyl, thiomorpholinyl, oxetanyl, tetrahydrothiopyranyl, and tetrahydrofuranyl. In some embodiments, when $L^1$ is absent, at least one $R^9$ is OXO.

As defined generally above, m is 0-4. In some embodiments, m is 0. In some embodiments, m is 1-4. In some embodiments, m is 1. In some embodiments, m is 2. In some embodiments, m is 3. In some embodiments, m is 4.

As defined generally above, n is 0-4. In some embodiments, n is 0. In some embodiments, n is 1-4. In some embodiments, n is 1. In some embodiments, n is 2. In some embodiments, n is 3. In some embodiments, n is 4. In some embodiments, n is 0-1. In some embodiments, n is 0-2. In some embodiments, n is 0-3.

As defined generally above, p is 0-3. In some embodiments, p is 0. In some embodiments, p is 1-3. In some embodiments, p is 1. In some embodiments, p is 2. In some embodiments, p is 3. In some embodiments, p is 0-6. In some embodiments, p is 4. In some embodiments, p is 5. In some embodiments, p is 6.

In certain embodiments, the present invention provides a compound of formula I, wherein when X is =N—, $R^3$ is phenyl.

In certain embodiments, the present invention provides a compound of formula I: or a pharmaceutically acceptable salt thereof, wherein:

each of X and Y is independently =C($R^6$)— or =N—, provided that X and Y are not simultaneously =C($R^6$)—;

Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;

each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$; or $R^1$ and $R^{1'}$ are taken together with their intervening atoms to form an optionally substituted 3-7 membered spiro-fused ring having 0-2 heteroatoms independently selected from nitrogen, oxygen, and sulfur;

each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic;

$R^5$ is a group selected from hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;

provided that when $R^3$ is other than phenyl, $R^5$ is not hydrogen or unsubstituted alkyl when $L^1$ is a covalent bond;

each instance of $R^6$, $R^7$, and $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4;

n is 0-4;

p is 0-6; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein $R^1$ and $R^{1'}$ are each hydrogen, thereby forming a compound of formula II:

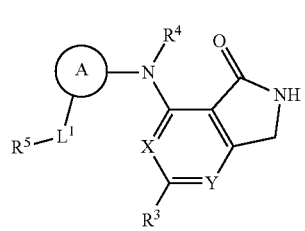

II or a pharmaceutically acceptable salt thereof, wherein each of X, Y, Ring A, $L^1$, $R^3$, $R^4$, and $R^5$ is as defined above and described in embodiments herein, both singly and in combination.

In certain embodiments, the present invention provides a compound of formula I, wherein X is =N— and Y is =C($R^6$)—; X is =C($R^6$)—; and Y is =N—; or each of X and Y are =N—, thereby forming a compound of formula III-a, III-b, or III-c, respectively:

III-a

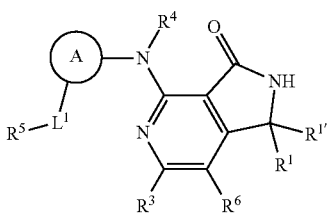

III-b

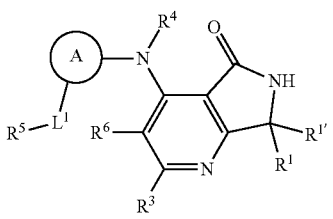

III-c

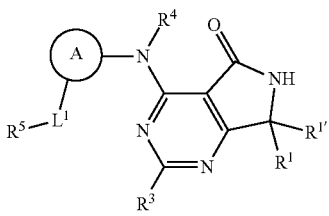

or a pharmaceutically acceptable salt thereof, wherein each of Ring A, $L^1$, $R^1$, $R^{1'}$, $R^3$, $R^4$, $R^5$, and $R^6$ is as defined above and described in embodiments herein, both singly and in combination.

In certain embodiments, the present invention provides a compound of formulae III-a, III-b, or III-c, wherein $R^1$ and $R^{1'}$ are each hydrogen, thereby forming a compound of formulae IV-a, IV-b, and IV-b, respectively:

IV-a

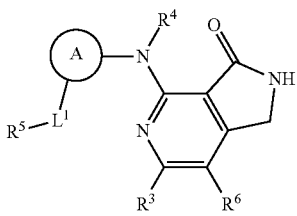

IV-b

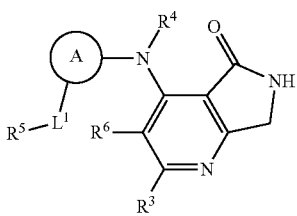

IV-c

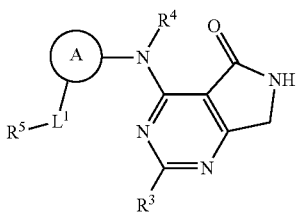

or a pharmaceutically acceptable salt thereof, wherein each of Ring A, $L^1$, $R^3$, $R^4$, and $R^5$ is as defined above and described in embodiments herein, both singly and in combination.

In some embodiments, the present invention provides a compound of formula IV-a or IV-b wherein $R^6$ is hydrogen.

In certain embodiments, the present invention provides a compound of formula I, wherein Ring A is phenyl, pyridin-2-yl, pyridine-3-yl, pyrazinyl, pyridazinyl, or pyrazol-4-yl. In certain embodiments, the present invention provides a compound of formula I, wherein Ring A is phenyl, pyridin-2-yl, pyridine-3-yl, pyrazinyl, pyridazinyl, or pyrazol-4-yl, and $L^1$ is para to —N($R^4$)—, thereby forming a compound of formulae V-a, V-b, V-c, V-d, V-e, and V-f respectively:

-continued

V-f

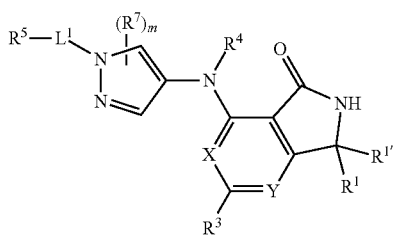

or a pharmaceutically acceptable salt thereof, wherein each of, X, Y, $L^1$, $R^1$, $R^{1'}$, $R^3$, $R^4$, $R^5$, $R^7$, and m is as defined above and described in embodiments herein, both singly and in combination.

In some embodiments, the present invention provides a compound of any one of formulae V-a, V-b, V-c, V-d, V-e, and V-f wherein m is 0.

In certain embodiments, the present invention provides a compound of one of formulae V-a, V-b, V-c, V-d, V-e, and V-f wherein X is =C($R^6$)— and Y is =N—, thereby forming a compound of formulae V-a-i, V-b-i, V-c-i, V-d-i, V-e-i, and V-f-i respectively:

V-a-i

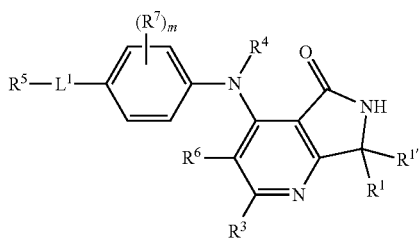

V-b-i

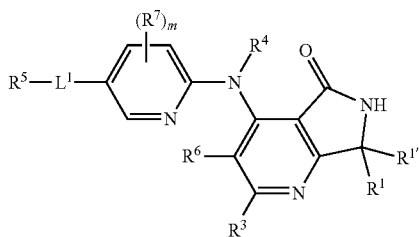

V-c-i

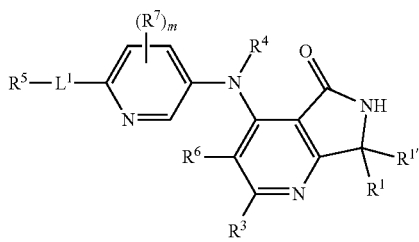

V-d-i

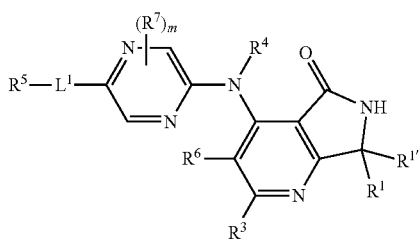

V-e-i

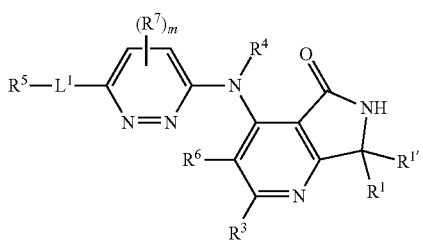

V-f-i

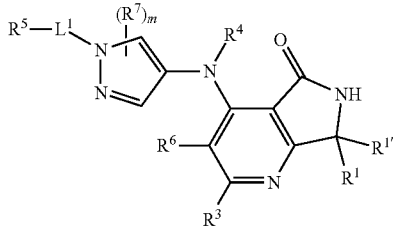

or a pharmaceutically acceptable salt thereof, wherein each of, $L^1$, $R^1$, $R^{1'}$, $R^3$, $R^4$, $R^5$, $R^7$, and m is as defined above and described in embodiments herein, both singly and in combination.

In certain embodiments, the present invention provides a compound of formula I, wherein $L^1$ is —$CH_2C(O)$—, thereby forming a compound of formula VI:

VI

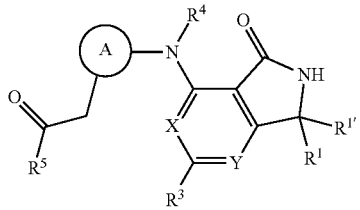

or a pharmaceutically acceptable salt thereof, wherein each of, X, Y, Ring A, $R^1$, $R^{1'}$, $R^3$, $R^4$, $R^5$, and p is as defined above and described in embodiments herein, both singly and in combination.

In certain embodiments, the present invention provides a compound of formula VI, wherein X is =CH— and Y is =N—, thereby forming a compound of formula VI-i:

VI-i

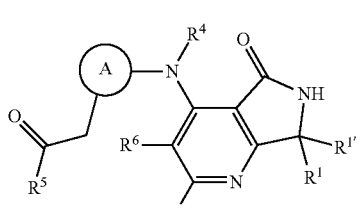

or a pharmaceutically acceptable salt thereof, wherein each of Ring A, $R^1$, $R^{1'}$, $R^3$, $R^4$, $R^5$, and p is as defined above and described in embodiments herein, both singly and in combination.

In certain embodiments, the present invention provides a compound of formula VI, wherein $R^3$ is phenyl, thereby forming a compound of formula VI-ii:

VI-ii

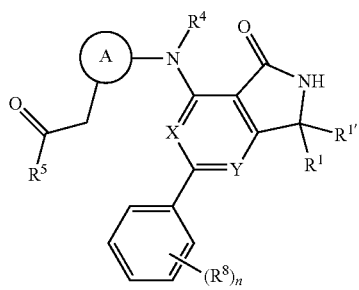

or a pharmaceutically acceptable salt thereof, wherein each of Ring A, $R^1$, $R^{1'}$, $R^3$, $R^4$, $R^5$, and p is as defined above and described in embodiments herein, both singly and in combination.

In certain embodiments, the present invention provides a compound of formula I, wherein $L^1$ is a covalent bond, $R^5$ is pyrrolidinyl or piperidinyl, and one instance of $R^9$ is oxo, thereby forming a compound of either one of formulae VII-a and VII-b:

VII-a

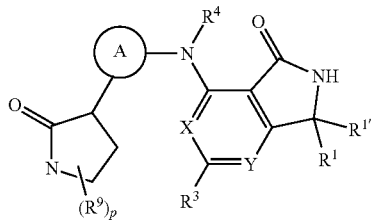

VII-b

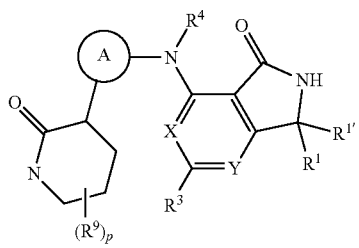

or a pharmaceutically acceptable salt thereof, wherein p is 0-2, and each of X, Y, Ring A, $R^1$, $R^{1'}$, $R^3$, $R^4$, $R^9$ is as defined above and described in embodiments herein, both singly and in combination.

In certain embodiments, the present invention provides a compound of one of formulae VII-a and VII-b, wherein X is =C($R^6$)— and Y is =N—, thereby forming a compound of formulae VII-a-i and VII-b-i respectively:

VII-a-i

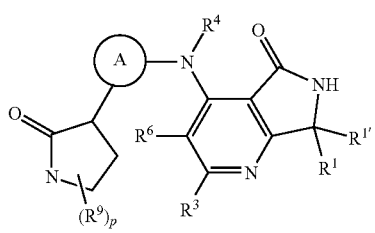

VII-b-i

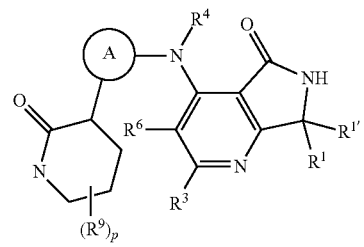

or a pharmaceutically acceptable salt thereof, wherein p is 0-2, and each of Ring A, $R^1$, $R^{1'}$, $R^3$, $R^4$, $R^9$ is as defined above and described in embodiments herein, both singly and in combination.

In certain embodiments, the present invention provides a compound of one of formulae VII-a and VII-b, wherein $R^3$ is phenyl, thereby forming a compound of formulae VII-a-ii and VII-b-ii respectively:

VII-a-ii

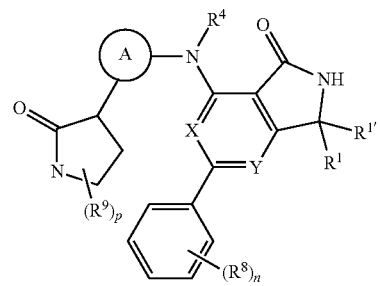

VII-b-ii

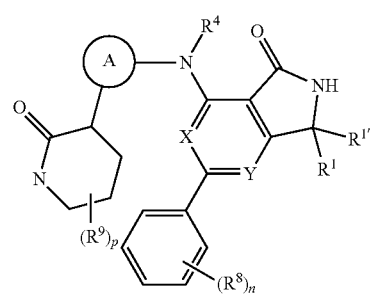

or a pharmaceutically acceptable salt thereof, wherein p is 0-2, and each of X, Y, Ring A, $R^1$, $R^{1'}$, $R^3$, $R^4$, $R^9$ is as defined above and described in embodiments herein, both singly and in combination.

In certain embodiments, the present invention provides a compound of formula I, wherein $R^3$ is phenyl, pyrrolidinyl, or piperidinyl, thereby forming a compound of formula VIII-a, VIII-b, or VIII-c, respectively:

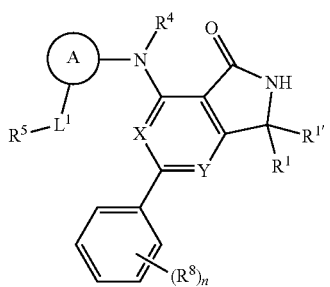

VIII-a

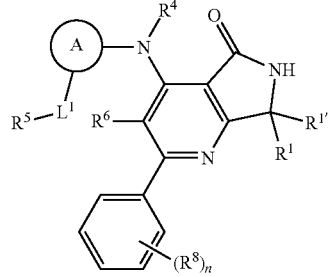

VIII-a-i

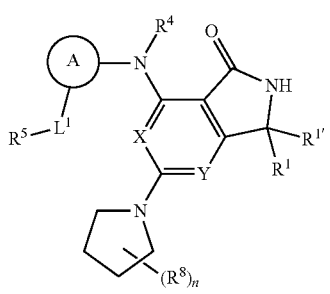

VIII-b

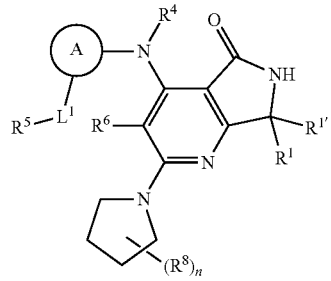

VIII-b-i

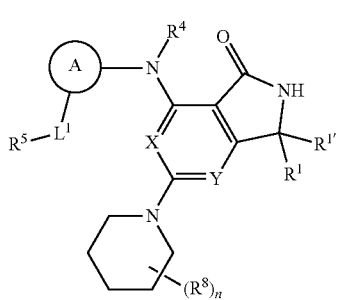

VIII-c

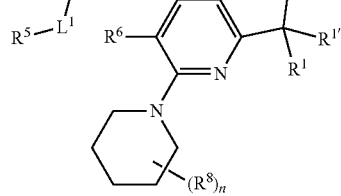

VIII-c-i or a pharmaceutically acceptable salt thereof, wherein each of X, Y, Ring A, L$^1$, R$^1$, R$^{1'}$, R$^4$, R$^5$, R$^8$, and n is as defined above for formula I and described in embodiments herein, both singly and in combination.

In certain embodiments, the present invention provides a compound of formula VIII-a, or a pharmaceutically acceptable salt thereof, wherein each of Ring A, L$^1$, R$^1$, R$^{1'}$, R$^4$, R$^5$, R$^8$, and n is as defined above for formula I and described in embodiments herein, both singly and in combination. In certain embodiments, the present invention provides a compound of formula VIII-a, or a pharmaceutically acceptable salt thereof, wherein n is 1-3. In some embodiments, and at least one R$^8$ substituent is ortho to the point of attachment. In certain embodiments, the present invention provides a compound of formula VIII-a, or a pharmaceutically acceptable salt thereof, wherein n is 1. In certain embodiments, the present invention provides a compound of formula VIII-a, or a pharmaceutically acceptable salt thereof, wherein n is 2.

In certain embodiments, the present invention provides a compound of one of formulae VIII-a, VIII-b, and VIII-c wherein X is =C(R$^6$)— and Y is =N—, thereby forming a compound of formula VIII-a-i, VIII-b-i, or VIII-c-i, respectively:

or a pharmaceutically acceptable salt thereof, wherein each of Ring A, L$^1$, R$^1$, R$^{1'}$, R$^4$, R$^5$, R$^8$, and n is as defined above for formula I and described in embodiments herein, both singly and in combination.

In certain embodiments, the present invention provides a compound of formula I, wherein L$^1$ is a covalent bond and R$^5$ is —OR, thereby forming a compound of formula IX:

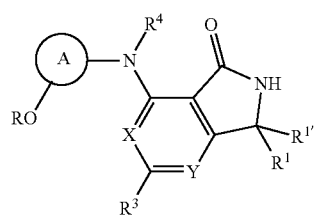

IX or a pharmaceutically acceptable salt thereof, wherein each of X, Y, Ring A, R, R$^1$, R$^{1'}$, R$^3$, and R$^4$ is as defined above and described in embodiments herein, both singly and in combination.

In certain embodiments, the present invention provides a compound of formula IX, wherein X is =C(R$^6$)— and Y is =N—, thereby forming a compound of formula IX-i:

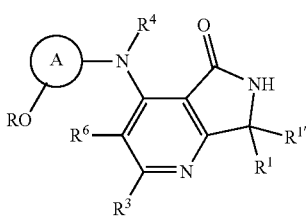

IX-i or a pharmaceutically acceptable salt thereof, wherein each of Ring A, R, $R^1$, $R^{1'}$, $R^3$, $R^4$, and $R^6$ is as defined above and described in embodiments herein, both singly and in combination.

In certain embodiments, the present invention provides a compound of formula IX, wherein $R^3$ is phenyl, pyrrolidinyl, or piperidinyl, thereby forming a compound of formula X-a, X-b, or X-c, respectively:

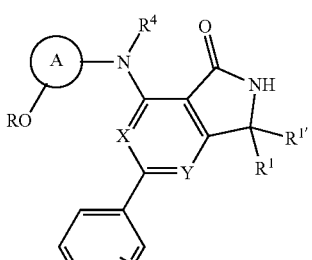

X-a

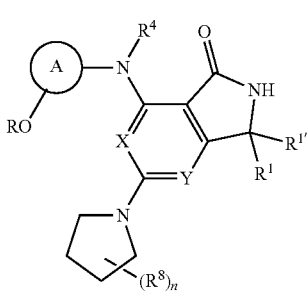

X-b

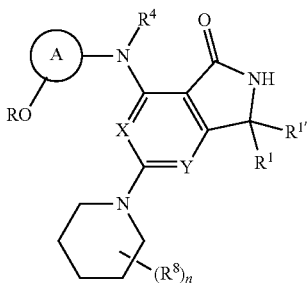

X-c or a pharmaceutically acceptable salt thereof, wherein each of X, Y, Ring A, $L^1$, R, $R^1$, $R^{1'}$, $R^4$, $R^8$, and n is as defined above for formula I and described in embodiments herein, both singly and in combination.

In certain embodiments, the present invention provides a compound of any one of formulae IX, IX-i, X-a, X-b, and X-c, wherein R is hydrogen. In certain embodiments, the present invention provides a compound of any one of formulae IX, IX-i, X-a, X-b, and X-c, wherein R is an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur. In certain embodiments, the present invention provides a compound of any one of formulae IX, IX-i, X-a, X-b, and X-c, wherein R is optionally substituted $C_{1-6}$ aliphatic. In certain embodiments, the present invention provides a compound of any one of formulae IX, IX-i, X-a, X-b, and X-c, wherein R is optionally substituted $C_{1-6}$ alkyl. In certain embodiments, the present invention provides a compound of any one of formulae IX, IX-i, X-a, X-b, and X-c, wherein R is methyl.

In certain embodiments, the present invention provides a compound of formula I, wherein $L^1$ is a covalent bond or —C(O)—, thereby forming a compound of formula XI or XII:

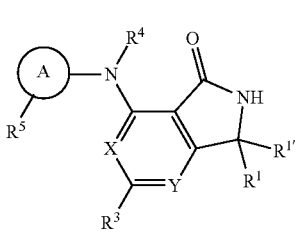

XI

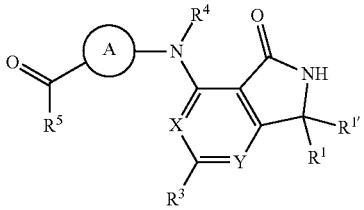

XII or a pharmaceutically acceptable salt thereof, wherein each of X, Y, Ring A, R, $R^1$, $R^{1'}$, $R^3$, $R^4$ and $R^5$ is as defined above and described in embodiments herein, both singly and in combination.

In certain embodiments, the present invention provides a compound of formula XI or XII, wherein X is $=C(R^6)-$ and Y is $=N-$, thereby forming a compound of formula XI-i or XII-i:

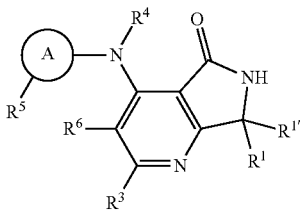

XI-i

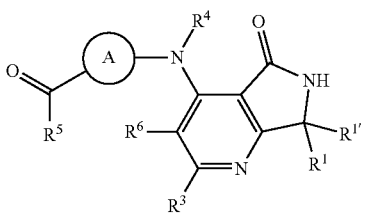

XII-i or a pharmaceutically acceptable salt thereof, wherein each of Ring A, R, $R^1$, $R^{1'}$, $R^3$, $R^4$, $R^5$, and $R^6$ is as defined above and described in embodiments herein, both singly and in combination.

In certain embodiments, the present invention provides a compound of formula XI or XII, wherein $R^3$ is phenyl, thereby forming a compound of formula XI-ii or XII-ii:

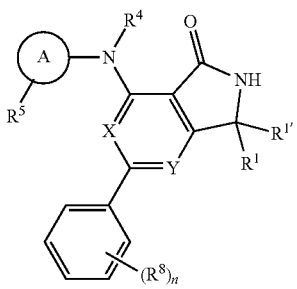

XI-ii

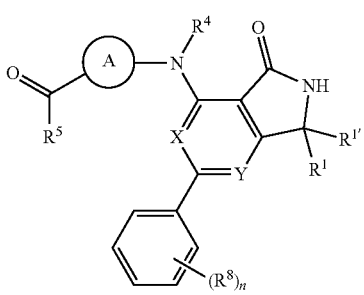

XII-ii or a pharmaceutically acceptable salt thereof, wherein each of Ring A, R, $R^1$, $R^{1'}$, $R^3$, $R^4$, $R^5$, $R^6$, $R^8$, and n is as defined above and described in embodiments herein, both singly and in combination.

In certain embodiments, the present invention provides a compound of any one of formulae I, III-a, III-b, III-c, V-a, V-b, V-c, V-d, V-a-i, V-b-i, V-c-i, V-d-i, VI, VII-a, VII-b, VIII-a, VIII-b, VIII-c, IX, IX-i, X-a, X-b, X-c, XI, XII, XI-i, XII-i, XI-ii, and XII-ii, or a pharmaceutically acceptable salt thereof, wherein each of $R^1$ and $R^{1'}$ is hydrogen.

In certain embodiments, the present invention provides a compound of any one of formulae I, II, V-a, V-b, V-c, V-d, VI, VII-a, VII-b, VIII-a, VIII-b, VIII-c, IX, X-a, X-b, and X-c or a pharmaceutically acceptable salt thereof, wherein X is =N—, and Y is =C($R^6$)—. In certain embodiments, the present invention provides a compound of any one of formulae I, II, V-a, V-b, V-c, V-d, VI, VII-a, VII-b, VIII-a, VIII-b, VIII-c, IX, X-a, X-b, X-c, XI, and XII or a pharmaceutically acceptable salt thereof, wherein X is =N—, and Y is =CH—.

In certain embodiments, the present invention provides a compound of any one of formulas I, II, V-a, V-b, V-c, V-d, VI, VII-a, VII-b, VIII-a, VIII-b, VIII-c, IX, X-a, X-b, X-c, XI, and XII or a pharmaceutically acceptable salt thereof, wherein X is =C($R^6$)—, and Y is =N—. In certain embodiments, the present invention provides a compound of any one of formulas I, II, V-a, V-b, V-c, V-d, VI, VII-a, VII-b, VIII-a, VIII-b, VIII-c, IX, X-a, X-b, X-c, XI, and XII or a pharmaceutically acceptable salt thereof, wherein X is =CH—, and Y is =N—.

In certain embodiments, the present invention provides a compound of any one of formulas I, II, V-a, V-b, V-c, V-d, VI, VII-a, VII-b, VIII-a, VIII-b, VIII-c, IX, X-a, X-b, X-c, XI, and XII or a pharmaceutically acceptable salt thereof, wherein both X and Y are =N—.

In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is —CH$_2$C(O)—; or $L^1$ is a covalent bond, and $R^5$ is a 3-7 membered saturated or partially unsaturated heterocyclic ring having 1-2 heteroatoms independently selected from nitrogen, oxygen, and sulfur. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is —CH$_2$C(O)—; or $L^1$ is a covalent bond, and $R^5$ is pyrrolidinyl. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is —CH$_2$C(O)—; or $L^1$ is a covalent bond, and $R^5$ is piperidinyl. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is —CH$_2$C(O)—; or $L^1$ is a covalent bond, and $R^5$ is pyrrolidinyl, and at least one $R^9$ is OXO.

In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond and $R^5$ is —OR. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond, and $R^5$ is —OR, where in this instance R is hydrogen. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond, and $R^5$ is —OR, where in this instance R is an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond, and $R^5$ is —OR, where in this instance R is optionally substituted $C_{1-6}$ aliphatic. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond, and $R^5$ is —OR, where in this instance R is optionally substituted $C_{1-6}$ alkyl. In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein $L^1$ is a covalent bond, and $R^5$ is —OR, where in this instance R is methyl.

In certain embodiments, the present invention provides a compound of any one of formulas I, II, III-a, III-b, III-c, IV-a, IV-b, IV-c, V-a, V-b, V-c, V-d, VIII-a, VIII-b, or VIII-c, or a pharmaceutically acceptable salt thereof, wherein L¹R⁵ taken together comprises at least one carbonyl (i.e. —C(O)—) group.

In certain embodiments, the present invention provides a compound of any one of formulas I, II, III-a, III-b, III-c, IV-a, IV-b, IV-c, V-a, V-b, V-c, V-d, VIII-a, or a pharmaceutically acceptable salt thereof, wherein n is 1-3. In certain embodiments, the present invention provides a compound of any one of formulas I, II, III-a, III-b, III-c, IV-a, IV-b, IV-c, V-a, V-b, V-c, V-d, VIII-a, or a pharmaceutically acceptable salt thereof, wherein n is 1-3, and each $R^8$ is halogen or $CF_3$.

Exemplary compounds of the invention are set forth in Table 1, below.

TABLE 1

| Compound | Structure |
|---|---|
| I-1 | 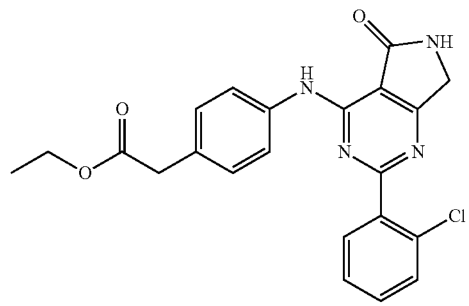 [SMILES: CCOC(=O)Cc1ccc(Nc2nc(-c3ccccc3Cl)nc3c2C(=O)NC3)cc1] |
| I-2 | 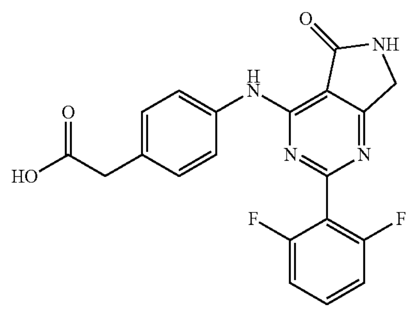 [SMILES: O=C(O)Cc1ccc(Nc2nc(-c3c(F)cccc3F)nc3c2C(=O)NC3)cc1] |
| I-3 | 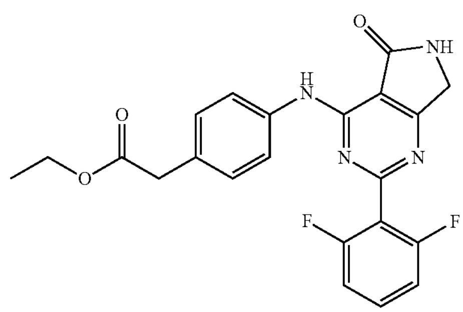 [SMILES: CCOC(=O)Cc1ccc(Nc2nc(-c3c(F)cccc3F)nc3c2C(=O)NC3)cc1] |
| I-4 | 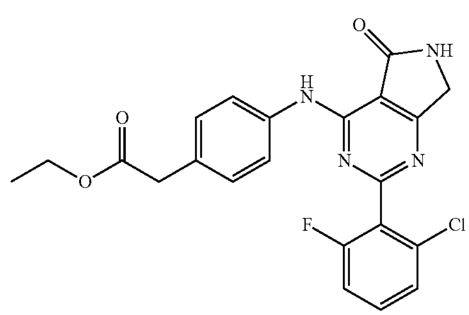 [SMILES: CCOC(=O)Cc1ccc(Nc2nc(-c3c(F)cccc3Cl)nc3c2C(=O)NC3)cc1] |

TABLE 1-continued

Exemplary Compounds

| Compound | Structure |
|---|---|
| I-5 | 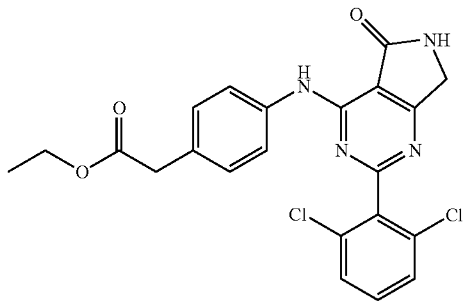 [SMILES: CCOC(=O)Cc1ccc(Nc2nc(-c3c(Cl)cccc3Cl)nc3c2C(=O)NC3)cc1] |
| I-6 | 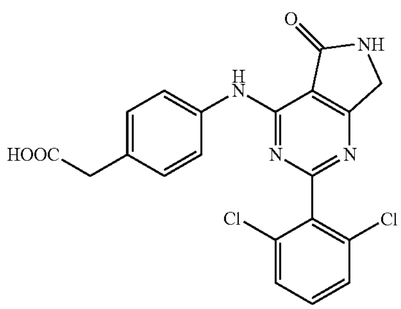 [SMILES: O=C(O)Cc1ccc(Nc2nc(-c3c(Cl)cccc3Cl)nc3c2C(=O)NC3)cc1] |
| I-7 | 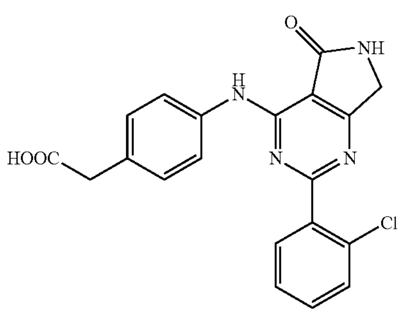 [SMILES: O=C(O)Cc1ccc(Nc2nc(-c3ccccc3Cl)nc3c2C(=O)NC3)cc1] |
| I-8 | 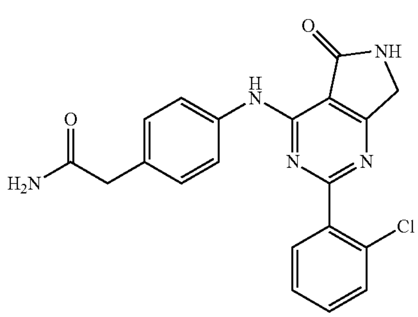 [SMILES: NC(=O)Cc1ccc(Nc2nc(-c3ccccc3Cl)nc3c2C(=O)NC3)cc1] |

TABLE 1-continued

Exemplary Compounds

| Compound | Structure |
|---|---|
| I-9 | (structure: 4-((2-(2,6-dichloro-4-cyanophenyl)-5-oxo-6,7-dihydro-5H-pyrrolo[3,4-d]pyrimidin-4-yl)amino)phenyl)acetic acid) |
| I-10 | (structure: 4-((2-(2-chloro-6-fluorophenyl)-5-oxo-6,7-dihydro-5H-pyrrolo[3,4-d]pyrimidin-4-yl)amino)phenyl)acetic acid) |
| I-11 | (structure: 2-(4-((2-(2,6-difluorophenyl)-5-oxo-6,7-dihydro-5H-pyrrolo[3,4-d]pyrimidin-4-yl)amino)phenyl)-N-(piperidin-4-yl)acetamide) |
| I-12 | (structure: N-(azetidin-3-yl)-2-(4-((2-(2,6-difluorophenyl)-5-oxo-6,7-dihydro-5H-pyrrolo[3,4-d]pyrimidin-4-yl)amino)phenyl)acetamide) |

TABLE 1-continued
Exemplary Compounds
| Compound | Structure |
|---|---|
| I-13 | 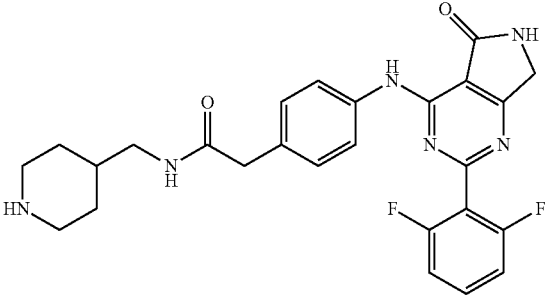 [SMILES: O=C(Cc1ccc(Nc2nc(-c3c(F)cccc3F)nc3c2C(=O)NC3)cc1)NCC1CCNCC1] |
| I-14 | 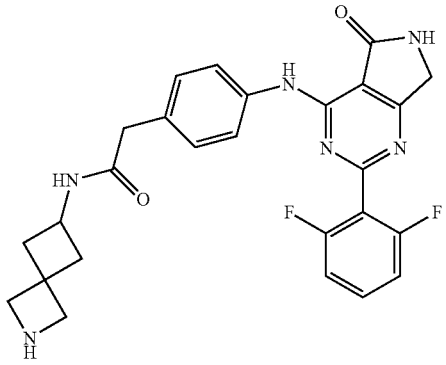 [SMILES: O=C(Cc1ccc(Nc2nc(-c3c(F)cccc3F)nc3c2C(=O)NC3)cc1)NC1CC2(CNC2)C1] |
| I-15 | 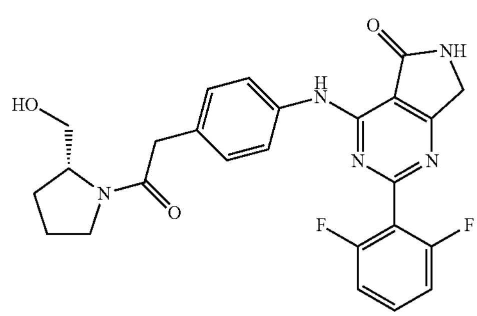 [SMILES: O=C1NCc2nc(-c3c(F)cccc3F)nc(Nc3ccc(CC(=O)N4CCC[C@@H]4CO)cc3)c21] |
| I-16 | 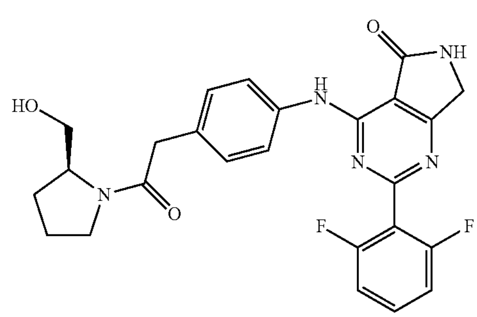 [SMILES: O=C1NCc2nc(-c3c(F)cccc3F)nc(Nc3ccc(CC(=O)N4CCC[C@H]4CO)cc3)c21] |

TABLE 1-continued

Exemplary Compounds

| Compound | Structure |
|---|---|
| I-17 | 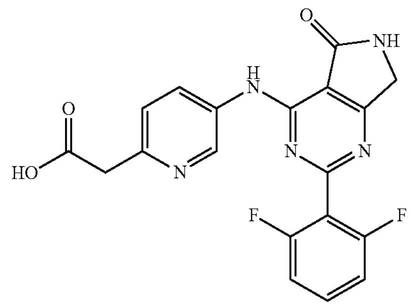 [SMILES: O=C(O)Cc1ccc(Nc2nc(-c3c(F)cccc3F)nc3c2C(=O)NC3)cn1] |
| I-18 | 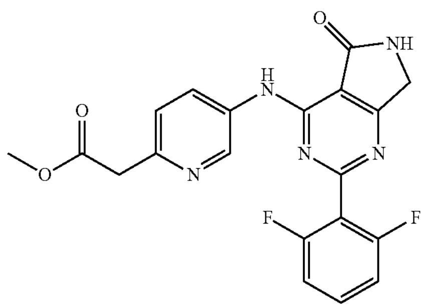 [SMILES: COC(=O)Cc1ccc(Nc2nc(-c3c(F)cccc3F)nc3c2C(=O)NC3)cn1] |
| I-19 | 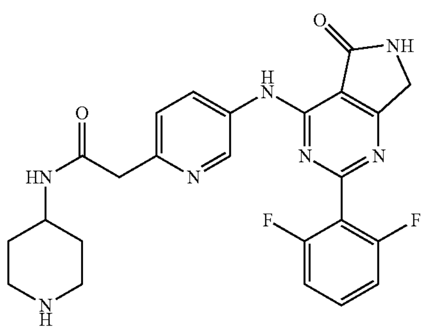 [SMILES: O=C(Cc1ccc(Nc2nc(-c3c(F)cccc3F)nc3c2C(=O)NC3)cn1)NC1CCNCC1] |
| I-20 | 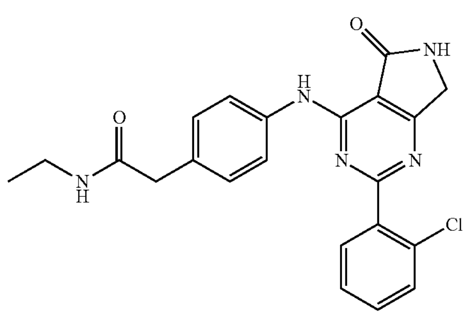 [SMILES: CCNC(=O)Cc1ccc(Nc2nc(-c3ccccc3Cl)nc3c2C(=O)NC3)cc1] |
| I-21 | 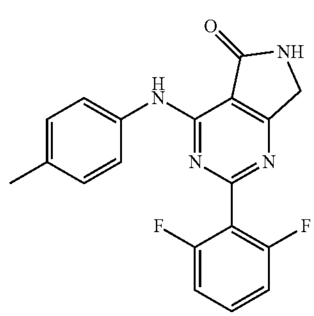 [SMILES: Cc1ccc(Nc2nc(-c3c(F)cccc3F)nc3c2C(=O)NC3)cc1] |

TABLE 1-continued

Exemplary Compounds

| Compound | Structure |
|---|---|
| I-22 | 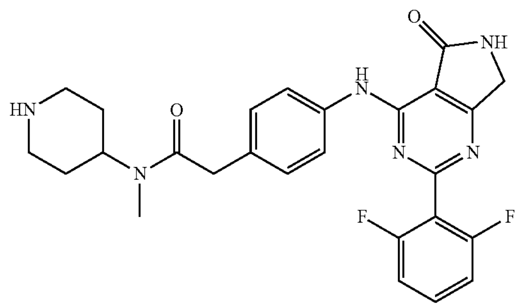 [SMILES: CN(C(=O)Cc1ccc(Nc2nc(-c3c(F)cccc3F)nc3c2C(=O)NC3)cc1)C1CCNCC1] |
| I-23 | 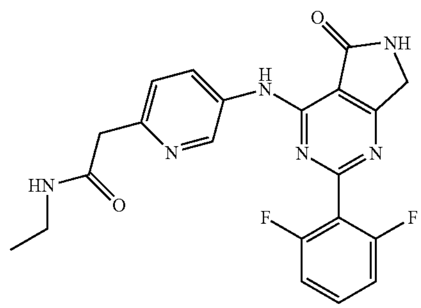 [SMILES: CCNC(=O)Cc1ccc(Nc2nc(-c3c(F)cccc3F)nc3c2C(=O)NC3)cn1] |
| I-24 | 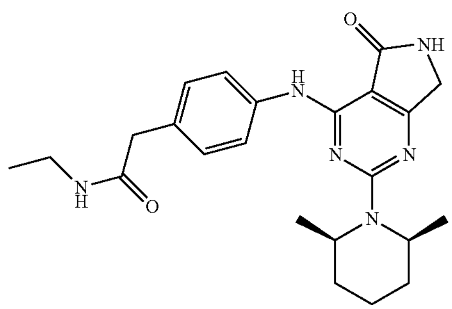 [SMILES: CCNC(=O)Cc1ccc(Nc2nc(N3[C@H](C)CCC[C@@H]3C)nc3c2C(=O)NC3)cc1] |
| I-25 | 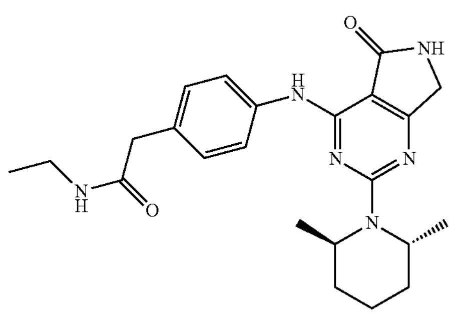 [SMILES: CCNC(=O)Cc1ccc(Nc2nc(N3[C@H](C)CCC[C@H]3C)nc3c2C(=O)NC3)cc1] |
| I-26 | 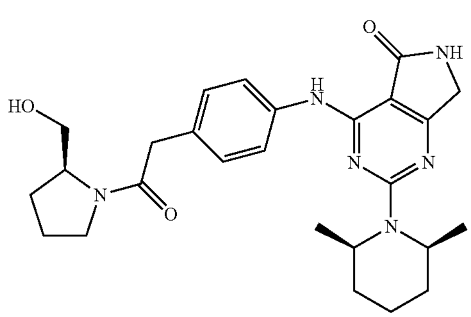 [SMILES: C[C@@H]1CCC[C@H](C)N1c1nc2c(c(Nc3ccc(CC(=O)N4CCC[C@H]4CO)cc3)n1)C(=O)NC2] |

TABLE 1-continued

Exemplary Compounds

| Compound | Structure |
|---|---|
| I-27 | 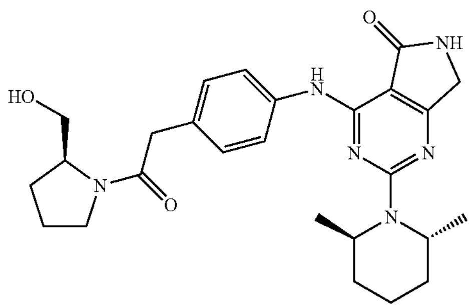 [SMILES: C[C@@H]1CCC[C@@H](C)N1c1nc2c(c(Nc3ccc(CC(=O)N4CCC[C@H]4CO)cc3)n1)C(=O)NC2] |
| I-28 | 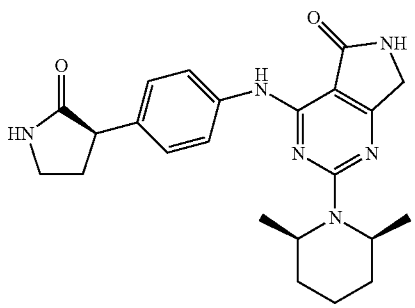 [SMILES: C[C@@H]1CCC[C@H](C)N1c1nc2c(c(Nc3ccc([C@H]4CCNC4=O)cc3)n1)C(=O)NC2] |
| I-29 | 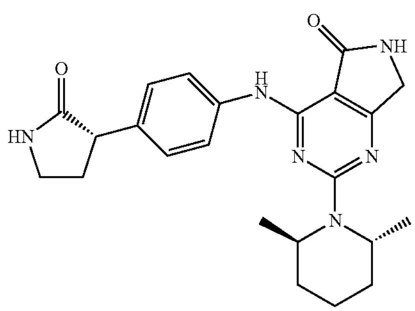 [SMILES: C[C@@H]1CCC[C@@H](C)N1c1nc2c(c(Nc3ccc([C@@H]4CCNC4=O)cc3)n1)C(=O)NC2] |
| I-30 | 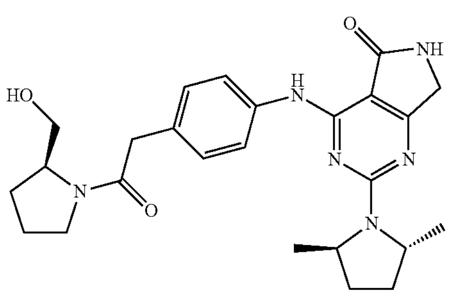 [SMILES: C[C@@H]1CC[C@@H](C)N1c1nc2c(c(Nc3ccc(CC(=O)N4CCC[C@H]4CO)cc3)n1)C(=O)NC2] |
| I-31 | 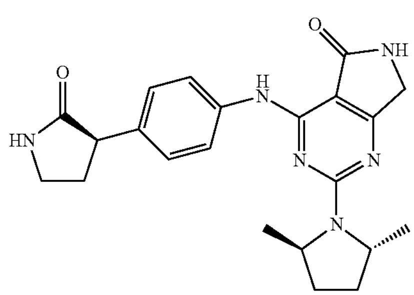 [SMILES: C[C@@H]1CC[C@@H](C)N1c1nc2c(c(Nc3ccc([C@H]4CCNC4=O)cc3)n1)C(=O)NC2] |

TABLE 1-continued

Exemplary Compounds

| Compound | Structure |
|---|---|
| I-32 | 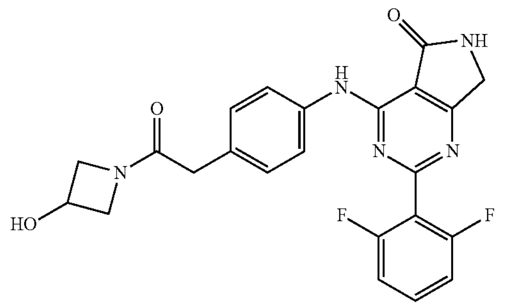 [SMILES: O=C1NCc2nc(-c3c(F)cccc3F)nc(Nc3ccc(CC(=O)N4CC(O)C4)cc3)c21] |
| I-33 | 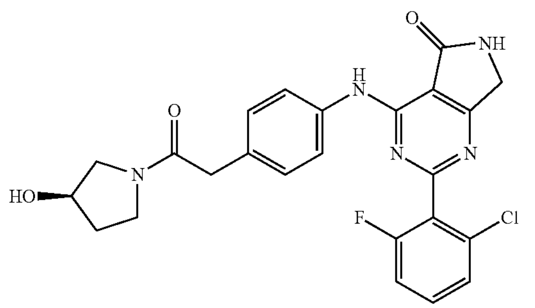 |
| I-34 | 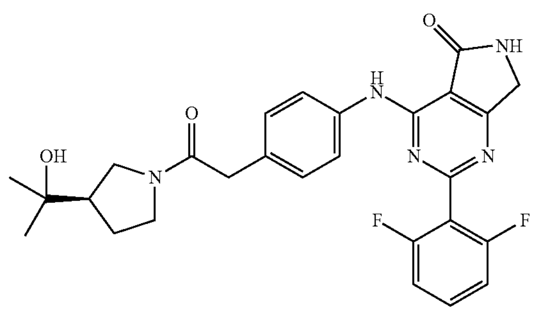 [SMILES: CC(C)(O)[C@@H]1CCN(C(=O)Cc2ccc(Nc3nc(-c4c(F)cccc4F)nc4c3C(=O)NC4)cc2)C1] |
| I-35 | 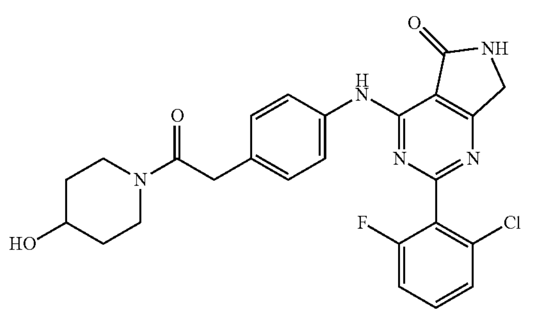 [SMILES: O=C1NCc2nc(-c3c(F)cccc3Cl)nc(Nc3ccc(CC(=O)N4CCC(O)CC4)cc3)c21] |
| I-36 | 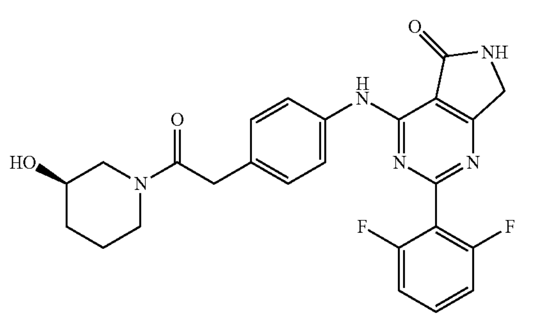 [SMILES: O=C1NCc2nc(-c3c(F)cccc3F)nc(Nc3ccc(CC(=O)N4CCC[C@@H](O)C4)cc3)c21] |

TABLE 1-continued

Exemplary Compounds

| Compound | Structure |
|---|---|
| I-37 | 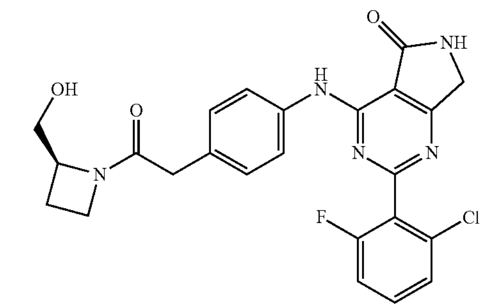 [SMILES: O=C1NCc2nc(-c3c(F)cccc3Cl)nc(Nc3ccc(CC(=O)N4CC[C@H]4CO)cc3)c21] |
| I-38 | 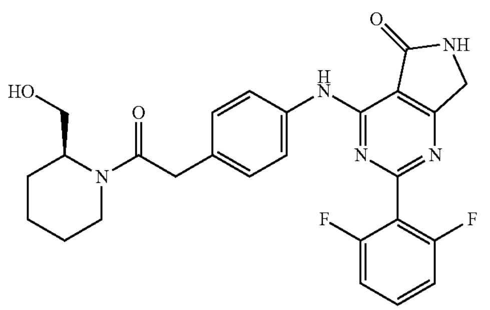 [SMILES: O=C1NCc2nc(-c3c(F)cccc3F)nc(Nc3ccc(CC(=O)N4CCCC[C@H]4CO)cc3)c21] |
| I-39 | 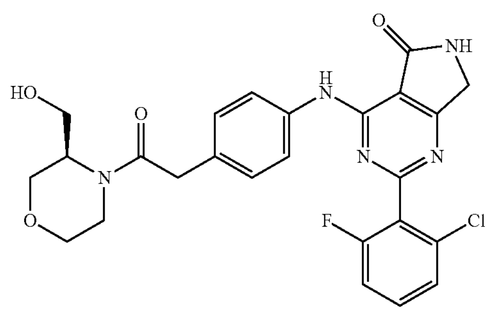 [SMILES: O=C1NCc2nc(-c3c(F)cccc3Cl)nc(Nc3ccc(CC(=O)N4CCOC[C@H]4CO)cc3)c21] |
| I-40 | 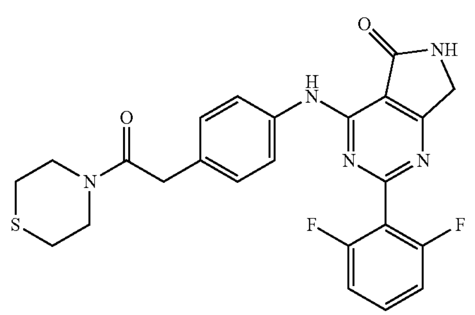 [SMILES: O=C1NCc2nc(-c3c(F)cccc3F)nc(Nc3ccc(CC(=O)N4CCSCC4)cc3)c21] |
| I-41 | 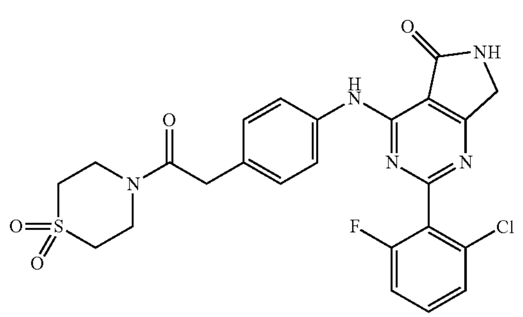 [SMILES: O=C1NCc2nc(-c3c(F)cccc3Cl)nc(Nc3ccc(CC(=O)N4CCS(=O)(=O)CC4)cc3)c21] |

TABLE 1-continued

Exemplary Compounds

| Compound | Structure |
|---|---|
| I-42 | 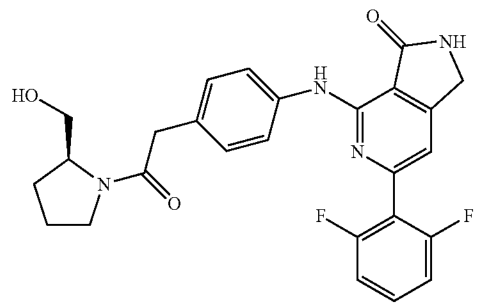 [SMILES: O=C1NCc2cc(-c3c(F)cccc3F)nc(Nc3ccc(CC(=O)N4CCC[C@H]4CO)cc3)c21] |
| I-43 | 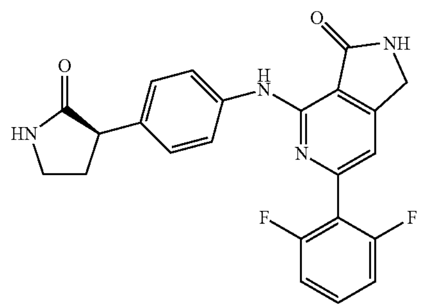 [SMILES: O=C1NCc2cc(-c3c(F)cccc3F)nc(Nc3ccc([C@H]4CCNC4=O)cc3)c21] |
| I-44 | 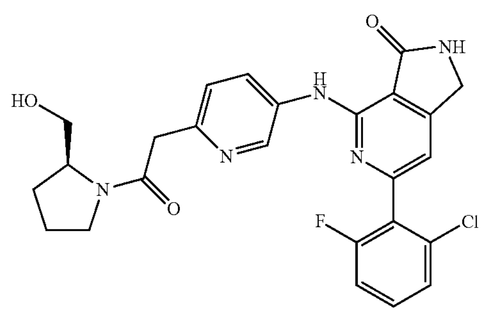 [SMILES: O=C1NCc2cc(-c3c(F)cccc3Cl)nc(Nc3ccc(CC(=O)N4CCC[C@H]4CO)nc3)c21] |
| I-45 | 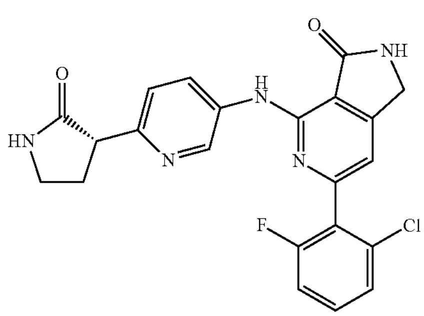 [SMILES: O=C1NCc2cc(-c3c(F)cccc3Cl)nc(Nc3ccc([C@@H]4CCNC4=O)nc3)c21] |
| I-46 | 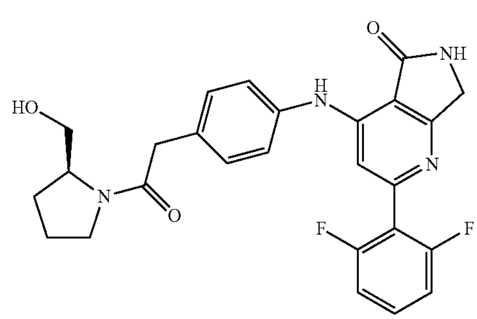 [SMILES: O=C1NCc2nc(-c3c(F)cccc3F)cc(Nc3ccc(CC(=O)N4CCC[C@H]4CO)cc3)c21] |

TABLE 1-continued

Exemplary Compounds

| Compound | Structure |
|---|---|
| I-47 | 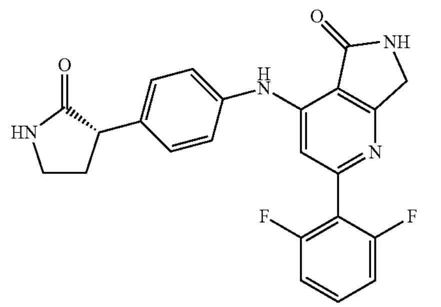 [SMILES: O=C1NCc2nc(-c3c(F)cccc3F)cc(Nc3ccc([C@@H]4CCNC4=O)cc3)c21] |
| I-48 | 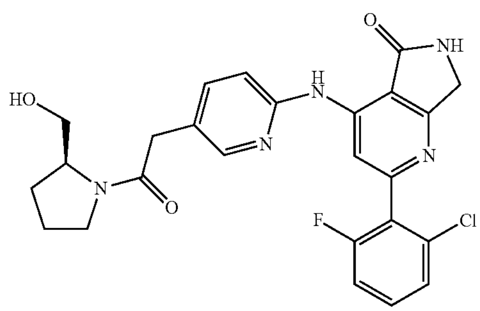 [SMILES: O=C1NCc2nc(-c3c(F)cccc3Cl)cc(Nc3ccc(CC(=O)N4CCC[C@H]4CO)cn3)c21] |
| I-49 | 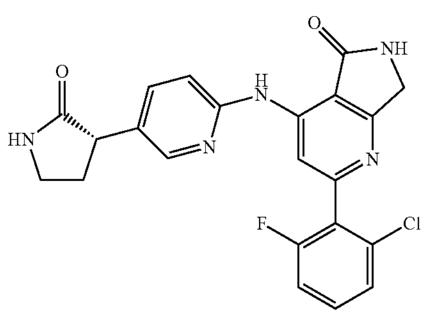 [SMILES: O=C1NCc2nc(-c3c(F)cccc3Cl)cc(Nc3ccc([C@@H]4CCNC4=O)cn3)c21] |
| I-50 | 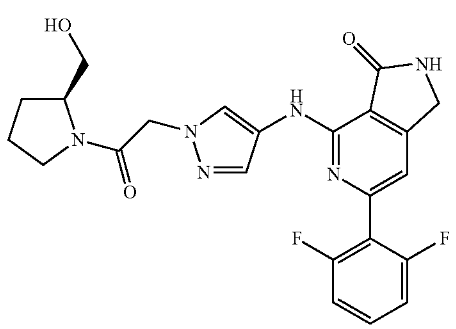 [SMILES: O=C1NCc2cc(-c3c(F)cccc3F)nc(Nc3cnn(CC(=O)N4CCC[C@H]4CO)c3)c21] |
| I-51 | 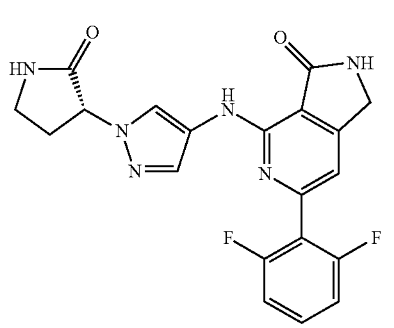 [SMILES: O=C1NCc2cc(-c3c(F)cccc3F)nc(Nc3cnn([C@@H]4CCNC4=O)c3)c21] |

TABLE 1-continued
Exemplary Compounds
| Compound | Structure |
|---|---|
| I-52 | 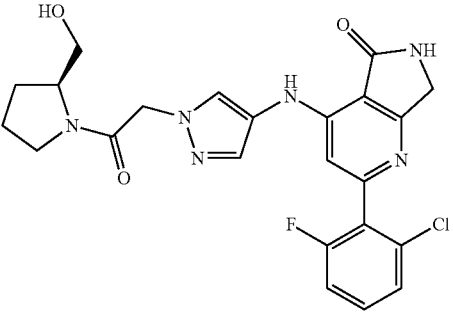 [SMILES: O=C1NCc2nc(-c3c(F)cccc3Cl)cc(Nc3cnn(CC(=O)N4CCC[C@H]4CO)c3)c21] |
| I-53 | 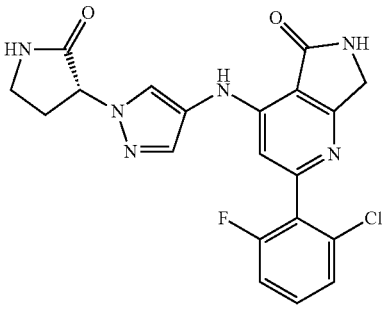 [SMILES: O=C1NCc2nc(-c3c(F)cccc3Cl)cc(Nc3cnn([C@@H]4CCNC4=O)c3)c21] |
| I-54 | 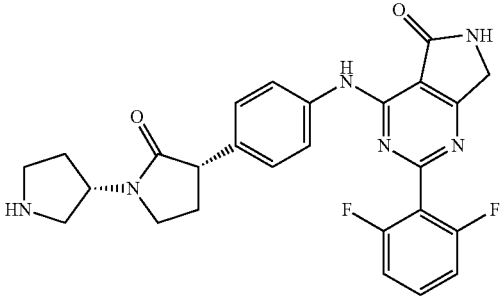 [SMILES: O=C1NCc2nc(-c3c(F)cccc3F)nc(Nc3ccc([C@@H]4CCN([C@H]5CCNC5)C4=O)cc3)c21] |
| I-55 | 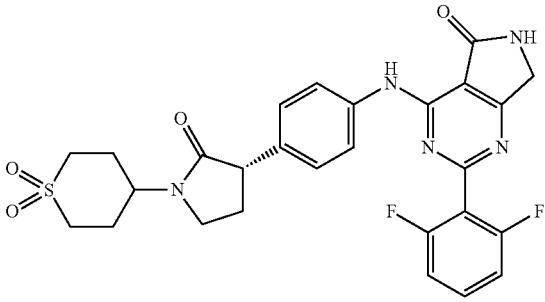 [SMILES: O=C1NCc2nc(-c3c(F)cccc3F)nc(Nc3ccc([C@@H]4CCN(C5CCS(=O)(=O)CC5)C4=O)cc3)c21] |

TABLE 1-continued
Exemplary Compounds
| Compound | Structure |
|---|---|
| I-56 | 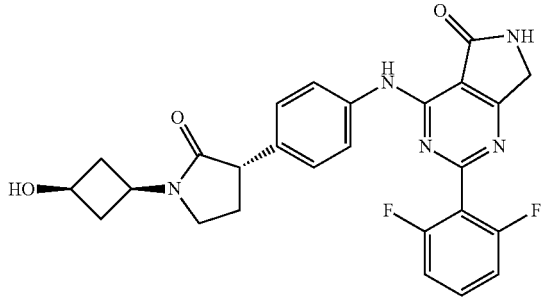 [SMILES: O=C1NCc2nc(-c3c(F)cccc3F)nc(Nc3ccc([C@@H]4CCN([C@H]5C[C@@H](O)C5)C4=O)cc3)c21] |
| I-57 | 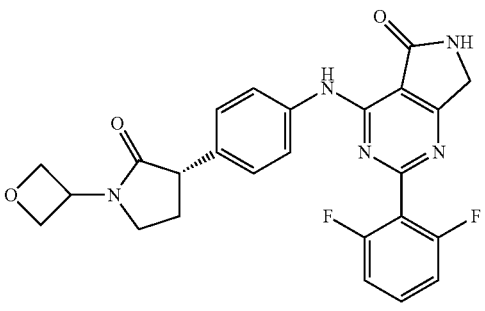 [SMILES: O=C1NCc2nc(-c3c(F)cccc3F)nc(Nc3ccc([C@@H]4CCN(C5COC5)C4=O)cc3)c21] |
| I-58 | 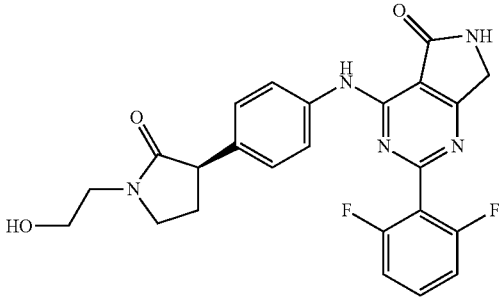 [SMILES: O=C1NCc2nc(-c3c(F)cccc3F)nc(Nc3ccc([C@H]4CCN(CCO)C4=O)cc3)c21] |
| I-59 | 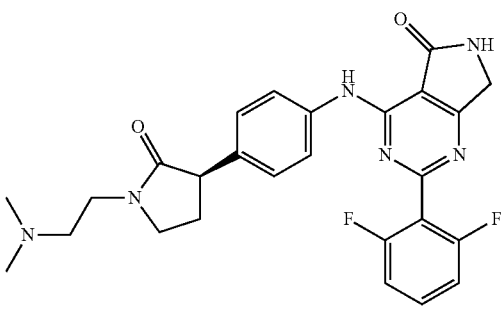 [SMILES: CN(C)CCN1CC[C@H](c2ccc(Nc3nc(-c4c(F)cccc4F)nc4c3C(=O)NC4)cc2)C1=O] |
| I-61 | 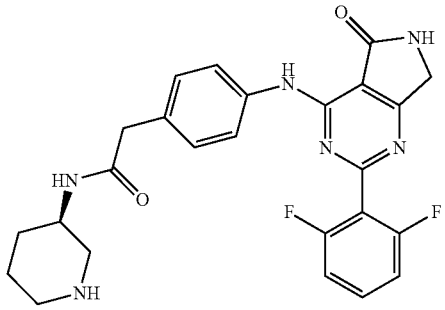 [SMILES: O=C(Cc1ccc(Nc2nc(-c3c(F)cccc3F)nc3c2C(=O)NC3)cc1)N[C@@H]1CCCNC1] |

TABLE 1-continued
Exemplary Compounds
| Compound | Structure |
|---|---|
| I-62 | 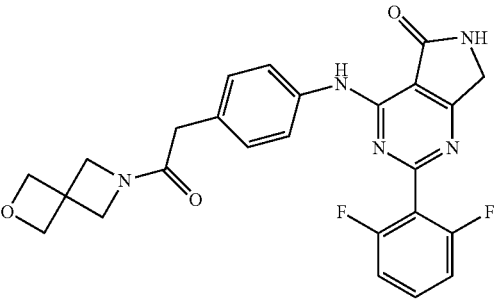 [SMILES: O=C1NCc2nc(-c3c(F)cccc3F)nc(Nc3ccc(CC(=O)N4CC5(COC5)C4)cc3)c21] |
| I-63 | 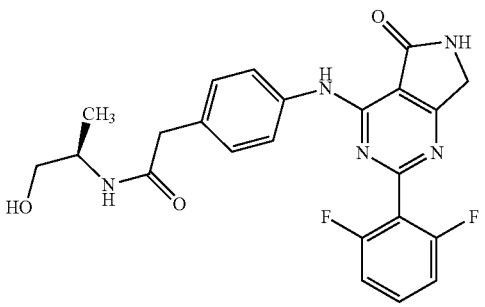 [SMILES: C[C@H](CO)NC(=O)Cc1ccc(Nc2nc(-c3c(F)cccc3F)nc3c2C(=O)NC3)cc1] |
| I-64 | 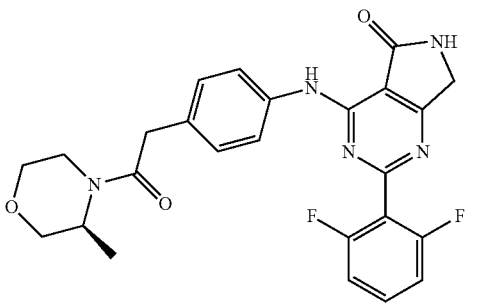 [SMILES: C[C@H]1COCCN1C(=O)Cc1ccc(Nc2nc(-c3c(F)cccc3F)nc3c2C(=O)NC3)cc1] |
| I-65 | 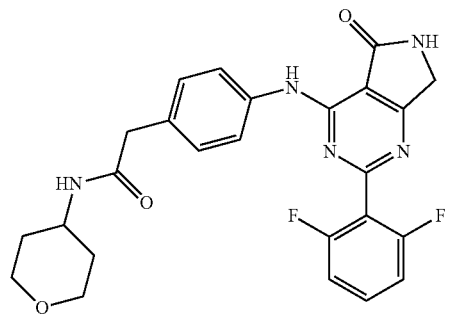 [SMILES: O=C(Cc1ccc(Nc2nc(-c3c(F)cccc3F)nc3c2C(=O)NC3)cc1)NC1CCOCC1] |
| I-66 | 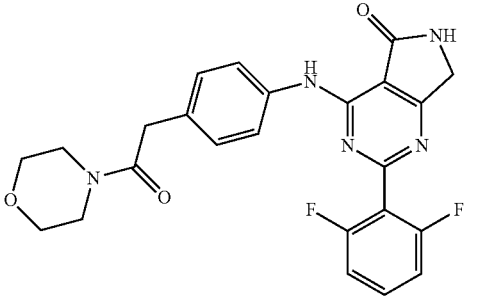 [SMILES: O=C1NCc2nc(-c3c(F)cccc3F)nc(Nc3ccc(CC(=O)N4CCOCC4)cc3)c21] |

TABLE 1-continued

Exemplary Compounds

| Compound | Structure |
|---|---|
| I-67 | |
| I-68 | |
| I-69 | |
| I-70 | |
| I-71 | |

TABLE 1-continued
Exemplary Compounds
| Compound | Structure |
|---|---|
| I-72 | 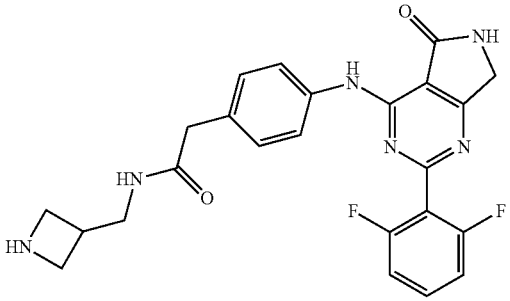 [SMILES: O=C(Cc1ccc(Nc2nc(-c3c(F)cccc3F)nc3c2C(=O)NC3)cc1)NCC1CNC1] |
| I-73 | 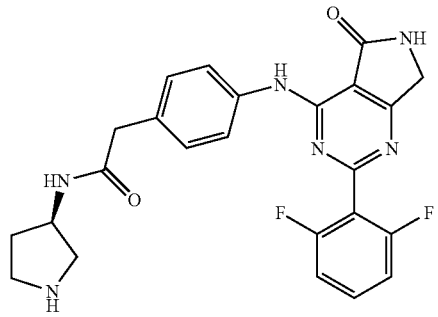 [SMILES: O=C(Cc1ccc(Nc2nc(-c3c(F)cccc3F)nc3c2C(=O)NC3)cc1)N[C@@H]1CCNC1] |
| I-74 | 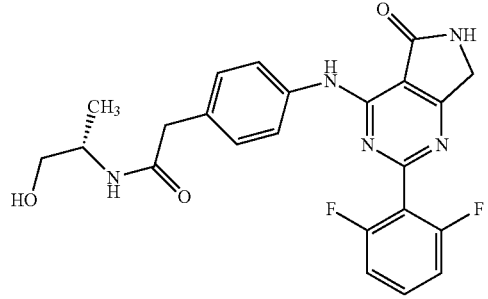 [SMILES: C[C@@H](CO)NC(=O)Cc1ccc(Nc2nc(-c3c(F)cccc3F)nc3c2C(=O)NC3)cc1] |
| I-75 | 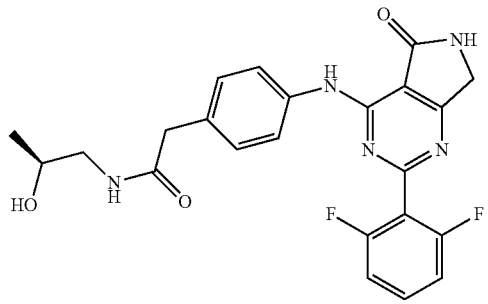 [SMILES: C[C@H](O)CNC(=O)Cc1ccc(Nc2nc(-c3c(F)cccc3F)nc3c2C(=O)NC3)cc1] |
| I-76 | 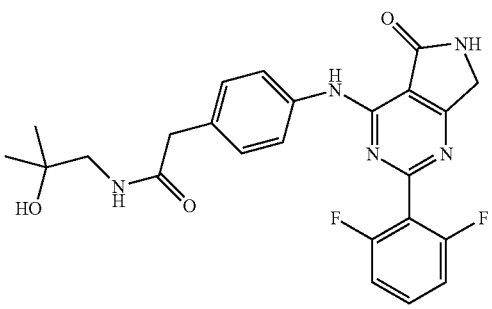 [SMILES: CC(C)(O)CNC(=O)Cc1ccc(Nc2nc(-c3c(F)cccc3F)nc3c2C(=O)NC3)cc1] |

TABLE 1-continued

Exemplary Compounds

| Compound | Structure |
|---|---|
| I-77 | |
| I-78 | |
| I-79 | |
| I-80 | |
| I-81 | |

TABLE 1-continued

Exemplary Compounds

| Compound | Structure |
|---|---|
| I-82 | |
| I-83 | |
| I-84 | |
| I-85 | |
| I-86 | |

TABLE 1-continued
Exemplary Compounds
| Compound | Structure |
|---|---|
| I-87 | 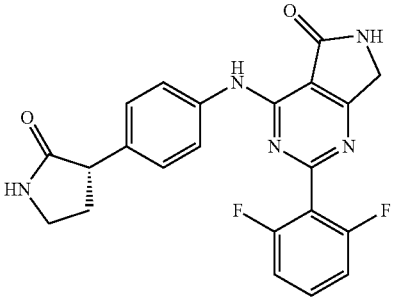 [SMILES: O=C1NCc2nc(-c3c(F)cccc3F)nc(Nc3ccc([C@@H]4CCNC4=O)cc3)c21] |
| I-88 | 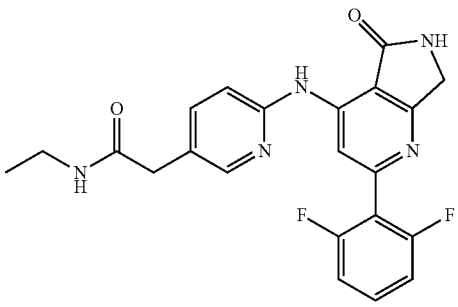 [SMILES: CCNC(=O)Cc1ccc(Nc2cc(-c3c(F)cccc3F)nc3c2C(=O)NC3)nc1] |
| I-89 | 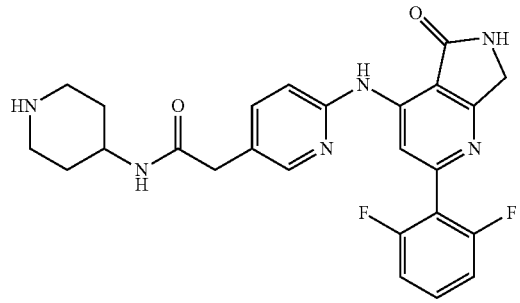 [SMILES: O=C(Cc1ccc(Nc2cc(-c3c(F)cccc3F)nc3c2C(=O)NC3)nc1)NC1CCNCC1] |
| I-90 | 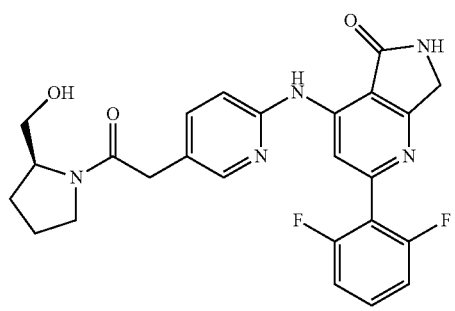 [SMILES: O=C1NCc2nc(-c3c(F)cccc3F)cc(Nc3ccc(CC(=O)N4CCC[C@H]4CO)cn3)c21] |
| I-91 | 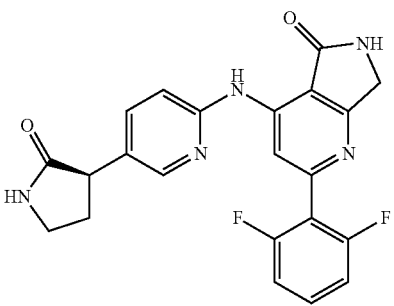 [SMILES: O=C1NCc2nc(-c3c(F)cccc3F)cc(Nc3ccc([C@H]4CCNC4=O)cn3)c21] |

TABLE 1-continued

Exemplary Compounds

| Compound | Structure |
|---|---|
| I-92 | 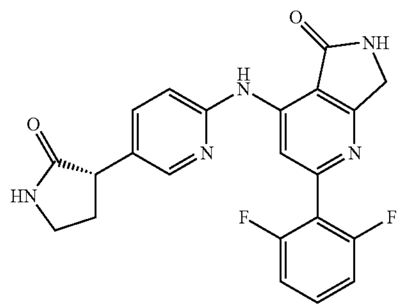 [SMILES: O=C1NCc2nc(-c3c(F)cccc3F)cc(Nc3ccc([C@@H]4CCNC4=O)cn3)c21] |
| I-93 | 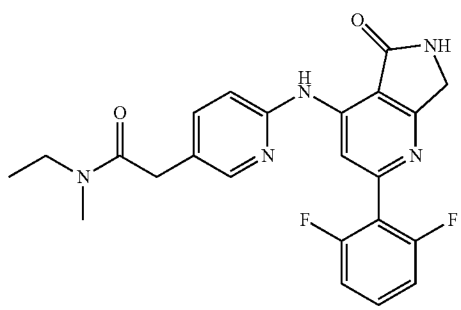 [SMILES: CCN(C)C(=O)Cc1ccc(Nc2cc(-c3c(F)cccc3F)nc3c2C(=O)NC3)nc1] |
| I-94 | 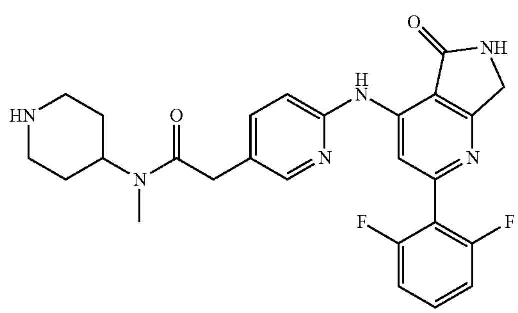 [SMILES: CN(C(=O)Cc1ccc(Nc2cc(-c3c(F)cccc3F)nc3c2C(=O)NC3)nc1)C1CCNCC1] |
| I-95 | 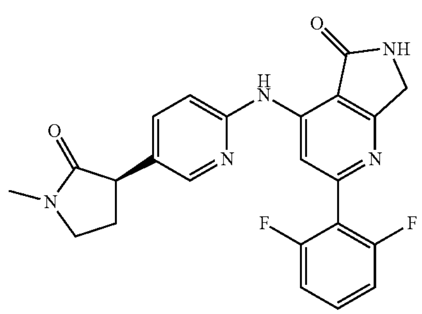 [SMILES: CN1CC[C@H](c2ccc(Nc3cc(-c4c(F)cccc4F)nc4c3C(=O)NC4)nc2)C1=O] |
| I-96 | 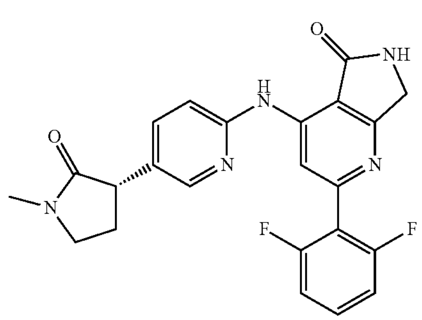 [SMILES: CN1CC[C@@H](c2ccc(Nc3cc(-c4c(F)cccc4F)nc4c3C(=O)NC4)nc2)C1=O] |

TABLE 1-continued
Exemplary Compounds
| Compound | Structure |
|---|---|
| I-97 | 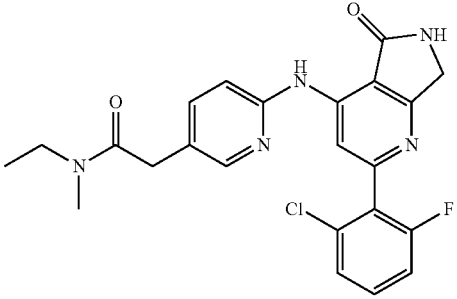 [SMILES: CCN(C)C(=O)Cc1ccc(Nc2cc(-c3c(F)cccc3Cl)nc3c2C(=O)NC3)nc1] |
| I-98 | 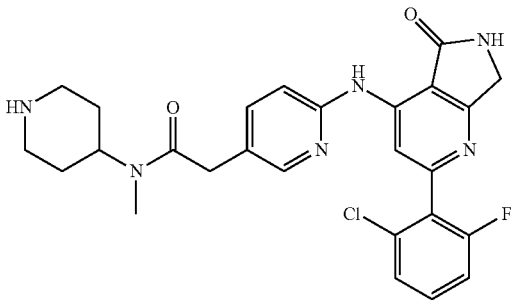 [SMILES: CN(C(=O)Cc1ccc(Nc2cc(-c3c(F)cccc3Cl)nc3c2C(=O)NC3)nc1)C1CCNCC1] |
| I-99 | 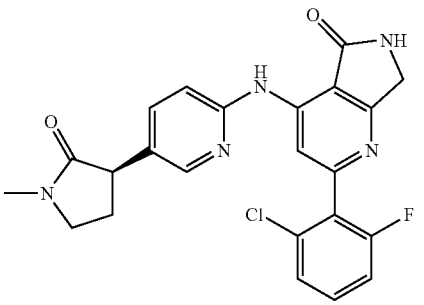 [SMILES: CN1CC[C@H](c2ccc(Nc3cc(-c4c(F)cccc4Cl)nc4c3C(=O)NC4)nc2)C1=O] |
| I-100 | 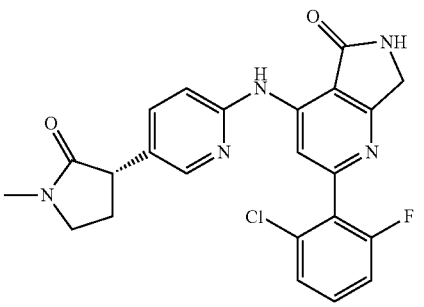 [SMILES: CN1CC[C@@H](c2ccc(Nc3cc(-c4c(F)cccc4Cl)nc4c3C(=O)NC4)nc2)C1=O] |
| I-101 | 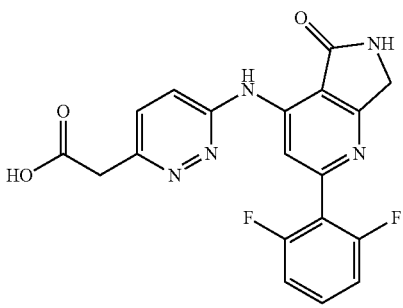 [SMILES: O=C(O)Cc1ccc(Nc2cc(-c3c(F)cccc3F)nc3c2C(=O)NC3)nn1] |

TABLE 1-continued

Exemplary Compounds

| Compound | Structure |
|---|---|
| I-102 | 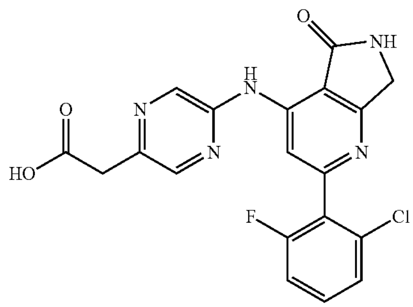 [SMILES: O=C(O)Cc1cnc(Nc2cc(-c3c(F)cccc3Cl)nc3c2C(=O)NC3)cn1] |
| I-103 | 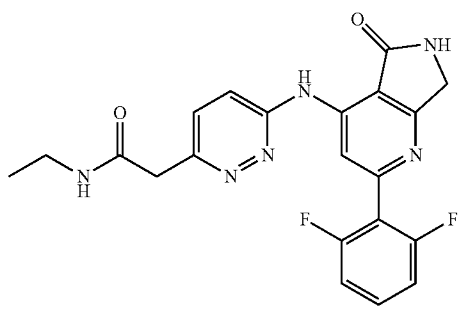 [SMILES: CCNC(=O)Cc1ccc(Nc2cc(-c3c(F)cccc3F)nc3c2C(=O)NC3)nn1] |
| I-104 | 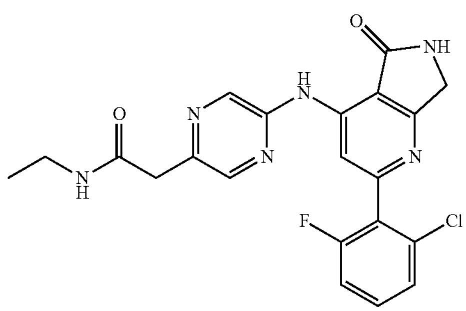 [SMILES: CCNC(=O)Cc1cnc(Nc2cc(-c3c(F)cccc3Cl)nc3c2C(=O)NC3)cn1] |
| I-105 | 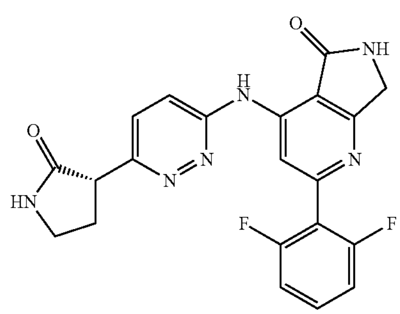 [SMILES: O=C1NCc2nc(-c3c(F)cccc3F)cc(Nc3ccc([C@@H]4CCNC4=O)nn3)c21] |
| I-106 | 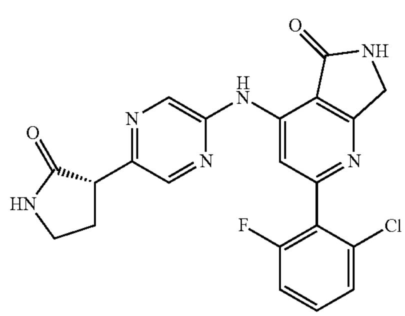 [SMILES: O=C1NCc2nc(-c3c(F)cccc3Cl)cc(Nc3cnc([C@@H]4CCNC4=O)cn3)c21] |

TABLE 1-continued

Exemplary Compounds

| Compound | Structure |
|---|---|
| I-107 | 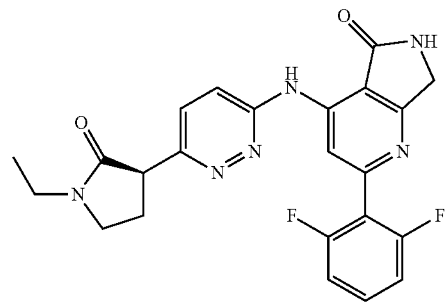 [SMILES: CCN1CC[C@H](c2ccc(Nc3cc(-c4c(F)cccc4F)nc4c3C(=O)NC4)nn2)C1=O] |
| I-108 | 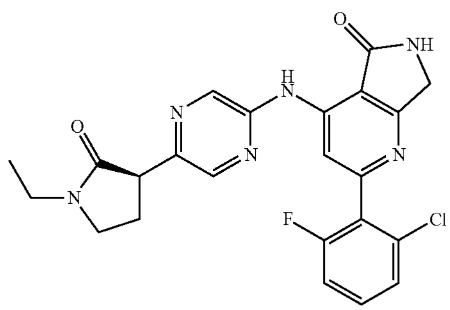 [SMILES: CCN1CC[C@H](c2cnc(Nc3cc(-c4c(F)cccc4Cl)nc4c3C(=O)NC4)cn2)C1=O] |
| I-109 | 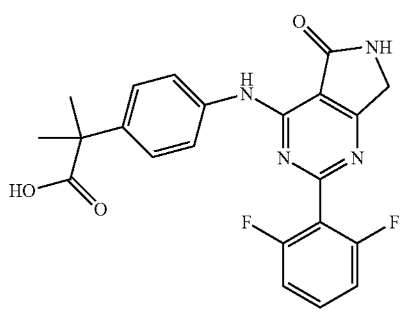 [SMILES: CC(C)(C(=O)O)c1ccc(Nc2nc(-c3c(F)cccc3F)nc3c2C(=O)NC3)cc1] |
| I-110 | 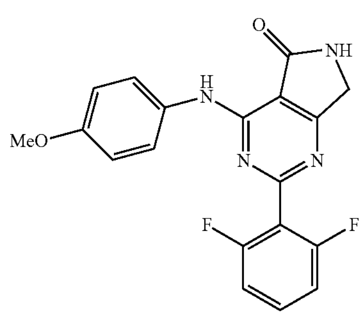 [SMILES: COc1ccc(Nc2nc(-c3c(F)cccc3F)nc3c2C(=O)NC3)cc1] |
| I-111 | 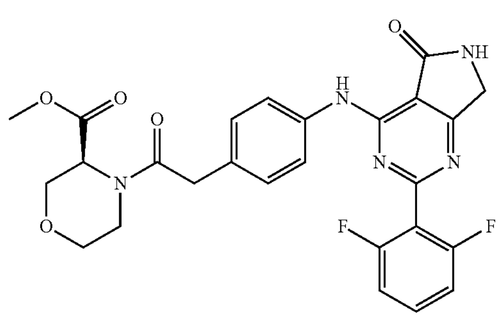 [SMILES: COC(=O)[C@@H]1COCCN1C(=O)Cc1ccc(Nc2nc(-c3c(F)cccc3F)nc3c2C(=O)NC3)cc1] |

TABLE 1-continued
Exemplary Compounds
| Compound | Structure |
|---|---|
| I-112 | 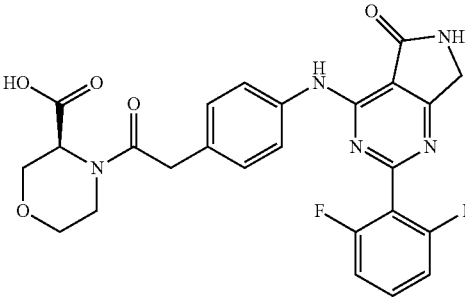 |
| I-113 | 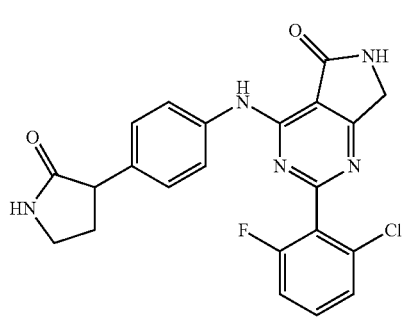 [SMILES: O=C1NCc2nc(-c3c(F)cccc3Cl)nc(Nc3ccc(C4CCNC4=O)cc3)c21] |
| I-114 | 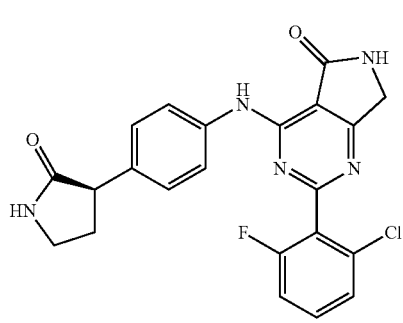 [SMILES: O=C1NCc2nc(-c3c(F)cccc3Cl)nc(Nc3ccc([C@H]4CCNC4=O)cc3)c21] |
| I-115 | 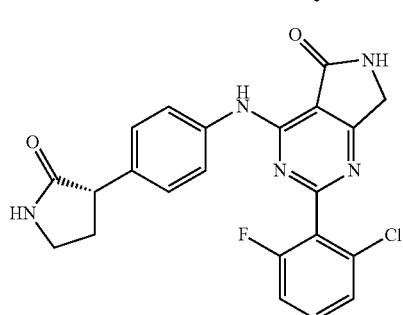 |
| I-116 | 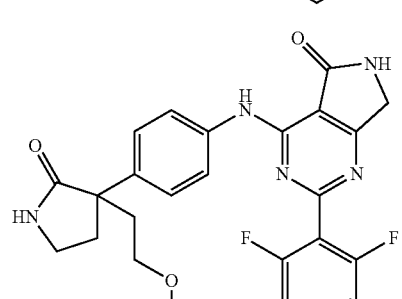 |

TABLE 1-continued

Exemplary Compounds

| Compound | Structure |
|---|---|
| I-117 | |
| I-118 | |
| I-119 | |
| I-120 | |
| I-121 | |

TABLE 1-continued

Exemplary Compounds

| Compound | Structure |
|---|---|
| I-122 | |
| I-123 | |
| I-124 | |
| I-125 | |
| I-126 | |

TABLE 1-continued
Exemplary Compounds
| Compound | Structure |
|---|---|
| I-127 | 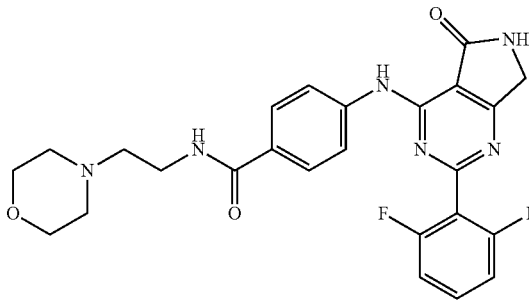 |
| I-128 | 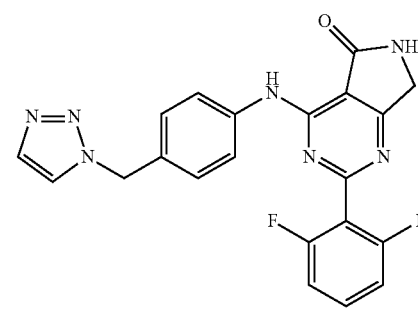 |
| I-129 | 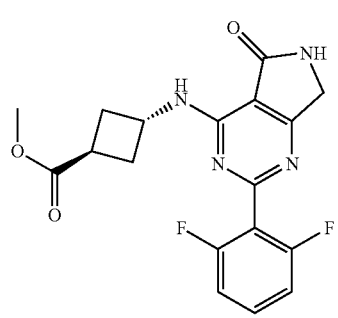 [SMILES: COC(=O)[C@H]1C[C@H](Nc2nc(-c3c(F)cccc3F)nc3c2C(=O)NC3)C1] |
| I-130 | 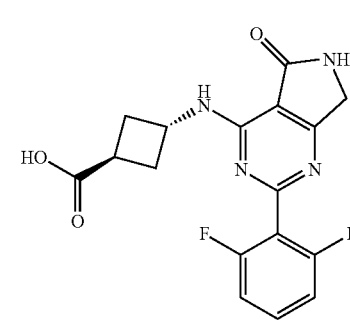 |
| I-131 | 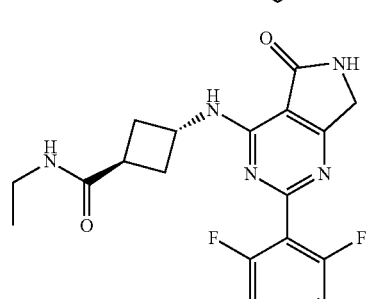 |

TABLE 1-continued
Exemplary Compounds
| Compound | Structure |
|---|---|
| I-132 | 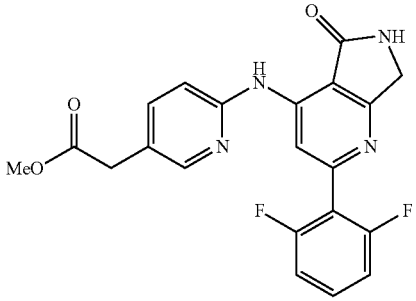 [SMILES: COC(=O)Cc1ccc(Nc2cc(-c3c(F)cccc3F)nc3c2C(=O)NC3)nc1] |
| I-133 | 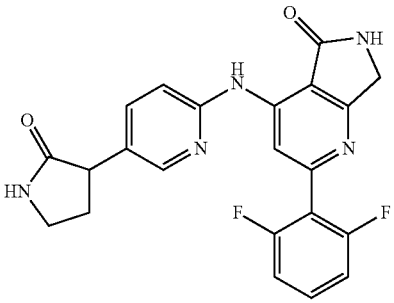 [SMILES: O=C1NCc2nc(-c3c(F)cccc3F)cc(Nc3ccc(C4CCNC4=O)cn3)c21] |
| I-134 | 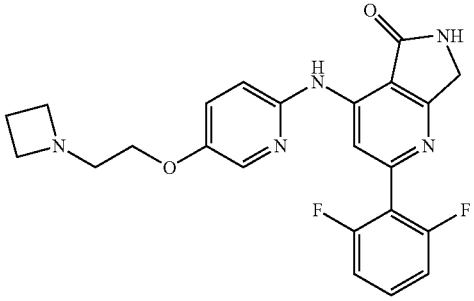 [SMILES: O=C1NCc2nc(-c3c(F)cccc3F)cc(Nc3ccc(OCCN4CCC4)cn3)c21] |
| I-135 | 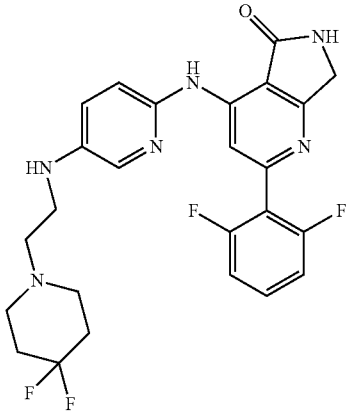 [SMILES: O=C1NCc2nc(-c3c(F)cccc3F)cc(Nc3ccc(NCCN4CCC(F)(F)CC4)cn3)c21] |

TABLE 1-continued

Exemplary Compounds

| Compound | Structure |
|---|---|
| I-136 | |
| I-137 | |
| I-138 | |
| I-139 | |
| I-140 | |

TABLE 1-continued

Exemplary Compounds

| Compound | Structure |
|---|---|
| I-141 | |
| I-142 | |
| I-143 | |
| I-144 | |
| I-145 | |

TABLE 1-continued

Exemplary Compounds

| Compound | Structure |
|---|---|
| I-146 | |
| I-147 | |
| I-148 | |
| I-149 | |
| I-150 | |

TABLE 1-continued

Exemplary Compounds

| Compound | Structure |
|---|---|
| I-151 | |
| I-152 | |
| I-153 | |
| I-154 | |
| I-155 | |

TABLE 1-continued

Exemplary Compounds

| Compound | Structure |
|---|---|
| I-156 | 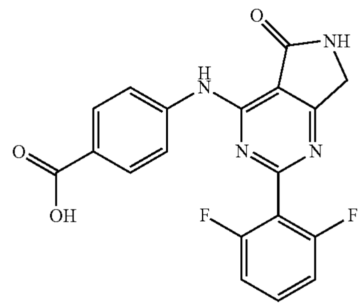 [SMILES: O=C(O)c1ccc(Nc2nc(-c3c(F)cccc3F)nc3c2C(=O)NC3)cc1] |
| I-157 | 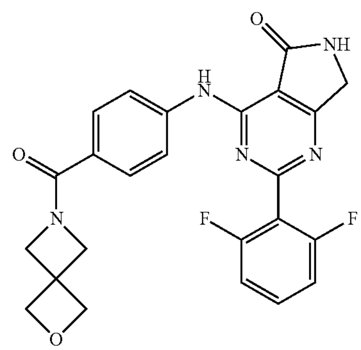 [SMILES: O=C1NCc2nc(-c3c(F)cccc3F)nc(Nc3ccc(C(=O)N4CC5(COC5)C4)cc3)c21] |
| I-158 | 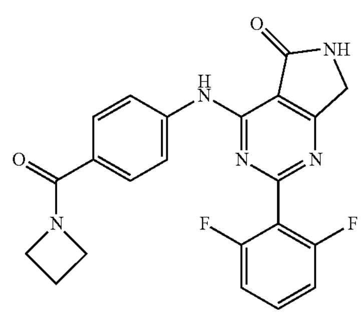 [SMILES: O=C1NCc2nc(-c3c(F)cccc3F)nc(Nc3ccc(C(=O)N4CCC4)cc3)c21] |
| I-159 | 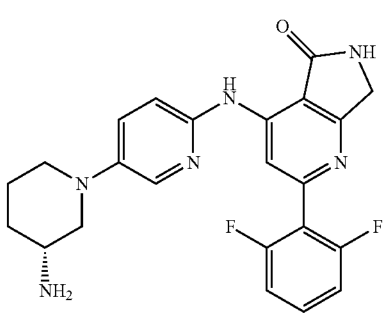 [SMILES: N[C@@H]1CCCN(c2ccc(Nc3cc(-c4c(F)cccc4F)nc4c3C(=O)NC4)nc2)C1] |

TABLE 1-continued

Exemplary Compounds

| Compound | Structure |
|---|---|
| I-160 | 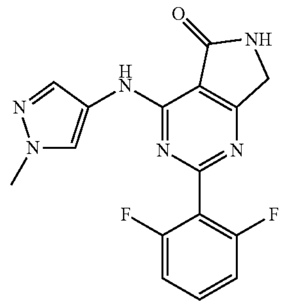 [SMILES: Cn1cc(Nc2nc(-c3c(F)cccc3F)nc3c2C(=O)NC3)cn1] |
| I-161 | 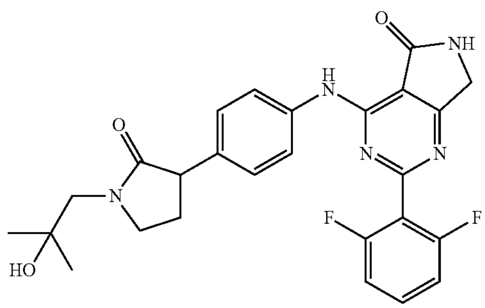 [SMILES: CC(C)(O)CN1CCC(c2ccc(Nc3nc(-c4c(F)cccc4F)nc4c3C(=O)NC4)cc2)C1=O] |
| I-162 | 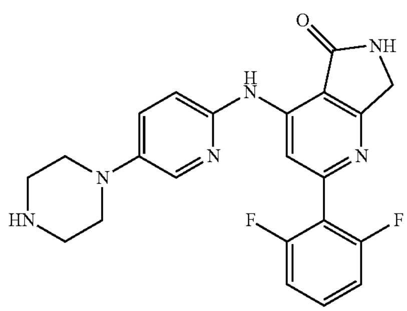 [SMILES: O=C1NCc2nc(-c3c(F)cccc3F)cc(Nc3ccc(N4CCNCC4)cn3)c21] |
| I-163 | 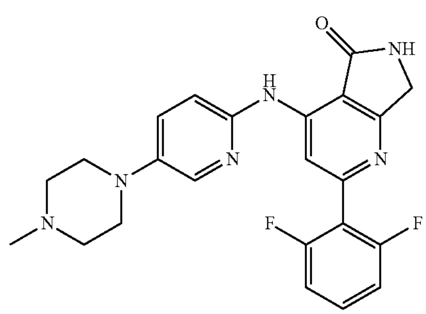 [SMILES: CN1CCN(c2ccc(Nc3cc(-c4c(F)cccc4F)nc4c3C(=O)NC4)nc2)CC1] |
| I-164 | 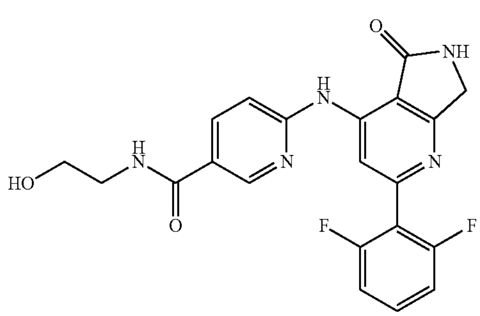 [SMILES: O=C(NCCO)c1ccc(Nc2cc(-c3c(F)cccc3F)nc3c2C(=O)NC3)nc1] |

TABLE 1-continued

Exemplary Compounds

| Compound | Structure |
|---|---|
| I-165 | 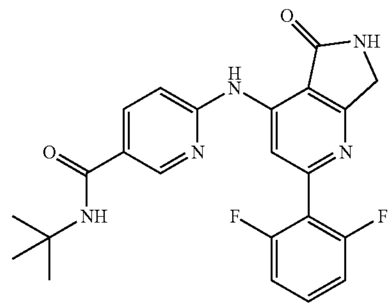 [SMILES: CC(C)(C)NC(=O)c1ccc(Nc2cc(-c3c(F)cccc3F)nc3c2C(=O)NC3)nc1] |
| I-166 | 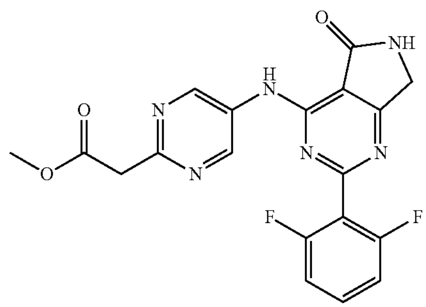 [SMILES: COC(=O)Cc1ncc(Nc2nc(-c3c(F)cccc3F)nc3c2C(=O)NC3)cn1] |
| I-167 | 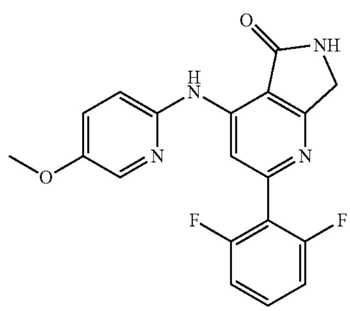 [SMILES: COc1ccc(Nc2cc(-c3c(F)cccc3F)nc3c2C(=O)NC3)nc1] |
| I-168 | 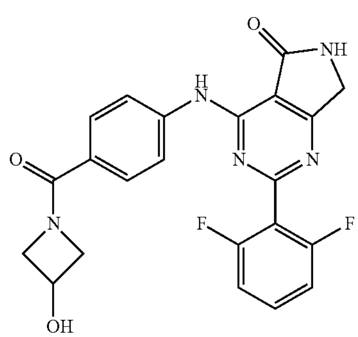 [SMILES: O=C1NCc2nc(-c3c(F)cccc3F)nc(Nc3ccc(C(=O)N4CC(O)C4)cc3)c21] |
| I-169 | 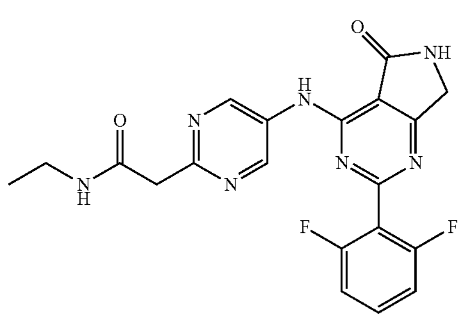 [SMILES: CCNC(=O)Cc1ncc(Nc2nc(-c3c(F)cccc3F)nc3c2C(=O)NC3)cn1] |

TABLE 1-continued
Exemplary Compounds
| Compound | Structure |
|---|---|
| I-170 | 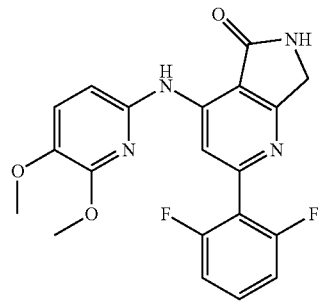 [SMILES: COc1ccc(Nc2cc(-c3c(F)cccc3F)nc3c2C(=O)NC3)nc1OC] |
| I-171 | 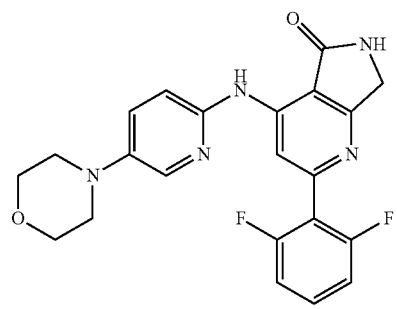 [SMILES: O=C1NCc2nc(-c3c(F)cccc3F)cc(Nc3ccc(N4CCOCC4)cn3)c21] |
| I-172 | 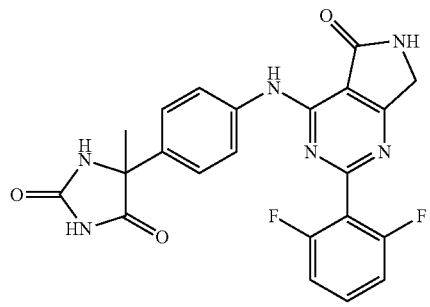 [SMILES: CC1(c2ccc(Nc3nc(-c4c(F)cccc4F)nc4c3C(=O)NC4)cc2)NC(=O)NC1=O] |
| I-173 | 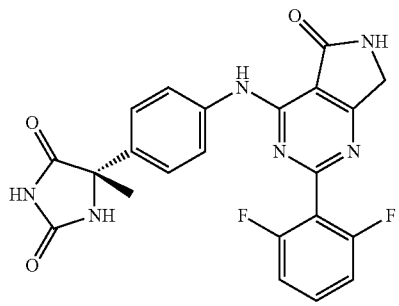 [SMILES: C[C@@]1(c2ccc(Nc3nc(-c4c(F)cccc4F)nc4c3C(=O)NC4)cc2)NC(=O)NC1=O] |
| I-174 | 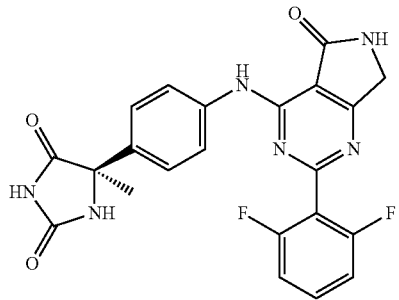 [SMILES: C[C@]1(c2ccc(Nc3nc(-c4c(F)cccc4F)nc4c3C(=O)NC4)cc2)NC(=O)NC1=O] |

TABLE 1-continued

Exemplary Compounds

| Compound | Structure |
|---|---|
| I-175 | 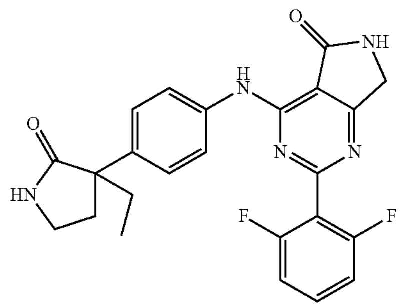 [SMILES: CCC1(c2ccc(Nc3nc(-c4c(F)cccc4F)nc4c3C(=O)NC4)cc2)CCNC1=O] |
| I-176 | 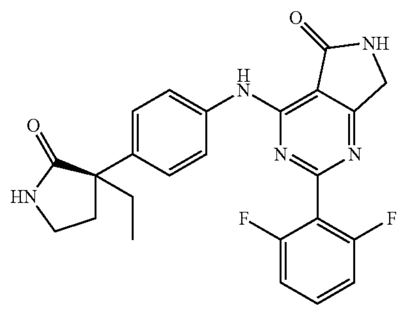 [SMILES: CC[C@@]1(c2ccc(Nc3nc(-c4c(F)cccc4F)nc4c3C(=O)NC4)cc2)CCNC1=O] |
| I-177 | 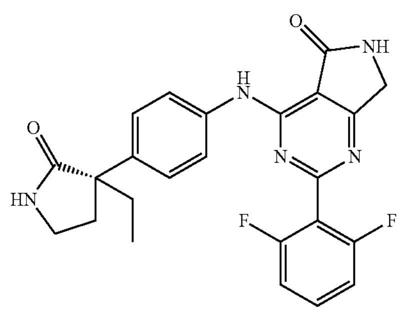 [SMILES: CC[C@]1(c2ccc(Nc3nc(-c4c(F)cccc4F)nc4c3C(=O)NC4)cc2)CCNC1=O] |
| I-178 | 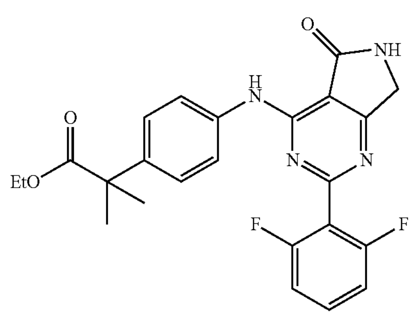 [SMILES: CCOC(=O)C(C)(C)c1ccc(Nc2nc(-c3c(F)cccc3F)nc3c2C(=O)NC3)cc1] |
| I-179 | 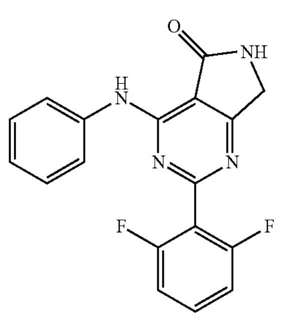 [SMILES: O=C1NCc2nc(-c3c(F)cccc3F)nc(Nc3ccccc3)c21] |

TABLE 1-continued
Exemplary Compounds
| Compound | Structure |
|---|---|
| I-180 | 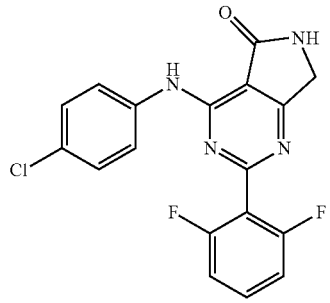 [SMILES: O=C1NCc2nc(-c3c(F)cccc3F)nc(Nc3ccc(Cl)cc3)c21] |
| I-181 | 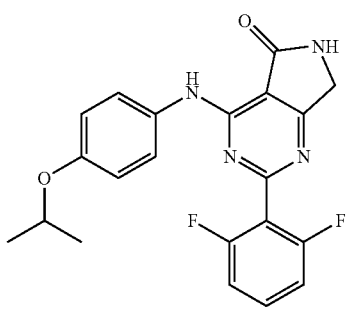 [SMILES: CC(C)Oc1ccc(Nc2nc(-c3c(F)cccc3F)nc3c2C(=O)NC3)cc1] |
| I-182 | 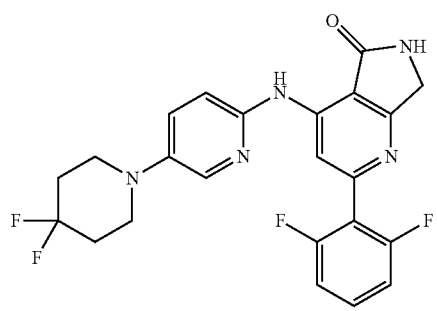 [SMILES: O=C1NCc2nc(-c3c(F)cccc3F)cc(Nc3ccc(N4CCC(F)(F)CC4)cn3)c21] |
| I-183 | 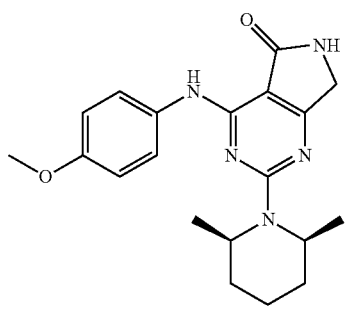 |
| I-184 | 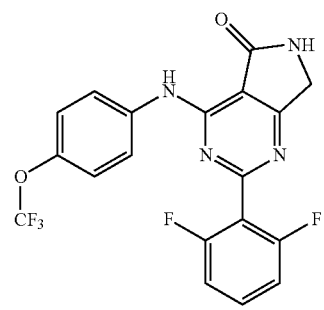 [SMILES: O=C1NCc2nc(-c3c(F)cccc3F)nc(Nc3ccc(OC(F)(F)F)cc3)c21] |

TABLE 1-continued

Exemplary Compounds

| Compound | Structure |
|---|---|
| I-185 | 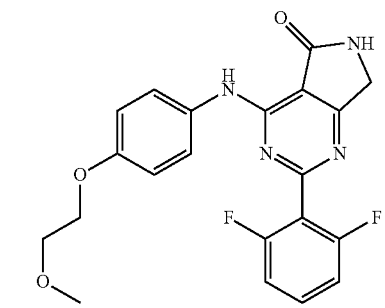 [SMILES: COCCOc1ccc(Nc2nc(-c3c(F)cccc3F)nc3c2C(=O)NC3)cc1] |
| I-186 | 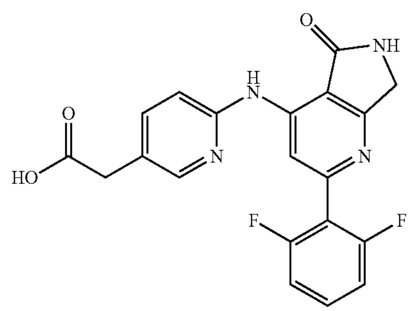 [SMILES: O=C(O)Cc1ccc(Nc2cc(-c3c(F)cccc3F)nc3c2C(=O)NC3)nc1] |
| I-187 | 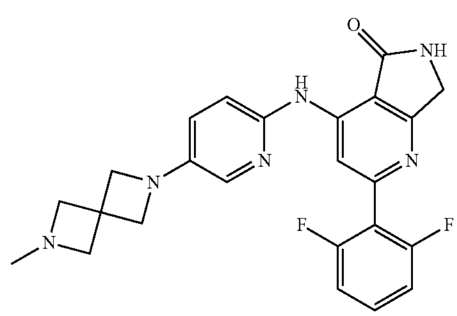 [SMILES: CN1CC2(C1)CN(c1ccc(Nc3cc(-c4c(F)cccc4F)nc4c3C(=O)NC4)nc1)C2] |
| I-188 | 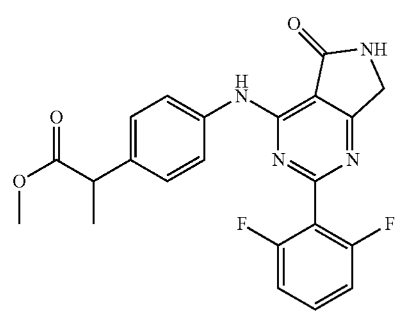 [SMILES: COC(=O)C(C)c1ccc(Nc2nc(-c3c(F)cccc3F)nc3c2C(=O)NC3)cc1] |
| I-189 | 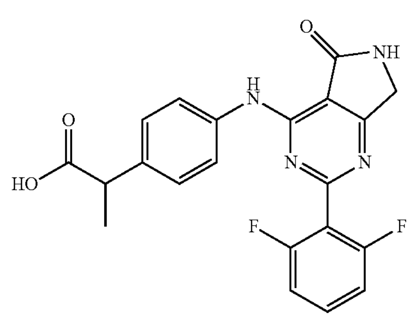 [SMILES: CC(C(=O)O)c1ccc(Nc2nc(-c3c(F)cccc3F)nc3c2C(=O)NC3)cc1] |

TABLE 1-continued
Exemplary Compounds
| Compound | Structure |
|---|---|
| I-190 | 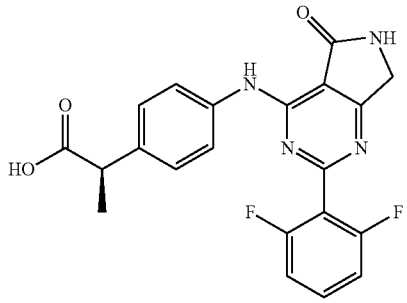 [SMILES: C[C@@H](C(=O)O)c1ccc(Nc2nc(-c3c(F)cccc3F)nc3c2C(=O)NC3)cc1] |
| I-191 | 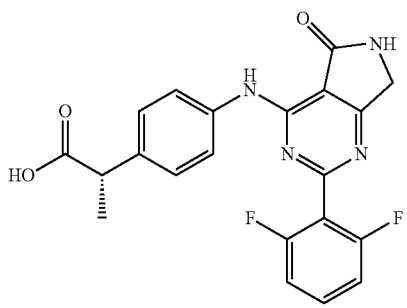 [SMILES: C[C@H](C(=O)O)c1ccc(Nc2nc(-c3c(F)cccc3F)nc3c2C(=O)NC3)cc1] |
| I-192 | 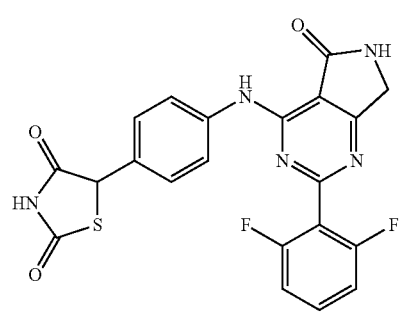 [SMILES: O=C1NC(=O)C(c2ccc(Nc3nc(-c4c(F)cccc4F)nc4c3C(=O)NC4)cc2)S1] |
| I-193 | 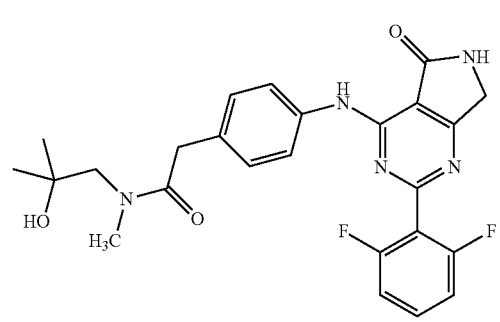 [SMILES: CN(CC(C)(C)O)C(=O)Cc1ccc(Nc2nc(-c3c(F)cccc3F)nc3c2C(=O)NC3)cc1] |
| I-194 | 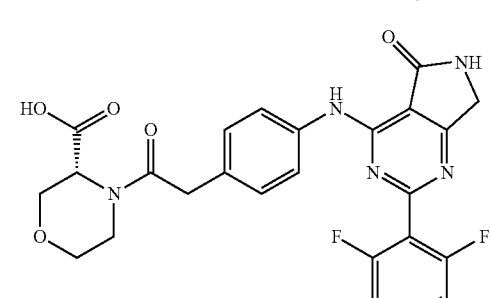 |

TABLE 1-continued

Exemplary Compounds

| Compound | Structure |
|---|---|
| I-195 | 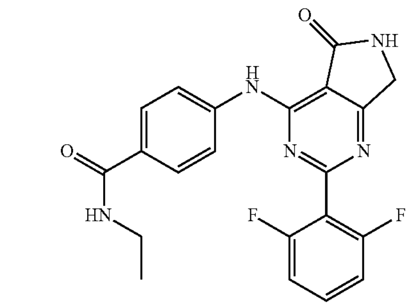 [SMILES: CCNC(=O)c1ccc(Nc2nc(-c3c(F)cccc3F)nc3c2C(=O)NC3)cc1] |
| I-196 | 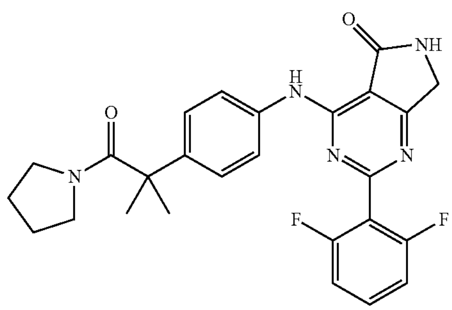 [SMILES: CC(C)(C(=O)N1CCCC1)c1ccc(Nc2nc(-c3c(F)cccc3F)nc3c2C(=O)NC3)cc1] |
| I-197 | 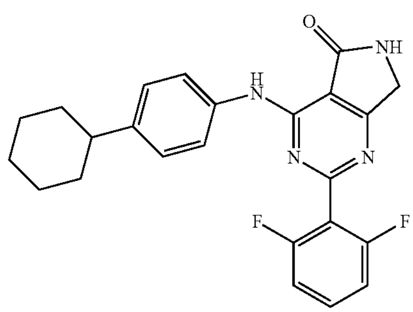 [SMILES: O=C1NCc2nc(-c3c(F)cccc3F)nc(Nc3ccc(C4CCCCC4)cc3)c21] |
| I-198 | 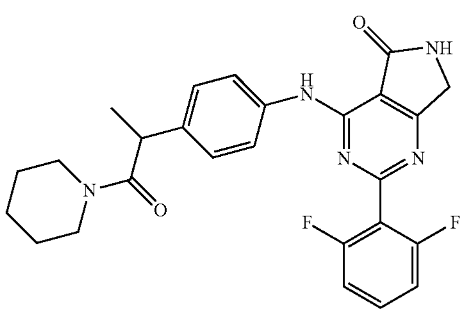 [SMILES: CC(C(=O)N1CCCCC1)c1ccc(Nc2nc(-c3c(F)cccc3F)nc3c2C(=O)NC3)cc1] |
| I-199 | 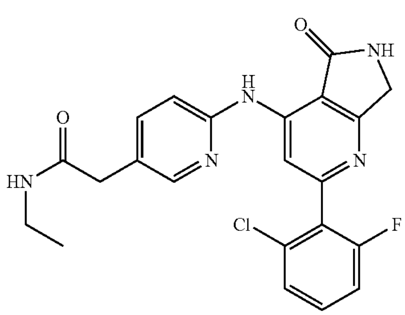 [SMILES: CCNC(=O)Cc1ccc(Nc2cc(-c3c(F)cccc3Cl)nc3c2C(=O)NC3)nc1] |

TABLE 1-continued
Exemplary Compounds
| Compound | Structure |
|---|---|
| I-200 | 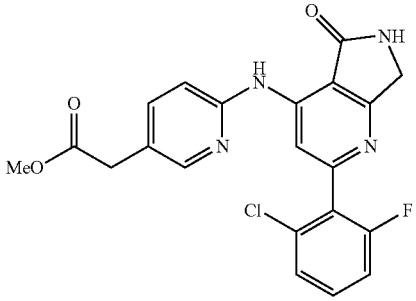 [SMILES: COC(=O)Cc1ccc(Nc2cc(-c3c(F)cccc3Cl)nc3c2C(=O)NC3)nc1] |
| I-201 | 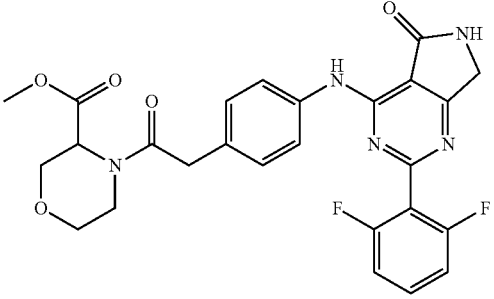 [SMILES: COC(=O)C1COCCN1C(=O)Cc1ccc(Nc2nc(-c3c(F)cccc3F)nc3c2C(=O)NC3)cc1] |
| I-202 | 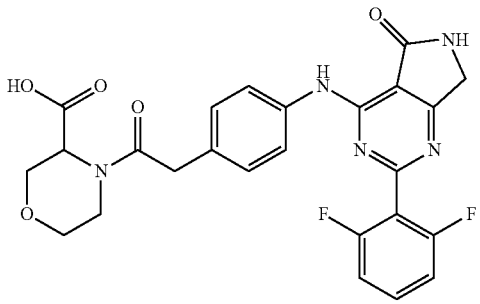 |
| I-203 | 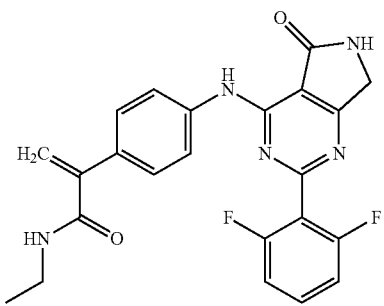 [SMILES: C=C(C(=O)NCC)c1ccc(Nc2nc(-c3c(F)cccc3F)nc3c2C(=O)NC3)cc1] |
| I-204 | 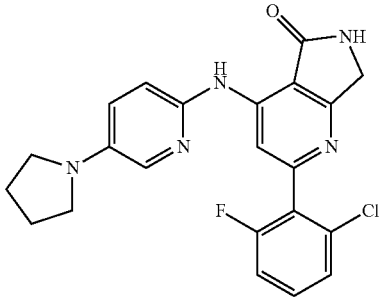 [SMILES: O=C1NCc2nc(-c3c(F)cccc3Cl)cc(Nc3ccc(N4CCCC4)cn3)c21] |

TABLE 1-continued
Exemplary Compounds
| Compound | Structure |
|---|---|
| I-205 | 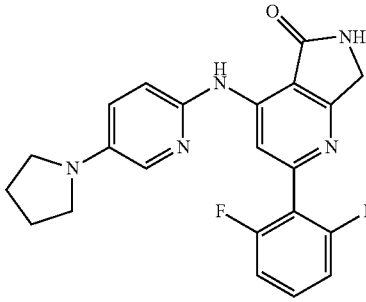 |
| I-206 | 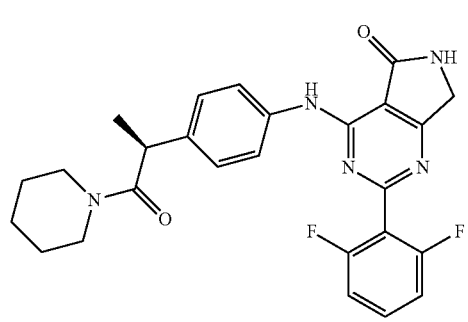 [SMILES: C[C@H](C(=O)N1CCCCC1)c1ccc(Nc2nc(-c3c(F)cccc3F)nc3c2C(=O)NC3)cc1] |
| I-207 | 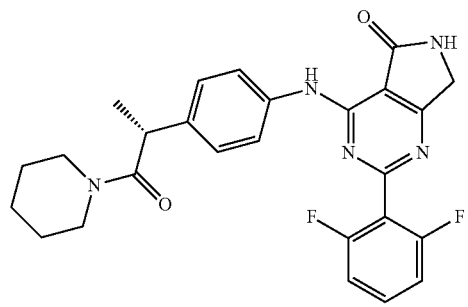 |
| I-208 | 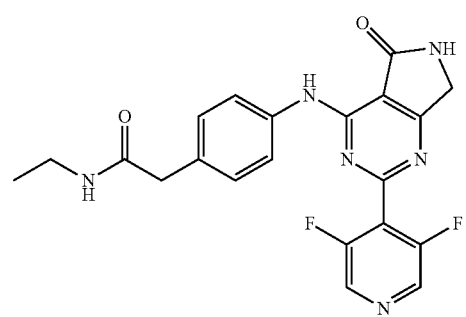 [SMILES: CCNC(=O)Cc1ccc(Nc2nc(-c3c(F)cncc3F)nc3c2C(=O)NC3)cc1] |
| I-209 | 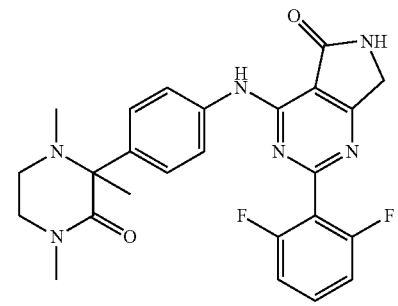 [SMILES: CN1CCN(C)C(C)(c2ccc(Nc3nc(-c4c(F)cccc4F)nc4c3C(=O)NC4)cc2)C1=O] |

TABLE 1-continued

Exemplary Compounds

| Compound | Structure |
|---|---|
| I-210 | 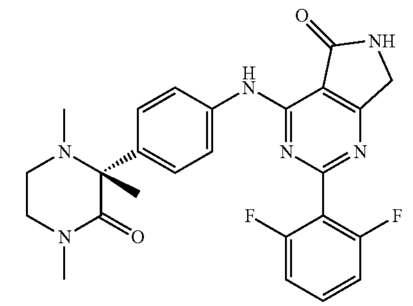 [SMILES: CN1CCN(C)[C@](C)(c2ccc(Nc3nc(-c4c(F)cccc4F)nc4c3C(=O)NC4)cc2)C1=O] |
| I-211 | 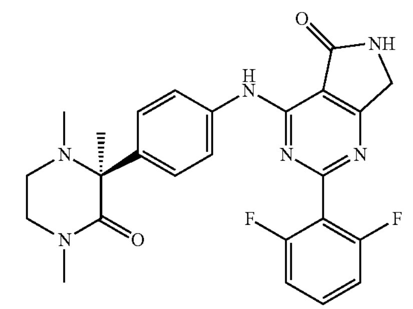 [SMILES: CN1CCN(C)[C@@](C)(c2ccc(Nc3nc(-c4c(F)cccc4F)nc4c3C(=O)NC4)cc2)C1=O] |
| I-212 | 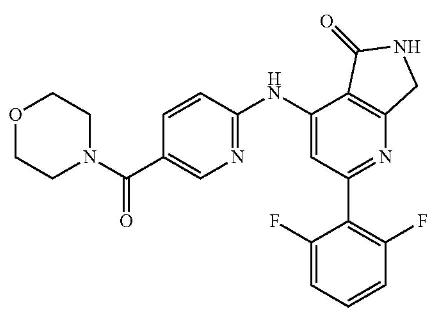 [SMILES: O=C1NCc2nc(-c3c(F)cccc3F)cc(Nc3ccc(C(=O)N4CCOCC4)cn3)c21] |
| I-213 | 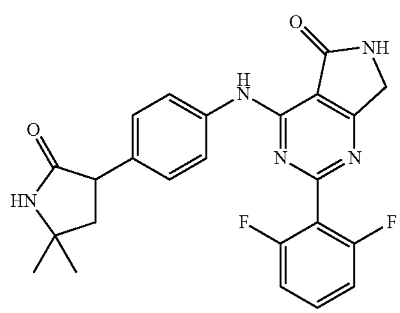 [SMILES: CC1(C)CC(c2ccc(Nc3nc(-c4c(F)cccc4F)nc4c3C(=O)NC4)cc2)C(=O)N1] |
| I-214 | 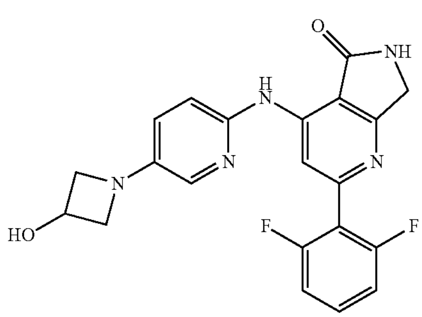 [SMILES: O=C1NCc2nc(-c3c(F)cccc3F)cc(Nc3ccc(N4CC(O)C4)cn3)c21] |

TABLE 1-continued

Exemplary Compounds

| Compound | Structure |
|---|---|
| I-215 | 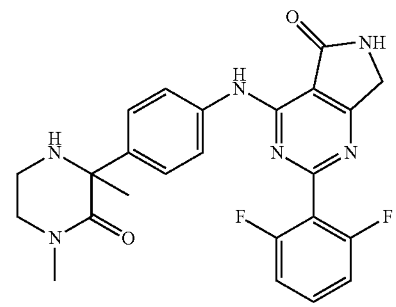 [SMILES: CN1CCNC(C)(c2ccc(Nc3nc(-c4c(F)cccc4F)nc4c3C(=O)NC4)cc2)C1=O] |
| I-216 | 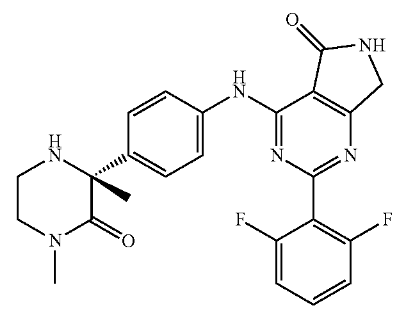 [SMILES: CN1CCN[C@](C)(c2ccc(Nc3nc(-c4c(F)cccc4F)nc4c3C(=O)NC4)cc2)C1=O] |
| I-217 | 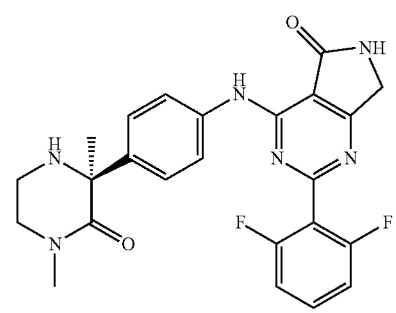 [SMILES: CN1CCN[C@@](C)(c2ccc(Nc3nc(-c4c(F)cccc4F)nc4c3C(=O)NC4)cc2)C1=O] |
| I-218 | 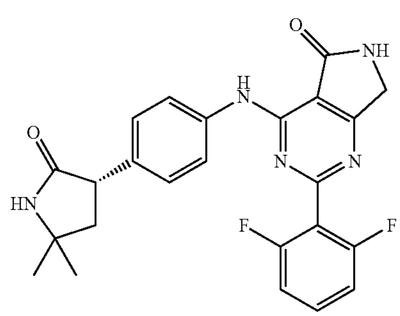 [SMILES: CC1(C)C[C@@H](c2ccc(Nc3nc(-c4c(F)cccc4F)nc4c3C(=O)NC4)cc2)C(=O)N1] |
| I-219 | 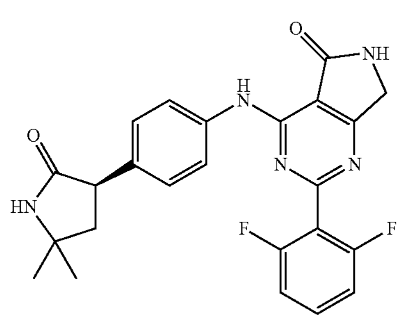 [SMILES: CC1(C)C[C@H](c2ccc(Nc3nc(-c4c(F)cccc4F)nc4c3C(=O)NC4)cc2)C(=O)N1] |

TABLE 1-continued

Exemplary Compounds

| Compound | Structure |
|---|---|
| I-220 | 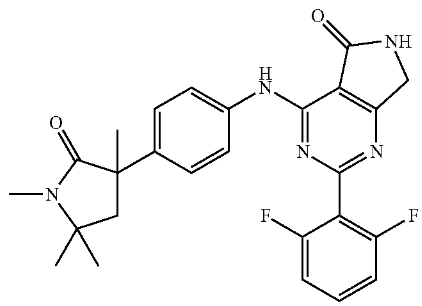 [SMILES: CN1C(=O)C(C)(c2ccc(Nc3nc(-c4c(F)cccc4F)nc4c3C(=O)NC4)cc2)CC1(C)C] |
| I-221 | 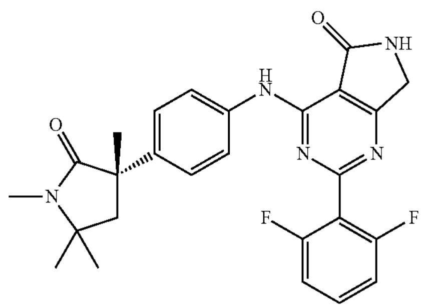 [SMILES: CN1C(=O)[C@](C)(c2ccc(Nc3nc(-c4c(F)cccc4F)nc4c3C(=O)NC4)cc2)CC1(C)C] |
| I-222 | 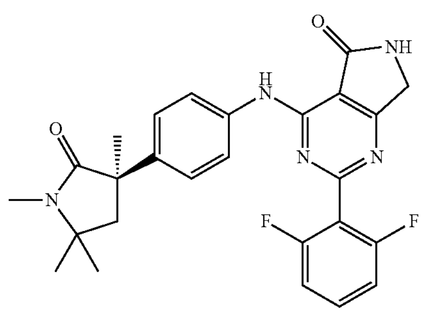 [SMILES: CN1C(=O)[C@@](C)(c2ccc(Nc3nc(-c4c(F)cccc4F)nc4c3C(=O)NC4)cc2)CC1(C)C] |
| I-223 | 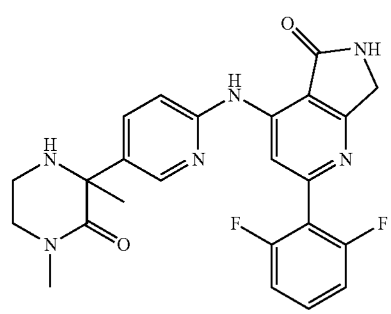 [SMILES: CN1CCNC(C)(c2ccc(Nc3cc(-c4c(F)cccc4F)nc4c3C(=O)NC4)nc2)C1=O] |
| I-224 | 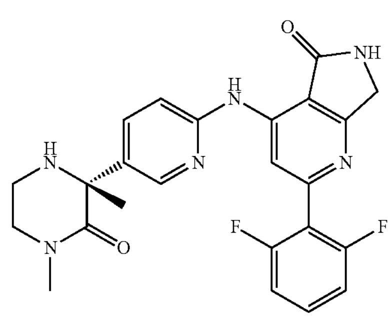 [SMILES: CN1CCN[C@](C)(c2ccc(Nc3cc(-c4c(F)cccc4F)nc4c3C(=O)NC4)nc2)C1=O] |

TABLE 1-continued

Exemplary Compounds

| Compound | Structure |
|---|---|
| I-225 | 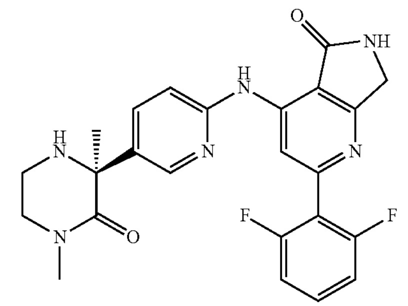 [SMILES: CN1CCN[C@@](C)(c2ccc(Nc3cc(-c4c(F)cccc4F)nc4c3C(=O)NC4)nc2)C1=O] |
| I-226 | 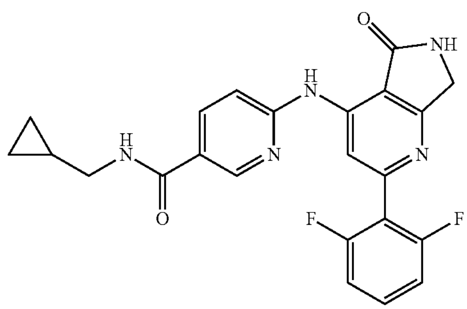 [SMILES: O=C(NCC1CC1)c1ccc(Nc2cc(-c3c(F)cccc3F)nc3c2C(=O)NC3)nc1] |
| I-227 | 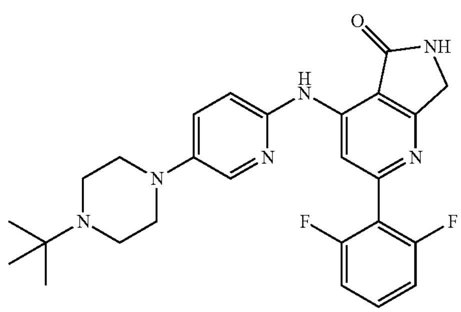 [SMILES: CC(C)(C)N1CCN(c2ccc(Nc3cc(-c4c(F)cccc4F)nc4c3C(=O)NC4)nc2)CC1] |
| I-228 | 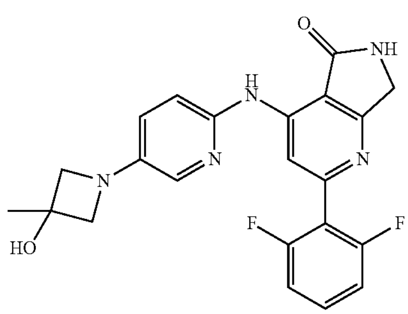 [SMILES: CC1(O)CN(c2ccc(Nc3cc(-c4c(F)cccc4F)nc4c3C(=O)NC4)nc2)C1] |
| I-229 | 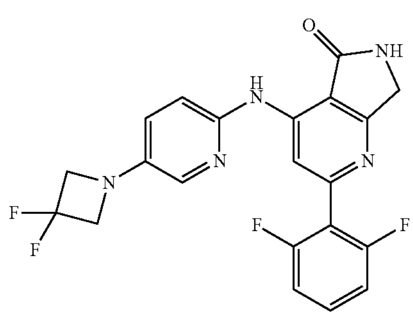 [SMILES: O=C1NCc2nc(-c3c(F)cccc3F)cc(Nc3ccc(N4CC(F)(F)C4)cn3)c21] |

TABLE 1-continued

Exemplary Compounds

| Compound | Structure |
|---|---|
| I-230 | 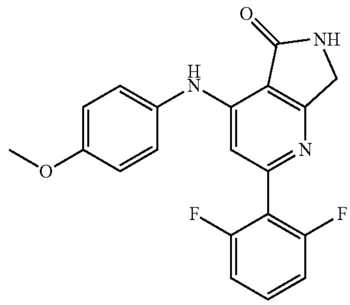 [SMILES: COc1ccc(Nc2cc(-c3c(F)cccc3F)nc3c2C(=O)NC3)cc1] |
| I-231 | 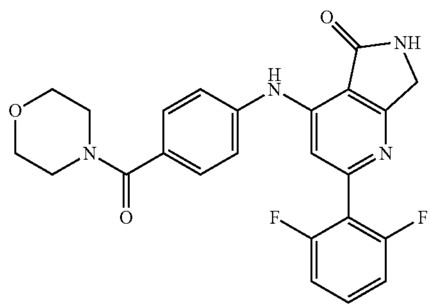 |
| I-232 | 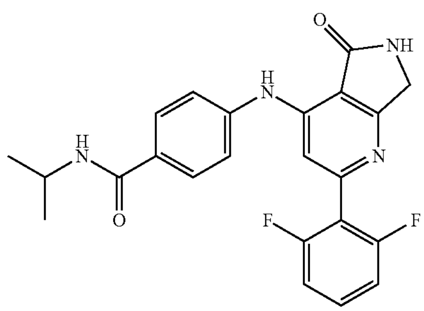 [SMILES: CC(C)NC(=O)c1ccc(Nc2cc(-c3c(F)cccc3F)nc3c2C(=O)NC3)cc1] |
| I-233 | 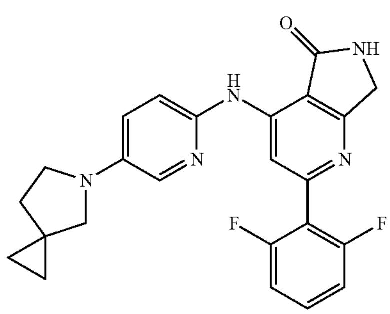 [SMILES: O=C1NCc2nc(-c3c(F)cccc3F)cc(Nc3ccc(N4CCC5(CC5)C4)cn3)c21] |
| I-234 | 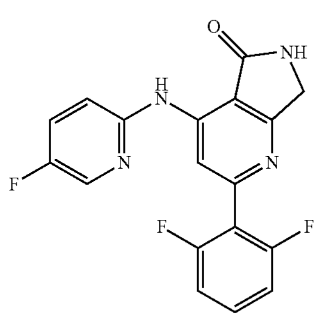 [SMILES: O=C1NCc2nc(-c3c(F)cccc3F)cc(Nc3ccc(F)cn3)c21] |

TABLE 1-continued

Exemplary Compounds

| Compound | Structure |
|---|---|
| I-235 | 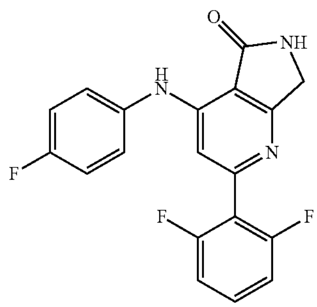 [SMILES: O=C1NCc2nc(-c3c(F)cccc3F)cc(Nc3ccc(F)cc3)c21] |
| I-236 | 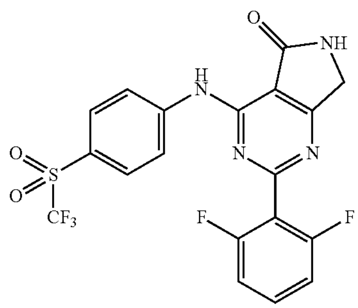 [SMILES: O=C1NCc2nc(-c3c(F)cccc3F)nc(Nc3ccc(S(=O)(=O)C(F)(F)F)cc3)c21] |
| I-237 | 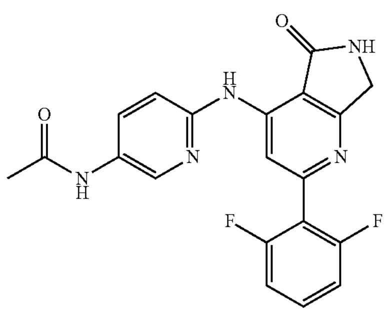 [SMILES: CC(=O)Nc1ccc(Nc2cc(-c3c(F)cccc3F)nc3c2C(=O)NC3)nc1] |
| I-238 | 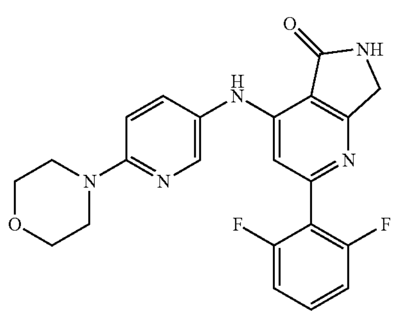 [SMILES: O=C1NCc2nc(-c3c(F)cccc3F)cc(Nc3ccc(N4CCOCC4)nc3)c21] |
| I-239 | 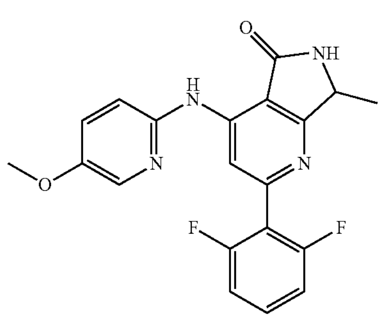 |

TABLE 1-continued

Exemplary Compounds

| Compound | Structure |
|---|---|
| I-240 | 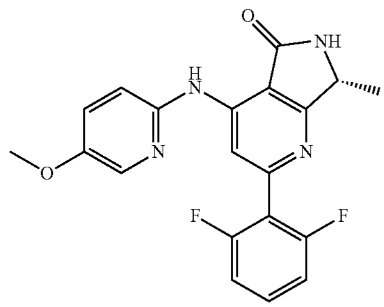 |
| I-241 | 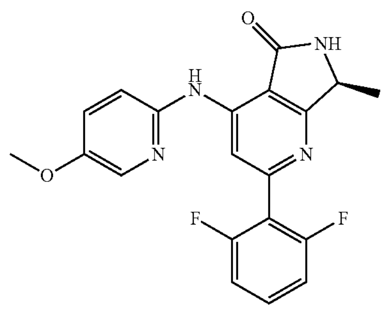 |
| I-242 | 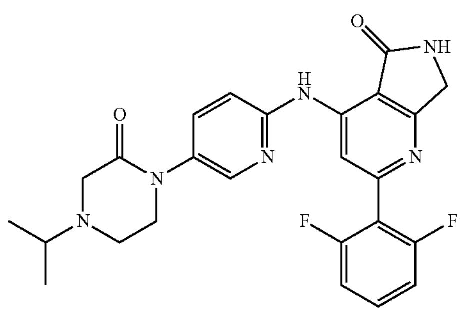 [SMILES: CC(C)N1CCN(c2ccc(Nc3cc(-c4c(F)cccc4F)nc4c3C(=O)NC4)nc2)C(=O)C1] |
| I-243 | 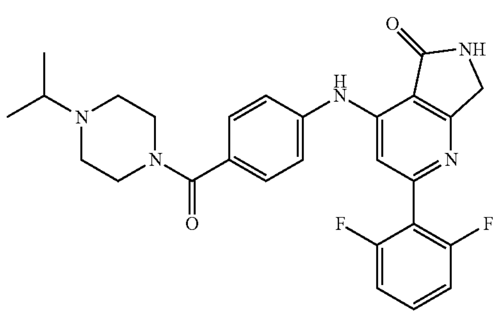 [SMILES: CC(C)N1CCN(C(=O)c2ccc(Nc3cc(-c4c(F)cccc4F)nc4c3C(=O)NC4)cc2)CC1] |
| I-244 | 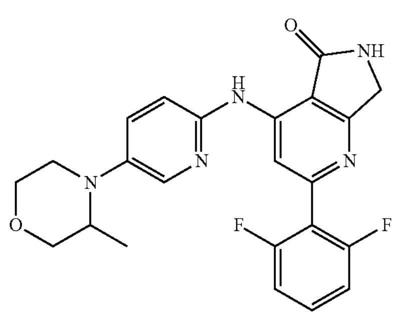 [SMILES: CC1COCCN1c1ccc(Nc2cc(-c3c(F)cccc3F)nc3c2C(=O)NC3)nc1] |

TABLE 1-continued

Exemplary Compounds

| Compound | Structure |
|---|---|
| I-245 | 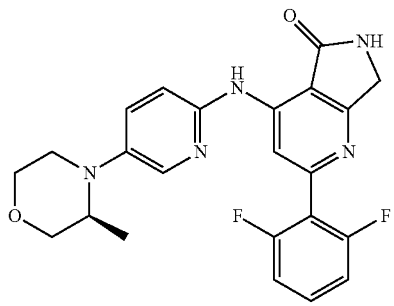 [SMILES: C[C@H]1COCCN1c1ccc(Nc2cc(-c3c(F)cccc3F)nc3c2C(=O)NC3)nc1] |
| I-246 | 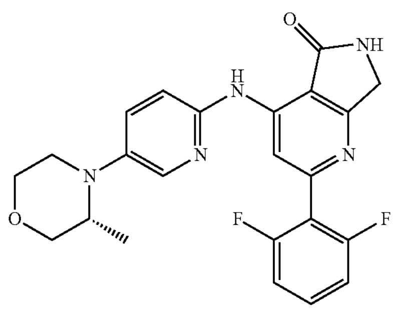 [SMILES: C[C@@H]1COCCN1c1ccc(Nc2cc(-c3c(F)cccc3F)nc3c2C(=O)NC3)nc1] |
| I-247 | 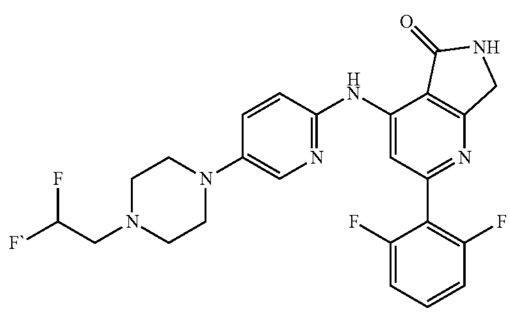 |
| I-248 | 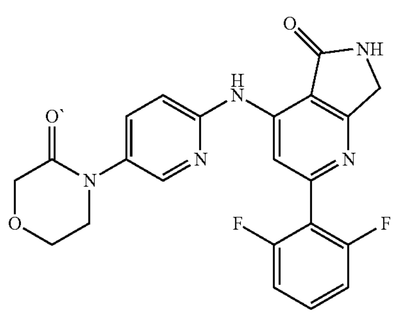 |
| I-249 | 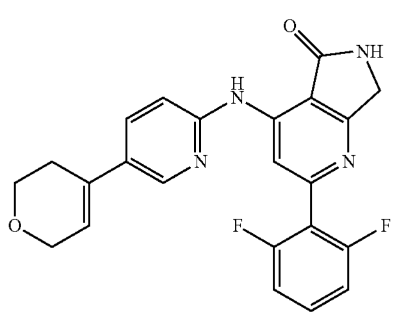 [SMILES: O=C1NCc2nc(-c3c(F)cccc3F)cc(Nc3ccc(C4=CCOCC4)cn3)c21] |

TABLE 1-continued
Exemplary Compounds
| Compound | Structure |
|---|---|
| I-250 | 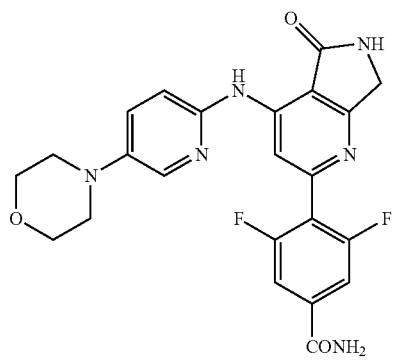 [SMILES: NC(=O)c1cc(F)c(-c2cc(Nc3ccc(N4CCOCC4)cn3)c3c(n2)CNC3=O)c(F)c1] |
| I-251 | 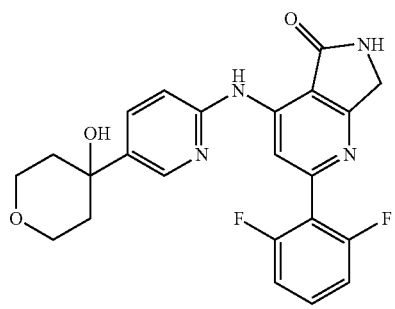 [SMILES: O=C1NCc2nc(-c3c(F)cccc3F)cc(Nc3ccc(C4(O)CCOCC4)cn3)c21] |
| I-252 | 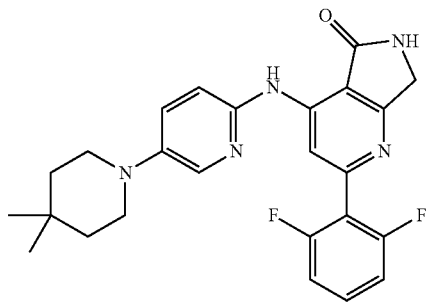 [SMILES: CC1(C)CCN(c2ccc(Nc3cc(-c4c(F)cccc4F)nc4c3C(=O)NC4)nc2)CC1] |
| I-253 | 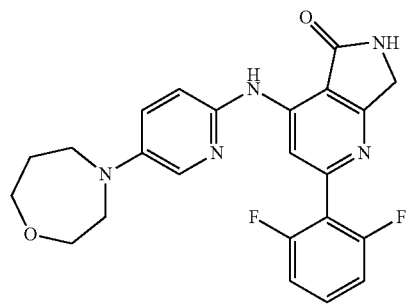 [SMILES: O=C1NCc2nc(-c3c(F)cccc3F)cc(Nc3ccc(N4CCCOCC4)cn3)c21] |

TABLE 1-continued

Exemplary Compounds

| Compound | Structure |
|---|---|
| I-254 | 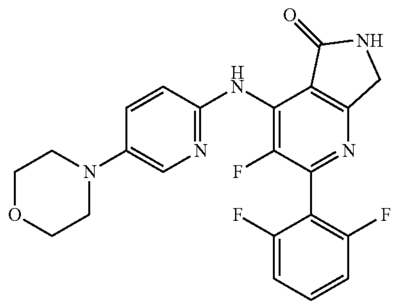 [SMILES: O=C1NCc2nc(-c3c(F)cccc3F)c(F)c(Nc3ccc(N4CCOCC4)cn3)c21] |
| I-255 | 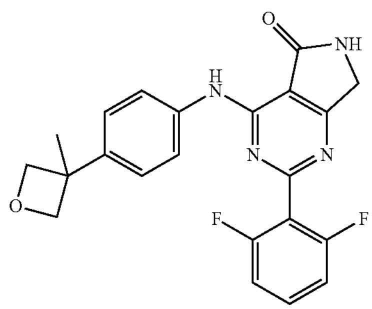 [SMILES: CC1(c2ccc(Nc3nc(-c4c(F)cccc4F)nc4c3C(=O)NC4)cc2)COC1] |
| I-256 | 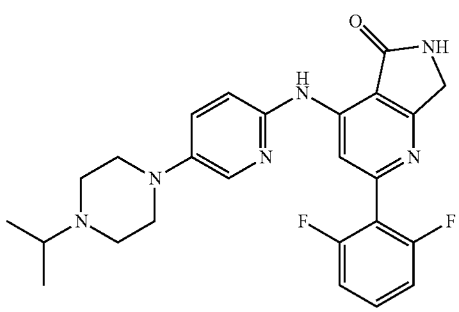 [SMILES: CC(C)N1CCN(c2ccc(Nc3cc(-c4c(F)cccc4F)nc4c3C(=O)NC4)nc2)CC1] |
| I-257 | 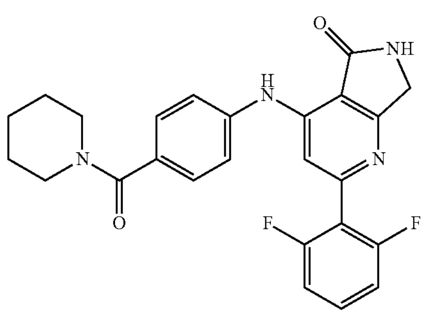 [SMILES: O=C1NCc2nc(-c3c(F)cccc3F)cc(Nc3ccc(C(=O)N4CCCCC4)cc3)c21] |
| I-258 | 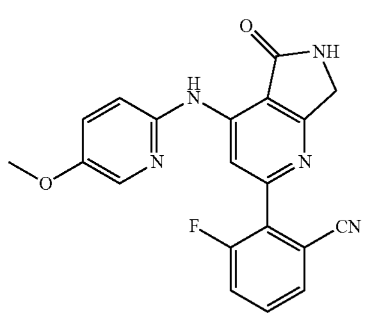 [SMILES: COc1ccc(Nc2cc(-c3c(F)cccc3C#N)nc3c2C(=O)NC3)nc1] |

TABLE 1-continued

Exemplary Compounds

| Compound | Structure |
|---|---|
| I-259 | 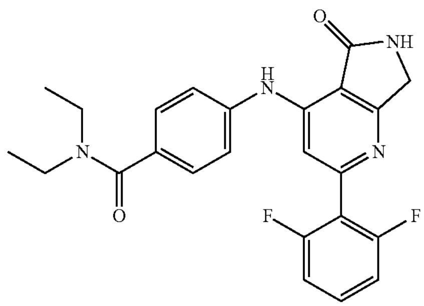 [SMILES: CCN(CC)C(=O)c1ccc(Nc2cc(-c3c(F)cccc3F)nc3c2C(=O)NC3)cc1] |
| I-260 | 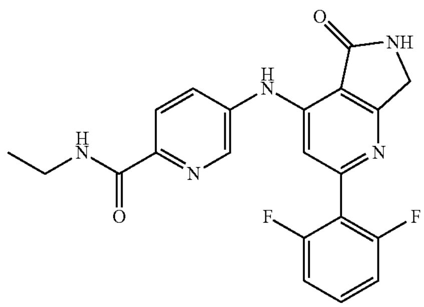 [SMILES: CCNC(=O)c1ccc(Nc2cc(-c3c(F)cccc3F)nc3c2C(=O)NC3)cn1] |
| I-261 | 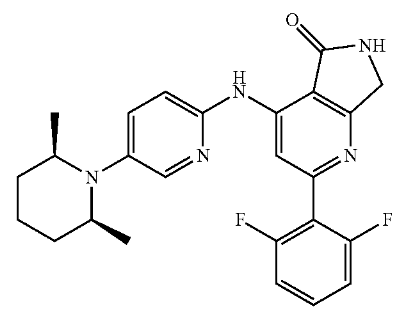 [SMILES: C[C@@H]1CCC[C@H](C)N1c1ccc(Nc2cc(-c3c(F)cccc3F)nc3c2C(=O)NC3)nc1] |
| I-262 | 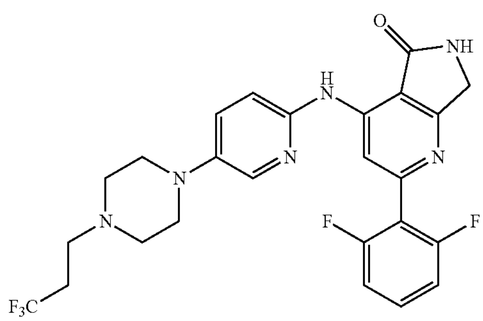 [SMILES: O=C1NCc2nc(-c3c(F)cccc3F)cc(Nc3ccc(N4CCN(CCC(F)(F)F)CC4)cn3)c21] |
| I-263 | 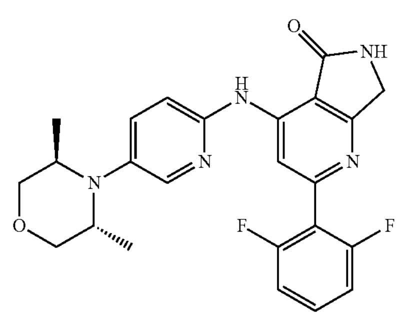 [SMILES: C[C@@H]1COC[C@@H](C)N1c1ccc(Nc2cc(-c3c(F)cccc3F)nc3c2C(=O)NC3)nc1] |

TABLE 1-continued

Exemplary Compounds

| Compound | Structure |
|---|---|
| I-264 | 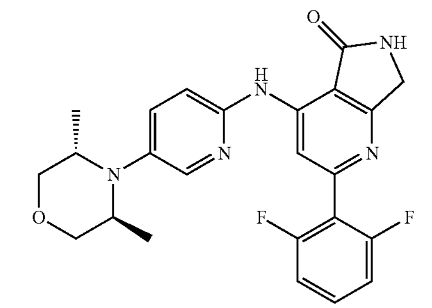 [SMILES: C[C@H]1COC[C@H](C)N1c1ccc(Nc2cc(-c3c(F)cccc3F)nc3c2C(=O)NC3)nc1] |
| I-265 | 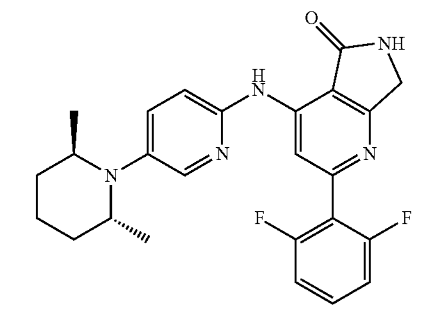 [SMILES: C[C@@H]1CCC[C@@H](C)N1c1ccc(Nc2cc(-c3c(F)cccc3F)nc3c2C(=O)NC3)nc1] |
| I-266 | 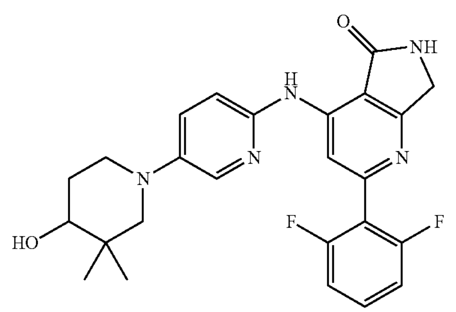 [SMILES: CC1(C)CN(c2ccc(Nc3cc(-c4c(F)cccc4F)nc4c3C(=O)NC4)nc2)CCC1O] |
| I-267 | 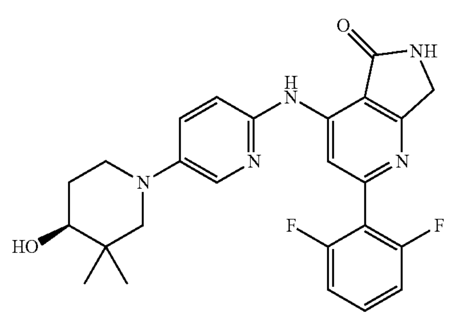 [SMILES: CC1(C)CN(c2ccc(Nc3cc(-c4c(F)cccc4F)nc4c3C(=O)NC4)nc2)CC[C@@H]1O] |
| I-268 | 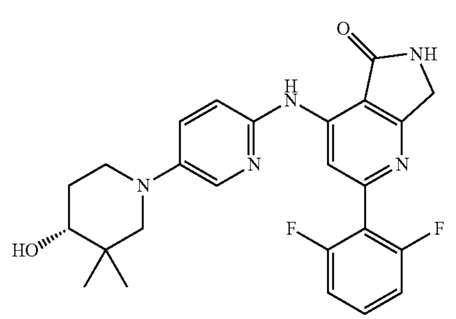 [SMILES: CC1(C)CN(c2ccc(Nc3cc(-c4c(F)cccc4F)nc4c3C(=O)NC4)nc2)CC[C@H]1O] |

TABLE 1-continued

Exemplary Compounds

| Compound | Structure |
|---|---|
| I-269 | (structure) |
| I-270 | (structure) |
| I-271 | (structure) |
| I-272 | (structure) |
| I-273 | (structure) |

TABLE 1-continued

Exemplary Compounds

| Compound | Structure |
|---|---|
| I-274 | 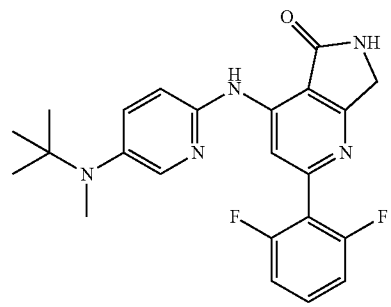 [SMILES: CN(c1ccc(Nc2cc(-c3c(F)cccc3F)nc3c2C(=O)NC3)nc1)C(C)(C)C] |
| I-275 | 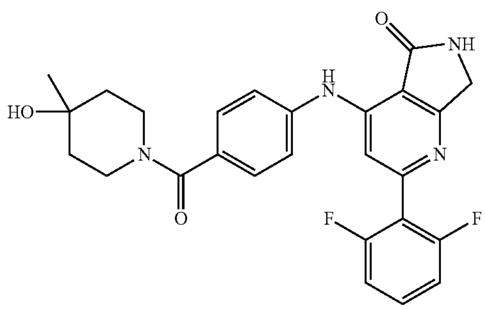 [SMILES: CC1(O)CCN(C(=O)c2ccc(Nc3cc(-c4c(F)cccc4F)nc4c3C(=O)NC4)cc2)CC1] |
| I-276 | 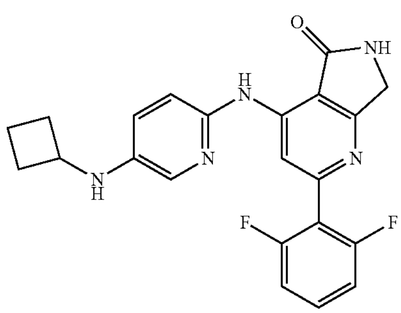 [SMILES: O=C1NCc2nc(-c3c(F)cccc3F)cc(Nc3ccc(NC4CCC4)cn3)c21] |
| I-277 | 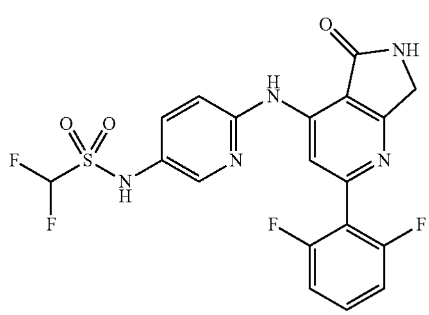 [SMILES: O=C1NCc2nc(-c3c(F)cccc3F)cc(Nc3ccc(NS(=O)(=O)C(F)F)cn3)c21] |
| I-278 | 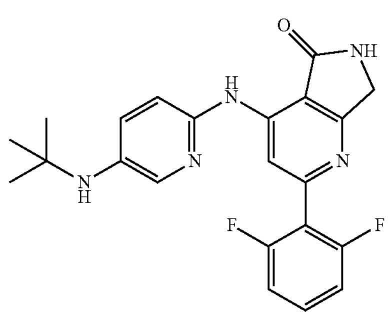 [SMILES: CC(C)(C)Nc1ccc(Nc2cc(-c3c(F)cccc3F)nc3c2C(=O)NC3)nc1] |

TABLE 1-continued
Exemplary Compounds
| Compound | Structure |
|---|---|
| I-279 | 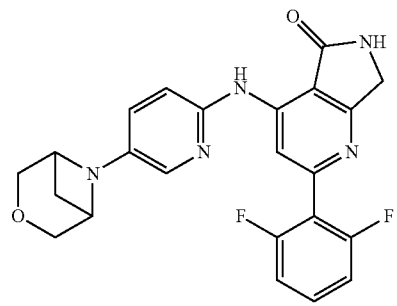 [SMILES: O=C1NCc2nc(-c3c(F)cccc3F)cc(Nc3ccc(N4C5COCC4C5)cn3)c21] |
| I-280 | 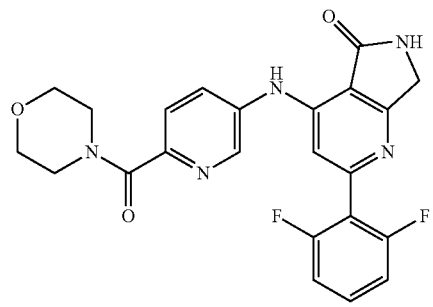 [SMILES: O=C1NCc2nc(-c3c(F)cccc3F)cc(Nc3ccc(C(=O)N4CCOCC4)nc3)c21] |
| I-281 | 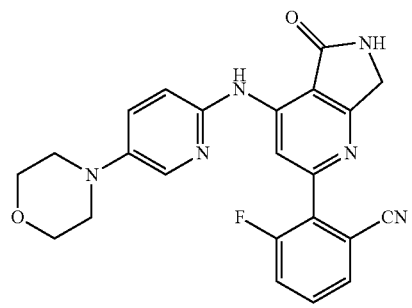 [SMILES: N#Cc1cccc(F)c1-c1cc(Nc2ccc(N3CCOCC3)cn2)c2c(n1)CNC2=O] |
| I-282 | 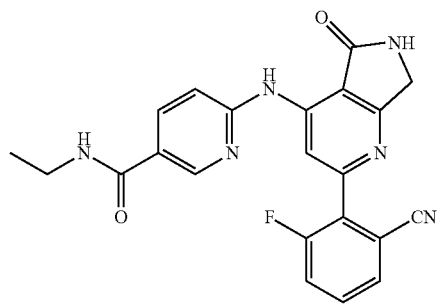 [SMILES: CCNC(=O)c1ccc(Nc2cc(-c3c(F)cccc3C#N)nc3c2C(=O)NC3)nc1] |

147
148
TABLE 1-continued
Exemplary Compounds
| Compound | Structure |
| --- | --- |
| I-283 | 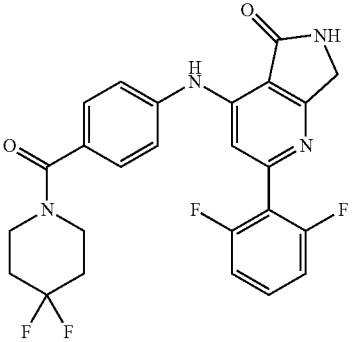 [SMILES: O=C1NCc2nc(-c3c(F)cccc3F)cc(Nc3ccc(C(=O)N4CCC(F)(F)CC4)cc3)c21] |
| I-284 | 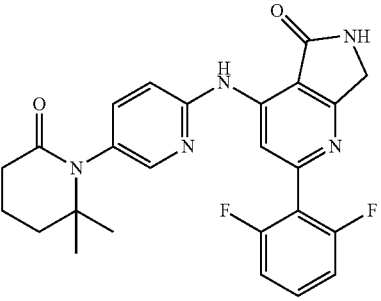 [SMILES: CC1(C)CCCC(=O)N1c1ccc(Nc2cc(-c3c(F)cccc3F)nc3c2C(=O)NC3)nc1] |
| I-285 | 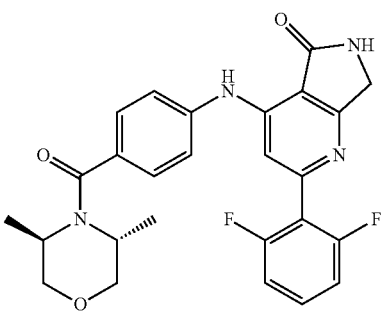 [SMILES: C[C@@H]1COC[C@@H](C)N1C(=O)c1ccc(Nc2cc(-c3c(F)cccc3F)nc3c2C(=O)NC3)cc1] |
| I-286 | 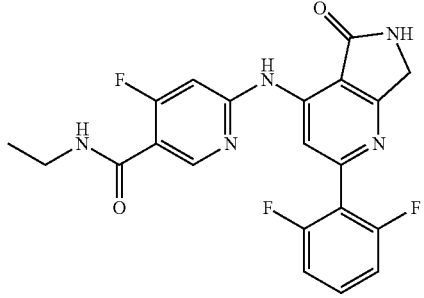 [SMILES: CCNC(=O)c1cnc(Nc2cc(-c3c(F)cccc3F)nc3c2C(=O)NC3)cc1F] |

TABLE 1-continued
Exemplary Compounds
| Compound | Structure |
|---|---|
| I-287 | 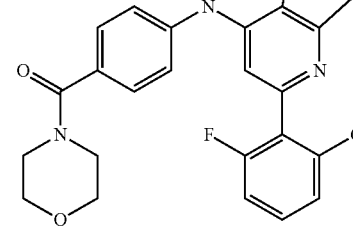 |
| I-288 | 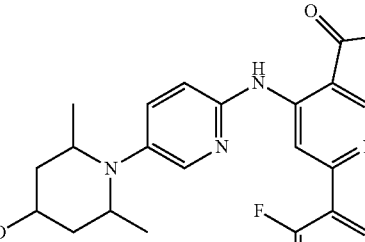 |
| I-289 | 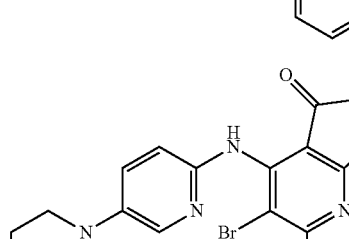 |
| I-290 | 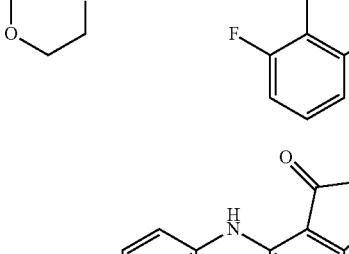 |
| I-291 | 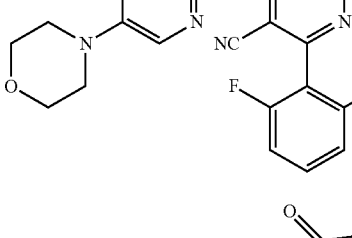 |

TABLE 1-continued

Exemplary Compounds

| Compound | Structure |
|---|---|
| I-292 | (structure: 4-(3-fluoro-4-methylphenylamino)-2-(2,6-difluorophenyl)-6,7-dihydro-5H-pyrrolo[3,4-d]pyrimidin-5-one) |

In some embodiments, the method employs a compound set forth in Table 1, above, or a pharmaceutically acceptable salt thereof. In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In some embodiments, compounds of the present invention of formula II are prepared according to the method depicted in Scheme 1.

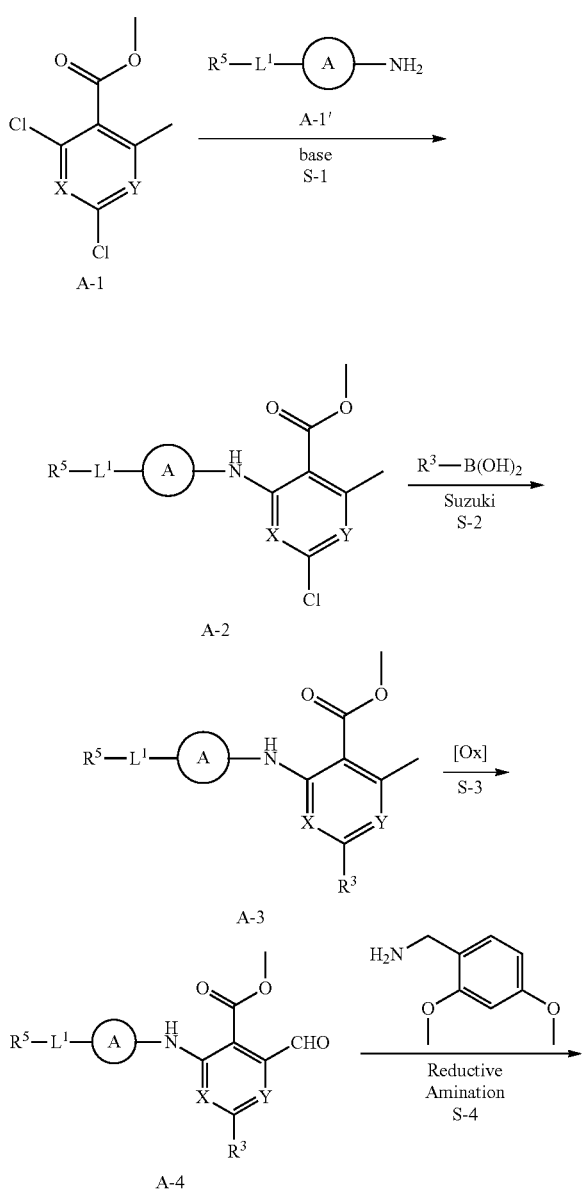

Scheme 1-Synthesis of Compounds of Formula II

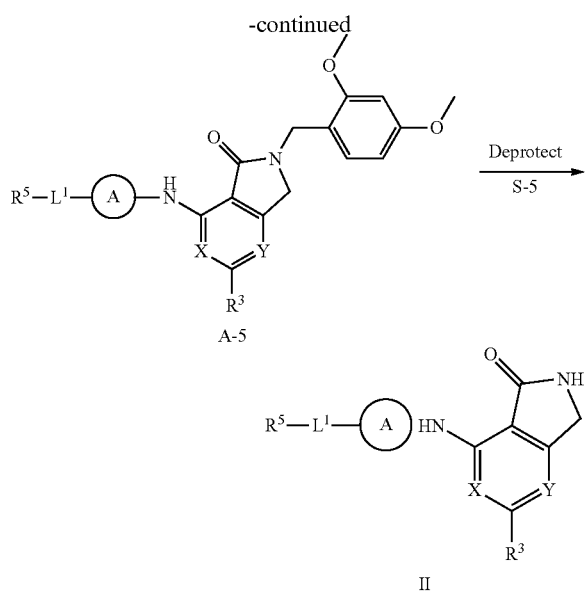

As depicted in Scheme 1 above, in step S-1, readily accessible starting materials of general formula A-1 are treated with amines of formula A-1' in the presence of base to form intermediate A-2. In some embodiments, the base is an amine. In some embodiments the base is DIPEA.

In step S-2, intermediate A-2 is contacted with boronic acids of the formula $R^3$—$B(OH)_2$ under Suzuki conditions to form a compound of formula A-3.

In step S-3, intermediate A-3 is contacted with an oxidizing agent to oxidize the methyl group to a carboxaldehyde, thereby providing an intermediate of formula A-4. In some embodiments the oxidizing agent is selenium dioxide.

In step S-4, intermediate A-4 is contacted with 2,4-dimethoxybenzylamine under reductive amination conditions, thereby providing a compound of formula A-5. In some embodiments the reducing agent is sodium cyanoborohydride.

In step S-5, intermediate the 2,4-dimethoxybenzyl protecting group of A-5 is removed, thereby providing a final compound of formula II. In some embodiments the deprotection is effected by trifluoroacetic acid.

Compounds of formula I bearing substituents $R^1$ and/or $R^{1'}$, can be produced by analogous procedures, for example by treating an imine of carboxaldehyde A-4 with appropriate nucleophiles corresponding to groups $R^1$ and/or $R^{1'}$.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition.

In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, L-13, IL-22, IL-23, L-27, L-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by L-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine L-23 is composed of IL-12Rβ1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene,"

Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calciparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplanltation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, no-small-cell lung cancer, myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787

(Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of Ethyl 2-(4-((2-(2-chlorophenyl)-5-oxo-6,7-dihydro-5H-pyrrolo[3,4-d]pyrimidin-4-yl)amino)phenyl)acetate, I-1
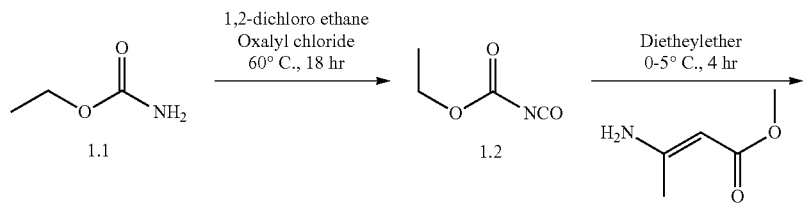
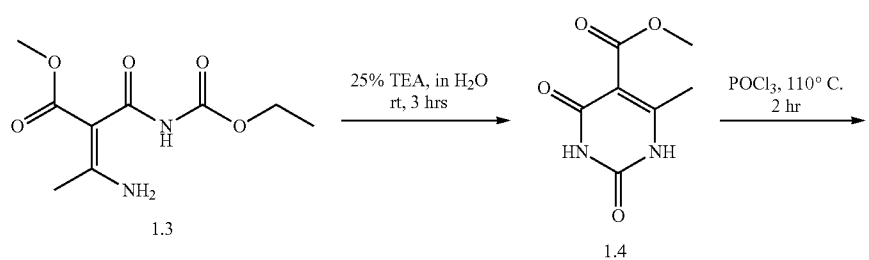
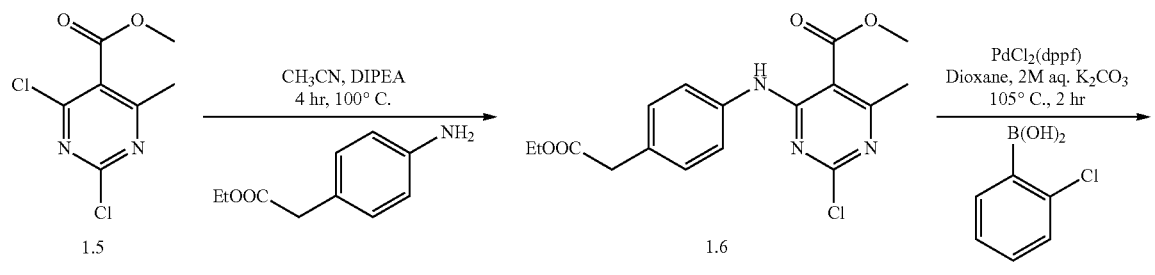
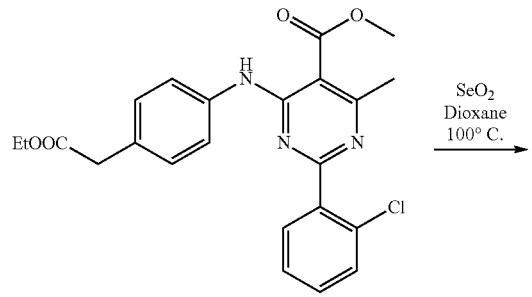
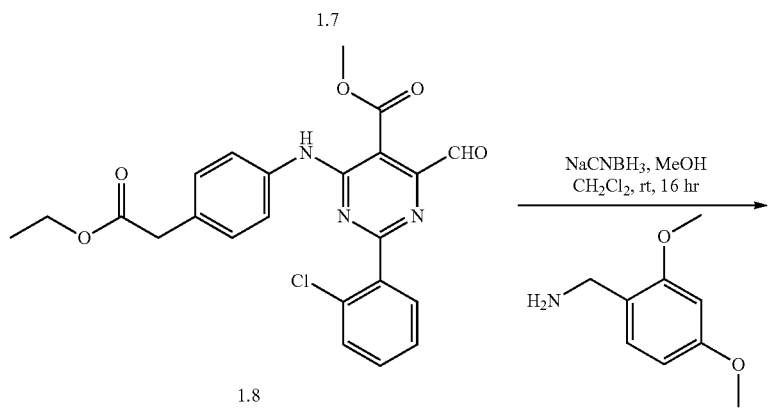

-continued

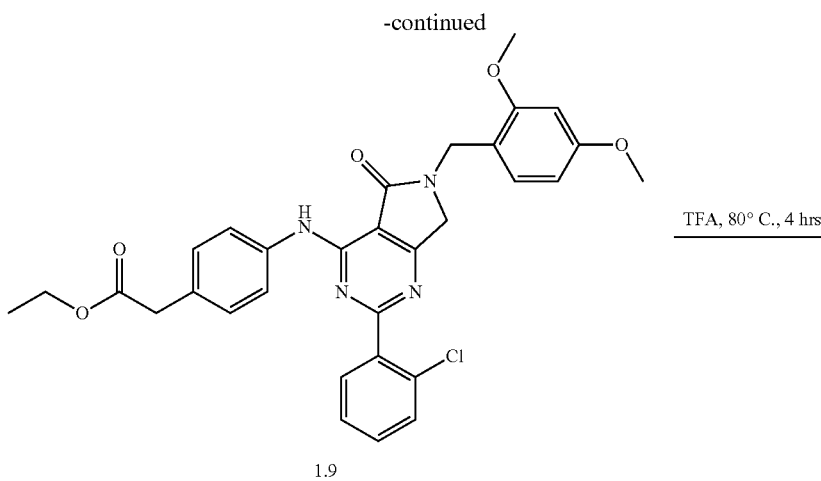

1.9

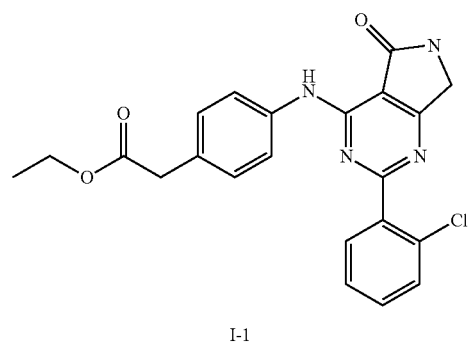

I-1

Synthesis of Compound 1.2.

To solution of 1 (50 g, 0.56 mol, 1.00 equiv) in dry 1,2-dichloroethane (260 ml) was added oxalyl-chloride (87 ml), dropwise keeping the temperature below 10° C. The mixture was heated to 60° C. for 18 hours. The excess oxalylchloride and 1,2-dichloroethane were removed under reduced pressure and the oily residue obtained was further purified by high vacuum distillation at 90° C. (1 mm Hg). This resulted in 20 g of 1.2 as 50% solution in 1,2-dichloroethane. It was used as such in the next step.

Synthesis of Compound 1.3.

To a solution of 3-aminocrotonate methyl ester (20 g, 0.1739 mol, 1.0 equiv) in dry diethyl ether (120 ml) was added solution 1.2 (50% solution in 1,2-dichloroethane, 20 g, 0.1739 mol, 1.0 equiv.) in dry diethyl ether (25 ml), dropwise at 0-5° C. The mixture was stirred for 4 hours at 0-5° C. After consumption of starting material, reaction mixture was directly purified via flash column chromatography to yield pure compound 1.3 (16 g, 40%). MS (ES) m/z=231.61 [M+H]$^+$ Synthesis of Compound 1.4

A solution of 1.3 (16 g, 0.06956 mol, 1.00 equiv) in 25% triethylamine (105 mL) was heated at 70° C. until starting material was consumed. Subsequently, the reaction was stopped and the mixture was acidified with acetic acid. The solid white crystals were filtered off and dried under vacuum to provide pure compound 1.4 (12.1 g, 94.53%). MS (ES) m/z 185.21 [M+H]$^+$.

Synthesis of Compound 1.5.

A solution of 1.4 (12.1 g, 0.06576 mol, 1.00 equiv) in phosphorusoxychloride (120 ml) was heated at 110° C. for 2 hrs. After completion, reaction mixture was concentrated under reduced pressure and residue was quenched in ice. The crude product was extracted twice with ethyl acetate. The organic layers were dried over sodium sulfate and concentrated under reduced pressure to afford crude material which was purified by flash column chromatography This resulted in pure compound 1.5 (10.2 g, 70.20%). MS (ES): m/z 222.8 [M+H]$^+$ Synthesis of Compound 1.6.

To a solution of 1.5 (2.37 g, 0.01072 mol, 1.00 equiv), in acetonitrile (35 mL) was added diisopropylethylamine (3.81 mL, 0.02144 mol, 2.0 equiv) and tert-butyl 2-(4-aminophenyl)acetate (2.0 g, 0.009648 mol, 0.9 equiv). The mixture was heated at 100° C. for 4 hours. After completion, reaction mixture was concentrated under reduced pressure and triturated with water to obtain solids. The precipitate was collected and dried under reduced pressure to yield pure compound 1.6 (2.45 g, 58.3%). MS (ES): m/z 392.14 [M+H]$^+$.

Synthesis of Compound 1.7.

To a solution of compound 1.6 (0.35 g, 0.9641 mmol, 1.00 equiv) in 1,4-dioxane (15 mL) was added 2-chlorophenylboronic acid (0.165 g, 1.06 mmol, 1.1 equiv) and 2M $K_2CO_3$ solution (2.0 mL). The mixture was degassed using argon gas for 10-15 minutes then $PdCl_2$(dppf) (0.049 g, 0.06741 mmol, 0.07 equiv) was added and mixture was again degassed under argon for 5 minutes. The mixture was heated at 105° C. for 2 hrs. After completion of the reaction, the mixture was poured into water and extracted twice with ethyl acetate. The organic layers were combined, dried over sodium sulfate, and concentrated under reduced pressure to obtain the crude material which was purified by preparative HPLC to furnish pure compound 1.7 (0.135 g, 32.14%). MS (ES): m/z 440.33 [M+H]$^+$.

Synthesis of Compound 1.8.

A solution of compound 1.7 (0.135 g, 0.3075 mmol, 1.00 equiv) and selenium dioxide (0.068 g, 0.612 mmol, 2.0 equiv) in 1,4-dioxane (3 mL) was heated at 100° C. until consumption of the starting material. The mixture was filtered through Celite and the filtrate was concentrated under reduced pressure to give crude 1.8 (0.14 g) which was used as such for the next step.

Synthesis of Compound 1.9.

To a solution of compound 1.8 (0.14 g, 0.31 mmol, 1.00 equiv) in dichloromethane (2.0 mL) and methanol (1.0 mL) was added 2,4-dimethoxybenzylamine (0.0567 g, 0.34 mmol, 1.1 equiv). The solution was stirred at ambient temperature for 30 minutes. Sodium cyanoborohydride (0.077 g, 1.23 mmol, 4.0 equiv) was added at 0° C. and stirred overnight. After completion, the mixture was poured into water and the product was extracted twice with ethyl acetate. The organic layers were dried over sodium sulfate and concentrated under reduced pressure to give the crude material which was purified by flash column chromatography to furnish pure 1.9 (0.097 g, 55.1%). MS (ES): m/z 573.62 [M+H]$^+$ Synthesis of Compound I-1.

A solution of compound 1.9 (0.097 g, 0.1695 mmol, 1.00 equiv) in trifluoroacetic acid (2.0 mL) was heated at 80° C. for 4 hours. After completion, reaction mixture was concentrated and residue was diluted with ethyl acetate and washed with saturated sodium bicarbonate solution. The organic layers were concentrated under reduced pressure to obtain the crude material which was purified by preparative TLC to furnish I-1, as a white solid (0.046 g, 64.56%). MS (ES): m/z 422.86 (M+H)$^+$ $^1$H NMR (400 MHz, DMSO-d$_6$): δ 9.04 (s, 1H), 8.86 (s, 1H), 7.78-7.74 (m, 3H), 7.61-7.47 (m, 3H), 7.25-7.23 (d, 2H) 4.47 (s, 2H), 4.07-4.06 (q, 2H), 3.63 (s, 2H), 1.18-1.15 (t, 3H).

Example 2: Synthesis of 2-(4-((2-(2,6-difluorophenyl)-5-oxo-6,7-dihydro-5H-pyrrolo[3,4-d]pyrimidin-4-yl) amino)phenyl)acetic Acid, I-2

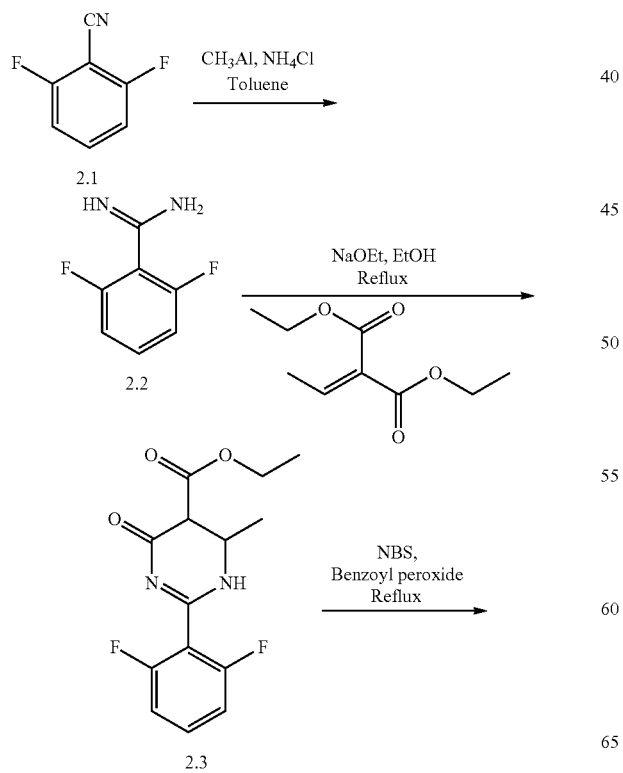

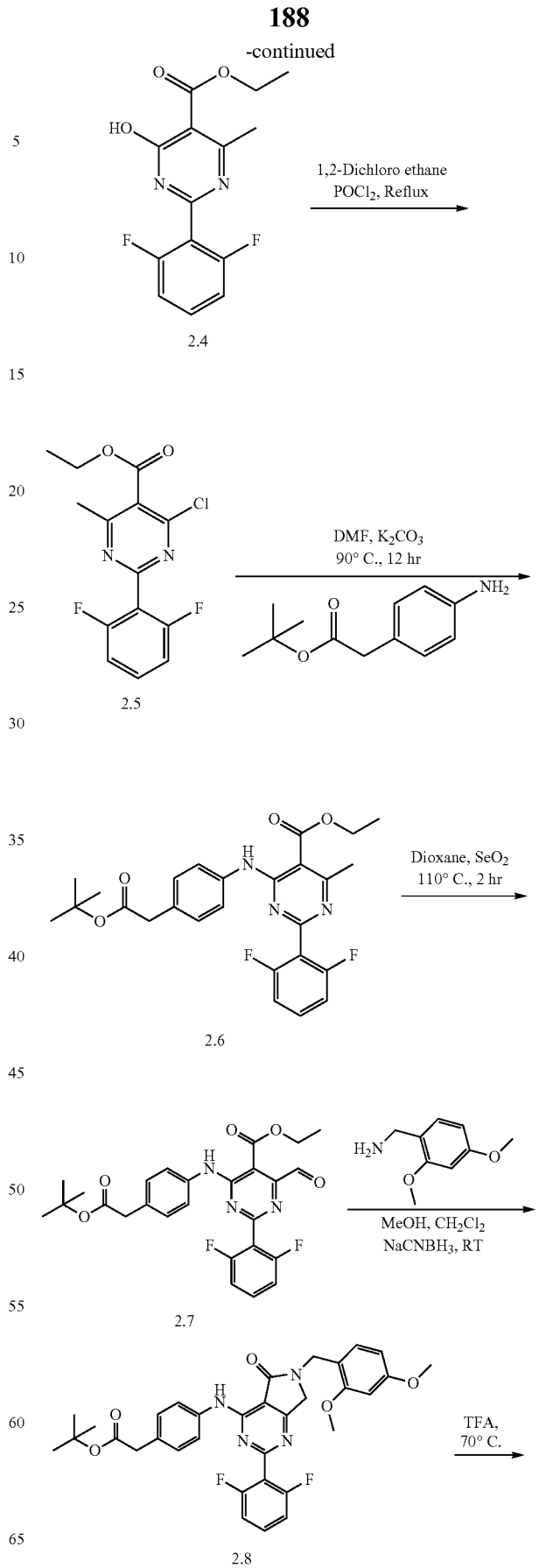

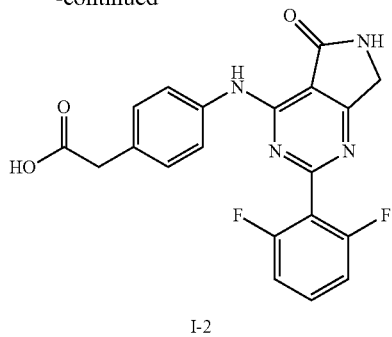

I-2

Synthesis of Compound 2.2.

Compound 2.1 (5 g, 35.97 mmol, 1.00 eq), NH₄Cl (2.11 g, 39.56 mmol, 1.1 eq) were suspended in toluene (100 ml). A solution of trimethylaluminium (2.0 M, 19.5 ml, 39.56 mmol, 1.1 eq) was added dropwise to the above reaction mixture at room temperature. The mixture was stirred for one hour at ambient temperature and subsequently refluxed for 16 hours. After completion of the reaction, toluene was evaporated and residue was diluted with 10% methanol in CH$_2$Cl$_2$ (100 mL). Silica gel (5.0 g) was added mixture and stirred for 30 minutes at ambient temperature. After 30 minutes, slurry was filtered and washed with CH$_2$Cl$_2$/methanol. The filtrate was concentrated under vacuum at 45° C. to afford the crude material which was purified using trituration with 20% ethyl acetate in hexane (50 ml). The solid obtained was filtered off and dried under vacuum to afforded pure compound 2.2 (4.5 g, 80.35%). LCMS: 99.27%. MS (ES): m/z 157.0 (M+H)⁺.

Synthesis of Compound 2.3.

To a solution of compound 2.2 (4.5 g, 28.8 mmol,) in ethanol (50 mL) was added diethyl ethylidene malonate (4.76 g, 25.96 mmol, 0.9 eq) followed by sodium ethoxide (3.44 g, 52.20 mmol, 1.81 eq). The mixture was heated to reflux for 2 hours under argon. After completion of the reaction, reaction mixture was concentrated under reduced pressure and residue was diluted with ethyl acetate and washed with water and brine. The organic layers were separated, dried over sodium sulfate, and concentrated under reduced pressure to afforded the crude material which was purified by flash column chromatography to afford pure compound 2.3 (5.5 g, 64.4%) LCMS: 95.12%, m/z=297.1 [M+H]⁺.

Synthesis of Compound 2.4

To a solution of compound 2.3 (4.0 g, 13.50 mmol, 1.0 eq) in 1,4-dioxane (40 mL) was added K$_2$CO$_3$ (2.80 g, 20.20 mmol, 1.5 eq), NBS (2.40 g, 13.5 mmol, 1.0 eq) and benzoyl peroxide (0.65 g, 2.70 mmol, 0.2 eq). The mixture was heated to reflux until starting material was consumed. After completion of the reaction, water was added and product was extracted with ethyl acetate (2×50 ml) and organic layer was separated and dried over Na$_2$SO$_4$ and concentrated under reduced pressure to afforded pure compound 2.4 (3.90 g, 98.2%). LCMS: 99.5% MS (ES): m/z 295.0 [M+H]⁺.

Synthesis of Compound 2.5.

A solution of compound 2.4 (3.0 g, 1.00 equiv) in dichloroethane (30 mL) and POCl$_3$ (30 ml) was heated to reflux for 3 h. After completion of the reaction, reaction mixture was concentrated and residue was quenched with ice. Obtained product was extracted with dichloromethane (2×50 ml). The organic layers were dried over sodium sulfate and concentrated under reduced pressure and the resulting crude material was purified by column chromatography to afford pure compound 2.5 (2.0 g, 62.9%). MS (ES): m/z 312.7 [M+H]⁺.

Synthesis of Compound 2.6.

A solution of compound 2.5 (1.0 g, 3.19 mmol, 1.0 eq), tert-butyl 2-(4-aminophenyl)acetate (0.661 g, 3.19 mmol, 1.00 eq) and K$_2$CO$_3$ (1.32 g, 9.57 mmol, 3.0 eq) in DMF (10.0 mL) was heated at 90° C. for 12 hours. Upon completion, the mixture was cooled to room temperature and poured into water. The product was extracted with ethyl acetate (50 mL×3). And the combined organic layers were washed with brine, dried over sodium sulfate and concentrated under reduced pressure. The crude material was purified using flash column chromatography to afford the compound 2.6 (1.10 g, 71.4%) MS (ES): m/z 484.2 [M+H]⁺.

Synthesis of Compound 2.7.

A solution of compound 2.7 (1.1 g, 2.27 mmol, 1.0 eq), selenium dioxide (0.50 g, 4.55 mmol, 2.00 eq) in 1,4-dioxane (10.0 mL) was stirred at 100° C. to 105° C. for 3 hours. After completion of the reaction, the resulting solution was filtered through Celite and washed with 1,4-dioxane. The filtrate was concentrated under reduced pressure to afford desired compound 1.6 (1.0 g, 100%) as a light yellow semisolid. MS (ES): m/z 498.2 [M+H]⁺.

Synthesis of Compound 2.8.

To a solution of Compound 1.7 (1.0 g, 2.0 mmol, 1.0 equiv) in mixture of CH$_2$Cl$_2$/methanol (10 mL, 2:8) was added 2,4-dimthoxybenzylamine (0.43 g, 2.61 mmol, 1.3 eq) at room temperature. The mixture was initially stirred for 30 minutes. After 30 minutes, NaCNBH$_3$ (0.50 g, 8.04 mmol, 4.0 eq) was added at 0-10° C. The reaction mixture was allowed to warm to room temperature and was stirred for 16 hours. After completion, the reaction was diluted with water and extracted with ethyl acetate (25 mL×3) followed by brine wash. The combined organic layers were dried and concentrated under vacuum. The residue was purified via flash column chromatography to afford compound 2.8 (0.95 g, 78.5%) as a yellowish solid. MS (ES): m/z 603.2 [M+H]⁺

Synthesis of Compound I-2.

A solution of compound 2.8 (0.95 g, 1.57 mmol, 1.0 equiv.) in trifluoroacetic acid (10 mL) was stirred for 4 hours at reflux temperature. After completion of the reaction, the mixture was concentrated under reduced pressure. The crude material was triturated with diethyl ether/methanol (9.5:0.5) solution to afford I-2 (0.5 g, 81.3%) as a yellow solid. MS (ES): m/z 397 [M+H]⁺, ¹H NMR (400 MHz, DMSO-d$_6$): δ 12.22 (s, 1H), 9.06 (s, 1H). 8.88 (s, 1H), 7.69-7.67 (d, 2H), 7.63-7.57 (m, 1H), 7.29-7.22 (m, 4H), 4.47 (s, 2H), 2.58 (s, 2H).

Example 3: Synthesis of ethyl 2-(4-((2-(2,6-difluorophenyl)-5-oxo-6,7-dihydro-5H-pyrrolo[3,4-d]pyrimidin-4-yl)amino)phenyl)acetate, I-3
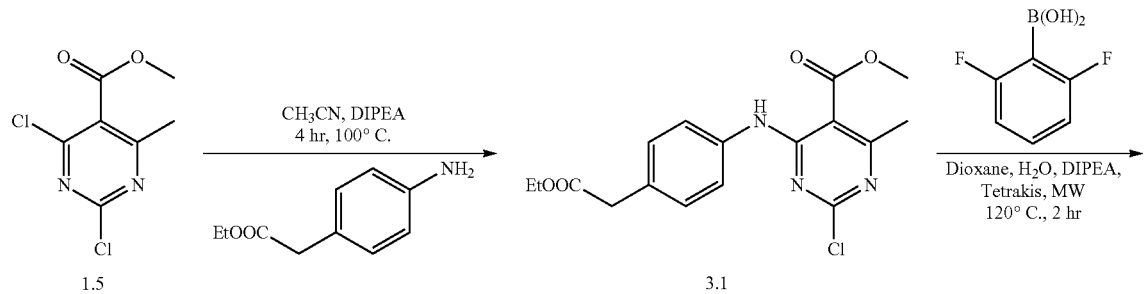
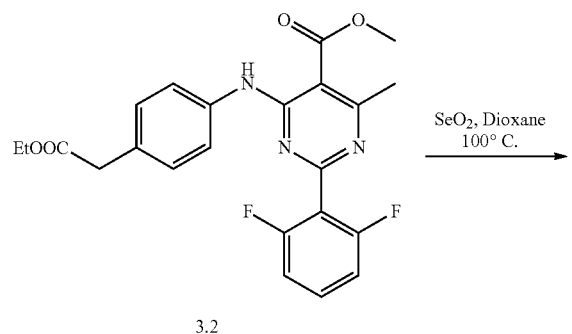
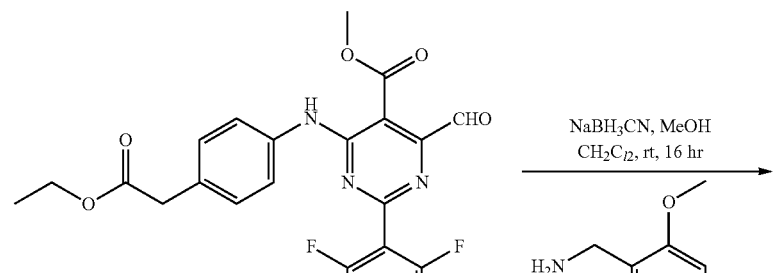
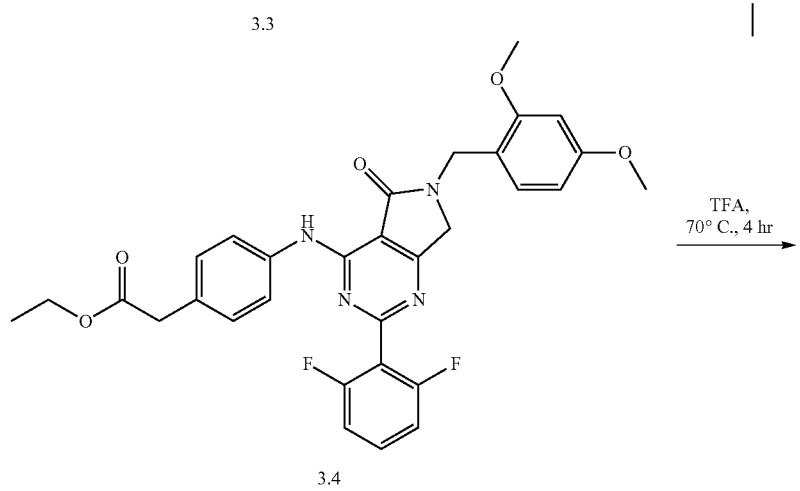

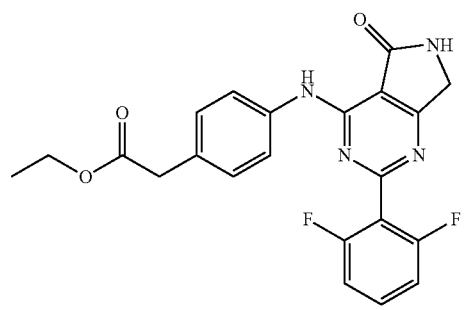

I-3

Synthesis of Compound 3.1.

To a solution of compound 1.5 (2.4 g, 10.7 mmol, 1.0 equiv), in acetonitrile (35 mL) was added diisopropylethylamine (3.81 mL, 21.44 mmol, 2.0 equiv) and ethyl-2-(4-aminophenyl)acetate (2.0 g, 9.64 mmol, 0.9 equiv) at room temperature. The mixture was heated to 100° C. for 4 hrs. After completion, the mixture was concentrated under reduced pressure and triturated with water to obtain a solid. The precipitate was filtered off to furnish pure 3.1 (2.4 g, 58.3%). MS (ES): m/z 364 [M+H]$^+$.

Synthesis of Compound 3.2.

To a solution of compound 3.2 (0.2 g, 0.55 mmol, 1.0 equiv) in 1,4-dioxane (8 mL) was added 2,6-difluorophenylboronic acid (0.17 g, 1.1 mmol, 2.0 equiv), water (2 mL) and diisopropylethylamine (0.4 mL, 2.0 mmol, 4.0 equiv). The mixture was degassed using argon gas for 10-15 min then Pd(PPh$_3$)$_4$ (0.063 g, 0.055 mmol, 0.1 equiv) was added and suspension was again degassed under argon for 5 min. The mixture was heated at 120° C. in a microwave oven for 2 hours. Upon completion, the mixture was poured into water and the product was extracted with ethyl acetate. The organic layers were combined, dried over sodium sulfate, and concentrated under reduced pressure to obtain the crude material. The crude product was purified using flash column chromatography to yield desired compound 3.2 (0.24 g, 24%). MS (ES): m/z 442 [M+H]$^+$.

Synthesis of Compound 3.3.

A solution of compound 3.2 (0.24 g, 0.544 mmol, 1.0 equiv) and selenium dioxide (0.120 g, 1.08 mmol, 2.0 equiv) in 1,4-dioxane (8 mL) was heated to 110° C. until consumption of starting material. The mixture was filtered through Celite and the filtrate was concentrated under reduced pressure to get crude 3.3 (0.24 g), which was used as such for the next step.

Synthesis of Compound 3.4.

To a solution of 3.3 (0.24 g, 0.52 mmol, 1.0 equiv) in dichloromethane (8 mL) and methanol (2 mL) was added 2,4-dimethoxybenzyl amine (0.1 g, 0.68 mmol, 1.3 equiv) and stirred at room temperature for 30 min. Sodium cyanoborohydride (0.13 g, 2.08 mmol, 4.0 equiv) was added at 0° C. and the mixture was stirred overnight. After completion, the mixture was poured into water and product was extracted twice with ethyl acetate. The organic layers were dried over sodium sulfate, the solvent removed under reduced pressure and the crude was purified via flash column chromatography to furnish 3.4 (0.17 g, 57%). MS (ES): m/z 575 [M+H]$^+$.

Synthesis of Compound I-3.

A solution of compound 3.4 (0.17 g, 0.29 mmol, 1.0 equiv) in trifluoroacetic acid (3 mL) was heated to 70° C. for 4 hours. After completion, the mixture was concentrated, diluted with ethyl acetate and washed with saturated sodium bicarbonate solution. The organic layers were concentrated under reduced pressure to obtain the crude material which was purified by flash column chromatography to furnish I-3 (0.070 g, 55%). MS (ES): m/z 425.15 (M+H)$^+$, $^1$H NMR (400 MHz, DMSO-d$_6$): δ 9.07 (s, 1H), 8.89 (s, 1H), 7.70-7.68 (d, 2H), 7.62-7.58 (m, 1H), 7.29-7.23 (m, 4H) 4.48 (s, 2H), 4.09-4.04 (q, 2H), 3.62 (s, 2H), 1.19-1.16 (t, 3H).

Example 4. Synthesis of ethyl 2-(4-((2-(2-chloro-6-fluorophenyl)-5-oxo-6,7-dihydro-5H-pyrrolo[3,4-d]pyrimidin-4-yl)amino)phenyl)acetate I-4, I-4

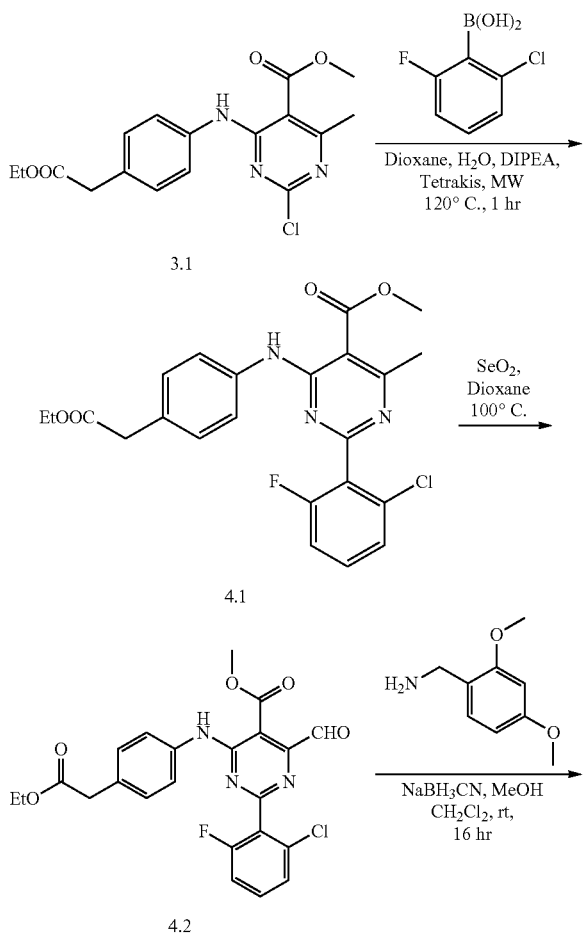

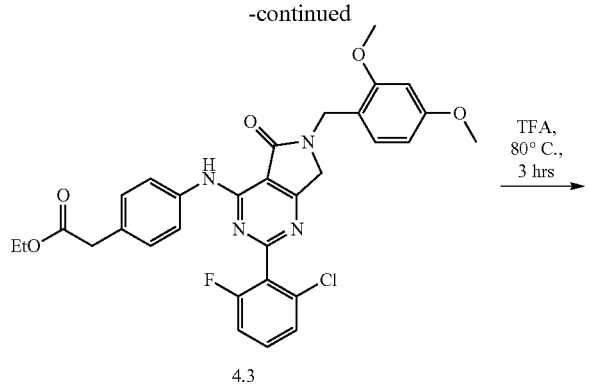

4.3

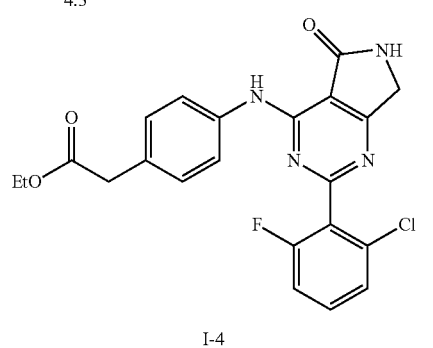

I-4

Synthesis of Compound 4.1.

To a solution of compound 3.1 (0.2 g, 0.55 mmol, 1.0 equiv) in 1,4-dioxane (8 mL) was added (2-chloro-6-fluorophenyl)boronic acid (0.19 g, 1.1 mmol, 2.0 equiv), water (2 mL) and diisopropylethylamine (0.4 mL, 2.0 mmol, 4.0 equiv). The mixture was degassed using argon gas for 15 minutes then Pd(PPh₃)₄ (0.063 g, 0.055 mmol, 0.1 equiv) was added and the suspension was degassed under argon for 5 minutes. The mixture was heated to 120° C. in a microwave oven for 1 hour. Upon completion, the mixture was poured into water and the product was extracted with ethyl acetate. The organic layers were combined, dried over sodium sulfate and concentrated under reduced pressure to obtain the crude material, which was purified by preparative HPLC to yield pure compound 4.1 (0.15 g, 59%). MS (ES): m/z 458.8 [M+H]⁺.

Synthesis of Compound 4.2.

A solution of 4.1 (0.15 g, 0.328 mmol, 1.0 equiv) and selenium dioxide (0.072 g, 0.65 mmol, 2.0 equiv) in 1,4-dioxane (4 mL) was heated at 100° C. until consumption of the starting material. The mixture was filtered through Celite and the filtrate was concentrated under reduced pressure to yield crude compound 4.2 (0.15 g) which was used as such for the next step.

Synthesis of Compound 4.3.

To a solution of 4.2 (0.15 g, 0.318 mmol, 1.0 equiv) in dichloromethane (6 mL) and methanol (2 mL) was added 2,4-dimethoxy benzyl amine (0.069 g, 0.41 mmol, 1.3 equiv). Reaction stirred at room temperature for 30 minuets. Sodium cynoborohydride (0.080 g, 1.27 mmol, 4.0 equiv) was added at 0° C. and stirred for overnight at room temperature. After completion, reaction mixture was poured into water and product was extracted twice with ethyl acetate. Organic layer was dried over sodium sulphate and concentrated under reduced pressure to get crude material which was purified by flash column chromatography to yield compound 4.3 (0.11 g, 58%). MS (ES): m/z 591 [M+H]⁺.

Synthesis of Compound I-4.

A solution of 4.3 (0.11 g, 0.18 mmol, 1.0 equiv) in trifluoroacetic acid (4 mL) was heated at 80° C. for 3 hours. Upon completion, the mixture was concentrated and residue was diluted with ethyl acetate and washed with saturated sodium bicarbonate solution. The organic layers were concentrated under reduced pressure to obtain crude material which was purified by flash column chromatography to furnish I-4 (0.040 g, 48%). MS (ES): m/z 440.7 [M+H]⁺, ¹H NMR (400 MHz, DMSO-d₆): δ 9.11 (s, 1H), 8.91 (s, 1H), 7.67-7.65 (d, 2H), 7.60-7.57 (m, 1H), 7.49-7.47 (d, 1H), 7.41-7.37 (t, 1H), 7.24-7.22 (d, 2H) 4.49 (s, 2H), 4.09-4.03 (q, 2H), 3.61 (s, 2H), 1.19-1.15 (t, 3H).

Example 5. Synthesis of ethyl 2-(4-((2-(2,6-dichlorophenyl)-5-oxo-6,7-dihydro-5H-pyrrolo[3,4-d]pyrimidin-4-yl)amino)phenyl)acetate, I-5

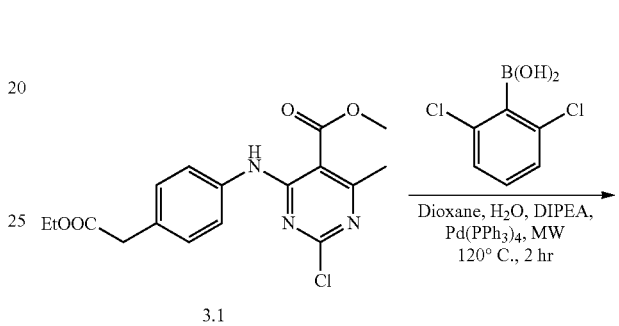

3.1

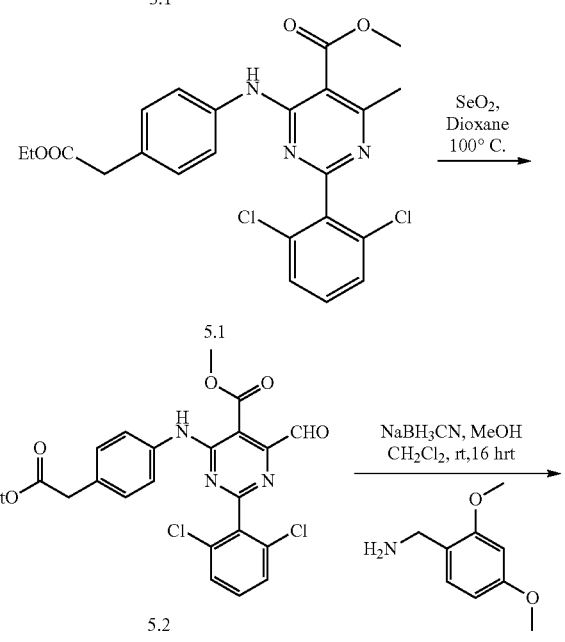

5.1

5.2

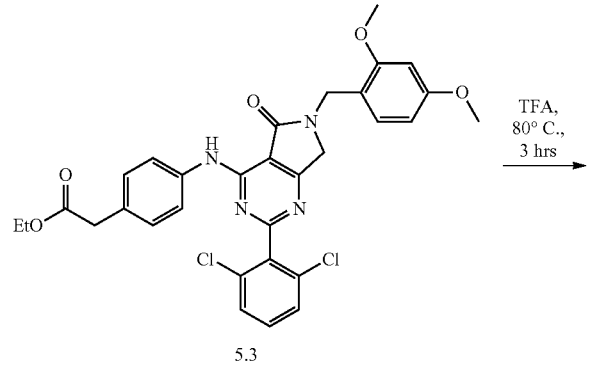

5.3

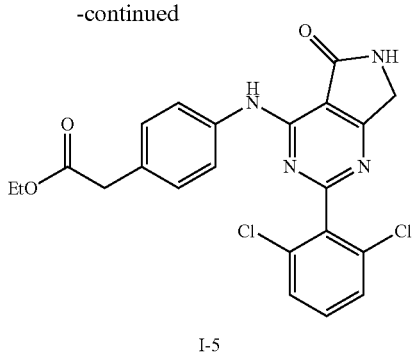

I-5

Synthesis of Compound 5.1.

To a solution of compound 3.1 (0.2 g, 0.55 mmol, 1.0 equiv) in 1,4-dioxane (8 mL) was added 2,6-dichloro phenylboronic acid (0.21 g, 1.1 mmol, 2.0 equiv), water (2 mL) and diisopropylethylamine (0.4 mL, 2.0 mmol, 4.0 equiv). The mixture was degassed under argon gas for 10-15 min then Pd(PPh$_3$)$_4$ (0.063 g, 0.055 mmol, 0.1 equiv) was added and the suspension was degassed under argon for 5 minutes. The mixture was heated to 120° C. in a microwave for 2 hours. Upon completion, the mixture was poured into water and extracted with ethyl acetate. The organic layers were combined and dried over sodium sulfate. The solvent was removed under reduced pressure to obtain crude material, which was purified using preparative HPLC to furnish compound 5.1 (0.170 g, 65%). MS (ES): m/z 474 [M+H]$^+$.

Synthesis of Compound 5.2.

A solution of 5.1 (0.17 g, 0.359 mmol, 1.0 equiv) and selenium dioxide (0.080 g, 0.71 mmol, 2.0 equiv) in 1,4-dioxane (3 mL) was heated at 110° C. until consumption of starting material. The mixture was filtered through Celite and the filtrate was concentrated under reduced pressure to get crude 5.2 (0.17 g) which was used as such for the next step.

Synthesis of Compound 5.3.

To a solution of compound 5.2 (0.17 g, 0.349 mmol, 1.0 equiv) in dichloromethane (6 mL) and methanol (2 mL) was added 2,4-dimethoxybenzyl amine (0.075 g, 0.45 mmol, 1.3 equiv) and stirred at room temperature for 30 minutes. Sodium cyanoborohydride (0.065 g, 1.04 mmol, 3.0 equiv) was added at 0° C. and stirred for 16 hours. After completion, reaction mixture was poured into water and product was extracted twice with ethyl acetate. The organic layers were combined and dried over sodium sulfate. The solvent was removed under reduced pressure to give the crude product which was purified using flash column chromatography to furnish 5.3 (0.130 g, 61%). MS (ES): m/z 607 [M+H]$^+$.

Synthesis of Compound I-5.

A solution of compound 5.3 (0.130 g, 0.21 mmol, 1.0 equiv) in trifluoroacetic acid (2.5 mL) was heated at 80° C. for 3 hours. After completion, reaction mixture was concentrated and residue was diluted with ethyl acetate and washed with saturated sodium bicarbonate solution. The organic layers were concentrated under reduce pressure to obtain crude material which was purified by flash column chromatography to furnish I-5 (0.077 g, 80%). MS (ES): m/z 457 [M+H]$^+$, $^1$H NMR (400 MHz, DMSO-d$_6$): δ 9.13 (s, 1H), 8.91 (s, 1H), 7.64-7.60 (m, 4H), 7.54-7.50 (m, 1H), 7.24-7.21 (d, 2H) 4.49 (s, 2H), 4.08-4.03 (q, 2H), 3.61 (s, 2H), 1.18-1.15 (t, 3H).

Example 6. Synthesis of Synthesis of 2-(4-((2-(2,6-dichlorophenyl)-5-oxo-6,7-dihydro-5H-pyrrolo[3,4-d]pyrimidin-4-yl)amino)phenyl)acetic Acid, I-6

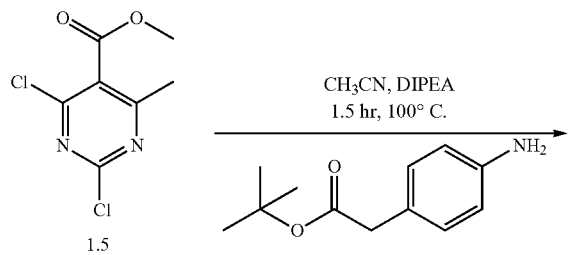

1.5

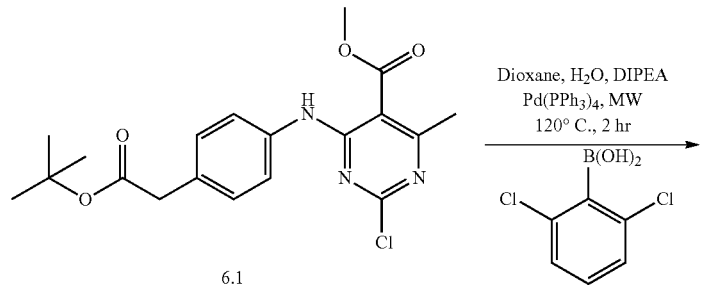

6.1

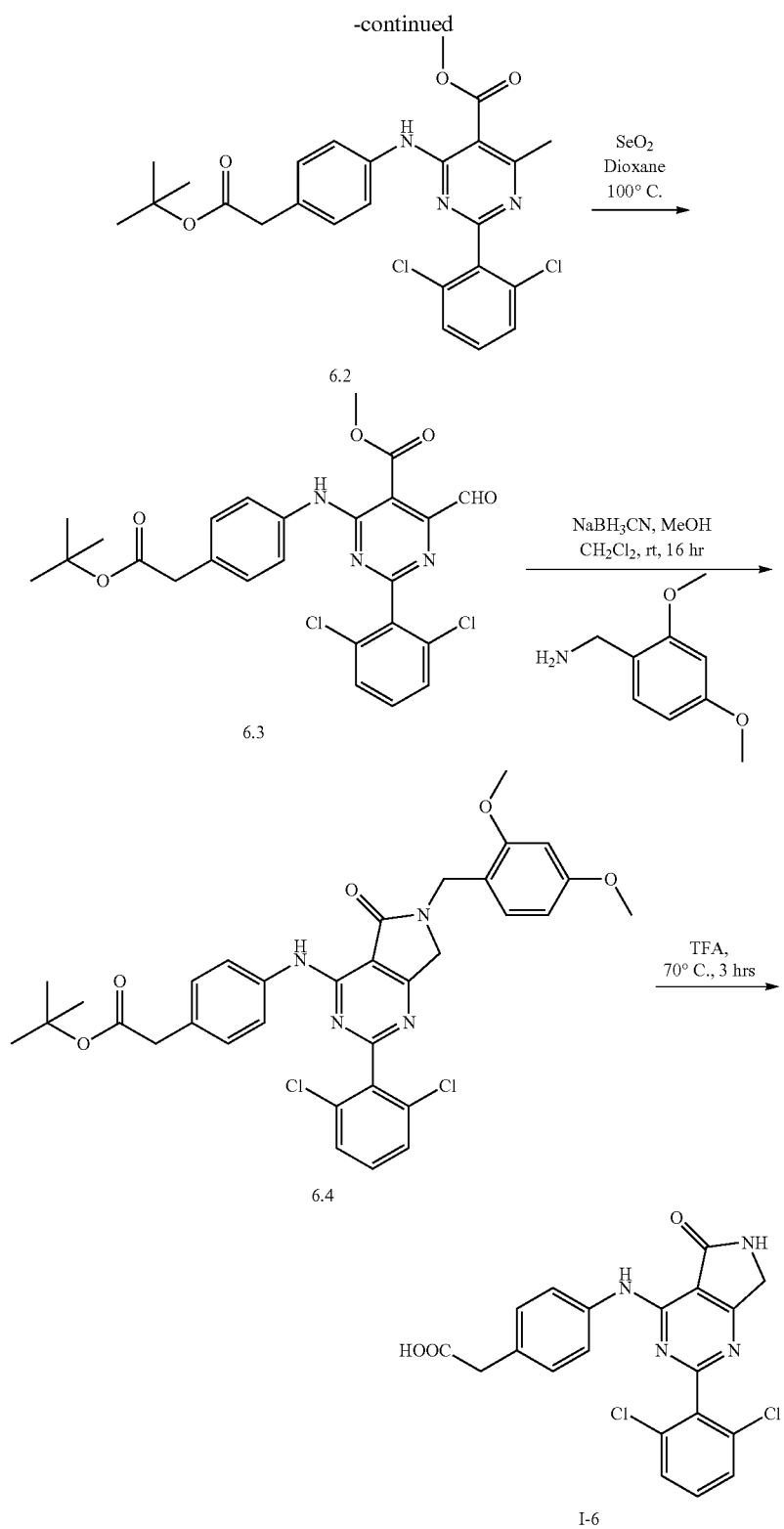

Synthesis of Compound 6.1.

To a solution of 1.5 (5.0 g, 22.6 mmol, 1.0 equiv), in acetonitrile (40 mL) was added diisopropylethylamine (12 mL, 67.8 mmol, 3.0 equiv) and tert-butyl 2-(4-aminophenyl) acetate (4.68 g, 22.6 mmol, 1.0 equiv). The reaction mixture was heated to 100° C. for 1.5 hours. After completion, the reaction was stopped and the solvent removed. The crude material was triturated with water to furnish compound 6.1 (8.5 g, 95%). MS (ES): m/z 392.14 [M+H]+.

Synthesis of Compound 6.2.

To a solution of 6.1 (0.2 g, 0.51 mmol, 1.0 equiv) in 1,4-dioxane (8 mL) was added 2,6-dichloro-phenylboronic acid (0.194 g, 1.0 mmol, 2.0 equiv), water (2 mL) and diisopropylethylamine (0.35 mL, 2.0 mmol, equiv). The mixture was degassed under argon gas for 15 minutes then Pd(PPh$_3$)$_4$ (0.059 g, 0.051 mmol, 0.1 equiv) was added and the suspension was heated at 120° C. in a microwave oven for 2 hours. After consumption of the starting material, the mixture was poured into water and the product was extracted with ethyl acetate. The organic layers were combined, dried over sodium sulfate, and concentrated under reduced pressure to obtain the crude material. The crude batches were purified by preparative HPLC to furnish compound 6.2 (0.140 g, 8%). MS (ES): m/z 502 [M+H]$^+$.

Synthesis of Compound 6.3.

A solution of compound 6.2 (0.14 g, 0.279 mmol, 1.0 equiv) and selenium dioxide (0.061 g, 0.558 mmol, 2.0 equiv) in 1,4-dioxane (5 mL) was heated at 100° C. until starting material was consumed. The mixture was filtered through Celite and the filtrate was concentrated under reduced pressure to give the crude compound 6.2 (0.14 g), which was used as such for the next step.

Synthesis of Compound 6.4.

To a solution of compound 6.3 (0.14 g, 0.278 mmol, 1.0 equiv) in dichloromethane (1.5 mL) and methanol (2.5 mL) was added 2,4-dimethoxybenzyl amine (0.051 g, 0.3 mmol, 1.1 equiv). The mixture was stirred at room temperature for 30 minutes. Sodium cyanoborohydride (0.052 g, 0.83 mmol, 3.0 equiv) was added at 0° C. and stirred for 16 hours. After completion, reaction mixture was poured into water and product was extracted twice with ethyl acetate. The organic layers were dried over sodium sulfate and concentrated under reduced pressure to give the crude material which was purified by column chromatography to provide compound 6.4 (0.089 g, 50%). MS (ES): m/z 635 [M+H]$^+$.

Synthesis of Compound I-6.

A solution of 6.4 (0.089 g, 0.14 mmol, 1.0 equiv) in trifluoroacetic acid (2.0 mL) was heated at 70° C. for 3 hrs. After reaction completion, reaction mixture was concentrated and residue was diluted with ethyl acetate and washed with saturated sodium bicarbonate solution. The solvent was removed under reduced pressure to obtain crude material which was purified by flash column chromatography to furnish I-6 (0.032 g, 53%). MS (ES): m/z 429 [M+H]$^{+1}$H NMR (400 MHz, DMSO-d$_6$): δ 12.3 (s, 1H), 9.12 (s, 1H), 8.91 (s, 1H), 7.63-7.60 (m, 4H), 7.53-7.49 (m, 1H), 7.23-7.2 (d, 2H), 4.49 (s, 2H), 3.52 (s, 2H).

Example 7. Example 1: Synthesis of 2-(4-((2-(2-chlorophenyl)-5-oxo-6,7-dihydro-5H-pyrrolo[3,4-d]pyrimidin-4-yl)amino)phenyl)acetic Acid, I-7

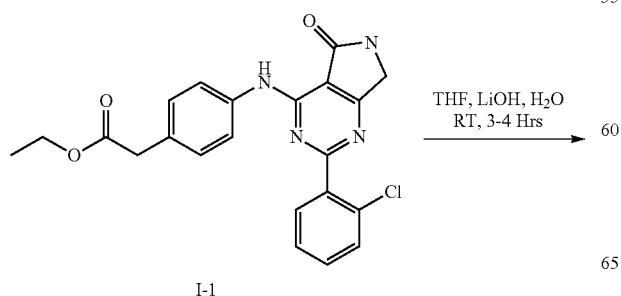

I-1

-continued

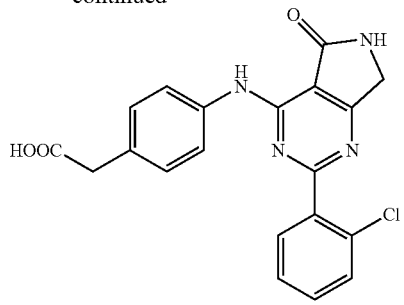

I-7

Synthesis of Compound I-7.

To a solution of compound I-1 (0.032 g, 0.07582 mmol, 1.00 equiv) in THF (1.0 mL) was added solution of lithium hydroxide monohydrate (0.0074 g, 0.2274 mmol, 3.0 equiv) in water (1.0 mL). The reaction mixture was stirred at room temperature for 4 hrs. After completion, reaction mixture was acidified with dilute HCl and the product was extracted with ethyl acetate twice to obtain the crude material, which was purified by preparative HPLC to furnish I-7. (0.016 g, 55.17%). MS (ES): m/z 394.86 (M+H)$^+$ $^1$H NMR (400 MHz, DMSO-d$_6$): δ 12.30 (s, 1H) 9.02 (s, 1H), 8.85 (s, 1H), 7.73-7.78 (m, 3H), 7.59-7.61 (d, 1H), 7.54-7.46 (m, 2H), 7.25-7.23 (d, 2H), 4.47 (s, 2H), 3.54 (s, 2H).

Example 8. Synthesis of 2-(4-((2-(2-chlorophenyl)-5-oxo-6,7-dihydro-5H-pyrrolo[3,4-d]pyrimidin-4-yl)amino)phenyl)acetamide, I-8

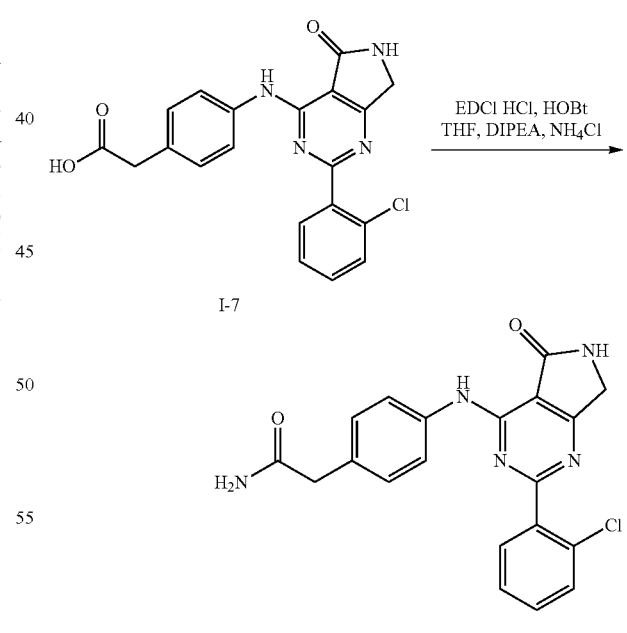

Synthesis of Compound I-8.

To a solution of 1 (0.09 g, 0.22 mmol, 1.0 eq.) in dry tetrahydrofuran (2.0 mL) at 0-5° C., was added 1-ethyl-3-(3-dimethylaminopropyl)-carbodiimide (0.065 g, 0.34 mmol, 1.5 eq.), 1-hydroxybezotriazole (0.040 g, 0.26 mmol, 1.2 eq.) and the mixture stirred for 20 minutes. To the above reaction mixture was added ammonium chloride (0.116 g, 0.22 mmol, 10 eq) and di-isopropyl ethyl amine (0.141 g, 1.1 mmol, 5.0 eq.) at 0-5° C. The reaction mixture was allowed to warm at room temperature and stirred for 24 hours. After completion of reaction, reaction mixture was poured into ice cold water and extracted using ethyl acetate. The organic layers were washed with brine, dried over sodium sulfate and concentrated under reduced pressure. The crude product was purified by flash column chromatography to furnish I-8 (0.032 g, 37%). MS (ES): m/z 394 [M+H]⁺, ¹H NMR (400 MHz, DMSO-d$_6$): δ 9.01 (s, 1H), 8.85 (s, 1H), 7.76-7.73 (m, 3H), 7.61-7.59 (dd, 1H), 7.53-7.45 (m, 3H), 7.24-7.2 (d, 2H), 6.88 (s, 1H), 4.46 (s, 2H), 3.34 (s, 2H).

Example 9. Synthesis of 2-(4-((2-(2,6-dichloro-4-cyanophenyl)-5-oxo-6,7-dihydro-5H-pyrrolo[3,4-d]pyrimidin-4-yl)amino)phenyl)acetic Acid I-9

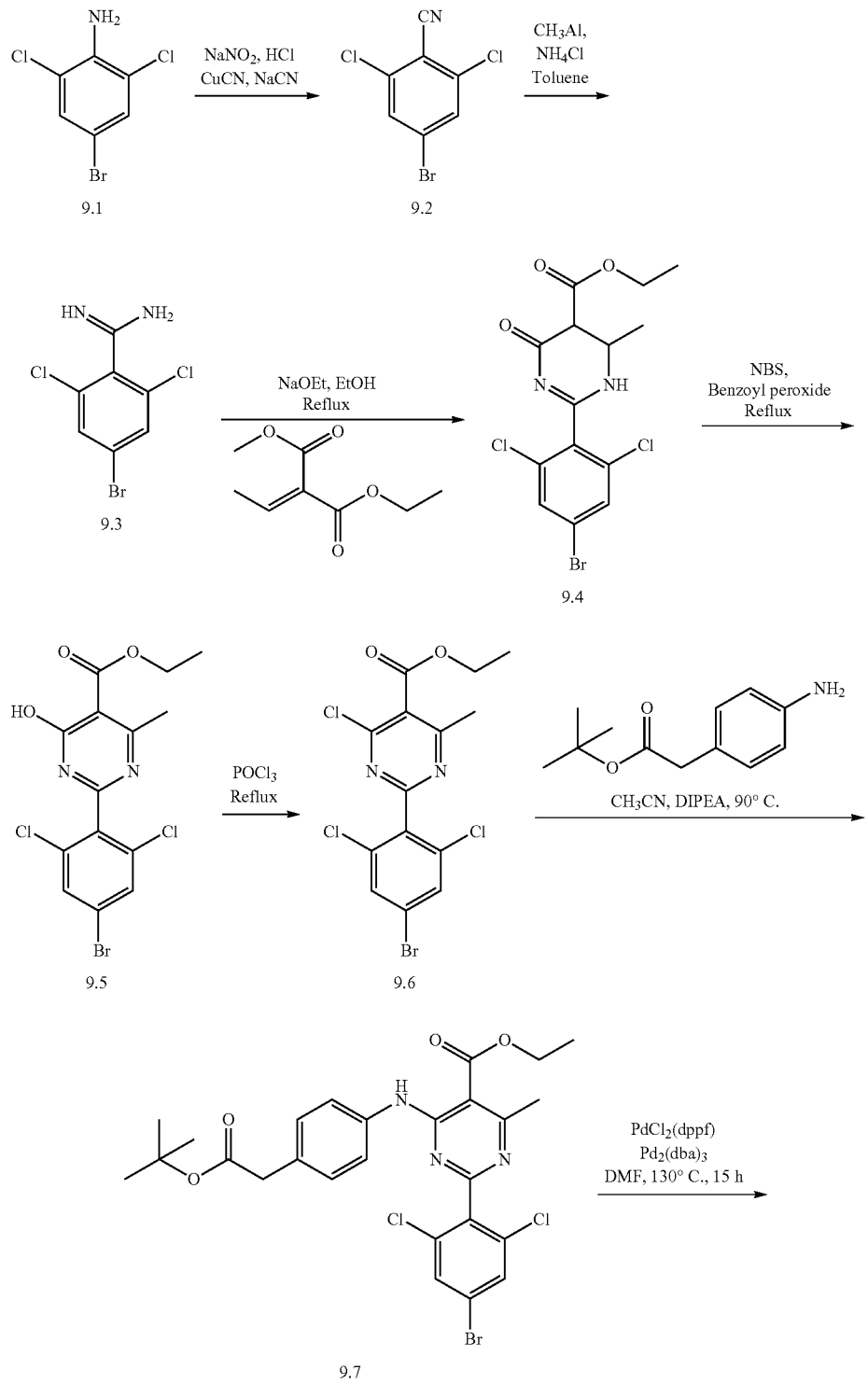

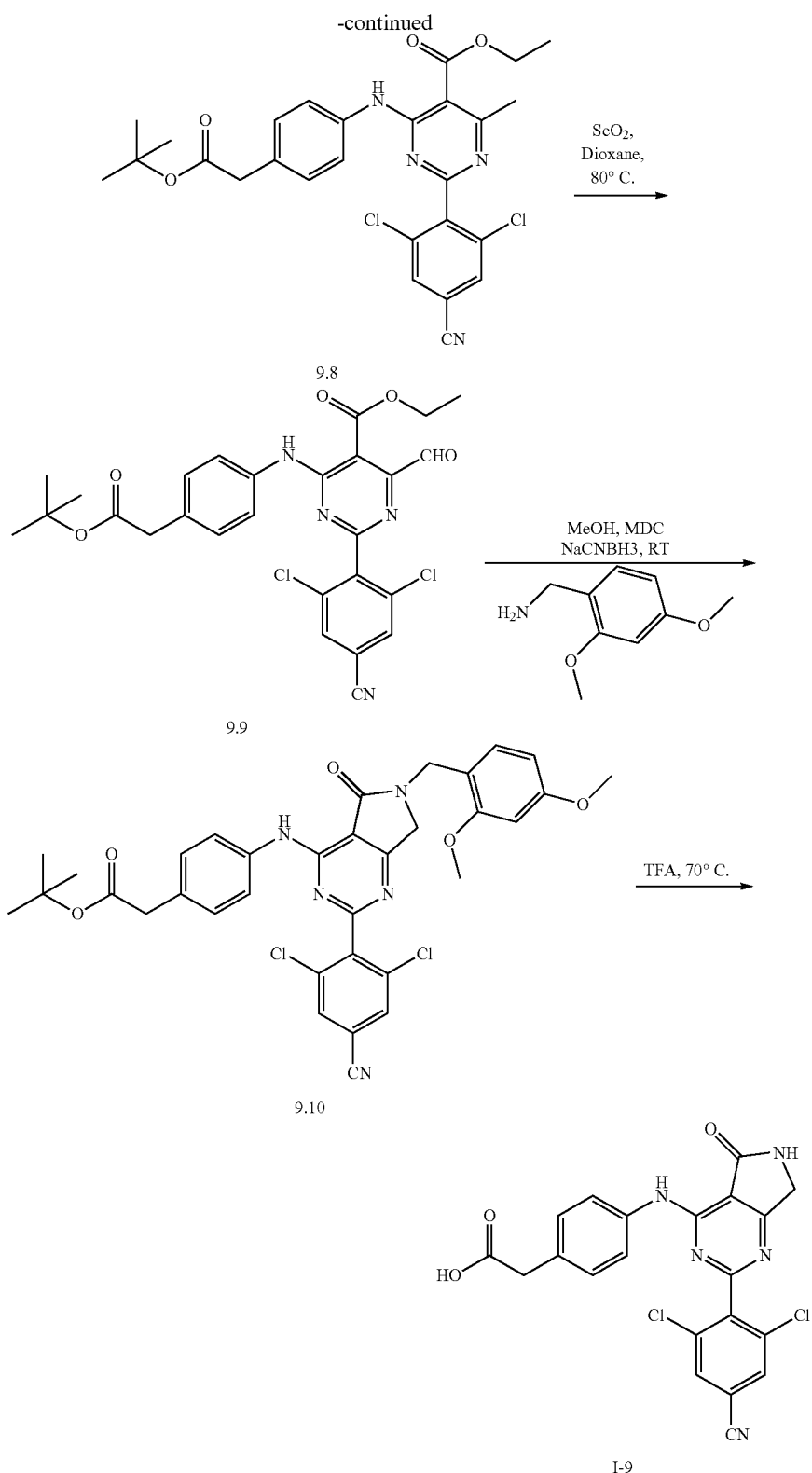

Synthesis of Compound 9.2.

To a suspension of compound 9.1 (7.0 g, 29 mmol, 1.0 equiv), in water (35 mL) was added conc. hydrochloric acid (14 mL). The suspension was cooled to 0° C. then sodium nitrite (2.2 g, 31.96 mmol, 1.1 equiv) in water (7 mL) was added dropwise at 0° C. and the reaction mixture was stirred for 30 minutes. In another flask, a solution of copper (I) cyanide (3.11 g, 37.86 mmol, 1.2 equiv) and sodium cyanide (2.13 g, 43.5 mmol, 1.5 equiv) in water (35 mL) was heated to 70° C. The diazonium salt mixture was neutralized by solid sodium bicarbonate and added portion wise to the cyanide mixture at 70° C. The mixture was heated at 70° C. for 30 minutes. Upon completion, the mixture was cooled to room temperature and extracted with toluene. The organic layers were combined, dried over sodium sulfate, and concentrated under reduced pressure to obtain the crude material which was purified via flash column chromatography to furnish compound 9.2 (1.6 g, 48%).

Synthesis of Compound 9.3.

To a solution of compound 9.2 (1.6 g, 6.37 mmol, 1.0 equiv) in toluene (28 mL) was added ammonium chloride (1.7 g, 31.8 mmol, 5.0 equiv) at room temperature. Trimethylaluminum solution (2M in toluene) (2.29 g, 31.8 mmol, 5.0 equiv) was added slowly under a nitrogen atmosphere. The mixture was heated at 110° C. for 48 hrs. Upon completion, the reaction mixture was cooled to room temperature and silica was added followed by chloroform (50 mL). The resulting suspension was stirred for 30 minutes, filtered and the filter cake washed with 20% methanol in dichloromethane. The filtrate was concentrated under reduced pressure to obtain crude material, which was triturated with 10% ethyl acetate in hexane to yield compound 9.3 (1.6 g, 93%). MS (ES): m/z 269 [M+H]$^+$.

Synthesis of Compound 9.4.

To a solution of compound 9.3 (1.3 g, 4.86 mmol, 1.0 equiv) and diethyl 2-ethylidenemalonate (0.9 g, 4.86 mmol, 1.0 equiv) in ethanol (13 mL) was added sodium ethoxide (0.59 g, 8.74 mmol, 1.8 equiv) at room temperature. The mixture was refluxed for 3 hours then the solvent was removed under reduced pressure. The crude material was purified via flash column chromatography to yield compound 9.4 (2.6 g, 65%). MS (ES): m/z 409 [M+H]$^+$.

Synthesis of Compound 9.5.

To a solution of compound 9.4 (2.6 g, 6.37 mmol, 1.0 equiv) in 1,4-dioxane (60 mL) was added N-bromosuccinimide (1.13 g, 6.37 mmol, 1.0 equiv), potassium carbonate (1.31 g, 9.55 mmol, 1.5 equiv), benzoylperoxide (0.23 g, 0.955 mmol, 0.15 equiv). The mixture was heated at 100° C. for 6 hours. After completion, reaction mixture was poured into water, acidified with dilute HCl and extracted twice with ethyl acetate. The organic layers were combined and dried over sodium sulfate. The solvent was removed and crude material was triturated with hexane to yield compound 9.5 (2.3 g, 88%). MS (ES): m/z 406.9 [M+H]$^+$.

Synthesis of Compound 9.6.

To a solution of compound 9.5 (2.3 g, 5.66 mmol, 1.0 equiv) in toluene (23 mL) was added phosphorous oxychloride (23 mL) and reaction mixture was heated at 100° C. for 45 minutes. Upon completion, the mixture was poured into ice-water and product was extracted twice with ethyl acetate. The organic layers were dried over sodium sulfate and concentrated under reduced pressure to give the crude material which was purified by flash chromatography to yield compound 9.6 (1.1 g, 45%). MS (ES): m/z 424.95 [M+H]$^+$.

Synthesis of Compound 9.7.

To a solution of compound 9.6 (1.1 g, 2.5 mmol, 1.0 equiv), in acetonitrile (20 mL) was added diisopropylethylamine (0.81 g, 6.25 mmol, 2.5 equiv) and tert-butyl 2-(4-aminophenyl) acetate (0.51 g g, 2.46 mmol, 0.95 equiv). The mixture was heated at 90° C. for 24 hours. Upon completion, the mixture was concentrated under reduced pressure and triturated with water and extracted with ethyl acetate to obtain crude material which was purified by flash chromatography to furnish 9.7 (0.7 g, 45%). MS (ES): m/z 596 [M+H]$^+$.

Synthesis of Compound 9.8.

To a solution of 9.7 (0.6 g, 1.0 mmol, 1.0 equiv), in N,N-dimethylformamide (12 mL) was added zinc cyanide (0.102 g, 1.0 mmol, 0.9 equiv). The mixture was degassed with argon for 15 minutes. To this reaction mixture was added tris(dibenzylideneacetone)dipalladium(0) (0.072 g, 0.08 mmol, 0.08 equiv) and [1,1'-Bis(diphenylphosphino) ferrocene] dichloro-palladium(II) (0.060 g, 0.08 mmol, 0.08 equiv). The mixture was degassed again for 15 minutes then heated at 130° C. for 8 hours. Upon completion, the mixture was poured in water and product was extracted twice with ethyl acetate. The organic layers were dried over sodium sulfate and concentrated under reduced pressure to give the crude material, which was purified by flash column chromatography to furnish compound 9.8 (0.28 g, 51%) MS (ES): m/z 541 [M+H]$^+$.

Synthesis of Compound 9.9.

A solution of compound 9.8 (0.17 g, 0.314 mmol, 1.0 equiv) and selenium dioxide (0.069 g, 0.628 mmol, 2.0 equiv) in 1,4-dioxane (4 mL) was heated at 100° C. for 24 hours. The reaction mixture was filtered through Celite and obtained filtrate was concentrated under reduced pressure to afford crude compound 9.9 (0.17 g) which was used as such for the next step.

Synthesis of Compound 9.10.

To a solution of 1.8 (0.17 g, 0.306 mmol, 1.0 equiv) in dichloromethane (1.5 mL) and methanol (0.8 mL) was added 2,4-dimethoxybenzyl amine (0.056 g, 0.33 mmol, 1.1 equiv) and stirred at room temperature for 30 min. Sodium cyanoborohydride (0.059 g, 0.91 mmol, 3.0 equiv) was added at 0° C. and stirred for 16 hours. Upon completion, the mixture was poured into water and product was extracted twice with ethyl acetate. Organic layer was dried over sodium sulfate and concentrated under reduced pressure to get crude material, which was purified by column chromatography to furnish compound 9.10 (0.1 g, 49%). MS (ES): m/z 660 [M+H]$^+$.

Synthesis of Compound I-9.

A solution of compound 9.10 (0.098 g, 0.14 mmol, 1.0 equiv) in trifluoroacetic acid (1.5 mL) was heated at 70° C. for 5 hours. After completion, the mixture was concentrated and the residue was diluted with ethyl acetate and washed with saturated sodium bicarbonate solution. The solvent was removed under reduced pressure to obtain crude material, which was purified by preparative HPLC to furnish I-9 (0.024 g, 53%). MS (ES): m/z 454 (M)+, LCMS purity: 100%, HPLC purity: 99%, $^1$H NMR (400 MHz, DMSO-d$_6$): δ 12.3 (s, 1H), 9.19 (s, 1H), 8.94 (s, 1H), 8.27 (s, 2H), 7.60-7.58 (d, 2H), 7.23-7.20 (d, 2H), 4.5 (s, 2H), 3.52 (s, 2H).

Example 10. Synthesis of 2-(4-((2-(2-chloro-6-fluorophenyl)-5-oxo-6,7-dihydro-5H-pyrrolo[3,4-d]pyrimidin-4-yl)amino)phenyl)acetic Acid, I-10

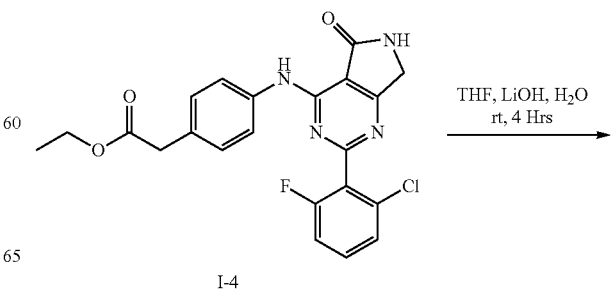

I-4

THF, LiOH, H$_2$O
rt, 4 Hrs

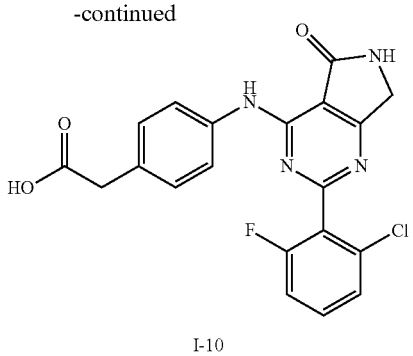

I-10

Synthesis of Compound I-10.

Starting from compound I-4, compound I-10 was obtained in 69% yield using the same protocol as described in Example 7. MS (ES): m/z 413 [M+H]+ 1H NMR (400 MHz, DMSO-d6): δ 12.33 (s, 1H), 9.0 (s, 1H), 8.51 (s, 1H), 7.65-7.63 (d, 1H), 7.58-7.54 (m, 2H), 7.48-7.46 (d, 1H), 7.41-7.36 (t, 1H), 7.23-7.20 (m, 2H) 4.49 (s, 2H), 3.52 (s, 2H).

Example 11. Synthesis of 2-(4-((2-(2,6-difluorophenyl)-5-oxo-6,7-dihydro-5H-pyrrolo[3,4-d]pyrimidin-4-yl)amino)phenyl)-N-(piperidin-4-yl)acetamide, I-11

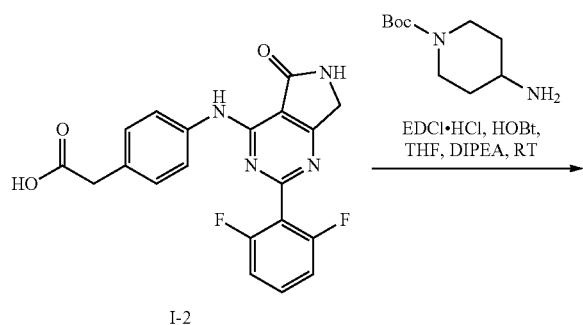

Synthesis of Compound 11.1

To a solution of I-2 (60 mg, 0.15 mmol, 1.0 eq.) in dry THF (4.0 mL) was added 1-ethyl-3-(3-dimethylaminopropyl)carbodiimide (43.5 mg, 0.22 mmol, 1.5 eq.), 1-hydroxybezotriazole (24.5 mg, 0.18 mmol, 1.2 eq.) at 0-5° C. and stirred for 20 minutes at same temperature. To the above reaction mixture was added tert-butyl 4-aminopiperidine-1-carboxylate (39 mg, 0.19 mmol, 1.3 eq.) and diisopropylethyl amine (78 mg, 0.6 mmol, 4.0 eq.) at 0-5° C. The reaction mixture was allowed to warm to room temperature and was stirred for 24 hours. After completion of the reaction, mixture was poured into ice cold water and extracted using ethyl acetate. The organic layers were washed with brine, dried over sodium sulfate, and concentrated under reduced pressure. The crude material was purified by flash column chromatography to furnish compound 11.1 48 mg (55%). MS (ES): m/z 579 [M+H]+.

Synthesis of Compound I-11.

To a solution of compound 11.1 (48 mg, 0.08 mmol, 1.0 eq.) in dry dichloromethane (1.0 mL) was added trifluoroacetic acid (0.3 mL) at 0° C. The reaction mixture was allowed to warm at room temperature and was stirred for 30 minutes. After completion of the reaction, the solvent was removed on a rotary evaporator. The crude material obtained was dissolved in methanol (3.0 mL) and tetraalkylammoniumcarbonate (polymer supported) was added until a pH=7 was obtained. The reaction mixture was filtered through a Millipore filter funnel and the solvent was removed under reduced pressure to afford 40 mg (98%) compound I-11 as an off-white solid. MS (ES): m/z 479 [M+H] 1H NMR (400 MHz, DMSO-d6): δ 9.04 (s, 1H), 8.89 (s, 1H), 8.21-8.19 (d, 1H), 7.66-7.64 (d, 2H), 7.62-7.56 (m, 1H), 7.28-7.21 (m 4H), 4.47 (s, 2H), 3.71 (bs, 1H), 3.25-3.12 (m, 4H), 2.82-2.77 (t, 2H), 1.82-1.79 (d, 2H), 1.52-1.44 (m, 2H).

Example 12. Synthesis of N-(azetidin-3-yl)-2-(4-((2-(2,6-difluorophenyl)-5-oxo-6,7-dihydro-5H-pyrrolo[3,4-d]pyrimidin-4-yl)amino)phenyl)acetamide I-12

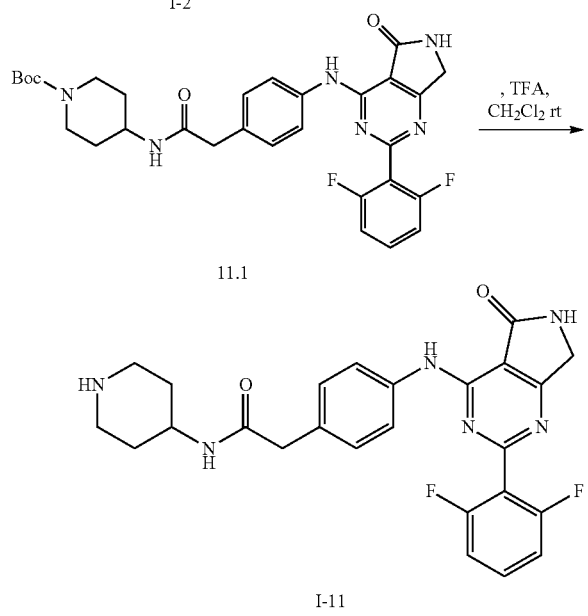

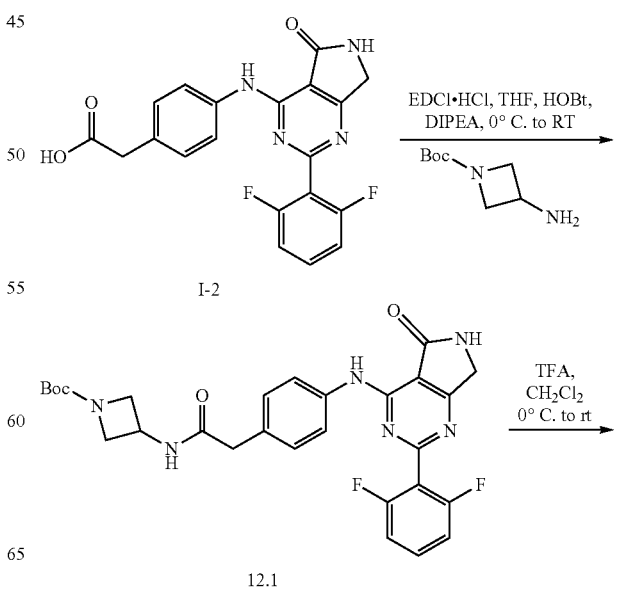

-continued

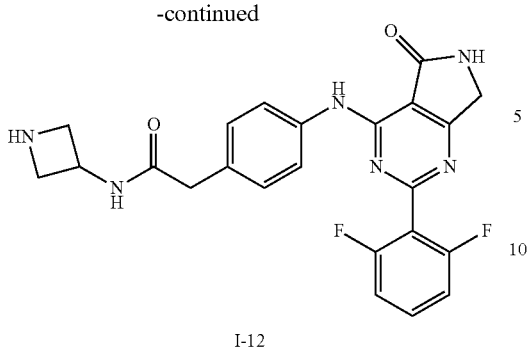

I-12

Compound I-12 was synthesized in 29% yield from compound I-2 using the same procedure described in Example 11. MS (ES): m/z 452 [M+H]$^{+1}$H NMR (400 MHz, DMSO-d$^6$): δ 9.04 (s, 1H), 8.90 (s, 1H). 8.84 (s, 1H), 8.36 (bs, 1H), 7.67-7.65 (d, 2H), 7.61-7.60 (d, 1H), 7.28-7.21 (m, 4H), 4.52 (s, 1H), 4.45 (s, 1H), 3.83-3.82 (d, 2H), 3.63 (s, 2H), 3.38 (s, 2H), 3.17 (s, 1H).

Example 13. Synthesis of 2-(4-((2-(2,6-difluorophenyl)-5-oxo-6,7-dihydro-5H-pyrrolo[3,4-d]pyrimidin-4-yl)amino)phenyl)-N-(piperidin-4-ylmethyl)acetamide, I-13

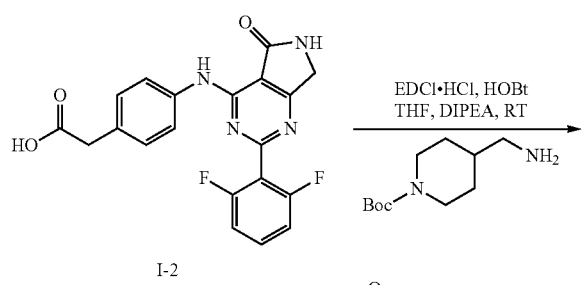

I-2

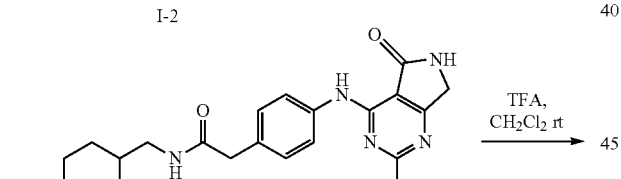

13.1

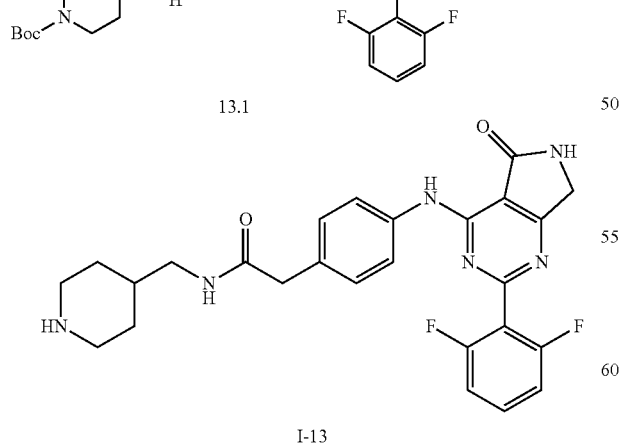

I-13

Compound I-13 was synthesized in 78% yield from compound I-2 using the same procedure described in Example 11. MS (ES): m/z 493 [M+H]$^+$ $^1$H NMR (400 MHz, DMSO-d$_6$): δ 9.04 (s, 1H), 8.88 (s, 1H). 7.99 (s, 1H), 8.36 (bs, 1H), 7.66-7.58 (m, 3H), 7.28-7.20 (m 4H), 4.47 (s, 2H), 3.36-3.34 (s, 2H), 2.90-2.87 (m, 4H), 2.36-2.30 (m, 2H), 1.53-1.50 (d, 2H), 0.99 (m, 2H).

Example 14. Synthesis of 2-(4-((2-(2,6-difluorophenyl)-5-oxo-6,7-dihydro-5H-pyrrolo[3,4-d]pyrimidin-4-yl)amino)phenyl)-N-(2-azaspiro[3.3]heptan-6-yl)acetamide, I-14


I-2


14.1

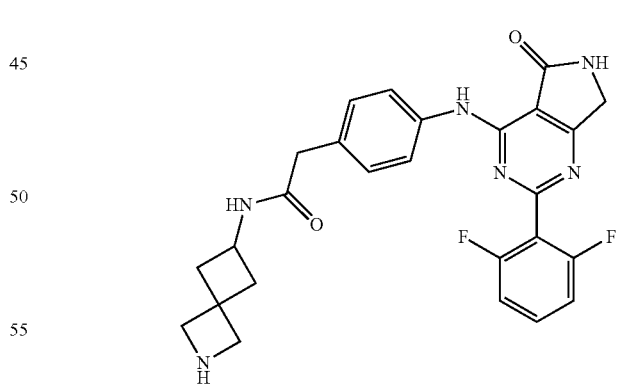

I-14

Compound I-14 was synthesized in 78% yield from compound I-2 using the same procedure described in Example 11. MS (ES): m/z 491 [M+H]$^+$ $^1$H NMR (400 MHz, DMSO-d$_6$): δ 9.03 (s, 1H), 8.89 (s, 1H). 8.23-8.22 (d, 1H), 7.66-7.58 (m, 3H), 7.28-7.24 (t, 2H), 7.20-7.18 (d, 2H) 4.47 (s, 2H), 3.98-3.97 (d, 1H), 3.71-3.65 (t, 2H), 3.39 (s, 2H), 2.33 (bs, 4H), 2.05-1.99 (d, 2H).

Example 15. Synthesis of (R)-2-(2,6-difluorophenyl)-4-((4-(2-(2-(hydroxymethyl)pyrrolidin-1-yl)-2-oxoethyl)phenyl)amino)-6,7-dihydro-5H-pyrrolo[3,4-d]pyrimidin-5-one, I-15

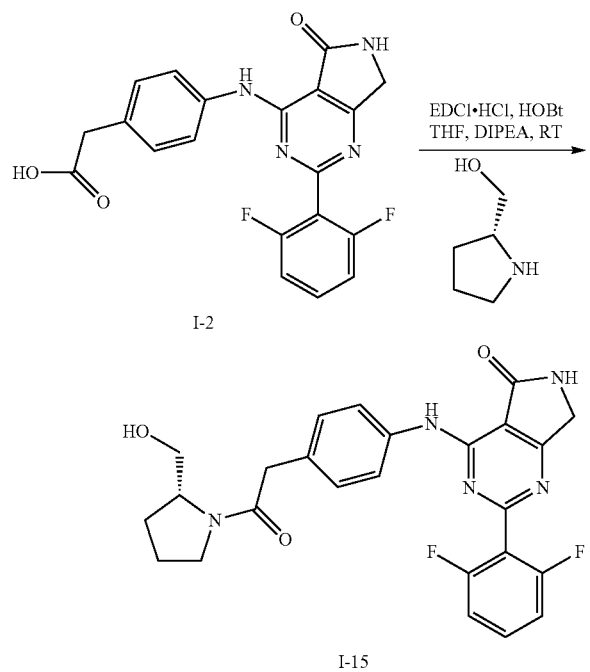

Compound I-15 was synthesized in 48% yield from compound I-2 using the procedure described in Example 8. MS (ES): m/z 480 (M+H)$^+$, $^1$H NMR (400 MHz, DMSO-d$_6$): δ 9.05 (s, 1H), 8.89 (s, 1H). 7.68-7.65 (m, 2H), 7.63-7.57 (m, 1H), 7.28-7.24 (t, 2H), 7.21-7.18 (m, 2H), 4.98-4.73 (m, 1H) 4.47 (s, 2H), 3.92 (bs, 1H), 3.71-3.65 (m, 2H), 3.47-3.39 (m, 2H), 3.27-3.21 (m, 2H), 1.91-1.76 (m, 4H).

Example 16. Synthesis of (S)-2-(2,6-difluorophenyl)-4-((4-(2-(2-(hydroxyl-methyl)pyrrolidin-1-yl)-2-oxoethyl)phenyl)amino)-6,7-dihydro-5H-pyrrolo[3,4-d]pyrimidin-5, I-16

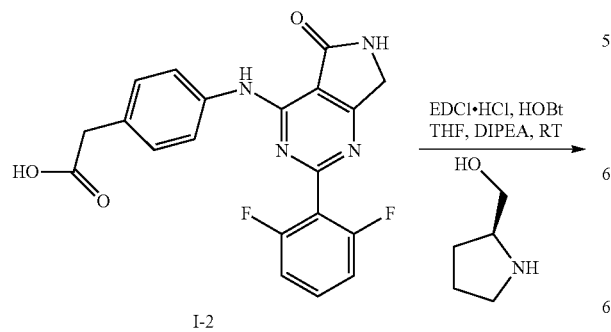

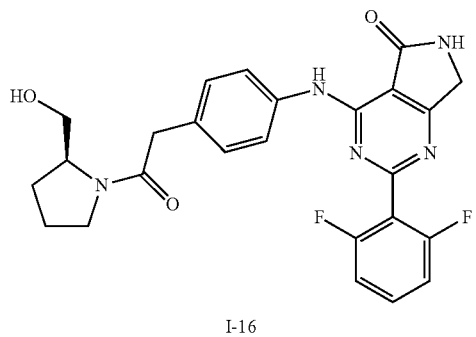

Compound I-16 was synthesized in 61% yield from compound I-2 using the procedure described in Example 8, MS (ES): m/z 480 [M+H]$^+$ $^1$H NMR (400 MHz, DMSO-d$_6$): δ 9.04 (s, 1H), 8.88 (s, 1H). 7.68-7.59 (m, 3H), 7.28-7.19 (m, 4H), 4.98-4.73 (t, 1H), 4.75-4.72 (t, 1H) 4.47 (s, 2H), 3.92 (bs, 1H), 3.65 (s, 2H), 3.47-3.41 (m, 2H), 3.29-3.21 (m, 2H), 1.93-1.77 (m, 4H).

Example 17. Synthesis of Compound, I-17

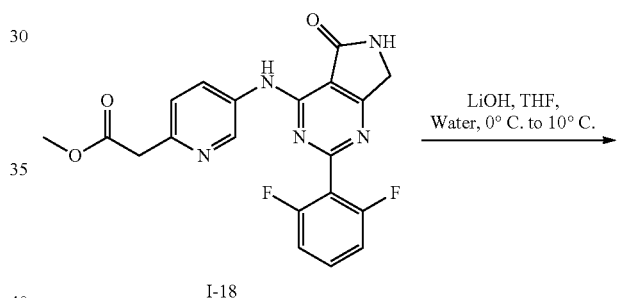

Compound I-17 was obtained from compound I-18 using the protocol described in Example 7. MS (ES): m/z 398 [M+H]$^+$ $^1$H NMR (400 MHz, DMSO-d$_6$): δ 9.25 (s, 1H), 8.88 (s, 1H), 8.85 (s, 1H), 8.07-8.05 (d, 1H), 7.61-7.57 (m, 1H), 7.33-7.24 (m, 3H), 4.49 (s, 2H), 3.67 (s, 2H).

Example 18. Synthesis of compound methyl 2-(5-((2-(2,6-difluorophenyl)-5-oxo-6,7-dihydro-5H-pyrrolo[3,4-d]pyrimidin-4-yl)amino)pyridin-2-yl)acetate I-18

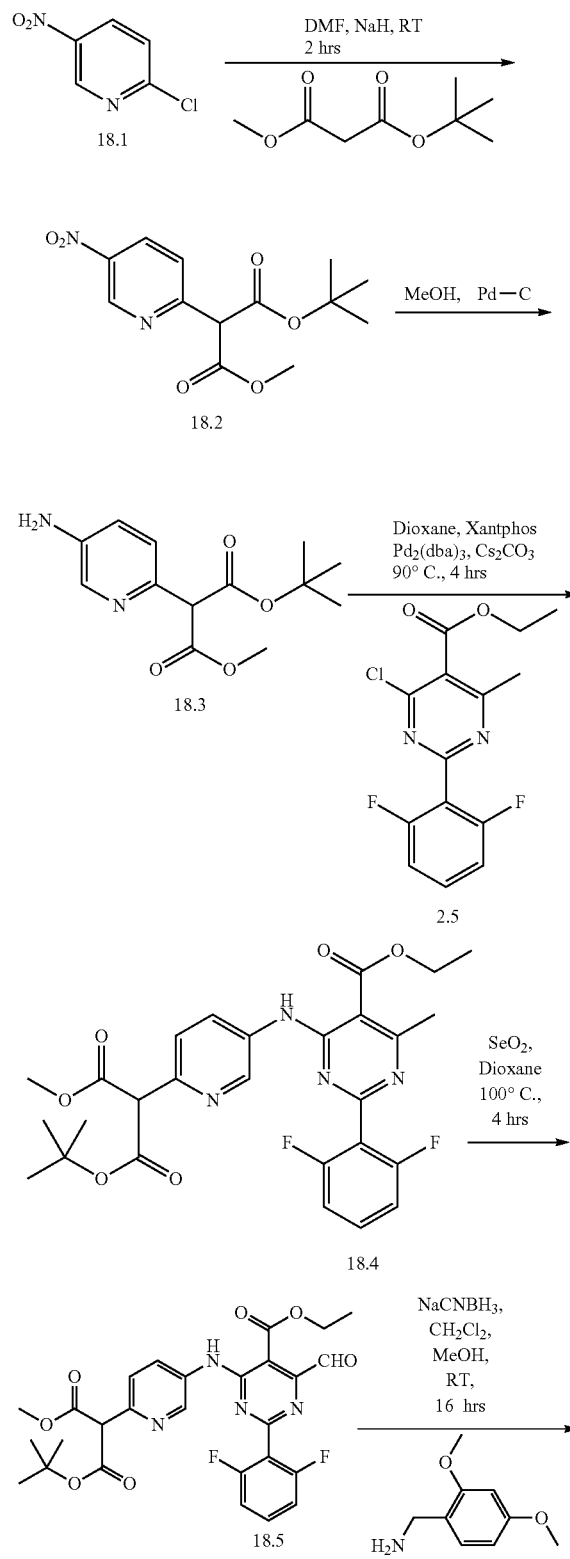

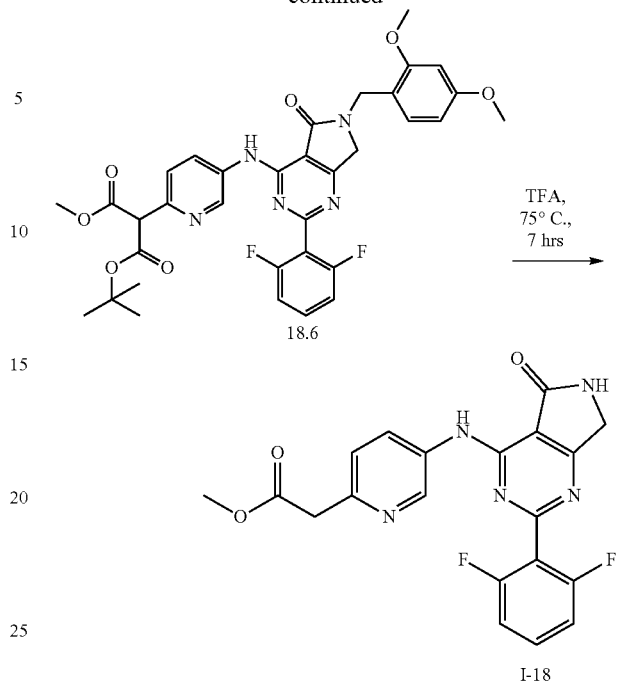

Synthesis of Compound 18.2.

To a solution of compound 18.1 (2.5 g, 15.8 mmol, 1.00 equiv) in dry DMF (25 mL) at 0° C., was added sodium hydride (60% suspension in mineral oil) (1.45 g, 36.2 mmol, 2.3 eq.) and the suspension was stirred at room temperature for 30 minutes. Tert-butyl methyl malonate (3.3 g, 18.9 mmol, 1.2 equiv.) was added dropwise to the above reaction mixture at 0° C. The reaction mixture was stirred at same temperature for 2 hours. The mixture was poured into water and extracted with ethyl acetate (100 mL×3). The combined organic layers were washed with water and brine. Then dried over sodium sulfate and the solvent was removed under reduced pressure. The crude material was purified by column chromatography to furnish compound 18.2 (2.4 g, 51%). MS (ES) m/z=297 [M+H]$^+$.

Synthesis of Compound 18.3.

To a suspension of Pd—C (250 mg, 10 mol %) in methanol was added 18.2 (2.4 g, 8.1 mmol, 1.0 equiv) at room temperature under a nitrogen atmosphere. Hydrogen gas was bubbled through the reaction mixture until the completion of the reaction. After completion of the reaction, the mixture was filtered through Celite and washed with methanol. The solvent was removed under reduced pressure to afford compound 18.3 (2.05 g, 95%). MS (ES) m/z=267 [M+H]$^+$.

Synthesis of Compound 18.4.

To a solution of ethyl 4-chloro-2-(2, 6-difluorophenyl)-6-methylpyrimidine-5-carboxylate (0.26 g, 0.8 mmol, 1.0 eq.), in dioxane (5 mL) was added 4,5-bis(diphenylphosphino)-9,9-dimethyl xanthene (97.0 mg, 0.16 mmol, 0.2 eq.), tris(dibenzylidene acetone)dipalladium (0) (76 mg, 0.08 mmol, 0.1 eq.), cesium carbonate (0.4 g, 1.2 mmol, 1.5 eq.), and compound 18.3 (0.22 g, 0.8 mmol, 1.0 eq.) under an argon atmosphere. The mixture was degassed under argon for 15 minutes. The reaction mixture was heated to 90° C. for 4 hrs. After completion of the reaction mixture was diluted with ethyl acetate (100 mL) at room temperature and filtered through Celite. The organic layers were washed with water and brine solution then dried over sodium sulfate and the solvent was removed under reduced pressure. The crude material was purified by column chromatography to provide compound 18.4 (240 mg, 53%). MS (ES) m/z=543 [M+H]⁺.

Synthesis of Compound 18.5.

A solution of compound 18.4 (0.3 g, 0.55 mmol, 1.0 eq.), selenium dioxide (0.12 g, 1.1 mmol, 2.0 eq.) in 1,4-dioxane (5 mL) was heated at 100° C. for 3 hrs. After completion of the reaction mixture was filtered and filtrate was concentrated under reduced pressure to provide crude 18.5 (0.3 g), which was used as such for the next step without further purification.

Synthesis of Compound 18.6.

To a solution of 18.5 (1.2 g, 2.1 mmol, 1.0 eq.) in dichloromethane (10.0 mL) and methanol (5.0 mL) was added 2,4-dimethoxy benzylamine (0.36 g, 2.1 mmol, 1.0 eq.). The reaction was stirred at room temperature for 30 minutes. Sodium cyanoborohydride (0.4 g, 6.4 mmol, 3.0 eq.) was added to the above reaction mixture at 0° C. The reaction mixture was allowed to warm at room temperature and stirred for overnight. After completion, reaction mixture was concentrated under high vacuum. Obtained residue was poured in water (25 mL) and product was extracted with ethyl acetate (100 mL×3). Organic layer was washed with brine, dried over sodium sulphate and concentrated under reduced pressure to get crude material which was purified by column chromatography using 30% ethyl acetate in hexane as mobile phase to afford compound 18.6 (430 mg, 30%). MS (ES): m/z=662 [M+H]⁺.

Synthesis of Compound I-18.

A solution of compound 18.6 (0.43 g, 0.6 mmol, 1.0 eq.) in trifluoroacetic acid (4.3 mL) was heated at 80° C. for 7 hours. Upon completion of the reaction, the solvent was removed under reduced pressure. The residue obtained was diluted with ethyl acetate (200 mL) and washed with saturated sodium bicarbonate solution. The organic layers were dried over sodium sulfate and concentrated under reduce pressure. The crude product was purified by flash column chromatography to afford I-18 (180 mg, 67%). MS (ES): m/z 412 [M+H]⁺, ¹H NMR (400 MHz, DMSO-d₆): δ 9.30 (s, 1H), 8.90 (d, 2H). 8.14-8.11 (dd, 1H), 7.62-7.58 (m, 1H), 7.39-7.36 (d, 1H), 7.28-7.24 (t, 2H) 4.49 (s, 2H), 3.83 (s, 2H), 3.62 (s, 3H).

Example 19. Synthesis of compound 2-(5-((2-(2,6-difluorophenyl)-5-oxo-6,7-dihydro-5H-pyrrolo[3,4-d]pyrimidin-4-yl)amino)pyridin-2-yl)-N-(piperidin-4-yl)acetamide I-19

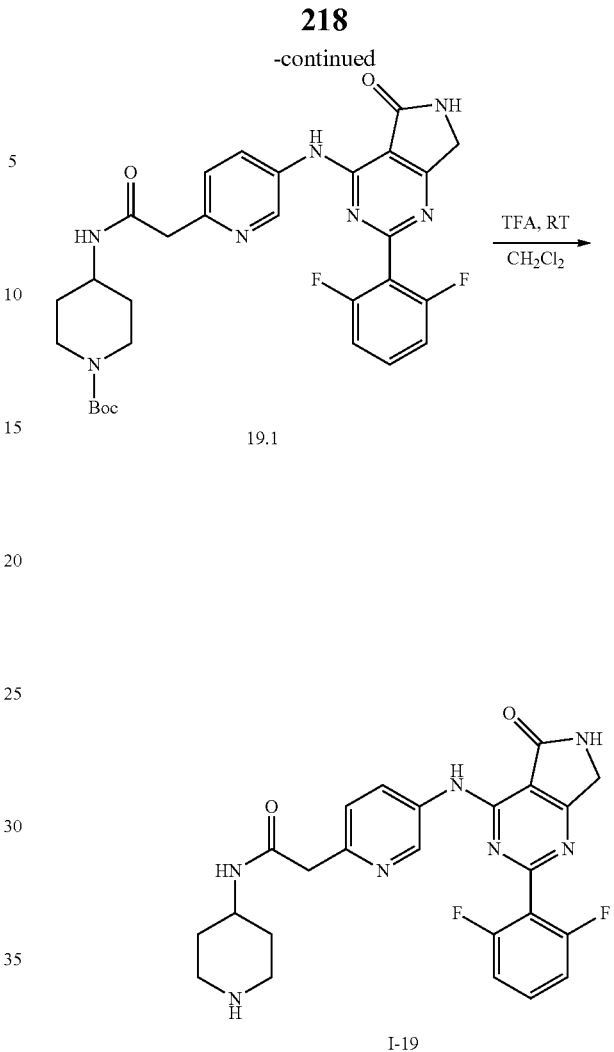

Compound I-19 was synthesized in 85% yield from compound I-19 using the same procedure described in Example 11. MS (ES): m/z 480 [M+H]⁺ ¹H NMR (400 MHz, DMSO-d₆): δ 9.24 (s, 1H), 8.88 (s, 1H). 8.84-8.83 (d, 1H), 8.11-8.09 (d, 1H), 8.05-8.02 (dd, 1H), 7.61-7.57 (m 1H), 7.30-7.24 (m, 3H), 4.49 (s, 2H), 3.66-3.63 (t, 1H), 3.55 (s, 2H), 3.02-2.99 (d, 2H), 2.64-2.58 (t, 2H), 1.74-1.71 (d, 2H), 1.37-1.32 (m, 2H).

Example 20. Synthesis of 2-(4-((2-(2-chlorophenyl)-5-oxo-6,7-dihydro-5H-pyrrolo[3,4-d]pyrimidin-4-yl)amino)phenyl)-N-ethylacetamide I-20

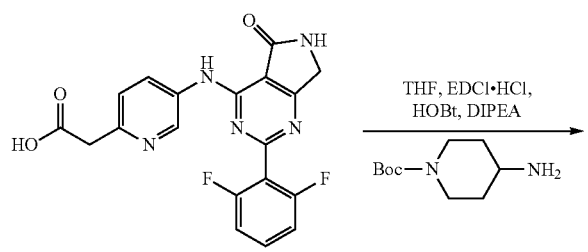

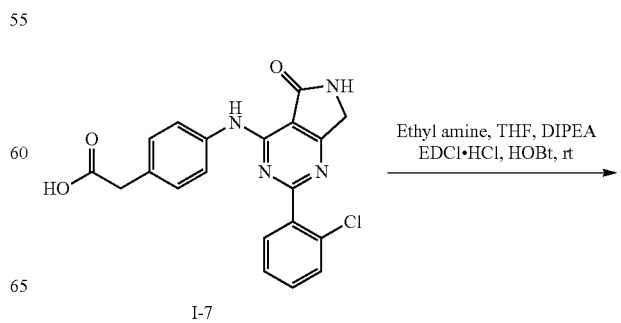

-continued

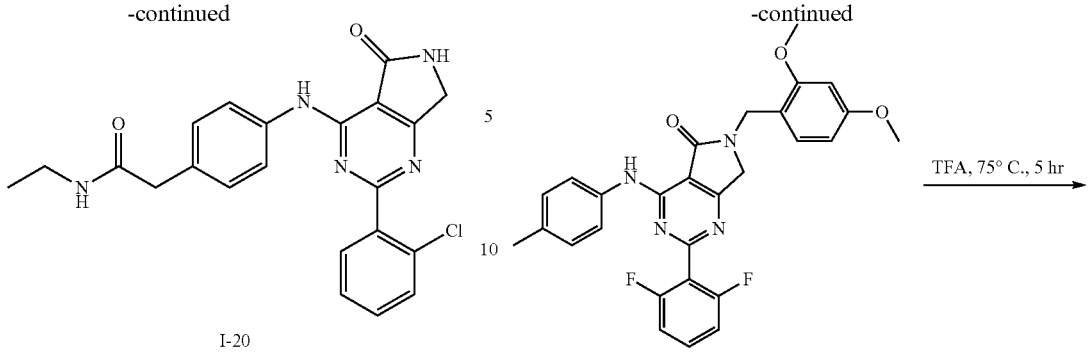

I-20

Compound I-20 was synthesized from compound I-7 in 63% yield using protocol described in Example 8. MS (ES): m/z 422 [M+H]$^+$, $^1$H NMR (400 MHz, DMSO-d$_6$): δ 9.00 (s, 1H), 8.85 (s, 1H), 8.01-8.00 (d, 1H), 7.75-7.73 (d, 3H), 7.61-7.59 (d, 1H), 7.53-7.45 (m, 2H), 7.23-7.21 (d, 2H) 4.46 (s, 2H), 3.65 (s, 2H), 3.06-3.03 (q, 2H), 1.02-0.98 (t, 3H).

Example 21. Synthesis of 2-(2,6-difluorophenyl)-4-(p-tolylamino)-6,7-dihydro-5H-pyrrolo[3,4-d]pyrimidin-5-one, I-21

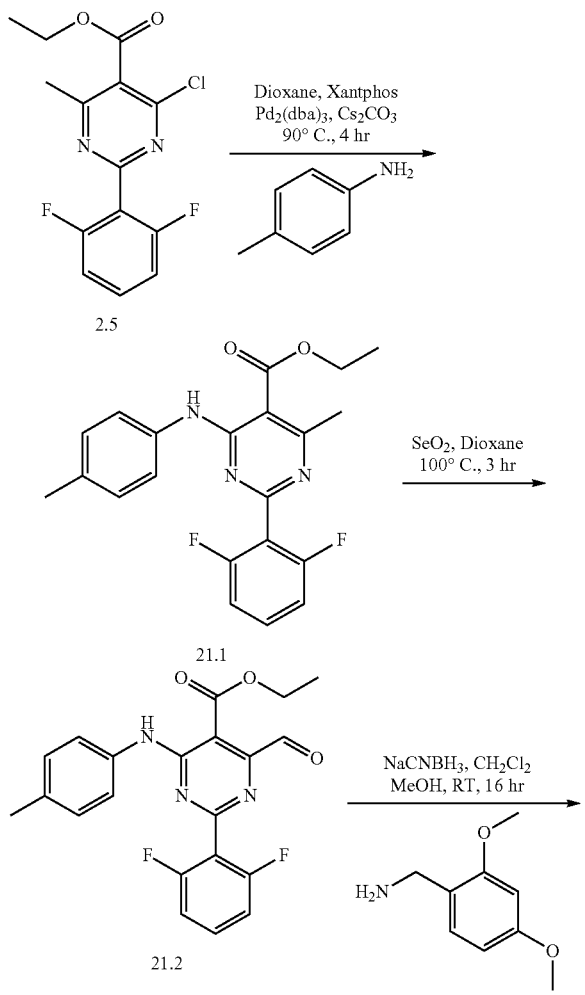

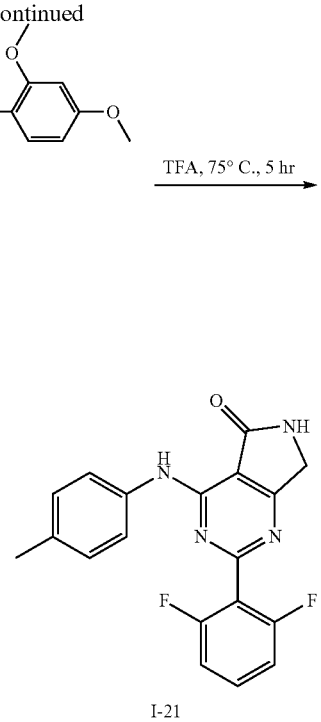

I-21

Synthesis of Compound 21.1.

To a solution of compound 2.5 (0.2 g, 0.64 mmol, 1.0 eq.) in dioxane (5 mL) was added 4,5-Bis(diphenylphosphino)-9,9-dimethyl xanthene (74.0 mg, 0.12 mmol, 0.2 eq.), tris(dibenzylidene acetone) dipalladium(0) (58 mg, 0.064 mmol, 0.1 eq.), cesium carbonate (0.31 g, 0.96 mmol, 1.5 eq.), and 4-methylaniline (75 mg, 0.7 mmol, 1.1 eq.) under an argon atmosphere. The mixture was degassed under argon for 15 minutes. The reaction mixture was heated at 90° C. for 4 hours. Upon completion of the reaction, the mixture was diluted with ethyl acetate (100 mL) at room temperature and filtered through Celite. The organic layers were washed with water and brine then dried over sodium sulfate and concentrated under reduced pressure. The resulting crude product was purified by column chromatography afford pure 21.1 (70 mg, 29%). MS (ES) m/z=384 [M+H]$^+$.

Synthesis of Compound 21.2.

A solution of compound 21.1 (70 mg, 0.18 mmol, 1.0 eq.), selenium dioxide (41 mg, 0.36 mmol, 2.0 eq.) in 1,4-dioxane (1.5 mL) was heated at 100° C. for 3 hours. After completion of the reaction mixture was filtered through and filtrate was concentrated under reduced pressure to get crude 21.2 (7 mg, 96%), which was used as such for the next step without further purification.

Synthesis of Compound 21.3.

To a solution of compound 21.2 (70 mg, 0.17 mmol, 1.0 eq.) in dichloromethane (2.0 mL) and methanol (1.0 mL) was added 2,4-dimethoxybenzylamine (32 mg, 0.19 mmol, 1.1 eq.) and stirred at room temperature for 30 minutes. Sodium cyanoborohydride (32 mg, 0.51 mmol, 3.0 eq.) was added to the above reaction mixture at 0° C. The reaction mixture was allowed to warm at room temperature and stirred for overnight. Upon completion, the mixture was concentrated under high vacuum. The residue obtained was poured into water (20 mL) and product was extracted with ethyl acetate (40 mL×3). The organic layers were washed with brine, dried over sodium sulfate, and concentrated under reduced pressure to give the crude material which was purified by column chromatography to afford compound 21.3 as a yellow solid (39 mg, 44%). MS (ES): m/z=503 [M+H]⁺.

Synthesis of Compound I-21.

A solution of 21.3 (39 mg, 0.08 mmol, 1.0 eq.) in trifluoroacetic acid (0.5 mL) was heated at 80° C. for 5 hours. Upon completion of the reaction, the mixture was concentrated under reduced pressure. The residue obtained was diluted with ethyl acetate (50 mL) and washed with saturated sodium bicarbonate solution. The organic layers were dried over sodium sulfate and concentrated under reduce pressure to give the crude material, which was purified by flash column chromatography to afford I-21 (25 mg, 91%); MS (ES): m/z 352 [M+H]⁺, ¹H NMR (400 MHz, DMSO-d₆): δ 9.00 (s, 1H), 8.86 (s, 1H). 7.62-7.55 (m, 3H), 7.29-7.23 (m, 2H), 7.17-7.15 (d, 2H), 4.47 (s, 2H), 2.33 (s, 3H).

Example 22. Synthesis of 2-(4-((2-(2,6-difluorophenyl)-5-oxo-6,7-dihydro-5H-pyrrolo[3,4-d]pyrimidin-4-yl)amino)phenyl)-N-methyl-N-(piperidin-4-yl)acetamide I-22

Example 23. Synthesis of 2-(5-((2-(2,6-difluorophenyl)-5-oxo-6,7-dihydro-5H-pyrrolo[3,4-d]pyrimidin-4-yl)amino)pyridin-2-yl)-N-ethylacetamide I-23

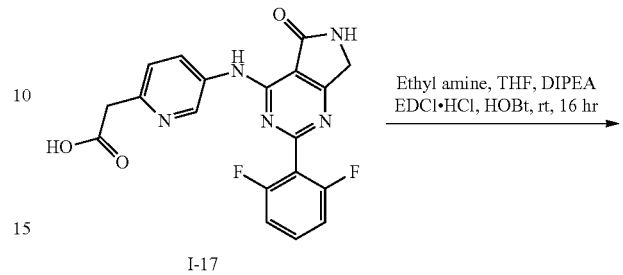

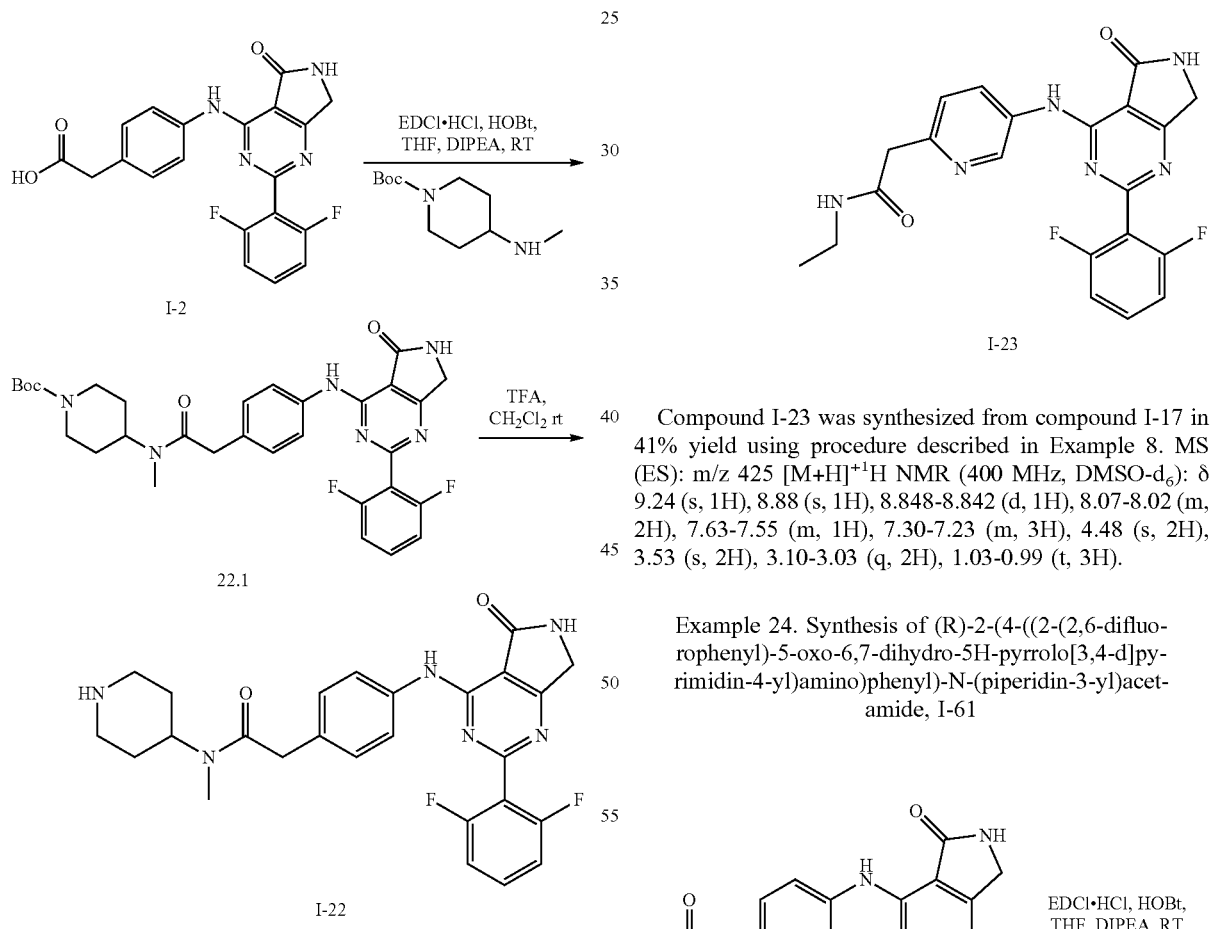

Compound I-23 was synthesized from compound I-17 in 41% yield using procedure described in Example 8. MS (ES): m/z 425 [M+H]⁺¹H NMR (400 MHz, DMSO-d₆): δ 9.24 (s, 1H), 8.88 (s, 1H), 8.848-8.842 (d, 1H), 8.07-8.02 (m, 2H), 7.63-7.55 (m, 1H), 7.30-7.23 (m, 3H), 4.48 (s, 2H), 3.53 (s, 2H), 3.10-3.03 (q, 2H), 1.03-0.99 (t, 3H).

Example 24. Synthesis of (R)-2-(4-((2-(2,6-difluorophenyl)-5-oxo-6,7-dihydro-5H-pyrrolo[3,4-d]pyrimidin-4-yl)amino)phenyl)-N-(piperidin-3-yl)acetamide, I-61

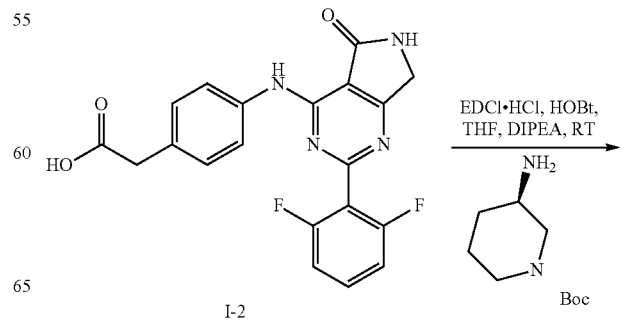

Compound I-22 was synthesized in 94% yield from compound I-2 using protocol described in Example 11. MS (ES): m/z 493 [M+H]⁺ ¹H NMR (400 MHz, DMSO-d₆): δ 9.05 (s, 1H), 8.89 (s, 1H), 7.69-7.67 (d, 1H), 7.62-7.56 (m, 1H), 7.28-7.17 (m, 4H), 4.47 (s, 2H), 3.65 (s, 2H), 3.17-3.07 (m, 2H), 2.89-2.73 (m, 5H), 1.68-1.61 (m, 2H), 1.52-1.40 (m, 2H).

223
-continued

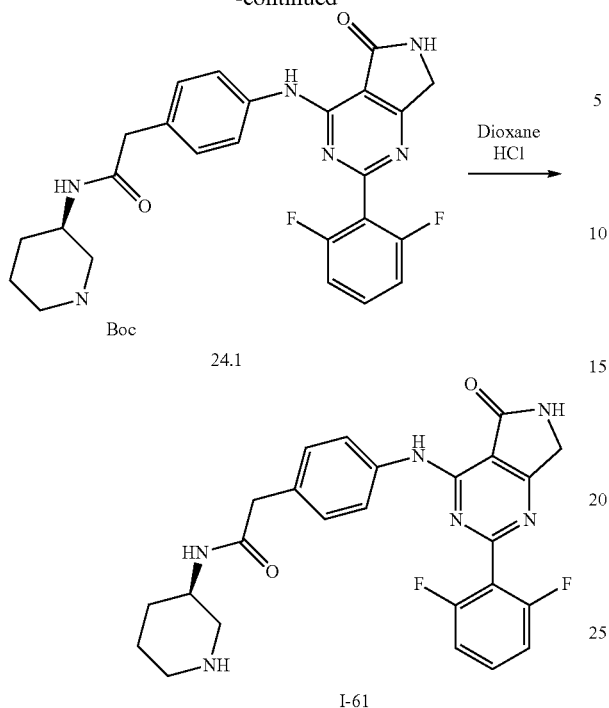

24.1

I-61

Synthesis of Compound 24.1

To a solution of compound I-2 (0.15 g, 0.378 mmol, 1.0 eq.) in dry THF (2 mL) at 0-5° C., was added 1-ethyl-3-(3-dimethylaminopropyl)-carbodiimide (0.108 g, 0.568 mmol, 1.5 eq.), 1-hydroxybenzotriazole (0.61 g, 0.453 mmol, 1.2 eq.) and the solution was stirred for 20 minutes. To the above reaction mixture was added tert-butyl (R)-3-aminopiperidine-1-carboxylate (0.113 g, 0.567 mmol, 1.5 eq.) and diisopropylethylamine (0.32 mL, 1.89 mmol, 5.0 eq.) at 0-5° C. The reaction mixture was allowed to warm to room temperature and stirred for 24 hours. Upon completion of reaction, the mixture was poured into ice cold water and extracted using ethyl acetate. The organic layers were washed with brine, dried over sodium sulfate, and concentrated under reduced pressure. The crude material was purified by column chromatography to afford compound 24.1 (0.087 g, 39%). MS (ES): m/z 579 [M+H]$^+$.

Synthesis of Compound I-61

To a solution of compound 24.1 (0.087 vg, 0.150 mmol, 1.0 eq.) in 1,4-dioxane (1.0 mL) was added dioxane-HCl (2 mL) at 0° C. The reaction mixture was allowed to warm at room temperature and stirred for 30 minutes. After completion of the reaction, mixture was concentrated under high vacuum. The crude salt obtained was dissolved in methanol (3.0 mL) and tetra-alkylammoniumcarbonate (polymer supported) was added until a neutral pH was obtained. The reaction mixture was filtered through a glass frit and the solvent was removed under reduced pressure at 45° C. to afford pure I-61 (0.070 g, 97%). MS (ES): m/z 479.26 [M+H]$^+$, $^1$H NMR (400 MHz, DMSO-d$_6$): δ 9.05 (s, 1H), 8.9 (s, 1H), 8.10-8.08 (d, 1H), 7.66-7.64 (d, 2H), 7.29-7.21 (m 4H), 4.47 (s, 2H), 3.67-3.43 (bs, 1H), 3.41-3.39 (s, 2H), 2.98-2.60 (m, 2H), 2.43-2.4 (m, 1H), 1.74-1.66 (m, 2H), 1.47-1.36 (m, 2H), 1.17-1.14 (m, 1H), 1.16-1.11 (m, 1H), 1.09-1.07 (d, 1H).

224

Example 25. Synthesis of 2-(2,6-difluorophenyl)-4-((4-(2-oxo-2-(2-oxa-6-azaspiro[3.3]heptan-6-yl)ethyl)phenyl)amino)-6,7-dihydro-5H-pyrrolo[3,4-d]pyrimidin-5-one I-62

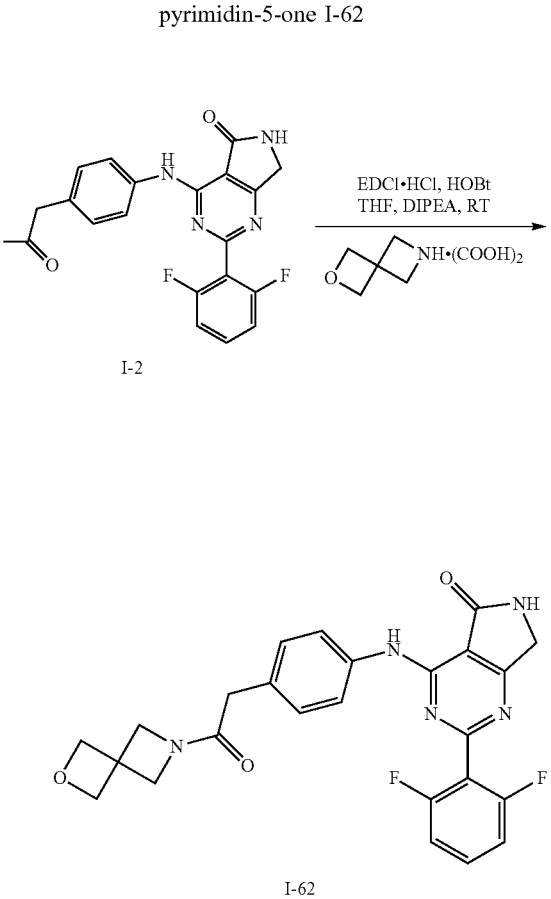

I-2

I-62

Compound I-62 was synthesized from compound I-2 in 37% yield using procedure described in Example 8. MS (ES): m/z 478.16 [M+H]$^+$, %, $^1$H NMR (400 MHz, DMSO-d$_6$): δ 9.05 (s, 1H), 8.88 (s, 1H), 7.67-7.65 (d, 2H), 7.61-7.58 (m, 1H), 7.28-7.24 (t, 2H), 7.20-7.18 (d, 2H), 4.66-4.64 (m, 4H), 4.47 (s, 2H), 4.33 (s, 2H), 4.0 (s, 2H), 3.34 (s, 2H).

Example 26. Synthesis of (R)-2-(4-((2-(2,6-difluorophenyl)-5-oxo-6,7-dihydro-5H-pyrrolo[3,4-d]pyrimidin-4-yl)amino)phenyl)-N-(1-hydroxypropan-2-yl)acetamide I-63

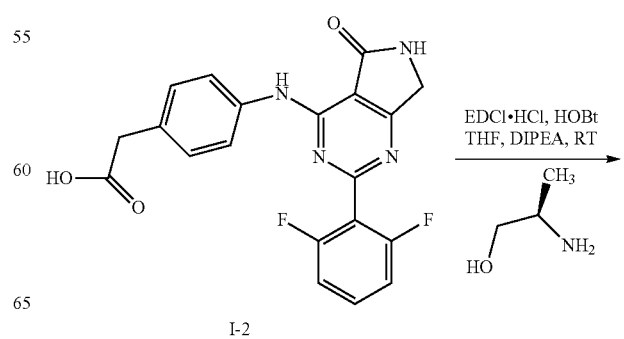

I-2

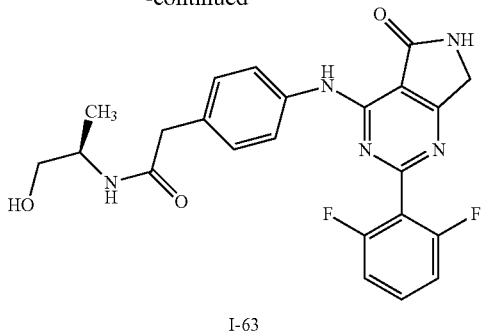

I-63

Compound I-63 was prepared from compound I-2 in 47% yield using protocol described in Example 8. MS (ES): m/z 454.21 [M+H]$^+$, $^1$H NMR (400 MHz, DMSO-d$_6$): δ 9.04 (s, 1H), 8.87 (s, 1H), 7.83-7.81 (d, 1H), 7.66-7.64 (d, 2H), 7.59-7.57 (m, 1H), 7.28-7.20 (m, 4H), 4.66 (s, 1H), 4.47 (s, 2H), 3.74-3.70 (m, 1H), 3.35-3.31 (m, 2H), 3.23-3.21 (m, 1H), 1.02-1.00 (d, 3H).

Example 27. Synthesis of (S)-2-(2,6-difluorophenyl)-4-((4-(2-(3-methylmorpholino)-2-oxoethyl)phenyl)amino)-6,7-dihydro-5H-pyrrolo[3,4-d]pyrimidin-5-one, I-64

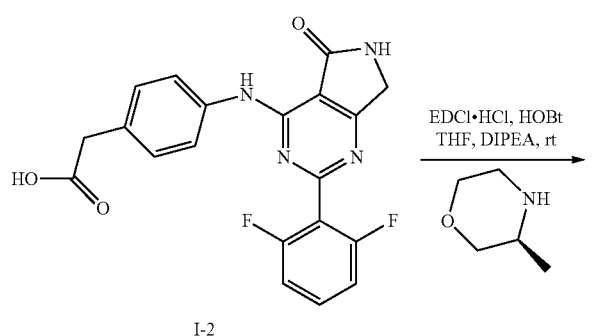

I-64

Compound I-64 was prepared in 37% yield from compound I-2 using protocol described in Example 8. MS (ES): m/z 480.21 [M+H]$^+$, $^1$H NMR (400 MHz, DMSO-d$_6$): δ 9.05 (s, 1H), 8.88 (s, 1H), 7.69-7.67 (d, 2H), 7.63-7.56 (m, 1H), 7.28-7.17 (m, 4H), 4.47 (s, 2H), 4.36 (bs, 1H), 4.06-4.02 (d, 1H), 3.81-3.74 (m, 2H), 3.64 (s, 2H), 3.41-3.38 (d, 1H), 3.24-3.22 (d, 2H), 1.12-1.08 (m, 3H).

Example 28. Synthesis of 2-(4-((2-(2,6-difluorophenyl)-5-oxo-6,7-dihydro-5H-pyrrolo[3,4-d]pyrimidin-4-yl)amino)phenyl)-N-(tetrahydro-2H-pyran-4-yl)acetamide, I-65

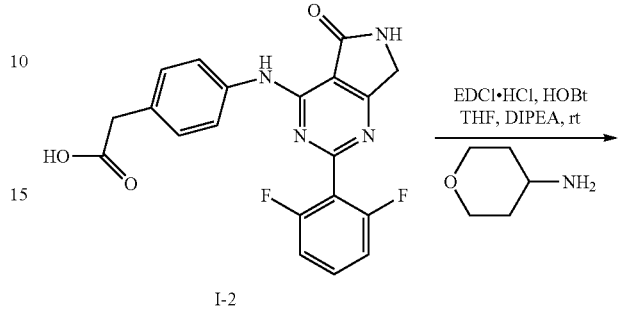

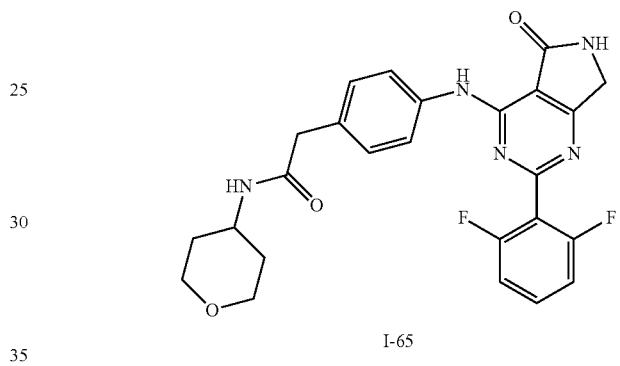

I-65

Compound I-65 was prepared in 37% yield from compound I-2 using protocol described in Example 8. MS (ES): m/z 480.16 [M+H]$^+$ $^1$H NMR (400 MHz, DMSO-d$_6$): δ 9.04 (s, 1H), 8.88 (s, 1H), 8.04 (s, 1H), 7.66 (bs, 2H), 7.60-7.59 (m, 1H), 7.33-7.23 (m, 3H), 4.47 (s, 2H), 3.81-3.79 (d, 2H), 3.72 (bs, 1H), 3.34-3.33 (m, 3H), 1.69-1.66 (d, 2H), 1.38 (bs, 2H).

Example 29. Synthesis of 2-(2,6-difluorophenyl)-4-((4-(2-morpholino-2-oxoethyl)phenyl)amino)-6,7-dihydro-5H-pyrrolo[3,4-d]pyrimidin-5-one, I-66

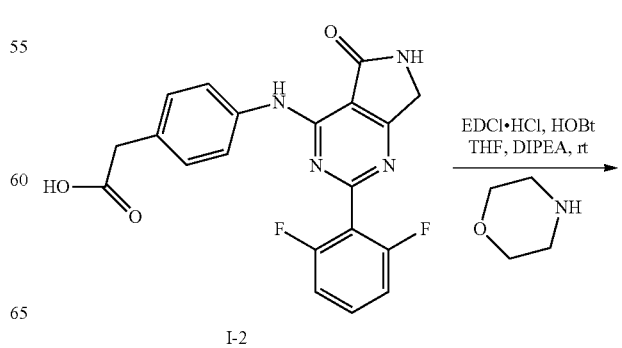

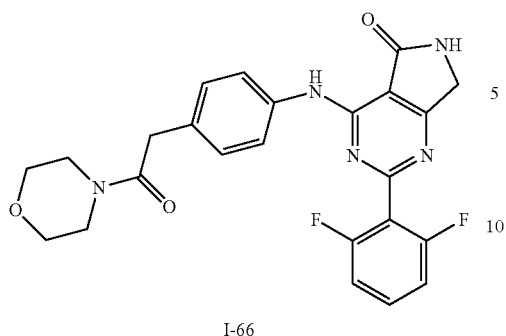

I-66

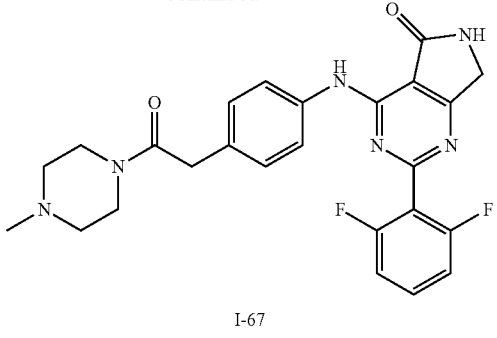

I-67

Compound I-66 was prepared from compound I-2 in 34% yield using protocol described in Example 8. MS (ES): m/z 466.2 [M+H]+ 1H NMR (400 MHz, DMSO-d6): δ 9.05 (s, 1H), 8.88 (s, 1H). 7.69-7.67 (d, 2H), 7.62-7.57 (m, 1H), 7.29-7.26 (m, 2H), 7.21-7.19 (d, 2H), 4.47 (s, 2H), 3.67 (s, 2H), 3.53-3.42 (m, 8H).

Compound I-67 was synthesized from compound I-2 in 44% yield using procedures described in Example 8. MS (ES): m/z 479.2 [M+H]+ 1H NMR (400 MHz, DMSO-d6): δ 9.05 (s, 1H), 8.89 (s, 1H). 7.68-7.66 (d, 2H), 7.63-7.57 (m, 1H), 7.28-7.24 (m, 2H), 7.20-7.18 (d, 2H), 4.47 (s, 2H), 3.66 (s, 2H), 3.46 (bs, 4H), 2.23 (bs, 4H), 2.15 (s, 3H).

Example 30. Synthesis of 2-(2,6-difluorophenyl)-4-((4-(2-(4-methylpiperazin-1-yl)-2-oxoethyl)phenyl)amino)-6,7-dihydro-5H-pyrrolo[3,4-d]pyrimidin-5-one, I-67

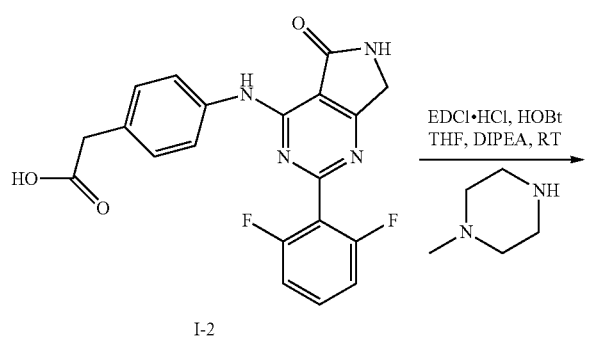

I-2

Example 31. Synthesis of Synthesis of 2-(4-((2-(2,6-difluorophenyl)-5-oxo-6,7-dihydro-5H-pyrrolo[3,4-d]pyrimidin-4-yl)amino)-1H-pyrazol-1-yl)acetic Acid, I-71

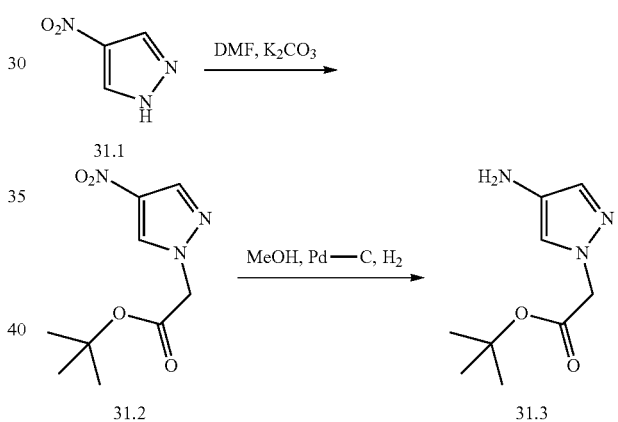

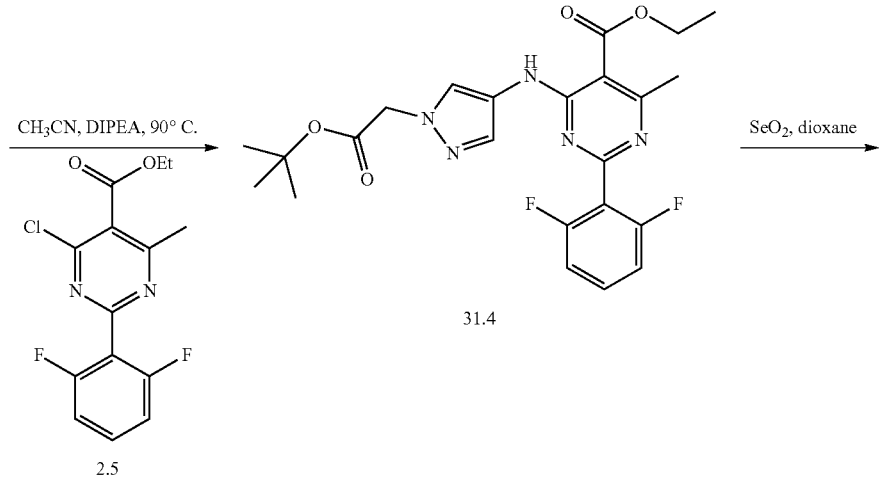

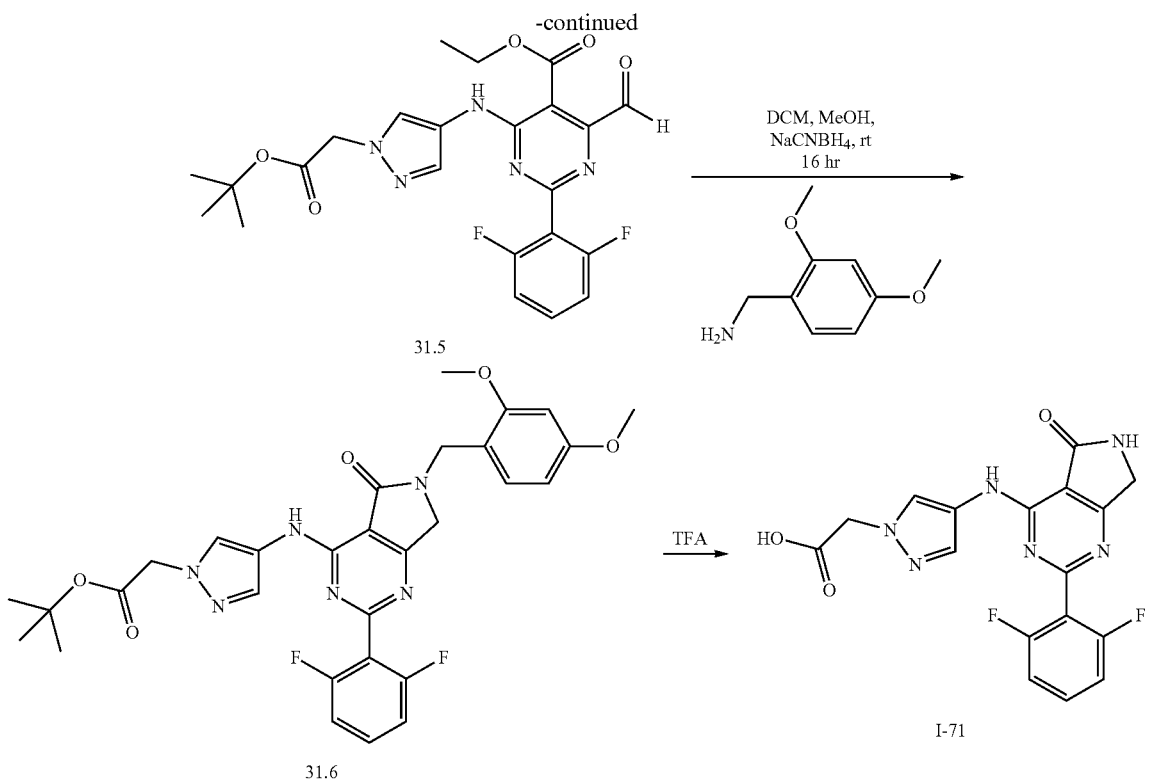

Synthesis of Compound 31.2.

To a solution of 31.1 (2 g, 17.68 mmol, 1.0 equiv), in DMF (20 mL) was added potassium carbonate (4.88 g, 35.37 mmol, 2.0 equiv) and tert-butyl bromoacetate (4.14 g, 21.22 mmol, 1.2 equiv). Reaction mixture was stirred at room temperature for 3 hours. After completion, reaction mixture was poured in water and product was extracted with ethyl acetate. Organic layer was dried over sodium sulfate and concentrated under reduced pressure to obtain crude material, which resulted in pure compound 31.2 (4 g, 99.5%).

Synthesis of Compound 31.3.

To a solution of 31.2 (2.5 g, 11.16 mmol, 1.0 equiv) in methanol (30 mL) was added 10% Pd/C (0.2 g, 10% w/w), Reaction mixture was bubbled under hydrogen gas for 3 h. After consumption of the starting material, the mixture was filtered over a Celite bed. The filtrate was concentrated under reduced pressure to yield crude material, which was purified by column chromatography to furnish 31.3 (2 g, 92.2%). MS (ES): m/z 197.9 [M+H]$^+$.

Synthesis of Compound 31.4.

To a solution of ethyl 4-chloro-2-(2,6-difluorophenyl)-6-methylpyrimidine-5-carboxylate, 2.5 (0.5 g, 1.60 mmol, 1.0 equiv), in acetonitrile (7 mL) was added diisopropylethylamine (0.82 mL, 4.80 mmol, 3.0 equiv) and tert-butyl 2-(4-amino-1H-pyrazol-1-yl)acetate (0.284 g, 1.44 mmol, 0.9 equiv). The mixture was heated at 100° C. for 15 hours. After completion, reaction mixture was concentrated under reduced pressure and reaction mixture was poured in water and product was extracted with ethyl acetate. Organic layer was dried over sodium sulfate and concentrated under reduced pressure to obtain crude material, which was purified by column chromatography to furnish compound 31.4 (0.550 g, 72.65%). MS (ES): m/z 474.2 [M+H]$^+$.

Synthesis of Compound 31.5.

A solution of compound 31.4 (0.550 g, 1.160 mmol, 1.0 equiv) and selenium dioxide (0.257 g, 2.320 mmol, 2.0 equiv) in 1,4-dioxane (5 mL) was heated at 90° C. until starting material was consumed. The mixture was filtered through Celite and obtained filtrate was concentrated under reduced pressure to get crude 31.5 (0.540 g), which was used as such for the next step.

Synthesis of Compound 31.6.

To a solution of compound 31.5 (0.550 g, 1.127 mmol, 1.0 equiv) in dichloromethane (3 mL) and methanol (1.5 mL) was added 2,4-dimethoxy benzyl amine (0.206 g, 1.239 mmol, 1.1 equiv) and stirred at room temperature for 30 min. Sodium cyanoborohydride (0.212 g, 3.381 mmol, 3.0 equiv) was added at 0° C. and reaction was stirred overnight. Upon completion, the mixture was poured into water and product was extracted twice with ethyl acetate. Organic layer was dried over sodium sulfate and concentrated under reduced pressure to get crude material, which was purified by column chromatography to furnish compound 31.6 (0.350 g, 52.4%). MS (ES): m/z 593.24 [M+H]$^+$.

Synthesis of Compound I-71.

A solution of compound 31.6 (0.350 g, 0.590 mmol, 1.0 equiv) in trifluoroacetic acid (3.0 mL) was heated at 70° C. for 5 hours. After completion, reaction mixture was concentrated, residue was triturated with diethyl ether to get solid compound, which was further washed with pentanes. Resulting solid was dried in vacuo to furnish 2-(4-((2-(2,6-difluorophenyl)-5-oxo-6,7-dihydro-5H-pyrrolo[3,4-d]pyrimidin-4-yl)amino)-1H-pyrazol-1-yl)acetic acid, compound I-71 (0.125 g, 50.40%). MS (ES): m/z 387.1 [M+H]$^{+1}$H NMR (400 MHz, DMSO-d$_6$): δ 13.02 (s, 1H), 9.29 (s, 1H), 8.74 (s, 1H), 8.05 (s, 1H), 7.85 (s, 1H), 7.63-7.57 (m, 1H), 7.28-7.24 (t, 2H), 4.91 (s, 2H), 4.44 (s, 2H).

Example 32. Synthesis of (S)-2-(2,6-difluorophenyl)-4-((1-(2-(2-(hydroxymethyl)pyrrolidin-1-yl)-2-oxoethyl)-1H-pyrazol-4-yl)amino)-6,7-dihydro-5H-pyrrolo[3,4-d]pyrimidin-5-one, I-68

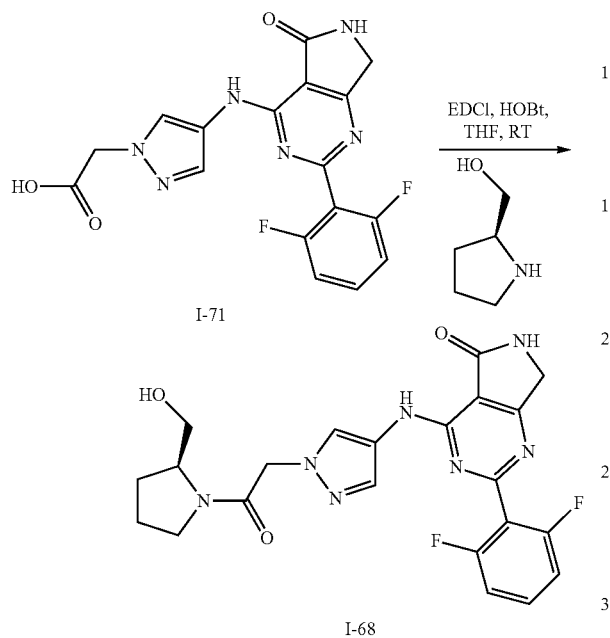

Example 33. Synthesis of 2-(4-((2-(2,6-difluorophenyl)-5-oxo-6,7-dihydro-5H-pyrrolo[3,4-d]pyrimidin-4-yl)amino)-1H-pyrazol-1-yl)-N-ethylacetamide, I-69

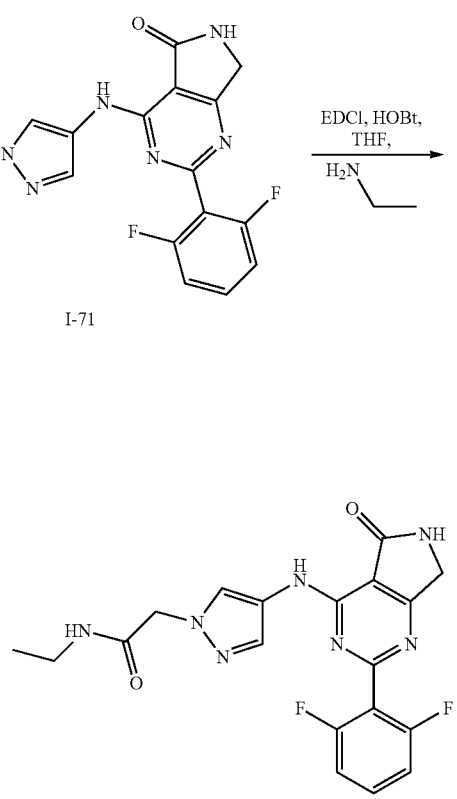

Synthesis of Compound I-68.

To a solution of 1 (0.050 g, 0.129 mmol, 1 equiv) in dry THF (2 ml) was added 1-Ethyl-3-(3 dimethylaminopropyl)-carbodiimide (0.037 g, 0.1942 mmol, 1.5 eq), hydroxybenzotriazole (0.023 g, 0.155 mmol, 1.2 equiv). Reaction mixture was stirred at room temperature for 1 hour. To the above reaction mixture was added (S)-pyrrolidin-2-ylmethanol (0.017 g, 0.168 mmol, 1.3 equiv) and di-isopropyl ethyl amine (0.066 g, 0.518 mmol, 4 equiv) at room temperature. Reaction mixture was stirred for 24 hours at room temperature. After completion of reaction, reaction mixture was poured into ice cold water and extracted using ethyl acetate. Organic layer was washed with aq. sodium bicarbonate solution followed by brine solution. Organic layer was dried over sodium sulfate and concentrated under reduced pressure. The crude material was purified by column chromatography to furnish (S)-2-(2,6-difluorophenyl)-4-((1-(2-(2-(hydroxymethyl)pyrrolidin-1-yl)-2-oxoethyl)-1H-pyrazol-4-yl)amino)-6,7-dihydro-5H-pyrrolo[3,4-d]pyrimidin-5-one, compound I-68. MS (ES): m/z 470.1[M+H]$^+$, 1H NMR (400 MHz, DMSO-d$_6$): δ 9.28 (s, 1H), 8.75 (s, 1H), 7.99-7.57 (d, 1H), 7.83-7.82 (d, 1H), 7.63-7.56 (m, 1H), 7.28-7.24 (t, 2H), 5.08-5.07 (d, 1H), 4.97-4.96 (d, 2H), 4.72 (bs, 1H), 4.73 (s, 2H), 4.07-4.05 (d, 1H), 3.91 (bs, 1H), 3.45-3.42 (m, 2H), 3.30-3.28 (m, 1H), 1.94-1.80 (m, 4H).

Compound I-69 was prepared from compound I-71 in 18% yield using protocol described in Example 32. MS (ES): m/z 414.1[M+H]$^+$ $^1$H NMR (400 MHz, DMSO-d$_6$): δ 9.29 (s, 1H), 8.75 (s, 1H), 8.07-8.04 (m, 1H), 7.84 (s, 1H), 7.59 (bs, 1H), 7.26 (bs, 2H), 4.69 (s, 2H), 4.43 (s, 2H), 3.9-3.6 (m, 2H), 3.07 (bs, 2H), 1.00 (t, 3H).

Example 34. Synthesis of (R)-2-(4-((2-(2,6-difluorophenyl)-5-oxo-6,7-dihydro-5H-pyrrolo[3,4-d]pyrimidin-4-yl)amino)-1H-pyrazol-1-yl)-N-(1-hydroxypropan-2-yl)acetamide, I-70

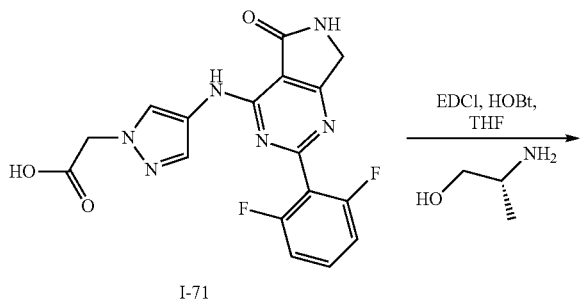

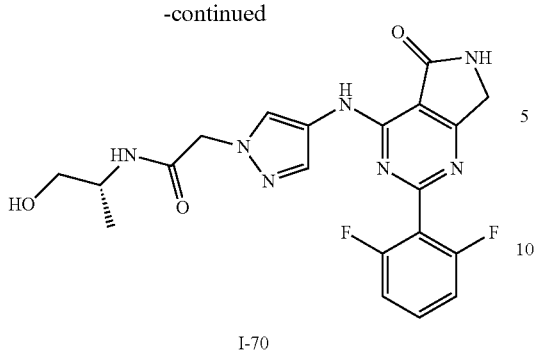

I-70

Compound I-70 was prepared from compound I-71 in 17.4% yield using procedure described in Example 32. MS (ES): m/z 444.1[M+H]+ 1H NMR (400 MHz, DMSO-d6): δ 9.28 (s, 1H), 8.75 (s, 1H), 8.0 (s, 1H), 7.95-7.93 (d, 1H), 7.83 (s, 1H), 7.61-7.58 (m, 1H), 7.28-7.24 (t, 2H), 4.75-4.71 (m, 3H), 4.43 (s, 2H), 3.75-3.72 (m, 1H), 3.26-3.22 (m, 1H), 1.03-1.01 (d, 2H).

Example 35. Synthesis of N-(azetidin-3-ylmethyl)-2-(4-((2-(2,6-difluoro-phenyl)-5-oxo-6,7-dihydro-5H-pyrrolo[3,4-d]pyrimidin-4-yl)amino)-phenyl)acetamide, I-72

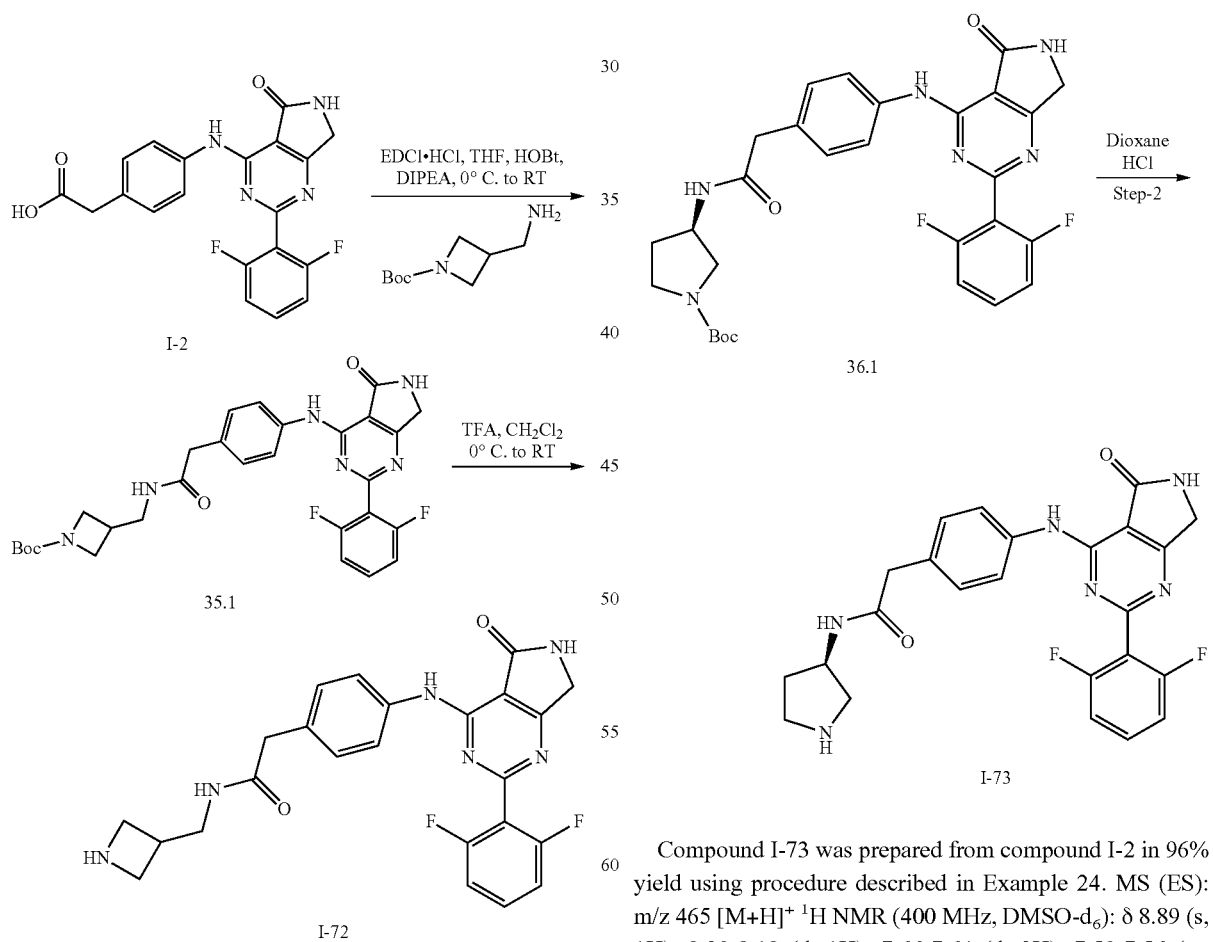

I-72

Compound I-72 was prepared from compound I-2 in 59% yield using protocol described in Example 11. MS (ES): m/z 465.26 [M+H]+ 1H NMR (400 MHz, DMSO-d6): δ 9.04 (s, 1H), 8.89 (s, 1H). 8.41 (s, 1H), 8.25 (bs, 1H), 7.71-7.67 (d, 2H), 7.62-7.56 (m, 1H), 7.28-7.21 (m, 3H), 4.47 (s, 2H), 3.80-3.76 (t, 2H), 3.56-3.53 (m, 2H), 3.39 (s, 2H), 3.26-3.23 (t, 2H), 2.84-2.82 (bs, 2H).

Example 36. Synthesis of (R)-2-(4-((2-(2,6-difluorophenyl)-5-oxo-6,7-dihydro-5H-pyrrolo[3,4-d]pyrimidin-4-yl)amino)phenyl)-N-(pyrrolidin-3-yl)acetamide, I-73

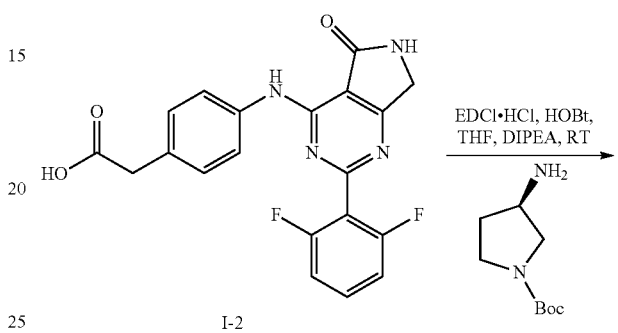

Compound I-73 was prepared from compound I-2 in 96% yield using procedure described in Example 24. MS (ES): m/z 465 [M+H]+ 1H NMR (400 MHz, DMSO-d6): δ 8.89 (s, 1H), 8.20-8.18 (d, 1H), 7.66-7.64 (d, 2H), 7.59-7.56 (m, 1H), 7.28-7.20 (m 4H), 4.47 (s, 2H), 4.06 (bs, 1H), 3.07 (bs, 1H), 3.34 (s, 2H), 2.57-2.54 (m, 1H), 2.96-2.90 (m, 2H), 2.80-2.70 (m, 2H), 1.93-1.85 (m, 1H), 1.55-1.50 (m, 1H).

Example 37. Synthesis of (S)-2-(4-((2-(2,6-difluorophenyl)-5-oxo-6,7-dihydro-5H-pyrrolo[3,4-d]pyrimidin-4-yl)amino)phenyl)-N-(1hydroxypropan-2-yl)acetamide, I-74

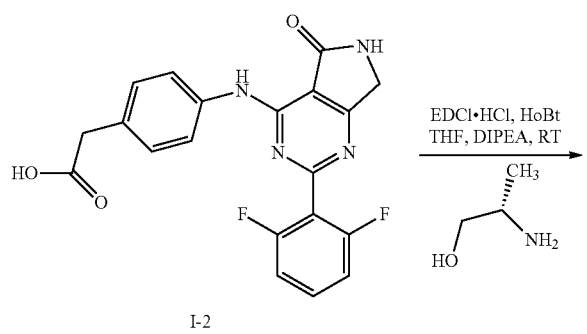

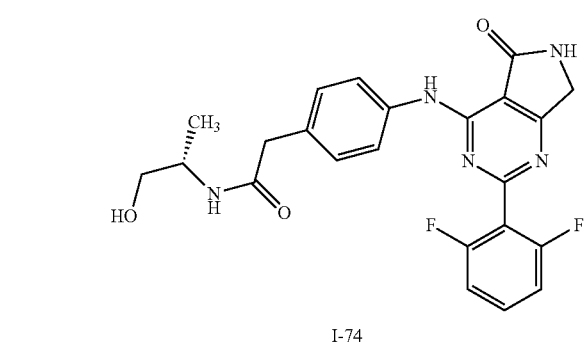

I-74

Compound I-74 was prepared from compound I-2 in 55% yield using procedure described in Example 8. MS (ES): m/z 454.21 [M+H]+ 1H NMR (400 MHz, DMSO-d6): δ 9.04 (s, 1H), 8.88 (s, 1H), 7.84-7.82 (d, 1H), 7.66-7.64 (d, 2H), 7.59-7.57 (m, 1H), 7.28-7.20 (m, 4H), 4.7-1.67 (t, 1H), 4.47 (s, 2H), 3.74-3.70 (m, 1H), 3.23-3.18 (m, 1H), 1.28-1.24 (m, 2H), 1.02-1.00 (d, 3H).

Example 38. Synthesis of (S)-2-(4-((2-(2,6-difluorophenyl)-5-oxo-6,7-dihydro-5H-pyrrolo[3,4-d]pyrimidin-4-yl)amino)phenyl)-N-(2-hydroxy-propyl)acetamide, I-75

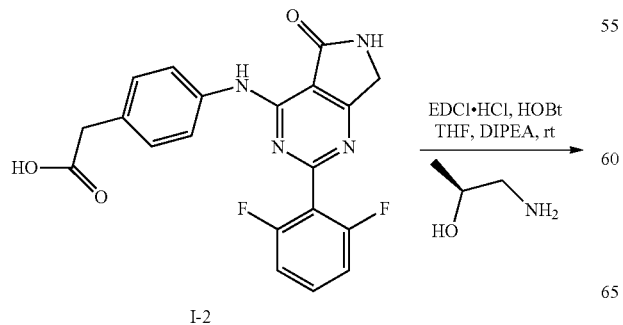

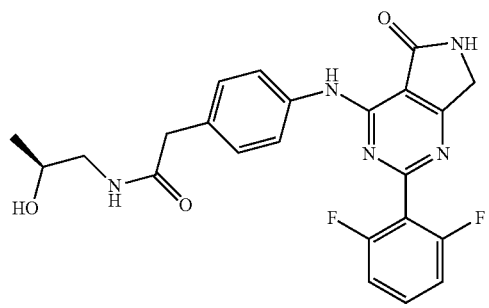

I-75

Compound I-75 was synthesized from compound I-2 in 54% yield using protocol described in Example 8. MS (ES): m/z 454.16 [M+H]+, 1H NMR (400 MHz, DMSO-d6): 9.04 (s, 1H), 8.88 (s, 1H), 7.99-7.96 (t, 1H), 7.66-7.64 (d, 2H), 7.61-7.57 (m, 1H), 7.29-7.22 (m, 4H), 4.67-4.66 (d, 1H), 4.47 (s, 2H), 3.63-3.60 (m, 1H), 3.39 (s, 2H), 3.0-2.96 (m, 2H), 0.99-0.98 (d, 3H).

Example 39. Synthesis of 2-(4-((2-(2,6-difluorophenyl)-5-oxo-6,7-dihydro-5H-pyrrolo[3,4-d]pyrimidin-4-yl)amino)phenyl)-N-(2-hydroxy-2-methylpropyl)acetamide, I-76


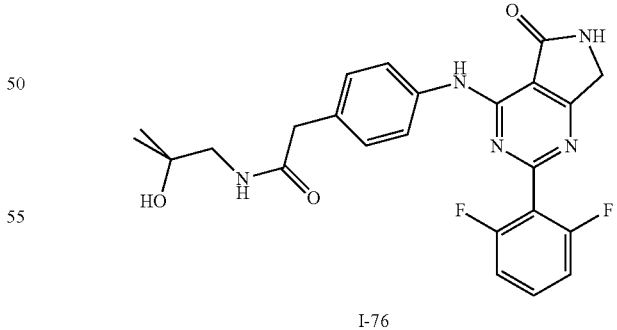

I-76

Compound I-76 was synthesized from compound I-2 in 45% yield using procedure described in Example 8. MS (ES): m/z 468.16 [M+H]+1H NMR (400 MHz, DMSO-d6): δ 9.03 (s, 1H), 8.87 (s, 1H), 7.87-7.84 (t, 1H), 7.66-7.64 (d, 2H), 7.61-7.57 (m, 1H), 7.28-7.23 (m, 4H), 4.47-4.43 (d, 3H), 3.43 (s, 2H), 3.01-3.00 (d, 2H), 1.01 (s, 6H).

Example 40. Synthesis of (R)-2-(4-((2-(2,6-difluorophenyl)-5-oxo-6,7-dihydro-5H-pyrrolo[3,4-d]pyrimidin-4-yl)amino)phenyl)-N-(2-hydroxy-propyl)acetamide, I-77

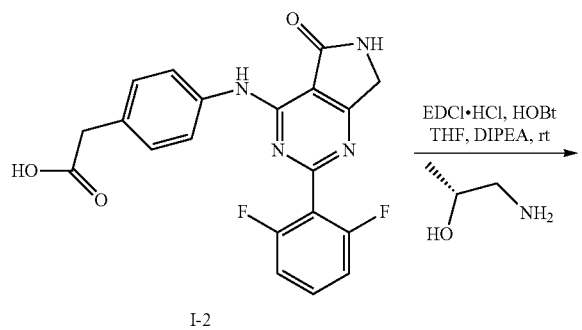

Compound I-77 was synthesized from compound I-2 in 61% yield using procedure described in Example 8. MS (ES): m/z 454.16 [M+H]+ 1H NMR (400 MHz, DMSO-d6): δ 9.04 (s, 1H), 8.88 (s, 1H), 7.99-7.96 (t, 1H), 7.66-7.61 (d, 2H), 7.59-7.58 (m, 1H), 7.28-7.21 (m, 4H), 4.68-4.66 (d, 1H), 4.47 (s, 2H), 3.64-3.59 (m, 1H), 3.39 (s, 2H), 3.0-2.96 (m, 2H), 0.99-0.97 (d, 3H).

Example 41. Synthesis of 4-((4-(2-(4-(2,2-difluoroethyl)piperazin-1-yl)-2-oxoethyl)phenyl)amino)-2-(2,6-difluorophenyl)-6,7-dihydro-5H-pyrrolo[3,4-d]pyrimidin-5-one, I-78

Compound I-78 was synthesized from compound I-2 in 54% yield using procedure described in Example 8. MS (ES): m/z 529.23 [M+H]+ 1H NMR (400 MHz, DMSO-d6): δ 9.05 (s, 1H), 8.88 (s, 1H), 7.68-7.66 (d, 2H), 7.63-7.56 (m, 1H), 7.28-7.23 (m, 2H), 7.20-7.18 (d, 2H), 6.26-5.98 (m, 1H), 4.47 (s, 2H), 3.66 (s, 2H), 3.49-3.43 (m, 4H), 2.75-2.66 (m, 2H), 2.46-2.42 (m, 4H).

Example 42. Synthesis of 2-(4-((2-(2,6-difluorophenyl)-5-oxo-6,7-dihydro-5H-pyrrolo[3,4-d]pyrimidin-4-yl)amino)phenyl)-N-(2-hydroxy-ethyl)acetamide, I-79

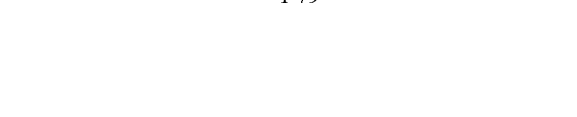

Compound I-79 was synthesized from compound I-2 in 38% yield using procedure described in Example 8. MS (ES): m/z 440.15 [M+H]+ 1H NMR (400 MHz, DMSO-d6): δ 9.04 (s, 1H), 8.88 (s, 1H), 8.02 (t, 1H), 7.66-7.64 (d, 2H), 7.59-7.56 (m, 1H), 7.28-7.2 (m, 4H), 4.68-1.66 (t, 1H), 4.47 (s, 2H), 3.4-3.37 (m, 4H), 3.1-3.01 (m, 2H).

Example 43. Synthesis of 2-(4-((2-(2,6-difluorophenyl)-5-oxo-6,7-dihydro-5H-pyrrolo[3,4-d]pyrimidin-4-yl)amino)phenyl)-N-ethylacetamide, I-80

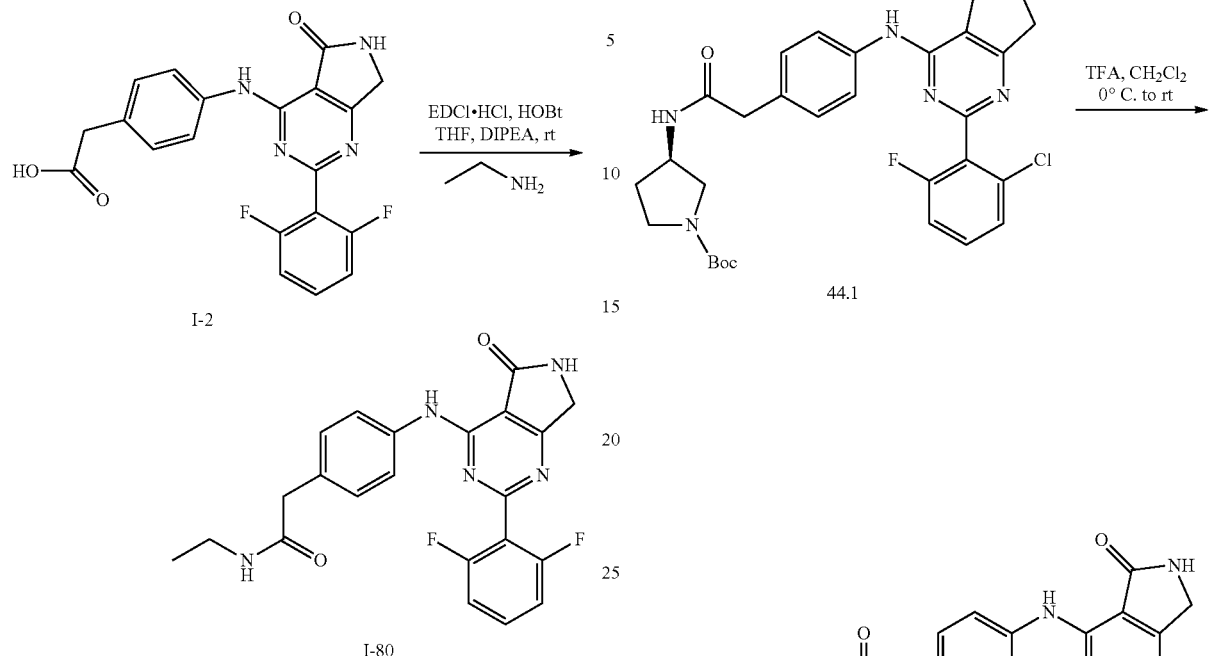

Compound I-80 was synthesized from compound I-2 in 56% yield using procedure described in Example 8. MS (ES): m/z [424.10] [M+H]+ $^1$H NMR (400 MHz, DMSO-$d_6$): δ 9.04 (s, 1H), 8.88 (s, 1H), 7.99 (m, 1H), 7.66-7.64 (d, 2H), 7.61-7.57 (m, 1H), 7.28-7.20 (m, 4H), 3.32 (s, 2H), 3.08-3.01 (q, 2H), 1.0 (t, 3H).

Example 44. Synthesis of (R)-2-(4-((2-(2-chloro-6-fluorophenyl)-5-oxo-6,7-dihydro-5H-pyrrolo[3,4-d]pyrimidin-4-yl)amino)phenyl)-N-(pyrrolidin-3-yl)acetamide, I-81

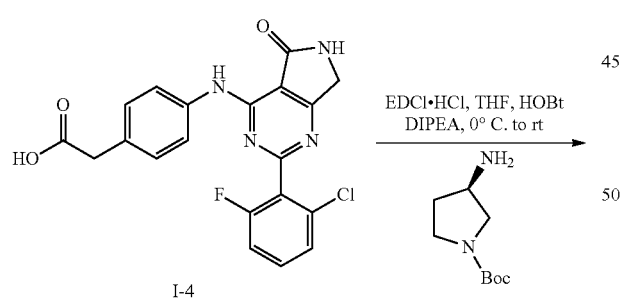

Compound I-81 was synthesized from compound I-4 in 89% yield using procedure described in Example 11. MS (ES): m/z [481.21] [M+H]+$^1$H NMR (400 MHz, DMSO-$d_6$): δ 9.09 (bs, 1H), 8.89 (s, 1H). 8.26-8.24 (d, 1H), 7.64-7.62 (d, 2H), 7.59-7.53 (m, 1H), 7.49-7.47 (d, 1H), 7.41-7.37 (t, 1H), 7.22-7.20 (d, 2H), 4.48 (s, 2H), 4.16-4.12 (m, 1H), 3.36-3.3 (m, 3H), 3.18-2.96 (m, 3H), 2.78-2.74 (m, 1H), 2.04-1.97 (m, 1H), 1.7-1.63 (m, 1H).

Example 45. Synthesis of 2-(4-((2-(2-fluoro-6-(trifluoromethyl)phenyl)-5-oxo-6,7-dihydro-5H-pyrrolo[3,4-d]pyrimidin-4-yl)amino)phenyl)acetic Acid, I-82

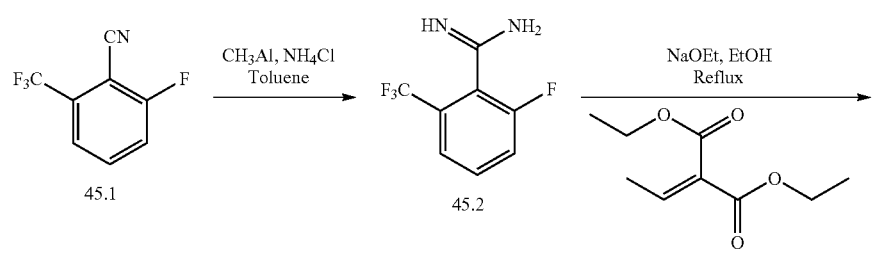

-continued
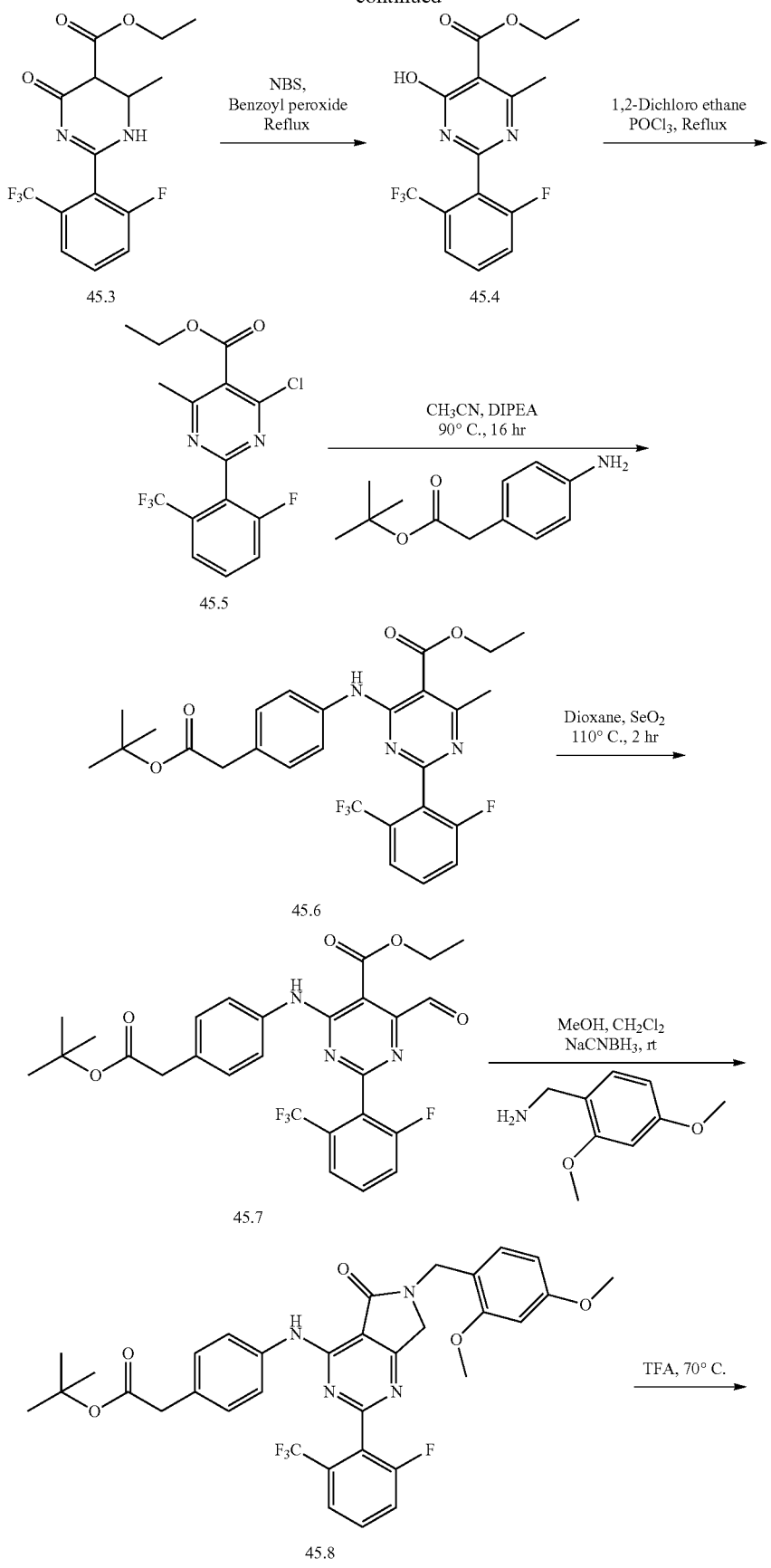

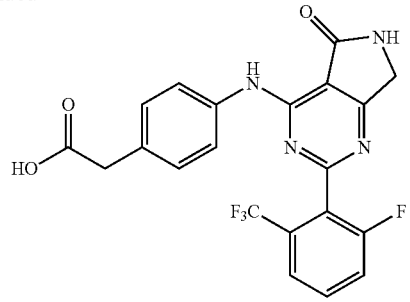

I-82

Synthesis of Compound 45.2.

Compound 45.1 (2 g, 10.57 mmol, 1.00 eq), NH$_4$Cl (0.58 g, 11.63 mmol, 1.1 eq) was dissolved in toluene (40 ml). A solution of trimethylaluminium (2.0 M sol. in toluene) (5.8 ml, 11.63 mmol, 1.1 eq) was added dropwise to the above reaction mixture at room temperature. Reaction mixture was stirred for 1 hour at room temperature then refluxed overnight. After completion of reaction, toluene was evaporated and residue was diluted with 10% methanol in dichloromethane (40 ml) Silica gel (2.0 g) was added to this reaction mixture and stirred for 30 minutes at ambient temperature. After 30 minutes, slurry was filtered and washed with dichloromethane & methanol filtrate was concentrated under vacuum to afford crude which was purified using trituration with 20% Ethyl acetate in hexane (50 mL). Obtained solid was filtered off and dried under vacuum to afforded compound 45.2 (2.0 g, 91%) as a white solid, MS (ES): m/z [207] [M+H]$^+$.

Synthesis of Compound 45.3.

To a solution of compound 45.2 (2.0 g, 9.7 mmol,) in ethanol (40 ml) was added diethyl ethylidene malonate (1.63 g, 8.7 mmol, 0.9 eq) followed by sodium ethoxide (1.2 g, 17.5 mmol, 1.81 eq). Reaction mixture was heated to reflux for 2 hours under argon atmosphere. After completion of the reaction, reaction mixture was concentrated under reduced pressure and residue was diluted with ethyl acetate and washed with water and brine. Organic layer was separated and dried over sodium sulfate and concentrated under reduced pressure to afforded crude material which was purified by column chromatography to furnish compound 45.3 (2.1 g, 62%) MS (ES): m/z [347] [M+H]$^+$.

Synthesis of Compound 45.4

To a solution of compound 45.3 (2.0 g, 5.77 mmol, 1.0 eq) in 1,4-dioxane (20 mL) was added potassium carbonate (1.2 g, 8.65 mmol, 1.5 eq), N-bromosuccinimide (1.0 g, 5.77 mmol, 1.0 eq) and benzoyl peroxide (0.28 g, 1.15 mmol, 0.2 eq). Reaction mixture was heated at reflux until starting material was consumed. After completion of the reaction, water was added and product was extracted with ethyl acetate (2×50 ml) and organic layer was separated and dried over Na$_2$SO$_4$ and concentrated under reduced pressure to afforded pure compound 45.4 (1.5 g, 75%). MS (ES): m/z [345] [M+H]$^+$.

Synthesis of Compound 45.5.

A solution of compound 45.4 (0.22 g, 1.00 equiv) in dichloroethane (2 ml) and phosphorous oxychloride (2 mL) was heated to reflux for 3 hours. After completion of the reaction, the mixture was concentrated and residue was drop wise quenched with ice. Obtained product was extracted with dichloromethane (2×10 mL). Organic layer was dried over sodium sulphate and concentrated under reduced pressure. Crude was purified by column chromatography to furnish compound 45.5 (0.15 g); MS (ES): m/z [363.7][M+H]$^+$.

Synthesis of Compound 45.6.

A solution of compound 45.5 (0.15 g, 0.41 mmol, 1.00 eq), tert-butyl 2-(4-aminophenyl)acetate (0.85 g, 0.41 mmol, 1.00 eq) and diisopropylethylamine (0.16 g, 1.24 mmol, 3.0 eq) in acetonitrile (2 mL) was heated at 90° C. for 16 hours. Reaction mixture was cooled to room temperature and poured in water. Product was extracted with ethyl acetate (20 mL×3). The combined organic layer was washed with brine, dried over sodium sulphate and concentrated under reduced pressure. The residue was purified via column column to afford the compound 45.6 (0.15 g, 68%) MS (ES): m/z [534.2] [M+H]$^+$.

Synthesis of Compound 45.7.

A solution of compound 45.6 (0.15 g, 0.28 mmol, 1.00 eq), selenium dioxide (0.062 g, 0.56 mmol, 2.00 eq) in 1,4-dioxane (5 mL) was stirred at 100° C. to 105° C. for 3 hours. After completion of the reaction, the resulting solution was filtered through celite and washed with 1,4-dioxane. Filtrate was concentrated under reduced pressure to afford compound 45.7 (0.15 g, quantitative) as a light yellow semisolid which was used as such for the next step. MS (ES): m/z [548.5] [M+H]$^+$.

Synthesis of Compound 45.8.

To a solution of compound 45.7 (0.15 g, 0.27 mmol, 1.00 eq) in mixture of dichloromethane: Methanol (10 mL, 2:8) was added 2,4-dimthoxybenzylamine (0.06 g, 0.35 mmol, 1.3 eq) at room temperature and stirred for 30 minutes. After 30 minutes, sodium cyanoborohydride (0.068 g, 1.092 mmol, 4.0 eq) was added at 0-10° C. The reaction mixture was allowed to warm at room temperature and stirred overnight. After completion, the reaction was diluted with water and product was extracted with ethyl acetate (25 mL×2) and washed with brine. The combined organic layers were dried and concentrated under vacuum. The residue was purified via flash column chromatography to afford compound 45.8 (0.015 g, 8.3%). MS (ES): m/z [653.2] [M+H]$^+$.

Synthesis of Compound I-82.

A solution of 45.8 (0.015 g, 0.229 mmol, 1.00 eq) in trifluoroacetic acid (2 mL) was stirred for 3-4 hours at reflux temperature. After completion of the reaction, mixture was concentrated under reduced pressure at 40° C. The residue was triturated with diethyl ether:Methanol (9.5:0.5) solution to afford pure 2-(4-((2-(2-fluoro-6-(trifluoromethyl)phenyl)-5-oxo-6,7-dihydro-5H-pyrrolo[3,4-d]pyrimidin-4-yl)amino) phenyl) acetic acid, compound I-82 (0.050 g, 49%). MS (ES): m/z [447] [M+H]$^+$, $^1$H NMR (400 MHz, DMSO-d$_6$): δ 9.11 (s, 1H). 8.93 (s, 1H), 7.78-7.75 (m, 3H), 7.62-7.60 (d, 2H), 7.21-7.19 (d, 2H), 4.48 (s, 2H), 3.51 (s, 2H).

Example 46. Synthesis of 2-(4-((2-(2-fluoro-6-(trifluoromethyl)phenyl)-5-oxo-6,7-dihydro-5H-pyrrolo[3,4-d]pyrimidin-4-yl)amino)phenyl)-N-(piperidin-4-yl)acetamide I-83

Compound I-83 was prepared from compound I-4 in 79% yield using procedure described in Example 11. MS (ES): m/z [529.18] [M+H]+ 1H NMR (400 MHz, DMSO-d6): δ 9.10 (s, 1H), 8.92 (s, 1H), 8.6-8.14 (d, 1H), 7.93-7.88 (bs, 1H), 7.75-7.72 (m, 3H), 7.60-7.58 (d, 2H), 7.20-7.18 (d, 2H), 4.48 (s, 2H), 3.75 (bs, 1H), 3.34 (s, 2H), 3.20-3.17 (m, 2H), 2.91-2.85 (t, 2H), 1.85-1.82 (m, 2H), 1.51-1.46 (m, 2H).

Example 47. Synthesis of 2-(2,6-difluorophenyl)-4-((4-(2-(1,1-dioxidothiomorpholino)-2-oxoethyl)phenyl)amino)-6,7-dihydro-5H-pyrrolo[3,4-d]pyrimidin-5-one, I-84

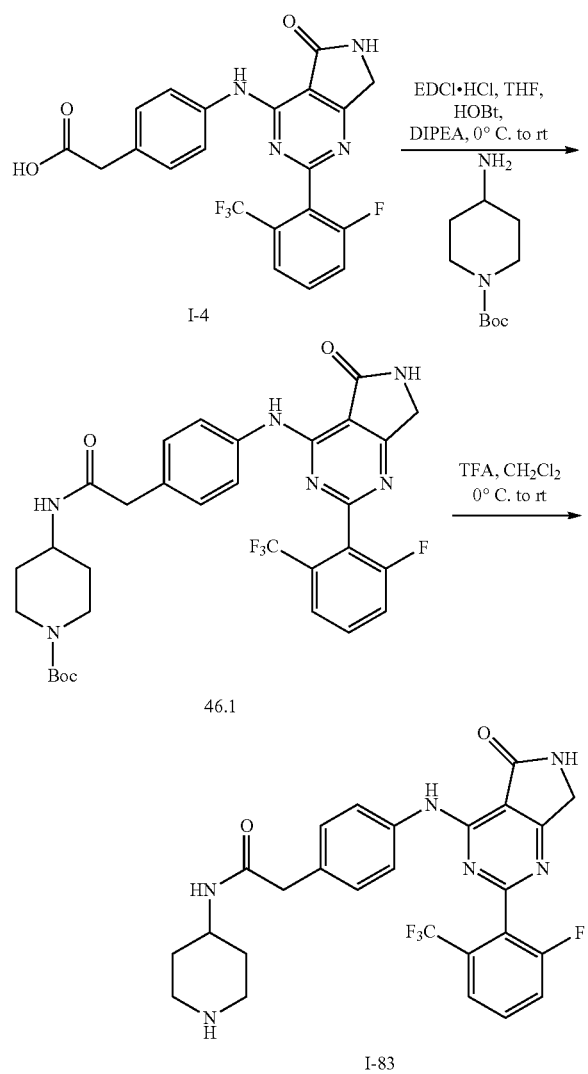

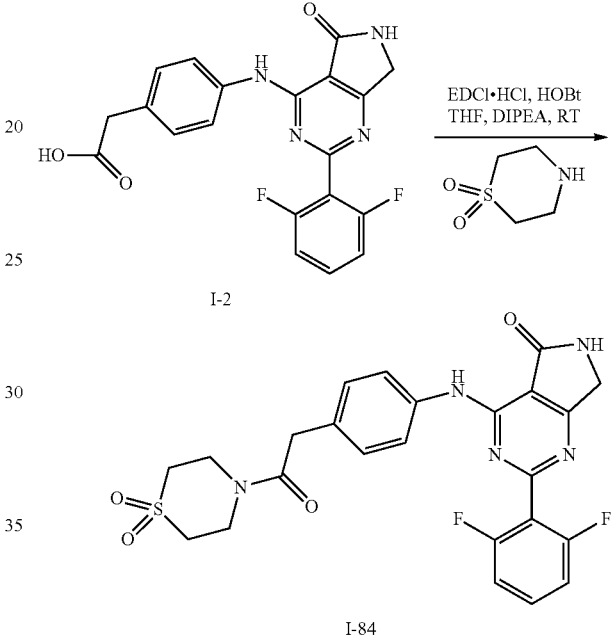

Compound I-84 was synthesized from compound I-2 in 57% yield using procedure described in Example 8. MS (ES): m/z [514.17] [M+H]+ 1H NMR (400 MHz, DMSO-d6): δ 9.06 (s, 1H), 8.89 (s, 1H), 7.70-7.68 (d, 2H), 7.62-7.58 (m, 1H), 7.28-7.20 (m, 4H), 4.47 (s, 2H), 3.87 (bs, 4H), 3.14-3.10 (d, 4H), 2.96-2.94 (m, 2H).

Example 48. Synthesis of 2-(4-((2-(3,5-difluoropyridin-4-yl)-5-oxo-6,7-dihydro-5H-pyrrolo[3,4-d]pyrimidin-4-yl)amino)phenyl)acetic Acid I-85

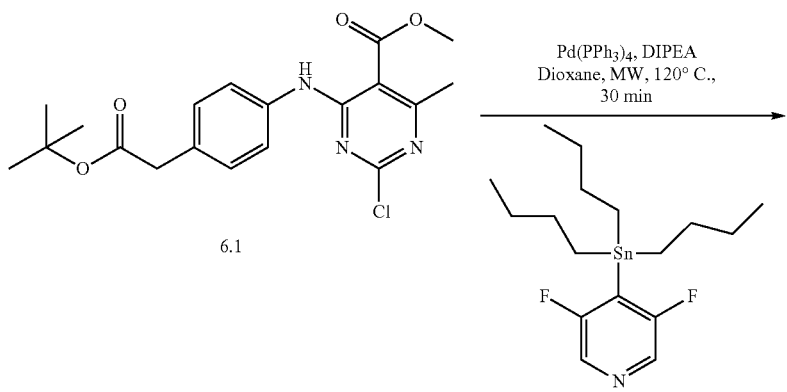

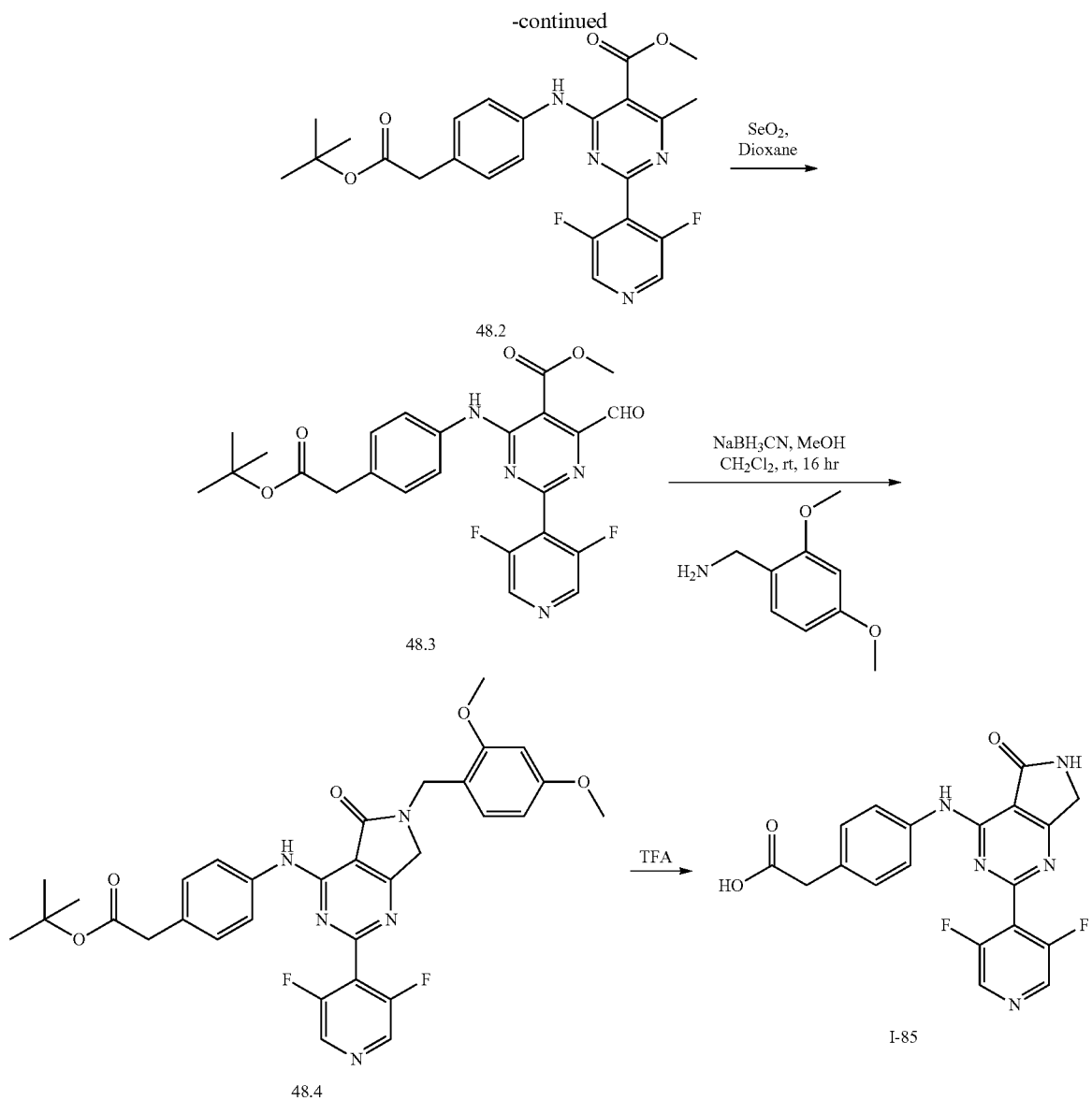

Synthesis of Compound 48.2.

A solution of 6.1 (0.1 g, 0.25 mmol, 1.00 eq), 3,5-difluoro-4-(tributylstannyl) pyridine (0.134 g, 0.33 mmol, 1.30 eq) and Copper Oxide (0.003 g, 0.025 mmol, 0.10 eq) in 1,4-dioxane was degassed with argon gas for 30 minutes. Tetrakis(triphenylphosphine) palladium(0) was added to reaction mixture and again degassed for 20 minutes. Reaction mixture was then subjected to microwave at 120° C. for 30 minutes. After completion of the reaction, water was added and product was extracted with ethyl acetate (2×50 mL) and organic layer was separated and dried over Na$_2$SO$_4$ and concentrated under reduced pressure. Crude was purified by column chromatography using to afforded pure compound 48.2 (0.038 g, 54.14%). MS (ES): m/Z [471.21] [M+H]$^+$.

Synthesis of Compound 48.3.

To a solution of 48.2 (0.250 g, 0.5 mmol, 1.0 eq) in dioxane (5 mL) was added selenium dioxide (0.118 g, 1.0 mmol, 2.0 eq) and it was heated at 100° C. for 6 h. After completion of the reaction, reaction mixture was filtered through celite bad to remove inorganic impurities. Filtrate was concentrated to afford crude compound 48.3, which was used as such in the next step. (0.25 g, 97.11%); MS (ES): m/z 484.16 [M+H]$^+$.

Synthesis of Compound 48.4.

A solution of 48.3 (0.25 g, 0.51 mmol, 1.00 eq) in dichloromethane (2.5 mL) and methanol (1.25 mL) was stirred at room temperature for 5 minutes. 2,4-dimethoxybenzylamine (0.094 g, 0.56 mmol, 1.1 eq) was added to it and reaction was stirred for 30 min. Reaction mixture then cooled at 0° C. and sodium cyanoborohydride was added slowly to it and reaction mixture was allowed to stir at room temperature for 12 h. After completion of reaction water was added and product was extracted with ethyl acetate (3×50 mL). Combined organic layer was washed with brine, dried over sodium sulfate and concentrated under reduced pressure. Crude was purified by column chromatography to afford pure compound 48.4. (0.19 g, 61.0%), MS (ES): m/z [604.23] [M+H]$^+$.

Synthesis of Compound I-85.

A solution of compound 48.4 (0.18 g, 0.4 mmol, 1.00 eq) in trifluoroacetic acid (2.0 mL) was stirred for 4 hours at reflux temperature. After completion of the reaction, reaction mixture was concentrated under reduced pressure. The residue was triturated with diethyl ether:methanol (9.5:0.5) solution to afford 2-(4-((2-(3,5-difluoropyridin-4-yl)-5-oxo-6,7-dihydro-5H-pyrrolo[3,4-d]pyrimidin-4-yl)amino)phenyl)acetic acid, compound I-85. (0.045 g, 37.9%); MS (ES): m/z [398.09] [M+H]$^+$, $^1$H NMR (400 MHz, DMSO-d$_6$): δ 12.303 (s, 1H), 9.161 (1H, s), 8.956 (1H, S), 8.735 (2H, s), 7.660-7.681 (1H, d), 7.231-7.252 (1H, d), 4.502 (1H, s), 3.554 (2H, s).

Example 49. Synthesis of compound 2-(2,6-difluorophenyl)-4-((4-(2-oxopyrrolidin-3-yl)phenyl)amino)-6,7-dihydro-5H-pyrrolo[3,4-d]pyrimidin-5-one, Intermediate 49.8

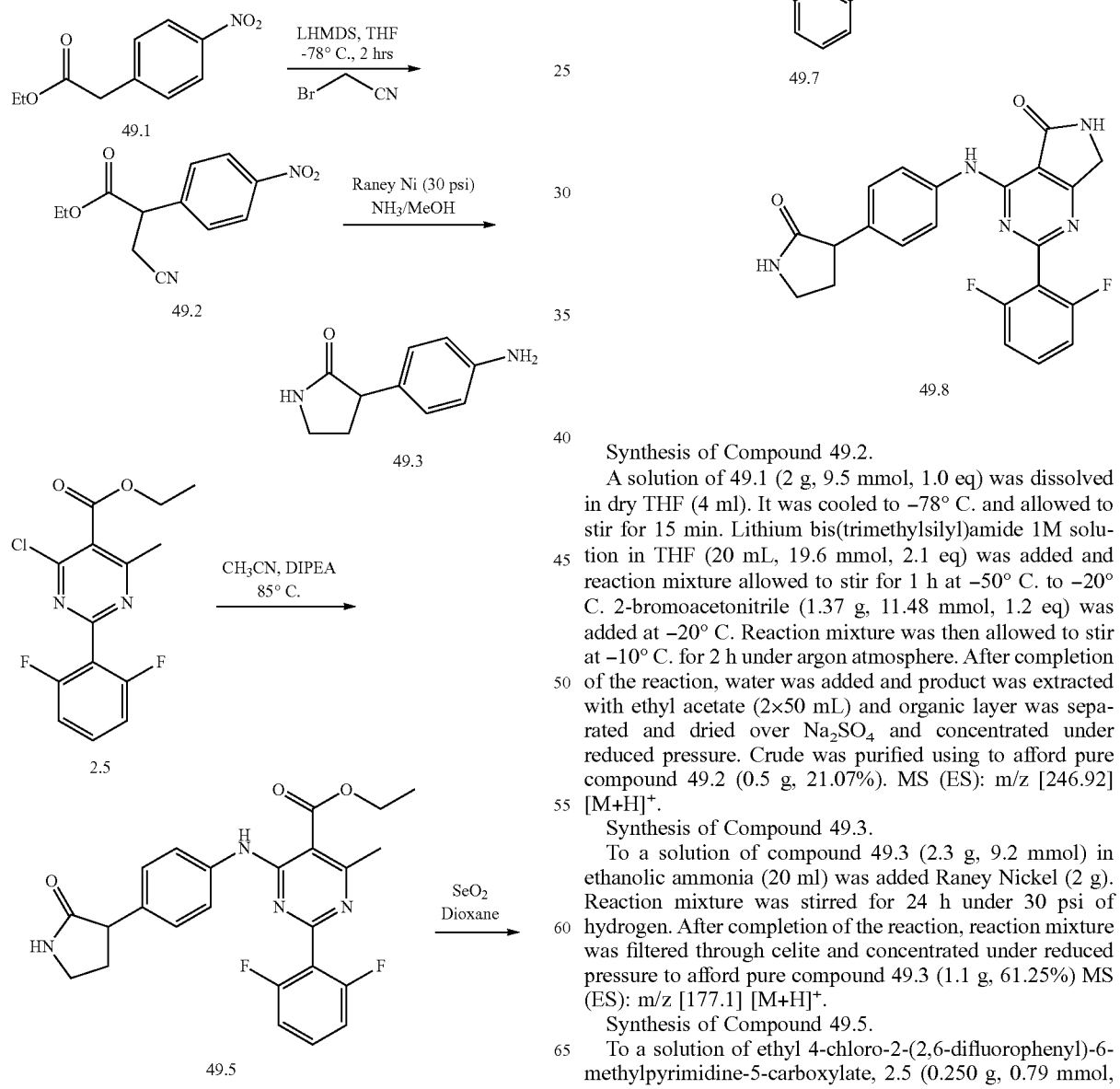

Synthesis of Compound 49.2.

A solution of 49.1 (2 g, 9.5 mmol, 1.0 eq) was dissolved in dry THF (4 ml). It was cooled to −78° C. and allowed to stir for 15 min. Lithium bis(trimethylsilyl)amide 1M solution in THF (20 mL, 19.6 mmol, 2.1 eq) was added and reaction mixture allowed to stir for 1 h at −50° C. to −20° C. 2-bromoacetonitrile (1.37 g, 11.48 mmol, 1.2 eq) was added at −20° C. Reaction mixture was then allowed to stir at −10° C. for 2 h under argon atmosphere. After completion of the reaction, water was added and product was extracted with ethyl acetate (2×50 mL) and organic layer was separated and dried over Na$_2$SO$_4$ and concentrated under reduced pressure. Crude was purified using to afford pure compound 49.2 (0.5 g, 21.07%). MS (ES): m/z [246.92] [M+H]$^+$.

Synthesis of Compound 49.3.

To a solution of compound 49.3 (2.3 g, 9.2 mmol) in ethanolic ammonia (20 ml) was added Raney Nickel (2 g). Reaction mixture was stirred for 24 h under 30 psi of hydrogen. After completion of the reaction, reaction mixture was filtered through celite and concentrated under reduced pressure to afford pure compound 49.3 (1.1 g, 61.25%) MS (ES): m/z [177.1] [M+H]$^+$.

Synthesis of Compound 49.5.

To a solution of ethyl 4-chloro-2-(2,6-difluorophenyl)-6-methylpyrimidine-5-carboxylate, 2.5 (0.250 g, 0.79 mmol, 1.0 eq) and compound 49.3 (0.126 g, 0.76 mmol, 0.9 eq) in acetonitrile (2.5 mL) was added diisopropylethylamine (0.309 g, 2.3 mmol, 4 eq). Reaction mixture was heated at reflux for 24 h. After completion of the reaction, water was added and product was extracted with ethyl acetate (2×50 mL), organic layers was separated and dried over $Na_2SO_4$ and concentrated under reduced pressure. Crude was purified by flash column chromatography to afford pure compound 49.5 (0.175 g, 48.38%). MS (ES): m/Z [453.16][M+H]$^+$.

Synthesis of Compound 49.6.

To a solution of compound 49.4 (0.19 g, 0.4 mmol, 1.0 eq) in Dioxane (4 mL) was added selenium dioxide (0.093 g, 0.84 mmol, 2.0 eq) Reaction was heated 100° C. reflux for 6 h. After completion of the reaction, reaction mixture was filtered through celite to remove inorganic impurities. Filtrate was concentrated to afford crude compound 49.6, which was used as such in the next step. (0.19 g, 97.0%); MS (ES): m/z [466.15][M+H]$^+$.

Synthesis of Compound 49.7.

A solution of 49.6 (0.36 g, 0.77 mmol, 1.00 eq) 10V dichloromethane (3.6 mL) and methanol (1.8 mL) was stirred at room temperature for 5 min. 2,4-dimethoxybenzylamine (0.142 g, 0.85 mmol, 1.1 eq) was added to it and allowed to stir for 30 min. Reaction mixture then cooed at 0° C. and sodium cyanoborohydride was added slowly to it and reaction mixture was allowed to stir at room temperature for 12 h. After completion of reaction water was added and product was extracted with ethyl acetate (3×50 mL). The combine organic layer was washed with brine, dried over sodium sulfate and concentrated under reduced pressure to afford crude compound 49.7, which was used as such in the next step. (0.36 g, 97%), MS (ES): m/Z [572.3] [M+H]$^+$.

Synthesis of Compound 49.8.

A solution of compound 49.7 (0.18 g, 0.31 mmol, 1.00 eq) in trifluoroacetic acid (1.8 mL) was stirred for 3-4 hours at reflux temperature. After completion of the reaction, mixture was concentrated under reduced pressure. The residue was triturated with diethyl ether:Methanol (9.5:0.5) solution to afford 2-(2,6-difluorophenyl)-4-((4-(2-oxopyrrolidin-3-yl)phenyl)amino)-6,7-dihydro-5H-pyrrolo[3,4-d]pyrimidin-5-one, 49.8 (0.016 g, 12%) as white solid. MS (ES): m/z 422.1 [M−H]$^+$, LCMS purity: 100%, HPLC purity: 98.79%, $^1$H NMR (400 MHz, DMSO-d$_6$): δ 7.784-7.805 (d, 1H), 7.542-7.574 (t, 1H). 7.280-7.301 (d, 1H), 7.127-7.168 (t, 2H), 4.512 (s, 2H), 3.667-3.711 (t, 2H), 3.429-3.473 (q, 2H), 2.616-2.680 (q, 1H), 2.175-2.260 (m, 1H), 1.309 (s, 1H), 0.905-0.938 (t, 1H).

Example 50. Synthesis of (R)-2-(2,6-difluorophenyl)-4-((4-(2-oxopyrrolidin-3-yl)phenyl)amino)-6,7-dihydro-5H-pyrrolo[3,4-d]pyrimidin-5-one, I-86

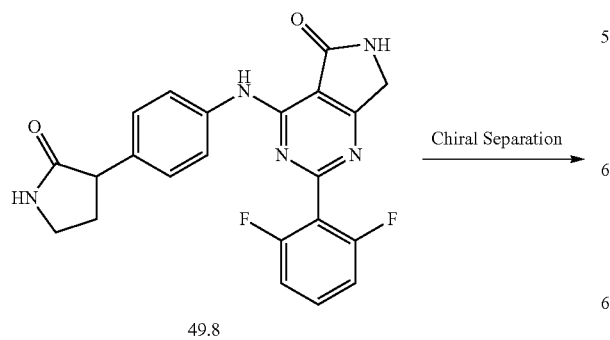

49.8

Chiral Separation →

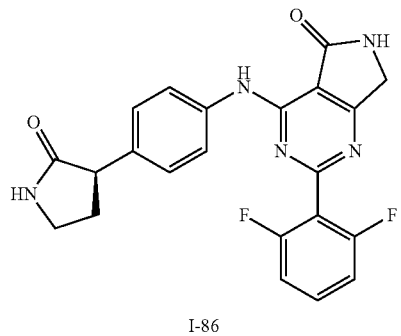

I-86

Compound I-86 was obtained by chiral purification of compound 49.8 to afford desired pure enantiomer as a white solid MS (ES): m/z [422.1] [M+H]$^+$, Chiral HPLC purity: 97.6%, $^1$H NMR (400 MHz, DMSO-d$_6$): δ 7.781-7.802 (d, 2H), 7.517-7.591 (m, 1H). 7.277-7.298 (d, 1H), 7.124-7.164 (t, 2H), 4.507 (s, 2H), 3.663-3.708 (t, 2H), 3.426-3.529 (m, 2H), 2.582-2.665 (m, 1H), 2.165-2.260 (m, 1H), 1.308 (s, 1H), 0.904-0.921 (t, 1H).

Example 51. Synthesis of(S)-2-(2,6-difluorophenyl)-4-((4-(2-oxopyrrolidin-3-yl)phenyl)amino)-6,7-dihydro-5H-pyrrolo[3,4-d]pyrimidin-5-I-87

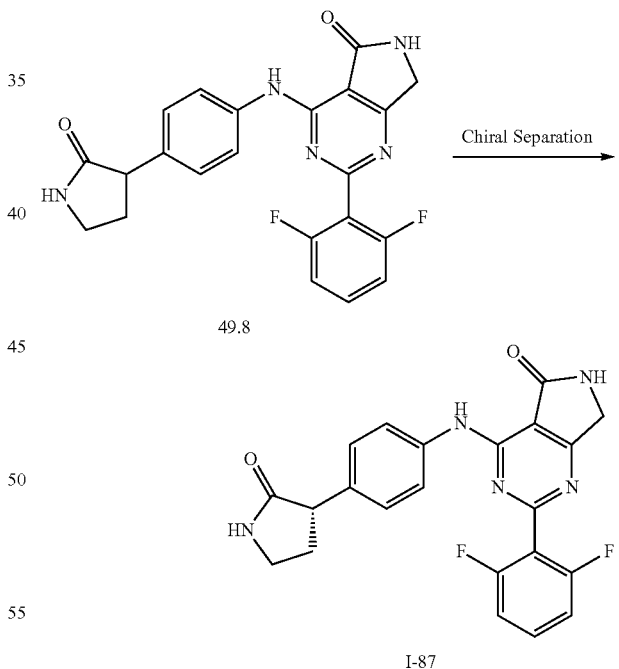

49.8

Chiral Separation →

I-87

Compound I-87 was obtained from chiral purification of compound 49.8 as white solid. MS (ES): m/z [422.1] [M+H]$^+$, Chiral HPLC purity: 97.6%, $^1$H NMR (400 MHz, DMSO-d$_6$): δ 7.779-7.801 (d, 2H), 7.516-7.590 (m, 1H). 7.275-7.297 (d, 1H), 7.114-7.171 (t, 2H), 4.504 (s, 2H), 3.662-3.707 (t, 2H), 3.425-3.528 (m, 2H), 2.581-2.664 (m, 1H), 2.163-2.258 (m, 1H), 1.308 (s, 1H), 0.903-0.920 (t, 1H).

Example 52. Synthesis of methyl (S)-4-(2-(4-((2-(2,6-difluorophenyl)-5-oxo-6,7-dihydro-5H-pyrrolo[3,4-d]pyrimidin-4-yl)amino)phenyl)acetyl)morpholine-3-carboxylate, I-111

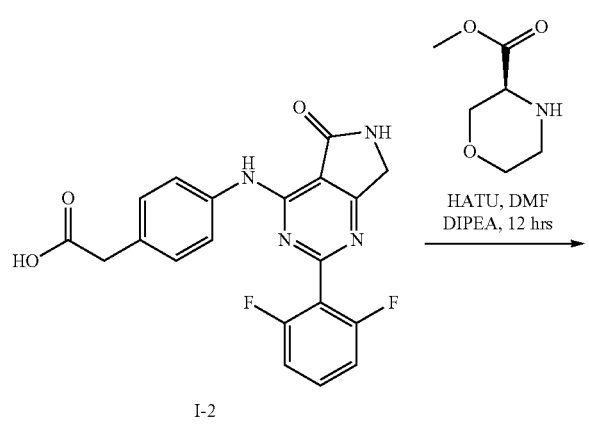

I-2

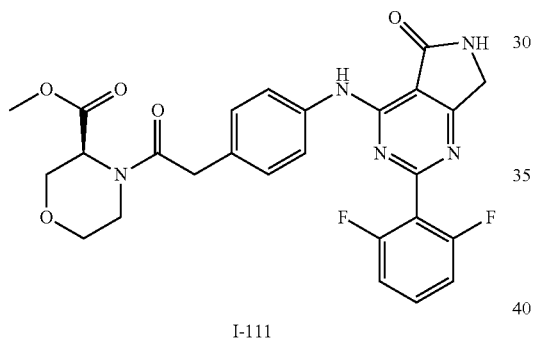

I-111

To a solution of compound I-2 (0.08 g, 0.20 mmol, 1.0 eq) in dry DMF (3 mL) was added HATU (0.115 g, 0.30 mmol, 1.5 eq) at 0° C. under argon atmosphere. Solution was allowed to stir for 1 hr at 0° C. Methyl (S)-morpholine-3-carboxylate (0.041 g, 0.24 mmol, 1.2 eq) was added followed by the addition of diisopropylethylamine (0.077 g, 0.60 mmol, 3.0 eq). The reaction was stirred at room temperature for 12 hr. After completion of reaction, reaction mixture was diluted with ethyl acetate (50 ml), washed with water (50 ml×3) and brine (50 ml). Organic layers were combined and dried over sodium sulphate. Solvents were removed under reduced pressure at 40° C. and crude product was purified by flash column chromatography to afford pure I-111 (0.025 g, 23.66%). MS (ES): m/Z 523.5 [M+H]$^+$; $^1$H NMR (400 MHz, DMSO-D6): δ 9.064 (s, 1H), 8.888 (s, 1H), 7.615-7.709 (m, 2H), 7.562-7.599 (t, 1H), 7.246-7.287 (t, 2H), 7.155-7.219 (dd, 2H), 4.905 (s, 1H), 4.479 (s, 2H), 4.182-4.223 (m, 1H), 3.680 (s, 4H), 3.652-3.680 (t, 2H), 3.535-3.571 (t, 2H), 3.384-3.396 (m, 1H), 3.236-3.275 (m, 1H).

Example 53. Synthesis of (S)-4-(2-(4-((2-(2,6-difluorophenyl)-5-oxo-6,7-dihydro-5H-pyrrolo[3,4-d]pyrimidin-4-yl)amino)phenyl)acetyl)morpholine-3-carboxylic Acid, I-112

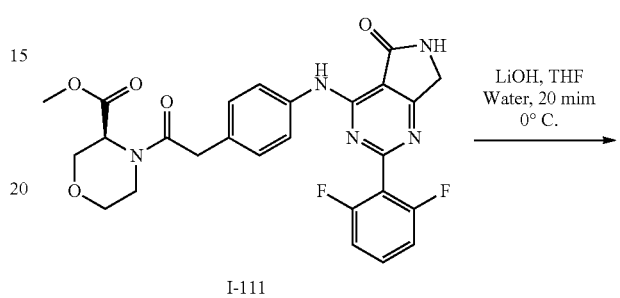

I-111

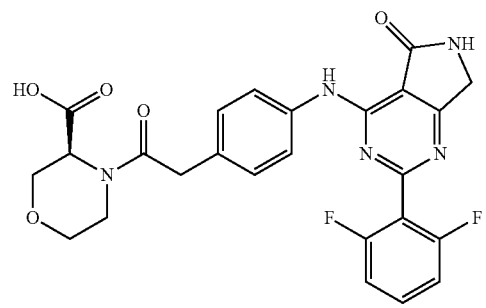

I-112

To a solution of compound I-111, (0.025 g, 0.04 mmol) in THF (1 mL) was added lithium hydroxide (0.05 g, 0.14 mmol, 3.0 eq) in water (1 mL) at 0° C. Reaction was stirred at 0° C. for 20 minutes. After completion of the reaction, pH was adjusted 5 using dilute HCl. Mixture was extracted with ethyl acetate (25 mL). Organic layer was separated out, washed with water (15 mL) and brine (10 mL) dried over sodium sulphate and concentrated under reduced pressure at 40° C. Crude product was purified by flash column chromatography to afford pure I-112 (0.010 g, 41.10%). MS (ES): m/Z 535.5 [M+H]$^+$; $^1$H NMR (400 MHz, DMSO-d$_6$): δ 13.109 (s, 1H), 9.050 (s, 1H), 8.871 (s, 1H), 7.648-7.694 (m, 2H), 7.561-7.614 (t, 1H), 7.244-7.284 (t, 2H), 7.155-7.227 (dd, 2H), 4.746 (s, 1H), 4.477 (s, 2H), 4.205-4.279 (m, 1H), 3.979-4.013 (d, 0.5H), 3.674-3.788 (m, 4H), 3.321-3.538 (m, 3H), 2.862-3.891 (t, 0.5H).

Example 54. Synthesis of 2-(2-chloro-6-fluorophenyl)-4-((4-(2-oxopyrrolidin-3-yl)phenyl)-amino)-6,7-dihydro-5H-pyrrolo[3,4-d]pyrimidin-5-one, I-113

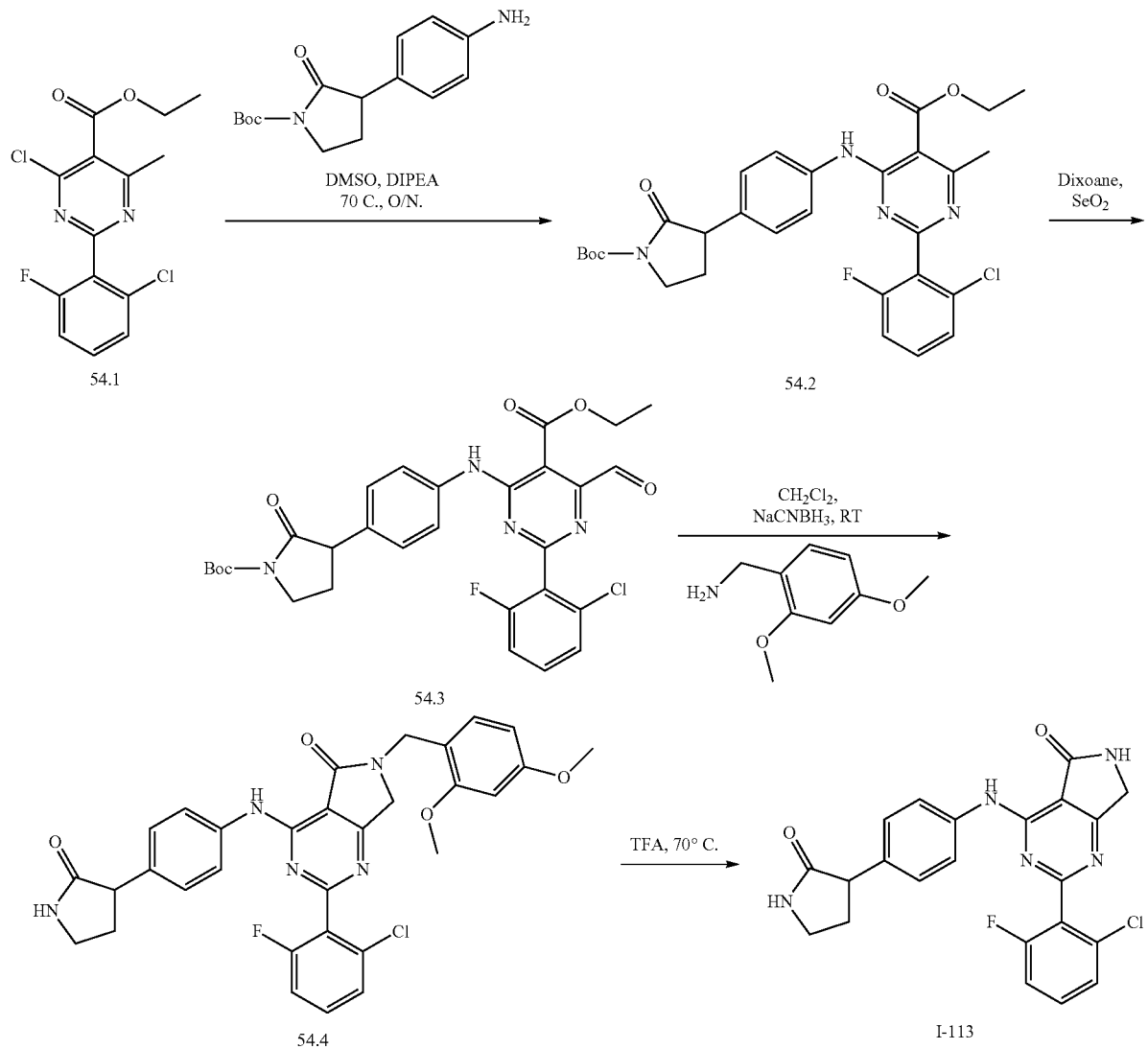

Synthesis of Compound 54.2.

To a solution of compound 54.1 (0.54 g, 1.60 mmol, 1.0 eq) in dry DMSO (5 mL) was added tert-butyl 3-(4-aminophenyl)-2-oxopyrrolidine-1-carboxylate (0.450 g, 1.60 mmol, 1.0 eq), DIPEA (0.527 g, 4.0 mmol, 2.5 eq). Reaction mixture was allowed to stir at 70° C. for overnight. After completion of reaction, reaction mixture was cooled to room temperature. Water (100 mL) was added to the reaction mixture and extracted with Ethyl acetate (100×2). Organic layer was washed with brine solution, dried over sodium sulfate and concentrated under reduced pressure to give crude product, which was purified by flash column chromatography to afford compound 54.2 (0.550 g, 58.92%). MS (ES): m/z=569.3 [M+H]$^+$.

Synthesis of Compound 54.3.

To a solution of compound 54.2 (0.550 g, 0.88 mmol, 1.0 eq) in Dioxane (10.0 mL) was added Selenium dioxide (0.195 g, 1.76 mmol, 2.0 eq.). Reaction mixture was heated at 90° C. temperature for 6 hours. After completion of the reaction, reaction mixture was poured into water and extracted with Ethyl acetate. Organic layer was washed with brine solution, dried over sodium sulfate and concentrated under reduced pressure to afford crude compound 54.3 (530 mg, 94.05%), which was used as such in next step. MS (ES): m/z 583.5 [M+H]$^+$.

Synthesis of Compound 54.4.

To a solution of compound 54.3 (0.530 g, 0.85 mmol, 1.0 eq) in dichloromethane (5.3 mL, 10V) and methanol (2.1 mL, 5V) was added 2,4-dimethoxybenzylamine (0.157 g, 0.94 mmol, 1.1 eq) at room temperature. Mixture was stirred for 30 minutes. Reaction mixture then cooled at 0° C. and sodium cyanoborohydride (0.161 g, 2.5 mmol, 3.0 eq) was added slowly. Reaction was stirred at room temperature for 12 h. After completion of the reaction, water was added and product was extracted with ethyl acetate (3×50 mL). Combined organic layers were washed with brine, dried over sodium sulphate and concentrated under reduced pressure to afford crude which was purified by flash column chromatography to afford compound 54.4. (0.388 g, 72.58%), MS (ES): m/Z [688.7] [M+H]$^+$.

Synthesis of Compound I-113.

A solution of compound 54.4 (0.388 g) in HBr/CH₃COOH (33%, 5 ml) was stirred at room temperature for 2 hours. After completion of the reaction, reaction mixture was poured into cold water, neutralized with NaHCO₃ and product was extracted with ethyl acetate (50 mL×2). Solvent was removed under reduced pressure at 45° C. to give crude product, which was purified by flash column chromatography to furnish compound I-113, (130 mg, 46.6%). MS (ES): m/z 438.16 [M+H]⁺; ¹H NMR (400 MHz, MeOD): δ 7.774 (s, 1H), 7.752 (s, 1H), 7.485-7.549 (m, 1H), 7.403-7.441 (t, 1H), 7.269-7.290 (m, 2H), 4.519 (s, 1H), 3.644-3.791 (m, 1H), 3.344-3.498 (m, 2H), 2.574-2.698 (m, 1H), 2.158-2.232 (m, 1H).

Example 55. Synthesis of (R)-2-(2-chloro-6-fluorophenyl)-4-((4-(2-oxopyrrolidin-3-yl)phenyl)amino)-6,7-dihydro-5H-pyrrolo[3,4-d]pyrimidin-5-one, I-114

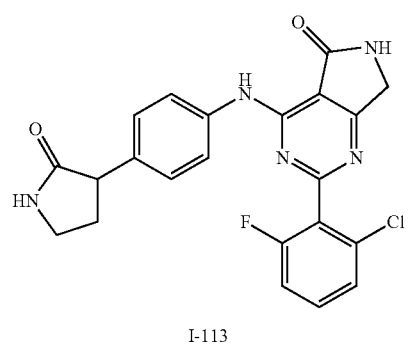

Compound I-114 was obtained by chiral separation of compound I-113. MS (ES): m/z 438.31 [M+H]⁺; Chiral HPLC: 100%. ¹H NMR (400 MHz, MeOD): δ 7.773 (s, 1H), 7.752 (s, 1H), 7.505-7.519 (d, 1H), 7.403-7.421 (d, 1H), 7.269-7.291 (t, 2H), 4.512 (s, 1H), 3.656-3.679 (d, 1H), 3.419-3.466 (m, 2H), 2.603-2.624 (m, 1H), 2.176-2.209 (m, 1H)

Example 56. Synthesis of (S)-2-(2-chloro-6-fluorophenyl)-4-((4-(2-oxopyrrolidin-3-yl)phenyl)amino)-6,7-dihydro-5H-pyrrolo[3,4-d]pyrimidin-5-one, I-115

Compound I-115 was obtained by chiral separation of compound I-113. MS (ES): m/z 438.26 [M+H]⁺. Chiral HPLC: 98.11%. ¹H NMR (400 MHz, MeOD): δ 7.773 (s, 1H), 7.752 (s, 1H), 7.484-7.540 (d, 1H), 7.402-7.422 (d, 1H), 7.237-7.291 (t, 3H), 4.512 (s, 1H), 3.656-3.700 (m, 1H), 3.419-3.466 (m, 2H), 2.592-2.625 (m, 1H), 2.176-2.212 (m, 1H).

Example 57. Synthesis of 2-(2,6-difluorophenyl)-4-((4-(3-(2-methoxyethyl)-2-oxopyrrolidin-3-yl)phenyl)amino)-6,7-dihydro-5H-pyrrolo[3,4-d]pyrimidin-5-one, I-116

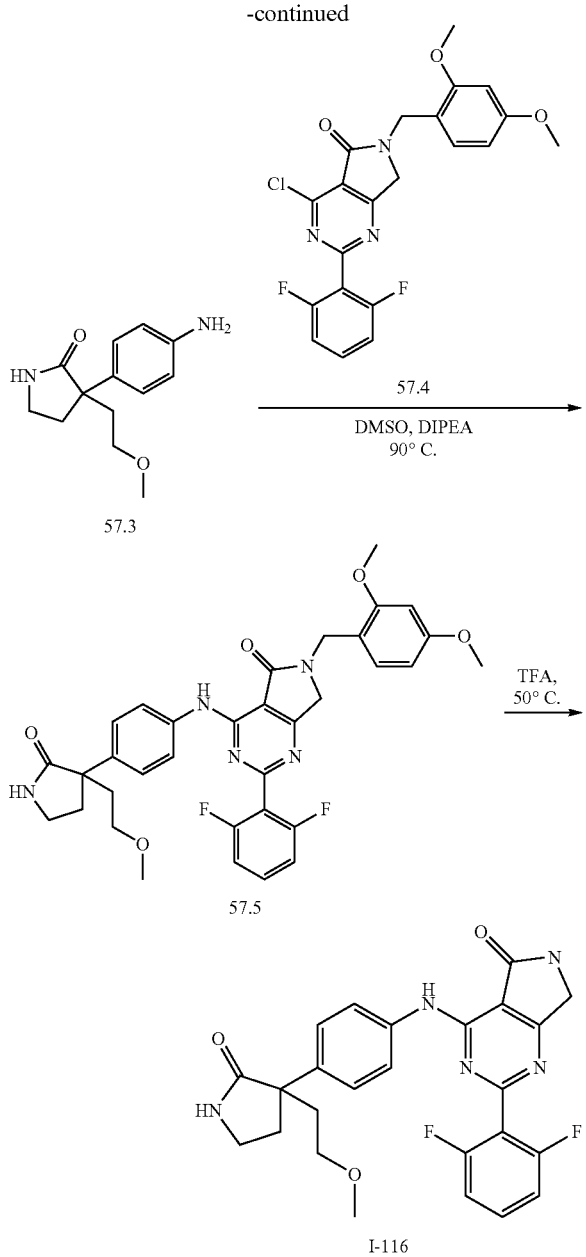

Synthesis of Compound 57.2

To a solution of compound 57.1 (0.400 g, 1.94 mmol, 1.0 eq) in dry acetonitrile (10 mL) were added 1-bromo-2-methoxyethane (0.404 g, 2.9 mmol, 1.5 eq) and cesium carbonate (1.26 g, 3.8 mmol, 2 eq). Reaction was irradiated in microwave at 150° C. for 15 minutes. After completion of reaction, reaction mixture was cooled to room temperature. Water (50 mL) was added to reaction mixture and extracted with ethyl acetate (50 mL×2). Organic layer was washed with by brine solution, dried over sodium sulfate and concentrated under reduced pressure. Crude product was purified by flash column chromatography to afford compound 57.2 (0.19 g, 37.1%). MS (ES): m/z=265.08 [M+H]$^+$ Synthesis of Compound 57.3.

To a suspension of Pd—C (0.050 g) in MeOH (5.0 mL) was added compound 57.2 (0.19 g, 1.2 mmol, 1.0 eq) in MeOH (2.0 mL). Suspension was purged with H$_2$ gas for 30 minutes. After completion of reaction, reaction mixture was filtered through celite and filtrate was concentrated under reduced pressure to afford crude which was purified by flash column chromatography to furnish compound 57.3. (0.050 g), MS (ES): m/z 235.06 [M+H]$^+$, Synthesis of Compound 57.5.

To a solution of compound 57.3 (0.050 g, 0.2 mmol, 1.0 eq) in dry DMSO (1.0 mL) were added compound 57.4 (0.088 g, 0.2 mmol, 1.0 eq), DIPEA (0.077 g, 0.6 mmol, 3 eq). Reaction mixture was allowed to stir at 70° C. for 16 hours. After completion of the reaction, reaction mixture was cooled to room temperature. Water (100 mL) was added to reaction mixture and mixture extracted with ethyl acetate (50 mL×2). Organic layer was washed with brine solution, dried sodium sulfate and concentrated under reduced pressure. Crude product, which was purified by flash column chromatography to furnish compound 57.5 (0.058 g, 43.2%). MS (ES): m/z 630.36 [M+H]$^+$.

Synthesis of Compound I-116.

A solution of compound 57.5 (0.058 g) in HBr/CH$_3$COOH (33%, 2 ml) was stirred at room temperature for 1 hour. After completion of the reaction, reaction mixture was poured in cold water, neutralized with NaHCO$_3$ and product was extracted with ethyl acetate (25 ml×2). Solvent was removed under reduced pressure at 45° C. This crude was purified by flash column chromatography to afford pure compound I-116 (17 mg, 38.49%). MS (ES): m/z 480.61 [M+H]$^+$ $^1$H NMR (400 MHz, CH$_3$OD): δ 7.826 (s, 1H), 7.804 (s, 1H), 7.490-7.583 (m, 3H), 7.133-7.174 (t, 2H), 4.515 (s, 2H), 3.113 (s, 2H), 3.231 (s, 3H), 2.601-2.642 (m, 1H), 2.407-2.625 (m, 1H), 2.118-2.297 (m, 2H), 2.046-2.100 (m, 2H).

Example 58. Synthesis of 4-((4-(1-cyclobutyl-2-oxopyrrolidin-3-yl)phenyl)amino)-2-(2,6-difluorophenyl)-6,7-dihydro-5H-pyrrolo[3,4-d]pyrimidin-5-one, I-117

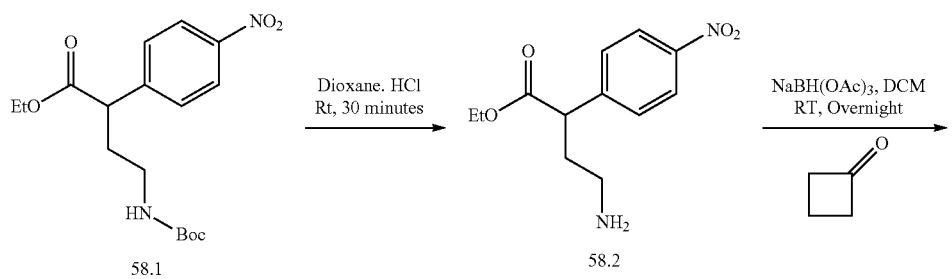

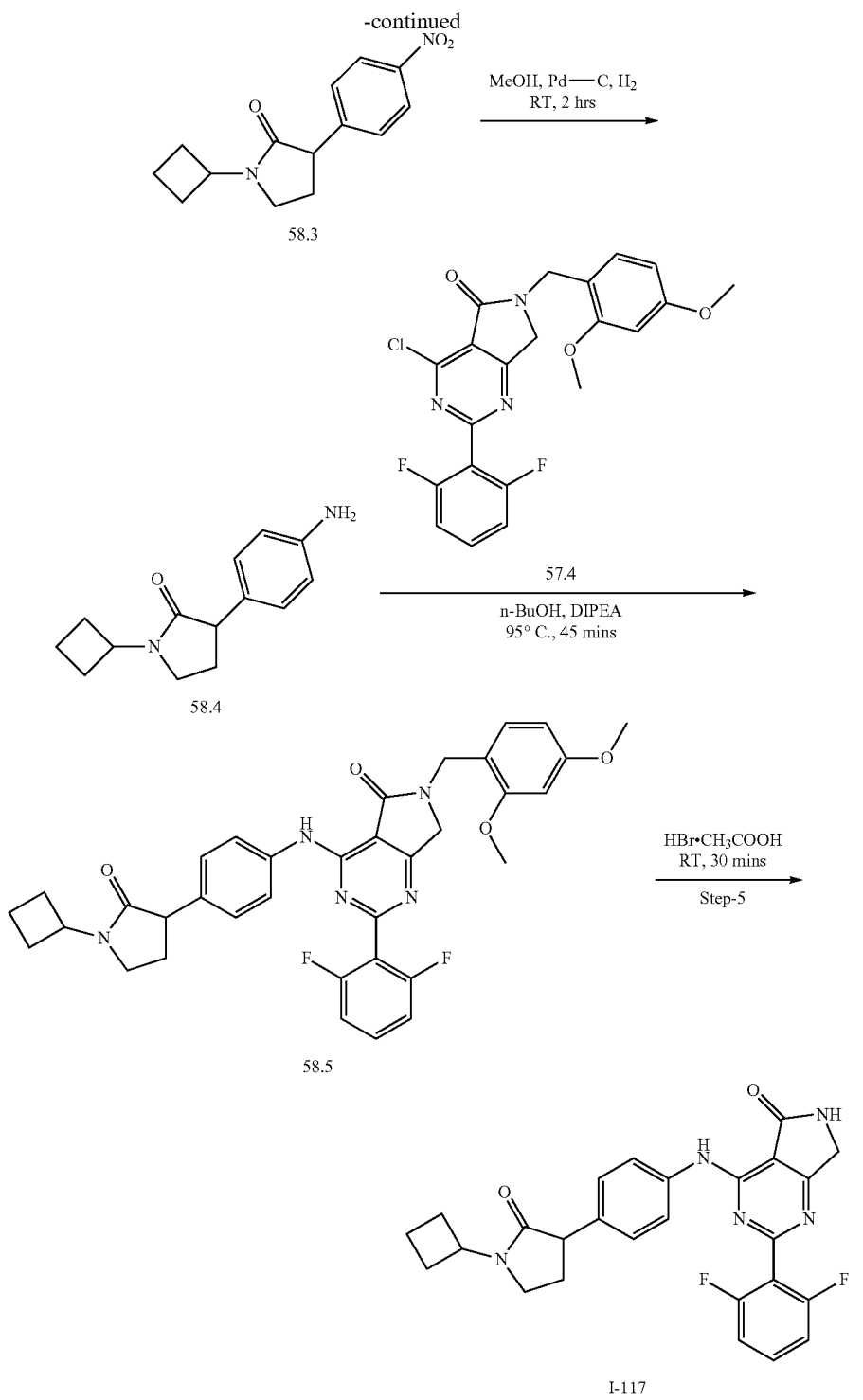

Synthesis of Compound 58.2.

A solution of 58.1 (1.1 g 3.12 mmol, 1.0 eq.) in dry hydrochloride solution in Dioxane (4.0M) (5.0 mL) was stirred at room temperature for 30 minutes. After completion of reaction, reaction mixture was poured into cold water and extracted using dichloromethane (15 mL×2). Organic layer was dried over sodium sulfate and used as such (without concentration).

Synthesis of Compound 58.3.

To a solution of compound 58.3 (0.65 g, 2.5 mmol, 1.0 eq) in dichloromethane was added cyclobutanone (0.18 g, 2.5 mmol, 1 eq.) at room temperature for 10 minutes. Sodium-triacetoxyborohydride was added portion wise (816 mg, 3.86 mmol, 1.5 eq.) and stirred for 16 hours at ambient temperature. After completion of the reaction, reaction mixture was diluted with dichloromethane (50 ml) and washed with bicarbonate (20 mL×2). Organic layer was dried over sodium sulphate and concentrate under reduced pressure at 45° C. Crude product was purified using flash column chromatography to afford compound 58.3 (0.49 g, 73%). MS (ES): m/z=261.3 [M+H]+.

Synthesis of Compound 58.4

To a suspension of Palladium on charcoal (200 mg) in methanol (20 ml) was added compound 58.3 (490 mg, 0.18 mmol. 1.0 eq.) under nitrogen atmosphere. A reaction mixture was flushed with $H_2$ (gas) at room temperature for 2 hours. After completion of reaction, mixture was filtered through celite. Solvent was removed under reduced pressure at 45° C. to afford compound 58.4 (380 mg, 95.36%). MS (ES): m/z 230.3 [M+H]+.

Synthesis of Compound 58.5.

To a solution of compound 57.4 (300 mg 0.69 mmol, 1.0 eq.) in 1-butanol (8.0 mL) were added compound 58.4 (160 mg, 0.69 mmol, 1.0 eq.) and diisopropylethylamine (224 mg, 1.74 mmol, 2.5 eq.) at room temperature. Reaction was heated at 85-95° C. for 2 hours. After completion of the reaction, reaction mixture was poured into water and extracted using ethyl acetate. Organic layer was washed with brine solution, dried over sodium sulfate and concentrated under reduced pressure. Crude was purified by column chromatography afford pure compound 58.5 (302 mg, 69.48%). MS (ES): m/z 626.6 [M+H]+

Synthesis of Compound I-117.

A solution of compound 58.5 (302 mg, 0.48 mmol, 1.0 eq.) in hydrobromic acid/$CH_3COOH$ solution (33%, 5 ml) was stirred at room temperature for 1 hour. After completion of reaction, reaction mixture was poured into cold water, neutralized with $NaHCO_3$ and extracted with ethyl acetate (50 ml×2). Solvent was removed under reduced pressure and crude was purified by flash column chromatography to furnish compound I-117 (170 mg, 74.07%). MS (ES): m/z 476.4 [M+H]+ $^1$H NMR (400 MHz, DMSO-d$^6$): δ 9.06 (s, 1H), 8.89 (s, 1H), 7.69-7.68 (d, 2H), 7.64-7.56 (m, 1H), 7.28-7.24 (t, 2H), 7.19-7.17 (d, 2H), 4.47 (S, 1H), 3.61 (m, 2H), 3.38 (m, 1H), 2.4 (m, 1H), 2.25 (m, 2H), 2.01 (m, 3H), 1.64 (m, 2H).

Example 59. Synthesis of (R)-4-((4-(1-cyclobutyl-2-oxopyrrolidin-3-yl)phenyl)amino)-2-(2,6-difluorophenyl)-6,7-dihydro-5H-pyrrolo[3,4-d]pyrimidin-5-one I-118

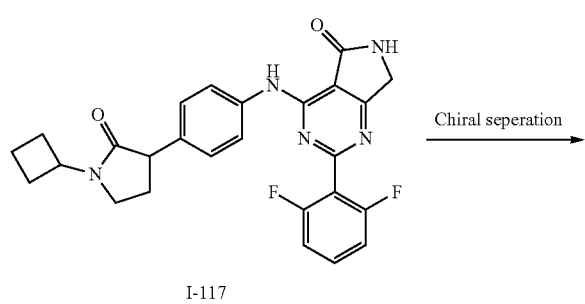

Compound I-118 was obtained by chiral separation of compound I-117. Chiral HPLC purity: 100%, $^1$H NMR (400 MHz, DMSO-d$_6$): δ 9.07 (s, 1H), 8.90 (s, 1H), 7.70-7.58 (m, 3H), 7.29-7.18 (m, 4H), 4.48 (s, 2H), 3.64-3.56 (m, 2H), 3.45-3.41 (m, 1H), 2.26-2.19 (m, 2H), 2.0 (bs, 4H), 1.65-1.57 (m, 2H) 1.24-1.17 (m, 1H)

Example 60. Synthesis of (S)-4-((4-(1-cyclobutyl-2-oxopyrrolidin-3-yl)phenyl)amino)-2-(2,6-difluorophenyl)-6,7-dihydro-5H-pyrrolo[3,4-d]pyrimidin-5-one, I-119

Compound I-119 was obtained by chiral separation of compound I-117. Chiral HPLC purity: 99.23%, $^1$H NMR (400 MHz, DMSO-d$_6$): δ 9.06 (s, 1H), 8.89 (s, 1H), 7.69-7.67 (d, 2H), 7.63-7.56 (m, 1H), 7.28-7.23 (t, 2H), 7.19-7.17 (d, 2H), 4.47 (s, 1H), 3.63-3.53 (m, 2H), 3.45 (m, 1H), 2.37 (m, 1H), 2.30 (m, 2H), 2.0 (bs, 1H) 1.68-1.61 (m, 1H).

Example 61. Synthesis of 2-(4-((2-(2,6-difluorophenyl)-5-oxo-6,7-dihydro-5H-pyrrolo[3,4-d]pyrimidin-4-yl)amino)phenyl)-N-ethyl-2-methylpropanamide, I-120

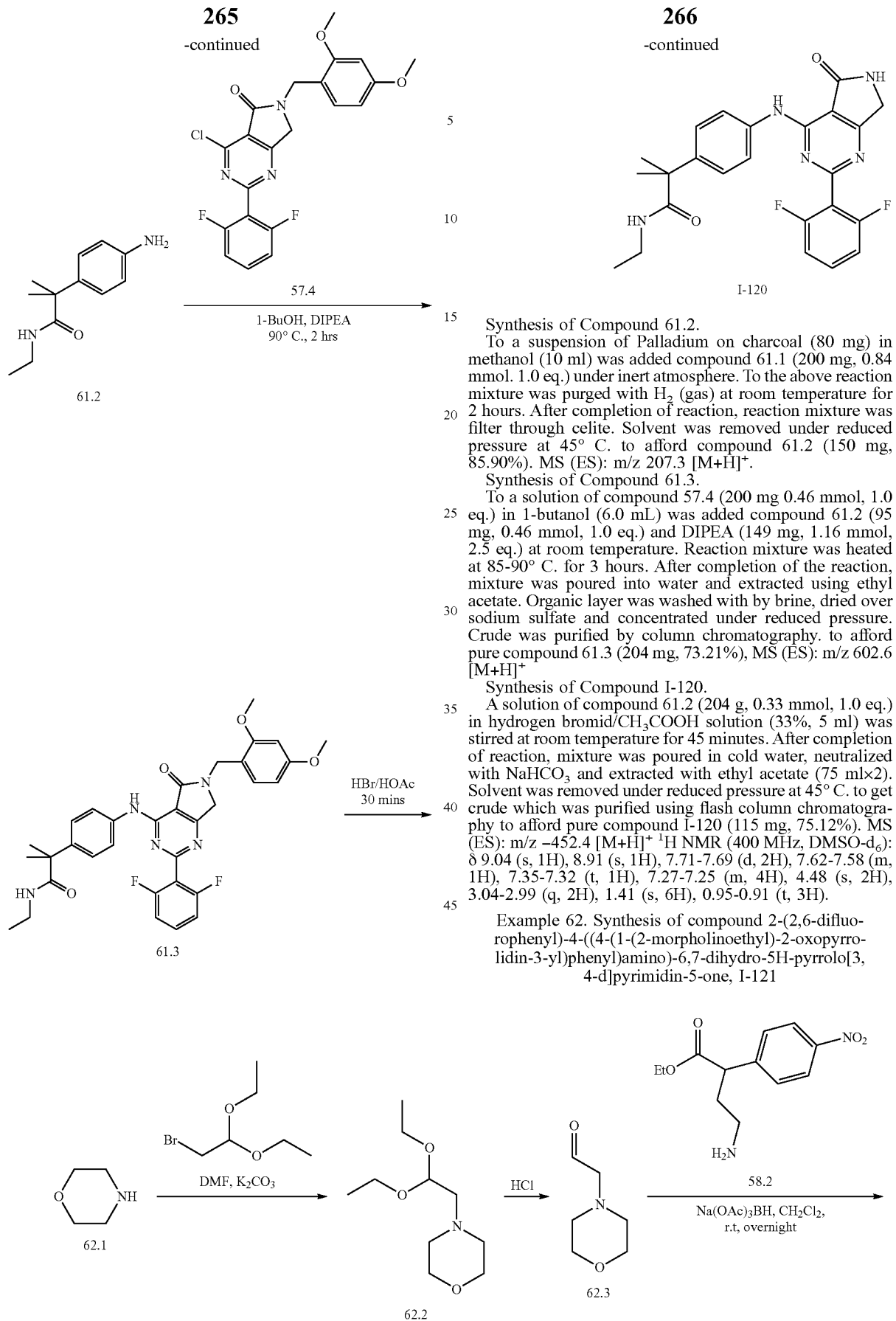

Synthesis of Compound 61.2.

To a suspension of Palladium on charcoal (80 mg) in methanol (10 ml) was added compound 61.1 (200 mg, 0.84 mmol. 1.0 eq.) under inert atmosphere. To the above reaction mixture was purged with $H_2$ (gas) at room temperature for 2 hours. After completion of reaction, reaction mixture was filter through celite. Solvent was removed under reduced pressure at 45° C. to afford compound 61.2 (150 mg, 85.90%). MS (ES): m/z 207.3 [M+H]$^+$.

Synthesis of Compound 61.3.

To a solution of compound 57.4 (200 mg 0.46 mmol, 1.0 eq.) in 1-butanol (6.0 mL) was added compound 61.2 (95 mg, 0.46 mmol, 1.0 eq.) and DIPEA (149 mg, 1.16 mmol, 2.5 eq.) at room temperature. Reaction mixture was heated at 85-90° C. for 3 hours. After completion of the reaction, mixture was poured into water and extracted using ethyl acetate. Organic layer was washed with by brine, dried over sodium sulfate and concentrated under reduced pressure. Crude was purified by column chromatography. to afford pure compound 61.3 (204 mg, 73.21%), MS (ES): m/z 602.6 [M+H]$^+$ Synthesis of Compound I-120.

A solution of compound 61.2 (204 g, 0.33 mmol, 1.0 eq.) in hydrogen bromid/$CH_3COOH$ solution (33%, 5 ml) was stirred at room temperature for 45 minutes. After completion of reaction, mixture was poured in cold water, neutralized with $NaHCO_3$ and extracted with ethyl acetate (75 ml×2). Solvent was removed under reduced pressure at 45° C. to get crude which was purified using flash column chromatography to afford pure compound I-120 (115 mg, 75.12%). MS (ES): m/z −452.4 [M+H]$^+$ $^1$H NMR (400 MHz, DMSO-d$_6$): δ 9.04 (s, 1H), 8.91 (s, 1H), 7.71-7.69 (d, 2H), 7.62-7.58 (m, 1H), 7.35-7.32 (t, 1H), 7.27-7.25 (m, 4H), 4.48 (s, 2H), 3.04-2.99 (q, 2H), 1.41 (s, 6H), 0.95-0.91 (t, 3H).

Example 62. Synthesis of compound 2-(2,6-difluorophenyl)-4-((4-(1-(2-morpholinoethyl)-2-oxopyrrolidin-3-yl)phenyl)amino)-6,7-dihydro-5H-pyrrolo[3,4-d]pyrimidin-5-one, I-121

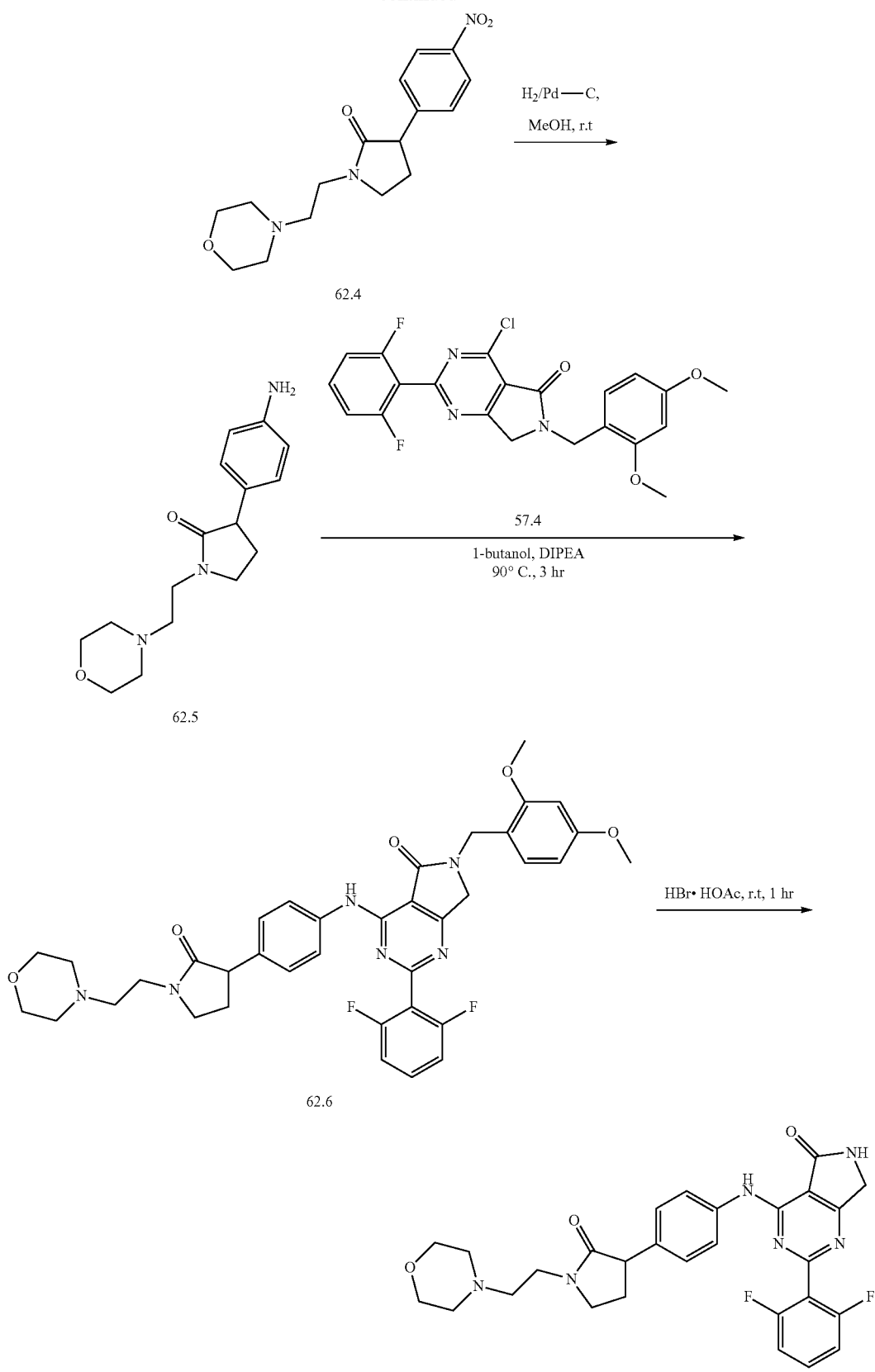

Synthesis of Compound 62.2.

Morpholine (2.0 g, 2.19 mmol, 1.0 eq), bromoacetaldehyde diethyl acetal (4.5 g, 2.54 mmol, 1.16 eq) and dry $K_2CO_3$ (6.04 g, 4.38 mmol, 2.0 eq) were mixed in dry dimethylformamide and heated at 120° C. for 5 h. After completion of reaction, reaction mixture was diluted with ethyl acetate (200 ml) and washed with water (200 ml×2) and then with brine (100 ml). Organic layer was dried over sodium sulphate and concentrated under reduced pressure at 45° C. Crude was purified by column chromatography to afford compound 62.2 (0.650 g, 14%). $^1$H NMR (400 MHz, $CDCl_3$): δ 4.660-4.686 (t, 1H), 3.686-3.738 (m, 6H), 3.528-3.3.581 (m, 2H), 3.554-3.577 (t, 6H), 1.216-1.252 (t, 6H).

Synthesis of Compound 62.3.

A solution of compound 62.2 (0.650 g, 0.37 mmol) in conc. HCl (10 mL) was refluxed for 2 h. After completion of the reaction, reaction mixture was allowed to cool at room temperature and dichloromethane (50 mL) was added to it. Organic layer was separated out, washed with water (50 mL) and brine (50 mL) dried over sodium sulphate and used as such in the next step considering 100% yield of compound 62.3 (0.413 g, 100%).

Synthesis of Compound 62.4.

To a solution of compound 58.2 (0.8 g, 3.17 mmol, 1.0 eq) in dichloromethane was added compound 62.3 (0.41 g, 3.17 mmol, 1 eq.) at room temperature and stirred for 10 minutes. Sodiumtriacetoxyborohydride (1.2 g, 4.7 mmol, 1.5 eq.) was added portion wise and stirred for overnight at room temperature. After completion of the reaction, reaction mixture was diluted with dichloromethane (50 ml) and washed with bicarbonate (20 ml×2). Organic layer was dried over sodium sulphate and concentrated under reduced pressure at 45° C. Crude was purified by column chromatography to afford compound 62.4 (0.23 g, 22.7%). MS (ES): m/z=320.3 $[M+H]^+$, Synthesis of Compound 62.5.

To a suspension of Pd/C (80 mg) in methanol (15 ml) was added compound 62.5 (230 mg, 0.72 mmol. 1.0 eq.) under nitrogen atmosphere. Reaction mixture was purged with $H_2$ (gas) at room temperature for 2 hours. After completion of reaction, mixture was filtered through celite. Solvent was removed under reduced pressure at 45° C. to afford compound 62.5 (180 mg, 86%). MS (ES): m/z 290.4 $[M+H]^+$, Synthesis of Compound 62.6.

To a solution of compound 57.4 (296 mg 0.68 mmol, 1.0 eq.) in 1-butanol (10.0 mL) was added compound 62.5 (198 mg, 0.68 mmol, 1.0 eq.) and diisopropylethylamine (221 mg, 1.71 mmol, 2.5 eq.) at room temperature. Reaction mixture was heated at 85-90° C. for 3 hours. After completion of reaction, mixture was poured into water and extracted using ethyl acetate. Organic layer was washed with by brine solution. Organic layer was dried over sodium sulfate and concentrated under reduced pressure. Crude was purified by column chromatography to afford pure compound 62.6 (385 mg, 82%). MS (ES): m/z 685.7 $[M+H]^+$ Synthesis of Compound I-121.

A solution of compound 62.6 (385 g, crude) in HBr/$CH_3COOH$ solution (33%, 7 ml) was stirred at room temperature for 1 hour. After completion of the reaction, reaction mixture was poured in cold water, neutralized with $NaHCO_3$ and extracted with ethyl acetate (75 ml×2). Solvent was removed under reduced pressure at 45° C. and resulting crude. was purified by column chromatography to afford pure compound I-121 (245 mg, 81.5%). MS (ES): m/z 535.5 $[M+H]^+$ $^1$H NMR (400 MHz, DMSO-d$^6$): δ 9.07 (s, 1H), 8.89 (s, 1H), 7.72-7.69 (d, 2H), 7.63-7.55 (m, 1H), 7.27-7.23 (m, 4H), 4.47 (s, 2H), 3.60-3.49 (m, 6H), 3.41-3.34 (m, 1H), 3.23-3.16 (m, 2H), 2.44-2.34 (m, 6H) 1.93-1.88 (m, 2H).

Example 63. Synthesis of (R)-2-(2,6-difluorophenyl)-4-((4-(1-(2-morpholinoethyl)-2-oxopyrrolidin-3-yl)phenyl)amino)-6,7-dihydro-5H-pyrrolo[3,4-d]pyrimidin-5-one, I-122

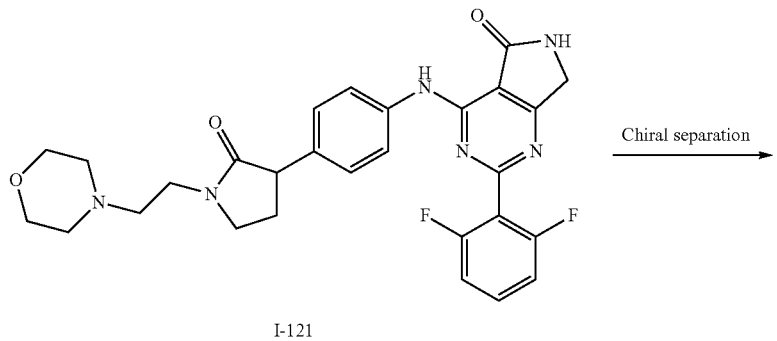

I-121

Chiral separation

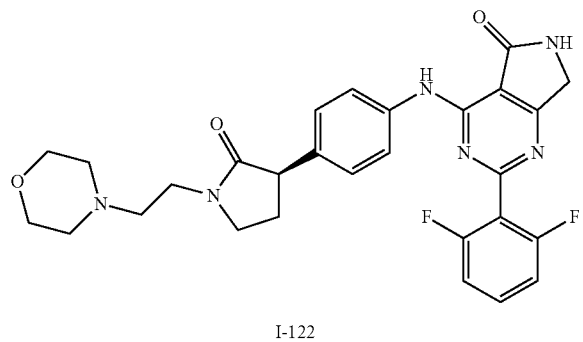

I-122

Compound I-122 was obtained by chiral separation of compound I-121. Chiral HPLC purity: 100%, $^1$H NMR (400 MHz, DMSO-d$_6$): δ 9.07 (s, 1H), 8.90 (s, 1H), 7.72-7.69 (d, 2H), 7.63-7.56 (m, 1H), 7.28-7.24 (m, 4H), 4.48 (s, 2H), 3.53 (bs, 6H), 3.39 (m, 1H), 3.21-3.10 (m, 2H), 2.41-2.30 (m, 6H) 1.92-1.90 (m, 2H).

Example 64. Synthesis of (S)-2-(2,6-difluorophenyl)-4-((4-(1-(2-morpholinoethyl)-2-oxopyrrolidin-3-yl)phenyl)amino)-6,7-dihydro-5H-pyrrolo[3,4-d]pyrimidin-5-one, I-123

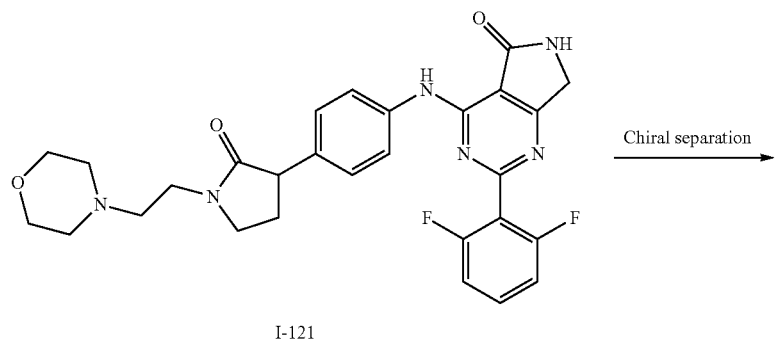

I-121

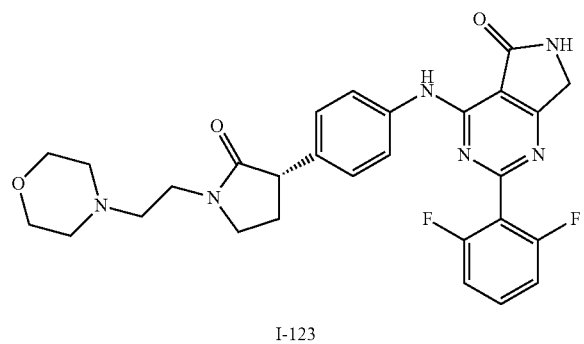 [SMILES: O=C1NCc2nc(-c3c(F)cccc3F)nc(Nc3ccc(C4CCN(CCN5CCOCC5)C4=O)cc3)c21]

I-123

Compound I-123 was obtained by chiral separation of compound I-121. Chiral HPLC purity: 98.57%, $^1$H NMR (400 MHz, DMSO-d$_6$): δ 9.07 (s, 1H), 8.89 (s, 1H), 7.72-7.69 (d, 2H), 7.61-7.55 (m, 1H), 7.28-7.23 (m, 4H), 4.47 (s, 2H), 3.58 (bs, 6H), 3.39 (m, 1H), 3.24-3.21 (m, 2H), 2.40-2.33 (m, 6H) 1.92-1.91 (m, 2H).

Example 65. Synthesis of compound 2-(2,6-difluorophenyl)-4-((4-(3-methyl-2-oxo-1-(tetrahydro-2H-pyran-4-yl)pyrrolidin-3-yl)phenyl)amino)-6,7-dihydro-5H-pyrrolo[3,4-d]pyrimidin-5-one, I-124

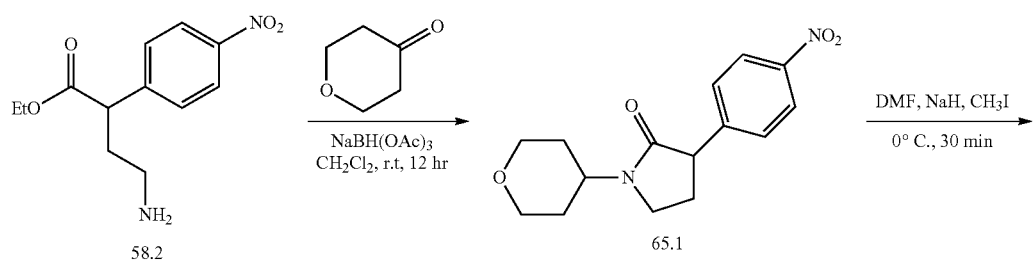

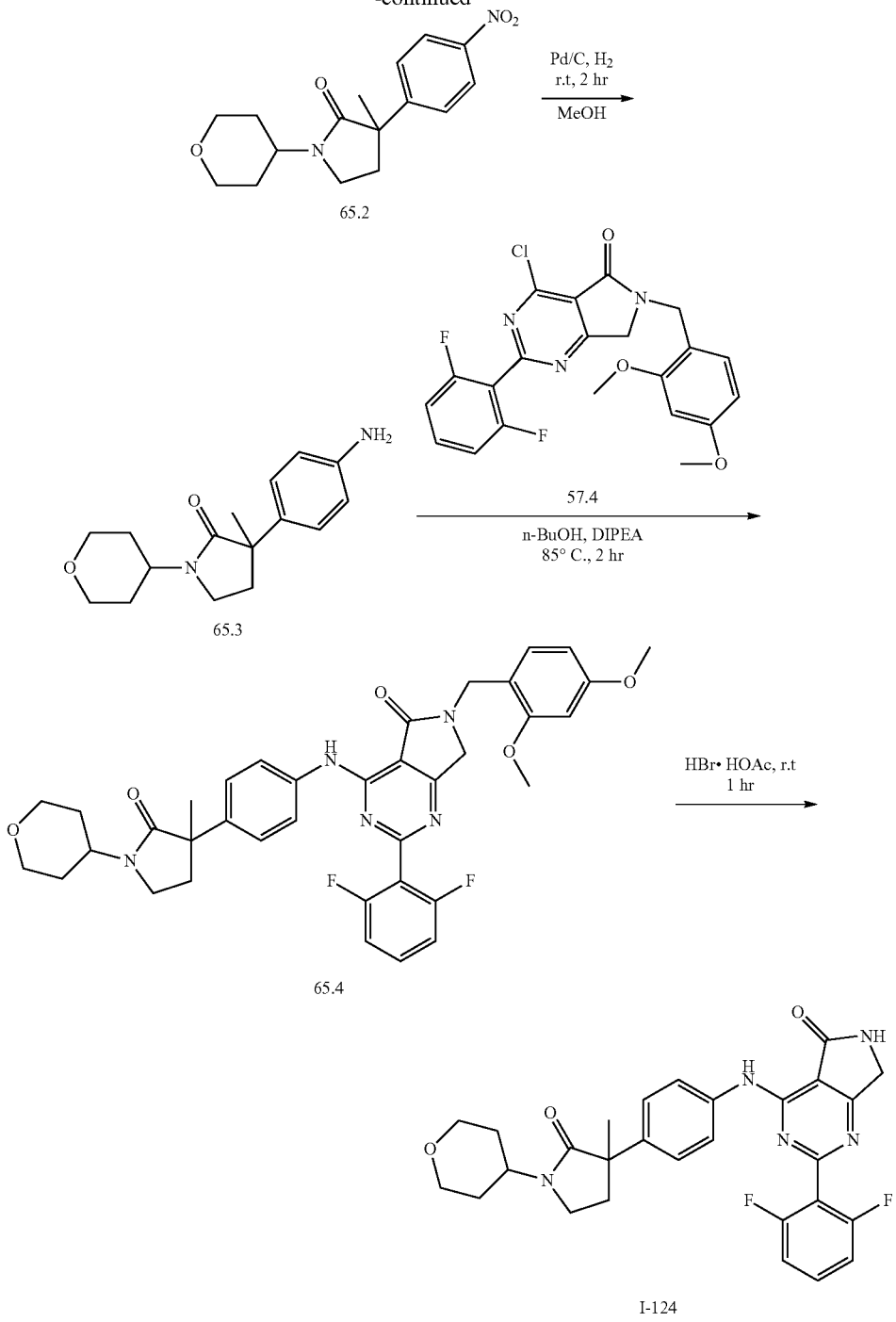

Synthesis of Compound 65.1.

To a solution of compound 58.2 (0.78 g, 3.12 mmol, 1.0 eq) was added tetrahydro-4H-pyran-4-one (0.31 g, 3.12 mmol, 1 eq.) at room temperature for 10 minutes. Sodium-triacetoxyborohydride was added portion wise (1.17 g, 4.6 mmol, 1.5 eq.). Reaction was stirred for overnight at room temperature. After completion of the reaction, reaction mixture was diluted with dichloromethane (50 ml) and washed with bicarbonate (20 ml×2). Organic layer was dried over sodium sulphate and concentrate under reduced pressure at 45° C. Crude was purified by column chromatography to afford compound 65.1 (0.5 g, 55%). MS (ES): m/z=291.3 [M+H]$^+$ Synthesis of Compound 65.2.

To a solution of compound 126.1 (0.5 g, 1.71 mmol. 1.0 eq.) in dry DMF (5.0 ml) was added NaH (60%) (105 mg, 2.57 mmol, 1.5 eq.) at 0° C. and stirred for 20 minutes. To the above reaction mixture was added drop wise methyl iodide (290 mg, 2.06 mmol, 1.2 eq.) and stirred for 30 minutes at 0-10° C. After completion of reaction, reaction mixture was poured into cold water and product was extracted with ethyl acetate (50 ml×2). Organic layer was washed with brine (25 ml×3) and dried over sodium sulphate. Solvent was removed under reduced pressure at 45° C. to get crude, Crude was purified by column chromatography to afford pure compound 65.2 (0.4 g, 76.31%). MS (ES): m/z 305.3 [M+H]⁺

Synthesis of Compound 65.3.

To a suspension of Pd/C (30 mg) in methanol (10 ml) was added compound 65.2 (114 mg, 0.37 mmol. 1.0 eq.) under nitrogen atmosphere. Above reaction mixture was purged with H₂ (gas) at room temperature for 2 hours. After completion of the reaction, reaction mixture was filter through celite. Solvent was removed under reduced pressure at 45° C. to afford compound 65.3 (98 mg, 95.36%). MS (ES): m/z 275.4 [M+H]⁺

Synthesis of Compound 65.4.

To a solution of compound 57.4 (157 g 0.36 mmol, 1.0 eq.) in 1-butanol (5.0 mL) was added compound 65.3 (98 mg, 0.36 mmol, 1.0 eq.) and diisopropylethylamine (117 mg, 0.91 mmol, 2.5 eq.) at room temperature. Reaction was heated at 85-90° C. for 2 hours. After completion of the reaction, mixture was poured into water and extracted using ethyl acetate. Organic layer was washed with by brine solution and dried over sodium sulfate and concentrated under reduced pressure. Crude was purified by column chromatograph to afford pure compound 65.4 (203 mg, 83%). MS (ES): m/z 670.7 [M+H]⁺

Synthesis of Compound I-124.

A solution of compound 65.4 (203 mg, crude) in HBr.CH₃COOH solution (33%, 5 ml) was stirred at room temperature for 1 hour. After completion of reaction, mixture was poured into cold water, neutralized with NaHCO₃ and product was extracted with ethyl acetate (50 ml×2). Solvent was removed under reduced pressure at 45° C. to get crude which was purified using column chromatography to afford pure compound I-124 (150 mg, 95.3%). MS (ES): m/z 520.3 [M+H]⁺, LCMS purity: 95.97%, ¹H NMR (400 MHz, DMSO-d⁶): δ 9.05 (s, 1H), 8.90 (s, 1H), 7.71-7.69 (d, 2H), 7.64-7.56 (m, 1H), 7.34-7.32 (d, 2H), 7.29-7.24 (t, 2H), 4.49 (S, 1H), 4.41 (s, 2H), 4.04-4.0 (m, 1H), 3.98-3.85 (m, 1H), 3.41-3.29 (m, 3H), 3.21-3.16 (m, 1H), 2.50-2.27 (m, 1H) 2.08-2.01 (m, 1H), 1.73-1.67 (m, 2H), 1.52-1.46 (T, 2H), 1.37 (s, 3H).

Example 66. Synthesis of compound (S)-2-(2,6-difluorophenyl)-4-((4-(3-methyl-2-oxo-1-(tetrahydro-2H-pyran-4-yl)pyrrolidin-3-yl)phenyl)amino)-6,7-dihydro-5H-pyrrolo[3,4-d]pyrimidin-5-one, I-125

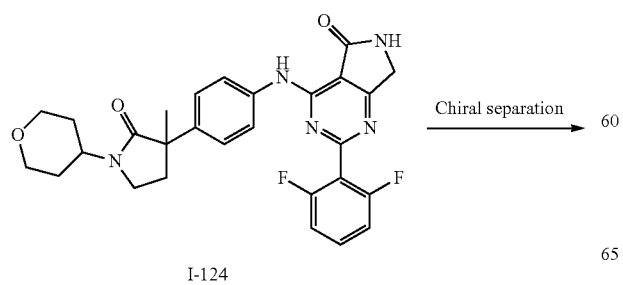

I-124

Chiral separation ⟶

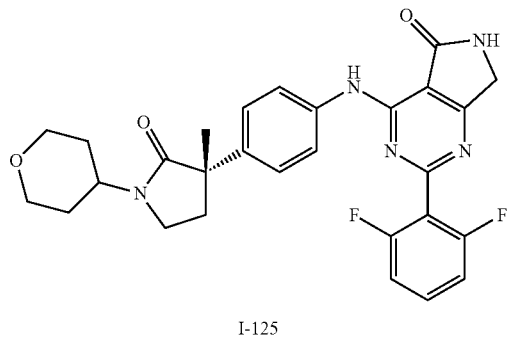

I-125

Compound I-125 was obtained by chiral separation of compound I-124. Chiral HPLC purity: 95.13%, ¹H NMR (400 MHz, DMSO-d⁶): δ 9.05 (s, 1H), 8.90 (s, 1H), 7.71-7.69 (d, 2H), 7.62-7.58 (m, 1H), 7.34-7.32 (d, 2H), 7.29-7.25 (t, 2H), 4.47 (S, 1H), 4.05-3.99 (m, 1H), 3.98-3.85 (m, 1H), 3.41-3.29 (m, 3H), 3.22-3.16 (m, 1H), 2.50-2.27 (m, 1H) 2.08-2.01 (m, 1H), 1.73-1.67 (m, 2H), 1.52-1.46 (T, 2H), 1.37 (s, 3H).

Example 67. Synthesis of (R)-2-(2,6-difluorophenyl)-4-((4-(3-methyl-2-oxo-1-(tetrahydro-2H-pyran-4-yl)pyrrolidin-3-yl)phenyl)amino)-6,7-dihydro-5H-pyrrolo[3,4-d]pyrimidin-5-one I-126

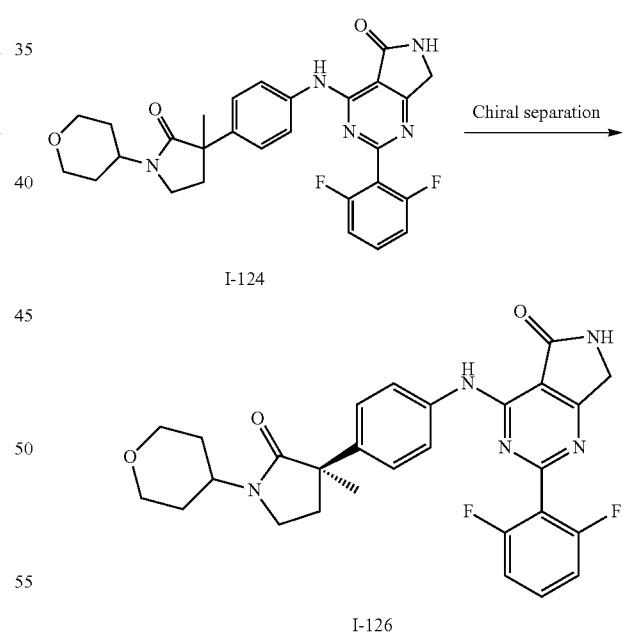

Compound I-126 was obtained by chiral separation of compound I-124. HPLC purity: 90.22%, ¹H NMR (400 MHz, DMSO-d⁶): δ 9.05 (s, 1H), 8.90 (s, 1H), 7.71-7.69 (d, 2H), 7.62-7.58 (m, 1H), 7.34-7.32 (d, 2H), 7.29-7.24 (t, 2H), 4.49 (S, 1H), 4.41 (s, 2H), 4.04-4.0 (m, 1H), 3.98-3.85 (m, 1H), 3.41-3.29 (m, 3H), 3.21-3.16 (m, 1H), 2.50-2.27 (m, 1H) 2.08-2.01 (m, 1H), 1.73-1.67 (m, 2H), 1.52-1.46 (T, 2H), 1.37 (s, 3H).

Example 68. Synthesis of 4-((2-(2,6-difluorophenyl)-5-oxo-6,7-dihydro-5H-pyrrolo[3,4-d]pyrimidin-4-yl)amino)-N-(2-morpholinoethyl)benzamide I-127

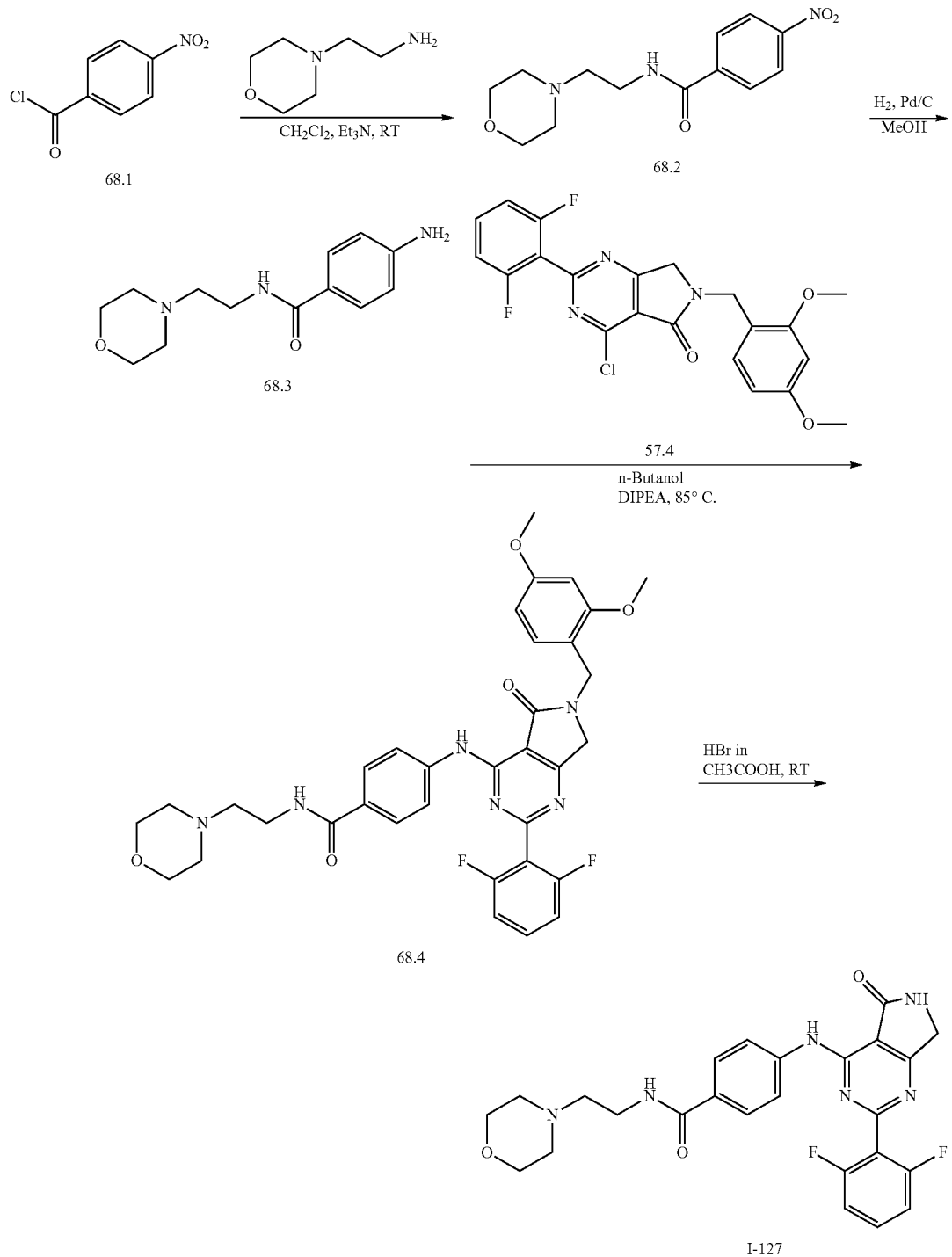

Synthesis of Compound 68.2.

A solution of 4-nitrobenzoyl chloride (0.2 g 1.0 mmol, 1.0 eq.) in dry dichloromethane (5.0 mL) was cooled to 0° C. Triethylamine (218 mg, 2.0 mmol, 2.0 eq.) and 2-morpholinoethan-1-amine (210 mg, 1.6 mmol, 1.5 eq.) were added at same temperature. The reaction mixture was allowed to warm at room temperature and was stirred for 2 hours. After completion of the reaction, mixture was poured into water and extracted using dichloromethane. Organic layer was washed with brine solution, dried over sodium sulfate and concentrated under reduced pressure. Crude was purified by column chromatography to afford pure compound 68.2 (0.17 g, 56.47%), MS (ES): m/z=280.3 [M+H]$^+$.

Synthesis of Compound 68.3.

To a suspension of Palladium on charcoal (80 mg) in methanol (10 ml) was added compound 68.2 (170 mg, 0.6 mmol. 1.0 eq.). The reaction mixture was purged with H$_2$ (gas) at room temperature for 2 hours. After completion of the reaction, mixture was filter through celite. Solvent was removed under reduced pressure at 45° C. to afford compound 68.3 (140 mg, 92.59%). MS (ES): m/z 250.3 [M+H]+

Synthesis of Compound 68.4.

To a solution of compound 57.4 (150 mg 0.34 mmol, 1.0 eq.) in 1-butanol (5.0 mL) were added 4-amino-N-(2-morpholinoethyl)benzamide (86 mg, 0.34 mmol, 1.0 eq.) and diisopropylethylamine (112 mg, 0.87 mmol, 2.5 eq.) at room temperature. Reaction was heated at 85-90° C. for 3 hours. After completion of the reaction, mixture was poured into water and extracted using ethyl acetate. Organic layer was washed with by brine solution, dried over sodium sulfate and concentrated under reduced pressure. Crude was purified by column chromatography to afford pure compound 68.4 (160 mg, 71.45%) MS (ES): m/z 645.7 [M+H]+

Synthesis of Compound I-127.

A solution of compound 68.4 (160 g, 0.24 mmol, 1.0 eq.) in HBr. CH₃COOH solution (33%, 5 ml) was stirred at room temperature for 45 minutes. After completion of the reaction, mixture was poured into cold water, neutralized with NaHCO₃ and extracted with ethyl acetate (75 ml×2). Solvent was removed under reduced pressure at 45° C. Crude was purified using column chromatography to furnish pure compound I-127 (80 mg, 65.18%). MS (ES): m/z −495.5 [M+H]+, ¹H NMR (400 MHz, DMSO-d₆): δ 9.25 (s, 1H), 8.95 (s, 1H), 8.34-8.31 (t, 1H), 7.89-7.82 (m, 4H), 7.64-7.61 (m, 1H), 7.31-7.27 (t, 2H), 4.51 (s, 2H), 3.57-3.55 (m, 4H), 3.39-3.36 (m, 2H), 2.45-2.43 (m, 2H), 2.41-2.33 (m, 4H).

Example 69. Synthesis of Compound 4-((4-((1H-1,2,3-triazol-1-yl)methyl)phenyl)amino)-2-(2,6-difluorophenyl)-6,7-dihydro-5H-pyrrolo[3,4-d]pyrimidin-5-one, I-128

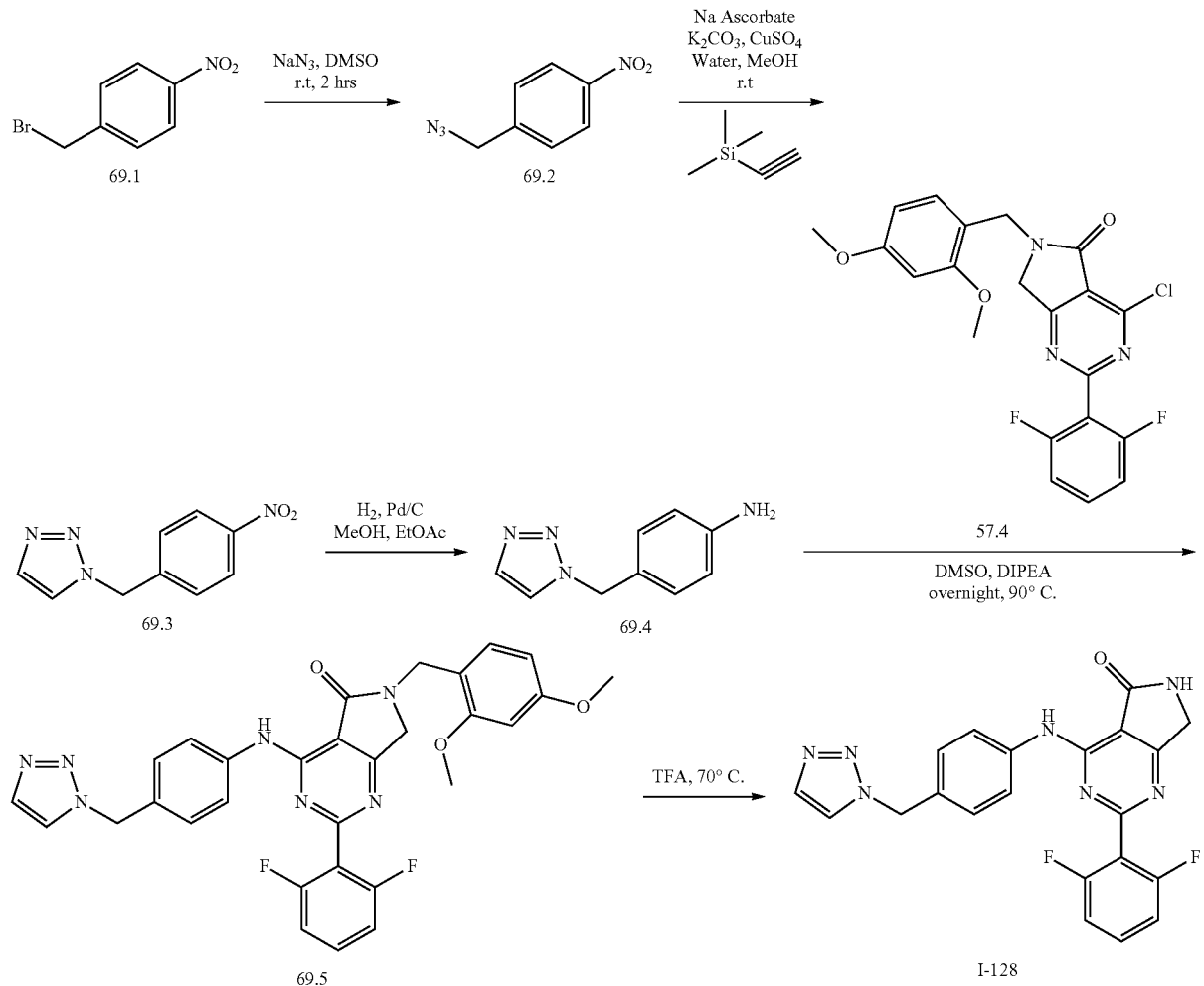

Synthesis of Compound 69.2.

To a solution of compound 69.1 (4 g 18.51 mmol, 1.0 eq.) in DMSO (20 mL) was added sodium azide (1.44 g, 22.22 mmol, 1.2 eq.) at room temperature Reaction mixture was stirred at room temperature for 2 hrs. After completion of the reaction, mixture was poured into water and extracted using ethyl acetate. Organic layer was dried over sodium sulfate and concentrated under reduced pressure to afford pure compound 69.2 (3.2 g, 97.01%). MS (ES): No ionisation [M+H]+, Synthesis of Compound 69.3.

Compound 69.2 (4.03 g, 22.6 mmol) was dissolved in methanol (6.3 mL) and water (6.3 mL). To the solution were added trimethylsilylacetylene (3.33 g, 33.93 mmol, 1.5 eq), potassium carbonate (3.74 g, 27.14 mmol, 1.2 q), copper sulfate (1.12 g, 4.52 mmol, 0.2 eq) and sodium ascorbate (1.79 g, 9.048 mmol, 0.4 eq). The reaction was stirred at room temperature for 24 hours. After completion of reaction, aq. ammonium hydroxide was added to the reaction and mixture was extracted with ethyl acetate. Organic layer was dried over sodium sulfate and concentrated under reduced pressure. Crude was purified using flash column chromatography to afford compound compound 69.3 (0.8 g, 17.32%). MS (ES): m/z 205.3 [M+H]$^+$.

Synthesis of Compound 69.4.

To a suspension of palladium on charcoal (0.800 g) in methanol (20 ml) was added compound 69.3 (0.8 g, 3.917 mmol, 1.0 eq.) under nitrogen atmosphere. The reaction mixture was purges using H$_2$ (gas) at room temperature for 3 hours. After completion of reaction, mixture was filtered through celite. Solvent was removed under reduced pressure at 45° C. to afford compound 69.4 (0.640 g, 93.77%). MS (ES): m/z 175.1 [M+H]$^+$, Synthesis of Compound 69.5.

To a solution of compound 57.4 (250 mg 0.0.578 mmol, 1.0 eq.) in DMSO (3.0 mL) was compound 69.4 (0.110 g, 0.636 mmol, 1.1 eq.) and diisopropylethylamine (0.3 ml, 0.1.736 mmol, 3 eq.) at room temperature. The reaction mixture was heated at 80° C. for 1 hour. After completion of reaction, mixture was poured into water and extracted using ethyl acetate. Organic layer was washed with brine, dried over sodium sulfate and concentrated under reduced pressure. Crude was purified by column chromatography to afford pure compound 69.5 (0.179 g, 54.28%), MS (ES): m/z 570.4 [M+H]$^+$.

Synthesis of Compound I-128.

A solution of compound 69.5 (0.179 g, 0.314 mmol, 1.0 eq.) in hydrogen bromide/acetic acid solution (33%, 4 ml) was stirred at room temperature for 45 minutes. After completion of reaction, reaction mixture was poured into cold water, neutralized with NaHCO$_3$ and extracted with ethyl acetate (75 ml×2). Solvent was removed under reduced pressure at 45° C. The crude was purified using column chromatography to afford pure compound I-128 (28 mg, 21.24%). MS (ES): m/z –420.20 [M+H]$^+$; $^1$H NMR (400 MHz, DMSO-d$_6$): δ 9.11 (s, 1H), 8.90 (s, 1H), 8.18 (d, 1H), 7.73 (m, 3H), 7.60 (m, 1H), 7.28 (m, 4H), 5.57 (s, 2H), 4.48 (s, 2H).

Example 70. Synthesis of methyl (1r,3r)-3-((2-(2,6-difluorophenyl)-5-oxo-6,7-dihydro-5H-pyrrolo[3,4-d]pyrimidin-4-yl)amino)cyclobutane-1-carboxylate, I-129

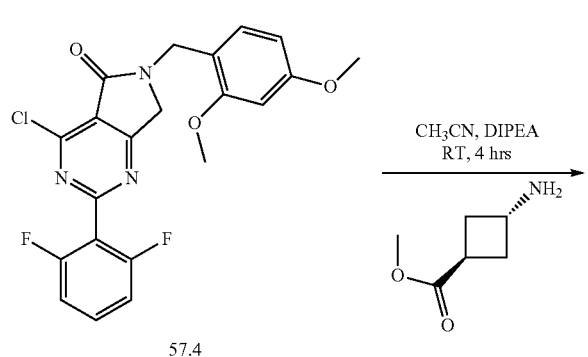

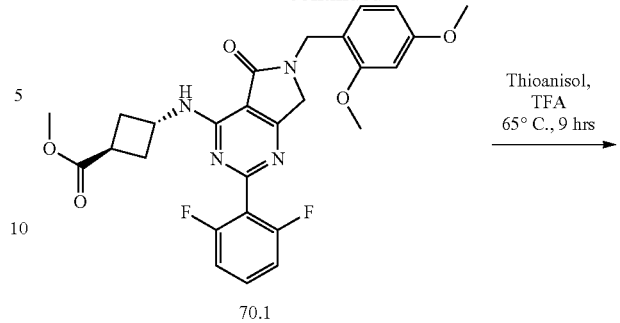

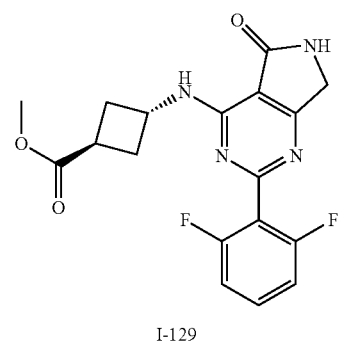

Synthesis of Compound 70.1.

To a solution of compound 57.4 (100 mg 0.23 mmol, 1.0 eq.) in acetonitrile (10.0 mL) was added methyl (1r,3r)-3-aminocyclobutane-1-carboxylate (39 mg, 0.23 mmol, 1.0 eq.) and diisopropylethylamine (75 mg, 0.58 mmol, 2.5 eq.) at room temperature. reaction was stirred for 3 hours at ambient temperature. After completion of reaction, mixture was poured into water and extracted using ethyl acetate. Organic layer was washed with by brine solution, dried over sodium sulfate and concentrated under reduced pressure. Crude was purified by triturated with diethyl ether to afford pure compound 70.1 (100 mg, 82.33%). MS (ES): m/z 525.5 [M+H]$^+$.

Synthesis of Compound I-129.

A solution of compound 70.1 (100 mg, 0.19 mmol, 1 eq.) in thioanisole (50 mg, 50%) and trifluoroacetic acid (1.0 mL) was stirred at 70° C. for 9 hours. After completion of the reaction, mixture was poured into cold water and product was extracted with ethyl acetate (75 ml×2) and dried over sodium sulphate. Solvent was removed under reduced pressure at 45° C. and crude, was purified by preparative TLC to afford pure compound I-129 (12 mg, 16.81%). MS (ES): m/z=375.4 [M+H]$^+$, $^1$H NMR (400 MHz, DMSO-d$_6$): δ 7.57-7.49 (m, 1H), 7.15-7.10 (m, 2H), 4.86 (m, 1H), 4.42 (s, 2H), 3.71 (s, 3H), 3.18-3.13 (m, 1H), 2.69-2.64 (m, 2H), 2.53-2.46 (m, 2H).

Example 71. Synthesis of compound (1r,3r)-3-((2-(2,6-difluorophenyl)-5-oxo-6,7-dihydro-5H-pyrrolo[3,4-d]pyrimidin-4-yl)amino)cyclobutane-1-carboxylic Acid, I-130

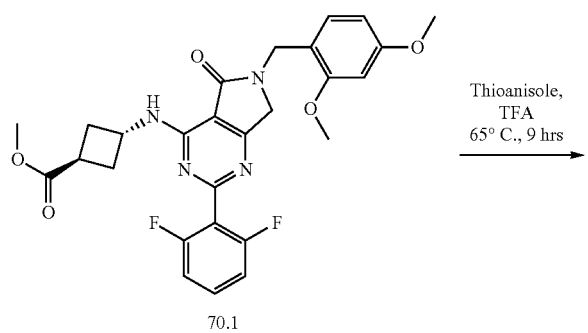

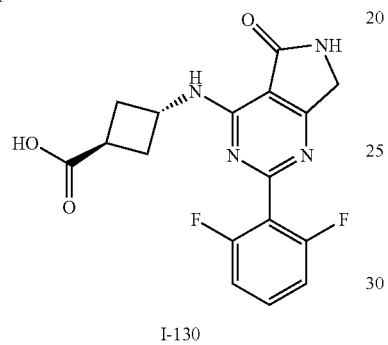

I-130

Synthesis of Compound I-130.

A solution of compound 70.1 (100 mg, 0.19 mmol, 1 eq.) in thioanisole (50 mg, 50%) and trifluoroaceticacid (1.0 ml) was stirred at 70° C. for 9 hours. After completion of the reaction, mixture was poured into cold water and product was extracted with ethyl acetate (75 ml×2) and dried over sodium sulphate. Solvent was removed under reduced pressure at 45° C. and crude was purified by preparative TLC to afford compound I-130 (8 mg, 11.6%). MS (ES): m/z 361.3 [M+H]+, 1H NMR (400 MHz, DMSO-$d_6$): δ 7.55-7.51 (m, 1H), 7.14-7.10 (m, 2H), 4.42 (s, 2H), 3.14-3.09 (m, 1H), 2.70-2.65 (m, 2H), 2.53-2.45 (m, 2H).

Example 72. Synthesis of compound (1r,3r)-3-((2-(2,6-difluorophenyl)-5-oxo-6,7-dihydro-5H-pyrrolo[3,4-d]pyrimidin-4-yl)amino)-N-ethylcyclobutane-1-carboxamide, I-131

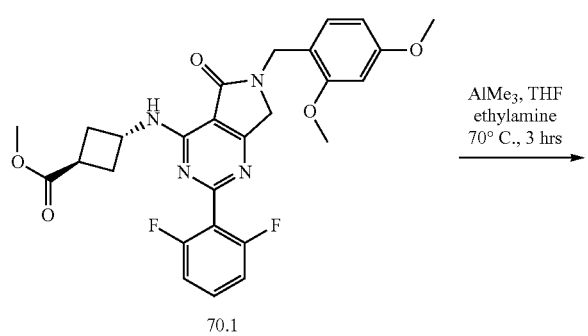

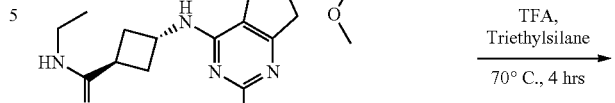

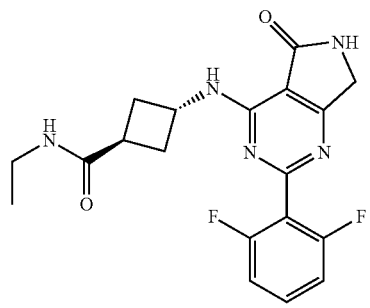

I-131

Synthesis of Compound 72.1.

To a solution of compound 70.1 (300 mg, 0.57 mmol, eq.) in dry THF (5.0 ml) were added Ethylamine (0.42 ml, 1.5 eq. 2M solution in THF) and diisopropylethylamine (147 mg, 11.4 mmol, 2.0 eq.) under nitrogen atmosphere at room temperature. The reaction mixture was cooled to 0° C. and Trimethyl aluminum (0.86 ml, 3.0 eq, 2M solution in toluene) was added at same temperature. Reaction mixture was stirred at 70° C. for 3 hours. After completion of reaction, mixture was poured into saturated bicarbonate and extracted using ethyl acetate. Organic layer was washed with brine solution, dried over sodium sulfate and concentrated under a reduced pressure. The crude was purified using column chromatography to provide compound 72.1 (220 mg, 71.55%). MS (ES): m/z 537.5 [M+H]+.

Synthesis of Compound I-131.

A solution of compound 72.1 (220 mg, 0.4 mmol, 1 eq.) in trifluoroaceticacid (2.0 ml) and triethylsilane (142 mg, 1.2 mmol, 3.0 eq.) was stirred at 70° C. for 9 hours. After completion of the reaction, mixture was concentrated and residue was poured into saturated bicarbonate. The product was extracted with ethyl acetate (75 ml×2) and dried over sodium sulphate. Solvent was removed under reduced pressure at 45° C. to get crude which was purified using column chromatography to afford pure compound I-131 (110 mg, 11.6%). MS (ES): m/z=388.4 [M+H]+, 1H NMR (400 MHz, DMSO-$d_6$): δ 8.62 (s, 1H), 7.78 (t, 1H), 7.57 (m, 1H), 7.48-7.46 (d, 1H), 7.24-7.20 (t, 2H), 4.83-4.81 (m, 1H), 4.35 (s, 1H), 3.07-3.03 (m, 2H), 2.84 (m, 1H), 2.39-2.34 (m, 4H), 1.00-0.97 (t, 3H).

Example 73. Synthesis of compound methyl 2-(6-((2-(2,6-difluorophenyl)-5-oxo-6,7-dihydro-5H-pyrrolo[3,4-b]pyridin-4-yl)amino)pyridin-3-yl)acetate, I-132
Synthesis of Compound 73.2.
To a solution of compound 73.1 (0.1 g, 0.427 mmol, 1.0 equiv) in 1,4-dioxane: water (8:2) was added 2,6-difluoro phenylboronic acid (0.135 g, 0.854 mmol, 2.0 equiv), and
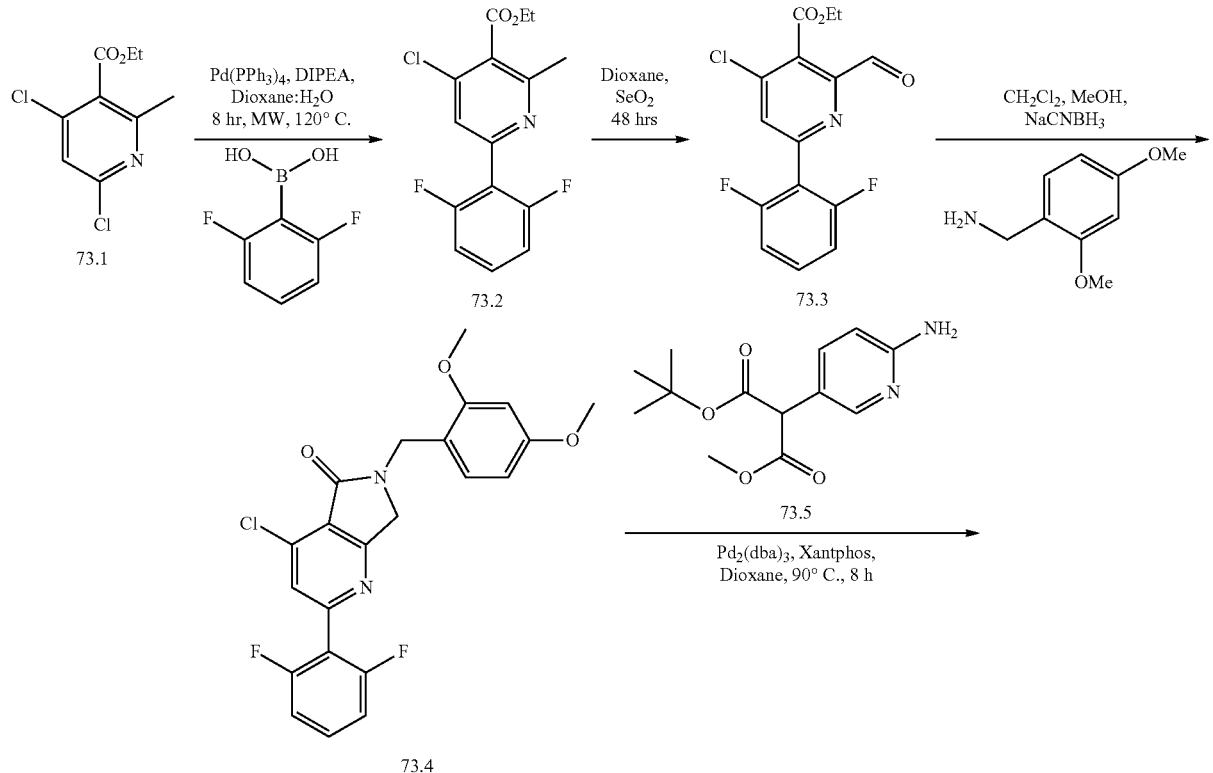
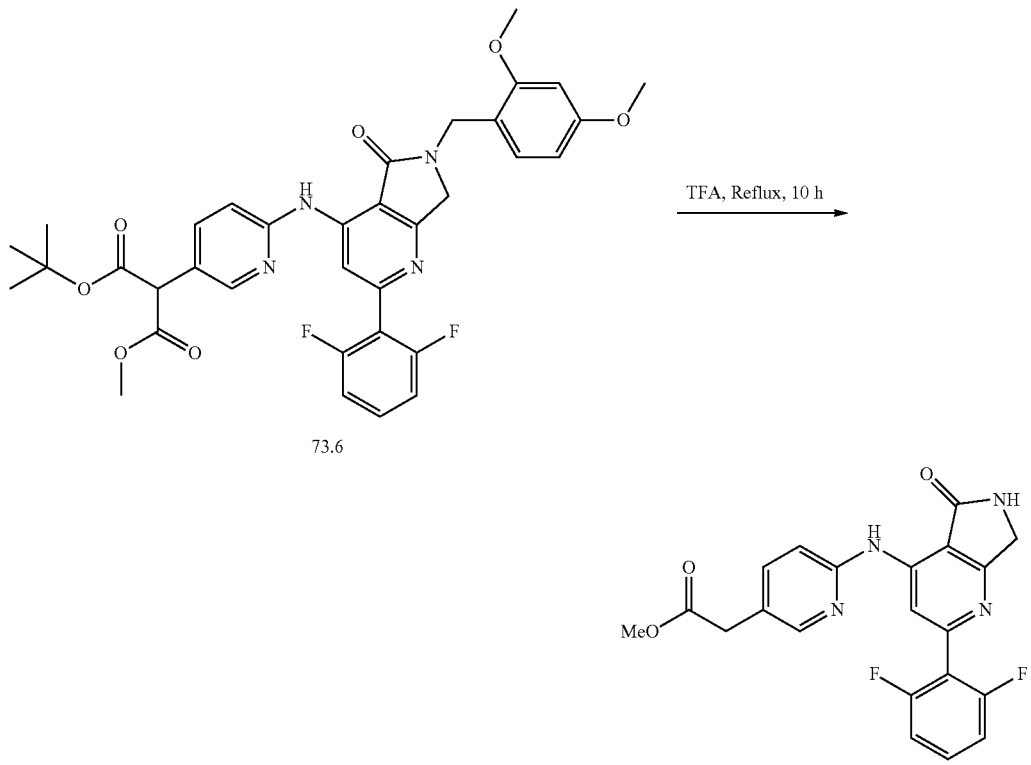

diisopropylethylamine (0.3 mL, 1.70 mmol, 4.0 equiv). Reaction mixture was degassed under argon gas for 5-10 min. and Pd(PPh$_3$)$_4$ (0.05 g, 0.0427 mmol, 0.1 equiv) was added. Mixture was degassed under argon for additional 5 minutes. Reaction mixture was heated at 120° C. in a microwave for 8 hours. Upon completion of the reaction, mixture was poured into water and product was extracted with ethyl acetate. Organic layers were combined and dried over sodium sulphate and concentrated under reduced pressure to obtain crude material which was purified using column chromatography to obtain pure 73.2 (0.045 g, 59.85%). MS (ES): m/z 312.05 [M+H]$^+$.

Synthesis of Compound 73.3.

A solution of compound 73.2 (0.375 g, 1.201 mmol, 1.0 equiv) and selenium dioxide (0.266 g, 2.402 mmol, 2.0 equiv) in 1,4-dioxane (10 mL) was heated at 110° C. until starting material was consumed (ca. 48 hrs). Reaction mixture was filtered through celite and filtrate was concentrated under reduced pressure to get crude compound 73.3 (0.375 g) which was used as such for in the next step without purification, MS (ES): m/z 326.0 [M+H]$^+$.

Synthesis of Compound 73.4.

To a solution of compound 73.3 (0.375 g, 0.1.153 mol, 1.0 equiv) in dichloromethane (8 mL) and methanol (2 mL) was added 2,4-dimethoxy benzyl amine (0.250 g, 1.499 mmol, 1.3 equiv) and stirred at room temperature for 30 min. Sodium cynoborohydride (0.290 g, 4.612 mmol, 4.0 equiv) was added at 0° C. Reaction was stirred at ambient temperature overnight. After completion, reaction mixture was poured into water and product was extracted twice with ethyl acetate. Organic layer was dried over sodium sulphate and concentrated under reduced pressure to get crude material which was purified by column chromatography to provide compound 73.4 (0.190 g, 36.67%). MS (ES): m/z 431.1 [M+H]$^+$ Synthesis of Compound 73.6.

To a solution of compound 73.4 (0.160 g, 0.372 mmol, 1.0 equiv) and compound 73.5 (0.109 g, 266.2 mmol, 1.1 equiv) in 1,4-dioxane was added and K$_2$CO$_3$ (0.128 mL, 0.930 mmol, 2.5 equiv). Reaction mixture was degassed under argon gas for 5-10 min. and Pd$_2$(dba)$_3$ (0.021 g, 0.0372 mmol, 0.1 equiv) and Xantphos (0.043 g, 0.0744 mmol, 0.2 equiv) were added. Mixture was degassed using argon for additional 5 min. Reaction mixture was heated at 100° C. for 8 hrs. After completion of the reaction, mixture was poured into water and product was extracted with ethyl acetate. Organic layers were combined and dried over sodium sulphate and concentrated under reduced pressure to obtain crude material which was purified using column chromatography to get pure compound 73.6 (0.210 g, 85.7%). MS (ES): m/z 611.5 [M+H]$^+$.

Synthesis of Compound I-132.

A solution of compound 73.6 (0.025 g, 0.037 mmol, 1.0 equiv) in trifluoroaceticacid acid (3 mL) was heated to 70° C. for 8 hours. After completion of the reaction, mixture was concentrated and residue was diluted with ethyl acetate and washed with saturated sodium bicarbonate solution. Organic layer was concentrated under the reduce pressure to obtain crude material which was purified by column chromatography to provide compound I-132. (0.010 g, 62.5%). MS (ES): m/z 411.4 [M+H]$^+$, $^1$H NMR (400 MHz, DMSO-d$_6$): δ 9.74 (s, 1H), 8.89 (s, 1H), 8.54 (s, 1H), 8.23-8.22 (d, 1H), 7.70-7.67 (dd, 1H), 7.62-7.54 (m, 1H), 7.28 (t, 2H), 7.17-7.15 (d, 1H), 4.44 (s, 2H), 3.68 (s, 2H), 3.37 (s, 3H).

Example 74. Synthesis of 2-(2,6-difluorophenyl)-4-((5-(2-oxopyrrolidin-3-yl)pyridin-2-yl)amino)-6,7-dihydro-5H-pyrrolo[3,4-b]pyridin-5-one, I-133

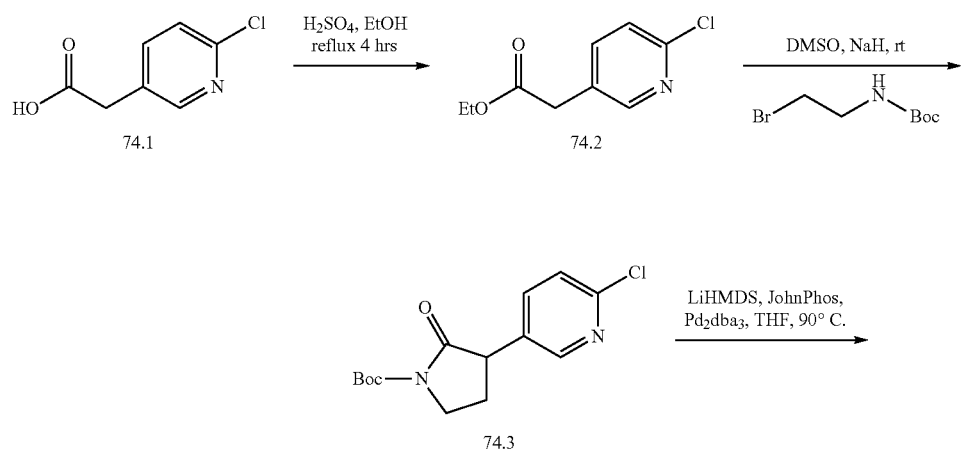

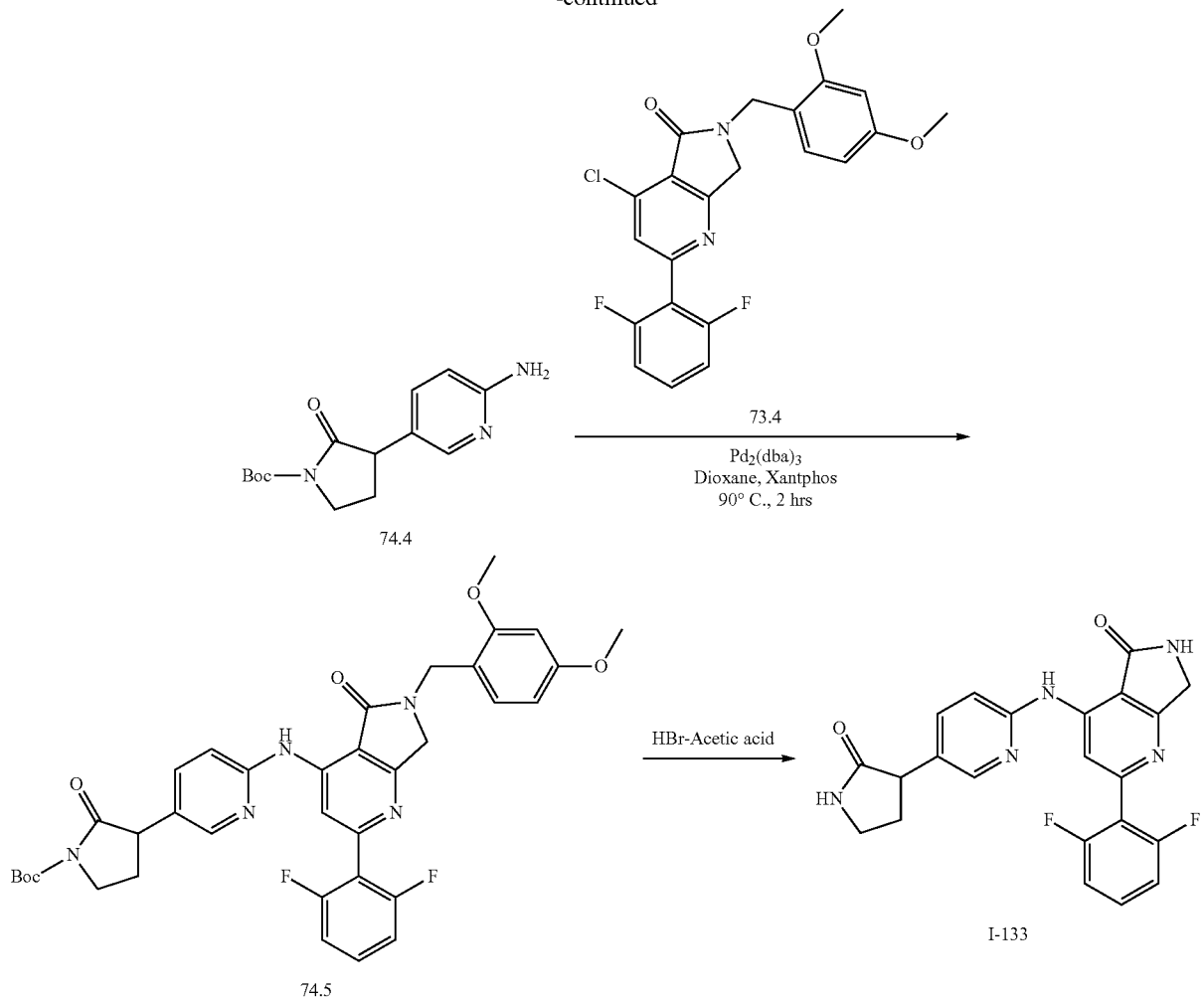

Synthesis of Compound 74.2.

To a solution of compound 74.1 (10 g, 0.0584 mol, 1.0 eq.) in ethanol (100 mL) was added drop wise $H_2SO_4$ (2 mL). Reaction was stirred for 4 hours at reflux temperature. After completion of the reaction, solvent was evaporated and water was added. Mixture was extracted using ethyl acetate (150 ml×2). Organic layer was washed with saturated sodium bicarbonate solution (70 ml×2), dried over sodium sulfate and concentrated under reduced pressure at 45° C. to afford compound 74.2 (8 g, 68.78%). MS (ES): m/z 200.4 $[M+H]^+$ Synthesis of Compound 74.3.

To a suspension of sodium hydride (0.72 g, 0.0180 mol, 1.2 eq) in DMSO (15 ml) was added compound 74.2 (3 g, 0.0150 mol, 1 eq.) at 10° C. Suspension was stirred for 20 minutes. Tert-butyl (2-bromoethyl) carbamate (4.14 g, 0.018 mol, 1.2 eq.) was added portion wise. Reaction was stirred for 1 hour at room temperature. After completion of the reaction, reaction mixture was diluted with ethyl acetate (50 ml) and washed with water (50 mL×2) followed by brine solution (50 ml×2). Organic layer was dried over sodium sulphate and concentrate under reduced pressure at 45° C. Crude was purified by column chromatography to afford compound 74.3 (0.420 g, 9.41%). MS (ES): m/z=297.1 $[M+H]^+$.

Synthesis of Compound 74.4.

To a solution of compound 74.3 (420 mg, 1.4189 mmol, 1.0 eq.) in THF (10 ml) was added (2-biphenyl)di-tert-butylphosphine. Suspension was de-gassed under argon for 30 minutes. Tris(dibenzylideneacetone)dipalladium(0) (129 mg, 0.1418 mmol, 0.1 eq.) was added and suspension de-gassed under argon for additional 30 minutes. 1M solution of Lithium bis (trimethylsilyl) amide (4.2 ml, 4.256 mmol, 3 eq.) was added and stirred at 90° C. for 3 hours. After completion of reaction, reaction mixture was poured into water and extracted using ethyl acetate. Organic layer was washed with brine solution. Organic layer was dried over sodium sulfate and concentrated under reduced pressure. Crude was purified by column chromatography to afford pure compound 74.4 (220 mg, 56.05%). MS (ES): m/z 278.3 [M+H]⁺, Synthesis of Compound 74.5.

To a solution of compound 73.4 (0.31 g, 0.720 mmol, 1 eq.) and compound 74.4 (0.22 g, 0.793 mmol, 1.1 eq.) in 1,4-dioxane (5 ml) was added and K₂CO₃ (0.243 g, 1.802 mmol, 2.5 eq.). Reaction mixture was de-gassed under argon for 10-15 minutes then xantphos (0.083 g, 0.144 mmol, 0.2 eq.) and Pd₂(dba)₃ (0.066 g, 0.072 mmol, 0.1 eq.) were added. Suspension was de-gassed under argon for additional 15 minutes. Reaction mixture was heated at 90° C. for 2 hours. After complication of the reaction, reaction mixture was poured in water and product was extracted with ethyl acetate. Organic layers were combined and dried over sodium sulphate and concentrated under reduced pressure to obtain crude material which was purified by column chromatography to afford compound 74.5 (0.35 g, 72.46%). MS (ES): m/z 672.01 [M+H]⁺

Synthesis of Compound I-133.

A solution of compound 74.5 (0.35 g, 0.5216 mmol, 1.0 eq.) in Hydrobromic acid/CH₃COOH solution (33%, 3 ml) was stirred at room temperature for 1 hour. After completion of the reaction, reaction mixture was poured into cold water, neutralized with NaHCO₃ and product was extracted with ethyl acetate (50 ml×2). Solvent was removed under reduced pressure at 45° C. to get crude which was purified by preparative HPLC to afford pure compound I-133 (73 mg, 33.33%). MS (ES): m/z 422.4 [M+H]⁺ ¹H NMR (400 MHz, DMSO-d⁶): δ 9.73 (s, 1H), 8.90 (s, 1H), 8.56-8.55 (d, 1H), 8.22 (d, 2H), 7.89 (S, 1H), 7.67-7.64 (dd, 2H), 7.60-7.56 (m, 1H), 7.28-7.24 (t, 2H), 7.17-7.15 (d, 1H), 4.43 (S, 2H), 3.58-3.53 (t, 1H), 3.32-3.27 (m, 1H), 2.46-2.45 (m, 1H), 2.14-2.08 (m, 1H).

Example 75. Synthesis of (R)-2-(2,6-difluorophenyl)-4-((5-(2-oxopyrrolidin-3-yl)pyridin-2-yl)amino)-6,7-dihydro-5H-pyrrolo[3,4-b]pyridin-5-one, I-91

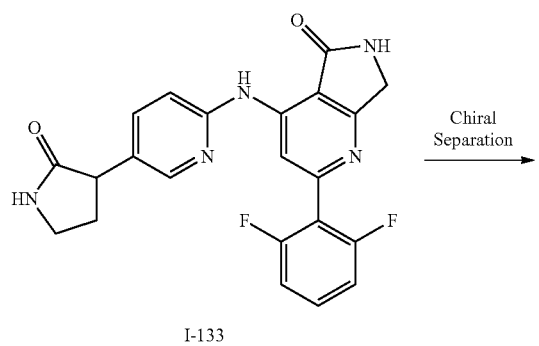

I-133

Chiral Separation →

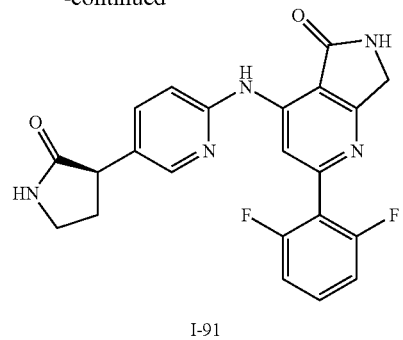

I-91

Compound I-91 was obtained by chiral separation of compound I-133. Chiral HPLC purity: 100%, ¹H NMR (400 MHz, DMSO-d₆): δ 9.77 (s, 1H), 8.92 (s, 1H), 8.57 (s, 1H), 8.23-8.22 (d, 1H), 7.90 (s, 1H), 7.68-7.65 (dd, 1H), 7.61-7.55 (m, 1H), 7.29-7.25 (t, 2H), 7.19-7.16 (d, 1H), 4.45 (s, 2H), 3.58-3.53 (t, 1H), 3.34-3.27 (m, 2H), 2.16-2.09 (m, 1H).

Example 76. Synthesis of (S)-2-(2,6-difluorophenyl)-4-((5-(2-oxopyrrolidin-3-yl)pyridin-2-yl)amino)-6,7-dihydro-5H-pyrrolo[3,4-b]pyridin-5-one, I-92

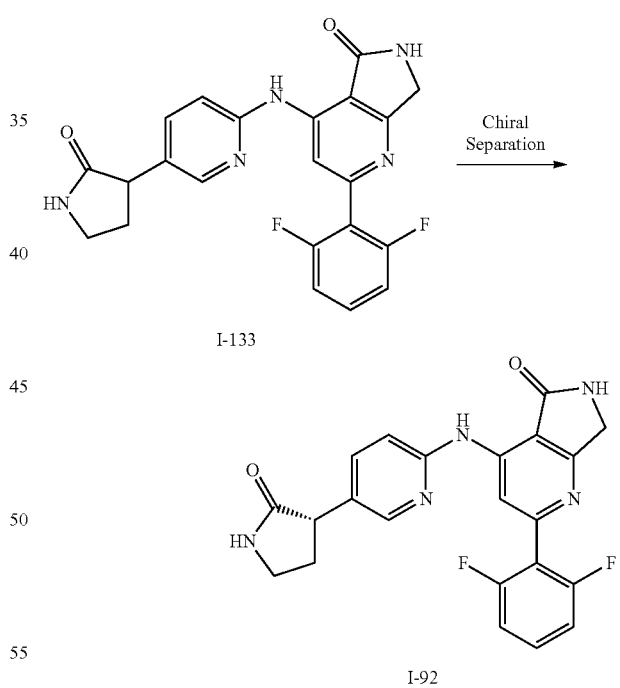

Compound I-92 was obtained by chiral separation of compound I-133. Chiral HPLC purity: 100%, ¹H NMR (400 MHz, DMSO-d₆): δ 9.76 (s, 1H), 8.92 (s, 1H), 8.57 (s, 1H), 8.23-8.22 (d, 1H), 7.89 (s, 1H), 7.6-7.65 (dd, 1H), 7.62-7.55 (m, 1H), 7.29-7.25 (t, 2H), 7.18-7.16 (d, 1H), 4.49 (s, 2H), 3.58-3.53 (t, 1H), 3.32-3.27 (m, 2H), 2.46-2.45 (m, 1H), 2.14-2.09 (m, 1H).

293
Example 77. Synthesis of 4-((5-(2-(azetidin-1-yl)ethoxy)pyridin-2-yl)amino)-2-(2,6-difluorophenyl)-6,7-dihydro-5H-pyrrolo[3,4-b]pyridin-5-one, I-134
294
Synthesis of Compound 77.2
To a solution of compound 77.1 (1.0 g, 5.7 mol, 1.0 equiv) and triphenylphosphine (2.1 g, 8.8 mol, 1.4 equiv) in THF
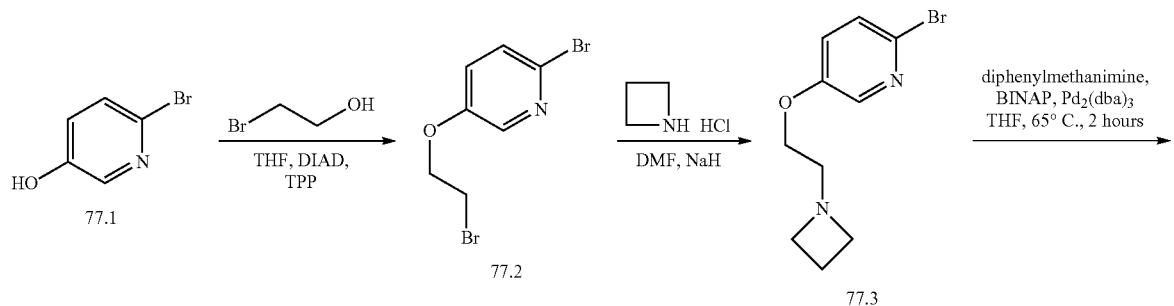
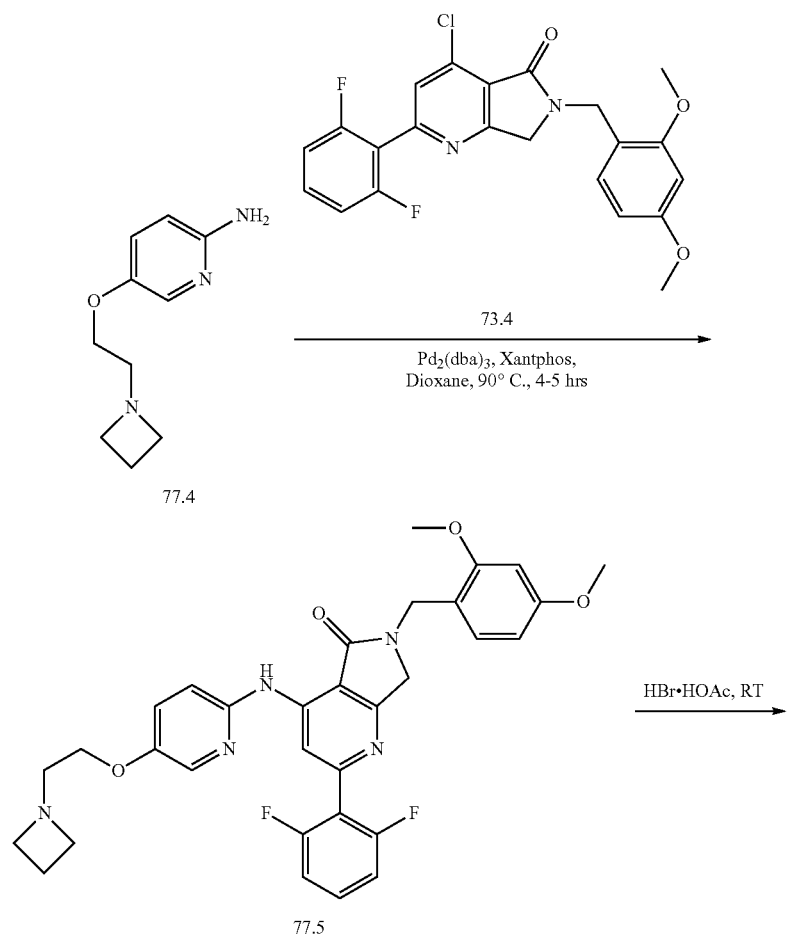
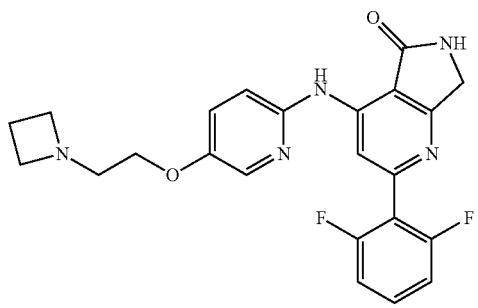

was added 2-bromoethan-1-ol (0.86 g, 6.8 mmol, 1.2 equiv), and diisopropyl azodicarboxylate (1.9 g, 9.97 mmol, 1.7 equiv) at 0° C. Reaction mixture was stirred at ambient temperature for 1 hour. Reaction mixture was poured in water (300 mL) and extracted with ethyl acetate (200 mL×3). Organic layers was combined and dried over sodium sulphate and concentrated under reduced pressure to obtain crude material. Which was purified purified by column chromatography to furnish compound 77.2 (1.0 g, 61.93%). MS (ES): m/z 282.09 [M+H]$^+$.

Synthesis of Compound 77.3.

To a solution of azetidine hydrochloride (0.250 g, 3.51 mmol, 2 equiv) and sodium hydride (50%) (0.122 g, 2.66 mmol, 1.5 equiv) in dimethylformamide (5 mL) was added compound 77.2 (0.5 g, 1.77 mmol, 1.0 equiv) at 0° C. Reaction mixture was stirred at ambient temperature for 1 hour. Reaction mixture was poured into water (100 mL) and extracted with ethyl acetate (50 mL×3). Organic layers were combined and dried over sodium sulphate and concentrated under reduced pressure to obtain crude material which was purified by column chromatography to provide compound 77.3 (0.2 g, 43.70%), MS (ES): m/z 257.2 [M+H]$^+$.

Synthesis of Compound 77.4

To a solution of compound 77.3 (0.2 g, 0.778 mmol, 1.0 equiv) and diphenylmethanimine (0.183 g, 1.01 mmol, 1.3 equiv) in toluene was added potassium acetate (0.26 g, 2.30 mmol, 3 equiv). Reaction mixture was degassed with argon gas for 5-10 min. and Pd$_2$(dba)$_3$ (0.071 g, 0.0778 mmol, 0.1 equiv) and BINAP (0.096 g, 0.15 mmol, 0.2 equiv) were added. Reaction mixture was heated at 100° C. for 2 hours. Reaction mixture was poured into water (50 mL) and extracted with ethyl acetate (20 mL×3). Organic layers were combined and dried over sodium sulphate and concentrated under reduced pressure to obtain crude material which purified by column chromatography to get pure 77.4 (0.06 g, 40%). MS (ES): m/z 194.2 [M+H]$^+$.

Synthesis of Compound 77.5.

To a solution of compound 73.4 (0.10 g 0.23 mmol, 1.0 eq.) in dry Dioxane (5.0 mL) was added compound 77.4 (50 mg, 0.25 mmol, 1.1 eq.), potassium carbonate (0.095 g, 0.60 mmol, 3.0 eq.) at room temperature. To the above reaction mixture was added Pd$_2$(dba)$_3$ (21 mg, 0.023 mmol, 0.1 eq.) and Xantphos (26 mg, 0.046 mmol, 0.2 eq.). Suspension was degassed using argon for 10 minutes. Reaction mixture was heated at 105° C. temperature for 3-4 hours. After completion of the reaction, mixture was poured into water and extracted using ethyl acetate. Organic layer was washed with by brine solution. and dried over sodium sulphate and concentrated under reduced pressure to obtain crude which was purified using column chromatography get pure compound 77.5 (0.06 g, 38.49%). MS (ES): m/z 611.5 [M+H]$^+$.

Synthesis of Compound I-134.

A solution of compound 77.5 (100 mg) in hydrobromic acid:acetic acid solution (33%, 5 ml) was stirred at room temperature for 1 hour. After completion of the reaction, mixture was poured in cold water, neutralized with sodium hydrogen carbonate and product was extracted with ethyl acetate (50 mL×2). Solvent was removed under reduced pressure at 45° C. to get the crude which was purified to afford I-134. (20 mg, 50%). MS (ES): m/z 438.2 [M+H]$^+$, $^1$H NMR (400 MHz, DMSO-d$^6$): δ 9.59 (s, 1H), 8.84 (s, 1H), 8.38 (s, 1H), 8.27 (s, 1H), 8.04 (d, 1H), 7.59-7.55 (m, 1H), 7.43 (dd, 1H), 7.28-7.24 (m, 2H), 7.16 (d, 1H), 4.42 (s, 2H), 3.95 (t, 2H), 3.27-3.13 (m, 4H), 2.71-2.68 (m, 2H), 1.99-1.94 (m, 2H).

Example 78. Synthesis of 2-(2,6-difluorophenyl)-4-((5-((2-(4,4-difluoropiperidin-1-yl)ethyl)amino)pyridin-2-yl)amino)-6,7-dihydro-5H-pyrrolo[3,4-b]pyridin-5-one, I-135

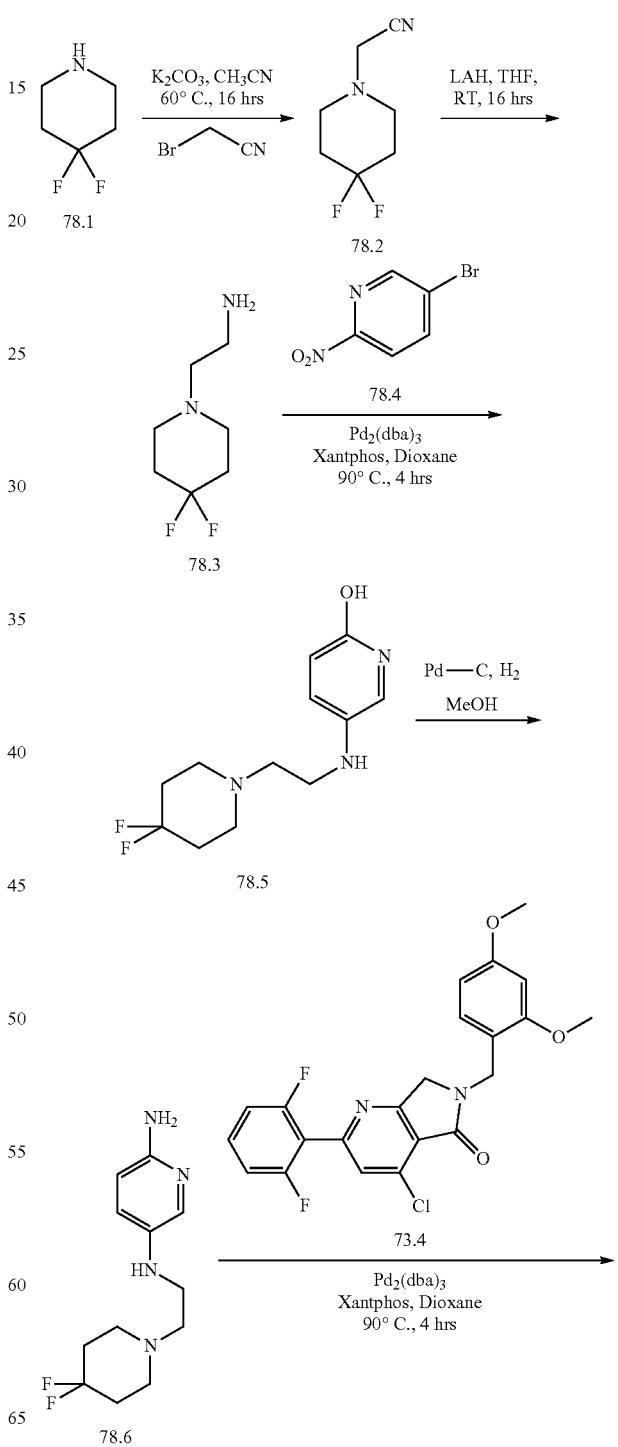

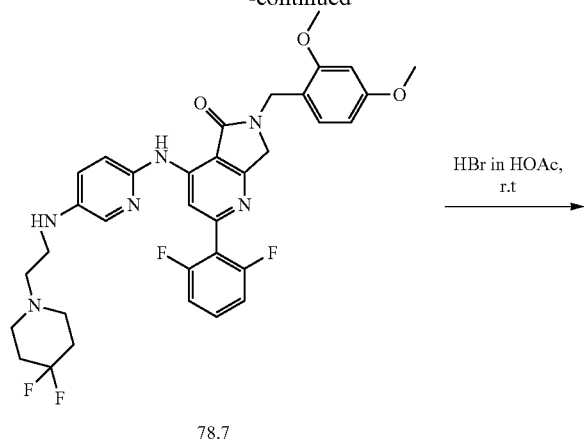

Synthesis of Compound 78.2

To a solution of compound 78.1 (1.0 g, 6.36 mol, 1.0 equiv) and 2-bromoacetonitrile (1.0 g, 8.2 mol, 1.3 equiv) in acetonitrile was added potassium carbonate (2.1 g, 15.9 mmol, 2.5 equiv). Reaction was stirred at room temperature for 1 hour. Reaction mixture was poured into water (300 mL) and extracted with ethyl acetate (200 mL×3). Organic layers were combined, dried over sodium sulphate and concentrated under reduced pressure to obtain crude material which was purified using column chromatography to provide compound 78.2 (0.96 g, 7.89%). MS (ES): m/z 160.2 [M+H]$^+$.

Synthesis of Compound 78.3.

To a solution of compound 78.2 (0.8 g, 4.99 mmol, 1 equiv) in THF (5 mL) was added LiAlH$_4$ (1M in THF) (12 mL) at 0° C. Reaction was stirred at RT for 1 hrs. Reaction mixture was poured in water (100 mL) and extracted with ethyl acetate (50 mL×3). Organic layers were combined and dried over sodium sulphate and concentrated under reduced pressure to obtain crude which was purified by column chromatography to furnish pure compound 78.3 (0.5 g, 61%), MS (ES): m/z 165.2 [M+H]$^+$.

Synthesis of Compound 78.5.

To a solution of 78.4 (0.5 g, 2.46 mmol, 1.0 equiv) in dry Dioxane (5.0 mL) was added 78.3 (404 mg, 2.46 mmol, 1.1 eq.) and potassium carbonate (1.01 g, 7.38 mmol, 3.0 eq.) at room temperature under argon purge for 15 minutes. To the above reaction mixture was added Pd$_2$(dba)$_3$ (22 mg, 0.246 mmol, 0.1 eq.) and Xantphos (27 mg, 0.48 mmol, 0.2 eq.) under argon purge for 10 minutes. Reaction mixture was heated at 105° C. for 4 hours. After completion of the reaction, reaction mixture was poured into water and extracted using ethyl acetate. Organic layer was washed with by brine solution. Organic layers were combined, dried over sodium sulphate and concentrated under reduced pressure to obtain crude material which was purified using column chromatography to get pure 78.5 (0.3 g, 42.54%). MS (ES): m/z 287.2 [M+H]$^+$.

Synthesis of Compound 78.6.

To a suspension of palladium on charcoal (80 mg) in methanol (15 ml) was added 78.5 (0.30 g, 1.05 mmol. 1.0 eq.) under nitrogen atmosphere. The above reaction mixture was purged with hydrogen at room temperature for 2 hours. After completion of the reaction, reaction mixture was filter through celite. Solvent was removed under reduced pressure at 45° C. to afford compound 78.6 (0.20 g, 74%). MS (ES): m/z 257.3 [M+H]$^+$ Synthesis of Compound 78.7.

To a solution of 73.4 (0.10 g 0.23 mmol, 1.0 eq.) in dry dioxane (5.0 mL) were added 78.6 (60 mg, 0.23 mmol, 1.0 eq.), potassium carbonate (0.095 g, 0.60 mmol, 3.0 eq.) at room temperature under argon bubbling for 15 minutes. To the above reaction mixture were added Pd$_2$(dba)$_3$ (21 mg, 0.023 mmol, 0.1 eq.) and Xantphos (26 mg, 0.046 mmol, 0.2 eq.) under argon purge for 10 minutes. Reaction mixture was heated at 105° C. temperature for 3-4 hours. After completion of reaction, reaction mixture was poured into water and extracted using ethyl acetate. Organic layer was washed with brine solution, dried over sodium sulphate and concentrated under reduced pressure to obtain crude material. Crude was purified using column chromatography to get pure 78.7 (0.08 g, 53.0%). MS (ES): m/z 651.20 [M+H]$^+$.

Synthesis of Compound I-135.

A solution of 78.7 (80 mg) in hydrobromic acid/acetic acid solution (33%, 5 ml) was stirred at room temperature for 1 hour. After completion of the reaction, mixture was poured into cold water, neutralized with sodium hydrogen carbonate and extracted with ethyl acetate (50 ml×2). Solvent was removed under reduced pressure at 45° C. to get crude which was purified using column chromatography to furnish I-135 (50 mg, 81%). MS (ES): m/z 501.58 [M+H]$^+$; $^1$H NMR (400 MHz, DMSO-d$^6$): δ 9.35 (s, 1H), 8.76 (s, 1H), 8.18 (s, 1H), 7.73 (d, 1H), 7.59-7.52 (m, 1H), 7.24 (t, 2H), 7.11 (dd, 1H), 6.99 (d, 1H), 5.50 (t, 1H), 4.42 (s, 2H), 3.15-3.11 (q, 2H), 2.67-2.53 (m, 4H), 2.00-1.95 (m, 4H).

Example 79. Synthesis of compound 6-((2-(2,6-difluorophenyl)-5-oxo-6,7-dihydro-5H-pyrrolo[3,4-b]pyridin-4-yl)amino)-N-ethylnicotinamide, I-136

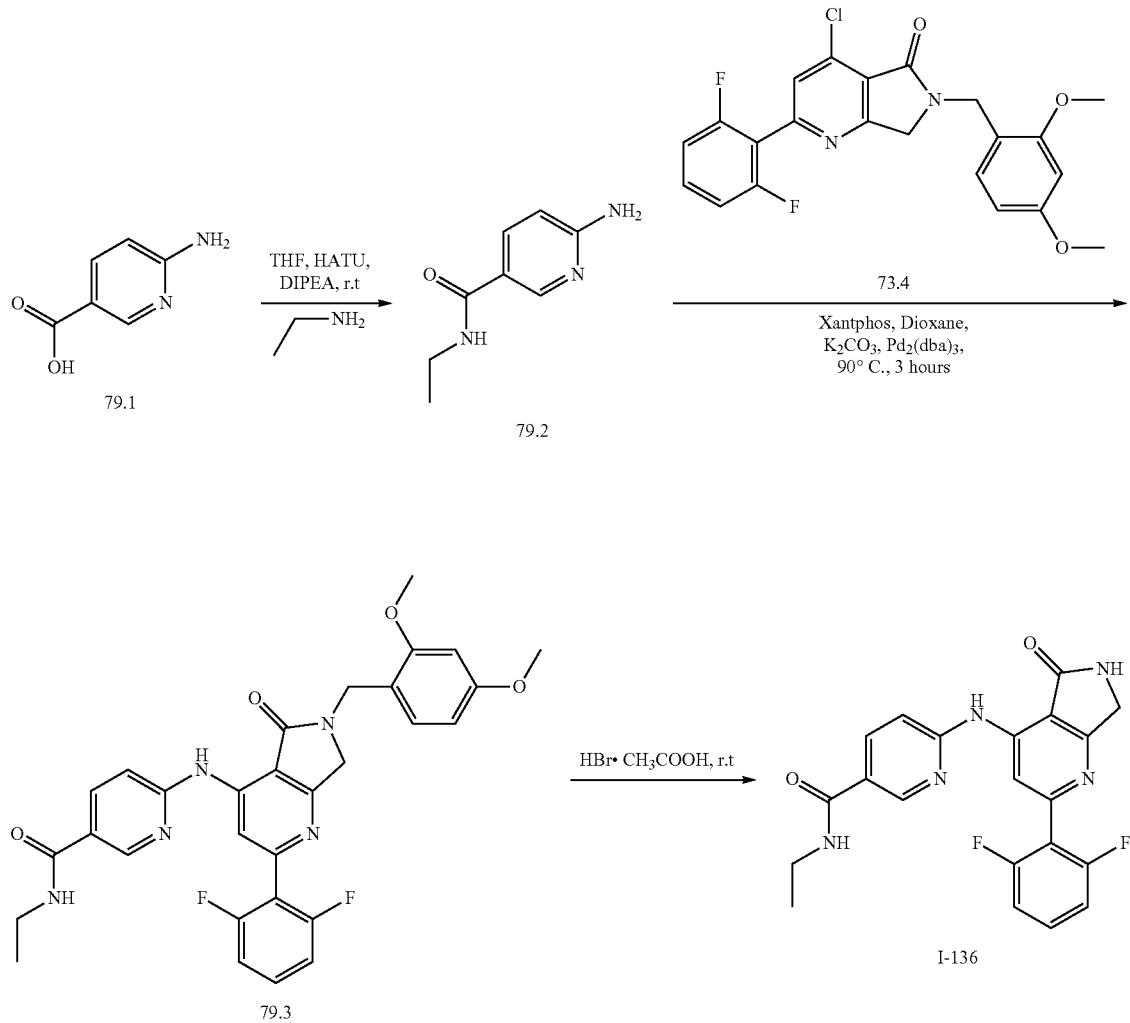

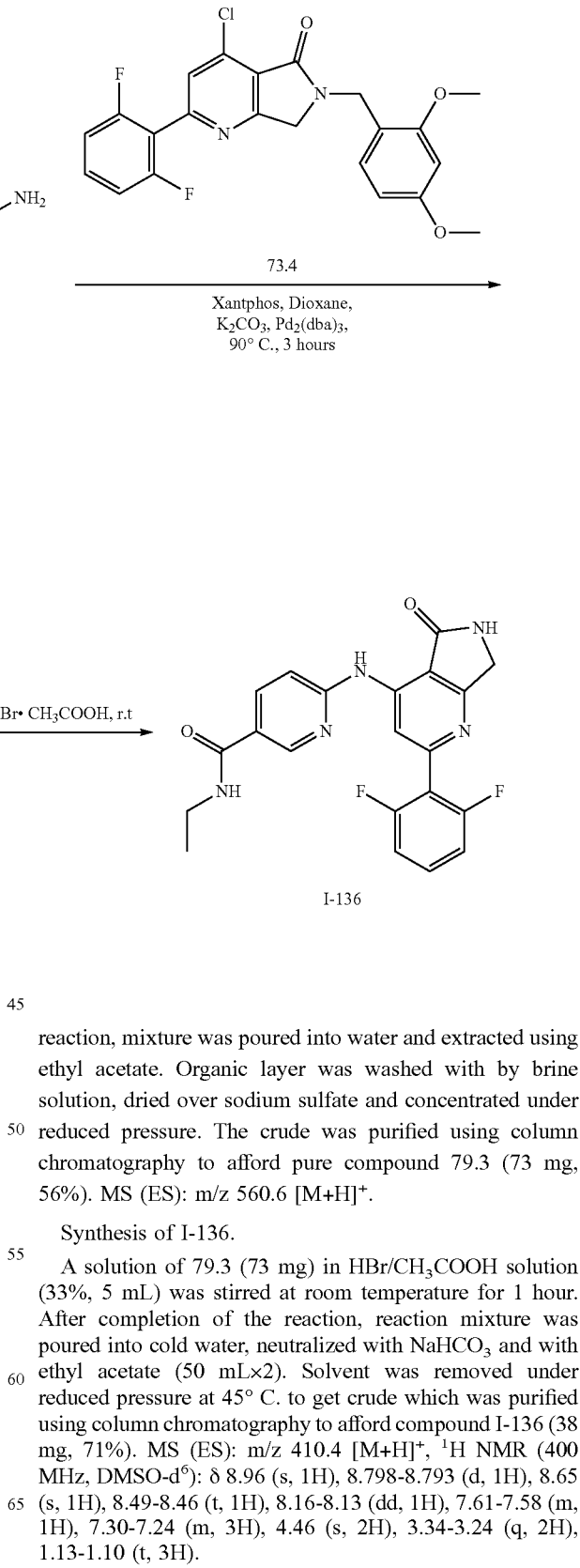

Synthesis of Compound 79.2

To a solution of 79.1 (0.2 g 1.44 mmol, 1.0 eq.) in dry THF (5.0 mL) were added HATU (826 mg, 2.17 mmol, 1.5 eq.), diisopropylethylamine (560 mg, 4.34 mmol, 3.0 eq.) and ethylamine (2M in tetrahydrofuran) (1.44 ml, 2.89, 2.0 eq.) at 0° C. while stirring. Reaction mixture was allowed to warm at room temperature and stirred for overnight. After completion of the reaction, mixture was poured into water and extracted using ethyl acetate. Organic layer was washed with by brine solution, dried over sodium sulfate and concentrated under reduced pressure. Crude was triturated with diethyether to afford compound 79.2 (0.1 g, 46%). MS (ES): m/z=166.2 [M+H]$^+$ Synthesis of Compound 79.3.

To a solution of 73.4 (0.1 g 0.23 mmol, 1.0 eq.) in dry Dioxane (3.0 mL) was added compound 79.2 (0.046 g, 0.27 mmol, 1.2 eq.), Potassium carbonate (0.064 g, 0.46 mmol, 2.0 eq.) at room temperature under argon gas purge for 15 minutes. To the above reaction mixture was added tris (dibenzylideneacetone)dipalladium(0) (0.021 g, 0.023 mmol, 0.1 eq.) and 4,5-Bis(diphenylphosphino)-9,9-dimethylxanthene (0.026 g, 0.046 mmol, 0.2 eq.) under argon purge for additional 10 minutes. Reaction mixture was heated at 105° C. temperature for 4 hours. After completion of the reaction, mixture was poured into water and extracted using ethyl acetate. Organic layer was washed with by brine solution, dried over sodium sulfate and concentrated under reduced pressure. The crude was purified using column chromatography to afford pure compound 79.3 (73 mg, 56%). MS (ES): m/z 560.6 [M+H]$^+$.

Synthesis of I-136.

A solution of 79.3 (73 mg) in HBr/CH$_3$COOH solution (33%, 5 mL) was stirred at room temperature for 1 hour. After completion of the reaction, reaction mixture was poured into cold water, neutralized with NaHCO$_3$ and with ethyl acetate (50 mL×2). Solvent was removed under reduced pressure at 45° C. to get crude which was purified using column chromatography to afford compound I-136 (38 mg, 71%). MS (ES): m/z 410.4 [M+H]$^+$, $^1$H NMR (400 MHz, DMSO-d$^6$): δ 8.96 (s, 1H), 8.798-8.793 (d, 1H), 8.65 (s, 1H), 8.49-8.46 (t, 1H), 8.16-8.13 (dd, 1H), 7.61-7.58 (m, 1H), 7.30-7.24 (m, 3H), 4.46 (s, 2H), 3.34-3.24 (q, 2H), 1.13-1.10 (t, 3H).

Example 80. Synthesis of 2-(2,6-difluorophenyl)-4-((5-(4-hydroxy-4-methylpiperidin-1-yl)pyridin-2-yl)amino)-6,7-dihydro-5H-pyrrolo[3,4-b]pyridin-5-one I-137 by brine (25 mL×3) solution, dried over sodium sulfate and concentrated under reduced pressure. Crude was purified by column chromatography to furnish compound 80.2 (0.19 g, 65%). MS (ES): m/z 238.2 [M+H]+.

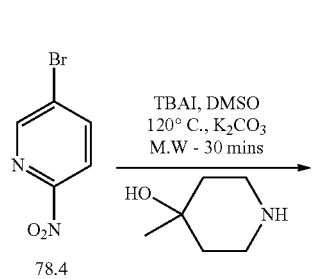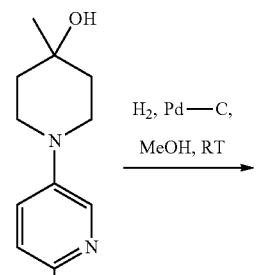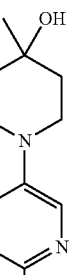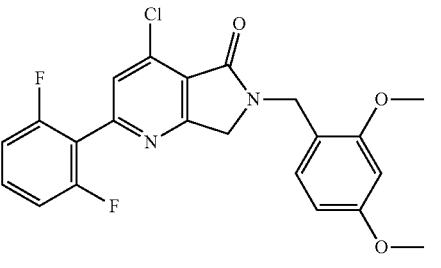

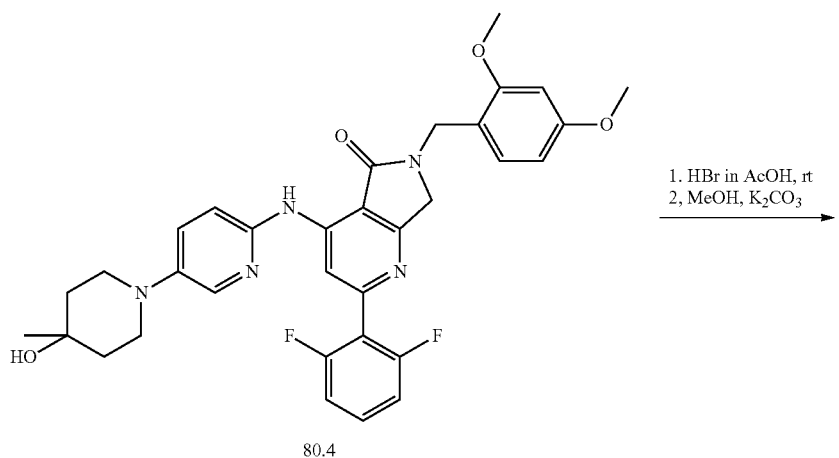

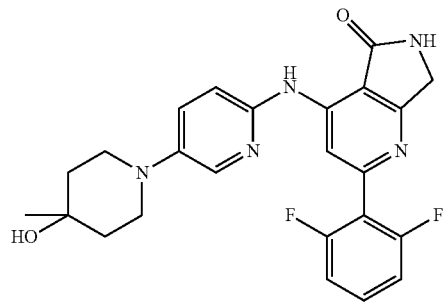

Synthesis of Compound 80.2.

To a solution of 78.4 (0.25 g 1.23 mmol, 1.0 eq.) in dry DMSO (3.0 mL) was added 4-methylpiperidin-4-ole (0.17 g, 1.47 mmol, 1.2 eq.), potassium carbonate (0.68 g, 4.92 mmol, 4.0 eq.) and tetrabutylammonium iodide (88 mg, 0.24 mmol, 0.2 eq.) at room temperature. Reaction mixture heated at 120° C. for 30 minutes in microwave. After completion of the reaction, mixture was poured into water and extracted using ethyl acetate. Organic layer was washed Synthesis of Compound 80.3.

To a suspension of Pd/C (80 mg) in methanol (15 ml) was added 80.2 (0.19 g, 0.81 mmol. 1.0 eq.) under nitrogen atmosphere. Above reaction mixture was purged with H₂ (gas) for 2 hours. After completion of the reaction, mixture was filtered through celite, solvent was removed under reduced pressure at 45° C. to afford compound 80.3 (0.14 g, 84%). MS (ES): m/z 208.1 [M+H]+

Synthesis of Compound 80.4.

To a solution of 73.4 (0.17 g 0.39 mmol, 1.0 eq.) in dry dioxane (3.0 mL) was added 80.3 (90 mg, 0.43 mmol, 1.1 eq.), potassium carbonate (0.1 g, 0.79 mmol, 2.0 eq.) at room temperature under argon purge for 15 minutes. To the above reaction mixture was added tris(dibenzylideneacetone)dipalladium(0) (36 mg, 0.039 mmol, 0.1 eq.) and 4,5-Bis(diphenylphosphino)-9,9-dimethylxanthene (45 mg, 0.08 mmol, 0.2 eq.) under argon purge for 10 minutes. Reaction mixture was heated at 105° C. temperature for 4 hours. After completion of the reaction, reaction mixture was poured into water and extracted using ethyl acetate. Organic layer was washed with by brine solution, dried over sodium sulfate and concentrated under reduced pressure. The crude was purified by column chromatography to afford pure compound 80.4 (0.165 g, 69.5%). MS (ES): m/z 602.2 [M+H]$^+$.

Synthesis of Compound I-137.

A solution of 80.4 (0.165 g, 0.27 mmol. 1.0 eq.) in HBr. CH$_3$COOH solution (33%, 5 mL) was stirred at room temperature for 1 hour. After completion of the reaction, reaction mixture was poured into cold water, neutralized with NaHCO$_3$ and product was extracted with ethyl acetate (50 mL×2). Solvent was removed under reduced pressure at 45° C. to get crude which was treated with K$_2$CO$_3$ (4 eq) in methanol (5 mL) at room temperature for 4 hours. Solvent was evaporated under reduced pressure at 40° C. Residue was poured into water and product was extracted with ethyl acetate (50 mL×2). Solvent was removed under reduced pressure at 45° C. to get crude which was purified by column chromatography to afford pure compound I-137 (80 mg, 64.61%). MS (ES): m/z 452.4 [M+H]$^+$, $^1$H NMR (400 MHz, DMSO-d$_6$): δ 9.49 (s, 1H), 8.80 (s, 1H), 8.35 (s, 1H), 8.02-8.01 (d, 1H), 7.59-7.55 (m, 1H), 7.46-7.43 (dd, 1H), 7.27-7.23 (t, 2H), 7.08-7.05 (d, 1H), 4.40 (s, 2H), 4.30 (s, 1H), 3.28-3.25 (m, 2H), 3.12-3.05 (m, 2H), 1.54-1.53 (m, 4H), 1.14 (s, 3H).

Example 81. Synthesis of 6-((2-(2,6-difluorophenyl)-5-oxo-6,7-dihydro-5H-pyrrolo[3,4-b]pyridin-4-yl)amino)-N-isopropylnicotinamide, I-138

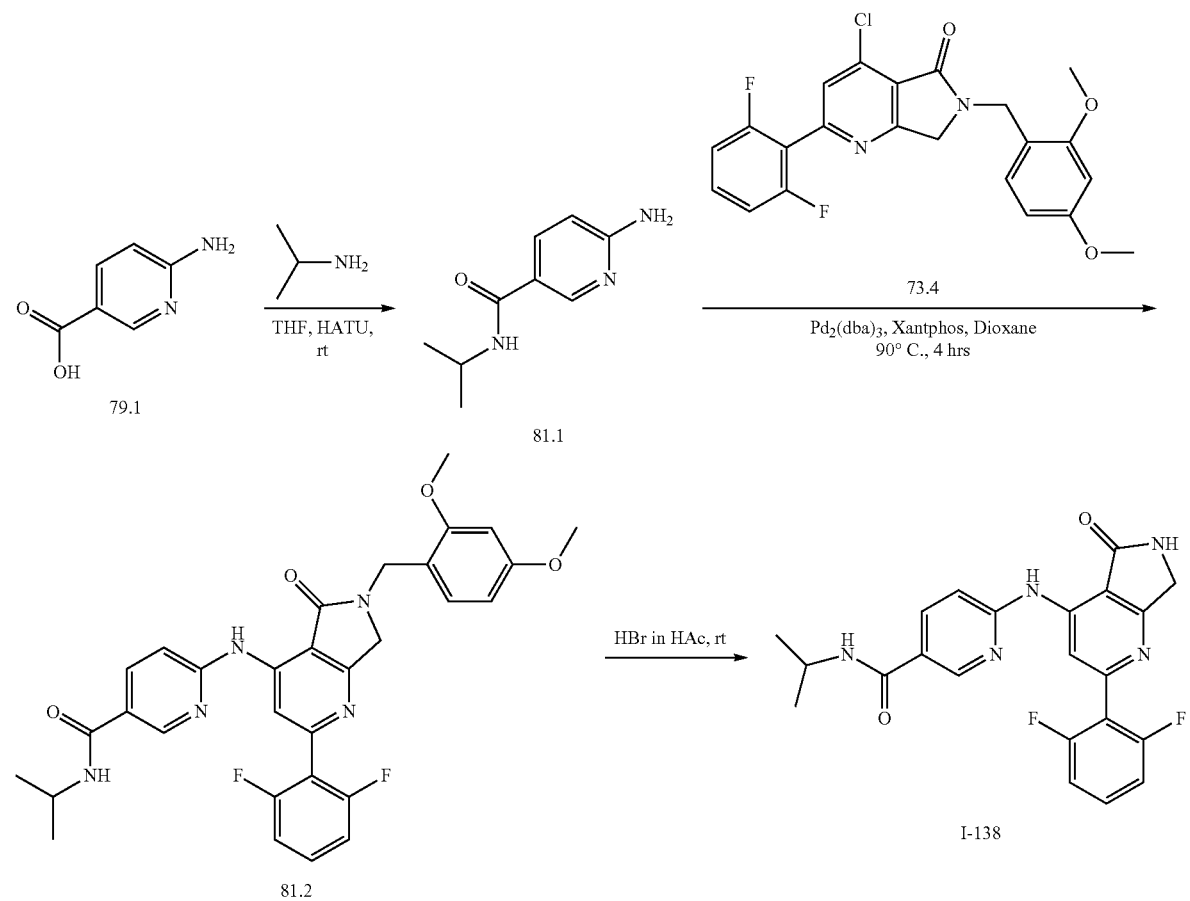

Synthesis of Compound 81.1.

To a solution of 79.1 (1.0 g 7.24 mmol, 1.0 eq.) in dry THF (10.0 mL) was added HATU (4.13 g, 10.8 mmol, 1.5 eq.), Diisopropylethylamine (2.8 g, 21.7 mmol, 3.0 eq.) and isopropylamine (615 mg, 8.69, 1.2 eq.) at 0° C. while stirring. Reaction mixture was allowed to warm at room temperature and was stirred overnight. After completion of reaction, reaction mixture was poured into water and extracted using ethyl acetate. Organic layer was washed with by brine solution, dried over sodium sulfate and concentrated under reduced pressure. Crude was triturated with methanol to afford compound 81.1 (0.51 g, 39%). MS (ES): m/z=180.2 [M+H]$^+$.

Synthesis of Compound 81.2.

To a solution of 73.4 (150 mg 0.34 mmol, 1.0 eq.) in dry Dioxane (4.0 mL) was added 81.1 (75 mg, 0.42 mmol, 1.2 eq.), K$_2$CO$_3$ (96 mg, 0.69 mmol, 2.0 eq.) at room temperature under argon purge for 15 minutes. To the above reaction mixture was added Pd$_2$(dba)$_3$ (0) (0.032 g, 0.035 mmol, 0.1 eq.) and Xantphos (0.040 g, 0.069 mmol, 0.2 eq.) under argon purge for 10 minutes. Reaction mixture was heated at 105° C. temperature for 4 hours. After completion of the reaction, reaction mixture was poured into water and extracted using ethyl acetate. Organic layer was washed with by brine solution, dried over sodium sulfate and concentrated under reduced pressure. Crude was purified by column chromatography to afford pure compound 81.2 (0.13 g, 65.1%). MS (ES): m/z 574.6 [M+H]$^+$, Synthesis of I-138.

A solution of 81.2 (130 mg) in HBr/HOAc solution (33%, 5 mL) was stirred at room temperature for 1 hour. After completion of the reaction, reaction mixture was poured in cold water, neutralized with NaHCO$_3$ and extracted with ethyl acetate (50 ml×2). Solvent was removed under reduced pressure at 45° C. to get crude, which was purified by column chromatography to afford pure I-138 (85 mg, 88.6%). MS (ES): m/z 424.4 [M+H]$^+$ $^1$H NMR (400 MHz, DMSO-d$^6$): δ 9.95 (s, 1H), 8.96 (s, 1H), 8.809-8.804 (d, 1H), 8.67 (s, 1H), 8.25-8.23 (d, 1H), 8.17-8.14 (dd, 1H), 7.61-7.57 (m, 1H), 7.30-7.24 (m, 3H), 4.46 (s, 2H), 4.10-4.05 (m, 1H), 1.16-1.14 (d, 6H).

Example 82. Synthesis of compound 6-((2-(2,6-difluorophenyl)-5-oxo-6,7-dihydro-5H-pyrrolo[3,4-b]pyridin-4-yl)amino)-N-(tetrahydro-2H-pyran-4-yl) nicotinamide, I-139

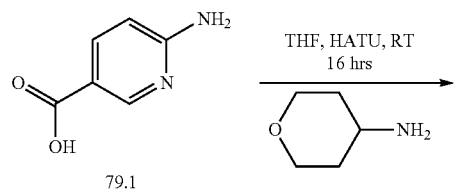

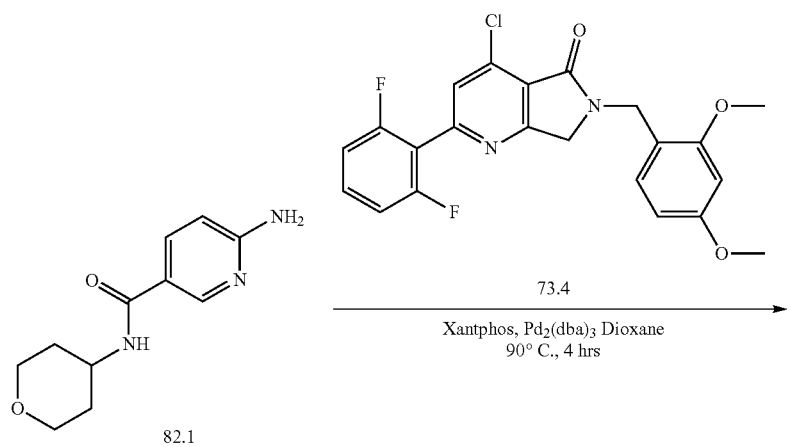

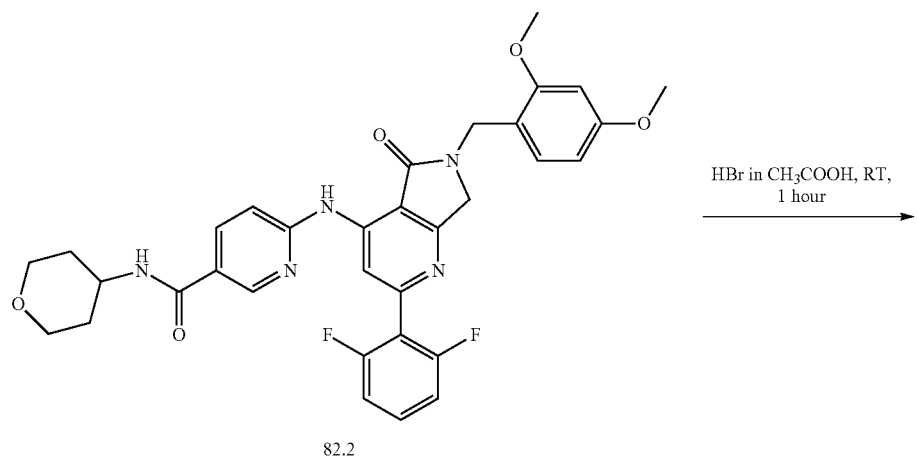

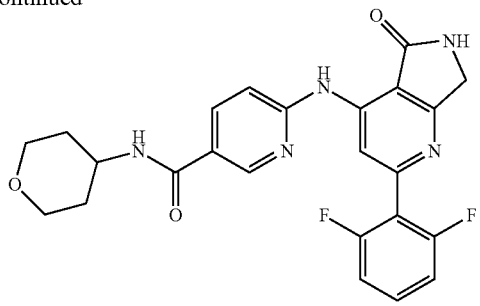

I-139

Synthesis of Compound 82.1.

To a solution of 79.1 (0.2 g 1.44 mmol, 1.0 eq.) in dry THF (5.0 mL) were added HATU (826 mg, 2.17 mmol, 1.5 eq.), diisopropylethylamine (560 mg, 4.34 mmol, 3.0 eq.) and tetrahydro-2H-pyran-4-amine hydrochloride (0.24, 2.16, 2.0 eq.) at 0° C. while stirring. Reaction mixture was allowed to warm at room temperature and stirred for overnight. After completion of the reaction, reaction mixture was poured into water and extracted using ethyl acetate. Organic layer was washed with brine solution, dried over sodium sulfate and concentrated under reduced pressure. Crude was triturated with diethyether to afford compound 82.1 (0.10 g, 31.21%). MS (ES): m/z=220.1 [M−H]−, Synthesis of Compound 82.2.

To a solution of 73.4 (0.15 g 0.34 mmol, 1.0 eq.) in dry Dioxane (5.0 mL) was added 82.1 (0.083 g, 0.38 mmol, 1.2 eq.), potassium carbonate (0.14 g, 1.2 mmol, 3.0 eq.) at room temperature under argon purge for 15 minutes. To the above reaction mixture was added Pd$_2$(dba)$_3$ (0.031 g, 0.034 mmol, 0.1 eq.) and Xantphos (0.035 g, 0.062 mmol, 0.2 eq.) under argon bubbling for 10 minutes. Reaction mixture was heated at 105° C. temperature for 4 hours. After completion of the reaction, reaction mixture was poured into water and extracted using ethyl acetate. Organic layer was washed with brine solution, dried over sodium sulfate and concentrated under reduced pressure. The crude was purified using column chromatography to afford compound 82.2 (75 mg, 35%). MS (ES): m/z 560.6 [M+H]+.

Synthesis of Compound I-139.

A solution of 82.2 (75 mg) in hydrobromic acid/acetic acid (33%, 5 ml) was stirred at room temperature for 1 hour. After completion of reaction, reaction mixture was poured into cold water, neutralized with sodium hydrogen carbonate and extracted with ethyl acetate (50 ml×2). Solvent was removed under reduced pressure at 45° C. to get crude which was purified using column chromatography to afford pure I-139 (25 mg, 50%). MS (ES): m/z 466.3 [M+H]+ $^1$H NMR (400 MHz, DMSO-d$^6$): δ 9.96 (s, 1H), 8.96 (s, 1H), 8.20 (d, 1H), 8.67 (s, 1H), 8.25 (d, 1H), 8.18-8.15 (dd, 1H), 7.59 (t, 1H), 7.30-7.25 (m, 3H), 4.46 (s, 2H), 4.00-3.98 (m, 1H), 3.88-3.86 (d, 2H), 3.40-3.34 (m, 2H), 1.77-1.74 (m, 2H) 1.58-1.50 (m, 2H).

Example 83. Synthesis of 6-((2-(2,6-difluorophenyl)-5-oxo-6,7-dihydro-5H-pyrrolo[3,4-b]pyridin-4-yl)amino)-N-(2,2,2-trifluoroethyl)nicotinamide, I-140

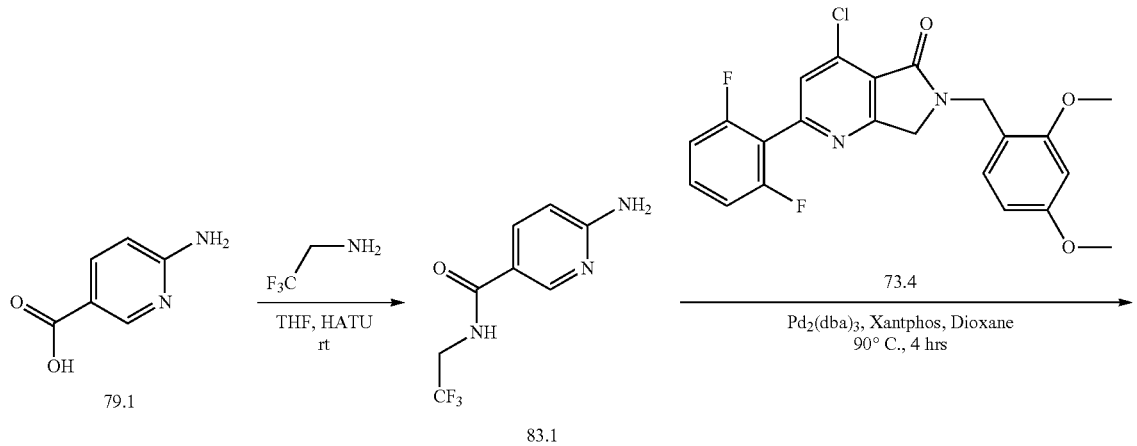

83.1

-continued

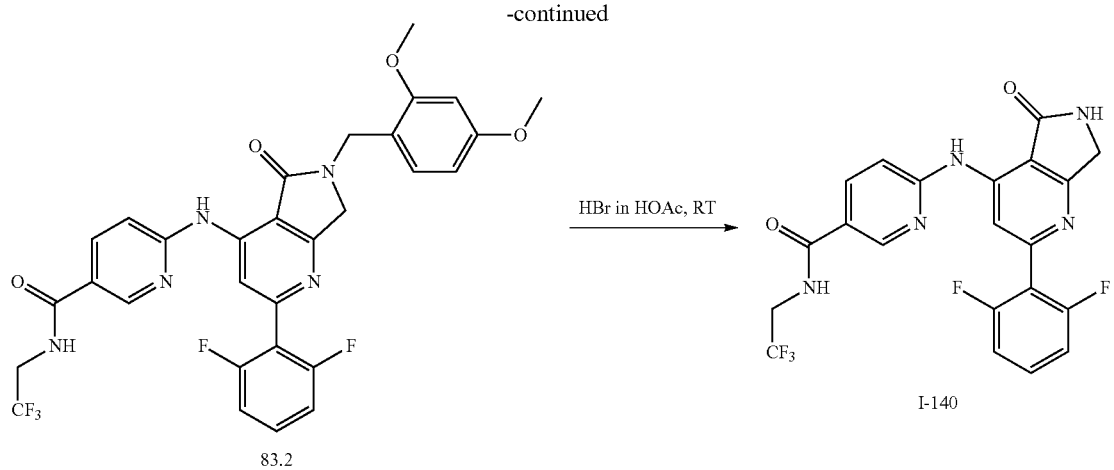

83.2

I-140

Synthesis of 83.1. To a solution of 79.1 (0.6 g, 0.4.343 mmol, 1.0 equiv) in THF (3 ml) were added HATU (2.47 g, 6.516 mmol, 1.2 equiv), diisopropyl ethyl amine (2.33 ml, 13.033 mmol, 3 equiv) and (0.162 g, 1.083 mmol, 1.1 equiv), 2,2,2-trifluoroethan-1-amine (0.51 g, 5.213 mmol, 1.2 equiv). The reaction mixture was stirred at room temperature for 3 hours. Upon completion reaction mixture was poured into water and extracted with ethyl acetate. Organic layers were combined, dried over sodium sulphate and concentrated under reduced pressure to obtain crude material which was purified by column chromatography to get pure 83.1 (0.4 g, 42.02%). MS (ES): m/z 220.09 [M+H]+.

Synthesis of Compound 83.2.

To a solution of 73.4 (0.2 g, 0.4645 mol, 1.0 equiv) in 1,4-dioxane (3 mL) were added 83.1 (0.107 g, 0.5109 mmol, 1.1 equiv) and potassium carbonate (0.160 g, 1.161 mmol, 2.5 equiv). The reaction mixture was degassed for 10 min. using argon, then Pd$_2$(dba)$_3$ (0.042 g, 0.0464 mmol, 0.1 equiv) and Xantphos (0.053 g, 0.0929 mmol, 0.2 equiv) were added. Suspension was degassed for additional 5 minutes. The reaction was then heated at 100° C. for 2 hours.

After completion of the reaction, reaction mixture was poured into water and extracted with ethyl acetate. Organic layers were combined, dried over sodium sulphate and concentrated under reduced pressure to obtain crude material which was purified using column chromatography to get pure 83.2 (0.2 g, 70.22%). MS (ES): m/z 614.15[M+H]+.

Synthesis of I-140. Compound 83.2 (0.2 g) was dissolved in HBr in acetic acid (2 ml) and stirred at room temperature for 1 h. After completion of the reaction, reaction mixture was poured into water, basified with saturated bicarbonate solution and extracted with ethyl acetate. Organic layers were combined, dried over sodium sulphate and concentrated under reduced pressure. The crude was purified using column chromatography to furnish compound I-140 (0.070 g, 46.34%). MS (ES): m/z 464.32 [M+H]+, 1H NMR (DMSO-d$_6$, 400 MHZ): 10.015 (s, 1H), 9.12 (t, 1H), 8.98 (s, 1H), 8.85 (d, 1H), 8.66 (s, 1H), 8.19 (dd, 1H), 7.59 (m, 1H), 7.28 (m, 3H), 4.46 (s, 2H), 4.11 (m, 2H), Example 84. Synthesis of 6-((2-(2,6-difluorophenyl)-5-oxo-6,7-dihydro-5H-pyrrolo[3,4-b]pyridin-4-yl)amino)-N-(2-methoxyethyl)nicotinamide I-141

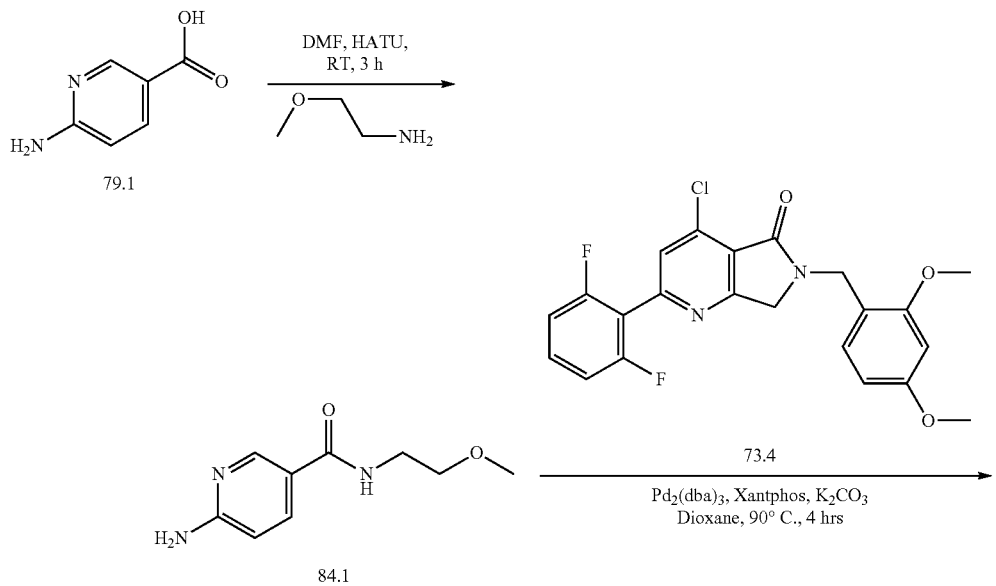

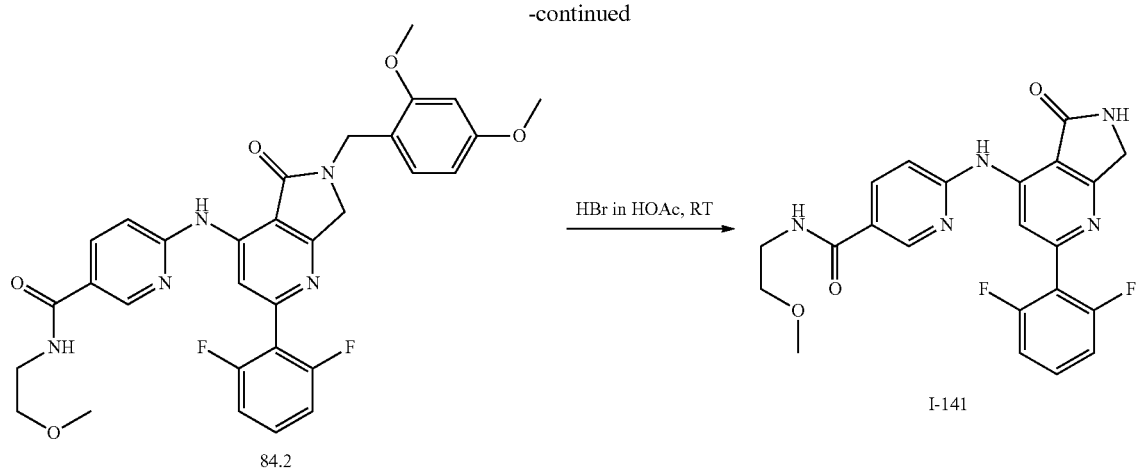

Synthesis of Compound 84.1.

A solution of 79.1 (0.300 g, 2.173 mmol, 1.0 equiv) in DMF (3 mL) were added HATU (1.235 g, 3.256 mmol, 1.5 equiv) in reaction mass and stirred for 15 min at room temperature, then added 2-methoxyethan-1-amine (0.195 g, 2.608 mmol, 1.2 equi.) and DIPEA (1.115 g, 6.519 mmol, 3.0 equiv). Reaction was stirred at room temperature for 3 hours. After completion of the reaction, reaction was quenched with water and extracted with ethyl acetate. Organic layer was washed with brine solution and dried over anhydrous sodium sulphate. Solvents were removed under reduce pressure to obtain crude material which was purified using column chromatography to afford compound 84.1 (0.100 g, 23.58%). MS (ES): m/z 196.2 [M+H]$^+$.

Synthesis of Compound 84.2.

To a solution of 73.4 (0.1 g, 0.232 mmol, 1.0 equiv) and 84.1 (0.045 g, 0.23 mmol, 1.0 equiv.) in 1,4-dioxane was (2 mL) added and potassium carbonate (0.08 mg, 0.58 mmol, 2.5 equiv). Reaction mixture was degassed under argon gas for 10 minutes and Pd$_2$(dba)$_3$ (0.018 g, 0.023 mmol, 0.1 equiv) and xanthpos (0.020 g, 0.046 mmol, 0.2 equiv.) were added. Suspension was degassed for additional five minutes using argon. Reaction mixture was heated at 90° C. for 4 hours. After completion of the reaction, mixture was poured into water and product was extracted with ethyl acetate. Organic layers were combined, dried over sodium sulphate and concentrated under reduced pressure to obtain crude material, which was purified using column chromatography to furnish 84.2 (0.112 g, 81.84%). MS (ES): m/z 589.5 [M+H]$^+$.

Synthesis of Compound I-141.

A solution of 84.2 (0.112 g, 1.904 mmol, 1.0 equiv) in HBr in acetic acid (2 mL) was stirred at room temperature for 1 hour. After completion, reaction mixture was concentrated and residue was diluted with water, basified with saturated bicarbonate solution and extracted with ethyl acetate. Organic layer was concentrated under reduced pressure to obtain crude material which was purified by preparative HPLC to furnish I-145. (0.022 g, 26.36%). MS (ES): m/z 385.3 [M+H]$^+$, $^1$H NMR (400 MHz, DMSO-d$_6$): δ 9.96 (s, 1H), 8.96 (s, 1H), 8.80 (s, 1H), 8.64 (s, 1H), 8.55 (d, 1H), 8.17-8.15 (d, 1H), 7.59 (s, 1H), 7.29-7.26 (m, 3H), 4.46 (s, 2H), 3.44-3.42 (t, 4H), 3.26 (s, 3H).

Example 85. Synthesis of 2-(2,6-difluorophenyl)-4-((5-(4-morpholinopiperidin-1-yl)pyridin-2-yl)amino)-6,7-dihydro-5H-pyrrolo[3,4-b]pyridin-5-one, I-142

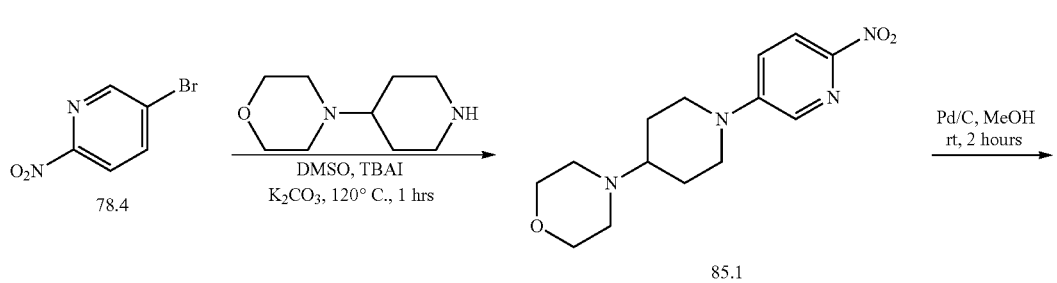

-continued

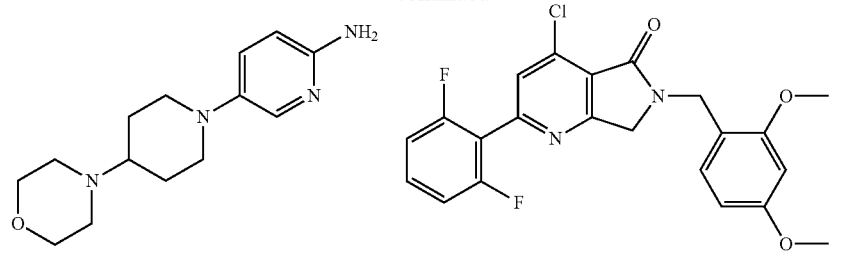

Xantphos, Pd$_2$(dba)$_3$, Dioxane
90° C., 4 hours

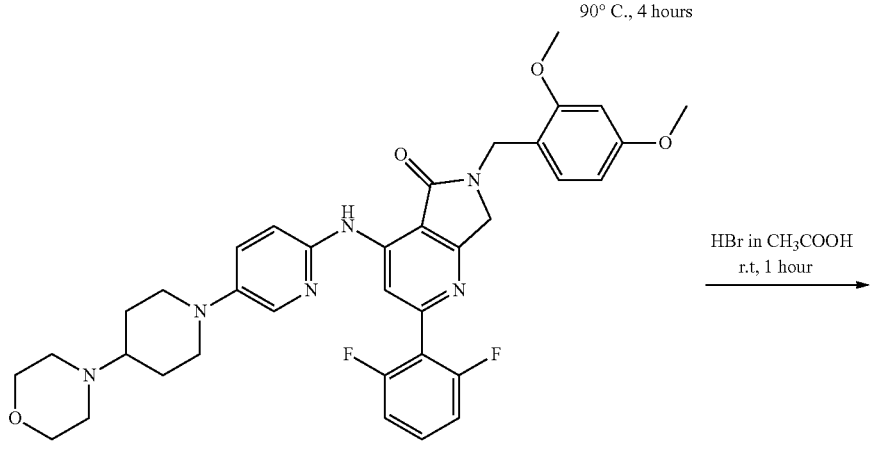

85.3

HBr in CH$_3$COOH
r.t, 1 hour

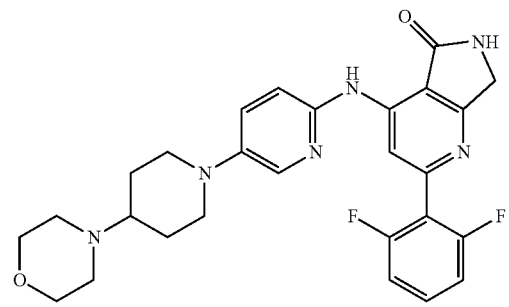

I-142

Synthesis of Compound 85.1.

To a solution of 78.4 (0.20 g 0.98 mmol, 1.0 eq.) in dry DMSO (3.0 mL) were added 4-(piperidin-4-yl)morpholine (0.2 g, 1.18 mmol, 1.2 eq.), K$_2$CO$_3$ (0.4 g, 3.0 mmol, 4.0 eq.) and tetrabutylammonium iodide (36 mg, 0.098 mmol, 0.2 equiv.) at ambient temperature. Reaction mixture was heated at 120° C. for one hour in microwave. After completion of the reaction, reaction mixture was poured into water and extracted using ethyl acetate. Organic layer was washed with by brine (25 ml×3) solution, dried over sodium sulfate and concentrated under reduced pressure. The crude was purified using column chromatography to afford pure compound 85.1 (0.2 g, 69%). MS (ES): m/z 293.3 [M+H]$^+$.

Synthesis of Compound 85.2.

To a suspension of palladium on charcoal (80 mg) in methanol (15 ml) was added 89.1 (0.19 g, 0.65 mmol. 1.0 eq.) under nitrogen atmosphere. Reaction mixture was purged using hydrogen gas and stirred for 2 hours at ambient temperature. After completion of the reaction, mixture was filter through celite. Solvent was removed under reduced pressure at 45° C. to afford compound 85.2 (0.14 g, 88%). MS (ES): m/z 263.2 [M+H]$^+$ Synthesis of Compound 85.3.

To a solution of 73.4 (0.15 g 0.39 mmol, 1.0 eq.) in dry dioxane (3.0 mL) were added 85.2 (118 mg, 0.45 mmol, 1.3 eq.), K$_2$CO$_3$ (0.14 g, 1.02 mmol, 2.0 eq.) at room temperature. Suspension was degassed using argon for 15 minutes. To mixture were added Pd$_2$(dba)$_3$ (28 mg, 0.031 mmol, 0.1 eq.) and Xantphos (35 mg, 0.062 mmol, 0.2 equiv.) Mixture was degassed for additional 10 minutes. Reaction mixture was heated at 105° C. temperature for 4 hours. After completion of the reaction, reaction mixture was poured into water and extracted using ethyl acetate. Organic layer was washed with brine, dried over sodium sulfate and concentrated under reduced pressure. Crude was purified using column chromatography to afford pure compound 85.3 (0.140 g, 61%). MS (ES): m/z 657.2 [M+H]$^+$.

Synthesis of Compound I-142.

A solution of 85.3 (0.14 g, 0.27 mmol. 1.0 eq.) in HBr/acetic acid solution (33%, 5 mL) was stirred at room temperature for 1 hour. After completion of the reaction, mixture was poured into cold water, neutralized with NaHCO$_3$ and extracted with ethyl acetate (50 ml×2). Solvent was removed under reduced pressure at 45° C. to get crude. The crude was purified using column chromatography to afford compound I-142 (52 mg, 48.2%). MS (ES): m/z 507.2 [M+H]+ 1H NMR (400 MHz, DMSO-d6): δ 9.50 (s, 1H), 8.81 (s, 1H), 8.37 (s, 1H), 8.01 (d, 1H), 7.60-7.53 (m, 1H), 7.467-7.44 (dd, 1H), 7.25 (t, 2H), 7.08 (d, 1H), 4.40 (s, 2H), 3.67 (d, 2H), 3.59 (s, 4H), 2.65 (t, 2H), 3.82 (s, 4H), 1.86-1.83 (m, 2H), 1.51-1.46 (m, 2H).

Example 86. Synthesis of (S)-4-((5-(3-aminopiperidin-1-yl)pyridin-2-yl)amino)-2-(2,6-difluorophenyl)-6,7-dihydro-5H-pyrrolo[3,4-b]pyridin-5-one, I-143 completion of the reaction, reaction mixture was poured into water and extracted using ethyl acetate. Organic layer was washed with brine (25 mL×3) solution. Organic layer was dried over sodium sulfate and concentrated under reduced pressure. The crude was purified by column chromatography to afford pure 86.1 (0.24 g, 60.45%). MS (ES): m/z 323.3 [M+H]+.

Synthesis of Compound 86.2.

To a suspension of Pd/C (80 mg) in methanol (15 ml) was added 86.1 (0.24 g, 0.74 mmol. 1.0 eq.) under nitrogen atmosphere. Above reaction mixture was purged with H2 (gas) at room temperature for 2 hours. After completion of the reaction, mixture was filtered through celite. Solvent was

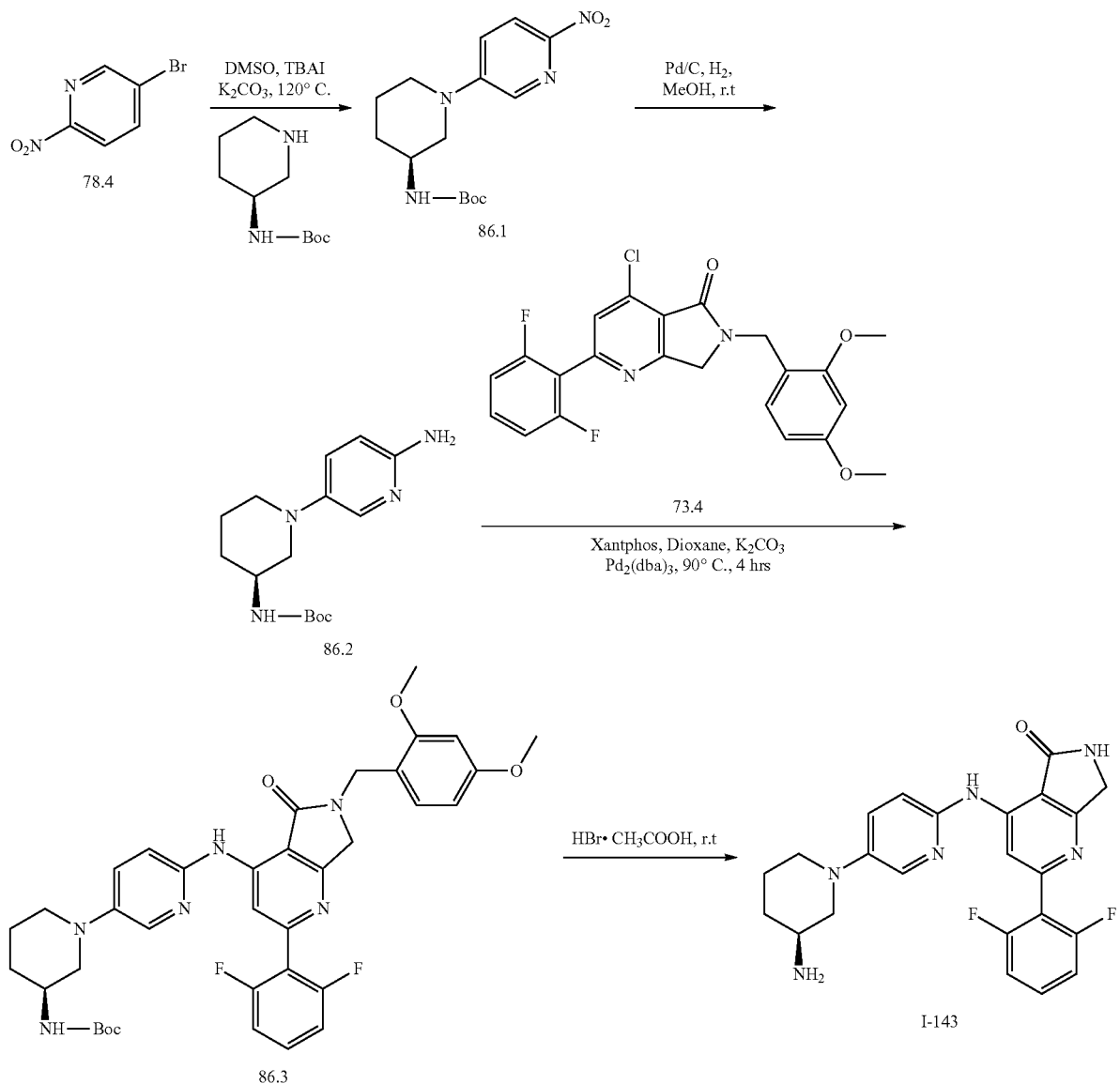

Synthesis of Compound 86.1.

To a solution of 78.4 (0.25 g 1.23 mmol, 1.0 eq.) in dry DMSO (3.0 mL) was added tert-butyl (S)-piperidin-3-ylcarbamate (0.246 g, 1.23 mmol, 1.0 eq.), K2CO3 (0.68 g, 4.92 mmol, 4.0 eq.) and tetrabutylammonium iodide (88 mg, 0.24 mmol, 0.2 eq.) at room temperature. Reaction mixture was heated at 120° C. for 30 minutes in microwave. After removed under reduced pressure to afford compound 86.2 (0.18 g, 82.7%). MS (ES): m/z 293.3 [M+H]+.

Synthesis of Compound 86.3.

To a solution of 73.4 (0.1 g 0.23 mmol, 1.0 eq.) in dry dioxane (3.0 mL) was added 86.2 (0.075 g, 0.25 mmol, 1.1 eq.), K2CO3 (0.064 g, 0.46 mmol, 2.0 eq.). Suspension was purged with argon for 15 minutes. To the above reaction mixture was added Pd$_2$(dba)$_3$ (0.021 g, 0.023 mmol, 0.1 eq.) and Xantphos (0.026 g, 0.046 mmol, 0.2 eq.). Reaction mixture was heated at 105° C. temperature for 4 hours. After completion of the reaction, reaction mixture was poured into water and extracted using ethyl acetate. Organic layer was washed with brine solution, dried over sodium sulfate and concentrated under reduced pressure. Crude was purified using column chromatography to provide compound 86.3 (0.175 g, crude). MS (ES): m/z 687.7 [M+H]$^+$.

Synthesis of Compound I-143.

A solution of 86.3 (0.175 g, crude) in HBr/CH$_3$COOH (33%, 5 ml) was stirred at room temperature for 1 hour. After completion of the reaction, reaction mixture was poured into cold water, neutralized with NaHCO$_3$ and with ethyl acetate (50 mL×2). Solvent was removed under reduced pressure and resulting crude was purified by column chromatography to afford compound I-143. (74 mg, 97.03%). MS (ES): m/z 437.4 [M+H]$^+$, $^1$H NMR (400 MHz, DMSO-d$_6$): δ 9.54 (s, 1H), 8.82 (s, 1H), 8.40 (s, 1H), 8.04-8.03 (d, 1H), 7.59-7.55 (m, 1H), 7.47-7.44 (dd, 1H), 7.28-7.24 (t, 2H), 7.15-7.13 (d, 1H), 4.41 (s, 2H), 3.53-3.47 (m, 1H), 3.23-3.17 (m, 1H), 2.91-2.87 (m, 2H), 1.90-1.87 (m, 1H), 1.81-1.77 (m, 1H) 1.61-1.55 (m, 1H), 1.52-1.47 (m, 1H).

Example 87. Synthesis of Compound 4-((5-(2-oxa-6-azaspiro[3.3]heptan-6-yl)pyridin-2-yl)amino)-2-(2, 6-difluorophenyl)-6,7-dihydro-5H-pyrrolo[3,4-b]pyridin-5-one, I-148

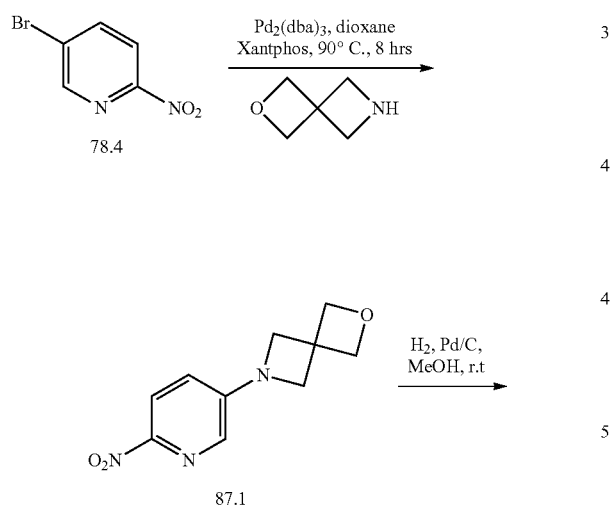

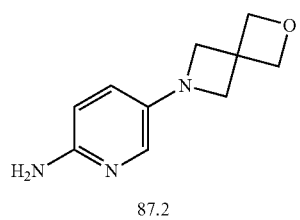

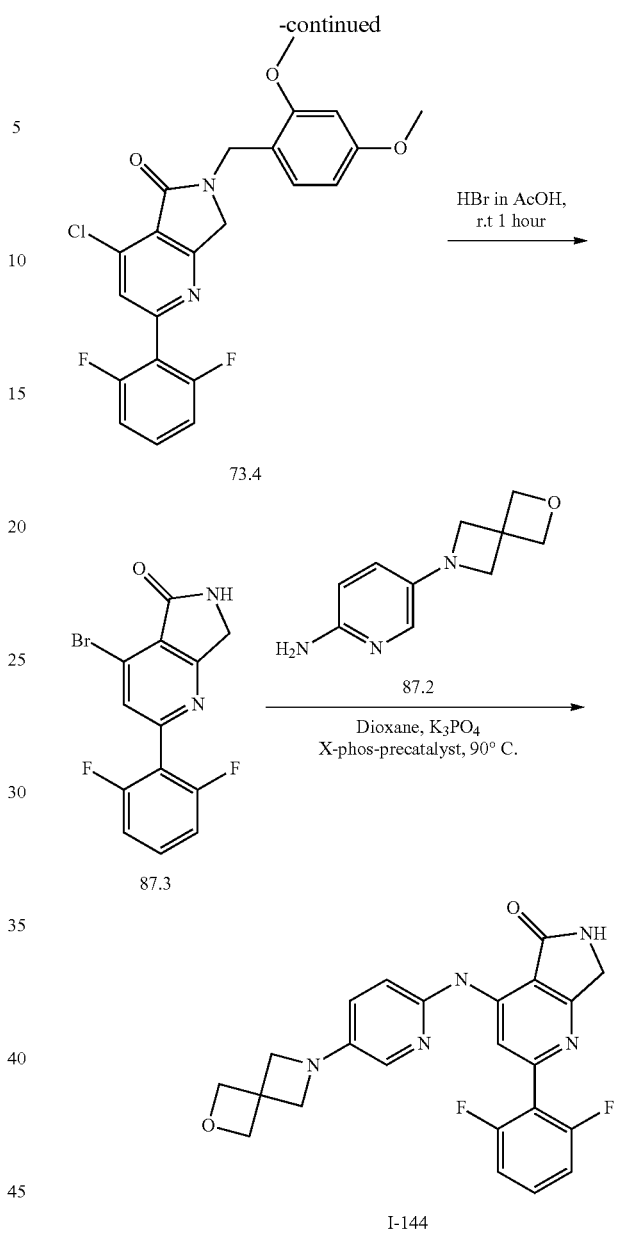

Synthesis of Compound 87.1.

To a solution of 78.4 (0.4 g 1.97 mmol, 1.0 eq.) in dry dioxane (2.0 mL) was added 2-oxa-6-azaspiro[3.3]heptane (0.41 g, 2.14 mmol, 1.1 eq.), K$_2$CO$_3$ (0.54 g, 3.94 mmol, 2.0 eq.). Mixture was purged with argon for 15 minutes. To the above reaction mixture was added Pd$_2$(dba)$_3$ (0.18 g, 0.39 mmol, 0.1 eq.) and Xantphos (0.22 g, 0.19 mmol, 0.2 eq.) under argon bubbling for 10 minutes. Reaction mixture was heated at reflux temperature for 8 hours. After completion of the reaction, reaction mixture was poured into water and extracted using ethyl acetate. Organic layer was washed with brine, dried over sodium sulfate and concentrated under reduced pressure. The crude was purified by column chromatography to afford pure compound 87.1 (0.18 g, 41%). MS (ES): m/z 222.1 [M+H]$^+$ Synthesis of Compound 87.2.

To a suspension of Pd/C (45 mg) in methanol (10 mL) was added 87.1 (0.18 g, 0.81 mmol. 1.0 eq.) under nitrogen atmosphere. Reaction mixture was purged with H$_2$ (gas) at room temperature for 2 hours. After completion of the reaction, reaction mixture was filter through celite, solvent removed under reduced pressure to afford compound 87.2 (0.13 g, 83.6%). MS (ES): m/z 192.2 [M+H]+, Synthesis of Compound 87.3.

A solution of 73.4 (0.6 g, 1.39 mmol. 1.0 eq.) in HBr/CH₃COOH (33%, 5 ml) was stirred at room temperature for 3 hours. After completion of the reaction, mixture was poured into cold water, neutralized with NaHCO₃ and product was extracted with ethylacetate (50 mL×2). Solvent was removed under reduced pressure to get the crude, which was triturated with diethyether to afford pure compound 87.3 (0.4 g, 88.4%). MS (ES): m/z 325.3 [M+H]+

Synthesis of Compound I-144.

To a solution of 87.3 (0.1 g 0.3 mmol, 1.0 eq.) in dry dioxane (2.0 mL) was added 87.2 (59 mg, 0.3 mmol, 1.0 eq.), K₃PO₄ (0.13 g, 0.61 mmol, 2.0 eq.) under argon purge for 15 minutes. To the mixture was added X-phos-precatalyst (45 mg, 0.06 mmol, 0.2 eq.) under argon purge for 10 minutes. Reaction mixture was heated at 90° C. for 20 minutes. After completion of the reaction, reaction mixture was poured into water and extracted using ethyl acetate. Organic layer was washed with by brine, dried over sodium sulfate and concentrated under reduced pressure. The crude was purified by column chromatography and preparative TLC to afford compound I-144 (16 mg, 11.9%). MS (ES): m/z 436.4 [M+H]+, ¹H NMR (400 MHz, DMSO-d₆): δ 9.45 (s, 1H), 8.78 (s, 1H), 8.29 (s, 1H), 7.63-7.53 (m, 2H), 7.30-7.23 (m, 2H), 7.08-7.06 (d, 1H), 6.98-6.95 (dd, 1H), 4.70 (s, 4H), 4.56 (s, 2H), 3.98 (s, 4H).

Example 88. Synthesis of 2-(4-((2-(2,6-difluorophenyl)-5-oxo-6,7-dihydro-5H-pyrrolo[3,4-d]pyrimidin-4-yl)amino)phenyl)-2-methylpropanoic Acid, I-109

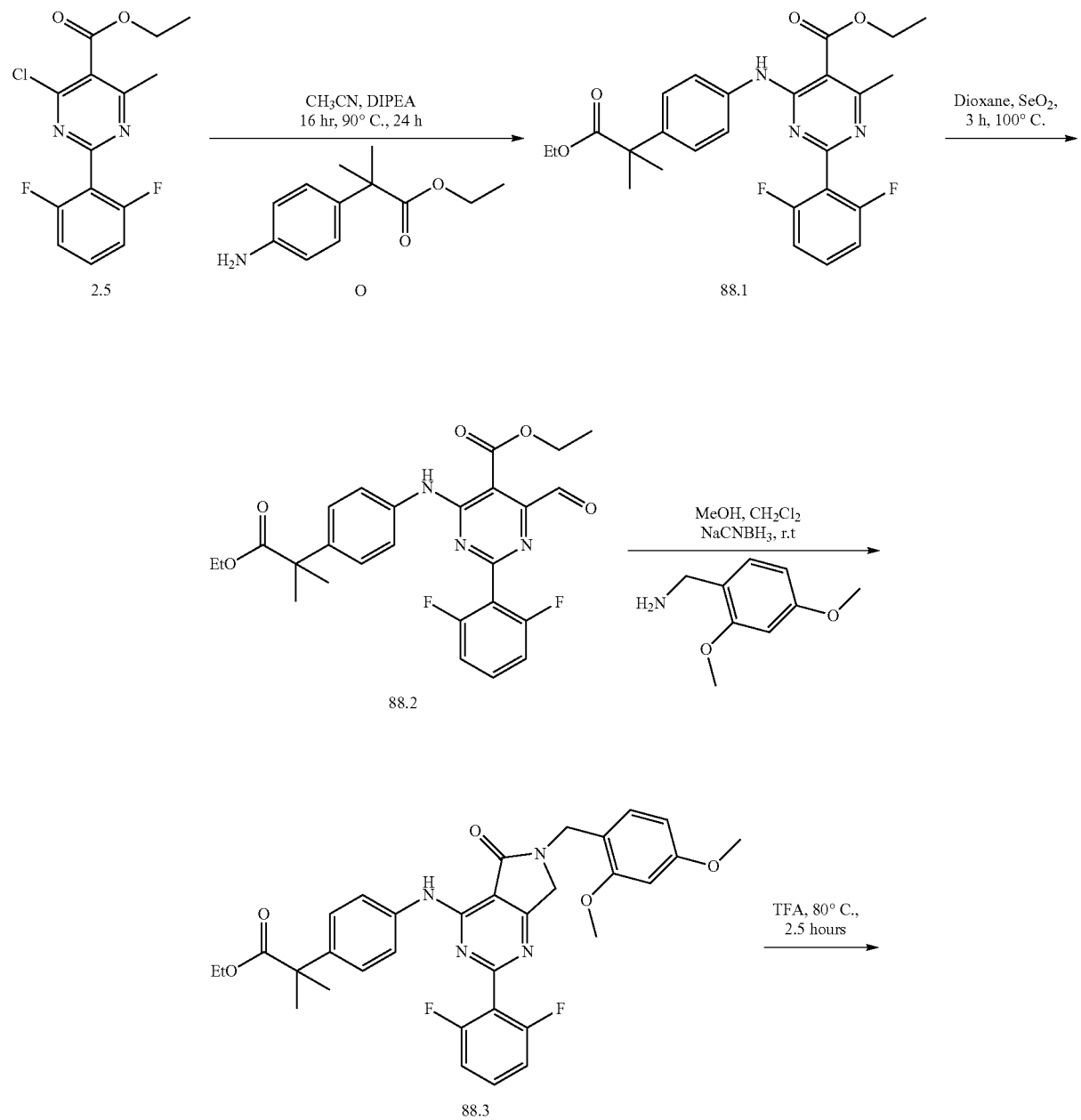

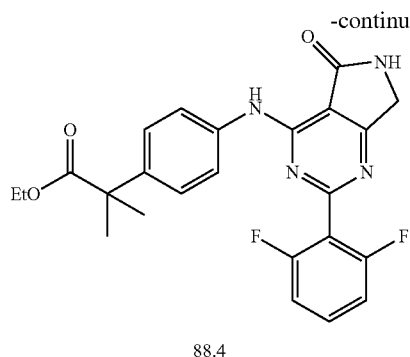

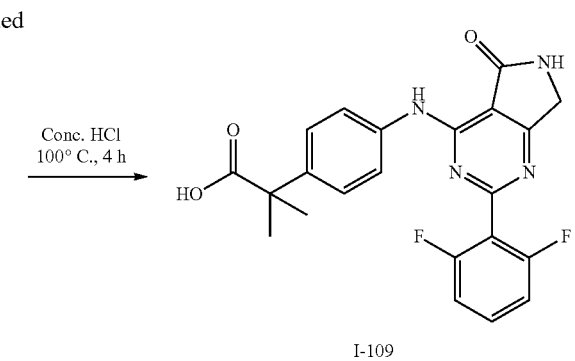

88.4

I-109

Synthesis of Compound 88.1.

A solution of 2.5 (0.5 g, 1.60 mmol, 1.00 eq), ethyl 2-(4-aminophenyl)-2-methylpropanoate (0.331 g, 1.06 mmol, 1.00 eq) and DIPEA (0.619 g, 4.8 mmol, 3.0 eq) in CH₃CN (8 mL) was heated at 100° C. for 24 h, Upon completion, reaction mixture was cooled to room temperature, poured into water and extracted with ethyl acetate (50 mL×3). Combined organic layer was washed with brine, dried over sodium sulphate and concentrated under reduced pressure. The crude was purified by column chromatography to afford compound 88.1 (0.5 g, 64%) LCMS-93%, MS (ES): m/z 484.5 [M+H]⁺.

Synthesis of Compound 88.2.

A solution of 88.1 (0.25 g, 0.517 mmol, 1.00 eq), selenium dioxide (0.143 g, 1.29 mmol, 2.5 eq) in 1,4-dioxane (6 mL) was stirred at 100° C. to 105° C. for 3 hours. After completion of the reaction, the resulting solution was filtered through celite and washed with 1,4-dioxane. Filtrate was concentrated under reduced pressure to afford 88.2 (0.250 g, quantitative) as a light yellow semisolid. Used as such crude for the next step. MS (ES): m/z 498.5 [M+H]⁺.

Synthesis of Compound 88.3.

To a solution of 88.2 (0.25 g, 0.5 mmol, 1.00 eq) in mixture of CH₂Cl₂: MeOH (5 mL, 1:4) was added 2,4-dimthoxybenzylamine (0.092 g, 0.55 mmol, 1.1 eq) at room temperature. Solution was stirred for 30 minutes. After 30 minutes, NaCNBH₃ (0.098 g, 1.51 mmol, 3.0 eq) was added at 0-10° C. The reaction mixture was allowed to warm at room temperature and was stirred 16 hours. After completion, the reaction was diluted with water and product was extracted with ethyl acetate (25 mL×3) and washed with brine. Combined organic layers were dried and concentrated under vacuum. Crude was purified using column chromatography to afford 88.3 (0.090 g, 30%) as a yellowish solid. MS (ES): m/z 603.2 [M+H]⁺.

Synthesis of Compound 88.4.

A solution of 88.3 (0.09 g, 0.149 mmol, 1.00 eq) in trifluoroaceticacid (1 mL) was stirred for 2.5 hours at 80° C. After completion of the reaction, mixture was concentrated under reduced pressure, diluted with water, extracted with ethyl acetate and washed with brine. Combined organic layers were dried and concentrated under vacuum. Crude was purified using column chromatography to afford the compound 88.4 (0.068 g, 99%) LCMS-94%, MS (ES): m/z 453.5 [M+H]⁺.

Synthesis of Compound I-109.

A solution of 88.4 (0.120 g, 0.264 mmol, 1.00 eq) in conc. HCl (2 mL) was stirred for 4 h at 100° C. After completion of the reaction, reaction mixture was diluted with water, extracted with ethyl acetate and washed with brine. Combined organic layers were dried and concentrated under reduced pressure. The crude was purified using column chromatography to afford compound I-109 (0.045 g, 40%) as a yellow solid. MS (ES): m/z 425.4 [M+H]⁺, ¹H NMR (400 MHz, DMSO-d₆): δ 12.31 (s, 1H), 9.06 (s, 1H), 8.9 (s, 1H), 7.73-7.70 (dd, 2H), 7.64-7.56 (m, 1H), 7.33-7.24 (m, 4H), 4.48 (s, 2H), 1.45 (s, 6H).

Example 89. Synthesis of 2-(2,6-difluorophenyl)-4-((4-methoxyphenyl)amino)-6,7-dihydro-5H-pyrrolo[3,4-d]pyrimidin-5-one, I-110

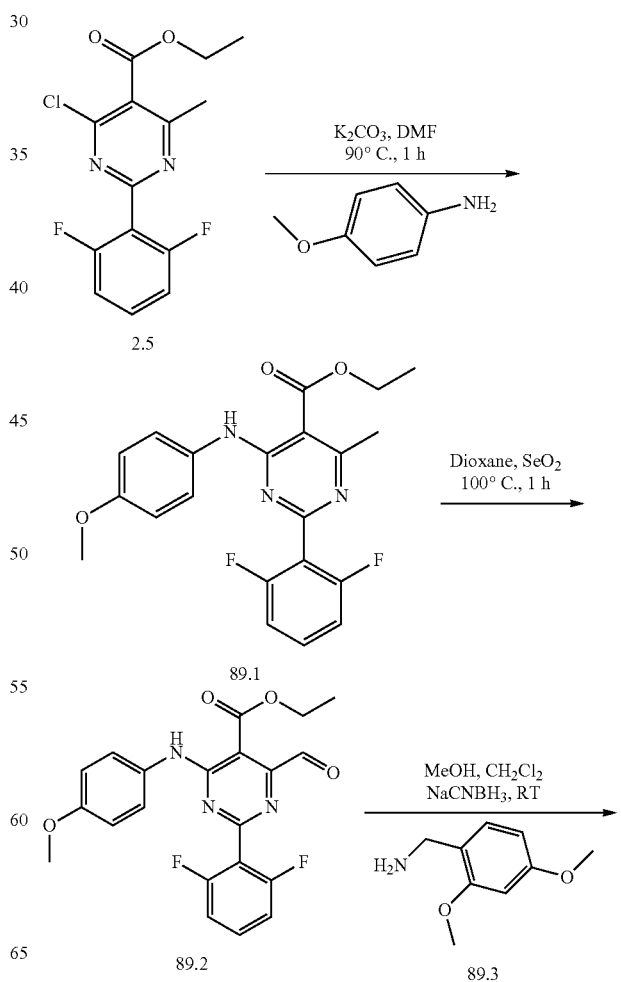

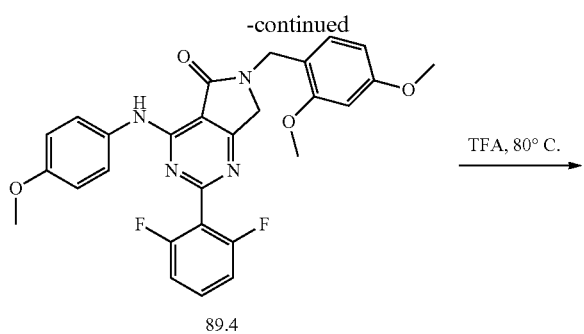

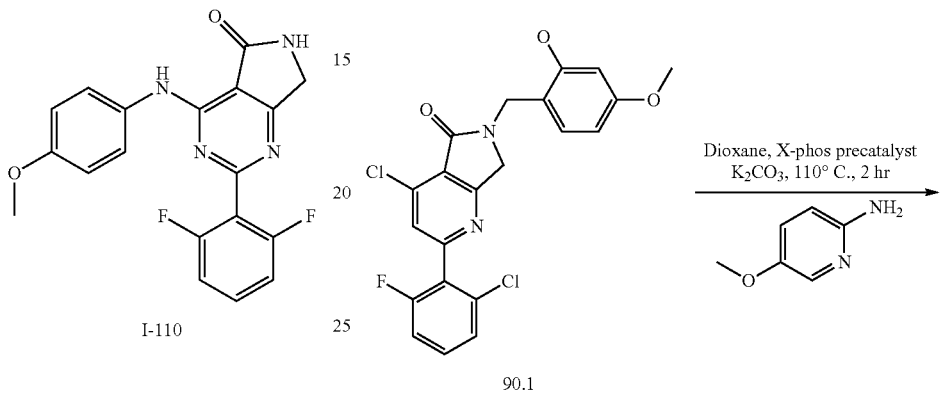

layers were dried and concentrated under vacuum. Crude was purified by column chromatography to afford compound I-110 (0.025 g, 39%) as a yellow solid. MS (ES): m/z 369 [M+H]$^+$, $^1$H NMR (400 MHz, DMSO-d$^6$): δ 8.96 (s, 1H), 8.83 (s, 1H), 7.64-7.57 (m, 3H), 7.27-7.23 (t, 2H), 6.93-6.91 (d, 2H), 4.46 (s, 2H), 3.73 (s, 3H).

Example 90. Synthesis of 2-(2-chloro-6-fluorophenyl)-4-((5-methoxypyridin-2-yl)amino)-6,7-dihydro-5H-pyrrolo[3,4-b]pyridin-5-one, I-145

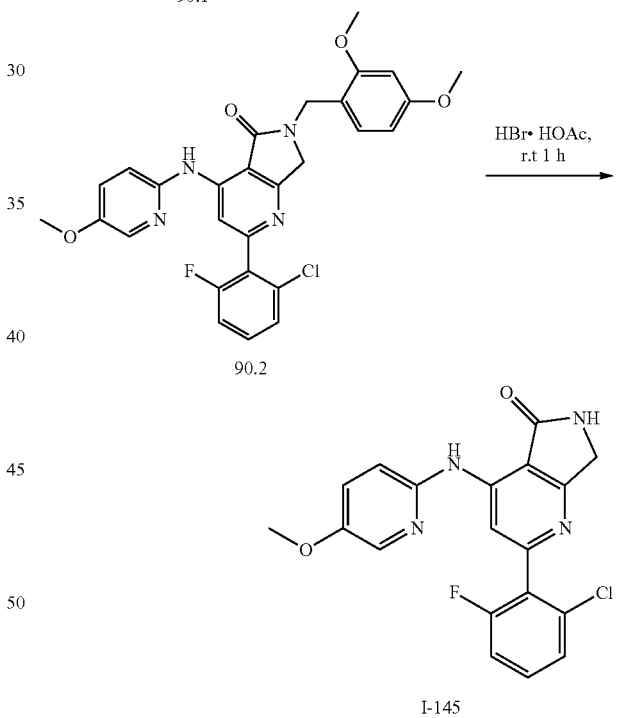

Synthesis of Compound 89.1.

A solution of 2.5 (0.3 g, 0.95 mmol, 1.00 eq), 4-methoxyaniline (0.141 g, 1.15 mmol, 1.2 eq) and K$_2$CO$_3$ (0.262 g, 1.9 mmol, 2.0 eq) in DMF (4 mL) was heated at 90° C. for 1 hour. Upon completion, reaction mixture was cooled to room temperature and poured into water and with ethyl acetate (25 mL×3). Combined organic layers were washed with brine, dried over sodium sulphate and concentrated under reduced pressure. Crude was purified using column chromatography to afford the compound 89.1 (0.28 g, 76%), MS (ES): m/z 400 [M+H]$^+$ Synthesis of Compound 89.2.

A solution of 89.1 (0.28 g, 0.76 mmol, 1.00 eq), selenium dioxide (0.169 g, 1.52 mmol, 2.0 eq) in 1,4-dioxane (3 mL) was stirred at 100° C. for 1 h. After completion of the reaction, the resulting solution was filtered through celite and washed with 1,4-dioxane. Filtrate was concentrated under reduced pressure to afford 89.2 (0.280 g, quantitative) as a light yellow semisolid. Used as such crude for the next step. MS (ES): m z 414.4 [M+H]$^+$.

Synthesis of Compound 89.4.

To a solution of 89.2 (0.28 g, 0.67 mmol, 1.00 eq) in mixture of CH$_2$Cl$_2$: MeOH (5 mL, 1:4) was added 89.3 (0.147 g, 0.88 mmol, 1.3 eq) at room temperature and stirred for 30 minutes. After 30 minutes, NaCNBH$_3$ (0.172 g, 2.68 mmol, 4.0 eq) was added at 0-10° C. The reaction mixture was allowed to warm at room temperature and stirred for overnight. After completion, the reaction was diluted with water and product was extracted with ethyl acetate (25 mL×3) and washed with brine. The combined organic layers were dried and concentrated under vacuum. The residue was purified using column chromatography to afford compound 89.4 (0.09 g, 26%) as a yellowish solid. MS (ES): m/z 519.5 [M+H]$^+$, Synthesis of Compound I-110.

A solution of 89.4 (0.090 g, 0.173 mmol, 1.00 eq) in trifluoroacetic acid (3 mL) was stirred for 3 hours at 80° C. After completion of the reaction, mixture was concentrated under reduced pressure, diluted with water, extracted with ethyl acetate and washed with brine. Combined organic Synthesis of Compound 90.2.

To a solution of compound 90.1 (0.60 g, 0.134 mmol, 1.0 equiv) and 5-methoxypyridin-2-amine (0.033 g, 0.268 mmol, 2.0 equiv) in 1,4-dioxane was added and K$_2$CO$_3$ (0.036 mg, 0.268 mmol, 2.0 equiv). Reaction mixture was degassed under argon gas for 5-10 minutes. Xanthpos precatalyst (0.019 g, 0.0268 mmol, 0.2 equiv) was added and suspension was degassed under argon for additional 5 minutes. Reaction mixture was heated at 110° C. for 2 hours. After completion of the reaction, reaction mixture was poured into water and product was extracted with ethyl acetate. Organic layers were combined and dried over sodium sulphate and concentrated under reduced pressure. The crude was purified using column chromatography to obtain compound 90.2 (0.052 g, 72.46%). MS (ES): m z 535.2 [M+H]⁺.

Synthesis of Compound I-145.

A solution of 90.2 (0.052 g, 0.971 mmol, 1.0 equiv) in HBr/Acetic acid (1 mL) was stirred at room temperature for one hour. After completion, reaction mixture was concentrated and residue was diluted with water. Crude was neutralized with NaHCO₃ and extracted with ethyl acetate. Organic layer was concentrated under reduce pressure to obtain crude material which was purified by column chromatography to afford compound I-145 (0.023 g, 61.5%). MS (ES): m/z 385.3 [M+H]⁺ ¹H NMR (400 MHz, DMSO-d₆): δ 9.62 (s, 1H), 8.84 (s, 1H), 8.33 (s, 1H), 8.08-8.07 (d, 1H), 7.56-7.47 (m, 1H), 7.45-7.42 (m, 2H), 7.41-7.36 (t, 1H), 7.19-7.17 (d, 1H), 4.41 (s, 2H), 3.82 (s, 3H).

Example 91. Synthesis of 6-((2-(2-chloro-6-fluorophenyl)-5-oxo-6,7-dihydro-5H-pyrrolo[3,4-b]pyridin-4-yl)amino)-N-ethylnicotinamide, I-146

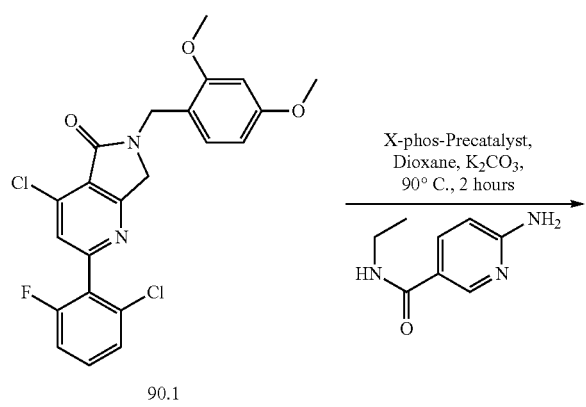

90.1

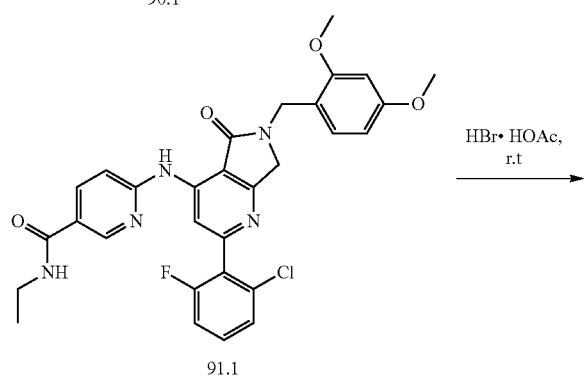

91.1

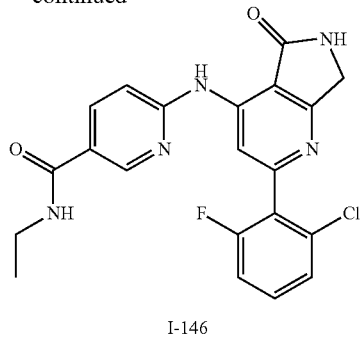

I-146

Synthesis of Compound 91.1.

To a solution of 90.1 (75 mg 0.167 mmol, 1.0 eq.) in dry Dioxane (2.0 mL) was added 6-amino-N-ethylnicotinamide (33 mg, 0.2 mmol, 1.2 eq.), K₂CO₃ (46 mg, 0.33 mmol, 2.0 eq.) at ambient temperature. Suspension was purged under argon for 15 minutes. To suspension was added X-phos-precatalyst (24 mg, 0.03 mmol, 0.2 eq.) Reaction mixture was purged with argon for additional ten minutes then heated at 90° C. for 20 minutes. After completion of the reaction, reaction mixture was poured into water and extracted using ethyl acetate. Organic layer was washed with by brine solution, dried over sodium sulfate and concentrated under reduced pressure. Crude was purified by column chromatography to furnish compound 91.1 (0.78 g, 53%). MS (ES): m/z 577 [M+H]⁺.

Synthesis of Compound I-146.

A solution of 91.1 (78 g, crude) in HBr/HOAc (33%, 5 ml) was stirred at room temperature for 1 hour. After completion of the reaction, reaction mixture was poured into cold water, neutralized with NaHCO₃ and extracted with ethyl acetate (50 ml×2). Solvent was removed under reduced pressure. The crude was purified by column chromatography to provide compound I-146 (28 mg, 94%). MS (ES): m/z 426.8 [M+H]⁺, ¹H NMR (400 MHz, DMSO-d₆): δ 9.97 (s, 1H), 8.98 (s, 1H), 8.78-8.77 (d, 1H), 8.57 (s, 1H), 8.47-8.44 (t, 1H), 8.15-8.13 (dd, 1H), 7.60-7.49 (m, 2H), 7.43-7.33 (t, 1H), 7.26-7.24 (d, 1H), 4.47 (s, 2H), 3.30-3.24 (q, 2H), 1.15-1.09 (t, 3H).

Example 92. Synthesis of 2-(2,6-difluorophenyl)-4-((5-(4-hydroxypiperidin-1-yl)pyridin-2-yl)amino)-6,7-dihydro-5H-pyrrolo[3,4-b]pyridin-5-one, I-147

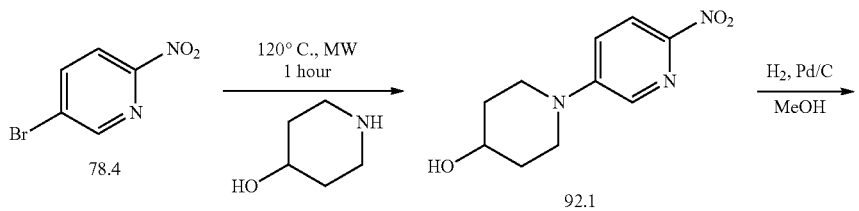

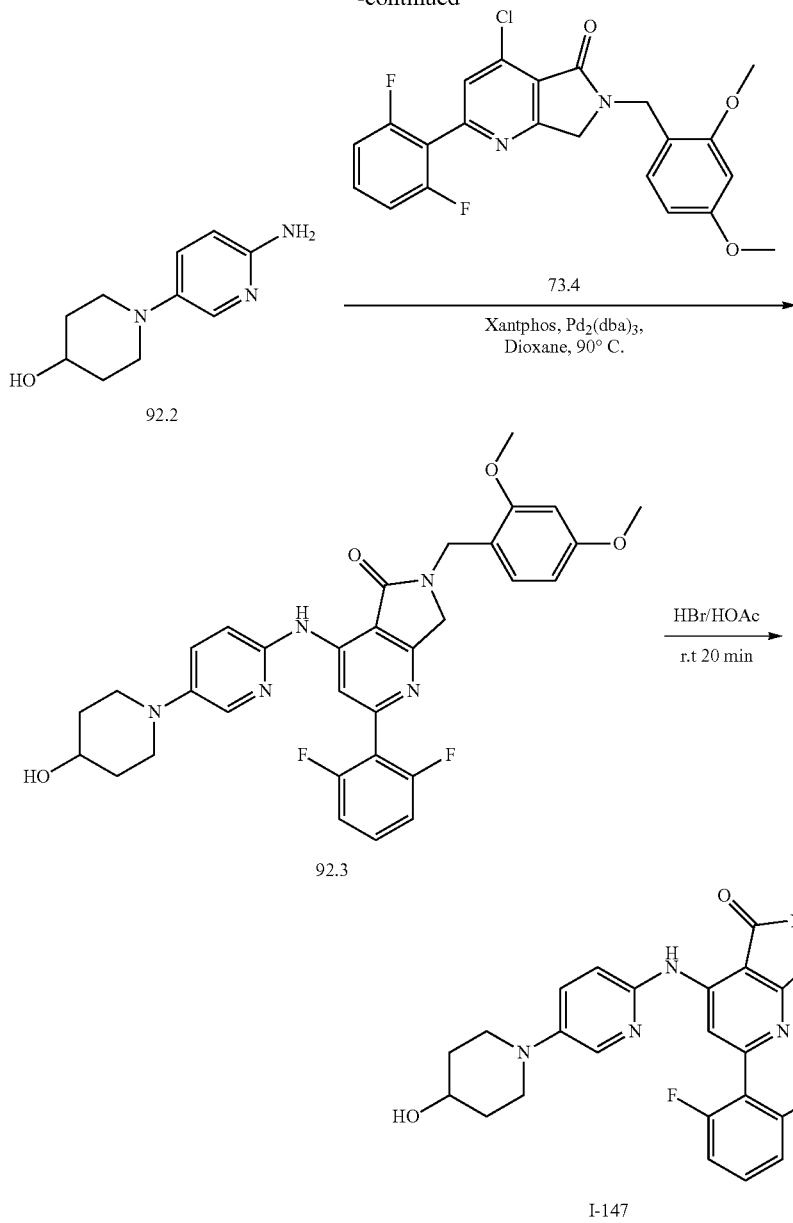

Synthesis of Compound 92.1

A mixture of 78.4 (1.0 g, 4.92 mmol, 1.0 eq) and piperidin-4-ol (1.0 g, 9.85 mmol, 2.0 eq) was heated in microwave for 2 hours at 120° C. After completion of the reaction, reaction mixture was poured into water and extracted using ethyl acetate (200 vmL×2). Organic layer was washed with by brine solution, dried over sodium sulfate and concentrated under reduced pressure. Crude was purified using column chromatography to afford 92.1 (0.25 g, 18.64%). MS (ES): m/z 224.1 [M+H]$^+$ Synthesis of Compound 92.2.

To a suspension of Pd/C (50 mg) in methanol (10 mL) was added 92.1 (0.25 g, 1.12 mmol, 1.0 eq) under nitrogen atmosphere. Suspension was purged with $H_2$ gas at room temperature for 1 hour. After completion of the reaction, reaction mixture was filtered through celite. Filtrate was concentrated under reduced pressure to afford 92.2 (0.12 g, 67.6%). MS (ES): m/z 194.1 [M+H]$^+$ Synthesis of Compound 92.3.

To a solution of 92.2 (0.05 g, 0.25 mmol, 1.1 eq) in dry 1,4-dioxane (3.0 mL) were added 73.4 (0.1 g, 0.23 mmol, 1.0 eq), Xantphos (0.026 g, 0.04 mmol, 0.2 eq) and $K_2CO_3$ (0.08 g, 0.46 mmol, 2.0 eq) at room temperature. Reaction mixture was degassed for 15 minutes using argon gas. To reaction mixture was added $Pd_2(dba)_3$ (0.021 g, 0.023 mmol, 0.1 eq) and suspension was purged for 20 minutes. Reaction mixture was heated at 100° C. for 4 hours. After completion of the reaction, mixture was poured into water and extracted using ethyl acetate (25 mL×2). Organic layers were washed with brine solution, dried over sodium sulfate and concentrated under reduced pressure. Crude was purified using column chromatography to afford 92.3 (0.090 g, 66%). MS (ES): m/z 588.6 [M+H]$^+$ Synthesis of Compound I-147.

A solution of 92.3 (0.09 g, 1.39 mmol. 1.0 eq.) in HBr/HOAc solution (33%, 3 mL) was stirred at room temperature for 2 hours. After completion of reaction, reaction mixture was poured in cold water, neutralized with sodium bicarbonate and extracted with ethyl acetate (50 mL×2). Solvent was removed under reduced pressure. Crude was treated with $K_2CO_3$/MeOH, and purified by column chromatography to afford pure I-147 (0.042 g, 62.7%). MS (ES): m/z 438.31 [M+H]+ 1H NMR (400 MHz, DMSO-$d_6$): δ 9.497 (s, 1H), 8.808 (s, 1H), 8.361 (s, 1H), 8.017-8.024 (d, 1H), 7.550-7.591 (m, 1H), 7.433-7.463 (dd, 1H), 7.236-7.276 (t, 2H), 7.062-7.085 (d, 1H), 4.686-4.697 (d, 1H), 4.407 (s, 2H), 3.584-3.627 (m, 2H), 3.468-3.501 (m, 2H), 2.797-2.861 (m, 2H), 1.781-1.812 (t, 2H), 1.431-1.508 (m, 2H).

Example 93. Synthesis of 2-(2,6-difluorophenyl)-4-((5-(2-morpholinoethoxy)pyridin-2-yl)amino)-6,7-dihydro-5H-pyrrolo[3,4-b]pyridin-5-one, I-148

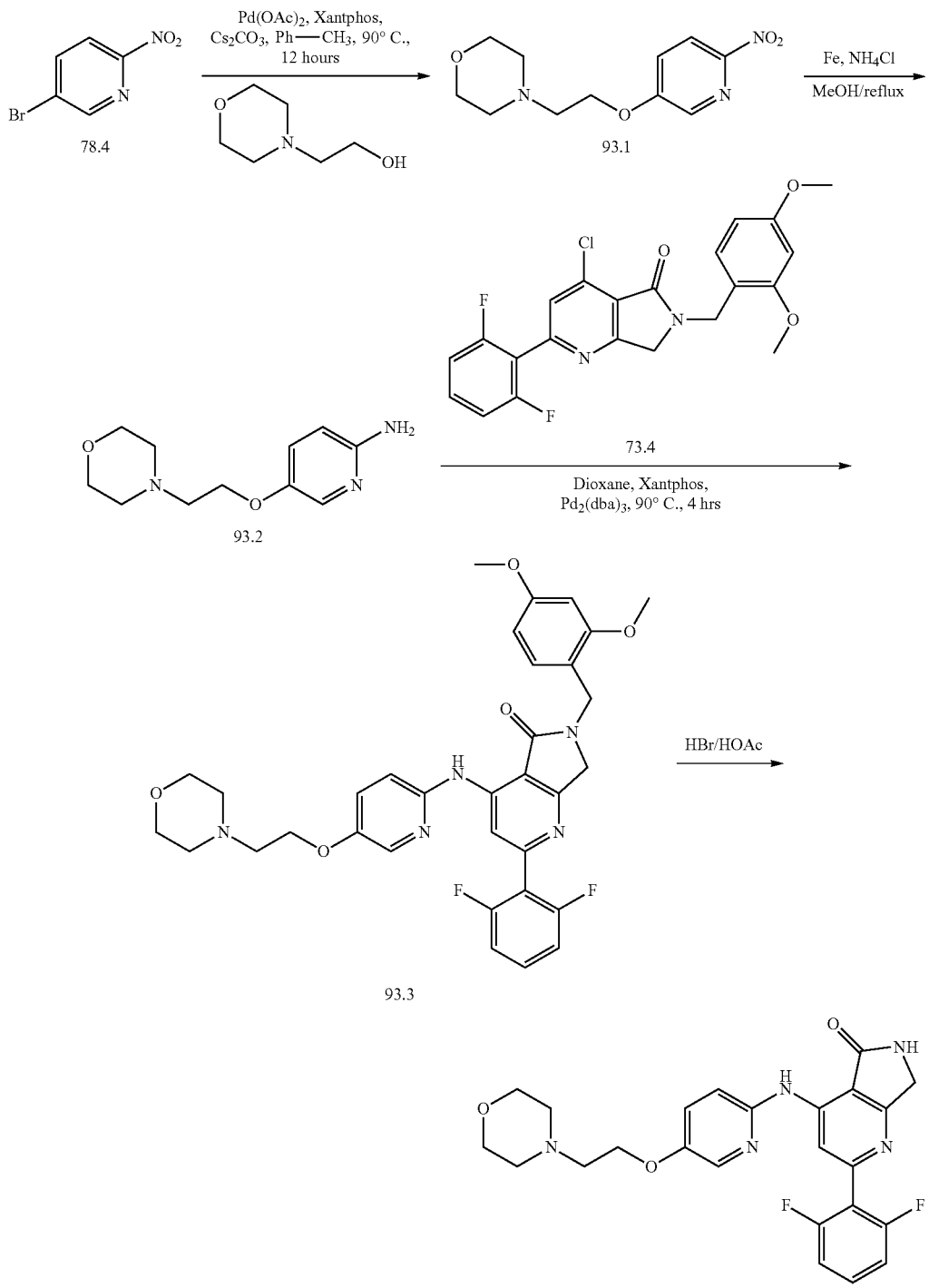

Synthesis of Compound 93.1.

To a solution of 78.4 (0.8 g 3.94 mmol, 1.0 eq) in dry toluene (8.0 mL) were added 2-morpholinoethan-1-ol (0.516 g, 3.94 mmol, 1.0 eq), $Cs_2CO_3$ (1.63 g, 11.82 mmol, 3.0 eq). Suspension was purged with argon for 15 minutes. To the above reaction mixture was added $Pd(OAc)_2$ (0.1 g, 0.39 mmol, 0.1 eq) and Xantphos (0.36 g, 0.39 mmol, 0.1 eq) under argon bubbling for 10 minutes. Reaction mixture was heated at 90° C. for 12 hours. After completion of the reaction, mixture was poured into water and extracted using ethyl acetate (100 mL×2). Organic layer was washed with brine, dried over sodium sulfate and concentrated under reduced pressure. Crude was purified using column chromatography to afford 93.1 (0.3 g, 30%). MS (ES): m/z 254.1 $[M+H]^+$.

Synthesis of Compound 93.2.

To a solution of 93.1 (0.15 g, 0.59 mmol, 1.0 eq) in methanol (2 mL) was added iron powder (0.165 g, 2.95 mmol, 5.0 eq), $NH_4Cl$ (0.157 g, 2.95 mmol, 5.0 eq) and water (2 mL). Reaction mixture was heated at 68° C. for 2 hours. After completion of reaction, mixture was filtered through celite. Filtrate was poured into water and extracted using ethyl acetate (50 mL×2). Organic layer was washed with by brine solution. Organic layer was dried over sodium sulfate and concentrated under reduced pressure at 45° C. to afford 93.2 (0.04 g, 30.2%). MS (ES): m/z 224.1 $[M+H]^+$.

Synthesis of Compound 93.3.

To a solution of 73.4 (0.08 g, 0.186 mmol, 1.0 eq) and 93.2 (0.041 g, 0.186 mmol, 1.0 eq) in 1,4-dioxane (2 mL) was added $K_2CO_3$ (0.051 g, 0.580 mmol, 3.0 eq). Reaction mixture was degassed under argon gas for 15 min. and $Pd_2(dba)_3$ (0.016 g, 0.018 mmol, 0.1 eq) and Xantphos (0.010 g, 0.018 mmol, 0.2 eq) were added. Suspension was degassed using argon for additional 15 minutes. Reaction mixture was heated at 90° C. for 4 hours. After completion of the reaction, reaction mixture was poured into water and product was extracted with ethyl acetate. Organic layers were combined, dried over sodium sulphate and concentrated under reduced pressure to obtain crude material. Crude was purified using column chromatography to afford 93.3 (0.80 g, 39.8%). MS (ES): m/z 618.1 $[M+H]^+$.

Synthesis of Compound I-148.

A solution of 93.3 (0.8 g, 0.129 mmol, 1.0 eq) in HBr/HOAc solution (33%, 2 mL) was stirred at room temperature for 1 hour. After completion of the reaction, mixture was poured into cold water, neutralized with sodium bicarbonate solution and extracted with ethyl acetate (2×50 mL). Solvent was removed under reduced pressure and crude purified using column chromatography to afford I-148 (0.040 g, 66.1%). MS (ES): m/z 468.1 $[M+H]^+$, LCMS purity: 98.75%, HPLC purity: 98.08%, $^1H$ NMR (400 MHz, DMSO-$d_6$): δ 9.60 (s, 1H), 8.84 (s, 1H), 8.38 (s, 1H), 8.08-8.07 (d, 1H), 7.61-7.75 (m, 1H), 7.47-7.44 (m, 1H), 7.28-7.23 (s, 2H), 7.18-7.16 (d, 1H), 4.42 (s, 2H), 4.14-4.11 (t, 2H), 3.58-3.55 (t, 4H), 2.68-2.66 (t, 2H), 2.45 (t, H).

Example 94. Synthesis of 2-(2,6-difluorophenyl)-4-((4-(1-(2-hydroxyethyl)-2-oxopyrrolidin-3-yl)phenyl)amino)-6,7-dihydro-5H-pyrrolo[3,4-d]pyrimidin-5-one I-149

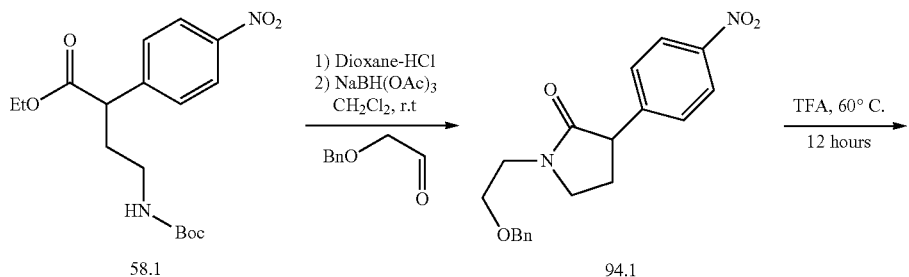

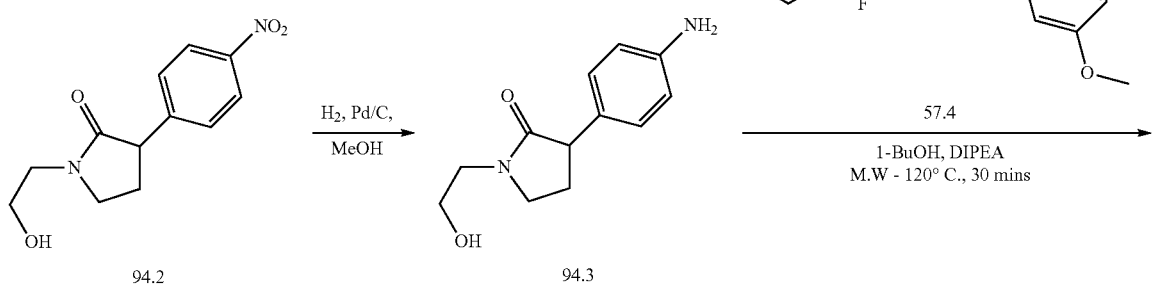

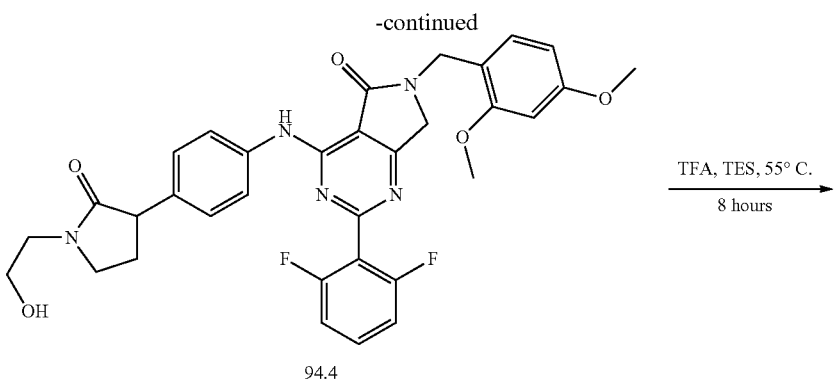

94.4

TFA, TES, 55° C.
8 hours

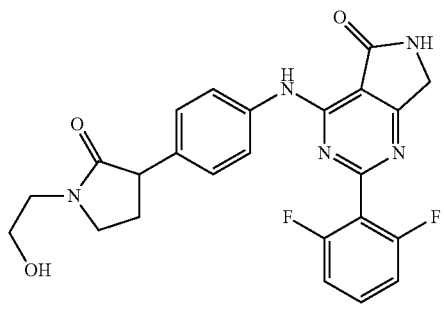

I-149

Synthesis of Compound 94.1.

To a solution of 58.1 (2.5 g, 7.09 mmol, 1.0 eq) in 1,4-dioxane (10 mL) was added 4N HCl in 1,4-dioxane (10 mL). Reaction mixture was allowed to stir at room temperature for 2 hours. Dioxane was removed under reduced pressure and $CH_2Cl_2$ (25 mL) was added. Sat. $NaHCO_3$ solution added to adjust pH to 8. Organic layer was separated out, washed with water and dried over sodium sulphate and transferred to separate round bottom flask. 2-(benzyloxy)acetaldehyde (1.06 g, 7.09 mmol, 1.0 eq) was added followed by portion wise addition of $NaCNBH_3$ (0.891 g, 14.1 mmol, 2.0 eq). After completion of the reaction, reaction mixture was cooled to room temperature. Water (50 mL) was added to reaction mixture and extracted with EtOAc (50 mL×2). Organic layer was washed with by brine, dried over sodium sulfate and concentrated under reduced pressure. Crude was purified using column chromatography to afford compound 94.1 (0.52 g, 21.53%). MS (ES): m/z=341.4 [M+H]$^+$ Synthesis of Compound 94.2.

Compound 94.1 (0.52 g, 1.53 mmol, 1.0 eq) was dissolved in trifluoroacetic acid (5 mL) and heated at 70° C. for 2 hours. After completion of the reaction, mixture was concentrated under reduced pressure to remove excess trifluoroacetic acid, then neutralized with saturated sodium bicarbonate solution to afford crude which was purified using column chromatography to provide 94.2. (0.250 g, 65.4%), MS (ES): m/z 251.2 [M+H]$^+$.

Synthesis of Compound 94.3.

To a suspension of Pd/C (0.050 g) in MeOH (5.0 mL) was added 94.2 (0.25 g, 1.0 mmol, 1.0 eq) in MeOH (5.0 mL). Suspension was purged with $H_2$ gas for 30 minutes. After completion of the reaction, mixture was filtered through celite and filtrate was concentrated under reduced pressure to afford crude which was purified by column chromatography to afford compound 94.3. (0.1 g, 45.4%), MS (ES): m/z 221.5 [M+H]$^+$.

Synthesis of Compound 94.4

To a solution of 94.3 (0.15 g, 0.69 mmol, 1.0 eq) in dry 1-butanol (2 mL) was added 57.4 (0.3 g, 0.69 mmol, 1 eq and DIPEA (2.67 g, 2.07 mmol, 3 eq). Reaction mixture was allowed to stir at 100° C. for 2 hours. After completion of the reaction, reaction mixture was cooled to room temperature. Water (100 mL) was added to reaction mixture and extracted with EtOAc (50 mL×2). Organic layer was washed with brine, dried over sodium sulfate and concentrated under reduced pressure. Crude was purified by column chromatography to afford 94.4 (0.11 g, 25.7%). MS (ES): m/z=616.74 [M+H]$^+$ Synthesis of Compound I-149.

A solution of 94.4 (0.11 g, 0.18 mmol, 1 eq) in trifluoroacetic acid (3 mL) and triethylsilane (0.207 g, 1.8 mmol, 10 eq) was stirred at 55° C. temperature for 8 hours. After completion of the reaction, mixture was poured into cold water, neutralized with sodium bicarbonate and product was extracted with ethyl acetate (25 mL×2). Solvent was removed under reduced pressure at 45° C. to get crude which was purified using column chromatography to afford pure I-149 (0.052 g, 62.52%). MS (ES): m/z 466.32 [M+H]$^+$ $^1$H NMR (400 MHz, DMSO-d$_6$): δ 8.765 (s, 1H), 7.779-7.800 (d, 2H), 7.387-7.460 (m, 1H), 7.295 (s, 1H), 7.274 (s, 1H), 7.024, 7.064 (t, 2H), 6.243 (s, 1H), 4.527 (s, 2H), 3.853-3.865 (d, 2H), 3.715-3.759 (t, 1H), 3.506-3.715 (m, 4H), 2.526-2.610 (m, 1H), 2.14-2.23.

Example 95. Synthesis of 2-(2,6-difluorophenyl)-4-((4-(1,3-dimethyl-2-oxopyrrolidin-3-yl)phenyl)amino)-6,7-dihydro-5H-pyrrolo[3,4-d]pyrimidin-5-one, I-150

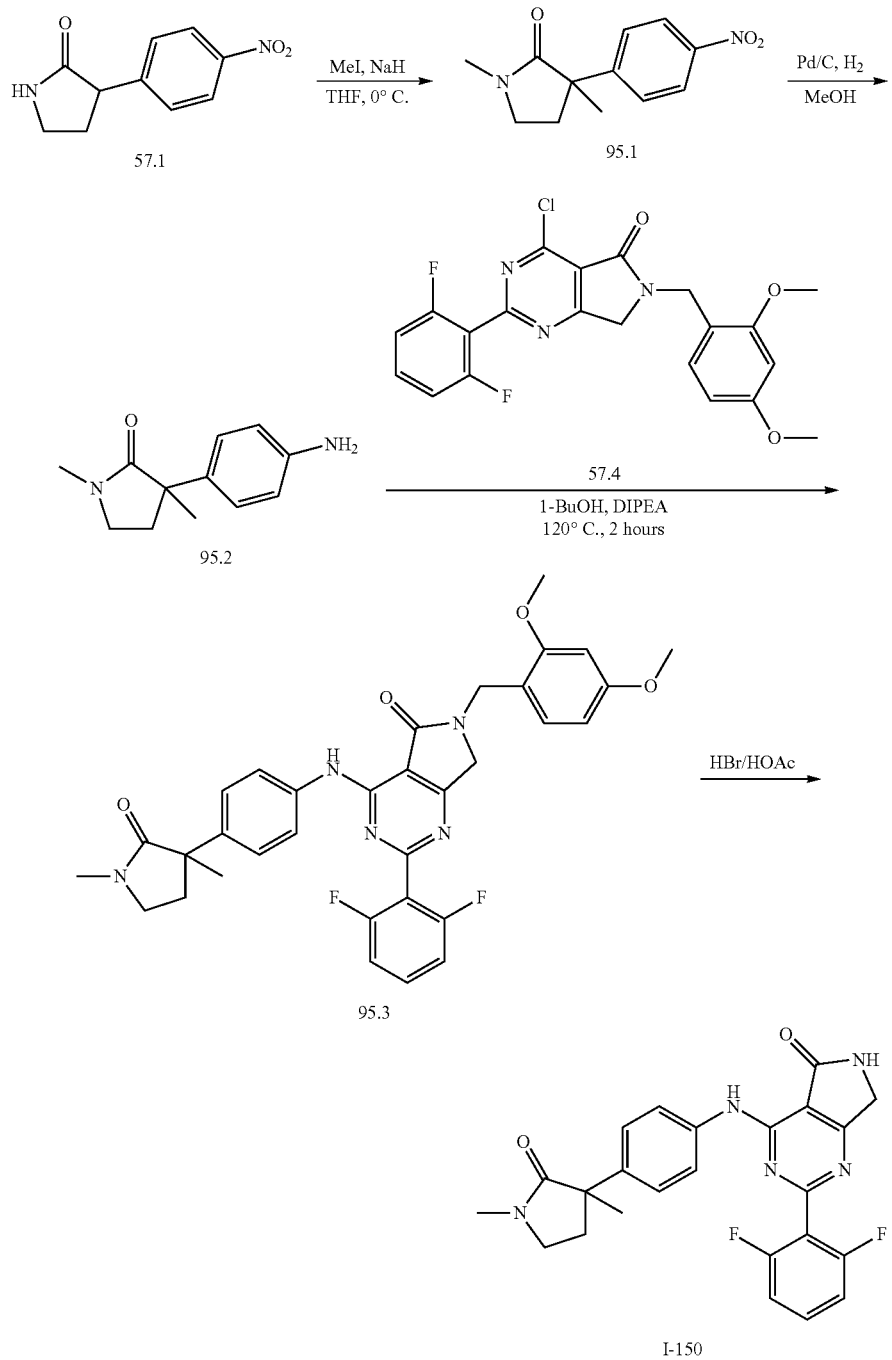

was separated out, washed with water, dried over sodium sulphate and concentrated under reduced pressure. Crude was purified by column chromatography to afford compound 95.1 (0.35 g, 61.6%). MS (ES): m/z=235.11 [M+H]$^+$ Synthesis of Compound 95.1.

To a solution of NaH (0.484 g, 12.1 mmol, 5.0 eq) in DMF (5 mL), was added 57.1 (0.5 g, 2.42 mmol, 1.0 eq) at 0° C. and allowed to stirred for 30 minutes. Methyl Iodide (1.03 g, 7.26 mmol, 3.0 eq) was added at 0° C. and reaction stirred at room temperature for 2 hours. After completion of the reaction, reaction mixture was quenched in ice and product was extracted with ethyl acetate (100 mL×2). Organic layer Synthesis of Compound 95.2.

To a suspension of Pd/C (0.1 g) in MeOH (5.0 mL) was added 103.1 (0.35 g, 1.49 mmol, 1.0 eq) in MeOH (3.0 mL). Suspension was purged with H$_2$ gas for 30 minutes. After completion of the reaction, mixture was filtered through celite and filtrate was concentrated under reduced pressure to afford crude which was purified to afford compound 95.2. (0.09 g, 29.5%), MS (ES): m/z 205.18 [M+H]$^+$ Synthesis of Compound 95.3.

To a solution of 95.2 (0.85 g, 0.42 mmol, 1.0 eq) in dry 1-butanol (2 mL) was added 57.4 (0.18 g, 0.42 mmol, 1 eq), DIPEA (1.62 g, 1.26 mmol, 3 eq). Reaction was stirred at 120° C. for 2 hours. After completion of the reaction, mixture was cooled to room temperature. Water (100 mL) was added to reaction and mixture was extracted with ethyl acetate (50 mL×2). Organic layers was washed with by brine solution, dried over sodium sulfate and concentrated under reduced pressure. Crude was purified by column chromatography to afford 95.3 (0.155 g, 62%). MS (ES): m/z=600.45 [M+H]$^+$ Synthesis of Compound I-150.

A solution of 95.3 (0.155 g, 0.18 mmol, 1 eq) in HBr/HOAc solution (33%, 3 mL) was stirred at room temperature for 2 hours. After completion of the reaction, mixture was poured into cold water, neutralized with NaHCO$_3$ and product was extracted with EtOAc (50 mL×2). Solvent was removed under reduced pressure, and resulting crude was purified using column chromatography to afford I-150 (0.070 g, 60.25%). MS (ES): m/z 450.42 [M+H]$^+$, $^1$H NMR (400 MHz, DMSO-d$_6$): δ 0.053 (s, 1H), 8.900 (s, 1H), 7.699-7.721 (d, 2H), 7.584-7.627 (m, 1H), 7.324-7.346 (d, 2H), 7.256-7.296 (t, 2H), 4.479 (s, 2H), 3.247-3.339 (m, 2H), 2.785 (s, 3H), 2.291-2.353 (m, 1H), 2.046-2.115 (s, 1H), 1.379 (s, 3H).

Example 96. Synthesis of (S)-2-(2,6-difluorophenyl)-4-((4-(1,3-dimethyl-2-oxopyrrolidin-3-yl)phenyl)amino)-6,7-dihydro-5H-pyrrolo[3,4-d]pyrimidin-5-one, I-151

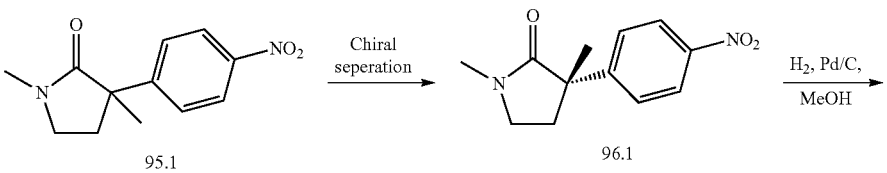

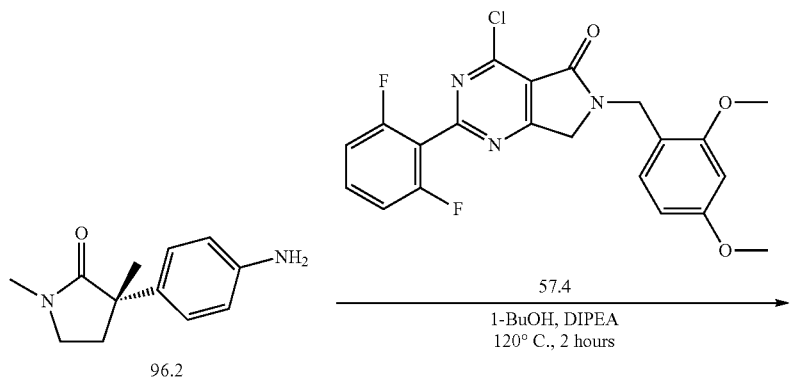

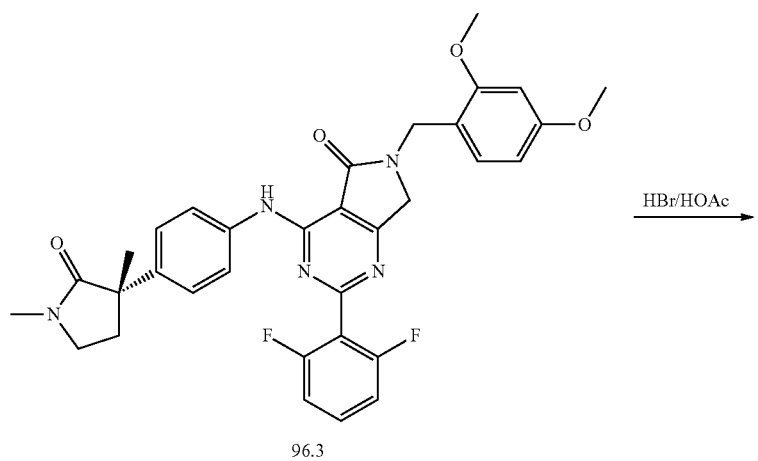

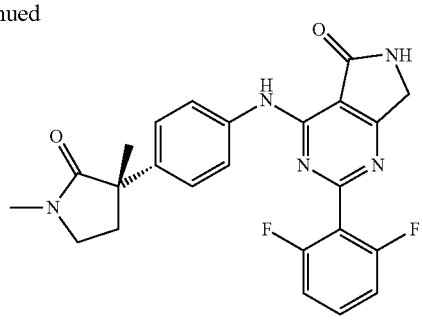

I-151

Synthesis of Compound 96.1.

Compound 96.1 was obtained by chiral separation of 95.1. MS (ES): m/z 438.26 [M+H]+ Chiral HPLC: 98.17%.

Synthesis of Compound 96.2.

To a suspension of Pd/C (0.1 g) in MeOH (5.0 mL) was 96.1 (0.080 g, 0.341 mmol, 1.0 eq) in MeOH (5.0 mL). Suspension was purged with $H_2$ gas for 30 minutes. After completion of the reaction, mixture was filtered through celite and filtrate was concentrated under reduced pressure to afford crude which was purified by column chromatography to provide 96.2 (0.73 g, 93.18%), MS (ES): m/z 205.2 [M+H]+, Chiral HPLC: 100%.

Synthesis of Compound 96.3.

To a a solution of 96.2 (0.66 g, 0.32 mmol, 1.0 eq) in dry 1-Butanol (2 mL) was added 57.4 (0.14 g, 0.32 mmol, 1 eq), followed by DIPEA (0.123 g, 0.96 mmol, 3 eq). Reaction was stirred at 120° C. for 2 hours. After completion of the reaction, mixture was cooled to room temperature. Water (100 mL) was added to the reaction, and mixture was extracted with EtOAc (50 mL×2). Organic layer was washed with brine, dried over sodium sulfate and concentrated under reduced pressure. Crude was purified using column chromatography to provide 96.3 (0.098 g, 50.4%). MS (ES): m/z 600.55 [M+H]+

Synthesis of Compound I-151.

A solution of 96.3 (0.095 g, 0.15 mmol, 1 eq) in HBr/HOAc solution (33%, 2 mL) was stirred at room temperature for 2 hours. After completion of the reaction, mixture was poured into cold water, neutralized with $NaHCO_3$ and extracted with EtOAc (50 mL×2). Solvent was removed under reduced pressure and resulting crude was purified using column chromatography to afford I-151 (0.048 g, 63.9%). MS (ES): m/z 450.42 [M+H]+; $^1$H NMR (400 MHz, DMSO-$d_6$): δ 9.055 (s, 1H), 8.909 (s, 1H), 7.698-7.719 (d, 2H), 7.568-7.642 (m, 1H), 7.322-7.343 (d, 2H), 7.256-7.297 (t, 2H), 4.478 (s, 2H), 3.226-3.399 (m, 2H), 2.783 (s, 3H), 2.289-2.350 (m, 1H), 2.043-2.113 (s, 1H), 1.376 (s, 3H).

Example 97. Synthesis of (R)-2-(2,6-difluorophenyl)-4-((4-(1,3-dimethyl-2-oxopyrrolidin-3-yl)phenyl)amino)-6,7-dihydro-5H-pyrrolo[3,4-d]pyrimidin-5-one, I-152

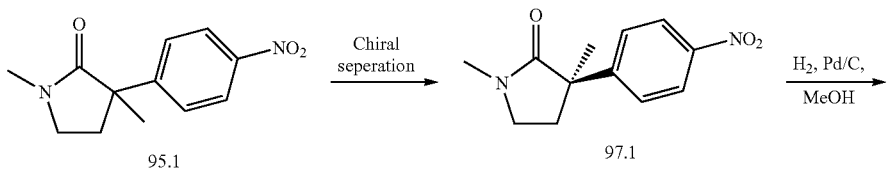

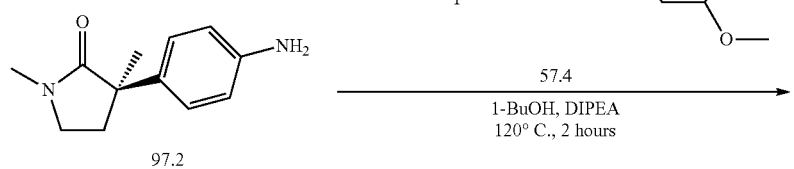

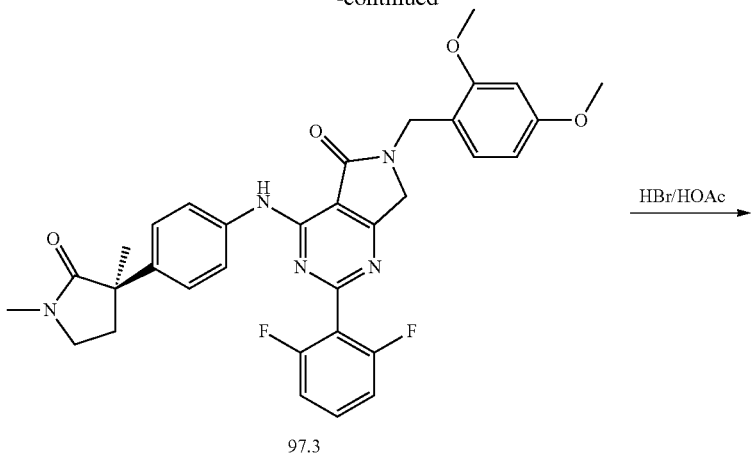

97.3

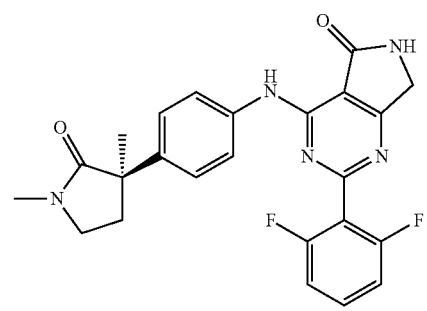

I-152

Synthesis of Compound 97.1

Compound 97.1 was obtained by chiral separation of 95.1 MS (ES): m/z 438.31 [M+H]⁺, Chiral HPLC: 94.87%

Synthesis of Compound 97.2.

To a suspension of Pd/C (0.1 g) in MeOH (5.0 mL) was added 97.1 (0.1 g, 0.47 mmol, 1.0 eq) in MeOH (5.0 mL). Suspension was purged with H₂ gas for 30 minutes. After completion of the reaction, reaction mixture was filtered through celite and filtrate was concentrated under reduced pressure to afford crude which was purified by column chromatography to furnish compound 97.2 (0.53 g, 55.3%), MS (ES): m/z 205.18 [M+H]⁺, Chiral HPLC: 95.8%.

Synthesis of Compound 97.3.

To a solution of 97.2 (0.054 g, 0.27 mmol, 1.0 eq) in dry 1-butanol (2 mL) were added 57.4 (0.11 g, 0.27 mmol, 1 eq) and DIPEA (0.104 g, 0.81 mmol, 3 eq). Reaction was stirred 120° C. for 2 hours. After completion of the reaction, reaction mixture was cooled to room temperature. Water (100 mL) was added to the reaction and mixture was extracted with EtOAc (50 mL×2). Organic layer was washed with brine, dried over sodium sulfate and concentrated under reduced pressure. Resulting crude was purified by column chromatography to afford compound 97.3 (0.070 g, 45.8%). MS (ES): m/z=600.60 [M+H]⁺,

Synthesis of Compound I-152.

A solution of 97.3 (0.070 g, 0.11 mmol, 1.0 eq) in HBr/HOAc solution (33%, 2 mL) was stirred at room temperature for 2 hours. After completion of the reaction, mixture was poured into cold water, neutralized with sodium bicarbonate and extracted with EtOAc (50 ml×2). Solvent was removed under reduced pressure to get crude product, which was purified by column chromatography to afford pure I-152 (0.040 g, 76.2%). MS (ES): m/z 450.22 [M+H]⁺;

¹H NMR (400 MHz, DMSO-d₆): δ 9.053 (s, 1H), 8.902 (s, 1H), 7.699-7.721 (d, 2H), 7.568-7.643 (m, 1H), 7.324-7.346 (d, 2H), 7.256-7.297 (t, 2H), 4.479 (s, 2H), 3.254-3.340 (m, 2H), 2.785 (s, 3H), 2.291-2.353 (m, 1H), 2.046-2.115 (s, 1H), 1.379 (s, 3H).

Example 98. Synthesis of 2-(2,6-difluorophenyl)-4-((4-(2-oxopiperidin-3-yl)phenyl)amino)-6,7-dihydro-5H-pyrrolo[3,4-d]pyrimidin-5-one, I-153

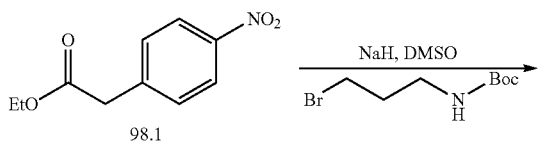

98.1

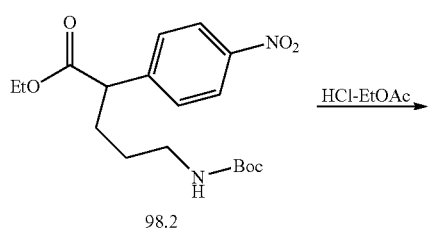

98.2

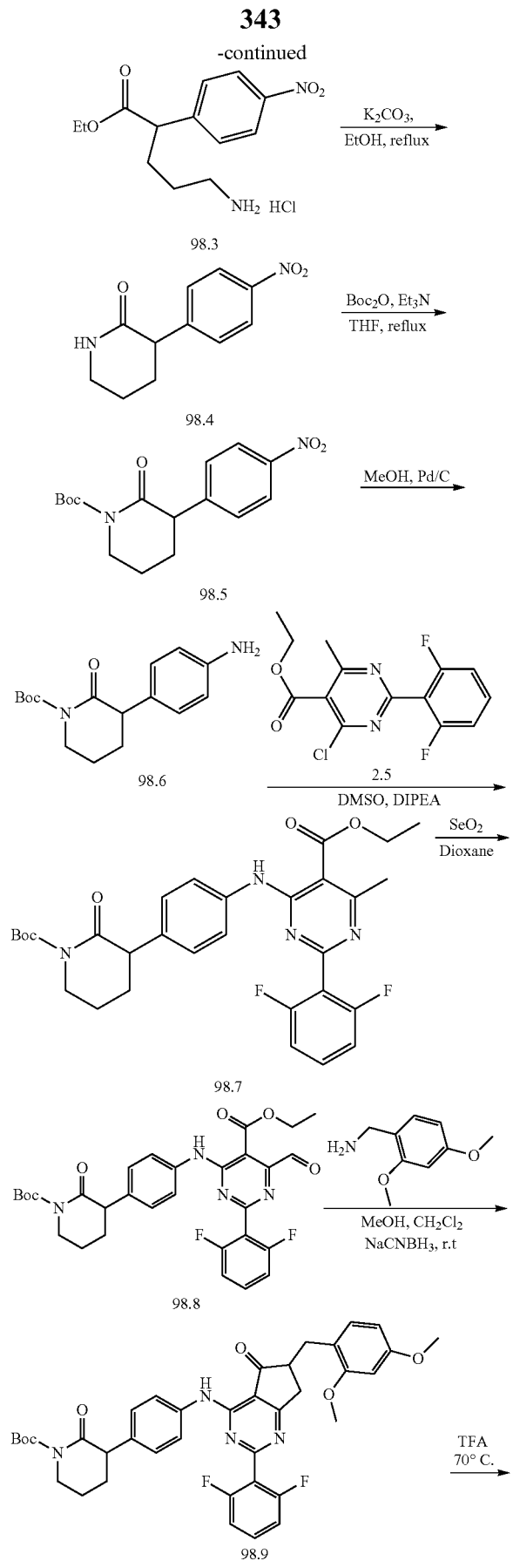

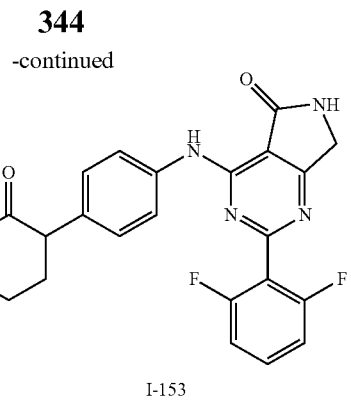

I-153

Synthesis of Compound 98.2

To a suspension of NaH (1.14 g, 28.7 mmol, 1.5 eq) in DMSO (35 mL) at 0° C. was added ethyl 2-(4-nitrophenyl)acetate (4.0 g, 19.13 mmol, 1 eq) and stirred for 10 minutes. Then tert-butyl (3-bromopropyl)carbamate (4.10 g, 17.22 mmol, 0.9 eq) was added to reaction mixture as solution in DMSO. The reaction mixture was stirred at room temp. for 5 hours. The reaction mixture was quenched with ice, and extracted with ethyl acetate (200 mL×2). Organic layers were combined and dried over sodium sulphate and concentrated under reduced pressure to obtain crude material. Crude was purified by column chromatography to provide 98.2 (3.5 g, 49.96%). MS (ES): m/z 367 [M+H]$^+$.

Synthesis of Compound 98.3.

A solution of 98.2 (3.5 g, 9.562 mmol, 1.0 eq) in HCl in ethyl acetate (35 mL) was stirred at room temperature for 4 hours. Reaction mixture was concentrated under reduced pressure to provide crude 98.3 (4.63 g) which was used as such for the next step, MS (ES): m/z 267.07 [M+H]$^+$.

Synthesis of Compound 98.4.

To a solution of 98.3 (4.63 g, 17.4 mmol, 1.0 eq) in ethanol (5 mL) was added K$_2$CO$_3$ (2.88 g, 20.9 mmol, 1.2 eq). Reaction was heated at 80° C. for 1 hour. After completion of the reaction, ethanol was evaporated. Water was added to the reaction mixture and was extracted with ethyl acetate (250 mL×2). Organic layers were combined and dried over sodium sulphate and concentrated under reduced pressure to to get pure 98.4 (1.7 g, 44.40%). MS (ES): m/z 221 [M+H]$^+$.

Synthesis of Compound 98.5.

The compound 98.4 (0.6 g, 2.27 mmol, 1.0 eq) dissolved in THF (1 mL), were added triethyl amine (0.57 mL, 4.090 mmol, 1.5 eq) and di-tert-butyl dicarbonate (0.713 g, 3.272 mmol, 1.2 eq). Reaction was heated at 70° C. for 3 hours. After completion of reaction, reaction mixture was poured into water and product was extracted with ethyl acetate (10 mL×2). Organic layers were combined, dried over sodium sulphate and concentrated under reduced pressure to obtain crude material, which was purified by column chromatography to furnish 98.5 (0.38 g, 43.5%). MS (ES): m/z 321 [M+H]$^+$.

Synthesis of Compound 98.6.

To a solution of 98.5 (0.38 g, 1.187 mmol, 1.0 eq) in MeOH (10 mL) was added 10% Pd/C (0.038 g) under nitrogen atmosphere. Reaction was purged with hydrogen for 3 hours. Reaction mixture was filtered through celite and obtained filtrate was concentrated under reduced pressure to get the crude which was purified by column chromatography to furnish 98.6 (0.320 g, 92.91%) MS (ES): m/z 291.2 [M+H]$^+$.

Synthesis of Compound 98.7.

To a solution of 98.6 (0.5 g, 1.60 mmol, 1.0 eq) in DMSO (5 mL) was added 2.5 (0.418 g, 1.44 mmol, 0.9 eq) and DIPEA (0.9 mL, 4.807 mmol, 3 eq). Reaction was heated at 90° C. for 6 hours. After completion of the reaction, mixture was poured into water and extracted with EtOAc (100 mL×2). Organic layers were combined, dried over sodium sulphate and concentrated under reduced pressure to obtain crude, which was purified by column chromatography to give 98.7 (0.490 g, 54.08%). MS (ES): m/z 567.3 [M+H]$^+$.

Synthesis of Compound 98.8.

To a solution 98.7 (0.490 g, 0.865 mmol, 1.0 eq) in 1,4-dioxane (5 mL) was added SeO$_2$ (0.24 g, 2.16 mmol, 2.5 eq). Reaction mixture was heated at 90° C. temperature for 6 hours. After completion of the reaction, reaction mixture was filtered through and concentrated to afford crude 98.8 (0.49 g, 97%), which was used as such in next step.

Synthesis of Compound 98.9.

To a solution of 98.8 (0.49 g, 0.844 mmol, 1.0 eq) in CH$_2$Cl$_2$ (4.9 ml) and methanol (2.5 mL,) was added 2,4-dimethoxybenzylamine (0.15 g, 0.929 mmol, 1.1 eq) at room temperature and allowed to stir for 30 minutes. Reaction mixture then cooled to 0° C. and NaCNBH$_3$ (0.159 g, 2.534 mmol, 3.0 eq) was added slowly to it. Reaction was stirred at room temperature for 12 hours. After completion of reaction water was added and product was extracted with EtOAc (3×50 mL). Combined organic layers were washed with brine, dried over sodium sulphate and concentrated under reduced pressure to afford crude, which was purified by column chromatography to afford compound 98.9 (0.16 g, 27.65%). MS (ES): m/Z 687.7 [M+H]$^+$.

Synthesis of Compound I-153.

Solution of 98.9 (0.16 g, 0.233 mmol, 1.0 eq) in trifluoroacetic acid (3 mL) was heated at 90° C. for 3 hours. After completion of the reaction trifluoroacetic acid removed in vacuo. Water was added and product was extracted with EtOAc (50 mL×2). Organic layer was washed with aqueous saturated bicarbonate solution. Combined organic layers were washed with brine, dried over sodium sulphate and concentrated under reduced pressure to provide crude which was purified by column chromatography to give pure I-153 (0.070 g, 68.90%) MS (ES): m/Z 436.2 [M+H]$^+$. $^1$H NMR (DMSO-d$_6$, 400 MHZ): 9.047 (s, 1H), 8.895 (s, 1H), 7.562-7.713 (m, 4H), 7.26 (t, 2H), 7.16 (d, 2H), 4.47 (s, sH), 3.443-3.508 (m, 1H), 3.20-3.29 (m, 2H), 2.0 (m, 3H), 1.75 (m, 4H), 1.50 (m, 2H).

Example 99. Synthesis of (R)-2-(2,6-difluorophenyl)-4-((4-(2-oxopiperidin-3-yl)phenyl)amino)-6,7-dihydro-5H-pyrrolo[3,4-d]pyrimidin-5-one, I-154

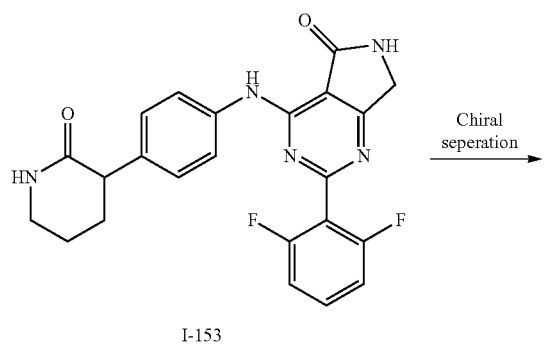

I-153

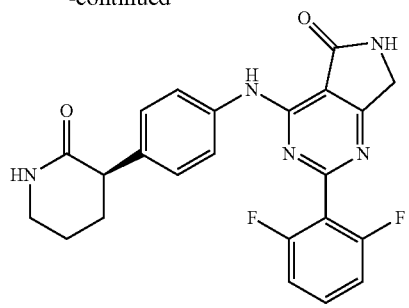

I-154

Compound I-154 was obtained by chiral separation of compound I-153. MS (ES): m/z 436.3 [M+H]$^+$, $^1$H NMR (400 MHz, DMSO-d$_6$): δ 9.044 (s, 1H), 8.887 (s, 1H), 7.57-7.67 (m, 4H), 7.26 (t, 2H), 7.16 (d, 2H), 4.47 (s, 2H), 3.44-3.48 (m, 1H), 3.23 (m, 2H), 2.0 (m 2H), 1.74 (m, 4H)

Example 100. Synthesis of (S)-2-(2,6-difluorophenyl)-4-((4-(2-oxopiperidin-3-yl)phenyl)-amino)-6,7-dihydro-5H-pyrrolo[3,4-d]pyrimidin-5-one, I-155

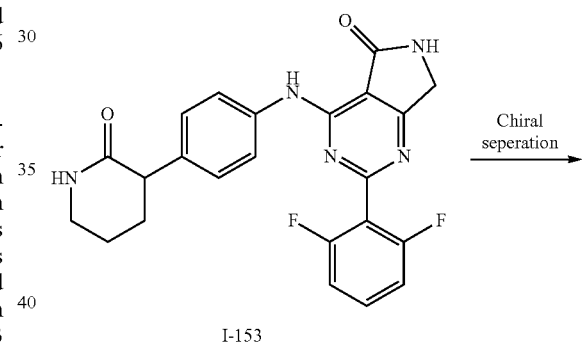

I-153

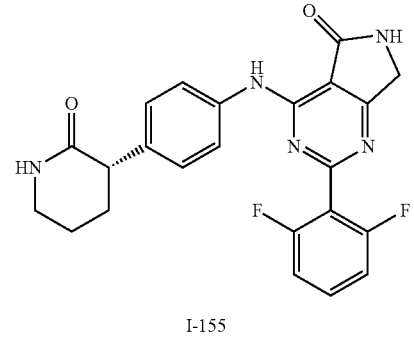

I-155

Compound I-153 was obtained by chiral separation of compound I-155. MS (ES): m/z 436.3 [M+H]$^+$; $^1$H NMR (400 MHz, DMSO): δ 9.044 (s, 1H), 8.887 (s, 1H), 7.581-7.674 (m, 4H), 7.26 (t, 2H), 7.16 (d, 2H), 4.47 (s, 2H), 3.443-3.482 (m, 1H), 3.21-3.26 (m, 2H), 2.022 (m, 1H), 1.65-1.82 (m 3H).

Example 101. Synthesis of 4-((2-(2,6-difluorophenyl)-5-oxo-6,7-dihydro-5H-pyrrolo[3,4-d]pyrimidin-4-yl)amino)benzoicacid, I-156

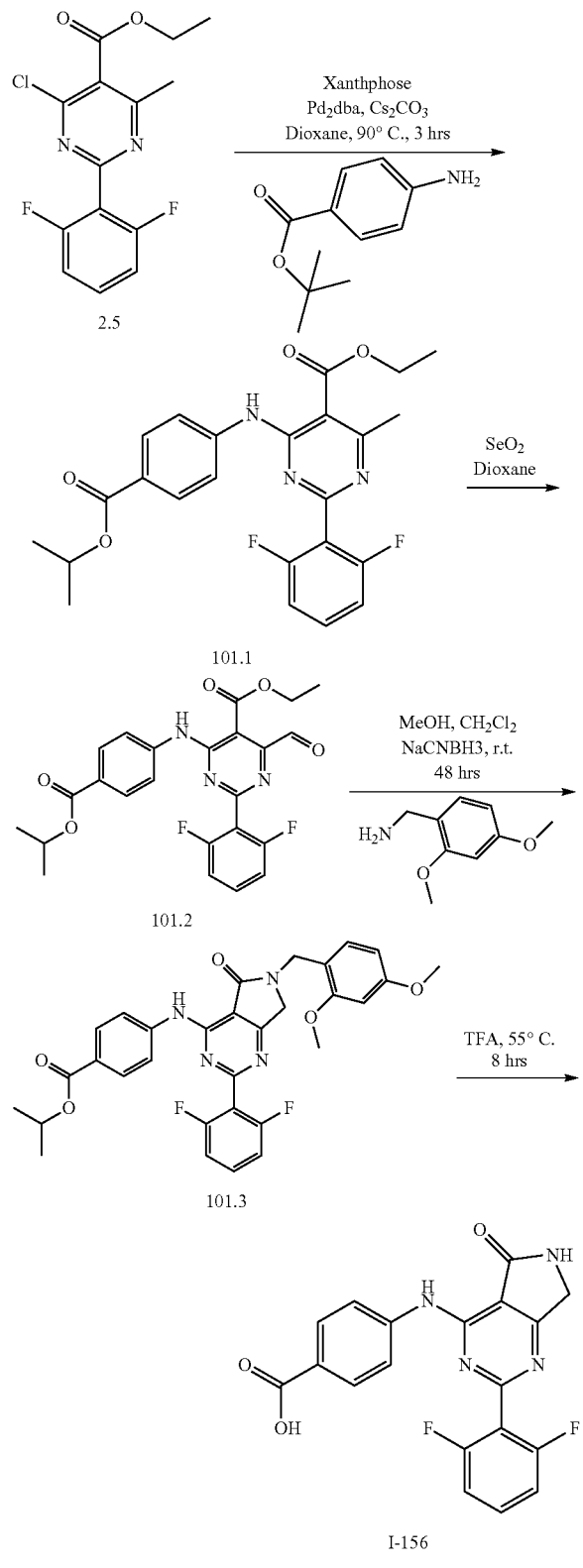

Synthesis of Compound 101.1.

To a solution of 2.5 (0.60 g, 1.91 mmol, 1.0 eq) in 1,4-dioxane (6 mL) were added tert-butyl 4-aminobenzoate (0.37 g, 1.91 mmol, 1.0 eq) and cesium carbonate (0.935, 2.87 mmol, 1.5 eq). The reaction mixture was degassed for 10 min. with argon, then Pd$_2$(dba)$_3$ 0.175 g, 0.191 mmol, 0.1 eq) and Xantphos (0.22 g, 0.383 mmol, 0.2 eq) were added, again degassed for 5 min. The reaction was heated at 90° C. for 3 hours. After completion of the reaction, mixture was poured into water and product was extracted with ethyl acetate. Organic layers were combined, dried over sodium sulphate and concentrated under reduced pressure to obtain crude material, which was purified by column chromatography to furnish 101.1 (0.320 g, 35.52%). MS (ES): m/z 470.5 [M+H]$^+$.

Synthesis of Compound 101.2.

A solution of compound 101.1 (0.32 g, 0.679 mmol, 1.0 eq), selenium dioxide (0.150 g, 1.35 mmol, 2.0 eq) in 1,4-dioxane (5 mL) was stirred at 100° C. to 105° C. for 3 hours. After completion of the reaction, the resulting solution was filtered through celite and washed with 1, 4-dioxane. Filtrate was concentrated under reduced pressure to afford crude compound 101.2 (0.289 g, 87.71) as a light yellow semisolid which was used as such for the next step. MS (ES): m/z 484.5 [M+H]$^+$.

Synthesis of Compound 101.3.

To a solution of compound 101.2 (0.289 g, 0.597 mmol, 1.0 eq) in mixture of CH$_2$Cl$_2$: MeOH (10 mL, 8:2) was added 2,4-dimthoxybenzylamine (0.1299 g, 0.77 mmol, 1.3 eq) at room temperature. Solution was stirred for 30 minutes. After 30 minutes, NaCNBH$_3$ (0.15 g, 2.39 mmol, 4.0 eq) was added at 0-10° C. The reaction mixture was allowed to warm at room temperature and was stirred for 48 hours. After completion, the reaction was diluted with water and product was extracted with ethyl acetate (25 mL×2) and washed with brine. The combined organic layers were dried and concentrated under vacuum. Crude was purified by column chromatography to provide 101.3 (0.15 g, 43.77%). MS (ES): m/z 589.6 [M+H]$^+$.

Synthesis of Compound I-156.

A solution of 101.3 (0.154 g, 0.26 mmol, 1.0 eq) in trifluoroacetic acid (2 mL) was stirred for 8 hours at 55° C. After completion of the reaction, mixture was concentrated under reduced pressure at 55° C. The crude was purified by column chromatography to provide I-156 (0.063 g, 62.98%). MS (ES): m/z 383.33 [M+H]$^+$, $^1$H NMR (DMSO-d$_6$, 400 MHz): 12.79 (brs, 1H), 9.31 (s, 1H), 8.97 (s, 1H), 7.90 (s, 4H), 7.66-7.58 (m, 1H), 7.31-7.27 (m, 2H), 4.51 (s, 2H).

Example 102. Synthesis of 4-((4-(2-oxa-6-azaspiro[3.3]heptane-6-carbonyl)phenyl)amino)-2-(2,6-difluorophenyl)-6,7-dihydro-5H-pyrrolo[3,4-d]pyrimidin-5-one I-157

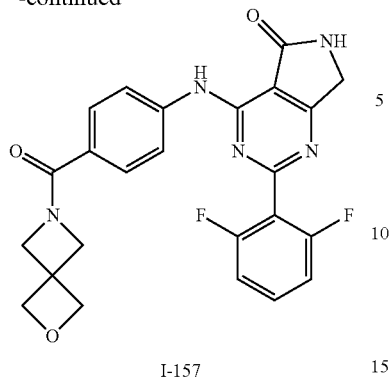

I-157

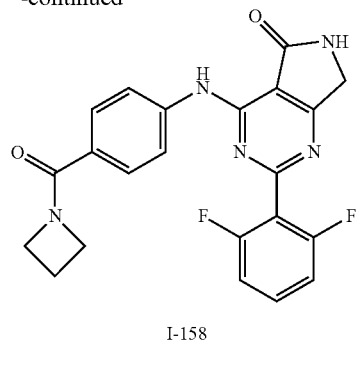

I-158

To a solution of I-156 (0.03 g, 0.0784 mmol, 1.0 eq) in THF (1 mL) was added EDCI (0.02254 g, 0.1176 mmol, 1.5 eq), HOBt (0.0127 g, 0.094 mmol, 1.2 eq) at 0° C. The reaction mixture was stirred at 0° C. for 15 min. After 15 min 2-Oxa-6-azaspiro[3.3]heptane (0.0163 g, 0.0862 mmol, 1.1 eq) and DIPEA (0.054 mL, 0.313 mmol, 4 eq) were added to reaction mixture at 0° C. Reaction was stirred at room temperature for 6 hours. After completion of reaction, reaction mixture was poured in water and extracted with ethyl acetate. Organic layers were combined, dried over sodium sulphate and concentrated under reduced pressure to obtain crude which was purified using column chromatography to provide I-157 (0.010 g, 27.52%). MS (ES): m/z 464.5 [M+H]$^+$, $^1$H NMR (DMSO-d$_6$, 400 MHZ): 9.27 (s, 1H), 8.97 (s, 1H), 7.86 (d, 2H), 7.63-7.60 (m, 3H), 7.31-7.27 (m, 2H), 4.66 (s, 4H), 4.51 (s, 4H), 4.19 (s, 2H).

Example 103. Synthesis of 4-((4-(azetidine-1-carbonyl)phenyl)amino)-2-(2,6-difluoro-phenyl)-6,7-dihydro-5H-pyrrolo[3,4-d]pyrimidin-5-one, I-158

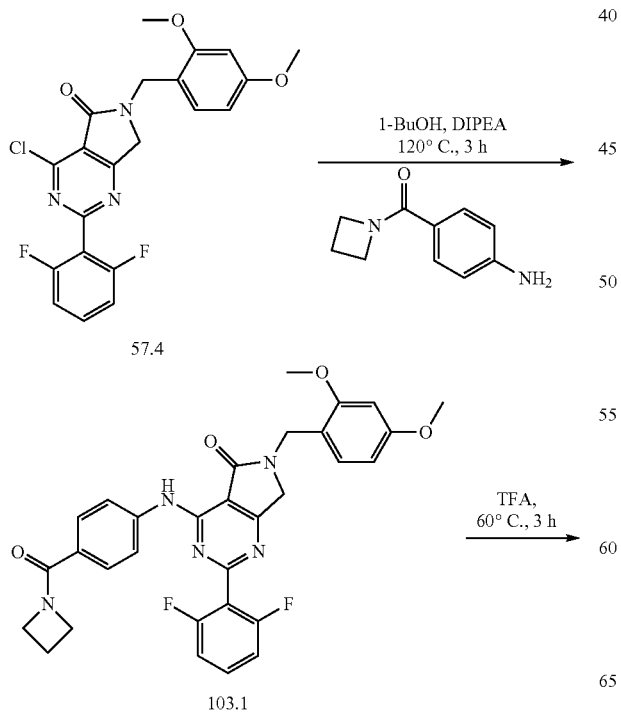

Synthesis of Compound 103.1.

To a solution of 57.4 (0.2 g, 0.46 mmol, 1.0 eq) in 1-butanol (5 mL) were added (4-aminophenyl)(azetidin-1-yl)methanone (0.1 g, 0.46 mmol, 1 eq) and DIPEA (0.3 mL, 1.38 mmol, 3 eq). The reaction mixture was stirred at 120° C. for 3 h. After completion of the reaction, mixture was poured into water and product was extracted with ethyl acetate (100 mL×2). Organic layers were combined, dried over sodium sulphate and concentrated under reduced pressure to obtain crude 103.1 which was uses as such for the following step. (0.1 g). MS (ES): m/z 572.1 [M+H]$^+$.

Synthesis of Compound I-158.

A solution of 103.1 (0.1 g, 0.17 mmol, 1.0 eq) in TFA (3 mL) was heated at 60° C. for 3 hours. After completion of the reaction trifluoroacetic acid was removed under reduced pressure. Water was added and product was extracted with ethyl acetate (50 mL×2). Organic layer was washed with aqueous saturated bicarbonate solution. Combined organic layers were washed with brine, dried over sodium sulphate and concentrated under reduced pressure. Crude was purified using column chromatography to give I-158 (0.045 g, 61.0%) MS (ES): m/Z 422.31 [M+H]$^+$. $^1$H NMR (DMSO-d6, 400 MHZ): 9.26 (s, 1H), 8.97 (s, 1H), 7.85 (d, 2H), 7.62 (t, 3H), 7.29 (t, 2H), 4.50 (s, 2H), 4.32-4.30 (m, 2H), 4.03-4.00 (m, 2H), 2.79-2.22 (m, 2H).

Example 104. Synthesis of compound (R)-4-((5-(3-aminopiperidin-1-yl)pyridin-2-yl)amino)-2-(2,6-difluorophenyl)-6,7-dihydro-5H-pyrrolo[3,4-b]pyridin-5-one, I-159

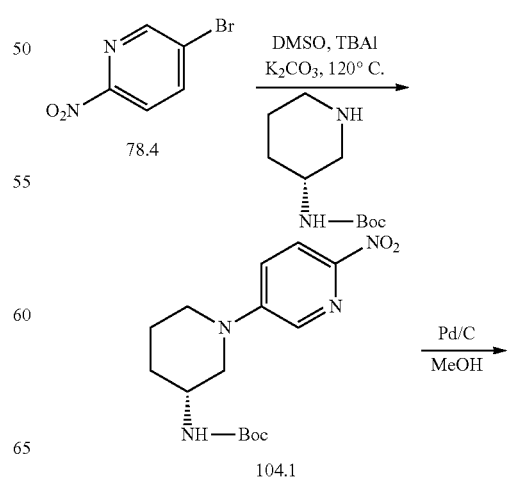

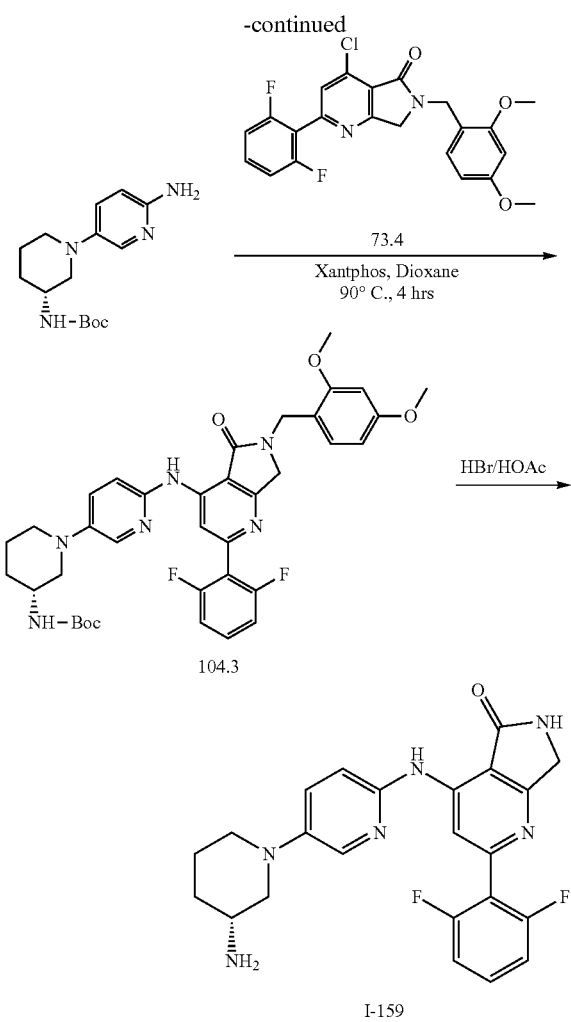

104.3

I-159

Synthesis of Compound 104.1

To a solution of 78.4 (0.2 g, 0.985 mmol, 1.0 eq) in DMSO (3 ml) was added TBAI (0.036, 0.098 mmol, 0.1 eq), tert-butyl (R)-piperidin-3-ylcarbamate (0.236 g, 1.182 mmol, 1.2 eq), and $K_2CO_3$ (0.408 g, 2.955 mmol, 3 eq). Reaction mixture was heated at 120° C. for 2 hours. Upon completion the reaction mixture was poured into water and extracted with ethyl acetate. Organic layers were combined, dried over sodium sulphate and concentrated under reduced pressure. Resulting crude was purified by column chromatography to provide 104.1 (0.150 g, 47.2%). MS (ES): m/z 323.4 $[M+H]^+$.

Synthesis of Compound 104.2.

To a solution of 104.1 (0.15 g, 0.465 mmol, 1.0 eq) in methanol (5 mL) was added 10% Pd/C (0.015 mg) under nitrogen atmosphere. Suspension was purged with hydrogen gas for 1 hour. Reaction mixture was filtered through celite and obtained filtrate was concentrated under reduced pressure to get crude 104.2 (0.120 g, 88.2%) which was used as such for the next step, MS (ES): m/z 293.38 $[M+H]^+$.

Synthesis of Compound 104.3.

To a solution of 73.4 (0.100 g, 0.232 mmol, 1.0 eq) in 1,4-dioxane (3 mL) were added 104.2 (0.081 g, 0.278 mmol, 1.2 eq) and $K_2CO_3$ (0.080 g, 0.58 mmol, 2.5 eq). The reaction mixture was degassed for 10 min. under argon atmosphere, then $Pd_2(dba)_3$ 0.021 g, 0.0232 mmol, 0.1 eq) and Xantphos (0.026 g, 0.0464 mmol, 0.2 eq) were added, and again suspension was degassed for 5 min. The reaction was heated at 90° C. for 4 h. After completion of the reaction, mixture was poured into water and product was extracted with ethyl acetate. Organic layers were combined, dried over sodium sulphate and concentrated under reduced pressure to obtain crude which was purified by column chromatography to get pure 104.3 (0.075 g, 47.05%). MS (ES): m/z 687.8 $[M+H]^+$.

Synthesis of Compound I-159.

Compound 104.3 (0.075 g, 0.109 mmol, 1.0 eq) was dissolved in HBr/HOAc (2 ml) and stirred at room temperature for 1 h. after completion of the reaction, mixture was poured into water, basified with saturated bicarbonate solution and extracted with ethyl acetate. Organic layers were combined, dried over sodium sulphate and concentrated under reduced pressure to obtain crude which was purified by column chromatography to get I-159 (0.046 g, 96.51%). MS (ES): m/z 437.5 $[M+H]^+$ $^1H$ NMR (DMSO-$d_6$, 400 MHZ): 9.51 (s, 1H), 8.81 (s, 1H), 8.38 (s, 1H), 8.01 (d, 1H), 7.59-7.55 (m, 1H), 7.43 (dd, 1H), 7.27-7.23 (m, 2H), 7.10 (d, 1H), 4.41 (s, 2H), 3.52 (d, 1H), 3.34 (s, 2H), 2.94-2.92 (m, 1H), 2.76-2.67 (m, 1H), 2.61-2.56 (m, 2H), 1.86-1.82 (m, 1H), 1.75-1.72 (m, 1H), 1.57-1.54 (m, 1H), 1.28-1.23 (m, 1H).

Example 105. Synthesis of 2-(2,6-difluorophenyl)-4-((1-methyl-1H-pyrazol-4-yl)amino)-6,7-dihydro-5H-pyrrolo[3,4-d]pyrimidin-5-one I-160

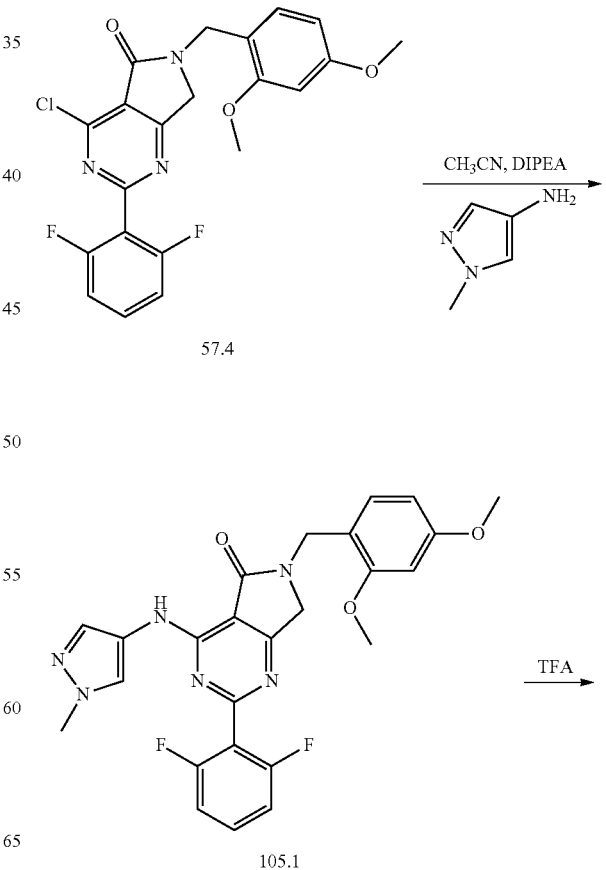

353

-continued

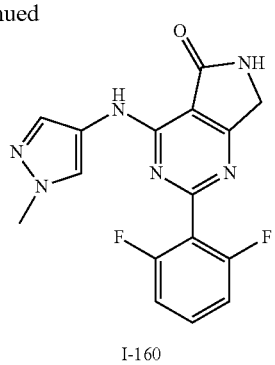

I-160

Synthesis of Compound 105.1.

To a solution of 57.4 (0.2 g 0.463 mmol, 1.0 eq.) in CH₃CN (2.0 mL) was added 1-methyl-1H-pyrazol-4-amine (0.0449 g, 0.4631 mmol, 1.0 eq.) and DIPEA (0.242 ml, 1.389 mmol, 3 eq.) at room temperature. Reaction mixture was heated at 70° C. for 30 minutes. After completion of the reaction, mixture was poured into water and extracted using ethyl acetate. Organic layer was washed with by brine, dried over sodium sulfate and concentrated under reduced pressure. Crude was purified by column chromatography to afford compound 105.1 (0.140 g, 61.38%), MS (ES): m/z 493.5[M+H]⁺.

Synthesis of Compound I-160.

A solution of 105.1 (0.14 g, 0.284 mmol, 1.0 eq.) in trifluoroaceticacid (2 mL) was stirred at 70° C. for 3 hours. After completion of the reaction, mixture was poured into cold water, neutralized with NaHCO₃ and extracted with ethyl acetate (75 ml×2). Solvent was removed under reduced pressure and resulting crude was purified using column chromatography to afford I-160 (0.045 g, 46.25%). MS (ES): m/z −343.5 [M+H]⁺ ¹H NMR (400 MHz, DMSO-d₆): δ 9.24 (s, 1H), 8.75 (s, 1H), 7.97 (s, 1H), 7.79 (s, 1H), 7.62-7.58 (m, 1H), 7.29-7.25 (m, 2H), 4.43 (s, 2H), 3.78 (s, 3H).

Example 106. Synthesis of 2-(2,6-difluorophenyl)-4-((4-(1-(2-hydroxy-2-methylpropyl)-2-oxopyrrolidin-3-yl)phenyl)amino)-6,7-dihydro-5H-pyrrolo[3,4-d]pyrimidin-5-one, I-161

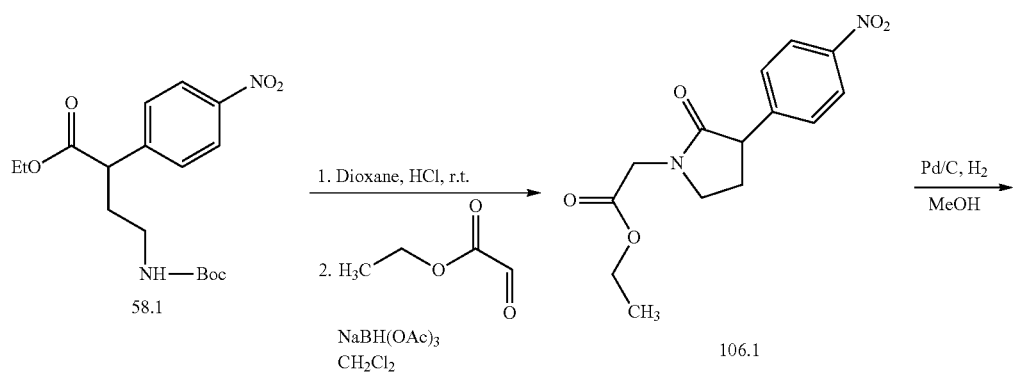

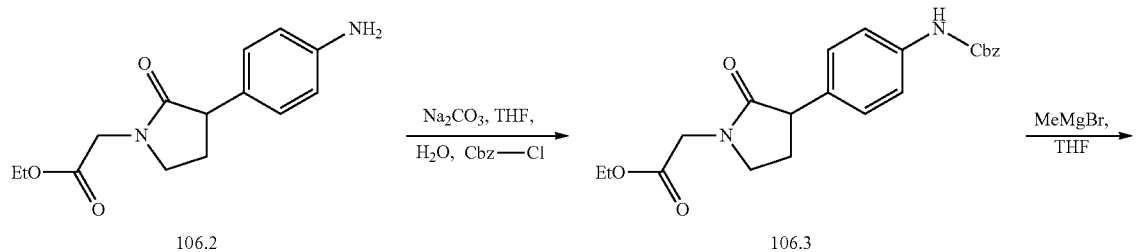

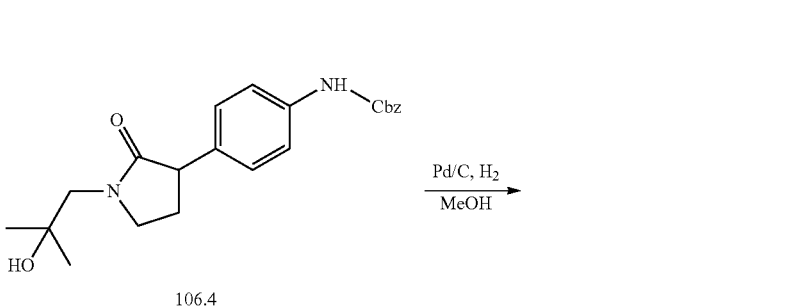

-continued

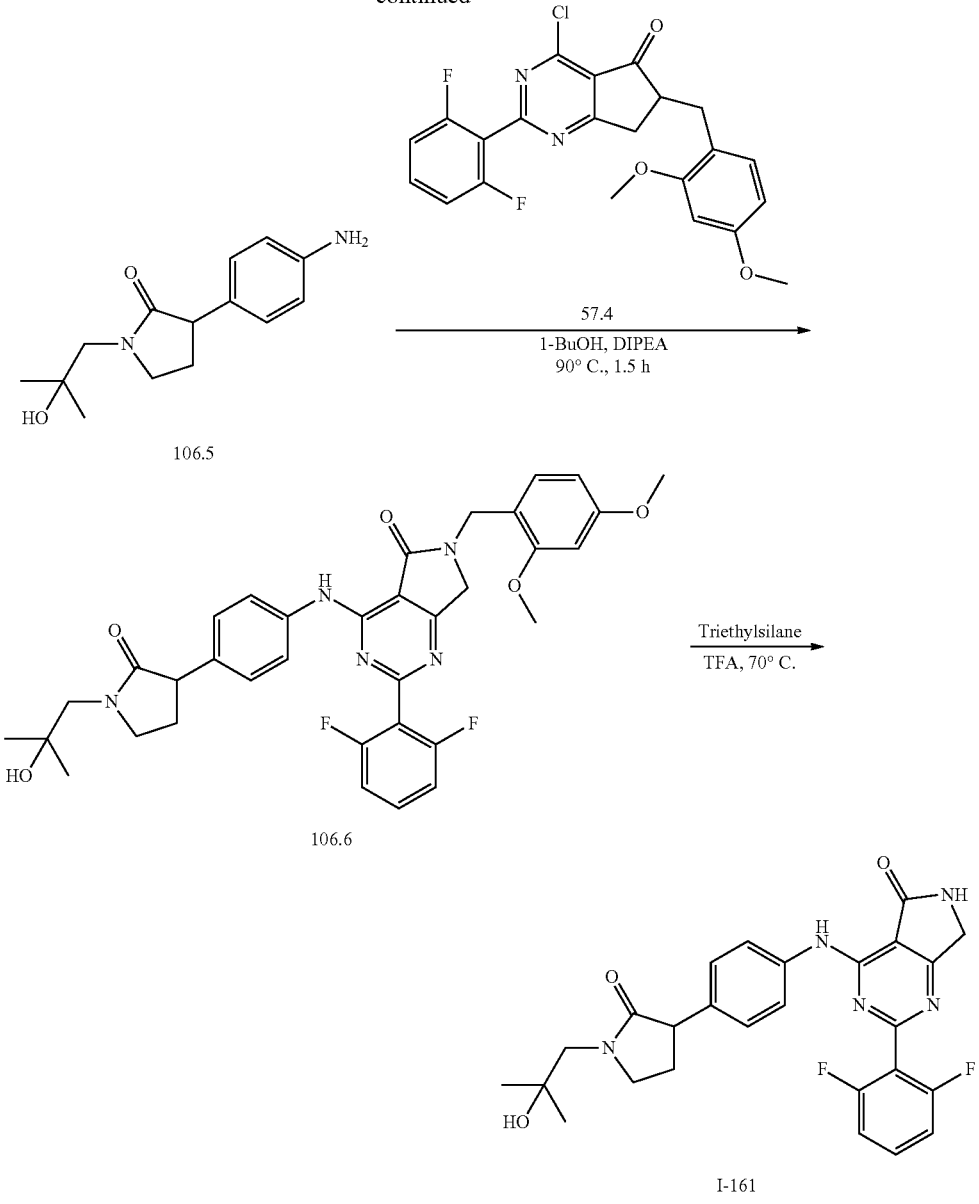

Synthesis of Compound 106.1.

A solution of 58.1 (1.5 g, 0.4.25 mol, 1.0 eq) in 1,4-dioxane HCl (15 mL) was stirred for 2 hours at room temperature. The reaction mixture was concentrated at reduced pressure and then dichloromethane (20 ml) was added and basified with saturated sodium bicarbonate solution, Organic layer was separated, dried over sodium sulfate and transferred to another 3-neck flask. Molecular sieves were added followed by ethyl 2-oxoacetate (0.405 g, 1.987 mmol, 0.7 eq) and mixture was stirred for 10 minutes. Sodium triacetoxy borohydride (0.902 g, 4.258 mmol, 1.5 eq) was portion wise for 30 minutes. The reaction mixture was then stirred at room temperature for 5 hours. After completion of the reaction, mixture was poured into water and product was extracted with $CH_2Cl_2$. Organic layer was washed with saturated sodium bicarbonate, dried over sodium sulphate and concentrated under reduced pressure to obtain crude which was purified by column chromatography to furnish 106.1 (0.726 g, 57%). MS (ES): m/z 294[M+H]$^+$.

Synthesis of Compound 106.2.

To a suspension of Pd/C (80 mg) in MeOH10 ml) was added 106.1 (0.72 g, 0. mmol. 1.0 eq) under nitrogen atmosphere. Suspension was purged with $H_2$ (gas) at room temperature for 2 h. After completion of the reaction, mixture was filtered through celite. Solvent was removed under reduced pressure to afford 106.2 (0.63 g, 97%). MS (ES): m/z 263 [M+H]$^+$, Synthesis of Compound 106.3.

To a solution of 106.2 (0.63 g, 2.42 mmol, 1.0 eq) in THF: $H_2O$ (3 ml: 10 ml) were added $Na_2CO_3$ (0.333 g, 3.15 mmol, 1.3 eq), benzyl chloroformate (0.35 ml, 2.42 mmol, 1.0 eq) at room temperature. Reaction mixture was stirred at room temperature for 3 hours. After completion of the reaction, mixture was poured into water and extracted using ethyl acetate. Organic layer was washed with brine solution, dried over sodium sulfate and concentrated under reduced pressure. Crude was purified by column chromatography, to afford 106.3 (0.5 g, 52%), MS (ES): m/z 397.1 [M+H]$^+$.

Synthesis of Compound 106.4.

To a solution of 106.3 (0.5 g, 1.26 mmol, 1.0 eq) in THF (5 mL) was added methyl magnesium bromide (8.41 ml, 25.2 mmol, 20 eq), at 0° C. Reaction was stirred at room temperature for 3 hours. After completion of the reaction, reaction mixture was quenched with satd $NH_4Cl$ and extracted using ethyl acetate. Organic layer was washed with brine, dried over sodium sulfate and concentrated under reduced pressure. Crude was purified by column chromatography to afford pure 106.4 (0.165 g, 34.21%), MS (ES): m/z 383.3 [M+H]$^+$.

Synthesis of Compound 106.5.

To a suspension of Pd/C (30 mg) in MeOH10 ml) was added 106.4 (0.160 g, 0.4186 mmol. 1.0 eq) under nitrogen atmosphere. Suspension was purged with $H_2$ (gas) at room temperature for 2 hours. After completion of reaction, reaction mixture was filtered through celite. Solvent was removed under reduced pressure at 45° C. to afford compound 106.5 (0.065 g, 62.57%). MS (ES): m/z 249.2 [M+H]$^+$ Synthesis of Compound 106.6.

To a solution of 57.4 (0.1 g, 0.231 mmol, 1.0 eq) in butanol (2 ml) was added 106.5 (0.063 g, 0.25 mmol, 1.1 eq) followed by DIPEA (0.15 ml, 0.694 mmol, 3 eq) at room temperature. Reaction mixture was heated at 90° C. for 1.5 h. After completion of the reaction, reaction mixture was poured into water and extracted using ethyl acetate. Organic layer was washed with by brine, dried over sodium sulfate and concentrated under reduced pressure. Crude was purified by column chromatography to afford 106.6 (0.070 g, 46.96%), MS (ES): m/z 645.3 [M+H]$^+$.

Synthesis of Compound I-161.

A solution of 106.6 (0.060 g, 0.093 mmol, 1.0 eq) in triethylsilane (0.032 g, 0.2796 mmol, 3 eq) and TFA (0.6 ml, 10 vol) was heated at 70° C. for 2 h. After completion, reaction mixture was concentrated and residue was diluted with ethyl acetate and washed with saturated sodium bicarbonate solution. Organic layer was concentrated under reduce pressure to obtain crude material which was purified by preparative TLC to provide I-161 (0.022 g, 47.8%). MS (ES): m/z 494.5 [M+H]$^+$, $^1$H NMR (DMSO-d6, 400 MHZ): 9.07 (s, 1H), 8.9 (s, 1H), 7.68-7.70 (d, 2H), 7.58-7.61 (t, 1H), 7.20-7.28 (m, 4H), 4.56 (s, 1H), 4.47 (s, 2H), 3.59-3.67 (m, 2H), 3.51-3.53 (d, 1H), 3.20-3.24 (d, 1H), 3.06-3.09 (d, 1H), 2.33-2.38 (m, 1H), 1.97- 2.02 (m, 1H), 1.07-1.08 (s, 6H).

Example 107. Synthesis of compound 2-(2,6-difluorophenyl)-4-((5-(piperazin-1-yl)pyridin-2-yl)amino)-6,7-dihydro-5H-pyrrolo[3,4-b]pyridin-5-one, I-162

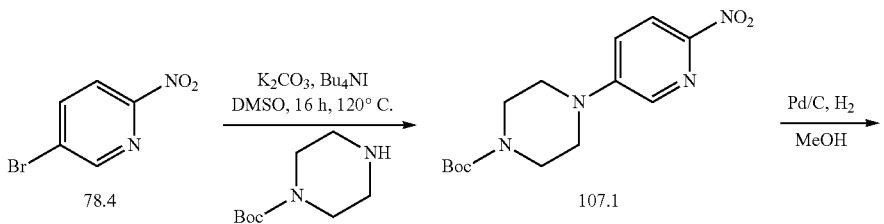

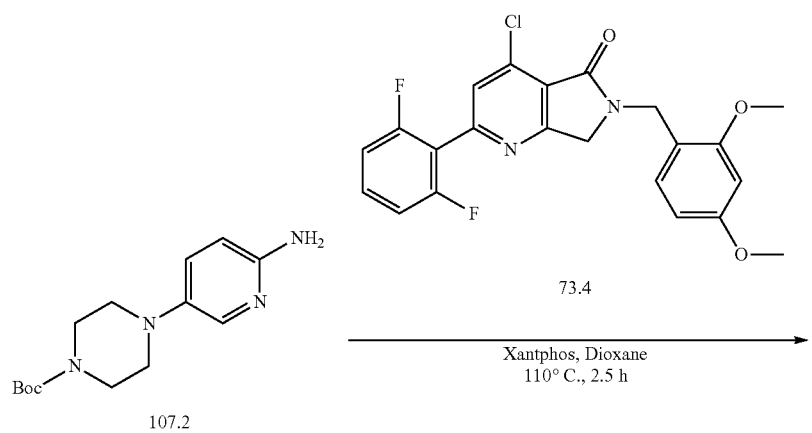

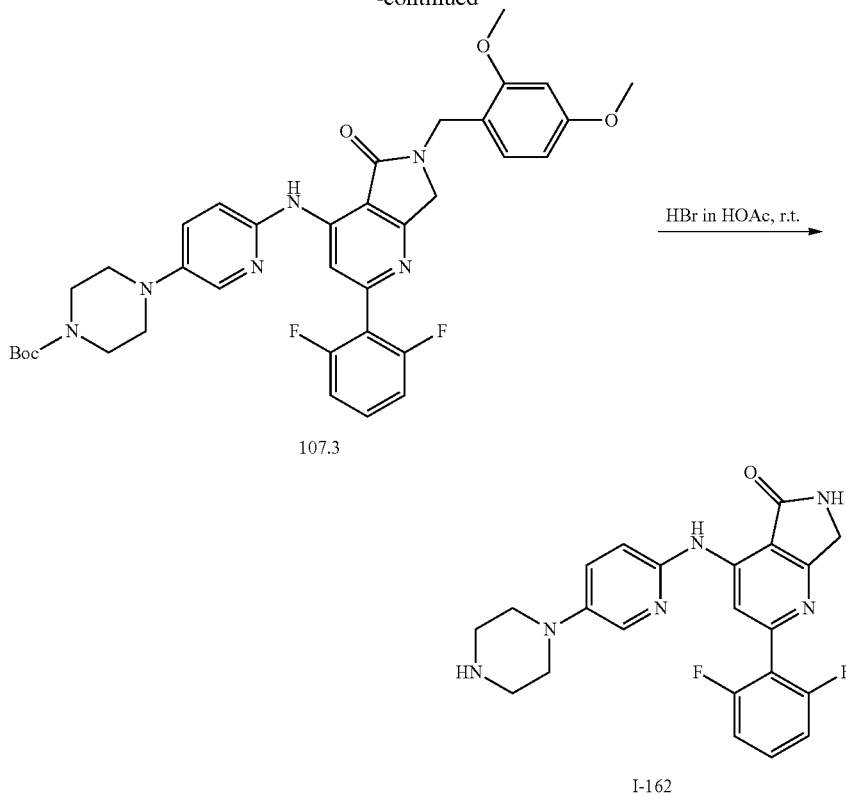

107.3

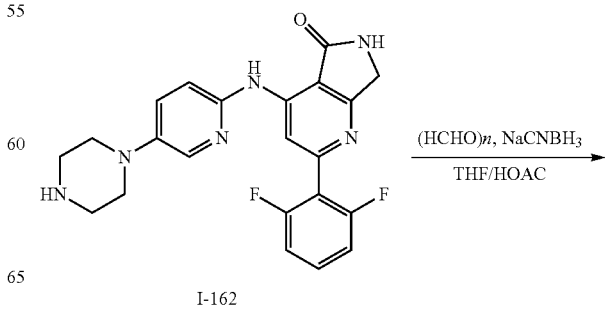

I-162

Synthesis of Compound 107.1

To a solution of 78.4 (1.0 g, 4.92 mmol, 1.0 eq) in DMSO (10 ml) was added Bu$_4$NI (0.18 g, 0.049 mmol, 0.1 eq), tert-butyl piperazine-1-carboxylate (1.37 g, 7.38 mmol, 1.5 eq), and K$_2$CO$_3$ (1.36 g, 9.85 mmol, 2 eq). Reaction mixture was heated at 120° C. for 16 hours. Upon completion reaction mixture was poured into water and product was extracted with ethyl acetate. Organic layers were combined, dried over sodium sulphate and concentrated under reduced pressure. The crude was purified using column chromatography to provide 107.1 (1.2 g, 79%). MS (ES): m/z 279.23 [M+H]$^+$.

Synthesis of Compound 107.2.

A solution of 107.1 (1.2 g, 3.89 mmol, 1.0 eq) in methanol (20 mL) was added with 10% Pd/C (120 g) under nitrogen atmosphere. Mixture was purged with H$_2$ gas for 3 hours. Reaction mixture was filtered through celite and obtained filtrate was concentrated under reduced pressure to get crude 107.2 (0.8 g, 73%) which was used as such for the next step, MS (ES): m/z 204.3 [M+H]$^+$.

Synthesis of Compound 107.3.

To a solution of 73.4 (0.1 g, 0.23 mmol, 1.0 eq) in 1,4-dioxane (2 mL) was added 107.3 (0.071 g, 0.255 mmol, 1.1 eq) and K$_2$CO$_3$ (0.080 g, 0.58 mmol, 2.5 eq). The reaction mixture was degassed for 10 minutes using argon gas, then Pd2(dba)3 (0.021 g, 0.023 mmol, 0.1 eq) and Xantphos (0.026 g, 0.046 mmol, 0.2 eq) were added. The reaction was stirred at 110° C. for 2.5 hours. After completion of the reaction, mixture was poured into water and product was extracted with ethyl acetate. Organic layer was dried over sodium sulphate and concentrated under reduced pressure to obtain crude which was purified using column chromatography to furnish 107.3 (0.080 g, 51.3%). MS (ES): m/z 673.7 [M+H]$^+$.

Synthesis of Compound I-162.

Compound 107.3. (0.08 g, 0.118 mmol, 1.0 eq) was dissolved in HBr/HOAc (2 ml) and stirred at room temperature for 1 hour. After completion of the reaction, mixture was poured into water, basified with saturated bicarbonate solution and extracted with ethyl acetate. Organic layers were combined, dried over sodium sulphate and concentrated under reduced pressure to obtain crude which was purified using column chromatography to furnish I-162 (0.020 g, 39.8%). MS (ES): m/z 423.5 [M+H]$^+$; $^1$H NMR (DMSO-d6, 400 MHZ): 9.54 (s, 1H), 8.83 (s, 1H), 8.39 (s, 1H), 8.04 (d, 1H), 7.53-7.59 (m, 1H), 7.46-7.48 (dd, 1H), 7.24-7.28 (t, 2H), 7.11-7.13 (d, 1H), 4.41 (s, 2H), 3.15 (br, 4H), 2.98 (br, 4H).

Example 108. Synthesis of 2-(2,6-difluorophenyl)-4-((5-(4-methylpiperazin-1-yl)pyridin-2-yl)amino)-6,7-dihydro-5H-pyrrolo[3,4-b]pyridin-5-one, I-163

I-162

361

-continued

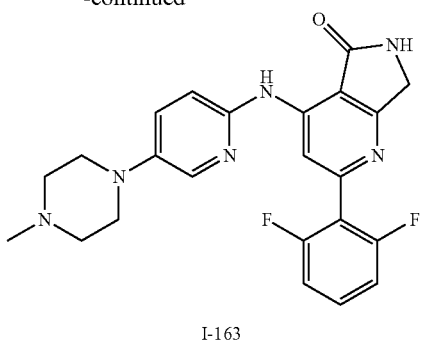

I-163

Compound I-162 (0.150 g, 0.355 mmol, 1.0 eq) was dissolved in THF 5 ml) followed by addition of acetic acid (0.5 mL) and paraformaldehyde (0.020 g, 0.533 mmol, 1.5 eq). Reaction mixture was stirred at room temperature for 30 min. To the mixture was added NaCNBH₃ (0.226 g, 1.06 mmol, 3.0 eq) portionwise and reaction was stirred at room temperature for 18 hours. After completion of the reaction, mixture was poured into water and extracted with ethyl acetate. Organic layers were combined, dried over sodium sulphate and concentrated under reduced pressure. Crude was purified by preparative HPLC to afford I-163 (0.022 g, 14%). MS (ES): m/z 437.9 [M+H]⁺; ¹H NMR (DMSO-d6, 400 MHZ): 9.59 (s, 1H), 8.84 (s, 1H), 8.44 (s, 1H), 8.11 (d, 1H), 7.53-7.61 (m, 2H), 7.24-7.28 (t, 2H), 7.16-7.19 (d, 1H), 4.42 (s, 2H), 3.81-3.84 (d, 2H), 3.49-3.52 (d, 2H), 3.15-3.17 (d, 2H), 2.94-3.0 (t, 2H), 2.85 (s, 3H).

Example 109. Synthesis of 6-((2-(2,6-difluorophenyl)-5-oxo-6,7-dihydro-5H-pyrrolo[3,4-b]pyridin-4-yl)amino)-N-(2-hydroxyethyl)nicotinamide, I-164

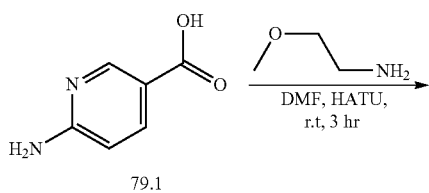

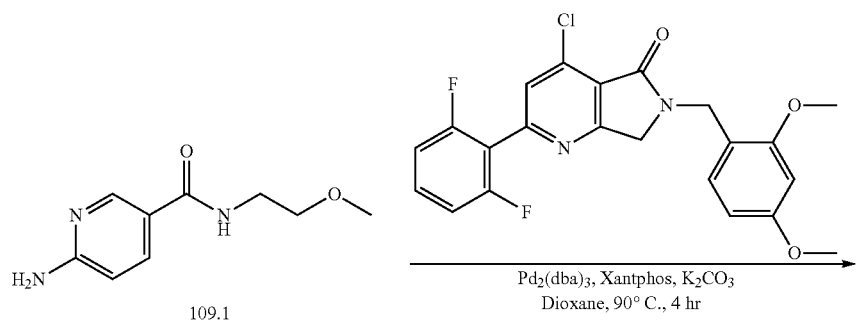

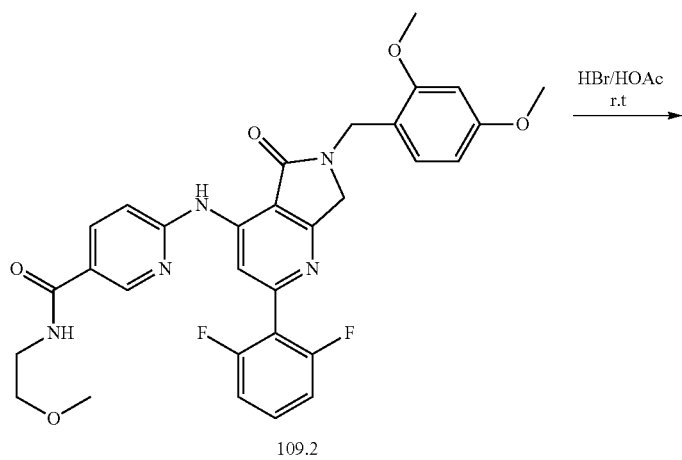

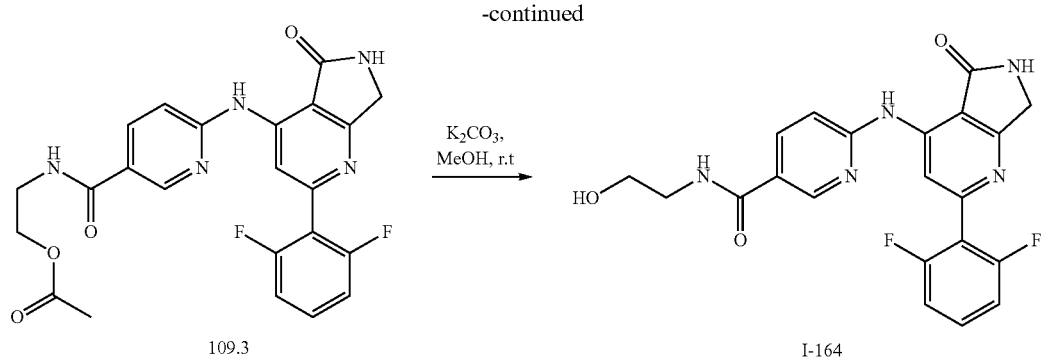

109.3 → I-164

K₂CO₃, MeOH, r.t

Synthesis of Compound 109.1.

To a solution of 79.1 (0.300 g, 2.173 mmol, 1.0 eq) in DMF (3 mL) was added HATU (1.235 g, 3.259 mmol, 1.5 eq) and stirred for 15 min at room temperature. To mixture were added 2-methoxyethan-1-amine (0.195 g, 2.608 mmol, 1.2 eq), DIPEA (1.115 g, 6.519 mmol, 3.0 eq.) and reaction was stirred at room temperature for 3 hours. After completion of the reaction, mixture was poured into water and extracted with ethyl acetate. Organic layer was washed with brine, dried over anhydrous sodium sulphate. Mixture was concentrated under reduced pressure to obtain crude material which was purified by column chromatography to afford 109.1 (0.10 g, 23.6%). MS (ES): m/z 196.2 [M+H]⁺.

Synthesis of Compound 109.2.

To a solution of 73.4 (0.1 g, 0.232 mmol, 1.0 eq) and 109.1 (0.045 g, 0.232 mmol, 1.0 eq.) in 1,4-dioxane (2 mL) was added K₂CO₃ (0.08 mg, 0.580 mmol, 2.5 eq). Reaction mixture was degassed under argon gas for 5-10 min. and Pd₂(dba)₃ (0.018 g, 0.023 mmol, 0.1 eq.) and Xantphos (0.020 g, 0.046 mmol, 0.2 eq.) were added. Reaction mixture was heated at 90° C. for 4 hours. After completion, reaction mixture was poured into water and product was extracted with ethyl acetate. Organic layers were combined and dried over sodium sulphate and concentrated under reduced pressure to obtain crude which was purified using column chromatography to provide 109.2 (0.112 g, 81.84%). MS (ES): m/z 589.5 [M+H]⁺.

Synthesis of Compound 109.3.

A solution of 109.2 (0.112 g, 1.9 mmol, 1.0 eq) in HBr in acetic acid (2 mL) was stirred at room temperature for 1 hour. After completion, reaction mixture was concentrated and residue was diluted with water, basified with saturated bicarbonate solution and extracted with ethyl acetate. Organic layer was concentrated under reduce pressure to obtain crude material which was purified by preparative HPLC to get 109.3 (0.012 g, 13.51%). MS (ES): m/z 468.5 [M+H]⁺.

Synthesis of Compound I-164.

A solution of 109.3 (0.012 g, 0.0256 mmol, 1.0 eq) and K₂CO₃ (0.01059 mg, 0.0768 mmol, 3.0 eq) in MeOH (1.5 mL) was stirred at room temperature for 2 hours. After completion, reaction mixture was concentrated and residue was diluted with water and extracted with ethyl acetate. Organic layer was concentrated under reduce pressure to obtain crude material which was purified by trituration in diethyl ether (0.5 mL) and methanol (0.1 mL) to get I-164 (0.006 g, 55.09%). MS (ES): m/z 426.5 [M+H]⁺; ¹H NMR (400 MHz, DMSO-d₆): δ 9.96 (s, 1H), 8.96 (s, 1H), 8.81-8.80 (d, 1H), 8.65 (s, 1H), 8.49-8.47 (m, 1H), 8.17-8.15 (m, 1H), 7.63-7.57 (m, 1H), 7.34-7.25 (m, 3H), 4.75 (s, 1H), 4.46 (s, 2H), 3.50 (s, 2H), 3.34 (s, 2H).

Example 110. Synthesis of compound N-(tert-butyl)-6-((2-(2,6-difluorophenyl)-5-oxo-6,7-dihydro-5H-pyrrolo[3,4-b]pyridin-4-yl)amino)nicotinamide, I-165

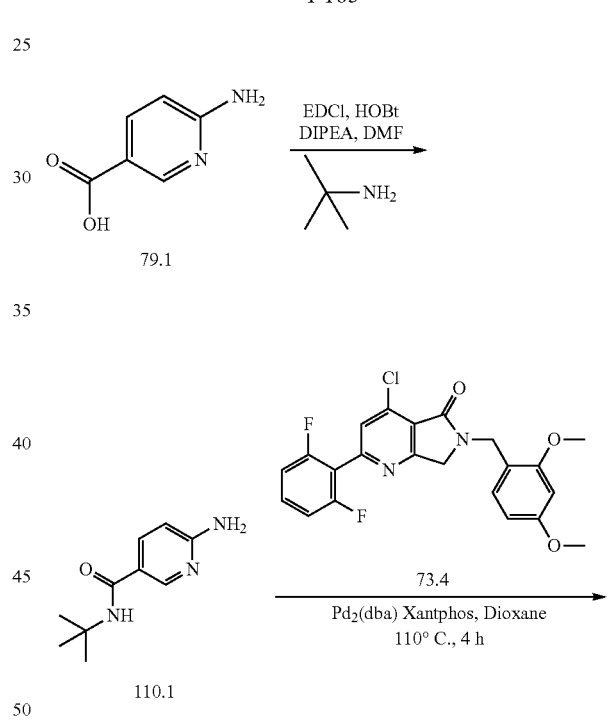

-continued

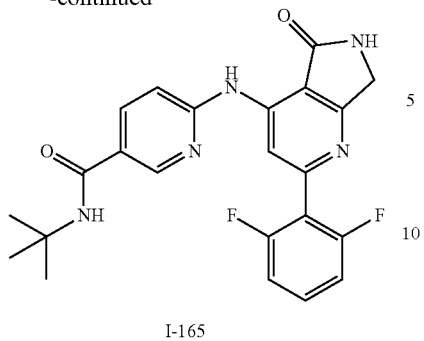

I-165

Synthesis of Compound 110.1.

To a solution of 79.1 (1.0 g, 7.2 mmol, 1.0 eq) in DMF (10 mL) was added EDCI (2.08 g, 10.86 mmol, 1.5 eq), HOBt (1.46 g, 10.86 mmol, 1.5 eq) at 0° C. Reaction was stirred at 0° C. for 15 min. After 15 min tert-butyl amine (0.794 g, 10.86 mmol, 1.5 eq) and DIPEA (2.72 mL, 15.9 mmol, 2.2 eq) ware added to reaction mixture at 0° C. Reaction was stirred at ambient temperature for 4 hours. After completion of the reaction, mixture was poured into water and product was extracted with ethyl acetate. Organic layers were combined and dried over sodium sulphate and concentrated under reduced pressure to obtain crude which was purified by column chromatography to afford 123.1 (1.0 g, 71%). MS (ES): m/z 194 [M+H]$^+$.

Synthesis of Compound 110.2.

To a solution of 73.4 (0.1 g, 0.23 mmol, 1.0 eq) in 1,4-dioxane (2 mL) was added 123.1 (0.049 g, 0.255 mmol, 1.1 eq) and K$_2$CO$_3$ (0.080 g, 0.58 mmol, 2.5 eq). The reaction mixture was degassed for 10 min. under argon atmosphere, then Pd$_2$(dba)$_3$ (0.021 g, 0.023 mmol, 0.1 eq) and Xantphos (0.026 g, 0.0464 mmol, 0.2 eq) were added. Reaction was then heated at 110° C. for 4 hours. After completion of the reaction, mixture was poured into water and product was extracted with ethyl acetate. Organic layers were combined and dried over sodium sulphate and concentrated under reduced pressure to obtain crude which was purified by column chromatography to furnish 110.2 (0.120 g, 87.9%). MS (ES): m/z 588.23 [M+H]$^+$.

Synthesis of Compound I-165.

Compound 110.2 (0.08 g, 0.136 mmol, 1.0 eq) was dissolved in HBr in acetic acid (2 ml) and stirred at room temperature for 1 hour. After completion of the reaction, mixture was poured into water, basified with saturated bicarbonate solution and extracted with ethyl acetate. Organic layers were combined, dried over sodium sulphate and concentrated under reduced pressure to obtain crude which was purified to furnish I-165 (0.050 g, 83.9%). MS (ES): m/z 438.46 [M+H]$^+$ $^1$H NMR (DMSO-d6, 400 MHZ): 9.93 (s, 1H), 8.96 (s, 1H), 8.77 (s, 1H), 8.66 (s, 1H), 8.11-8.13 (d, 1H), 7.81 (s, 1H), 7.60 (s, 1H), 7.22-7.29 (m, 3H), 4.46 (s, 2H), 1.36 (s, 9H).

Example 111. Synthesis of methyl 2-(5-((2-(2,6-difluorophenyl)-5-oxo-6,7-dihydro-5H-pyrrolo[3,4-d]pyrimidin-4-yl)amino)pyrimidin-2-yl)acetate, I-166

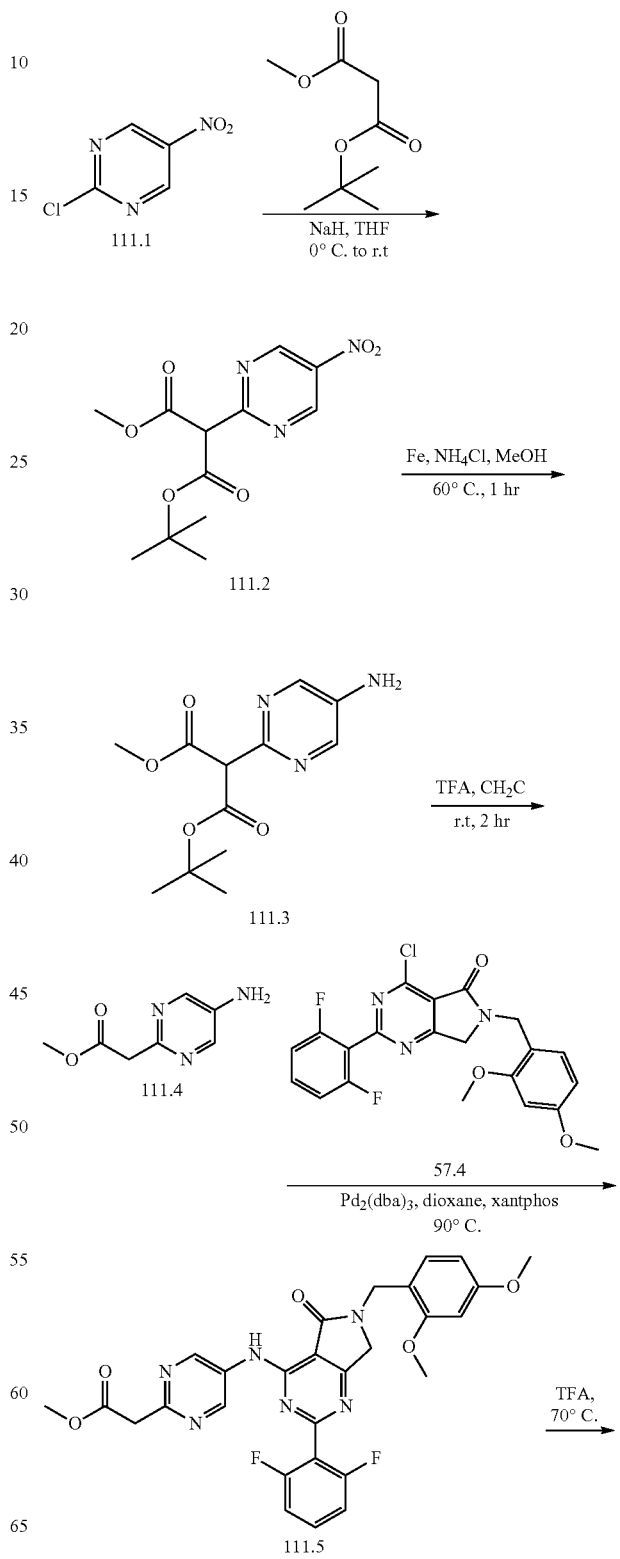

-continued

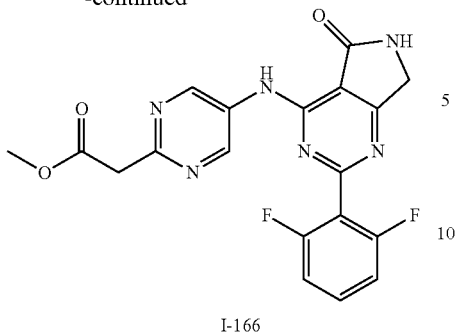

I-166

Synthesis of Compound 111.2.

A solution of malonic ester (3.93 g 2.25 mmol, 1.2 eq.) in THF (30 mL) was cooled to 0° C. and NaH (60% in oil) was added slowly at 0° C. Reaction mixture was stirred for 30 minutes at room temperature. A solution of 111.1 (3.0, 18.8 mmol, 1.0 eq) in THF (30 mL), was added slowly and reaction mixture was stirred for 30 min at 0-5° C. After completion of the reaction, mixture was poured into cold water and extracted using ethyl acetate (50 mL×2). Organic layer was dried over sodium sulfate and concentrated under reduced pressure. Crude compound was purified by flash column chromatography afford 111.2 (2.8 g, 50%). MS (ES): m/z 297.3 [M+H]$^+$ Synthesis of Compound 111.3.

To a solution of 111.2 (0.8 g, 2.6 mmol, 1.0 eq) in MeOH (8.0 mL) at room temperature was added a solution of NH$_4$Cl (0.84 g, 13.4 mmol, 5.0 eq) in water (8 mL) followed by Fe powder (0.75 g, 13.4 mmol, 5.0 eq). Reaction mixture was stirred at 60° C. for 1 hour. After completion of reaction, mixture was filtered through celite bed, diluted with water (50 ml) and extracted with EtOAC (20 ml×2). Organic layer was dried over sodium sulphate and concentrate under reduced pressure to afford 111.3 (0.7 g, 97.32%). MS (ES): m/z=267.3 [M+H]$^+$.

Synthesis of Compound 111.4.

A solution of Compound 111.3 (0.5 g) in CH$_2$Cl$_2$ (5 mL) was cooled at 0° C. TFA (5 mL) was added dropwise at 0° C. and reaction mixture was warmed to room temperature and stirred for 2 hours. After completion of the reaction, solvent was removed under reduced pressure to afford 111.4 (0.25 g, 79.8%). MS (ES): m/z 167.3 [M+H]$^+$.

Synthesis of Compound 111.5.

To a solution of 57.4 (0.250 g, 0.58 mmol, 1.0 eq.) in dioxane (8.0 mL) was added 124.4 (0.096 g, 0.58 mmol, 1.0 eq.) and K$_2$CO$_3$ (0.160 g, 1.16 mmol, 2.0 eq.) at room temperature. Reaction was degassed for 5 to 10 min, followed by addition of Xantphos (0.067 g, 0.11 mmol, 0.2 eq) and Pd$_2$(dba)$_3$ (0.053 g, 0.058 mmol, 0.1 eq), Reaction was degassed for 5t to 10 min and then heated at 90-100° C. for 2 hours. After completion of reaction, reaction mixture was poured into water and extracted using ethyl acetate. Organic layer was washed with brine solution, dried over sodium sulfate and concentrated under reduced pressure. Crude was purified by column chromatography to afford 111.5 (0.170 g, 52.20%). MS (ES): m/z 562.6 [M+H]$^+$ Synthesis of Compound I-166.

A solution of 111.5 (0.170 g, 0.30 mmol, 1.0 eq) in TFA (16 ml) was heated at 70° C. for 2 hours. After completion of the reaction, mixture was poured in cold water, neutralized with saturated sodium bicarbonate solution and product was extracted with EtOAc (50 mL×2). Solvent was removed under reduced pressure to get crude compound which was purified by column chromatography to furnish I-166 (0.052 g, 41.73%). MS (ES): m/z 412.4 [M+H]$^+$; $^1$H NMR (400 MHz, DMSO-d$_6$): δ 3.63 (s, 3H), 3.95 (s, 2H), 4.50 (s, 2H), 7.25-7.29 (m, 2H), 7.59-7.63 (m, 1H), 8.92 (s, 1H), 9.12 (s, 2H), 9.52 (s, 1H).

Example 112. Synthesis of 2-(2,6-difluorophenyl)-4-((5-methoxypyridin-2-yl)amino)-6,7-dihydro-5H-pyrrolo[3,4-b]pyridin-5-one, I-167

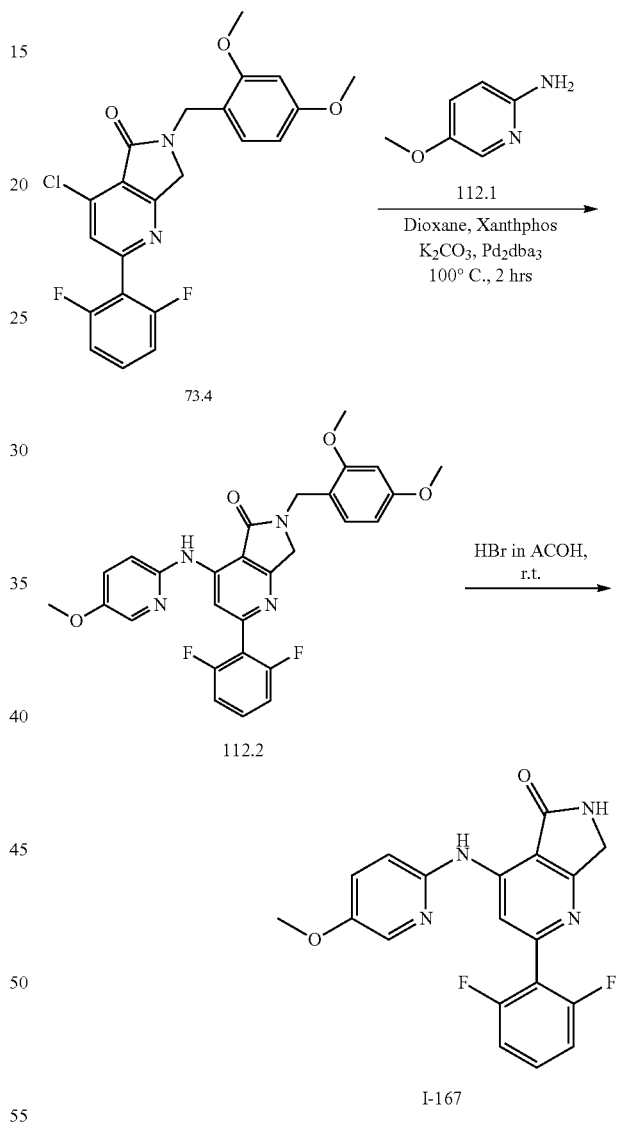

Synthesis of Compound 112.2.

To a solution of 73.4 (0.100 g, 0.232 mmol, 1.0 eq) in 1,4-dioxane (2 mL) was added 180.1 (0.031 g, 0.255 mmol, 1.1 eq) and K$_4$CO$_3$ (0.080 g, 0.580 mmol, 2.5 eq). The reaction mixture was degassed for 10 minutes using argon, then Pd$_2$(dba)$_3$ (0.021 g, 0.023 mmol, 0.1 eq) and Xantphos (0.026 g, 0.046 mmol, 0.2 eq) were added. The reaction was heated at 100° C. for 2 hours. After completion of reaction, mixture was poured into water and product was extracted with EtOAc. Organic layer were combined, dried over sodium sulphate and concentrated under reduced pressure to obtain crude which was purified to furnish 112.2 (0.080 g, 66.5%). MS (ES): m/z 519.5 [M+H]+.

Synthesis of Compound I-167.

Compound 112.2 (0.080 g, 0.154 mmol, 1.0 eq.) was dissolved in HBr/HOAc (2 ml) and stirred at room temperature for 1 hour. After completion of the reaction, mixture was poured into water, basified with saturated bicarbonate solution and extracted with EtOAc. Organic layers were combined, dried over sodium sulphate and concentrated under reduced pressure to obtain crude which was purified by column chromatography to furnish I-167 (0.050 g, 88.03%). MS (ES): m/z 369.3 [M+H]+, $^1$H NMR (DMSO-$d_6$, 400 MHZ): 9.60 (s, 1H), 8.83 (s, 1H), 8.40 (s, 1H), 8.08 (d, 1H), 7.57 (m, 1H), 7.45 (dd, 1H), 7.26 (t, 2H), 7.19 (d, 1H), 4.42 (s, 2H), 3.80 (s, 3H).

Example 113. Synthesis of 2-(2,6-difluorophenyl)-4-((4-(3-hydroxyazetidine-1-carbo-nyl)phenyl)amino)-6,7-dihydro-5H-pyrrolo[3,4-d]pyrimidin-5-one I-168

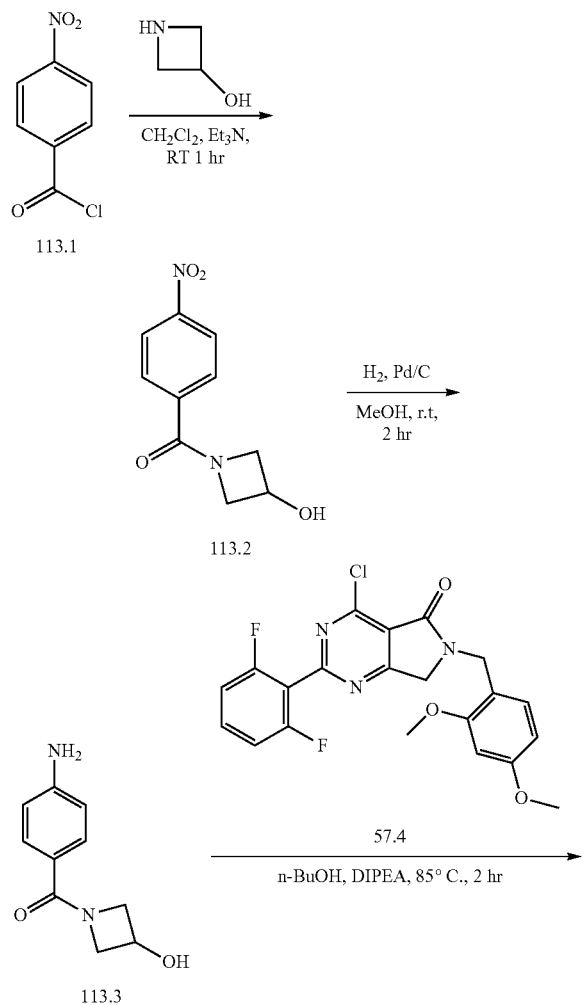

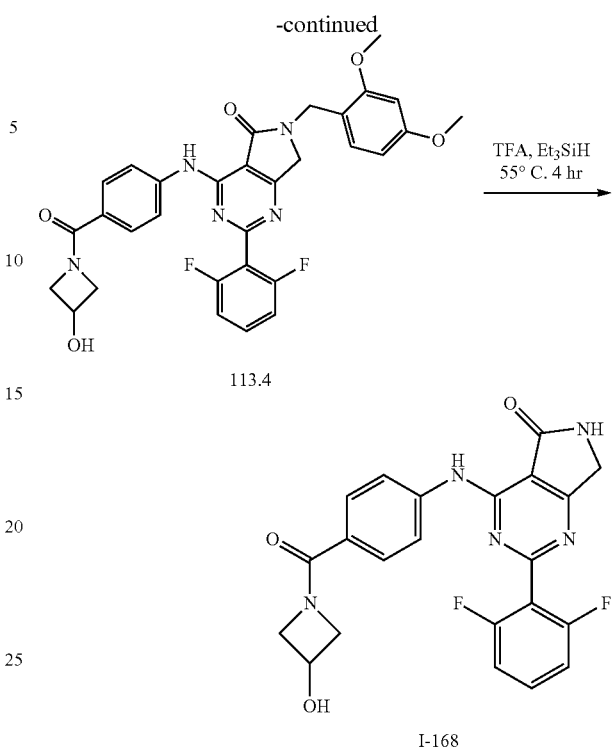

Synthesis of Compound 113.2.

To a solution of 113.1 (1.0 g 5.43 mmol, 1.0 eq.) in dry CH$_2$Cl$_2$ (15.0 mL) was added azetidin-3-ol (476 mg, 6.52 mmol, 1.2 eq) at 0° C. Triethylamine (1.64 g, 16.43 mmol, 3 eq) was added drop wise at same temperature. The reaction mixture was allowed to warm at room temperature and stirred for 1 hour. After completion of the reaction, mixture was poured in water and extracted using EtOAc (75 mL×2). Organic layer was dried over sodium sulfate and concentrated under reduced pressure to get the crude which was purified by column chromatography to afford pure 113.2 (0.4 g, 33.40%). MS (ES): m/z 223.2 [M+H]+

Synthesis of Compound 113.3.

To a suspension of Pd/C (100 mg) in MeOH (20 mL) was added 113.2 (400 mg, 1.8 mmol. 1.0 eq.) under nitrogen atmosphere. To the above reaction mixture was purged with H$_2$ (gas) at room temperature for 2 hours. After completion of the reaction, mixture was filter through celite. Solvent was removed under reduced pressure to afford 113.3 (300 mg, 86.70%). MS (ES): m/z 193.2 [M+H]+.

Synthesis of Compound 113.4.

To a solution of 57.4 (200 mg, 0.46 mmol, 1.0 eq.) in n-butanol (5.0 mL) was added 129.3 (90 mg, 0.46 mmol, 1.0 eq.) and DIPEA (149 mg, 1.16 mmol, 2.5 eq.) at room temperature. Reaction mixture was heated at 85° C. for 2 hours. After completion of the reaction, mixture was poured into water and extracted using EtOAc. Organic layer was washed with brine, dried over sodium sulfate and concentrated under reduced pressure. Crude was purified by column chromatography to afford pure 113.4 (175 mg, 64.31%). MS (ES): m/z 588.5 [M+H]+

Synthesis of Compound I-168.

To a solution of 113.4 (175 mg, 0.299 mmol, 1.0 eq) in TFA (2 ml) was added Triethylsilane (113 mg, 0.897 mmol, 3.0 eq) and heated at 55° C. for 4 hours. After completion of the reaction, mixture was concentrated under reduced pressure at 45° C. Obtained residue was poured in cold water, neutralized with NaHCO₃ and product was extracted with EtOAc (50 ml×2). Solvent was removed under reduced pressure to get crude, which was purified by column chromatography to afford pure I-168 (65 mg, 51.4%). MS (ES): m/z 438.4 [M+H]⁺, LCMS purity: 97.75%, HPLC purity: 96.30%, ¹H NMR (400 MHz, DMSO-d⁶): δ 9.26 (s, 1H), 8.96 (s, 1H), 7.86-7.84 (d, 2H), 7.68-7.60 (m, 3H), 7.31-7.27 (t, 2H), 4.51-4.48 (d, 4H), 4.22 (s, 1H), 4.04 (s, 1H), 3.78-3.76 (d, 2H).

Example 114. Synthesis of 2-(5-((2-(2,6-difluoro-phenyl)-5-oxo-6,7-dihydro-5H-pyrrolo[3,4-d]pyrimidin-4-yl)amino)pyrimidin-2-yl)-N-ethylacetamide, I-169

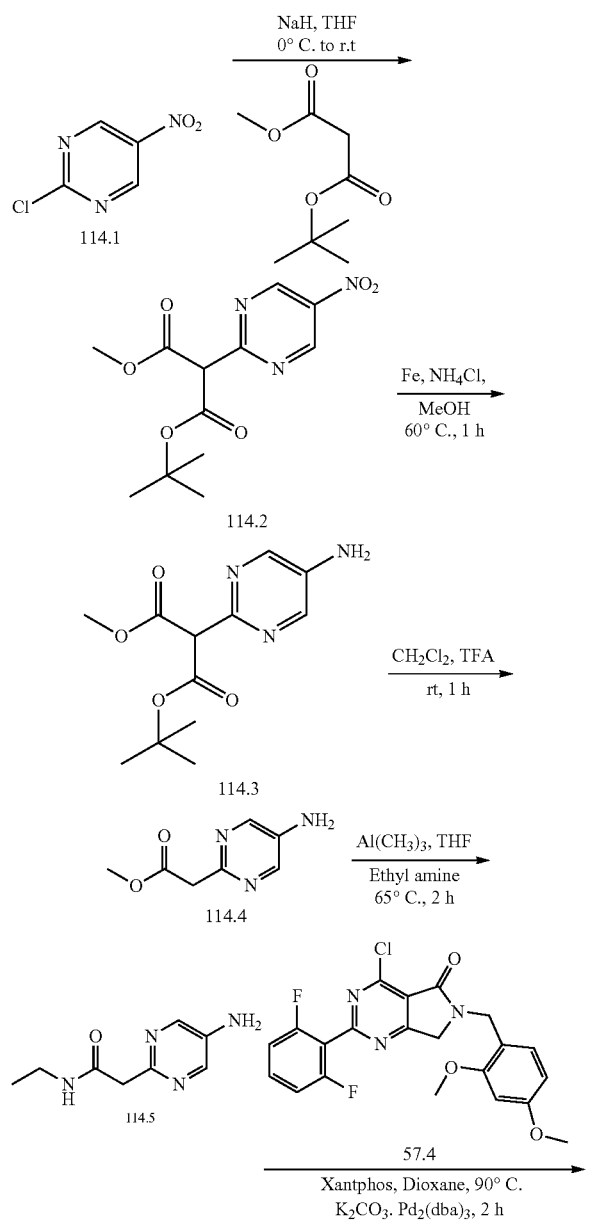

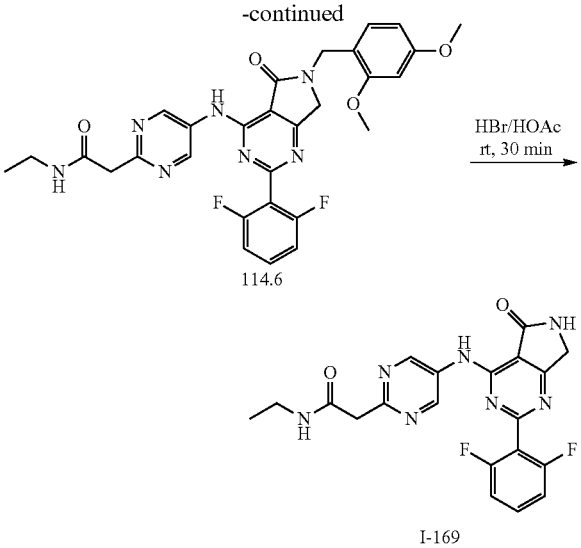

Synthesis of Compound 114.2.

A solution of Malonic ester (5.2 g, 30.0 mmol, 1.2 eq.) in THF (60 mL) was cooled at 0° C. and NaH (60% in oil) (2.3 g, 57.0 mmol, 2.3 eq) was added slowly at 0° C. Reaction mixture was stirred for 30 minutes at room temperature. A solution of 114.1 (4.0 g, 25.0 mmol, 1.0 eq) in THF (60 mL), was added slowly and reaction mixture was stirred for 30 min at 0-5° C. After completion of the reaction, mixture was poured into cold water and extracted using EtOAc (50 ml×2). Organic layer was dried over sodium sulfate and concentrated under reduced pressure. Crude was purified by flash column chromatography to afford 114.2 5.5 g, 60.37%). MS (ES): m/z 297.3 [M+H]⁺

Synthesis of Compound 114.3.

To a solution of Compound 114.2 (5.5 g, 18.5 mmol, 1.0 eq) in MeOH (55 mL) at room temperature was added a solution of NH₄Cl (5.79 g, 92.0 mmol, 5.0 eq) in water (55 mL) followed by Fe powder (5.18 g, 92.0 mmol, 5.0 eq). Reaction mixture was stirred at 60° C. for 1 hour. After completion of the reaction, mixture was filtered through celite bed, diluted with water (50 ml) and extracted with EtOAc (20 ml×2). Organic layer was dried over sodium sulphate and concentrated under reduced pressure to afford 114.3 (4.0 g, 80.89%). MS (ES): m/z=267.3 [M+H]⁺.

Synthesis of Compound 114.4.

A solution of 114.3 (2.7 g, 7.18 mmol, 1.0 eq) in CH₂Cl₂ (5 mL) was cooled at 0° C. Trifluoroacetic acid (5 mL) was added dropwise at 0° C. and reaction mixture was warmed to room temperature and stirred for 2 hours. After completion of the reaction, solvent was removed under reduced pressure to afford 114.4 (1.2 g, 59.22%). MS (ES): m/z 167.3 [M+H]⁺.

Synthesis of Compound 114.5.

To a solution of 114.4 (1.2 g, 7.18 mmol, 1.0 eq) in THF (20 mL), Et₃N in 2M THF (10.7 mL, 21.55 mmol, 3.0 eq) and DIPEA (2.4 mL, 14.37 mmol, 2 eq) were added. Reaction mixture was cooled at 0° C. and Me₃Al (10.7 mL, 21.55 mmol, 3.0 eq) was added dropwise at 0° C. Reaction mixture was heated at 65° C. and stirred for 2 hours. After completion of the reaction, reaction was cooled and quenched with 20% MeOH in CH₂Cl₂. Reaction was filter through celite and wash with 20% MeOH in CH₂Cl₂. Crude product was purified by column chromatography to afford 114.5 (0.430 g, 33.2%). MS (ES): m/z 181.3 [M+H]⁺.

Synthesis of Compound 114.6.

To a solution of 57.4 (0.579 g, 1.34 mmol, 1.0 eq.) in dioxane (12.0 mL) was added 114.5 (0.145 g, 0.80 mmol, 0.6 eq.) and K$_2$CO$_3$ (0.278 g, 2.01 mmol, 1.5 eq) at room temperature. Reaction was degassed for 5 to 10 min and Xantphos (0.155 g, 0.26 mmol, 0.2 eq) followed by Pd$_2$(dba)$_3$ (0.122 g, 0.134 mmol, 0.1 eq) were added. Reaction was degassed for 5 to 10 min and heated at 90-100° C. for 2 hours. After completion of the reaction, mixture was poured into water and extracted using EtOAc. Organic layer was washed with brine, dried over sodium sulfate and concentrated under reduced pressure. Crude was purified by column chromatography to afford pure 114.6 (0.400 g, 51.83%). MS (ES): m/z 575.6 [M+H]$^+$ Synthesis of Compound I-169.

A solution of Compound 114.6 (0.400 g) in HBr/HOAc (12 ml) was stirred for 2 hours at room temperature. After completion of the reaction, mixture was poured into cold water, neutralized with saturated NaHCO$_3$ solution and extracted with EtOAc (50 mL×2). Solvent was concentrated under reduced pressure to get the crude which was purified by column chromatography to afford I-169 (0.064 g, 21.65%). MS (ES): m/z 425.4 (M+H)$^+$; $^1$H NMR (400 MHz, DMSO-d$_6$): δ 9.07 (s, 1H), 8.93 (s, 1H), 8.50 (s, 2H), 8.10 (s, 1H), 7.62-7.58 (m, 1H), 7.29-7.24 (t, 2H), 4.50 (s, 2H), 3.68 (s, 2H), 3.09-3.06 (q, 2H), 1.04-1.00 (t, 3H).

Example 115. Synthesis of 2-(2,6-difluorophenyl)-4-((5,6-dimethoxypyridin-2-yl)amino)-6,7-dihydro-5H-pyrrolo[3,4-b]pyridin-5-one, I-170

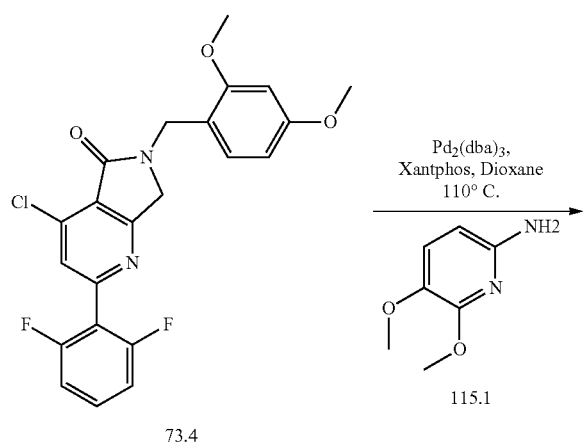

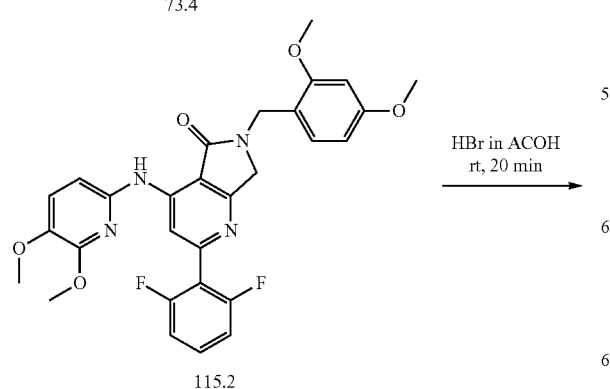

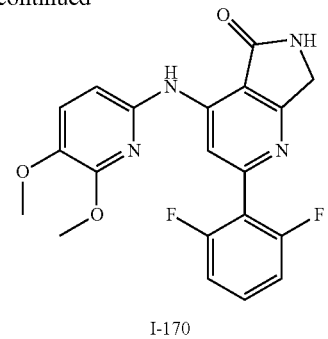

I-170

Synthesis of Compound 115.2.

To a solution of 73.4 (0.10 g, 0.23 mmol, 1.0 eq) in 1,4-dioxane (2 mL) was added 131.1 (0.039 g, 0.255 mmol, 1.1 eq) and K$_2$CO$_3$ (0.08 g, 0.58 mmol, 2.5 eq). The reaction mixture was degassed for 10 min. under argon atmosphere, then Pd$_2$(dba)$_3$ (0.021 g, 0.023 mmol, 0.1 eq) and Xantphos (0.026 g, 0.046 mmol, 0.2 eq) were added. The reaction was then heated at 110° C. for 2 hours. After completion of the reaction, mixture was poured into water and product was extracted with EtOAc. Organic layer were combined and dried over sodium sulphate and concentrated under reduced pressure to obtain crude which was purified by column chromatography to get pure 115.2 (0.070 g, 54.98%). MS (ES): m/z 549.6 [M+H]$^+$.

Synthesis of Compound I-170.

Compound 115.2 (0.070 g, 0.127 mmol, 1.0 eq.) was dissolved in HBr/HOAc (2 ml) and stirred at room temperature for 1 hour. After completion of the reaction, mixture was poured into water and basified with saturated Na$_2$CO$_3$ and extracted with EtOAc. Organic layer was dried over sodium sulphate and concentrated under reduced pressure to obtain crude which was purified by column chromatography get pure I-170 (0.023 g, 45.24%). MS (ES): m/z 399.37 [M+H]$^+$, $^1$H NMR (DMSO-d$_6$, 400 MHz): 9.48 (s, 1H), 8.82 (s, 1H), 8.35 (s, 1H), 7.56 (m, 1H), 7.37 (d, 1H), 7.24 (t, 2H), 6.74 (d, 1H), 4.41 (s, 2H), 3.81 (s, 3H), 3.75 (s, 3H).

Example 116. Synthesis of 2-(2,6-difluorophenyl)-4-((5-morpholinopyridin-2-yl)amino)-6,7-dihydro-5H-pyrrolo[3,4-b]pyridin-5-one, I-171

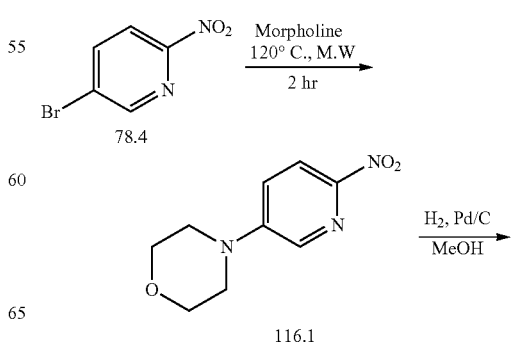

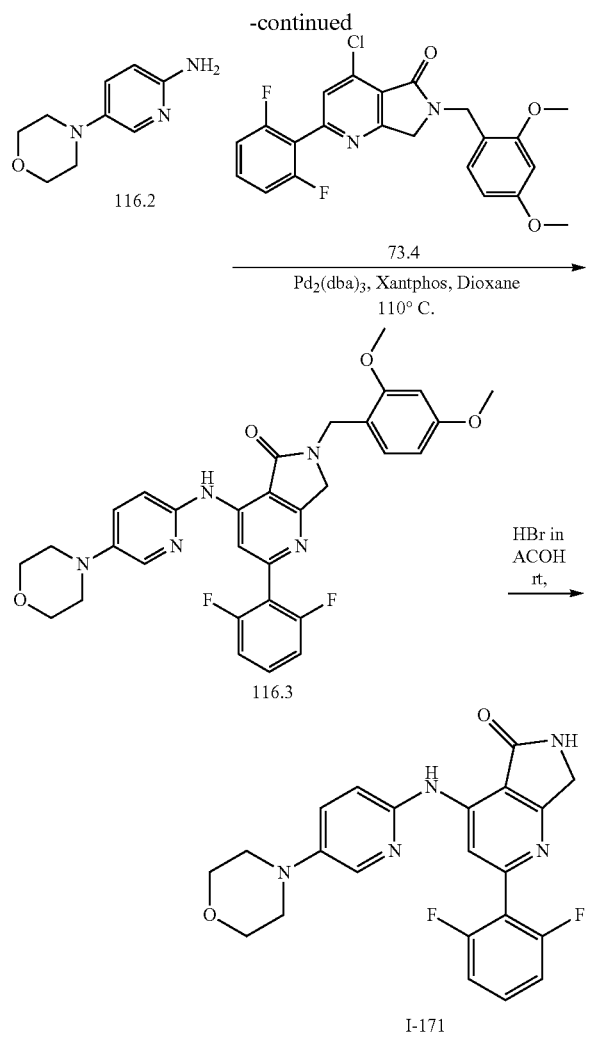

Synthesis of Compound 116.1.

To a solution of 78.4 (1.0 g g, 4.93 mmol, 1.0 eq) in DMSO (3 mL) was added morpholine (0.514 g, 5.911 mmol, 1.2 eq). Reaction mixture was heated at 120° C. in microwave for 2 h. The reaction mixture was poured into water and product was extracted with EtOAc. Organic layers were combined, dried over sodium sulphate and concentrated under reduced pressure to obtain crude which was purified by column chromatography to get 116.1 (0.390 g, 37.84%). MS (ES): m/z 210.3 [M+H]$^+$.

Synthesis of Compound 116.2.

A solution of 116.1 (0.39 g, 1.864 mmol, 1.0 eq) in MeOH (5 mL) was added with 10% Pd/C (0.039 mg) under nitrogen atmosphere. Suspension was purged with hydrogen gas for 1 h. Reaction mixture was filtered through celite and obtained filtrate was concentrated under reduced pressure to get crude 116.2 (0.210 g, 62.87%) which was used as such for the next step, MS (ES): m/z 180.3 [M+H]$^+$.

Synthesis of Compound 116.3.

To a solution of 73.4 (0.100 g, 0.232 mmol, 1.0 eq) in 1,4-dioxane (2 mL) was added 116.2 (0.045 g, 0.255 mmol, 1.1 eq) and K$_2$CO$_3$ (0.080 g, 0.580 mmol, 2.5 eq). The reaction mixture was degassed for 10 minutes under argon atmosphere, then Pd$_2$(dba)$_3$ (0.0212 g, 0.0232 mmol, 0.1 eq) and Xantphos (0.026 g, 0.046 mmol, 0.2 eq) were added, again degassed for 5 min. The reaction was then heated at 110° C. for 2 hours. After completion of reaction, mixture was poured into water and product was extracted with EtOAc. Organic layers were combined, dried over sodium sulphate and concentrated under reduced pressure to obtain crude which was purified by column chromatography get pure 116.3 (0.080 g, 60.09%). MS (ES): m/z 574.6 [M+H]$^+$.

Synthesis of Compound I-171.

Compound 116.3 (0.080 g, 0.139 mol, 1.0 eq.) was dissolved in Hbr/HOAc (2 ml) and stirred at room temperature for 1 hour. After completion of the reaction, reaction mixture was poured into water, basified with saturated bicarbonate solution and product was extracted with EtOAC. Organic layers were combined, dried over sodium sulphate and concentrated under reduced pressure to obtain crude which was purified by column chromatography to I-171 (0.035 g, 59.3%). MS (ES): m/z 424.5 [M+H]$^+$; $^1$H NMR (DMSO-d$_6$, 400 MHz): 9.53 (s, 1H), 8.81 (s, 1H), 8.39 (s, 1H), 8.07 (d, 1H), 7.57 (m, 1H), 7.47 (dd, 1H), 7.25 (m, 2H), 7.12 (d, 1H), 4.41 (s, 2H), 3.73 (t, 4H), 3.09 (t, 4H).

Example 117. Synthesis of 5-(4-((2-(2,6-difluorophenyl)-5-oxo-6,7-dihydro-5H-pyrrolo[3,4-d]pyrimidin-4-yl)amino)phenyl)-5-methylimidazolidine-2,4-dione, I-172

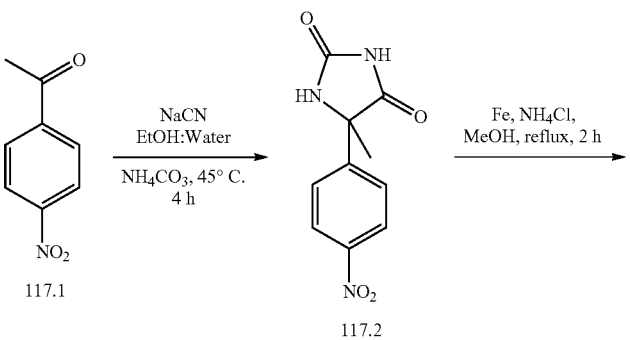

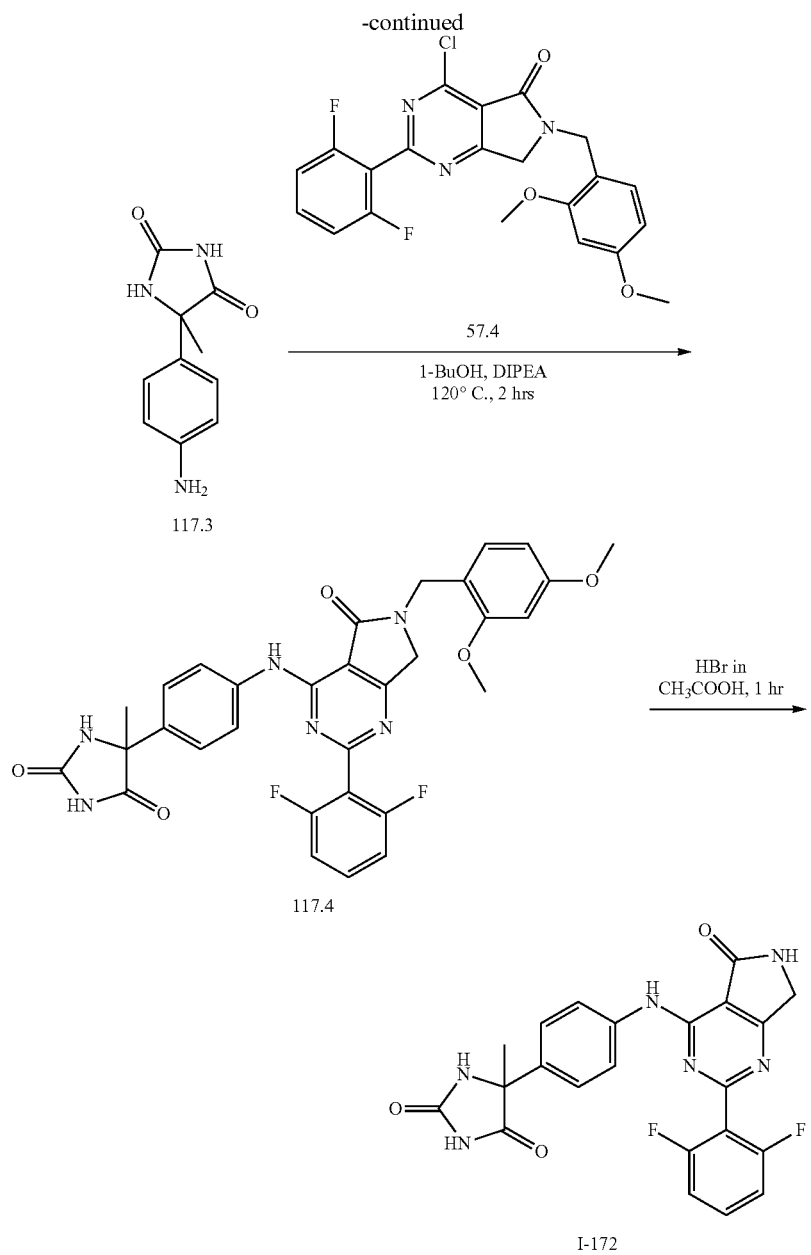

Synthesis of Compound 117.2.

To a suspension of 117.1 (10 g, 6.0 mmol, 1.0 eq), Ammonium carbonate (40.97 g, 45.58 mmol, 7.58 eq) in EtOH (80 mL) and H2O (80 mL) was added NaCN (3.96 g, 7.9 mmol, 1.3 eq) at room temperature. The reaction mass was sonicated at 45° C. for 5 hours. The reaction mixture was acidified with dil. HCl (1.2 L). The obtained solid was filtered and air dried for 24 h to obtain 117.2 (12 g, 84%). MS (ES): m/z no ionisation [M+H]$^+$.

Synthesis of Compound 117.3.

To a solution of 117.2 (2.0 g, 8.5 mmol, 1.0 eq) in MeOH (3 mL) and H$_2$O (3 mL) was added NH$_4$Cl (2.25 g, 42.5 mmol, 5.0 eq) followed by Fe powder (2.4 g, 42.5 mmol, 5.0 eq) for 1 hour. Reaction mixture was heated at 80° C. for 2 hours. Reaction mixture was filtered through celite, washed with methanol and obtained filtrate was concentrated under reduced pressure to get crude 117.3 (1.5 g, 85.9%) which was used as such for the next step, MS (ES): m/z 206.5 [M+H]$^+$.

Synthesis of Compound 117.4.

To a solution of 57.4 (0.2 g, 0.46 mmol, 1.0 eq) in 1-butanol (5 mL) was added 136.3 (0.159 g, 0.764 mmol, 1.1 eq) and DIPEA (0.3 mL, 1.38 mmol, 3 eq). The reaction mixture was then heated at 120° C. for 2 hours. After completion of the reaction, mixture was poured into water and product was extracted with EtOAc (100 mL×2). Organic layer was dried over sodium sulphate and concentrated under reduced pressure to obtain crude 117.4 (0.25 g), which was used as such. MS (ES): m/z 601.3 [M+H]$^+$.

Synthesis of Compound I-172.

Compound 117.4 (0.25 g, 0.41 mmol, 1.0 eq) was dissolved in HBr/HOAc (3 mL) and stirred at room temperature for 1 hour. After completion of the reaction, reaction mixture was poured in water and basified with saturated bicarbonate solution and product was extracted with EtOAC (100 mL×2). Organic layer was dried over sodium sulphate and concentrated under reduced pressure to obtain crude which was purified by column chromatography to get pure I-172 (0.14 g, 74.7%). MS (ES): m/z 451.6 [M+H]$^+$. $^1$H NMR (DMSO-d$_6$, 400 MHz): 10.77 (s, 1H), 9.13 (s, 1H), 8.92 (s, 1H), 8.58 (s, 1H), 7.78 (d, 2H), 7.60 (m, 1H), 7.42 (d, 2H), 7.27 (t, 2H), 4.48 (s, 2H), 1.63 (s, 3H).

Example 118. Synthesis of compound (S)-5-(4-((2-(2,6-difluorophenyl)-5-oxo-6,7-dihydro-5H-pyrrolo[3,4-d]pyrimidin-4-yl)amino)phenyl)-5-methylimidazolidine-2,4-dione, I-173 heated at 100° C. for 2 hours. After completion of the reaction, mixture was poured into water and product was extracted with EtOAC (100 mL×2). Organic layers were combined, dried over sodium sulphate and concentrated under reduced pressure to obtain crude 118.2 (0.09 g) which was use as such. MS (ES): m/z 601.3 [M+H]$^+$.

Synthesis of Compound I-173.

Compound 118.2 (0.09 g,) was dissolved in HBr/HOAc (3 mL) and stirred at room temperature for 1 hour. After completion of the reaction, mixture was poured into water and basified with saturated bicarbonate solution and

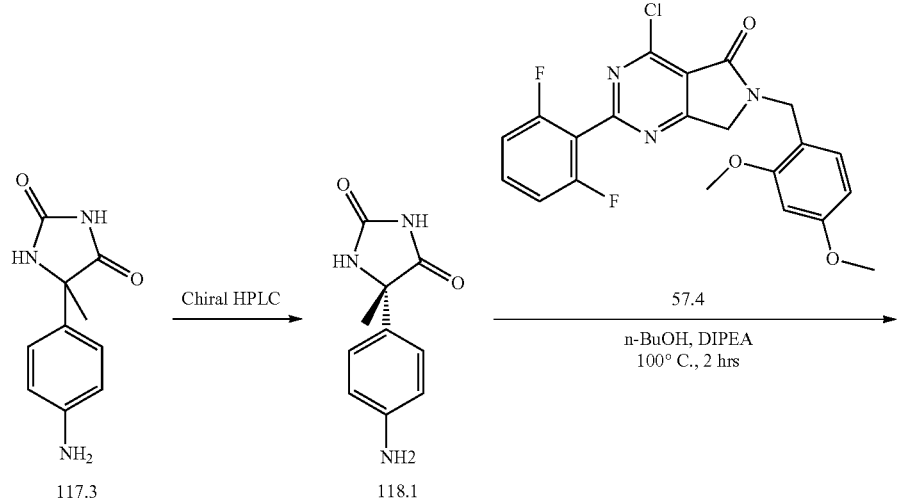

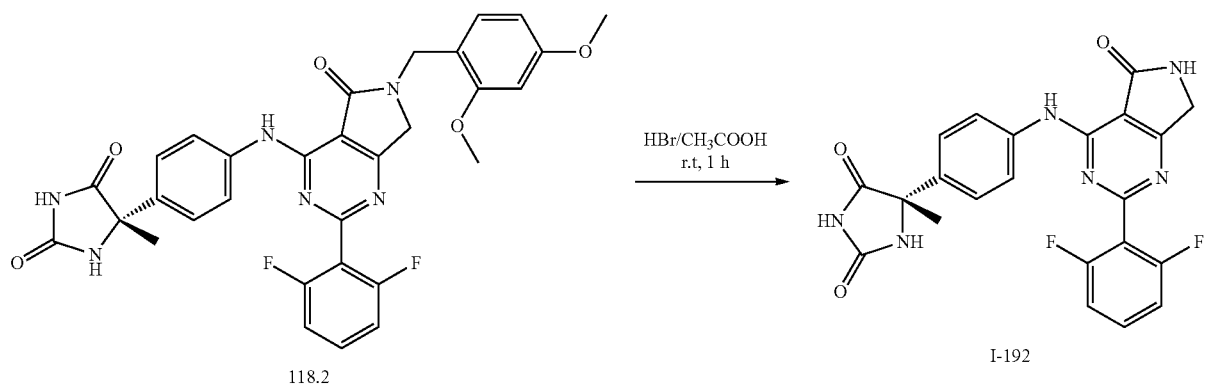

Synthesis of Compound 118.1.

Racemic mixture of 117.3 (0.300 mg) was separated using preparative chiral HPLC to afford pure 118.1 (75 mg), MS (ES): m/z 206.5 [M+H]$^+$, LCMS purity: 100%, Chiral HPLC: 100%

Synthesis of Compound 118.2.

To a solution of 57.4 (0.12 g, 0.27 mmol, 1.0 eq) in 1-butanol (5 mL) was added 118.1 (0.075 g, 0.36 mmol, 1.3 eq) and DIPEA (0.14 mL, 0.81 mmol, 3 eq). Reaction was extracted with EtOAC (100 mL×2). Organic layers were combined and dried over sodium sulphate and concentrated under reduced pressure to obtain crude which was purified by column chromatography to get pure I-173 (0.06 g, 89%). MS (ES): m/z 451.4 [M+H]$^+$. $^1$H NMR (DMSO-d$_6$, 400 MHz): 10.76 (s, 1H), 9.13 (s, 1H), 8.91 (s, 1H), 8.57 (s, 1H), 7.79 (d, 2H), 7.62-7.59 (m, 1H), 7.42 (d, 2H), 7.27 (t, 2H), 4.48 (s, 2H), 1.63 (s, 3H).

Example 119. Synthesis of compound (R)-5-(4-((2-(2,6-difluorophenyl)-5-oxo-6,7-dihydro-5H-pyrrolo[3,4-d]pyrimidin-4-yl)amino)phenyl)-5-methylimidazolidine-2,4-dione, I-174

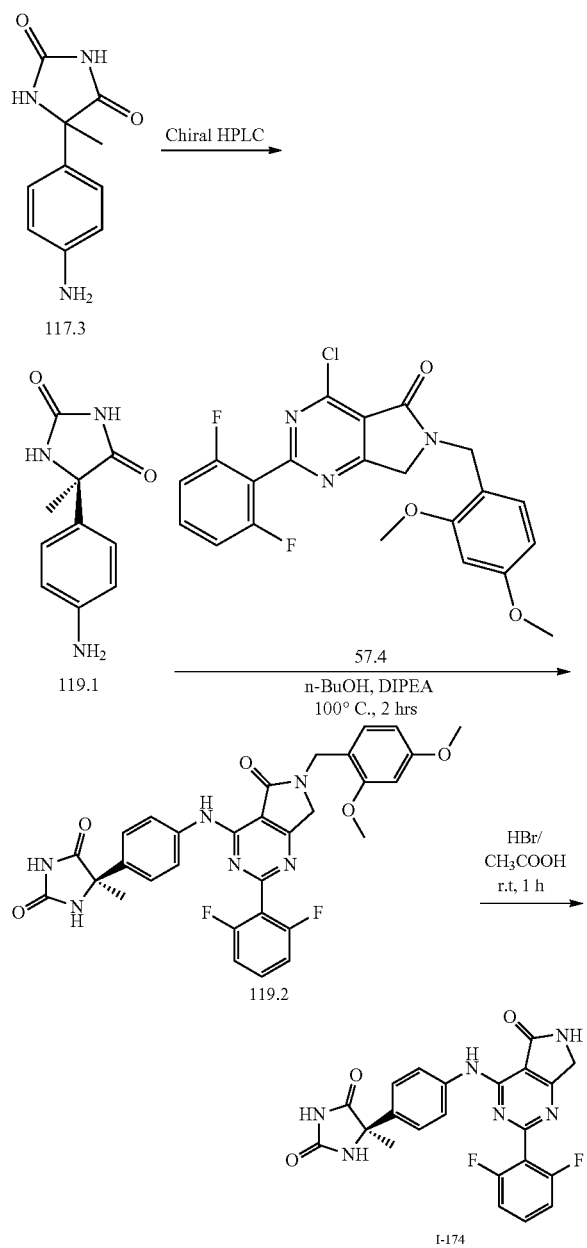

Synthesis of Compound 119.1.
A racemic mixture of 117.3 (0.300 mg) was separated using preparative HPLC to afford pure 119.1 (75 mg), MS (ES): m/z 206.5 [M+H]+, LCMS purity: 100%, Chiral HPLC: 100%

Synthesis of Compound 119.2.
To a solution of 57.4 (0.12 g, 0.27 mmol, 1.0 eq) in 1-butanol (5 mL) was added 119.1 (0.075 g, 0.36 mmol, 1.3 eq) and DIPEA (0.14 mL, 0.81 mmol, 3 eq). Reaction was stirred at 100° C. for 2 hours. After completion of the reaction, mixture was poured into water and product was extracted with EtOAc (100 mL×2). Organic layer was dried over sodium sulphate and concentrated under reduced pressure to obtain crude 119.2 (0.09 g) which was uses as such. MS (ES): m/z 601.3 [M+H]+.

Synthesis of Compound I-174.
Compound 119.2 (0.09 g,) was dissolved in HBr/HOaAc (3 mL) and stirred at room temperature for 1 hour. After completion of the reaction, mixture was poured into water, basified with saturated bicarbonate solution and extracted with EtOAc (100 mL×2). Organic layers were combined, dried over sodium sulphate and concentrated under reduced pressure to obtain crude which was purified by column chromatography to get pure I-174 (0.06 g, 89%). MS (ES): m/z 451.6 [M+H]+. 1H NMR (DMSO-d6, 400 MHz): 10.77 (s, 1H), 9.13 (s, 1H), 8.91 (s, 1H), 8.57 (s, 1H), 7.78 (d, 2H), 7.64-7.54 (m, 1H), 7.42 (d, 2H), 7.27 (t, 2H), 4.48 (s, 2H), 1.63 (s, 3H).

Example 120. Synthesis of 2-(2,6-difluorophenyl)-4-((4-(3-ethyl-2-oxopyrrolidin-3-yl)phenyl)amino)-6,7-dihydro-5H-pyrrolo[3,4-d]pyrimidin-5-one, I-175

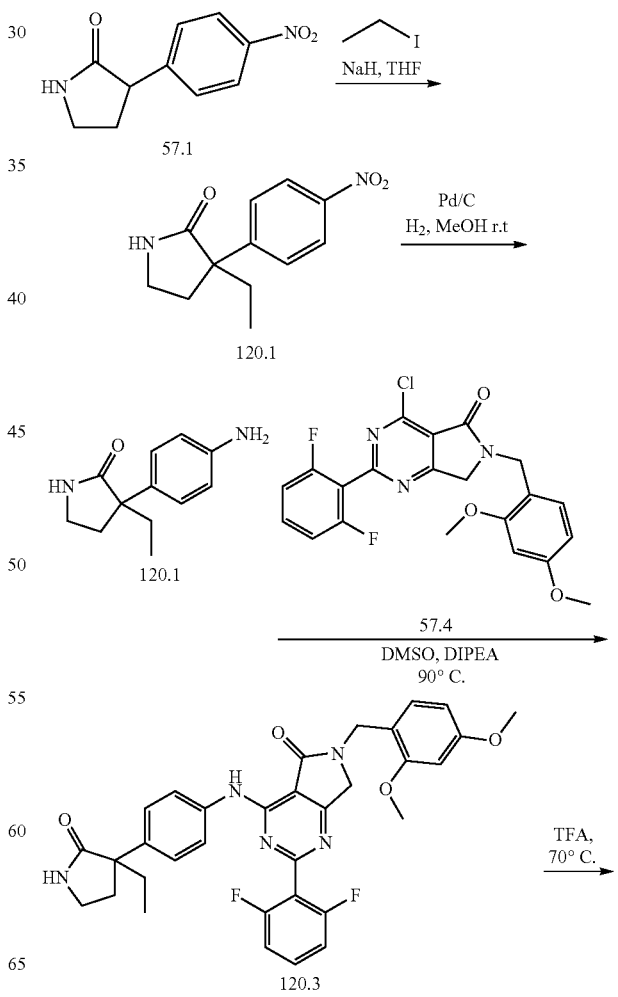

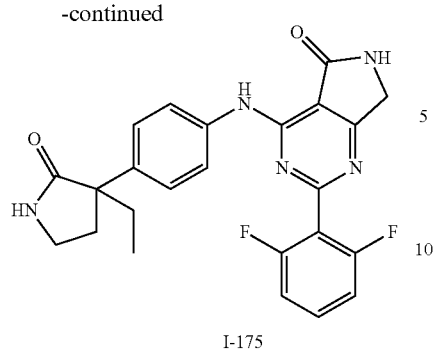

I-175

Synthesis of Compound 120.1.

A solution of 57.1 (0.325 g 1.50 mmol, 1.0 eq.) in DMF (2 mL) was cooled to 0° C. and NaH as 60% in oil (0.161 g, 3.9 mmol, 2.5 eq) was added portion wise. Reaction mixture was stirred for 20 minutes at 0° C. Ethyl iodide (0.27 g, 1.73 mmol, 1.1 eq) was added dropwise and reaction mixture was stirred for 30 minutes at 0° C. After completion of the reaction, mixture was poured into cold water and extracted using EtOAc (20 mL×2). Organic layer was dried over sodium sulfate and concentrate under reduced pressure. Crude was purified by column chromatography to afford 120.1 (0.185 g, 50.51%). MS (ES): m/z 234.2 [M+H]+

Synthesis of Compound 120.2.

To a suspension of 10% Pd/C (0.05 g) in MeOH (10 mL), Compound 120.1 (0.185 g, 0.79 mmol, 1.0 eq) was added at room temperature. Hydrogen gas was bubbled through reaction mixture for 2-3 h. After completion of the reaction, the mixture was filtered through celite bed and wash with methanol. Organic layer was concentrated under reduced pressure to afford compound 120.2 (0.100 g, 61.99%). MS (ES): m/z=204.27 [M+H]+.

Synthesis of Compound 120.3.

To a solution of compound 57.4 (0.175 g, 0.40 mmol, 1.0 eq.) in DMSO (2 mL), 142.2 (0.083 g, 0.40 mmol, 1.0 eq) and DIPEA (0.17 mL, 1.0 mmol, 2.5 eq) were added at room temperature. Reaction mixture was stirred at 90° C. for 30 minutes. After completion of the reaction, mixture was poured into cold water and extracted using EtOAc (20 mL×2). Organic layer was dried over sodium sulfate and concentrate under reduced pressure. Crude was purified by column chromatography to afford compound 120.3 (0.120 g, 49.4%). MS (ES): m/z 599.6 [M+H]+.

Synthesis of Compound I-175.

A solution of 120.3 (0.120 g, 0.200 mmol, 1.0 eq) in TFA (3 mL) was heated at 70° C. for 8 hours. After completion of the reaction, mixture was poured into cold water, neutralized with NaHCO3 and extracted with EtOAC (10 mL×2). Solvent was removed under reduced pressure to get crude. which was purified by column chromatography to afford I-175 (0.048 g, 69.80%). MS (ES): m/z 449.4 [M+H]+; 1H NMR (400 MHz, DMSO-d6): δ 9.04 (s, 1H), 8.90 (s, 1H), 7.74-7.71 (m, 3H), 7.64-7.57 (m, 1H), 7.45-7.43 (d, 2H), 7.30-7.25 (t, 2H), 5.76 (s, 1H), 4.48 (s, 2H), 3.20-3.16 (m, 1H), 3.10-3.04 (m, 1H), 2.19-2.12 (m, 1H), 1.88-1.83 (m, 1H), 1.69-1.64 (m, 1H), 0.74 (t, 3H).

Example 121. Synthesis of (S)-2-(2,6-difluorophenyl)-4-((4-(3-ethyl-2-oxopyrrolidin-3-yl)phenyl)amino)-6,7-dihydro-5H-pyrrolo[3,4-d]pyrimidin-5-one I-176

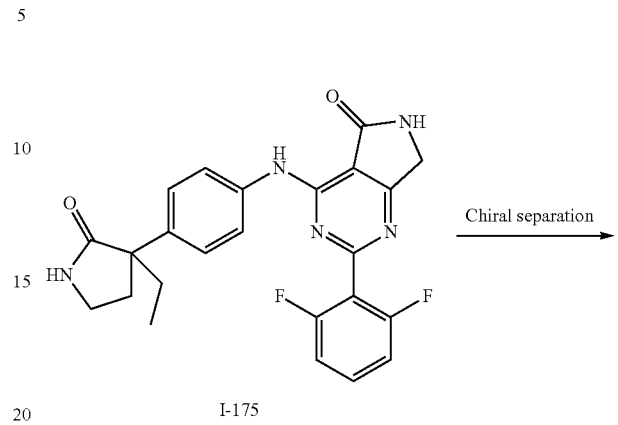

Compound I-176 was obtained by chiral separation of compound I-175. MS (ES): m/z 449.4 [M+H]+; 1H NMR (400 MHz, MeOD): δ 7.81-7.79 (d, 2H), 7.56-7.47 (m, 3H), 7.17-7.13 (m, 2H), 4.51 (s, 2H), 4.00 (s, 1H), 3.38-3.26 (m, 2H), 2.56-2.51 (m, 1H), 2.39-2.33 (m, 1H), 2.05-2.00 (m, 1H), 1.88-1.83 (m, 1H), 0.92-0.86 (t, 3H).

Example 122. Synthesis of (R)-2-(2,6-difluorophenyl)-4-((4-(3-ethyl-2-oxopyrrolidin-3-yl)phenyl)amino)-6,7-dihydro-5H-pyrrolo[3,4-d]pyrimidin-5-one, I-177

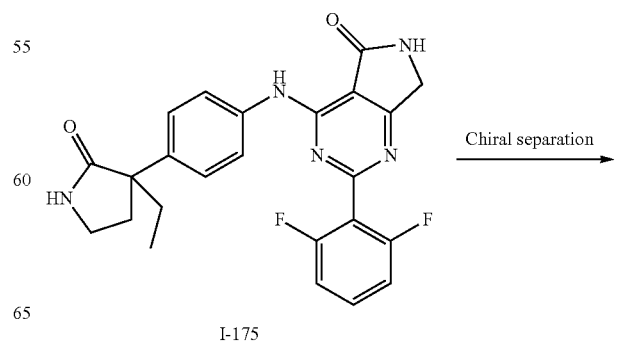

I-175

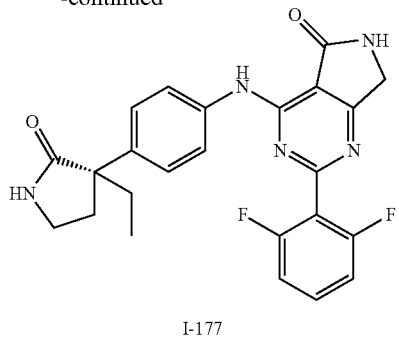

I-177

Compound I-177 was obtained by chiral separation of compound I-175. MS (ES): m/z 449.4 [pM+H]+; 1H NMR (400 MHz, MeOD): δ 7.81-7.78 (d, 2H), 7.58-7.52 (m, 1H), 7.49-7.47 (d, 2H), 7.17-7.13 (m, 2H), 4.51 (s, 2H), 4.00 (s, 1H), 3.38-3.24 (m, 2H), 2.57-2.51 (m, 1H), 2.39-2.31 (m, 1H), 2.05-2.00 (m, 1H), 1.88-1.83 (m, 1H), 0.92-0.86 (t, 3H).

Example 123. Synthesis of ethyl 2-(4-((2-(2,6-difluorophenyl)-5-oxo-6,7-dihydro-5H-pyrrolo[3,4-d]pyrimidin-4-yl)amino)phenyl)-2-methylpropanoate, I-178

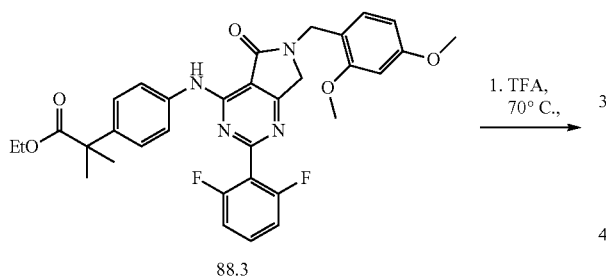

88.3

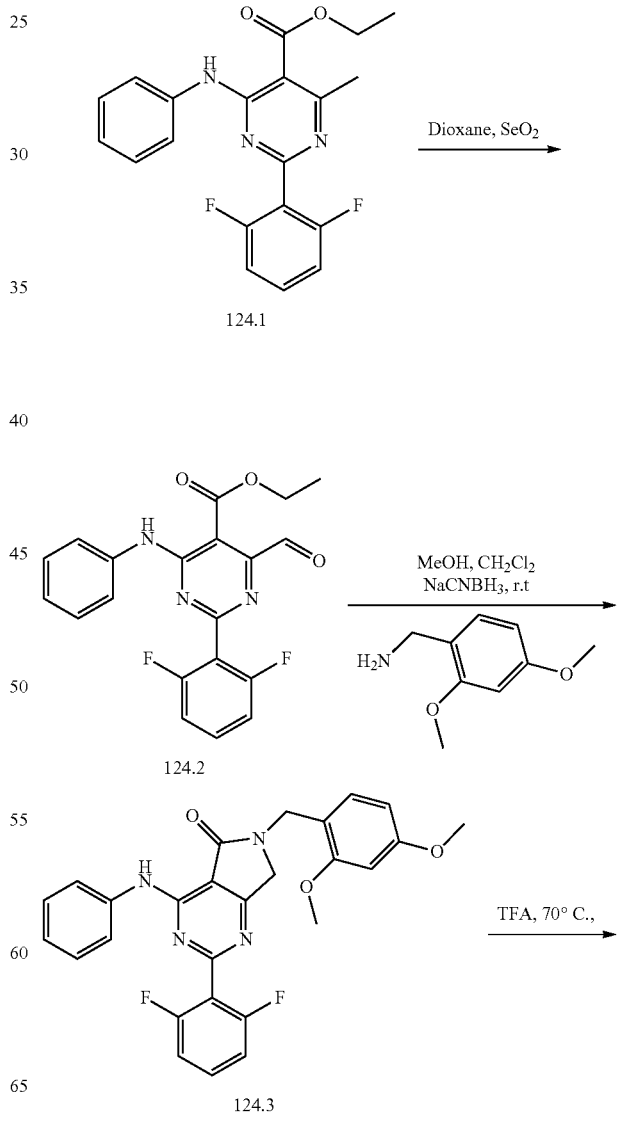

I-178

A solution of compound 88.3 (0.220 g, 0.36 mmol, 1.0 eq) in TFA (2.0 ml) was heated at 70° C. for 3 hours. After completion of the reaction, the mixture was poured into cold water, neutralized with sodium bicarbonate and product was extracted with EtOAc (20 ml×2). Solvent was removed under reduced pressure to get crude which purified by column chromatography to furnish I-178: (0.068 g, 43.89%) MS (ES): m/z 453.11 [M+H]+; 1H NMR (400 MHz, MeOD): δ 7.77-7.75 (d, 2H), 7.56-7.52 (m, 1H), 7.35-7.32 (m, 2H), 7.16-7.12 (m, 2H), 4.48 (s, 2H), 4.14-4.08 (q, 2H), 1.55 (s, 6H), 1.20-1.16 (t, 3H).

Example 124. Synthesis of 2-(2,6-difluorophenyl)-4-(phenylamino)-6,7-dihydro-5H-pyrrolo[3,4-d]pyrimidin-5-one, I-179

-continued

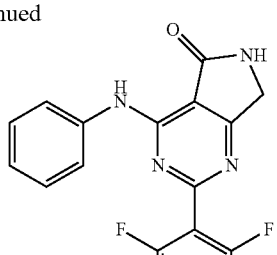

I-179

Synthesis of Compound 124.1.

To a solution of 2.5 (0.300 g, 9.60 mmol, 1.0 eq) in dry DMF (3 mL) was added aniline (0.093 g, 1.15 mmol, 1.2 eq) and K$_2$CO$_3$ (0.138 g, 1.92 mmol, 2.0 eq). Reaction mixture was stirred at 90° C. for 3 to 4 hrs. After completion of reaction, mixture was cooled to room temperature. Water (10 mL) was added to the mixture and extracted with EtOAc (20×2). Organic layer was washed with brine solution, dried over sodium sulfate and concentrated under reduced pressure to give crude product, which was purified by column chromatography to afford compound 124.1 (0.300 g, 84.66%). MS (ES): m/z=369.3 [M+H]$^+$.

Synthesis of Compound 124.2.

To a solution 124.1 (0.300 g, 0.81 mmol, 1.0 eq) in Dioxane (5.0 mL) was added Se$_2$O (0.180 g, 1.62 mmol, 2.0 eq.). Reaction mixture was stirred at 90° C. for 4 hours. After completion of the reaction, mixture was poured into water and extracted with EtOAc. Organic layer was washed with brine, dried over sodium sulfate and concentrated under reduced pressure to afford crude Compound 124.2 (300 mg, 96.4%), which was used as such in next step. MS (ES): m/z 383.5 [M+H]$^+$.

Synthesis of Compound 124.3.

To a solution of 124.2 (0.300 g, 0.81 mmol, 1.0 eq) in CH$_2$Cl$_2$ (0.6 mL) and MeOH (2.4 mL) was added 2,4-dimethoxybenzylamine (0.177 g, 1.06 mmol, 1.3 eq) at room temperature and allowed to stir for 30 minutes. Reaction mixture was then cooled at 0° C. and NaCNBH$_3$ (0.205 g, 3.2 mmol, 4.0 eq) was added portion wise. Reaction was stirred at room temperature for 12 hours. After completion of reaction water was added and product was extracted with ethyl acetate (3×50 mL). Combined organic layers were washed with brine, dried over sodium sulphate and concentrated under reduced pressure at 45° C. to afford crude, which was purified by column chromatography to afford compound 124.3 (0.190 g, 49.70%), MS (ES): m/Z (488.4) [M+H]$^+$.

Synthesis of Compound I-179.

A solution of 124.3 (0.190 g, 0.38 mmol, 1 eq) in TFA (5 ml) was stirred at room temperature for 2 hours. After completion of the reaction, the mixture was poured into cold water, neutralized with sodium bicarbonate and extracted with EtOAc (50 ml×2). Solvent was removed under reduced pressure to give crude which was purified by column chromatography to afford pure I-179 (0.09 mg, 68.4%). MS (ES): m/z 338.16 [M+H]$^{+1}$H NMR (400 MHz, DMSO-d$_6$): δ 9.08 (s, 1H), 8.90 (s, 1H), 7.77-7.75 (d, 2H), 7.64-7.56 (m, 1H), 7.38-7.34 (t, 2H), 7.30-7.24 (m, 2H), 7.13-7.09 (t, 1H), 4.48 (s, 2H).

Example 125. Synthesis of 4-((4-chlorophenyl)amino)-2-(2,6-difluorophenyl)-6,7-dihydro-5H-pyrrolo[3,4-d]pyrimidin-5-one, I-180

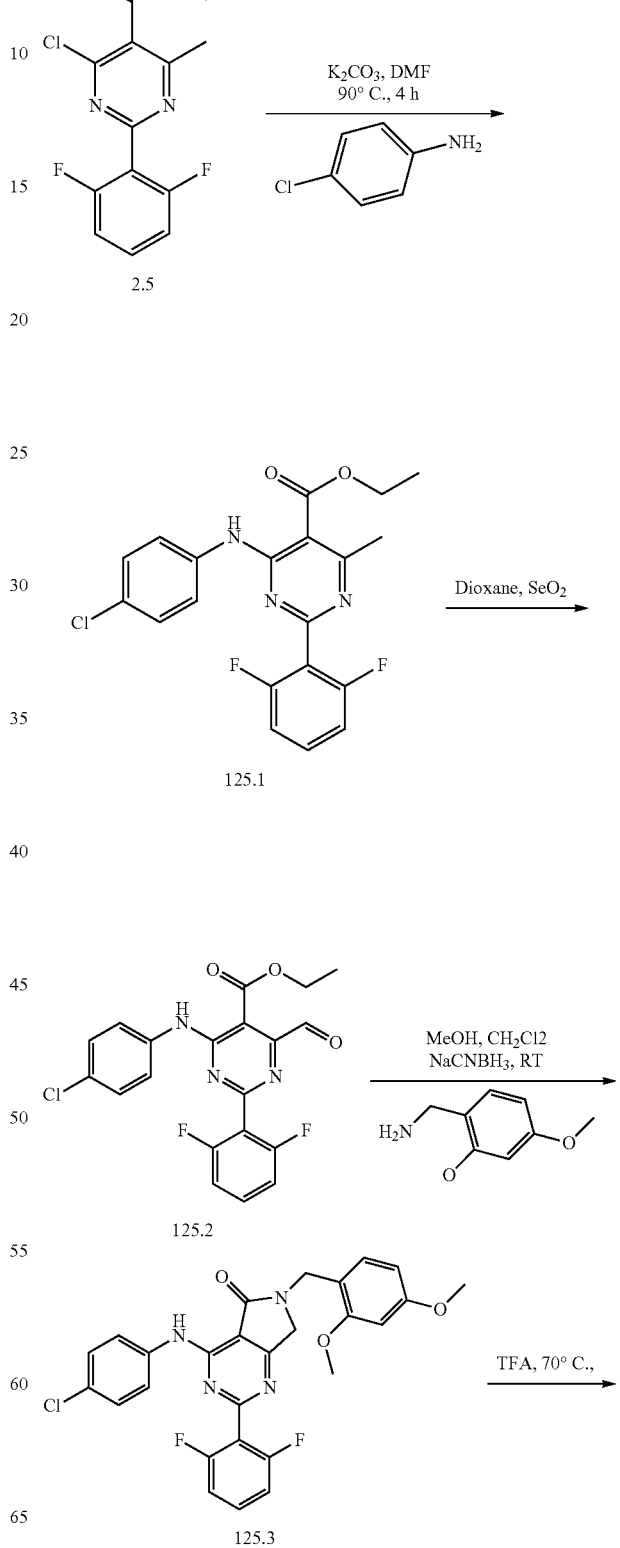

389

-continued

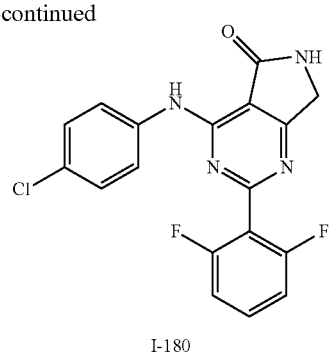

I-180

Synthesis of Compound 125.1.

To a solution of 2.5 (0.300 g, 9.60 mmol, 1.0 eq) in dry DMF (3 mL) was added 4-chloroaniline (0.146 g, 1.15 mmol, 1.2 eq) and K₂CO₃ (0.138 g, 1.92 mmol, 2.0 eq). Reaction mixture was stirred at 90° C. for 3 to 4 hrs. After completion of the reaction, mixture was cooled to room temperature. Water (10 mL) was added and mixture was extracted with EtOAc (20 mL×2). Organic layer was washed with brine, dried over sodium sulfate and concentrated under reduced pressure to give crude product, which was purified by column chromatography to afford compound 125.1 (0.148 g, 38.20%). MS (ES): m/z=403.8 [M+H]⁺.

Synthesis of Compound 125.2.

To a solution 125.1 (0.148 g, 0.34 mmol, 1.0 eq) in Dioxane (3.0 mL) was added SeO₂ (0.076 g, 0.69 mmol, 2.0 eq.). Reaction mixture was stirred at 100° C. for 4 hours. After completion of the reaction, mixture was poured into water and extracted with EtOAc. Organic layer was washed with brine, dried over sodium sulfate and concentrated under reduced pressure to afford crude compound 125.2 (0.148 g, 96.65%), which was used as such in next step. MS (ES): m/z 417.5 [M+H]⁺.

Synthesis of Compound 125.3.

To a solution of 125.2 (0.148 g, 0.35 mmol, 1.0 eq) in CH₂Cl₂ (2.0 mL) and MeOH (1.0 mL) was added 2,4-dimethoxybenzylamine (0.065 g, 0.39 mmol, 1.1 eq) Mixture was stirred for 30 minutes. Reaction mixture was then cooed at 0° C. and NaCNBH₃ (0.066 g, 1.06 mmol, 3.0 eq) was added slowly. Mixture was allowed to stir at room temperature for 12 hours. After completion of the reaction water was added and product was extracted with EtOAc (3×50 mL). Combined organic layers were washed with brine, dried over sodium sulphate and concentrated under reduced pressure to afford crude, which was purified by column chromatography to afford compound 125.3. (0.07 g, 37.79%), MS (ES): m/Z (522.13) [M+H]⁺.

Synthesis of Compound I-180.

A solution of 125.3 (0.07 g, 0.13 mmol, 1 eq) in TFA (3 mL) was heated at 90° C. for 5 h. After completion of the reaction, mixture was poured into cold water, neutralized with sodium bicarbonate and extracted with EtOAc (50 ml×2). Solvent was removed under reduced pressure to give crude which was purified by column chromatography to afford compound I-180 (0.025 g, 50.4%). MS (ES): m/z 372.7 [M+H]⁺, ¹H NMR (400 MHz, DMSO-d6): δ 9.06 (s, 1H), 8.89 (s, H), 7.80-7.77 (d, 2H), 7.64-7.56 (m, 1H), 7.42-7.40 (d, 2H), 7.272 (t, 2H), 4.49 (s 2H).

390

Example 126. Synthesis of 2-(2,6-difluorophenyl)-4-((4-isopropoxyphenyl)amino)-6,7-dihydro-5H-pyrrolo[3,4-d]pyrimidin-5-one, I-181

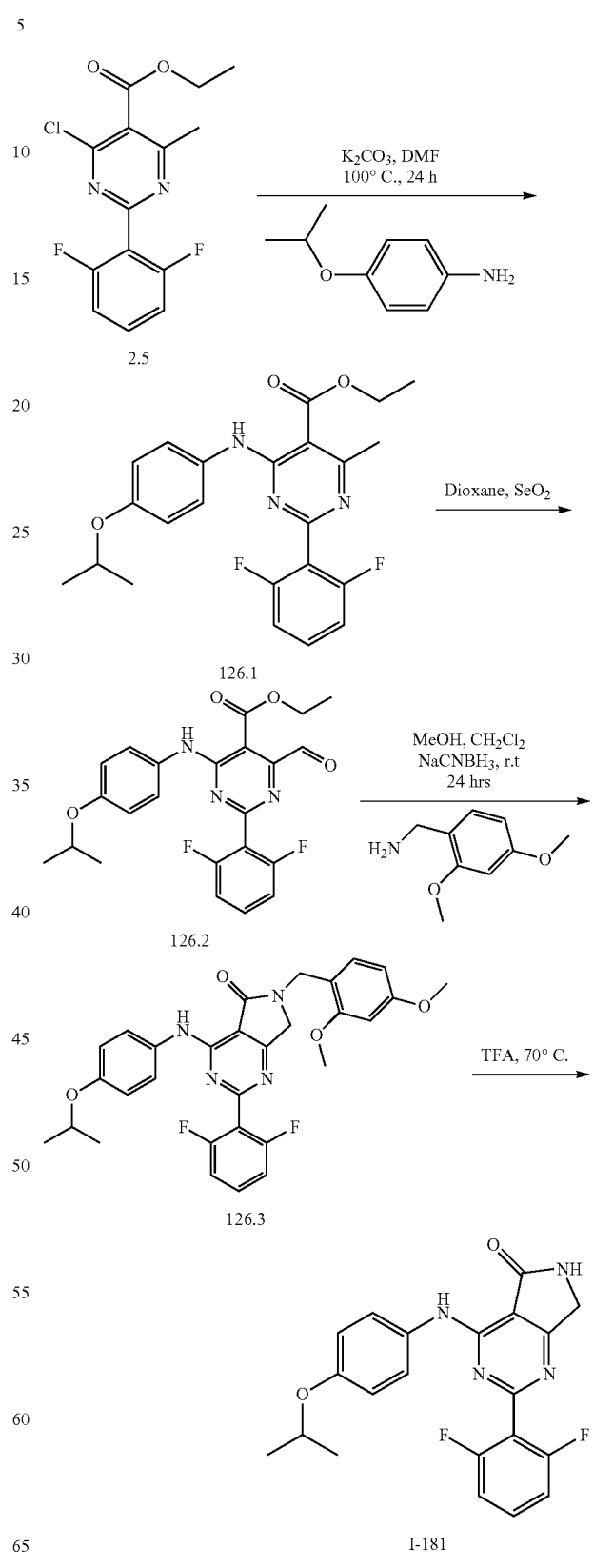

Synthesis of Compound 126.1.

To a solution of 2.5 (0.30 g, 0.96 mmol, 1.0 eq) in dry CH$_3$CN (5 mL) were added 4-isopropoxyaniline (0.145 g, 0.96 mmol, 1.0 eq), and DIPEA (0.49 mL, 2.88 mmol, 3.0 eq). Reaction mixture was allowed to stir at 100° C. for 24 hours. After completion of the reaction, the mixture was cooled to room temperature. Water (10 mL) was added to the mixture and extracted with EtOAc. Organic layer was washed with brine, dried over sodium sulfate and concentrated under reduced pressure to give crude which was purified by column chromatography to afford compound 126.1 (0.300 g, 73.15%). MS (ES): m/z=427.4 [M+H]$^+$.

Synthesis of Compound 126.2.

To a solution 126.1 (0.30 g, 0.70 mmol, 1.0 eq) in Dioxane (5.0 mL) was added SeO$_2$ (0.233 g, 2.10 mmol, 2.0 eq.). Reaction mixture was stirred at 100° C. temperature for 1 hour. After completion of the reaction, mixture was poured into water and extracted with EtOAc. Organic layer was washed with brine, dried over sodium sulfate and concentrated under reduced pressure to afford crude compound 126.2 (0.30 g, 96.8%), which was used as such in next step. MS (ES): m/z 441.4 [M+H]$^+$.

Synthesis of Compound 126.3.

A solution of 126.2 (0.30 g, 0.67 mmol, 1.0 eq) in CH$_2$Cl$_2$ (4.0 mL) and MeOH (2.0 mL) was added 2,4-dimethoxybenzylamine (0.147 g, 0.88 mmol, 1.3 eq) at room temperature and allowed to stir for 30 minutes. Reaction mixture wad then cooled at 0° C. and NaCNBH$_3$ (0.136 g, 2.03 mmol, 3.0 eq) was added slowly to it and the mixture was allowed to stir at room temperature for 12 hours. After completion of the reaction water was added and product was extracted with EtOAc (3×20 mL). Combined organic layers was washed with brine, dried over sodium sulphate and concentrated under reduced pressure at 45° C. to afford crude, which was purified by column chromatography to afford compound 126.3 (0.108 g, 29.1%), MS (ES): m/Z (547.5) [M+H]$^+$.

Synthesis of Compound I-181.

A solution of 126.2 (0.108 g, 0.19 mmol, 1 eq) in TFA acid (5 mL) was stirred at 85° C. for 2 hours. After completion of the reaction, mixture was poured into cold water, neutralized with NaHCO$_3$ and extracted with EtOAc (20 ml×2). Solvent was removed under reduced pressure to give crude which was purified by column chromatography to afford pure I-181 (0.04 g, 51.1%). MS (ES): m/z 396.4 [M+H]$^+$, $^1$H NMR (400 MHz, DMSO-d6): δ 8.95 (s, 1H), 8.84 (s, 1H), 7.61-7.56 (m, 3H), 7.27-7.23 (m, 2H), 6.90-6.88 (d, 2H), 4.58-4.55 (q, 1H), 4.45 (s, 2H), 1.24-1.23 (d, 6H).

Example 127. Synthesis of 2-(2,6-difluorophenyl)-4-((5-(4,4-difluoropiperidin-1-yl)pyridin-2-yl)amino)-6,7-dihydro-5H-pyrrolo[3,4-b]pyridin-5-one, I-182

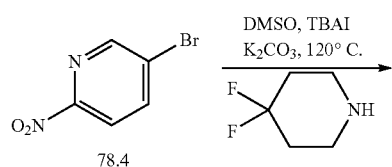

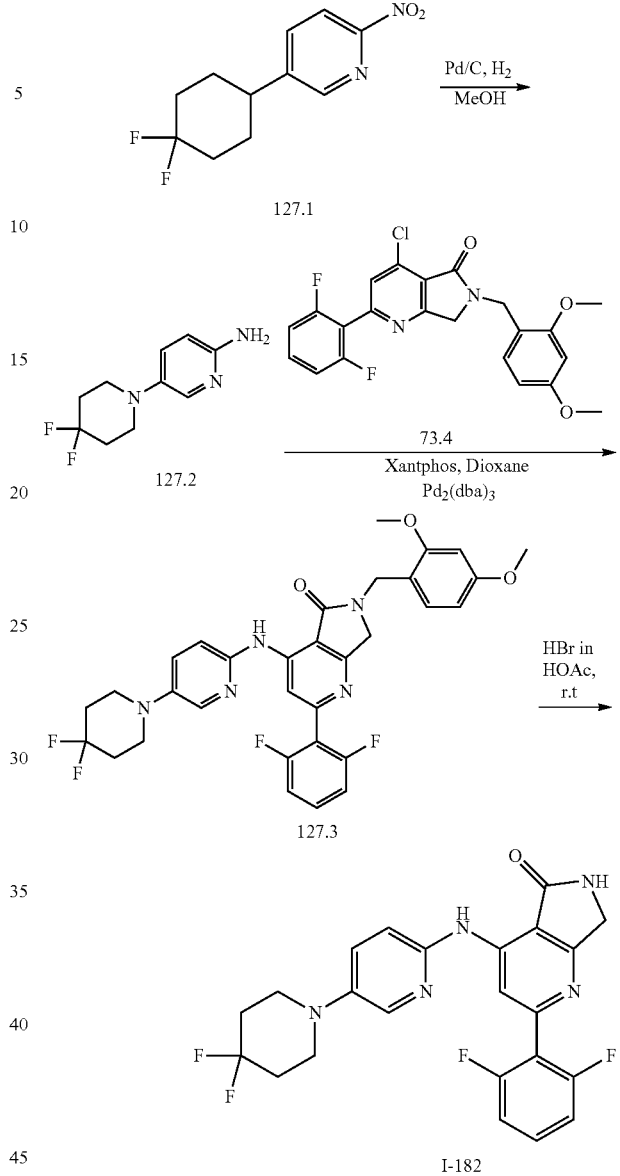

Synthesis of Compound 127.1.

To a solution of 78.4 (0.15 g, 0.738 mmol, 1.0 eq) in DMSO (3 mL) were added tetrabutyl ammonium iodide (0.027 g, 0.0738 mmol, 0.1 eq), 4,4-difluoropiperidine (0.12 g, 0.81 mmol, 1.1 eq), and K$_2$CO$_3$ (0.305 g, 0.0022 mmol, 3.0 eq). Reaction mixture was heated in microwave at 120° C. for 4 hours. The reaction mixture was poured in water and product was extracted with EtOAc. Organic layers were combined and dried over sodium sulphate and concentrated under reduced pressure to obtain crude which was purified by column chromatography to furnish 127.1 (0.070 g, 38.9%). MS (ES): m/z 244.2 [M+H]$^+$.

Synthesis of Compound 127.2.

To a solution of 127.1 (0.070 g, 0.287 mmol, 1.0 eq) in MeOH (5 mL) was added 10% Pd/C (0.0070 g) under nitrogen atmosphere. Suspension was purged with H$_2$ gas for 1 hour. Reaction mixture was filtered through celite and obtained filtrate was concentrated under reduced pressure to get crude 127.2 (0.045 g, 73.32%) which was used as such for the next step, MS (ES): m/z 214.23 [M+H]$^+$.

Synthesis of Compound 127.3.

To a solution of 73.4 (0.09 g, 0.21 mmol, 1.0 eq) in 1,4-dioxane (3 mL) was added 127.2 (0.045 g, 0.211 mmol, 1.0 eq) and $K_2CO_3$ (0.087 g, 0.633 mmol, 3.0 eq). The reaction mixture was degassed for 10 min. using argon, then Pd2(dba)3 (0.019 g, 0.0211 mmol, 0.1 eq) and Xantphos (0.024 g, 0.0422 mmol, 0.2 eq) were added. Reaction was stirred at 110° C. for 4 hours. After completion of the reaction, mixture was poured into water and product was extracted with EtOAc. Organic layers were combined, dried over sodium sulphate and concentrated under reduced pressure to obtain crude which was purified by column chromatography to furnish 127.3 (0.070 g, 55.17%). MS (ES): m/z 608.6 $[M+H]^+$.

Synthesis of Compound I-182.

Compound 127.3 (0.07 g, 0.115 mmol, 1.0 eq) was dissolved in HBr/HOAc (2 mL) and stirred at room temperature for 1 hour. After completion of the reaction, mixture was poured in water and basified with satd. $NaHCO_3$ and extracted with EtOAc. Organic layers were combined, dried over $Na_2SO_4$, concentrated under reduced pressure to obtain crude which was purified by column chromatography to furnish I-182 (0.038 g, 72.11%). MS (ES): m/z 458.4 $[M+H]^+$; $^1$H NMR (DMSO-$d_6$, 400 MHz): 9.54 (s, 1H), 8.82 (s, 1H), 8.41 (s, 1H), 8.10 (s, 1H), 7.59-7.53 (m, 2H), 7.28-7.24 (t, 2H), 7.13-7.11 (d, 1H), 4.41 (s, 2H), 2.05-1.99 (m, 4H), 1.23-1.16 (m, 4H).

Example 128. Synthesis of compound 2-((2R,6S)-2,6-dimethylpiperidin-1-yl)-4-((4-methoxyphenyl)amino)-6,7-dihydro-5H-pyrrolo[3,4-d]pyrimidin-5-one, I-183

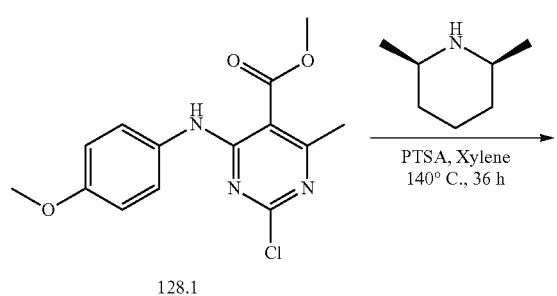

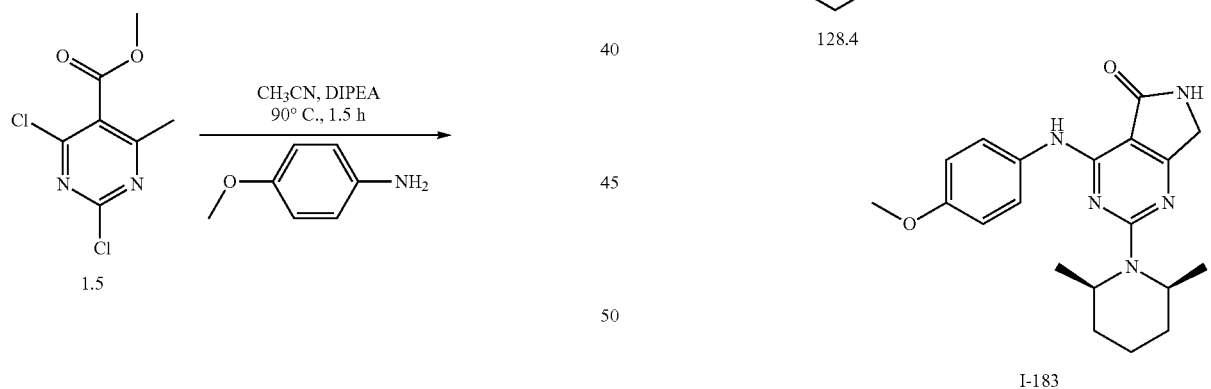

Synthesis of Compound 128.1.

To a solution of 1.5 (0.770 g, 3.5 mmol, 1.0 eq) in $CH_3CN$ (5.0 mL) at room temperature was added 4-methoxyaniline (0.473 g, 3.8 mmol, 1.1 eq) and DIPEA (0.71 mL, 4.2 mmol, 1.2 eq). Reaction mixture was stirred at 90° C. for 1.5 hour. After completion of the reaction, water was added in to the mixture, filtered, washed with water. Solid product was triturated with hexane to afford 128.1 (1.0 g, 93.28%). MS (ES): m/z=307.7 $[M+H]^+$.

Synthesis of Compound 128.2.

To solution of 128.1 (1.0 g, 3.2 mmol, 1.0 eq) in xylene (30 mL), 2,6-dimethylpiperidine (0.736 g, 6.5 mmol, 2 eq) and p-toluenesulfonic acid (0.092 g, 0.48 mmol, 0.15 eq)

395 were added. Reaction was stirred at 140° C. for 36 hours. After completion of reaction, mixture diluted with water and extracted with EtOAc. Solvent was removed under reduced pressure and crude was purified by column chromatography to afford 128.2 (0.440 g, 35.22%). MS (ES): m/z 384.4 [M+H]+.

Synthesis of Compound 128.3.

To a solution of 128.2 (0.440 g, 1.14 mmol, 1.0 eq) in dioxane (3.0 ml) was added SeO$_2$ (0.254 g, 2.29 mmol, 2 eq). Reaction was heated at 100° C. for 9 hours. After completion of reaction, the mixture was filtered through celite bed. Solvent was removed under reduced pressure to afford 128.3 (0.080 g, 17.54%) MS (ES): m/z 398.4. [M+H]+.

Synthesis of Compound 128.4.

To a solution of 128.3 (0.08 g, 0.20 mmol, 1.0 eq) in CH$_2$Cl$_2$ (3.0 ml) was added (2,4-dimethoxyphenyl)methanamine (0.027 g, 0.160 mmol, 0.8 eq). Reaction was stirred at room temperature for 30 min. NaBH(OAc)$_3$ (0.064 g, 0.301 mmol, 1.5 eq) was added portion wise at room temperature. Reaction was stirred over night at room temperature. After completion of the reaction, mixture was diluted with water and extracted with EtOAc. Solvent was removed under reduced pressure to afford 128.4 (0.060 g, 57.73%) MS (ES): m/z 517.4. [M+H]+.

Synthesis of Compound I-183.

A solution of 128.4 (0.06 g, 0.11 mmol, 1.0 eq) in HBr/HOAc (3.0 ml) was stirred at room temperature for 30 minutes. After completion of the reaction, mixture was diluted with NaHCO$_3$ solution and extracted with EtOAc. Solvent was removed under reduced pressure to afford pure I-183 (0.018 g, 42.26%) MS (ES): m/z 367.4, [M+H]+. $^1$H NMR (400 MHz, DMSO-d6): δ 8.46 (s, 1H), 8.04 (s, 1H), 7.65-7.63 (d, 2H), 6.94-6.91 (d, 2H), 4.88 (s, 2H), 4.16 (s, 2H), 3.75 (s, 3H), 1.91-1.83 (m, 1H), 1.64-1.61 (m, 3H), 1.50-1.47 (m, 1H), 1.27-1.21 (m, 6H).

Example 129. Synthesis of compound 2-(2,6-difluorophenyl)-4-((4-(trifluoro-methoxy)phenyl)amino)-6,7-dihydro-5H-pyrrolo[3,4-d]pyrimidin-5-one, I-184

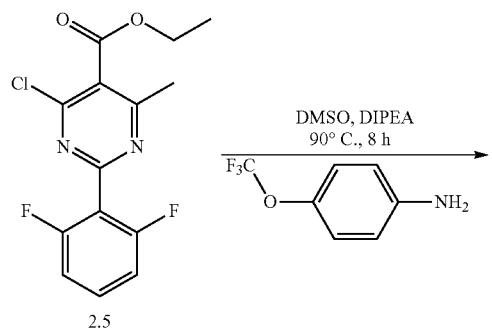

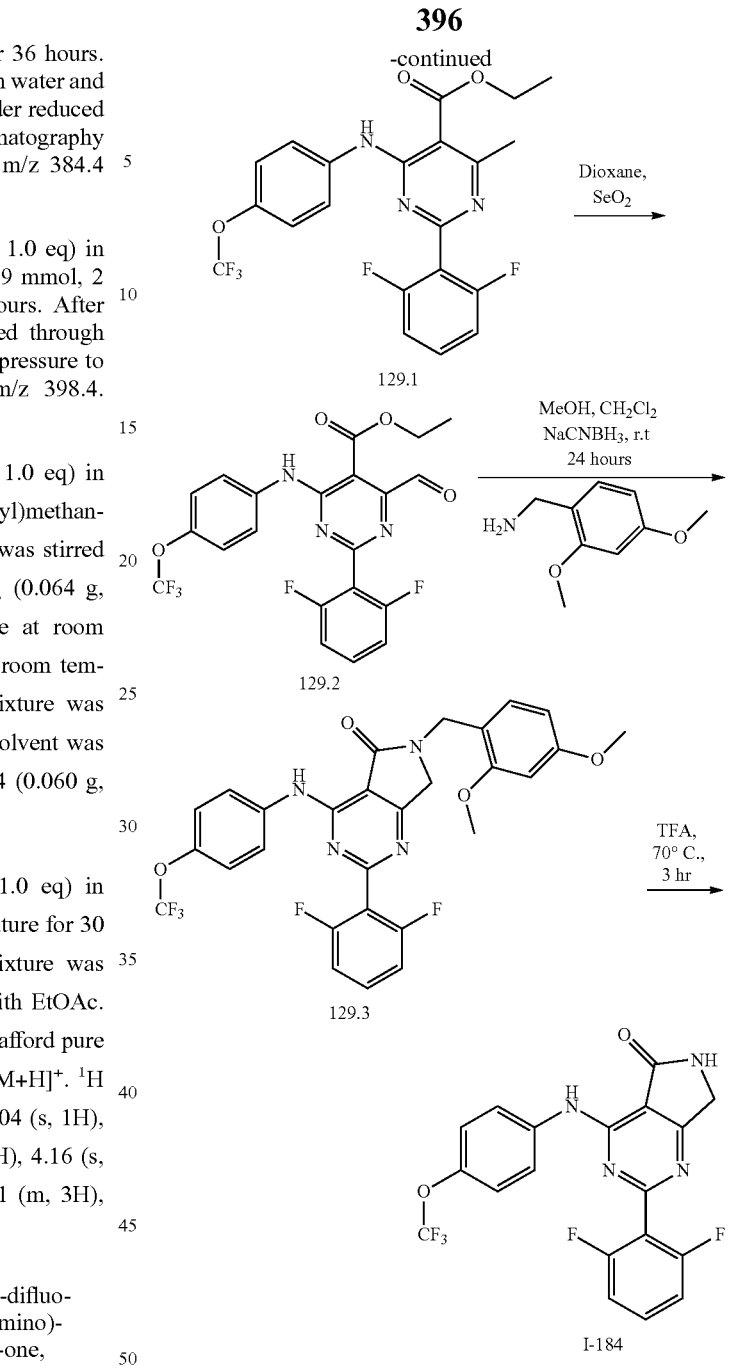

Synthesis of Compound 129.1.

To a solution of 2.5 (0.250 g 0.80 mmol, 1.0 eq.) in DMSO (2 mL), 4-(trifluoromethoxy)aniline (0.141 g, 0.80 mmol, 1.0 eq) and DIPEA (0.41 mL, 2.40 mmol, 3.0 eq) were added at room temperature. Reaction mixture was stirred at 90° C. for 8 h. After completion of the reaction, mixture was poured into cold water and extracted using EtOAc. Organic layer was dried over sodium sulfate and concentrate under reduced pressure. Crude was purified by column chromatography to furnish 129.1 (0.21 g, 58.5%). MS (ES): m/z 453.3 [M+H]+

Synthesis of Compound 129.2.

To a solution of 129.1 (0.212 g, 0.460 mmol, 1.0 eq) in Dioxane (4.0 mL) at room temperature SeO$_2$ (0.10 g, 0.94 mmol, 2.0 eq) was added. Reaction mixture was stirred at 90° C. for 3-4 h. After completion of the reaction, the mixture was filtered through celite bed and washed with CH₂Cl₂ (25 ml). Organic layer was concentrated under reduced pressure. to afford 129.2 (0.180 g, 82.37%). MS (ES): m/z=467.3 [M+H]⁺.

Synthesis of Compound 129.3.

A solution of 129.2 (0.180 g, 0.38 mmol, 1.0 eq) in CH₂Cl₂ (4 mL), and MeOH (2 mL), (2,4-dimethoxyphenyl)methanamine (0.064 g, 0.38 mmol, 1 eq) was added dropwise at room temperature. NaCNBH₃ (0.072 g, 1.15 mmol, 3.0 eq) was added in portions. Reaction was stirred for 16 hours. After completion of reaction solvent was removed under reduced pressure, residue was diluted with water and extracted with EtOAc. Solvent was removed under reduced pressure, and crude was purified using column chromatography to afford 129.3 (0.126 g, 57.14%). MS (ES): m/z 572.5 [M+H]⁺.

Synthesis of Compound I-184.

A solution of 129.3 (0.126 g, 0.22 mmol, 1.0 eq) in TFA (2.0 ml) was heated at 70° C. for 3 hours. After completion of the reaction, mixture was poured into cold water, neutralized with NaHCO₃ and extracted with EtOAc Solvent was removed under reduced pressure to get crude which was purified by column chromatography to afford I-184 (0.038 g, 42.93%) MS (ES): m/z 422.3 [M+H]⁺, ¹H NMR (400 MHz, DMSO-d₆): δ 9.24 (s, 1H), 8.93 (s, 1H), 7.89-7.87 (m, 2H), 7.63-7.58 (m, 1H), 7.38-7.36 (d, 2H), 7.29-7.25 (m, 2H), 4.49 (s, 2H).

Example 130. Synthesis of compound 2-(2,6-difluorophenyl)-4-((4-(2-methoxy-ethoxy)-phenyl)amino)-6,7-dihydro-5H-pyrrolo[3,4-d]pyrimidin-5-one, I-185

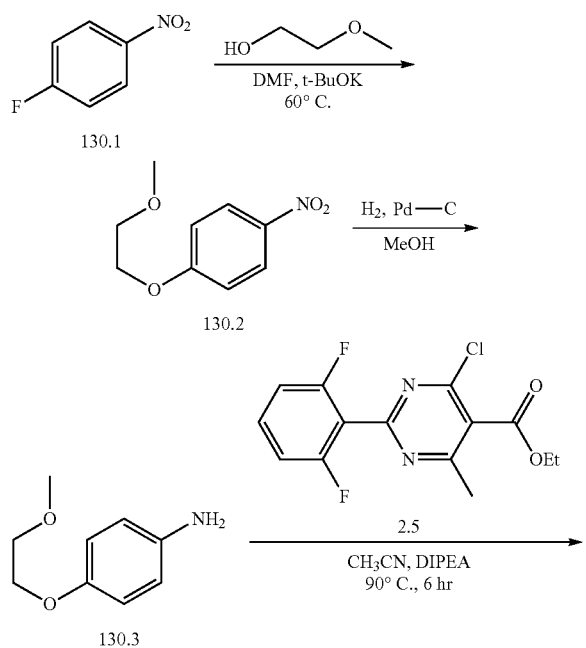

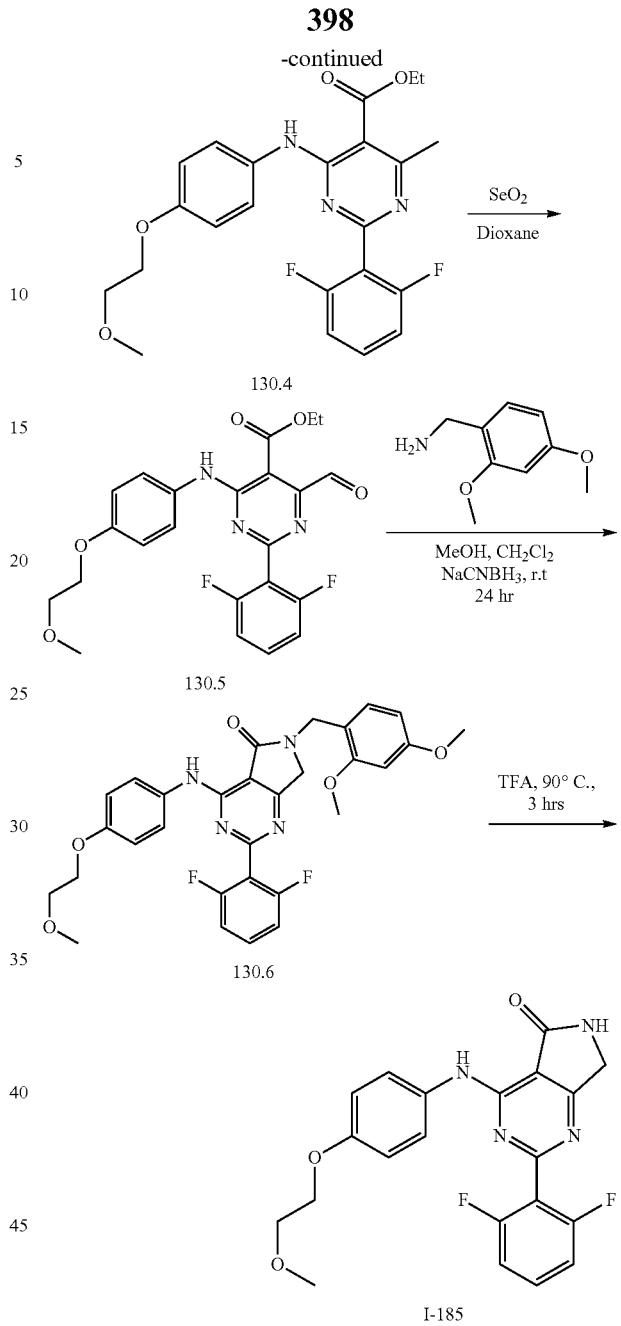

Synthesis of Compound 130.2.

To a solution of 130.1 (2.0 g, 14.18 mmol, 1.0 eq) in DMF (25 mL) were added 2-methoxyethan-1-ol (7.0 g, 92.13 mmol, 6.5 eq) and potassium tert-butoxide (1.43, 12.8 mmol, 0.95 eq). The reaction mixture was stirred at 60° C. for 16 hours. After completion of the reaction, mixture was poured into water and product was extracted with EtOAc. Organic layers were combined, dried over sodium sulphate and concentrated under reduced pressure to obtain crude which was purified by column chromatography to get pure 130.2 (1.5 g, 53.7%). MS (ES): m/z 197.1 [M+H]⁺.

Synthesis of Compound 130.3.

To a suspension of Pd/C (0.200 g,) in MeOH (20 ml) was added compound 130.2 (1.5 g, 7.61 mmol, 1.0 eq) under nitrogen atmosphere. Reaction mixture was purged with H₂ (gas) at room temperature for 2 hours. After completion of the reaction, mixture was filtered through celite. Solvent was removed under reduced pressure to afford compound 130.3 (1.2 g, 94.34%). MS (ES): m/z 167.2 [M+H]+.

Synthesis of Compound 130.4.

To a solution of 2.5 (0.300 g, 0.96 mmol, 1.0 eq) in CH₃CN (5 mL) was added 4-(2-methoxyethoxy) aniline (0.144 g, 0.86 mmol, 0.9 eq) and DIPEA (0.5 mL, 2.88 mmol, 3.0 eq). The reaction mixture was stirred at 90° C. for 6 hours. After completion of the reaction, mixture was poured into water and product was extracted with EtOAC. Organic layers were combined, dried over Na₂SO₄ and concentrated under reduced pressure to obtain crude which was purified by column chromatography to get compound 130.4 (0.360 g, 84.62%). MS (ES): m/z 443.4 [M+H]+.

Synthesis of Compound 130.5.

A solution of compound 130.4 (0.360 g, 0.81 mmol, 1.0 eq), SeO₂ (0.180 g, 1.62 mmol, 2.0 eq) in 1,4-dioxane (5 mL) was stirred at 90° C. for 4 hours. After completion of the reaction, the resulting solution was filtered through celite and washed with 1, 4-dioxane. Filtrate was concentrated under reduced pressure to afford compound 130.5 (0.360 g, 96.94%). MS (ES): m/z 457.4 [M+H]+.

Synthesis of Compound 130.6.

To a solution of compound 130.5 (0.360 g, 0.78 mmol, 1.0 eq) in mixture of CH₂Cl₂ (2 mL), MeOH (1 mL) was added 2,4-dimthoxybenzylamine (0.144 g, 0.86 mmol, 1.1 eq) at room temperature and stirred for 30 minutes. After 30 minutes, NaCNBH₃ (0.148 g, 2.36 mmol, 3.0 eq) was added at 0-10° C. Reaction mixture was allowed to warm to room temperature and stirred overnight. After completion, the reaction was diluted with water, extracted with EtOAc and washed with brine. Combined organic layers were dried and concentrated under vacuum. Crude was purified using column chromatography to furnish 130.6 (0.160 g, 36.14%). MS (ES): m/z 562.5 [M+H]+.

Synthesis of Compound I-185.

A solution of 130.6 (0.160 g, 0.28 mmol, 1.0 eq) in TFA (2 mL) was stirred for 3 h at 90° C. After completion of the reaction, the mixture was concentrated under reduced pressure. Crude compound was triturated with diethyl ether and pentane to get pure I-185 (0.060 g, 51.16%). MS (ES): m/z 413.33 [M+H]+ ¹H NMR (400 MHz, DMSO-d6): δ 8.97 (s, 1H), 8.84 (s, 1H), 7.63-7.56 (m, 3H), 7.27-7.23 (m, 2H), 6.94-6.92 (d, 2H), 4.46 (s, 2H), 4.06 (s, 2H), 3.74 (s, 2H), 3.29 (s, 3H).

Example 131. Synthesis of compound 2-(6-((2-(2,6-difluorophenyl)-5-oxo-6,7-dihydro-5H-pyrrolo[3,4-b]pyridin-4-yl)amino)pyridin-3-yl)acetic Acid, I-186

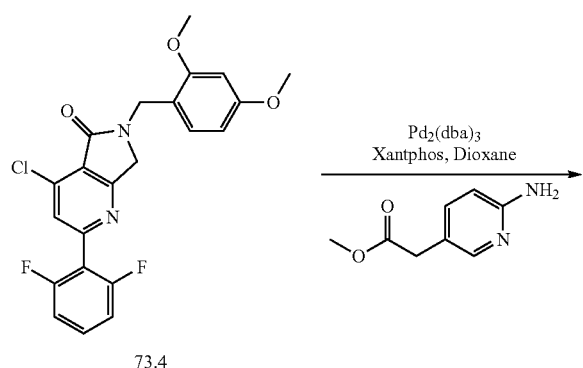

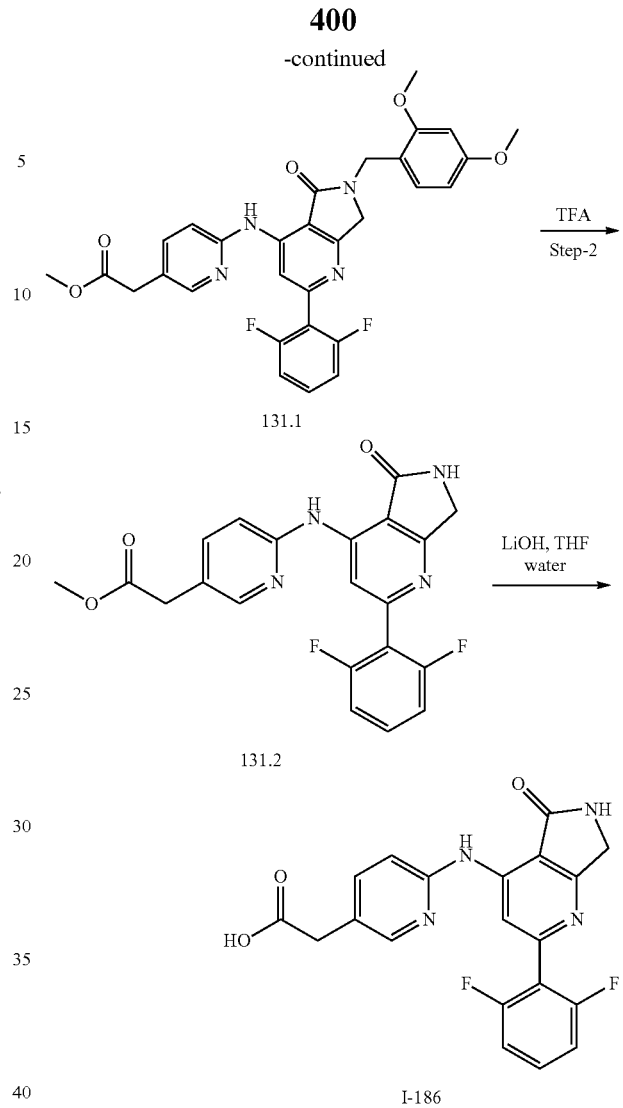

Synthesis of Compound 131.1.

To a solution of 73.4 (0.17 g, 0.395 mmol, 1.0 eq) in 1,4-dioxane (3 mL) was added methyl 2-(6-aminopyridin-3-yl) acetate (0.0655 g, 0.3945 mmol, 1.0 eq) and K₂CO₃ (0.136, 0.9862 mmol, 2.5 eq). The reaction mixture was degassed for 10 min. using argon, then Pd₂(dba)₃ (0.036 g, 0.03945 mmol, 0.1 eq) and Xantphos (0.0456 g, 0.079 mmol, 0.2 eq) were added. The reaction was stirred at 110° C. for 2 hours. After completion of the reaction, mixture was poured into water and product was extracted with EtOAc. Organic layers were combined, dried over sodium sulphate and concentrated under reduced pressure to obtain crude which was purified by column chromatography to furnish 131.1 (0.120 g, 52.26%). MS (ES): m/z 561.6 [M+H]+.

Synthesis of Compound 131.2.

A solution of 131.2 (0.12 g, 0.214 mmol, 1.0 eq) in TFA (3 mL) was heated at 60° C. for 3 h. After completion of reaction trifluroacetic acid was evaporated. Water was added and product was extracted with EtOAc. Organic layer was washed with aqueous saturated bicarbonate solution. Combined organic layers were washed with brine, dried over sodium sulphate and concentrated under reduced pressure to afford crude, which was purified by combiflash to furnish 131.2 (0.120 g, 52.26%). MS (ES): m/z 561.6 [M+H]+.

Synthesis of Compound I-186.

Compound 131.2 (0.070 g, 0.170 mmol, 1.0 eq) was dissolved in THF (2 ml) and water (0.5 ml). Lithium hydroxide (0.020 g, 0.511 mmol, 3.0 eq) was added to the mixture and it was stirred at room temperature for 3 hours. After completion of the reaction, mixture was poured into water and acidified with dil. HCl solution. Product was filtered dried, and further purified by trituration using n-pentane to get pure I-186 (0.035 g, 51.8%). MS (ES): m/z 397.5 [M+H]+, 1H NMR (DMSO-d6, 400 MHZ): 9.74 (s, 1H), 8.89 (s, 1H), 8.54 (s, H), 8.22 (d, 1H), 7.70-7.67 (dd, 1H), 7.60-7.56 (m, 1H), 7.28-7.24 (t, 2H), 7.17-7.15 (d, 1H), 4.44 (s, 2H), 3.68 (s, 2H).

Example 132. Synthesis of 2-(2,6-difluorophenyl)-4-((5-(6-methyl-2,6-diazaspiro-[3.3]heptan-2-yl)pyridin-2-yl)amino)-6,7-dihydro-5-pyrrolo[3,4-b]pyridin-5-one, I-187

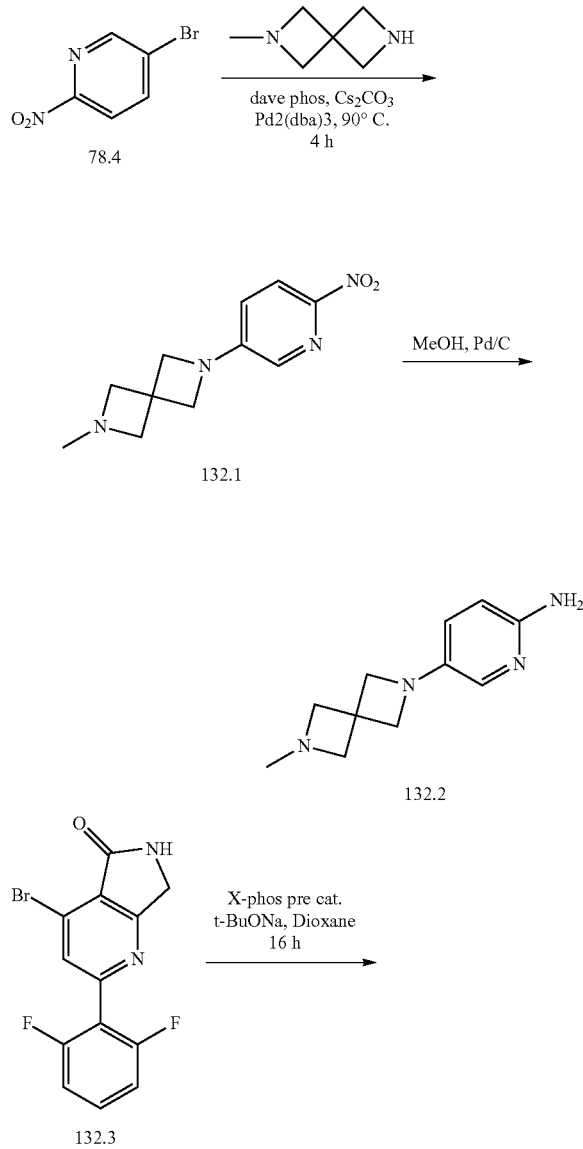

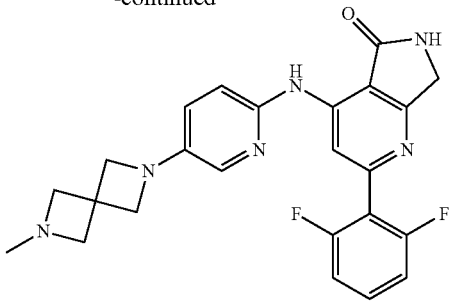

I-187

Synthesis of Compound 132.1

To a solution of 78.4 (0.5 g, 2.46 mmol, 1.0 eq) in 1,4-dioxane (3 ml) was added 2-methyl-2,6-diazaspiro[3.3]heptane (0.275 g, 2.46 mmol, 1.0 eq) and Cs2CO3 (1.01 g, 7.38 mmol, 3.0 eq). The reaction mixture was degassed for 10 min. under argon atmosphere, then Pd2(dba)3 0.225 g, 0.24 mmol, 0.1 eq) and 2-Dicyclohexylphosphino-2'-(N,N-dimethylamino)biphenyl (0.284 g, 0.49 mmol, 0.2 eq) were added. The reaction was stirred at 100° C. for 4 h. After completion of the reaction, mixture was poured into water and product was extracted with EtOAc. Organic layers were combined, dried over sodium sulphate and concentrated under reduced pressure to obtain crude which was purified by column chromatography to get pure 132.1 (0.3 g, 51.99%). MS (ES): m/z 234.2 [M+H]+.

Synthesis of Compound 132.2.

To a solution of 132.1 (0.3 g, 1.28 mmol, 1.0 eq) in MeOH (30 mL) was added 10% Pd/C (0.03 g) under nitrogen atmosphere. Suspension was purged with hydrogen for 1 hour. Reaction mixture was filtered through celite and obtained filtrate was concentrated under reduced pressure to get crude 132.1 (0.150 g, 57.34%) which was used as such for the next step, MS (ES): m/z 204.28 [M+H]+.

Synthesis of Compound of I-187.

To a solution of 132.3 (0.2 g, 0.61 mmol, 1.0 eq) in 1,4-dioxane (3 mL) was added 132.2 (0.136 g, 0.67 mmol, 1.1 eq) and Sodium t-butoxide (0.116 g, 1.23 mmol, 2.0 eq). The reaction mixture was degassed for 10 min. under argon, then 4,5-Bis(diphenylphosphino)-9,9-dimethylxanthene (0.091 g, 0.12 mmol, 0.2 eq) was added. Reaction was then stirred at 100° C. for 20 min. After completion of the reaction, mixture was poured into water and product was extracted with EtOAc. Organic layer was dried over sodium sulphate and concentrated under reduced pressure to obtain crude which was purified using preparative HPLC get pure I-187 (0.011 g, 3.99%). MS (ES): m/z 448.4 [M+H]+. 1H NMR (MeOD, 400 MHZ): 8.56 (s, 2H), 8.31 (s, 1H), 7.65 (s, 1H), 7.53 (m, 1H), 7.15-7.11 (m, 2H), 7.03 (s, 2H), 4.46 (s, 2H), 4.32 (s, 4H), 4.09 (s, 4H), 2.89 (s, 3H).

Example 133. Synthesis of methyl 2-(4-((2-(2,6-difluorophenyl)-5-oxo-6,7-dihydro-5H-pyrrolo[3,4-d]pyrimidin-4-yl)amino)phenyl)propanoate, I-188

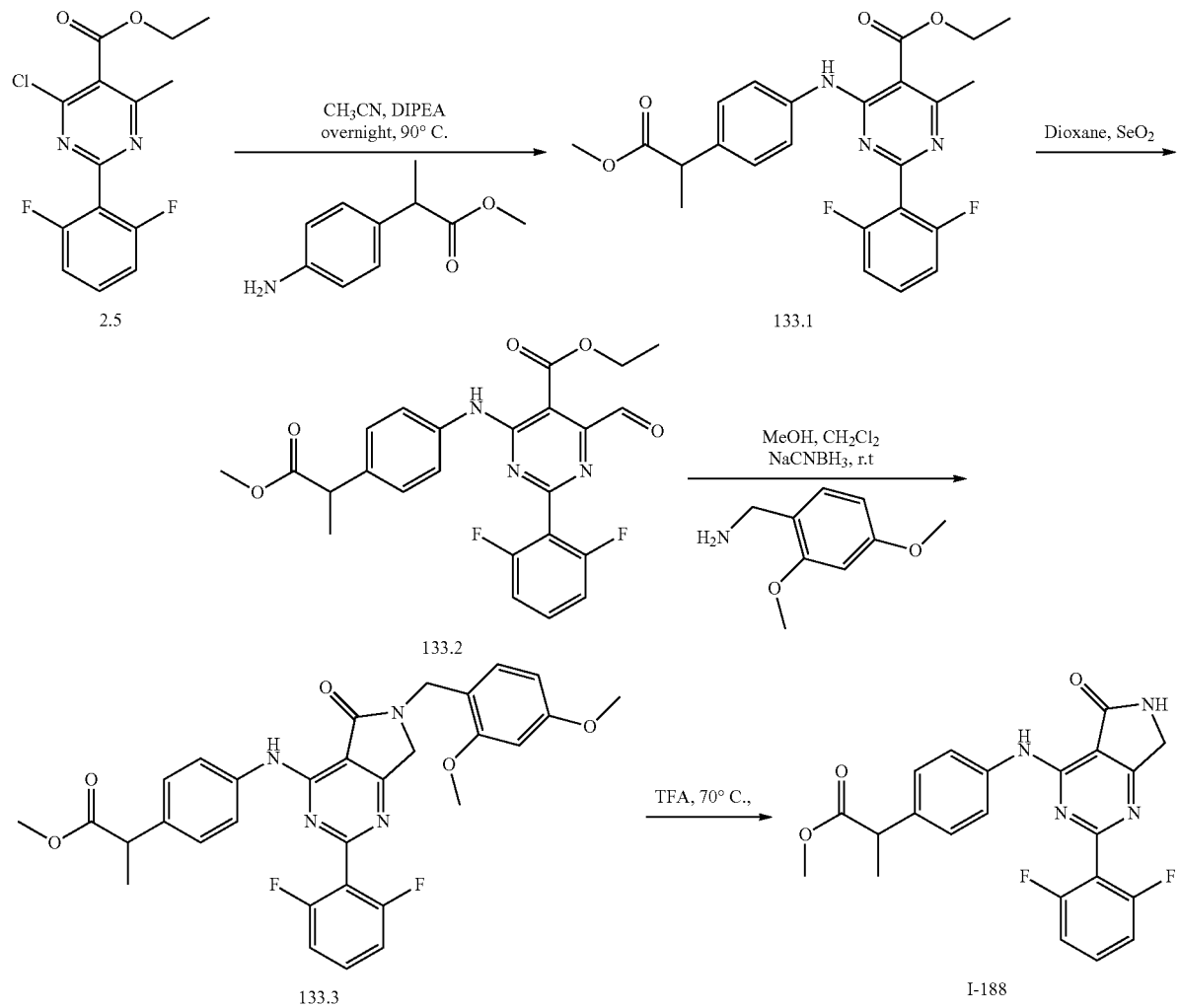

Synthesis of Compound 133.1.

To a solution of 2.5 (0.50 g, 1.60 mmol, 1.0 eq) in CH₃CN (8 mL), methyl 2-(4-aminophenyl) propanoate (0.285 g, 1.60 mmol, 1.0 eq) and DIPEA (0.82 mL, 4.80 mmol, 3.0 eq) were added at room temperature. Reaction mixture was heated at 90° C. for 24 hours. After completion of the reaction, mixture was poured into cold water and extracted using ethyl acetate (20 ml×2). Organic layer was dried over sodium sulfate and concentrate under reduced pressure. Crude was purified by column chromatography to afford 133.1 (0.50 g, 68.7%). MS (ES): m/z 455.4 [M+H]⁺

Synthesis of Compound 133.2.

To a solution of Compound 133.1 (0.50 g, 1.1 mmol, 1.0 eq) in Dioxane (6.0 mL) at room temperature, was added SeO₂ (0.304 g, 2.74 mmol, 2.5 eq). Reaction mixture was stirred at 100° C. for 1 hour. After completion of the reaction, mixture was filtered through celite, washed with CH₂Cl₂ (25 mL). Organic layer was concentrated under reduced pressure to afford 133.2 (0.500 g, 97.0%). MS (ES): m/z=469.4 [M+H]⁺.

Synthesis of Compound 133.3.

To a solution of 133.2 (0.500 g, 0.50 mmol, 1.0 eq) in CH₂Cl₂ (4 mL), and MeOH (2 mL), (2,4-dimethoxyphenyl) methanamine (0.195 g, 1.17 mmol, 1.1 eq) was added dropwise at room temperature. NaCNBH₃ (0.199 g, 3.1 mmol, 3.0 eq) was added portionwise and the reaction was stirred at room temperature for overnight. After completion of reaction, solvent was removed under reduced pressure; residue was diluted with water and extracted in to EtOAC. Solvent was removed under reduced pressure and crude was purified by column chromatography to afford 133.3 (0.250 g, 40.85%). MS (ES): m/z 574.5 [M+H]⁺.

Synthesis of Compound I-188.

A solution of Compound 133.3 (0.25 g, 0.43 mmol, 1.0 eq) in TFA (3.0 ml) was heated at 70° C. for 2.5 hours. After completion of the reaction, mixture was poured into cold water, neutralized with NaHCO₃ and product was extracted with EtOAc. Solvent was removed under reduced pressure to get crude, which was purified by column chromatography to afford I-188. (0.180 g, 97.48%) MS (ES): m/z 424.4 [M+H]⁺, ¹H NMR (400 MHz, DMSO-d₆): δ 9.07 (s, 1H), 8.91 (s, 1H), 7.72-7.69 (d, 2H), 7.62-7.58 (m, 1H), 7.29-7.24 (m, 4H), 4.48 (s, 2H), 3.80-3.75 (q, 1H), 3.57 (s, 3H), 1.38-1.36 (d, 3H).

Example 134. Synthesis of 2-(4-((2-(2,6-difluorophenyl)-5-oxo-6,7-dihydro-5H-pyrrolo[3,4-d]pyrimidin-4-yl)amino)phenyl)propanoic Acid, I-189

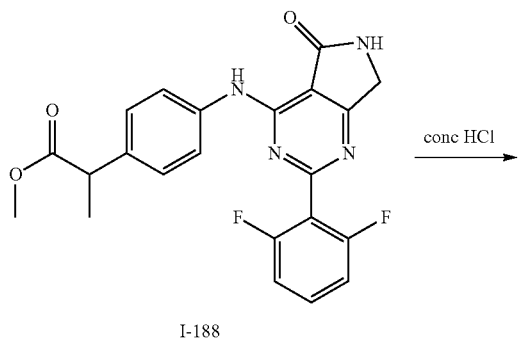

I-188

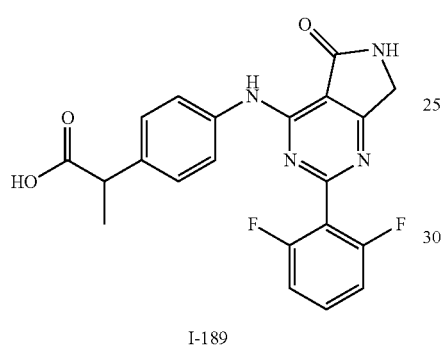

I-189

A solution of I-188 (0.080 g, 0.18 mmol, 1.0 eq) in Conc. HCl (3.0 mL) was heated at 80° C. for 2 hours. After completion of the reaction, reaction mixture was poured into cold water, neutralized with sodium bicarbonate and extracted with EtOAc. Solvent was removed under reduced pressure to get crude I-189 (0.044 g, 56.88%). MS (ES): m/z 410.3 [M+H]$^+$, $^1$H NMR (400 MHz, DMSO-d$_6$): δ 9.06 (s, 1H), 8.89 (s, 1H), 7.71-7.69 (d, 2H), 7.63-7.56 (m, 1H), 7.33-7.25 (m, 4H), 4.47 (s, 2H), 3.67-3.62 (q, 1H), 1.35-1.34 (d, 3H).

Example 135. Synthesis of (R)-2-(4-((2-(2,6-difluorophenyl)-5-oxo-6,7-dihydro-5H-pyrrolo-[3,4-d]pyrimidin-4-yl)amino)phenyl)propanoic Acid, I-190

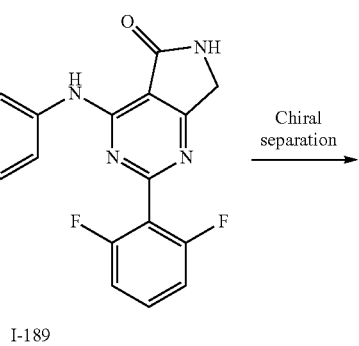

I-189

→ Chiral separation

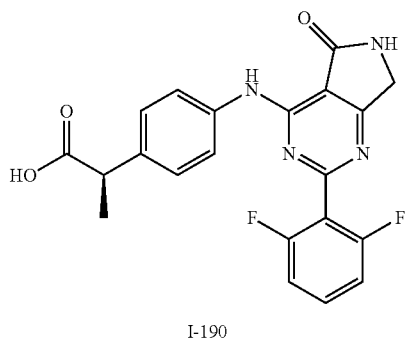

I-190

Compound I-190 was prepared by chiral separation of compound I-189. MS (ES): m/z 410.3 [M+H]$^+$, $^1$H NMR (400 MHz, DMSO-d$_6$): δ 12.21 (s, 1H), 9.06 (s, 1H), 8.90 (s, 1H), 7.70-7.68 (d, 2H), 7.62-7.58 (m, 1H), 7.29-7.25 (m, 4H), 4.47 (s, 2H), 3.64-3.62 (m, 1H), 1.33-1.32 (d, 3H).

Example 136. Synthesis of (S)-2-(4-((2-(2,6-difluorophenyl)-5-oxo-6,7-dihydro-5H-pyrrolo-[3,4-d]pyrimidin-4-yl)amino)phenyl)propanoic Acid I-214

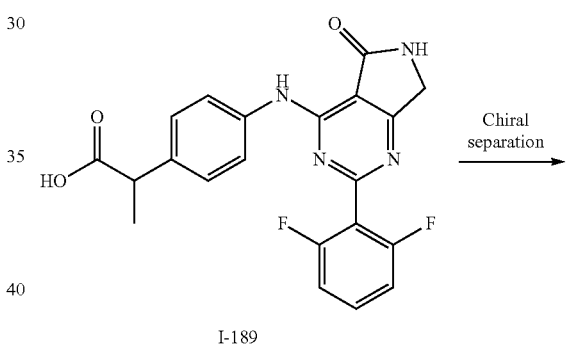

I-189

→ Chiral separation

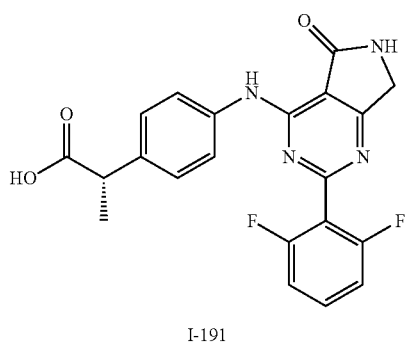

I-191

Compound I-191 was prepared by chiral separation of compound I-189. MS (ES): m/z 410.3 [M+H]$^+$,%, $^1$H NMR (400 MHz, DMSO-d$_6$): δ 9.04 (s, 1H), 8.89 (s, 1H), 7.67-7.57 (m, 3H), 7.29-7.24 (m, 4H), 4.47 (s, 2H), 3.57-3.56 (q, 1H), 1.32-1.30 (d, 3H).

Example 137. Synthesis of compound 5-(4-((2-(2,6-difluorophenyl)-5-oxo-6,7-dihydro-5H-pyrrolo[3,4-d]pyrimidin-4-yl)amino)phenyl)thiazolidine-2,4-dione, I-192
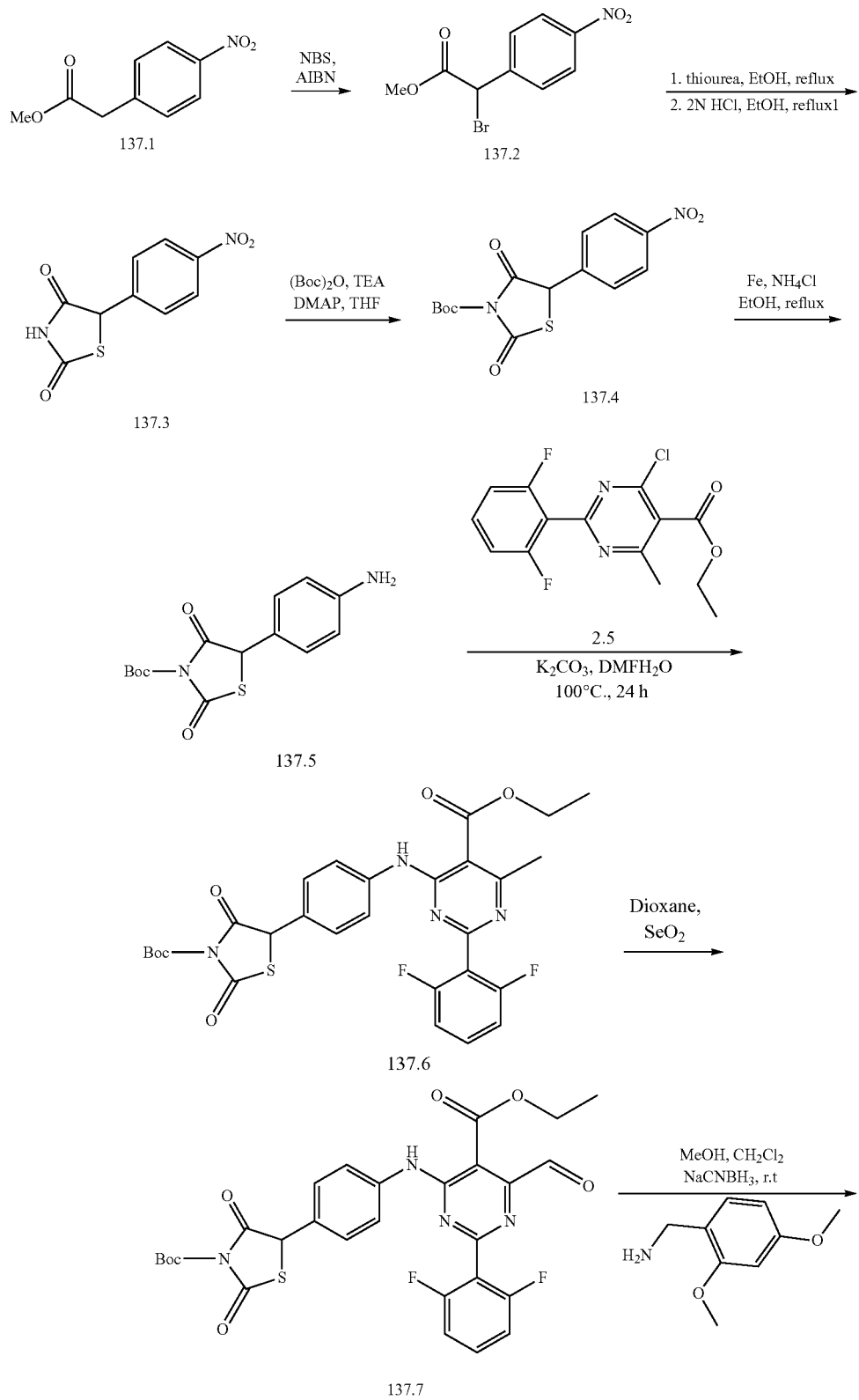

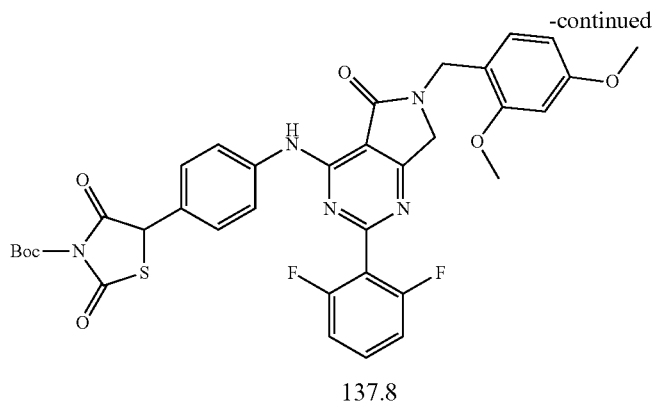

Synthesis of Compound 137.2.

To a solution of compound 137.1 (3.0 g, 14.35 mmol, 1.0 eq) in CCl₄ (30 mL) was added NBS (3.0 g, 15.9 mmol, 2.5 eq) and AIBN (0.082 g, 1.43 mmol, 0.1 eq) Reaction was stirred at 100° C. and for 24 h. Reaction mixture was poured into water (300 mL) and extracted with EtOAc (100 mL×3). Organic layers were combined, dried over sodium sulphate and concentrated under reduced pressure to obtain crude which was purified by column chromatography get pure compound 137.2 (2.8 g, 66.47%). MS (ES): m/z 275.07 [M+H]⁺.

Synthesis of Compound 137.3.

To a solution of compound 137.2 (2.8 g, 10.21 mmol, 1 eq) in EtOH (10 mL) was added Thiourea (0.854 g, 11.23 mmol, 1.1 eq). Reaction mixture was stirred at 70° C. for 1.5 hours. Reaction mixture was poured into water (100 mL) and extracted with EtOAc (50 mL×3). Organic layers were combined, dried over sodium sulphate and concentrated under reduced pressure to obtain crude material. To the crude was added concentrated HCl (25 mL) and EtOH (30 mL). Reaction was heated at 70° C. overnight. Reaction mixture was poured into water (100 mL) and extracted with EtOAc (50 mL×3). Organic layers were combined, dried over sodium sulphate and concentrated under reduced pressure to obtain crude which was purified by column chromatography, to get pure compound 137.3 (2.0 g, 82.18%), MS (ES): m/z 239.2 [M+H]⁺.

Synthesis of Compound 137.4.

To a solution of compound 137.3 (0.5 g, 2.10 mmol, 1.0 eq) in dry THF (5.0 mL) was added DMAP (0.012 g, 0.21 mmol, 0.1 eq.) and Et₃N (0.424 g, 4.20 mmol, 2.0 eq) at 0° C. Reaction was stirred for 10 min. To the above reaction mixture was added Di-tert-butyl-dicarbonate (0.686 g, 3.15 mmol, 1.5 eq). Reaction mixture was stirred at room temperature for 1 h. After completion of the reaction, mixture was poured into water and extracted using EtOAc. Organic layers were washed with brine, combined, dried over sodium sulphate and concentrated under reduced pressure to obtain crude compound 137.4 (0.5 g, 70.41%). MS (ES): m/z 338.2 [M+H]⁺.

Synthesis of Compound 137.5.

To a solution of 137.4 (0.5 g, 1.47 mmol, 1.0 eq) in EtOH (6 ml) and water (2 mL) was added Fe powder (0.414 g, 7.3 mmol. 5.0 eq) and NH₄Cl (0.459 g, 7.3 mmol, 5.0 eq). The reaction mixture was heated at 80° C. for 1 hour. After completion of the reaction, mixture was filter through celite. Reaction mixture was poured into water and extracted using EtOAc. Combined layers was washed with brine, dried over sodium sulphate and concentrated under reduced pressure to afford compound 137.5 (0.3 g, 65.83%). MS (ES): m/z 308.3 [M+H]⁺.

Synthesis of Compound 137.6.

To a solution of 2.5 (0.250 g 0.80 mmol, 1.0 eq) in DMSO (2.5 mL), compound 137.5 (0.141 g, 0.80 mmol, 1.0 eq) and DIPEA (0.34 mL, 2.0 mmol, 2.5 eq) were added at room temperature and reaction mixture was stirred at 100° C. for 24 h. After completion of the reaction, mixture was poured into cold water and extracted using EtOAc (20 mL×2). Organic layer was dried over sodium sulfate and concentrated under reduced pressure. Crude was purified by column chromatography to afford 137.6 (0.170 g, 36.37%). MS (ES): m/z 585.3 [M+H]⁺

Synthesis of Compound 137.7.

To a solution of 137.6 (0.170 g, 0.290 mmol, 1.0 eq) in Dioxane (4.0 mL) at room temperature, SeO₂ (0.102 g, 0.873 mmol, 3.0 eq) was added. Reaction mixture was stirred at 90° C. for 6 h. After completion of the reaction, mixture was filtered through celite bed, washed with CH₂Cl₂ (25 ml). Organic layer was concentrated under reduced pressure to afford compound 137.7 (0.150 g, 87.17%). MS (ES): m/z=599.3 [M+H]⁺.

Synthesis of Compound 137.8.

A solution of 137.7 (0.150 g, 0.25 mmol, 1.0 eq) in CH₂Cl₂ (2 mL), and MeOH (1 mL), (2,4-dimethoxyphenyl)methanamine (0.046 g, 0.27 mmol, 1.1 eq) was added dropwise at room temperature. NaCNBH₃ (0.050 g, 0.75 mmol, 3.0 eq) was added portion wise and reaction was stirred at room temperature overnight. After completion of the reaction, solvent was removed under reduced pressure, residue was diluted with water and extracted with EtOAc. Solvent was removed under reduced pressure and crude was purified by column chromatography to afford 137.8 (0.080 g, 45.36%). MS (ES): m/z 704.5 [M+H]⁺.

Synthesis of Compound I-192.

A solution of 137.8 (0.080 g, 0.11 mmol, 1.0 eq) in TFA (2.0 ml) was heated at 70° C. for 3 h. After completion of the reaction, mixture was poured into cold water, neutralized with NaHCO₃ and extracted with EtAOc. Solvent was removed under reduced pressure and crude was purified by column chromatography to afford I-192: (0.025 g, 48.5%) MS (ES): m/z 454.11 [M+H]⁺, ¹H NMR (400 MHz, MeOD): δ 7.89-7.87 (d, 2H), 7.60-7.52 (m, 1H), 7.45-7.42 (d, 2H), 7.18-7.13 (m, 2H), 5.63 (s, 1H), 4.52 (s, 2H).

Example 138. Synthesis of 2-(4-((2-(2,6-difluoro-phenyl)-5-oxo-6,7-dihydro-5H-pyrrolo[3,4-d]pyrimidin-4-yl)amino)phenyl)-N-(2-hydroxy-2-methylpropyl)-N-methylacetamide, I-193

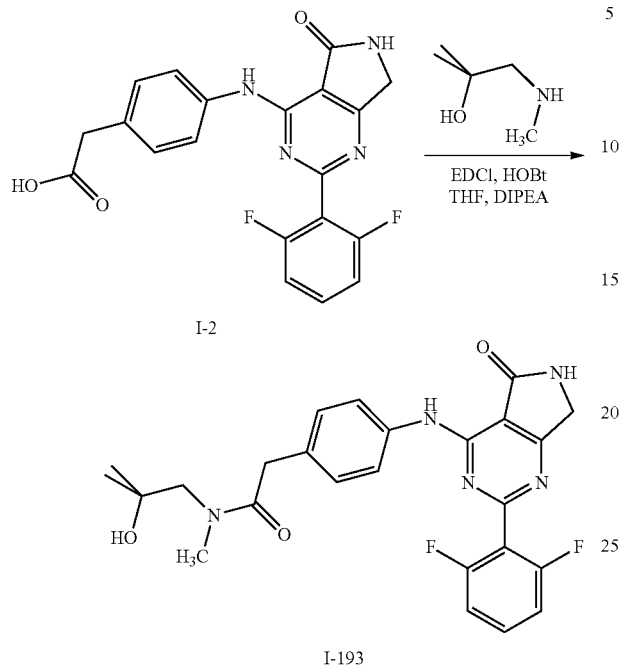

A solution of compound I-2 (0.080 g 0.20 mmol, 1.0 eq.) in THF (4 mL) was cooled to 0° C. 1-EDCI (0.057 g, 0.30 mmol, 1.5 eq), HOBt (0.032 g, 0.24 mmol, 1.2 eq) were added at 0° C. Reaction mixture was stirred for 20 minutes then, 2-methyl-1-(methylamino)propan-2-ol (0.027, 0.26 mmol, 1.3 eq), and DIPEA (0.13 mL, 0.80 mmol, 4.0 eq) were added at 0° C. Reaction mixture was stirred for 18 h at room temperature. After completion of the reaction, mixture was poured into cold water and extracted using EtOAc. Organic layer was dried over sodium sulfate and concentrated under reduced pressure. Crude was purified by column chromatography to afford I-193 (0.06 g, 61.74%). MS (ES): m/z 481.5 [M+H]+ 1H NMR (400 MHz, DMSO-d6): δ 9.05 (s, 1H), 8.88 (s, 1H), 7.69-7.57 (m, 3H), 7.28-7.17 (m, 4H), 4.47 (s, 2H), 3.72-3.67 (d, 2H), 3.33-3.27 (m, 2H), 3.09 (s, 2H), 2.90 (s, 2H), 1.12-1.09 (d, 3H), 1.01 (s, 3H).

Example 139. Synthesis of (R)-4-(2-(4-((2-(2,6-difluorophenyl)-5-oxo-6,7-dihydro-5H-pyrrolo[3,4-d]pyrimidin-4-yl)amino)phenyl)acetyl)morpholine-3-carboxylic Acid, I-194

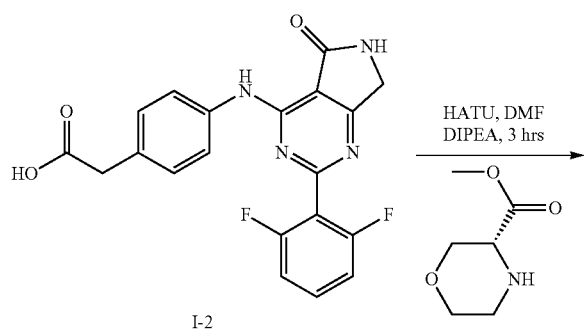

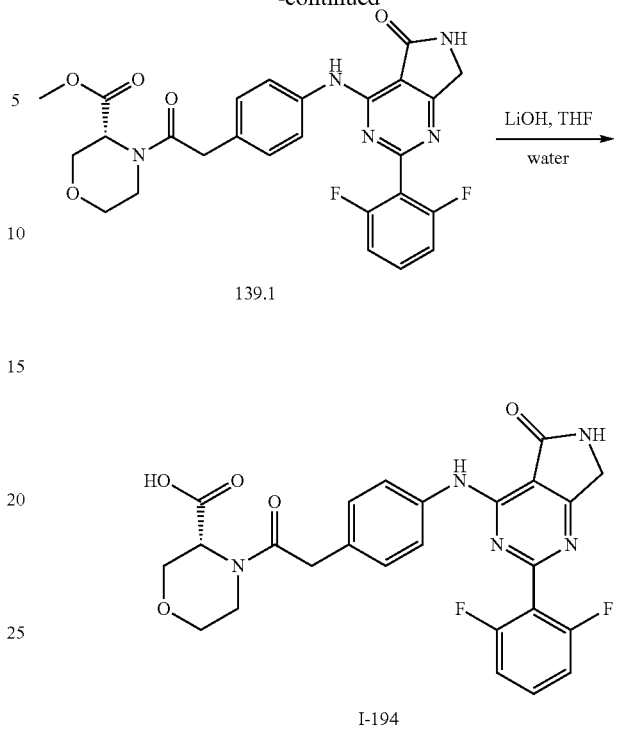

Synthesis of Compound 139.1

To a solution of I-2 (0.080 g, 0.2 mmol, 1.0 eq) in DMF (3 mL) were added methyl (R)-morpholine-3-carboxylate (0.034 g, 0.24 mmol, 1.2 eq), DIPEA (0.077 g, 0.6 mmol, 3 eq) and HATU (0.115 g, 0.3 mmol, 1.5 eq). The reaction mixture was stirred at ambient temperature for 3 hours. Reaction mixture was diluted with EtOAc and washed with saturated NaHCO3 solution. Organic layer was dried over sodium sulphate, concentrated under reduced pressure to obtain crude which was purified by column chromatography to obtain compound 139.1 (0.070 g, 66%). MS (ES): m/z 524.50 [M+H]+.

Synthesis of Compound I-194.

To a solution of compound 139.1 (0.063 g, 0.12 mmol, 1.0 eq) in THF (1 mL) was added LiOH (0.051 g, 0.36 mmol, 3.0 eq) in water (1 mL) at 0° C. Reaction was stirred at 0° C. for 20 minutes. After completion of the reaction, mixture was neutralized using HOAc and extracted with EtOAc. Organic layer was separated, washed with water and brine, dried over sodium sulphate and concentrated under reduced pressure. Crude product was purified by preparative HPLC to afford I-194 (0.002 g, 3%). MS (ES): m/Z 510.22 [M+H]+, 1H NMR (400 MHz, MeOD): δ 7.75-7.79 (m, 2H), 7.51-7.59 (m, 1H), 7.24-7.30 (m, 2H), 7.12-7.16 (t, 2H), 4.94 (s, 1H), 4.37-4.55 (m, 3H), 3.73-3.91 (m, 3H), 3.53-3.67 (m, 2H), 3.38-3.42 (m, 1H), 3.11-3.15 (m, 1H).

Example 140. Synthesis of 4-((2-(2,6-difluorophenyl)-5-oxo-6,7-dihydro-5H-pyrrolo[3,4-d]pyrimidin-4-yl)amino)-N-ethylbenzamide, I-195

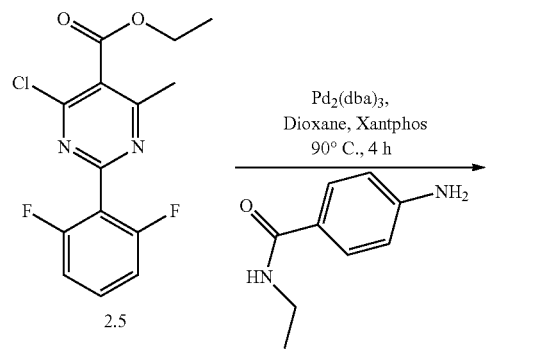

2.5

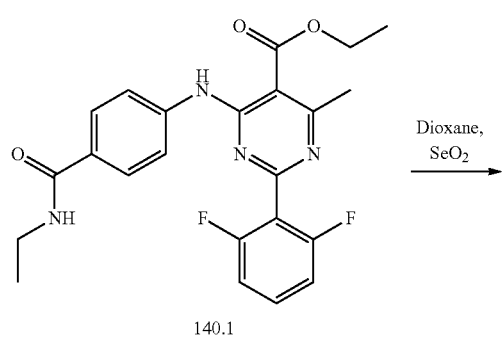

140.1

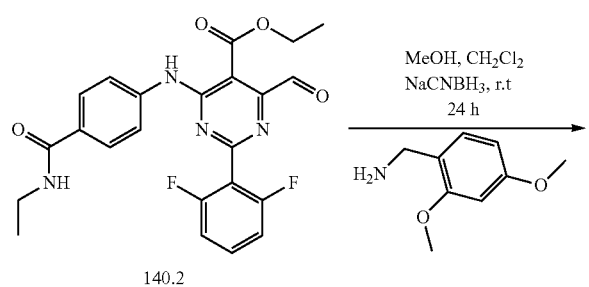

140.2

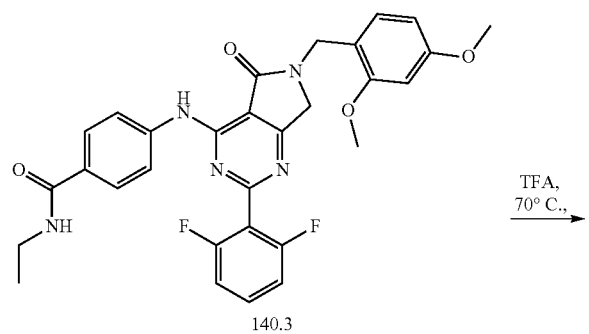

140.3

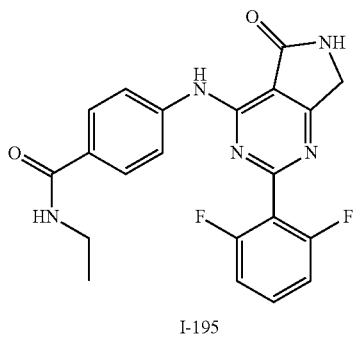

I-195

Synthesis of Compound 140.1.

To a solution of 2.5 (0.150 g, 0.47 mmol, 1.0 eq.) in Dioxane (4 mL), 4-amino-N-ethylbenzamide (0.074, 0.456 mmol, 0.95 eq) and K$_2$CO$_3$ (0.09 g, 0.71 mmol, 1.5 eq) were added at room temperature. Reaction mixture was degassed for 10 minutes at room temperature and Xantphos (0.055, 0.095 mmol, 0.2 eq), Pd$_2$(dba)$_3$ (0.044 g, 0.047 mmol, 0.1 eq) were added. Reaction mixture was stirred for 4 h at 90° C. After completion of reaction, mixture was poured into cold water and extracted using EtOAc. Organic layer was dried over sodium sulfate and concentrated under reduced pressure. Crude was purified by column chromatography to afford 140.1 (0.210 g, 99.39%). MS (ES): m/z 440.4 [M+H]$^+$ Synthesis of Compound 140.2.

To a solution of 140.1 (0.210 g, 0.476 mmol, 1.0 eq) in Dioxane (4.0 mL) at room temperature, SeO$_2$ (0.105 g, 0.953 mmol, 2.0 eq) was added. Reaction mixture was stirred at 90° C. for 2 h. After completion of the reaction, mixture was filter through celite bad, washed with CH$_2$Cl$_2$ (25 mL). Organic layer was concentrated under reduced pressure to afford 140.2 (0.180 g, 83.08%). MS (ES): m/z=454.3 [M+H]$^+$.

Synthesis of Compound 140.3.

To a solution of compound 140.2 (0.180 g, 0.396 mmol, 1.0 eq) in CH$_2$Cl$_2$ (4 mL), and MeOH (2 mL), (2,4-dimethoxyphenyl)methanamine (0.066 g, 0.396 mmol, 1 eq) was added dropwise at room temperature. NaCNBH$_3$ (0.074 g, 1.18 mmol, 3.0 eq) was added portionwise and reaction was stirred at room temperature overnight. After completion of reaction, solvent was removed under reduced pressure at to afford 140.3 (0.110 g, 46.63%). MS (ES): m/z 559.5 [M+H]$^+$.

Synthesis of Compound I-195.

A solution of 140.3 (0.110 g, 0.196 mmol, 1.0 eq) in TFA (2.6 ml) was heated at 70° C. for 2 hour. After completion of the reaction, mixture was poured in cold water, neutralized with NaHCO$_3$ and extracted with EtOAc. Solvent was removed under reduced pressure to get crude which was purified by column chromatography to afford pure I-195 (0.038 g, 47.22%). MS (ES): m/z 409.4 [M+H]$^+$, $^1$H NMR (400 MHz, MeOD): δ 7.96-7.94 (d, 2H), 7.85-7.83 (d, 2H), 7.60-7.56 (m, 1H), 7.19-7.19 (m, 2H), 4.53 (s, 2H), 3.44-3.39 (q, 2H), 1.25-1.21 (t, 3H).

Example 141. Synthesis of 2-(2,6-difluorophenyl)-4-((4-(2-methyl-1-oxo-1-(pyrrolidin-1-yl)propan-2-yl)phenyl)amino)-6,7-dihydro-5H-pyrrolo[3,4-d]pyrimidin-5-one, I-196

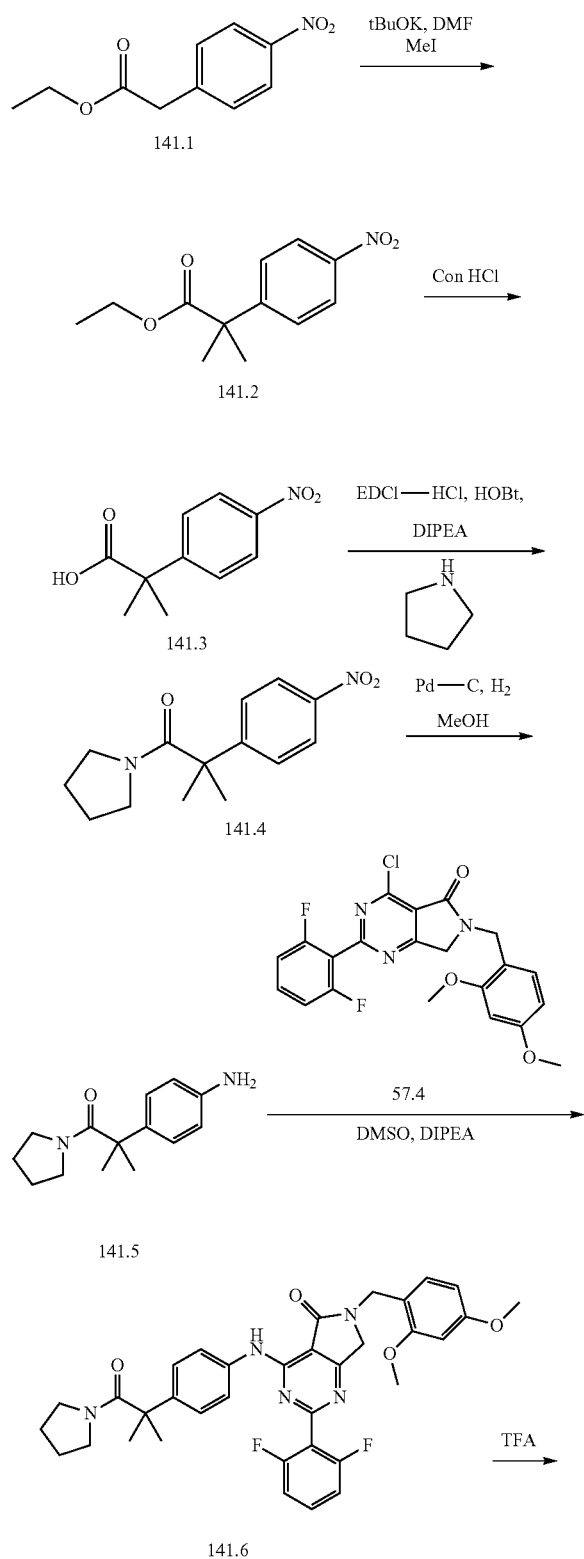

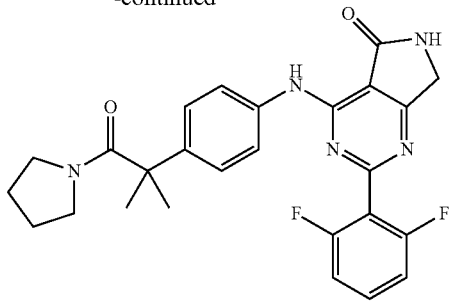

I-196

Synthesis of Compound 141.2.

To a solution of 141.1 (2.0 g, 9.5 mmol, 1.0 eq) in DMF (10 mL), MeI (3.37 g, 23.9 mmol, 2.5 eq) were added at room temperature. Reaction mixture was heated at 60° C. for 1 h. 1M solution of potassium tert-butoxide in THF (28 mL, 28.5 mmol, and 3.0 eq) was added to reaction mixture. Reaction mixture was stirred at 60° C. for 1 h. After completion of reaction, mixture was poured into cold water and extracted using EtOAc. Organic layer was dried over sodium sulfate and concentrated under reduced pressure. Crude was purified by column chromatography to afford 141.2 (1.6 g, 70.53%). MS (ES): m/z 238.26 [M+H]$^+$ Synthesis of Compound 141.3.

To a solution of 141.2 (0.6 g, 2.52 mmol, 1.0 eq) conc. HCl (10 ml) was added at room temperature. Reaction mixture was stirred at 80° C. for 4 h. After completion of the reaction, mixture was poured into cold water and extracted using EtOAc. Organic layer was dried over sodium sulfate and concentrate under reduced pressure to afford 141.3 (0.4 g, 75.61%). MS (ES): m/z=210.2 [M+H]$^+$.

Synthesis of Compound 141.4.

To a solution of 141.3 (0.3 g, 1.43 mmol, 1.0 eq) in THF (3 mL) was added EDCI (0.356 g, 1.86 mmol, 1.3 eq), HOBt (0.251 g, 1.86 mmol, 1.3 eq) at 0° C. The reaction mixture was stirred at 0° C. for 15 minutes. Pyrrolidine (0.121 g, 1.71 mmol, 1.2 eq) and DIPEA (0.55 g, 4.30 mmol, 3.0 eq) were added to reaction mixture at 0° C. Reaction was stirred at room temperature for 4 h. After completion of the reaction, mixture was poured into water and product was extracted with EtOAc. Organic layers were combined, dried over sodium sulphate and concentrated under reduced pressure to obtain crude which was purified to afford compound 141.4 (0.320 g, 63.80%). MS (ES): m/z 263.31 [M+H]$^+$.

Synthesis of Compound 141.5.

To a solution of 141.4 (0.320 g, 1.21 mmol, 1.0 eq) in MeOH (5 mL) was added with 10% Pd/C (0.032 g) under nitrogen atmosphere. It was purged with hydrogen for 1 h. Reaction mixture was filtered through celite and obtained filtrate was concentrated under reduced pressure to get crude 141.5 (0.270 g, 95.26%) which was used as such for the next step, MS (ES): m/z 233.33 [M+H]$^+$.

Synthesis of Compound 141.6.

To a solution of 57.4 (0.2 g 0.4631 mmol, 1.0 eq.) in DMSO (2.0 mL) was added 141.5 (0.107 g, 0.4631 mmol, 1.0 eq.) and DIPEA (0.242 ml, 1.389 mmol, 3 eq.) at room temperature. Reaction mixture was heated at 70° C. for 30 min. After completion of the reaction, mixture was poured into water and extracted using EtOAc. Organic layer was washed with by brine, dried over sodium sulfate and concentrated under reduced pressure. Crude was purified by column chromatography afford pure 141.6 (0.120 g, 41.28%), MS (ES): m/z 628.69 [M+H]$^+$ Synthesis of Compound I-196.

A solution of 141.6 (0.120 g, 0.191 mmol, 1.0 eq.) in TFA (2 mL) was stirred at 70° C. for 3 h. After completion of the reaction, mixture was poured into cold water, neutralized with NaHCO$_3$ and extracted with ethyl acetate. Solvent was removed under reduced pressure at 45° C. to get crude, which was purified by column chromatography to afford pure I-196 (0.060 g, 65.75%). MS (ES): m/z −478.5 [M+H]$^+$, $^1$H NMR (400 MHz, DMSO-d$^6$): δ 9.06 (s, 1H), 8.91 (s, 1H), 7.77-7.75 (d, 2H), 7.61 (m, 1H), 7.29-7.25 (t, 2H), 7.18-7.16 (d, 2H), 4.48 (s, 2H), 3.37-3.32 (m, 2H), 2.70-2.68 (m, 2H), 1.60-1.58 (m, 2H), 1.50-1.48 (m, 2H), 1.41 (s, 6H).

Example 142. Synthesis of 4-((4-cyclohexylphenyl)amino)-2-(2,6-difluorophenyl)-6,7-dihydro-5H-pyrrolo[3,4-d]pyrimidin-5-one I-197

Synthesis of Compound I-197.

A solution of 142.1 (0.070 g, 0.122 mmol, 1 eq) in TFA (6 ml) was stirred at 70° C. for 8 h. After completion of the reaction, mixture was poured into cold water, neutralized with NaHCO$_3$ and extracted with EtOAc. Solvent was removed under reduced pressure to get crude which was purified by column chromatography to afford pure I-197 (0.036 g, 69.80%). MS (ES): m/z 420.4 [M+H]$^+$, $^1$H NMR (400 MHz, DMSO-d$^6$): δ 9.01 (s, H), 8.88 (s, 1H), 7.65-7.57 (m, 3H), 7.29-7.19 (m, 4H), 4.47 (s, 2H), 3.75-3.74 (m, 1H), 2.51-2.46 (m, 1H), 1.78-1.67 (m, 5H), 1.39-1.29 (m, 4H).

Example 143. Synthesis of 2-(2,6-difluorophenyl)-4-((4-(1-oxo-1-(piperidin-1-yl)propan-2-yl)phenyl)amino)-6,7-dihydro-5H-pyrrolo[3,4-d]pyrimidin-5-one, I-198

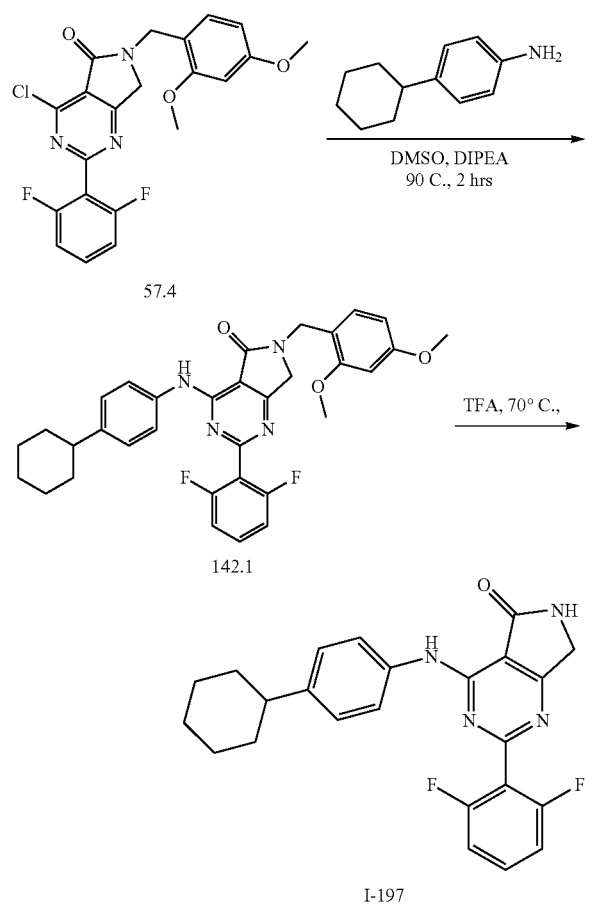

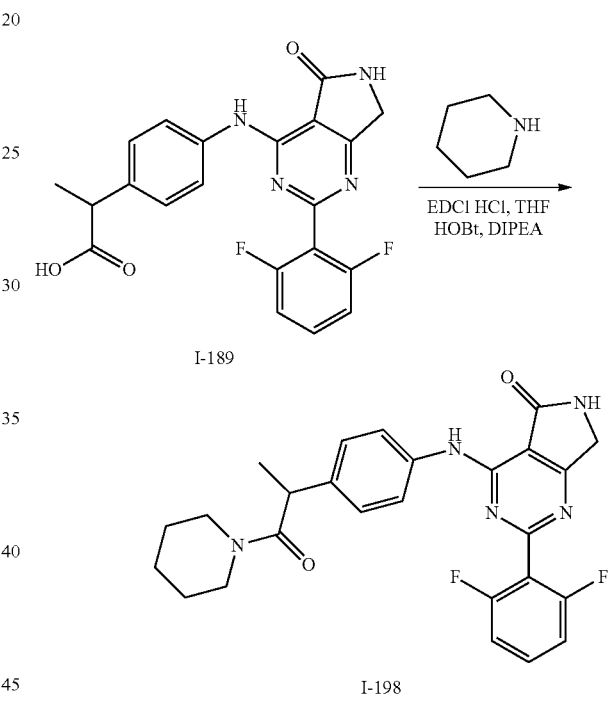

Synthesis of Compound 142.1.

To a solution of compound 57.4 (0.130 g, 0.30 mmol, 1.0 eq.) in DMSO (2 mL), 4-cyclohexylaniline (0.050 g, 0.280 mmol, 0.95 eq), DIPEA (0.15 mL, 0.90 mmol, 3.0 eq) were added at room temperature. Reaction mixture was heated at 90° C. for 2 h. After completion of the reaction, mixture was poured into cold water and extracted using EtOAc Organic layer was dried over sodium sulfate and concentrated under reduced pressure. Crude was purified by column chromatography to afford 142.1 (0.070 g, 40.75%). MS (ES): m/z 570.6 [M+H]$^+$ To a solution of I-189 (0.020 g, 0.048 mmol, 1.0 eq) in THF (1 mL) were added EDCI (0.014 g, 0.073 mmol, 1.5 eq) and HOBt (0.008 g, 0.057 mmol, 1.2 eq) at 0° C. The reaction mixture was stirred at 0° C. for 15 minutes. After 15 minutes piperidine (0.005 g, 0.057 mmol, 1.2 eq) and DIPEA (0.019 g, 0.144 mmol, 3.0 eq) were added at 0° C. The reaction was stirred at room temperature for 4 h. After completion of the reaction, mixture was poured into water and product was extracted with EtOAc. Organic layers were combined and dried over sodium sulphate, concentrated under reduced pressure to obtain crude which was purified by preparative TLC to get I-198 (0.004 g, 17%). MS (ES): m/z 478.56 [M+H]$^+$; $^1$H NMR (MeOD, 400 MHZ): δ 7.76-7.79 (d, 2H), 7.53-7.59 (m, 1H), 7.26-7.28 (d, 2H), 7.12-7.16 (t, 2H), 4.61 (s, 1H), 4.51 (s, 2H), 4.05-4.10 (q, 1H), 3.74-3.79 (m, 1H), 3.45-3.50 (m, 1H), 3.38-3.41 (m, 1H), 1.55-1.61 (m, 3H), 1.35-1.42 (m, 3H), 1.30 (d, 3H)

Example 144. Synthesis of 2-(6-((2-(2,6-difluorophenyl)-5-oxo-6,7-dihydro-5H-pyrrolo[3,4-b]pyridin-4-yl)amino)pyridin-3-yl)-N-ethylacetamide, I-88

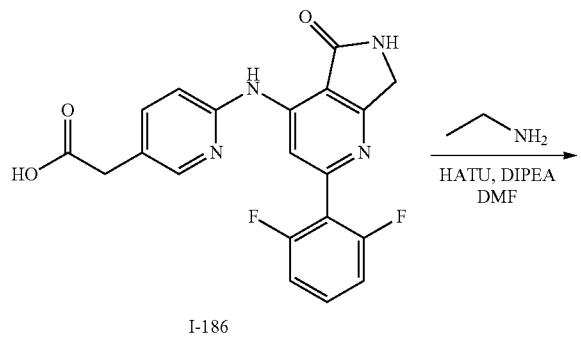

To a solution of I-186 (0.013 g, 0.032 mmol, 1.0 eq) in dry DMF (3 mL) was added HATU (0.022 g, 0.059 mmol, 1.5 eq) at 0° C. under argon atmosphere and allowed to stir for 30 min at 0° C. Ethyl amine (0.02 mL, 0.039 mmol, 1.2 eq) was added followed by the addition of DIPEA (0.01 g, 0.082 mmol, 2.5 eq). Reaction was stirred at room temperature for 1 hour. After completion of reaction, mixture was diluted with EtOAc (50 ml) and washed with water (50 ml×3) and then with brine (50 ml). Organic layer was dried over sodium sulphate and concentrated under reduced pressure. Crude product was purified by column chromatography to afford pure I-88 (0.005 g, 36.00%). MS (ES): m/Z 423.5 [M+H]$^+$, $^1$H NMR (DMSO-d6, 400 MHZ): 9.71 (s, 1H), 8.89 (s, 1H), 8.53 (s, 1H), 8.18 (s, 1H), 8.05 (s, 1H), 7.66-7.54 (m, 2H), 7.28-7.24 (m, 2H), 7.14-7.12 (d, 1H), 4.43 (s, 2H), 3.34 (s, 2H), 3.09-3.02 (m, 2H), 1.02-0.99 (t, 3H).

Example 145. Synthesis of 2-(6-((2-(2-chloro-6-fluorophenyl)-5-oxo-6,7-dihydro-5H-pyrrolo[3,4-b]pyridin-4-yl)amino)pyridin-3-yl)-N-ethylacetamide I-199

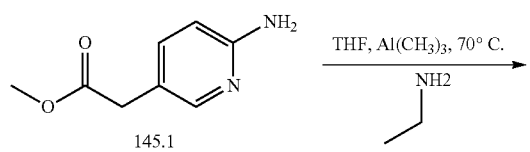

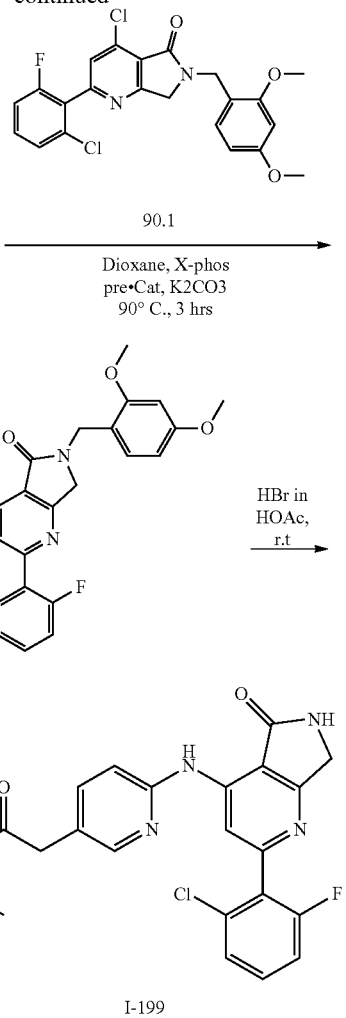

Synthesis of Compound 145.2

To a solution of methyl 2-(6-aminopyridin-3-yl) acetate (0.250 g, 1.6 mmol, 1.0 eq) in THF (5 mL) was added Ethyl amine (0.044 g, 0.260 mmol, 2.0 eq) and DIPEA (0.56 mL, 3.28 mmol, 2.0 eq). The reaction mixture was cooled at 0° C., and then AlMe$_3$ (4.2 mL, 8.0 mmol, 5.0 eq) was added. The reaction was then heated at 70° C. for 3 h. After completion of reaction, mixture was poured into water and product was extracted with EtOAC. Organic layer were combined, dried over sodium sulphate and concentrated under reduced pressure to obtain crude which was purified by column chromatography to get pure 145.2 (0.075 g, 27.82%). MS (ES): m/z 179.01 [M+H]$^+$.

Synthesis of Compound 145.3

To a solution of compound 90.1 (0.100 g, 0.22 mmol, 1.0 eq) in 1,4-dioxane (2.5 mL) was added compound 145.2 (0.071 g, 0.39 mmol, 1.8 eq) and K$_2$CO$_3$ (0.061 g, 0.44 mmol, 2.0 eq). The reaction mixture was degassed for 10 min. under argon atmosphere, then Chloro(2-dicyclohexylphosphino-2',4',6'-triisopropyl-1,1'-biphenyl)[2-(2-aminoethyl)phenyl)]palladium(II) (0.032 g, 0.040 mmol, 0.2 eq) was added, again degassed for 5 min. The reaction was stirred at 90° C. for 3 h. After completion of the reaction, mixture was poured into water and extracted with EtOAC. Organic layer was combined, dried over sodium sulphate and concentrated under reduced pressure to obtain crude which was purified to get pure 145.3 (0.085 g, 64.43%). MS (ES): m/z 590.01 [M+H]$^+$.

Synthesis of Compound I-199.

Compound 145.3 (0.085 g, 0.14 mmol, 1.0 eq) was dissolved in HBr/HOAc (2 ml) and stirred at room temperature for 1 h. After completion of reaction, mixture was poured in water and basified with NaHCO$_3$ and extracted with ethyl acetate. Organic layers were combined, dried over sodium sulphate and concentrated under reduced pressure to obtain crude which was purified by column chromatography to get I-199 (0.025 g, 37.5%). $^1$H NMR (MeOD, 400 MHz): 8.70 (s, 1H), 8.26 (s, 1H), 7.73-7.71 (dd, 1H), 7.55-7.51 (m, 1H), 7.46-7.44 (d, 1H), 7.31-7.27 (t, 1H), 7.11-7.09 (d, 1H), 4.52 (s, 2H), 3.48 (s, 2H), 3.24-3.18 (q, 2H), 1.14-1.11 (t, 3H).

Example 146. Synthesis of methyl 2-(6-((2-(2-chloro-6-fluorophenyl)-5-oxo-6,7-dihydro-5H-pyrrolo[3,4-b]pyridin-4-yl)amino)pyridin-3-yl)acetate, I-200

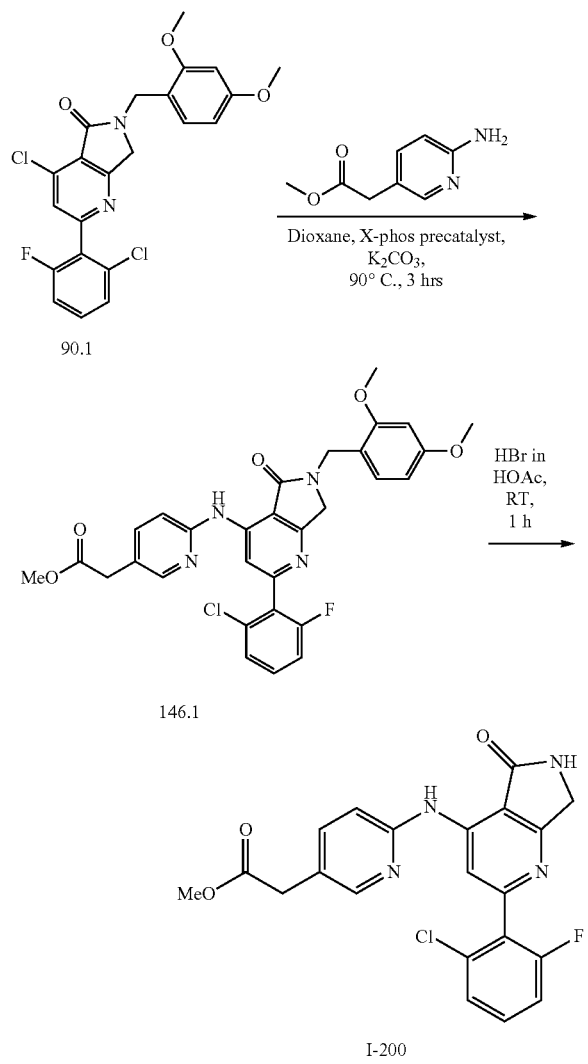 [SMILES: COc1ccc(CN2Cc3nc(-c4c(F)cccc4Cl)cc(Cl)c3C2=O)c(OC)c1 ; COC(=O)Cc1ccc(N)nc1 ; COC(=O)Cc1ccc(Nc2cc(-c3c(F)cccc3Cl)nc3c2C(=O)N(Cc2ccc(OC)cc2OC)C3)nc1 ; COC(=O)Cc1ccc(Nc2cc(-c3c(F)cccc3Cl)nc3c2C(=O)NC3)nc1]

Synthesis of Compound 146.1.

To a solution of compound 90.1 (0.06 g, 0.134 mmol, 1.0 eq) in 1,4-dioxane (2 mL) was added methyl 2-(6-aminopyridin-3-yl)acetate (0.044 g, 0.260 mmol, 2.0 eq) and K$_2$CO$_3$ (0.037 g, 0.26 mmol, 2.0 eq). The reaction mixture was degassed for 10 min. under argon atmosphere, then Chloro(2-dicyclohexylphosphino-2',4',6'-triisopropyl-1,1'-biphenyl)[2-(2-aminoethyl)phenyl)]palladium(II) (0.019 g, 0.026 mmol, 0.2 eq) was added, again degassed for 5 minutes. The reaction was stirred at 90° C. for 3 hours. After completion of the reaction, mixture was poured into water and product was extracted with EtOAC. Organic layer was combined, dried over sodium sulphate and concentrated under reduced pressure to obtain crude which was purified by column chromatography to get pure 146.1 (0.035 g, 45.22%). MS (ES): m/z 578.01 [M+H]$^+$.

Synthesis of Compound I-200.

Compound 146.1 (0.036 g, 0.062 mmol, 1.0 eq) was dissolved in HBr/HOAc (2 ml) and stirred at room temperature for 1 hour. After completion of the reaction, mixture was poured into water and basified with saturated bicarbonate solution and extracted with ethyl acetate. Organic layers were combined, dried over Na$_2$SO$_4$ and concentrated under reduced pressure to obtain crude which was purified by column chromatography to get pure I-200 (0.010 g, 39.8%). MS (ES): m/z 427.8 [M+H]$^+$, $^1$H NMR (MeOD, 400 MHZ): 8.66 (s, 1H), 8.24 (s, 1H), 7.72-7.70 (dd, 1H), 7.54-7.48 (m, 1H), 7.43-7.42 (d, 1H), 7.29-7.24 (s, 1H), 7.08-7.06 (d, 1H), 4.48 (s, 2H), 3.71 (s, 3H), 3.67 (s, 2H).

Example 147. Synthesis of methyl 4-(2-(4-((2-(2,6-difluorophenyl)-5-oxo-6,7-dihydro-5H-pyrrolo[3,4-d]pyrimidin-4-yl)amino)phenyl)acetyl)morpholine-3-carboxylate, I-201

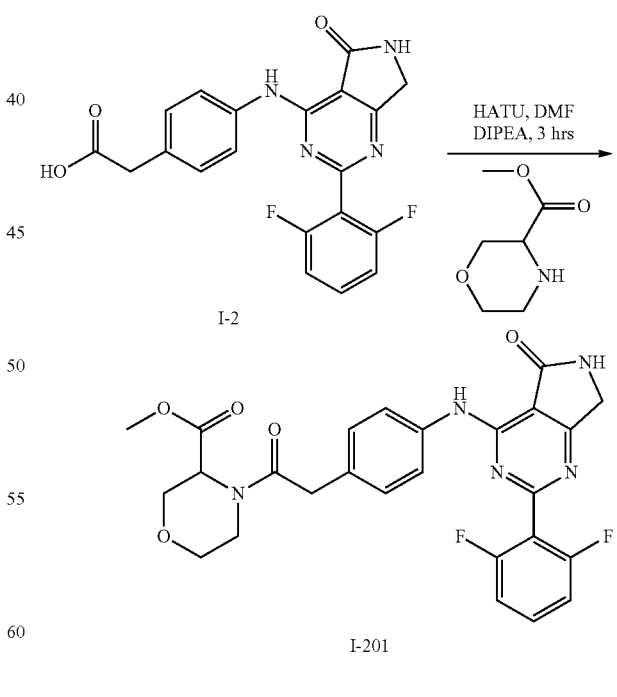

A solution of compound I-2 (0.080 g 0.20 mmol, 1.0 eq.) in DMF (2 mL) was cooled to 0° C. and HATU (0.115 g, 0.30 mmol, 1.5 eq) was added. Reaction mixture was stirred for 20 minutes. Methyl morpholine-3-carboxylate (0.034, 0.24 mmol, 1.2 eq), DIPEA (0.101 mL, 0.60 mmol, 3.0 eq)

were added. Reaction mixture was stirred for 3 hours at room temperature. After completion of the reaction, reaction mixture was poured into cold water and extracted using EtOAC. Organic layer was dried over sodium sulfate and concentrate under reduced pressure. Crude was purified column chromatography to afford I-201 (0.07 g, 66.3%). MS (ES): m/z 523.5 [M+H]+; 1H NMR (400 MHz, DMSO-d6): δ 9.06 (s, 1H), 9.05 (s, 1H), 7.70-7.56 (m, 3H), 7.28-7.15 (m, 4H), 4.90 (s, 1H), 4.48 (s, 2H), 4.22-4.18 (m, 1H), 3.83-3.76 (m, 3H), 3.71-3.67 (m, 5H), 3.58-3.54 (m, 1H), 3.27-3.20 (m, 1H).

Example 148. Synthesis of 4-(2-(4-((2-(2,6-difluorophenyl)-5-oxo-6,7-dihydro-5H-pyrrolo-[3,4-d]pyrimidin-4-yl)amino)phenyl)acetyl)morpholine-3-carboxylic Acid, I-202

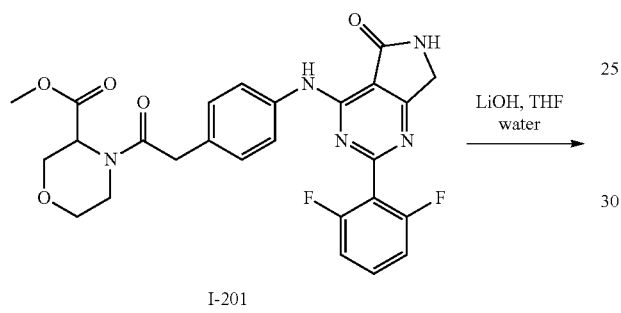

I-201

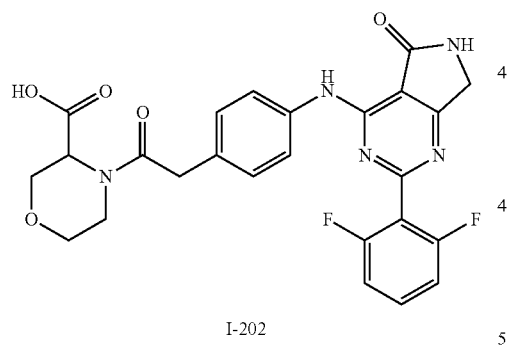

I-202

To a solution of I-201 (0.063 g, 0.120 mmol, 1.0 eq) in THF (2 mL), LiOH (0.015 g, 0.36 mmol, 3.0 eq) solution in water (2 mL) was added at room temperature. Reaction mixture was stirred for 15 minutes. After completion of the reaction, reaction mixture was neutralized with acetic acid, and extracted using EtOAC (10 mL×2). Organic layer was dried over sodium sulfate and concentrate under reduced pressure. Crude product was purified by preparative HPLC to afford I-202 (0.06 g, 97.9%). MS (ES): m/z=509.3 [M+H]+; 1H NMR (400 MHz, DMSO-d6): δ 9.03 (s, 1H), 8.88 (s, 1H), 8.32 (s, 1H), 7.68-7.55 (m, 3H), 7.28-7.22 (m, 3H), 7.16-7.14 (d, 1H), 4.47 (s, 2H), 4.34-4.25 (m, 1H), 3.76-3.63 (m, 4H), 3.46-3.36 (m, 4H).

Example 149. Synthesis of 2-(4-((2-(2,6-difluorophenyl)-5-oxo-6,7-dihydro-5H-pyrrolo[3,4-d]pyrimidin-4-yl)amino)phenyl)-N-ethylacrylamide, I-203

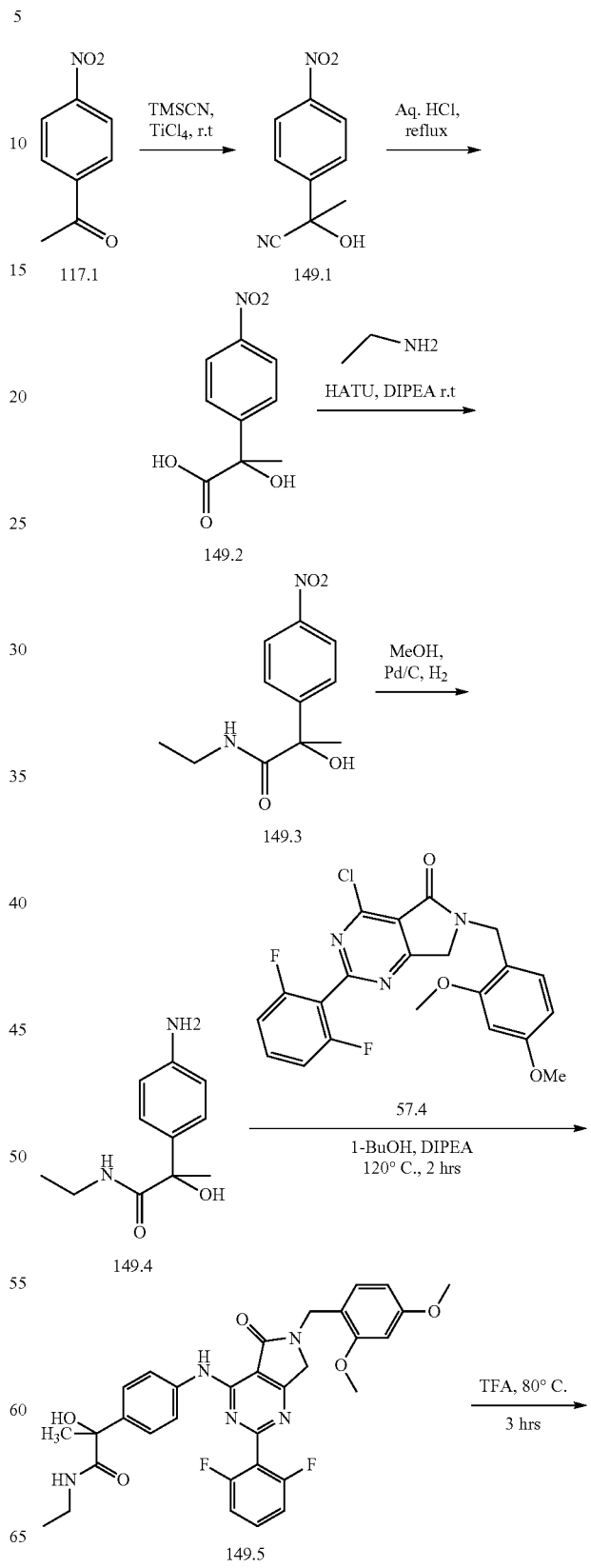

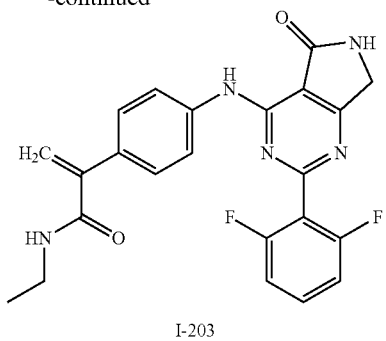

I-203

Synthesis of Compound 149.1.

To a solution of 117.1 (5.0 g, 30.3 mmol, 1.0 eq) in CH$_2$Cl$_2$ (50 mL) was added TMSCN (4.55 mL, 36.34 mmol, 1.2 eq) followed by TiCl$_4$ (1.14 g, 6.05 mmol, 0.2 eq) drop wise at room temperature. Reaction was stirred at room temperature for 18 hours. The reaction mixture was quenched with ice/cold water and product was extracted with CH$_2$Cl$_2$ (50 mL×2). Organic layers were combined, dried over sodium sulphate and concentrated under reduced pressure to obtain 149.1 (5.8 g, 99.7%). MS (ES): m/z No ionisation [M+H]$^+$.

Synthesis of Compound 149.2.

To a solution of 149.1 (5.8 g, 30.2 mmol, 1.0 eq) in 1,4-dioxane (100 mL) was added conc. HCl (50 mL, eq). Reaction mixture was heated at 120° C. for 5 hours. Reaction mixture was concentrated under reduced pressure. Residue was dissolved in EtOAc, washed with saturated NaHCO$_3$ solution. Organic layer was separated, dried over Na$_2$SO$_4$ and concentrated under reduced pressure to obtain 149.2 (4.7 g, 73.7%) which was used as such for the next step, MS (ES): m/z 210 [M−H]$^+$ Synthesis of Compound 149.3.

To a solution of 149.3 (4.7 g, 22.26 mmol, 1.0 eq) in DMF (50 mL) was added ethyl amine (13.4 mL, 26.7 mmol, 1.2 eq), DIPEA (7.62 mL, 44.53 mmol, 2 eq) and HATU (10.16 g, 26.7 mmol, 1.2 eq). Reaction was stirred at room temperature for 1 h. Reaction mixture was diluted with EtOAc and washed with saturated NaHCO$_3$ solution. Organic layer was dried over sodium sulphate and concentrated under reduced pressure to obtain 149.3 (3.6 g, 67.89%). MS (ES): m/z 239.3 [M+H]$^+$.

Synthesis of Compound 149.4.

Compound 149.3 (3.6 g, 15.1 mmol, 1.0 eq) was dissolved in MeOH (3 mL) and added to 10% Pd/C. Reaction mixture was purged with H$_2$ gas for 2 hours. After completion of the reaction, reaction mixture was filtered through celite bed. Filtrate was concentrated under reduced pressure to obtain get 149.4 (3.12 g, 99.14%). MS (ES): m/z 209.2 [M+H]$^+$.

Synthesis of Compound 149.5.

To a solution of 57.4 (0.3 g, 0.69 mmol, 1.0 eq) in 1-butanol (5 mL) was added 149.4 (0.16 g, 0.764 mmol, 1.1 eq) and DIPEA (0.4 mL, 2.083 mmol, 3 eq). The reaction mixture was then heated at 120° C. for 2 hours. After completion of the reaction, mixture was poured into water and product was extracted with EtOAc. Organic layers were combined and dried over Na$_2$SO$_4$ and concentrated under reduced pressure to obtain crude which was purified using column chromatography to get 149.5 (0.35 g, 83.46%). MS (ES): m/z 604.5 [M+H]$^+$.

Synthesis of Compound I-203.

Solution of 149.5 (0.040 g, 0.066 mmol, 1.0 eq) in TFA (2.0 ml) was heated at 80° C. for 3 hours. After completion of the reaction, mixture was poured into cold water, neutralized with NaHCO$_3$ and extracted with EtOAC. Solvent was removed under reduced pressure to get crude which was purified using column chromatography to afford pure I-203 (0.015 g, 52.03%). MS (ES): m/z 436.5 [M+H]$^+$. $^1$H NMR (DMSO-d$_6$, 400 MHz): δ 9.15 (s, 1H), 8.93 (s, 1H), 8.20-8.18 (t, 1H), 7.78-7.76 (d, 2H), 7.64-7.57 (m, 1H), 7.42-7.40 (d, 2H), 7.30-7.26 (m, 2H), 5.73 (s, 1H), 5.50 (s, 1H), 4.49 (s, 2H), 3.22-3.15 (m, 2H), 1.09-1.02 (t, 3H).

Example 150. Synthesis of 2-(2-chloro-6-fluorophenyl)-4-((5-(pyrrolidin-1-yl)pyridin-2-yl)amino)-6,7-dihydro-5H-pyrrolo[3,4-b]pyridin-5-one, I-204

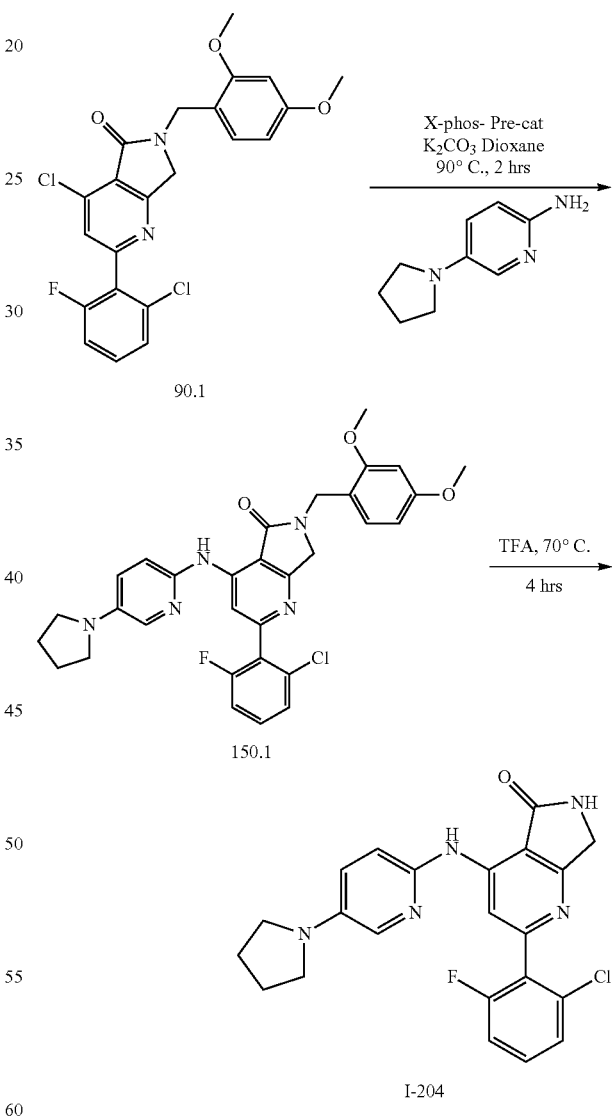

Synthesis of Compound 150.1.

To a solution of compound 90.1 (0.09 g, 0.20 mmol, 1.0 eq) in 1,4-dioxane (2 mL) was added 5-(pyrrolidin-1-yl) pyridin-2-amine (0.065 g, 0.40 mmol, 2.0 eq) and K$_2$CO$_3$ (0.055 g, 0.40 mmol, 2.0 eq). The reaction mixture was degassed for 10 min. under argon atmosphere, then Chloro (2-dicyclohexylphosphino-2',4',6'-triisopropyl-1,1'-biphenyl)[2-(2-aminoethyl)phenyl)]palladium(II) (0.029 g, 0.04 mmol, 0.2 eq) was added, again degassed for 5 min. The reaction was stirred at 90° C. for 2 hours. After completion of the reaction, mixture was poured into water and product was extracted with EtOAC. Organic layer was dried over Na$_2$SO$_4$ and concentrated under reduced pressure to obtain crude which was purified using column chromatography to get pure 150.1 (0.068 g, 58.87%). MS (ES): m/z 573.01 [M+H]$^+$.

Synthesis of Compound I-204.

Compound 150.1 (0.068 g, 0.011 mmol, 1.0 eq) was dissolved in TFA (2 mL) and stirred at 70° C. for 4 hours. After completion of the reaction, mixture was poured into water and basified with saturated bicarbonate solution and product was extracted with ethyl acetate. Organic layers were combined and dried over Na$_2$SO$_4$ and concentrated under reduced pressure to obtain crude which was purified using column chromatography to get pure I-204 (0.035 g, 69.7%). MS (ES): m/z 423.8 [M+H]$^+$, $^1$H NMR (DMSO-d$_6$, 400 MHz): 9.47 (s, 1H), 8.82 (s, 1H), 8.17 (s, 1H), 7.708-7.701 (s, 1H), 7.58-7.47 (m, 2H), 7.41-7.37 (m, 1H), 7.11-7.04 (m, 2H), 4.46 (s, 2H), 3.21 (s, 4H), 1.93 (s, 4H).

Example 151. Synthesis of 2-(2,6-difluorophenyl)-4-((5-(pyrrolidin-1-yl)pyridin-2-yl)ami-no)-6,7-dihydro-5H-pyrrolo[3,4-b]pyridin-5-one, I-205

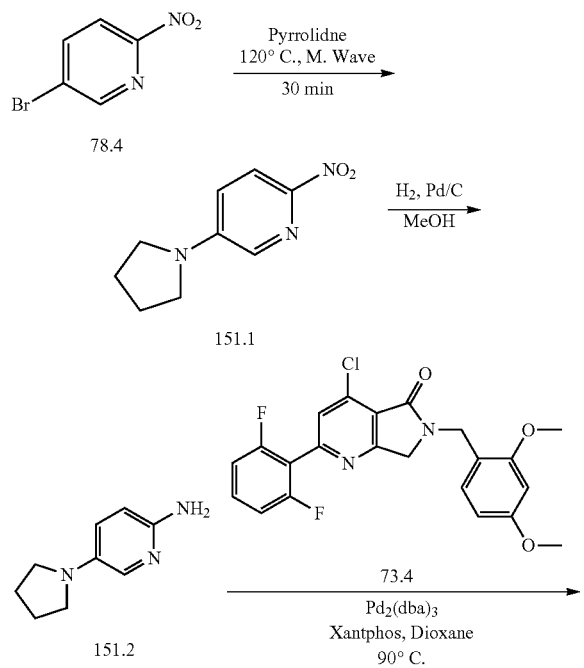

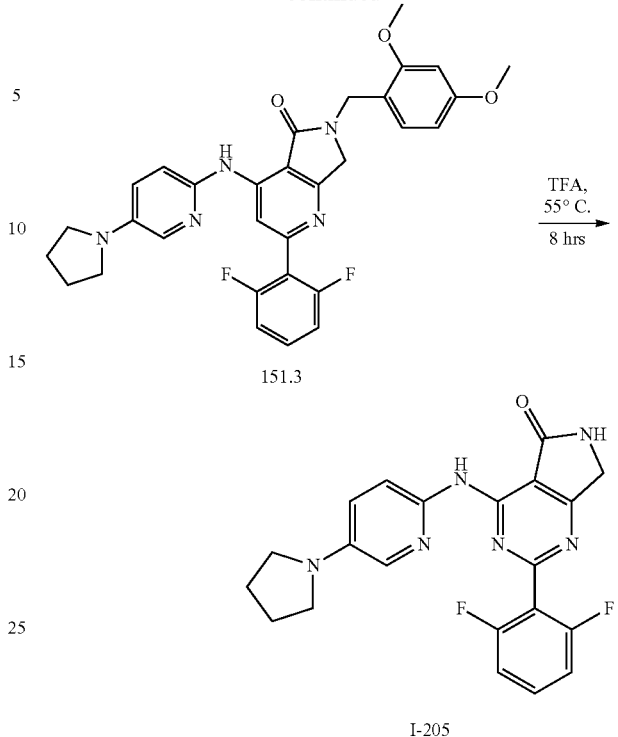

Synthesis of Compound 151.1.

To a solution of 78.4 (1.0 g, 4.90 mmol, 1.0 eq) was added pyrrolidine (0.350 g, 4.9 mmol, 1.0 eq). Reaction was stirred at 120° C. for 30 minutes in microwave. The reaction mixture was poured into water and product was extracted with EtOAc. Organic layers were combined and dried over Na$_2$SO$_4$ and concentrated under reduced pressure to obtain crude which was purified to get 151.1 (0.550 g, 57.79%). MS (ES): m/z 193.21 [M+H]$^+$.

Synthesis of Compound 151.2.

A solution of 151.1 (0.55 g, 2.84 mmol, 1.0 eq) in MeOH (10 mL) was added 10% Pd/C (0.055 g) under nitrogen atmosphere. Reaction was purged with H$_2$ gas for 3 h. Reaction mixture was filtered through celite and obtained filtrate was concentrated under reduced pressure to get crude 151.2 (0.35 g, 75.3%) which was used as such for the next step, MS (ES): m/z 164.3 [M+H]$^+$.

Synthesis of Compound 151.3.

To a solution of compound 73.4 (0.085 g, 0.18 mmol, 1.0 eq) in 1,4-dioxane (3 mL) was added 174.2 (0.034 g, 0.20 mmol, 1.1 eq) and K$_2$CO$_3$ (0.065 g, 0.45 mmol, 2.5 eq). The reaction mixture was degassed for 10 min. under argon atmosphere, then Pd$_2$(dba)$_3$ (0.010 g, 0.01 mmol, 0.1 eq) and Xantphos (0.021 g, 0.036 mmol, 0.2 eq) were added, and again suspension was degassed for 5 min. The reaction was stirred at 90° C. for 2.5 hours. After completion of the reaction, mixture was poured into water and product was extracted with EtOAc. Organic layer was dried over Na$_2$SO$_4$ and concentrated under reduced pressure to obtain crude which was purified by column chromatography to get pure 151.3 (0.045 g, 40.9%). MS (ES): m/z 557.6 [M+H]$^+$.

Synthesis of Compound I-205.

Compound 151.3 (0.045 g, 0.08 mmol, 1.0 eq) was dissolved in TFA (2 mL) and stirred at 55° C. for 8 hours. After completion of the reaction, mixture was poured into water and basified with satd. NaHCO$_3$ solution and was extracted with EtOAC. Organic layer was dried over Na₂SO₄ and concentrated under reduced pressure to obtain crude which was purified by column chromatography to furnish I-205 (0.024 g, 72.99%). MS (ES): m/z 407.4 [M+H]⁺, ¹H NMR (DMSO-d₆, 400 MHz): 9.41 (s, 1H), 8.78 (s, 1H), 8.23 (s, 1H), 7.70 (s, 1H), 7.58-7.55 (m, 1H), 7.27-7.23 (m, 2H), 7.10-7.04 (m, 2H), 4.40 (s, H), 3.22 (s, 4H), 1.94 (s, 4H).

Example 152. Synthesis of (S)-2-(2,6-difluorophenyl)-4-((4-(1-oxo-1-(piperidin-1-yl)propan-2-yl)phenyl)amino)-6,7-dihydro-5H-pyrrolo[3,4-d]pyrimidin-5-one, I-206

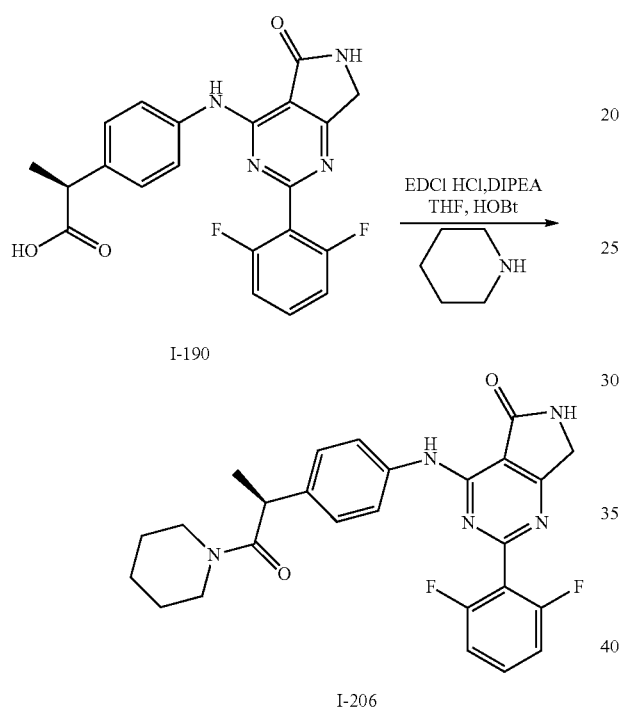

To a solution of I-190 (0.017 g, 0.041 mmol, 1.0 eq) in THF (1 mL) was added EDCI (0.011 g, 0.061 mmol, 1.5 eq), HOBt (0.007 g, 0.057 mmol, 1.2 eq) at 0° C. The reaction mixture was stirred at 0° C. for 15 minutes. After 15 minutes piperidine (0.005 g, 0.057 mmol, 1.2 eq) and DIPEA (0.016 g, 0.123 mmol, 3.0 eq) were added to reaction mixture at 0° C. The reaction mixture was stirred at room temperature for 4 hours. After completion of the reaction, mixture was poured into water and product was extracted with EtOAC. Organic layers were combined and dried over Na₂SO₄ and concentrated under reduced pressure to obtain crude which was purified by preparative TLC to get pure I-206 (0.003 g, 15%). MS (ES): m/z 478.43 [M+H]⁺, ¹H NMR (MeOD, 400 MHz): δ 7.76-7.79 (d, 2H), 7.53-7.58 (m, 1H), 7.26-7.28 (d, 2H), 7.12-7.17 (t, 2H), 4.64 (s, 1H), 4.51 (s, 2H), 4.05-4.10 (q, 1H), 3.74-3.79 (m, 1H), 3.45-3.50 (m, 1H), 3.36-3.41 (m, 1H), 1.55 (brs, 3H), 1.37-1.42 (m, 6H), Example 153. Synthesis of (R)-2-(2,6-difluorophenyl)-4-((4-(1-oxo-1-(piperidin-1-yl)propan-2-yl)phenyl)amino)-6,7-dihydro-5H-pyrrolo[3,4-d]pyrimidin-5-one, I-207

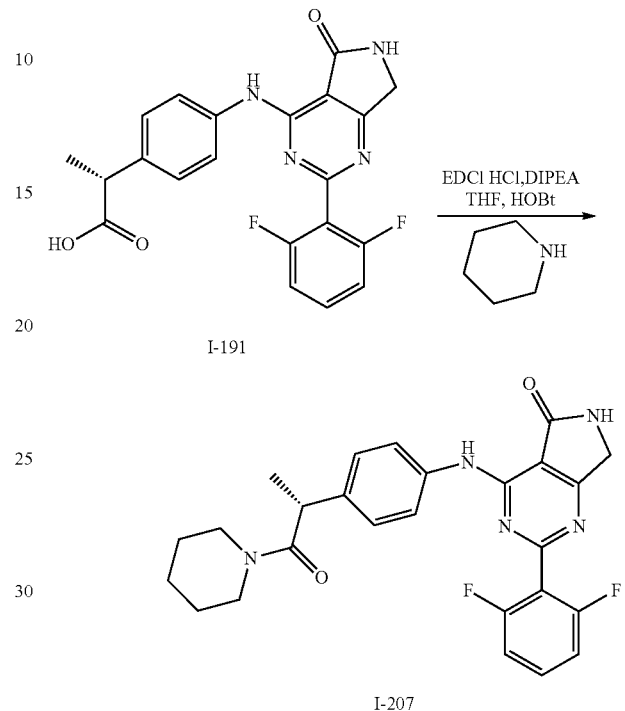

Compound I-207 was prepared from compound I-191 using the same procedure as described in Example 152. MS (ES): m/z 478.61 [M+H]⁺ ¹H NMR (MeOD, 400 MHz): δ 7.76-7.78 (d, 2H), 7.52-7.59 (m, 1H), 7.26-7.28 (d, 2H), 7.12-7.16 (t, H), 4.51 (s, 2H), 4.05-4.10 (q, 1H), 3.74-3.79 (m, 1H), 3.45-3.50 (m, 1H), 3.38-3.41 (m, 1H), 1.55 (brs, 3H), 1.35-1.45 (m, 4H), 1.30 (s, 3H)

Example 154. Synthesis of 2-(4-((2-(3,5-difluoropyridin-4-yl)-5-oxo-6,7-dihydro-5H-pyrrolo[3,4-d]pyrimidin-4-yl)amino)phenyl)-N-ethylacetamide, I-208

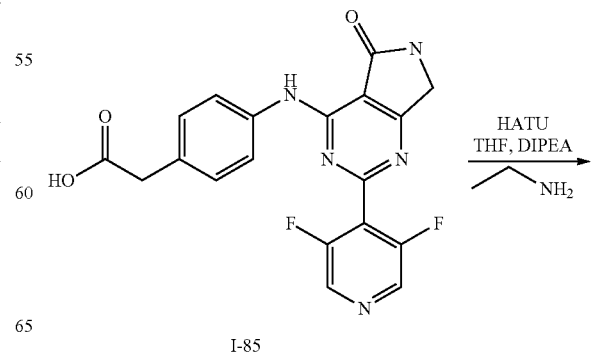

-continued

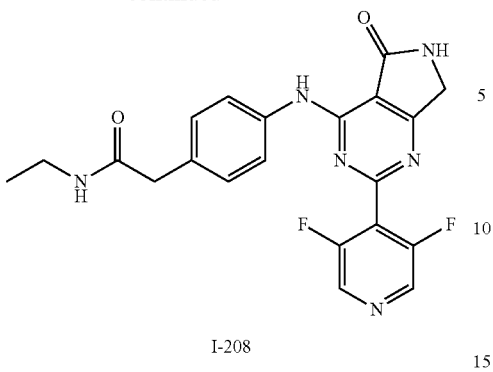

I-208

A solution of I-85 (0.305 g, 0.76 mmol, 1 eq) in THF (6 mL) was cooled at 0° C., HATU (0.437 g, 1.15 mmol, 1.5 eq) was added at 0° C. Reaction mixture was stirred at 0° C. for 30 min, DIPEA (0.39 mL, 2.30 mmol, 3 eq), and ethylamine (0.059 g, 0.92 mmol, 1.2 eq) were added, and reaction mixture was stirred at room temperature for 3 hours. After completion of the reaction, mixture was poured into cold water; product was extracted with EtOAc. Solvent was removed under reduced pressure to get which was purified by column chromatography to afford pure I-208 (0.25 g, 66.9%). MS (ES): m/z 424.4 [M+H]$^+$, $^1$H NMR (400 MHz, DMSO-d$_6$): δ 9.14 (s, 1H), 8.96 (s, 1H), 8.73 (s, 2H), 8.49 (s, 1H), 8.02 (s, 1H), 7.65-7.63 (d, 2H), 7.23-7.21 (d, 2H), 4.49 (s, 2H), 3.07-3.01 (q, 2H), 2.02-1.97 (m, 1H), 1.02-0.98 (t, 3H).

Example 155. Synthesis of 2-(2,6-difluorophenyl)-4-((4-(1,2,4-trimethyl-3-oxopiperazin-2-yl)phenyl)amino)-6,7-dihydro-5H-pyrrolo[3,4-d]pyrimidin-5-one, I-209

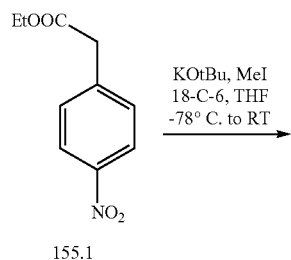

155.1

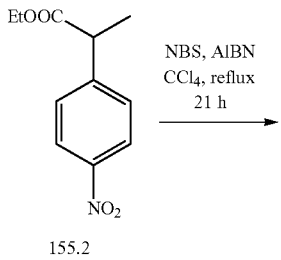

155.2

-continued

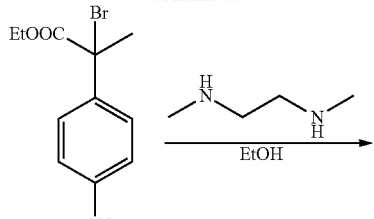

155.3

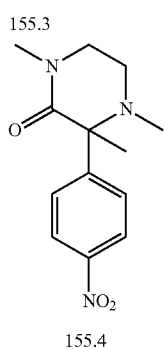

155.4

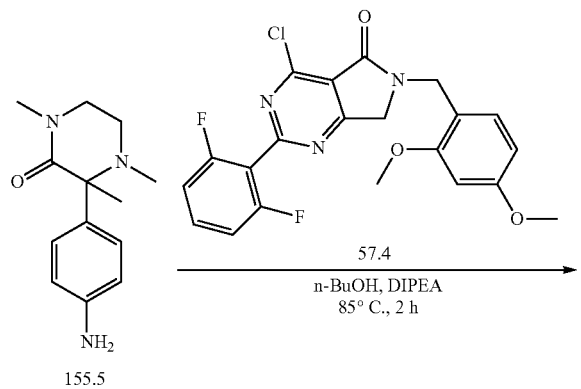

155.5

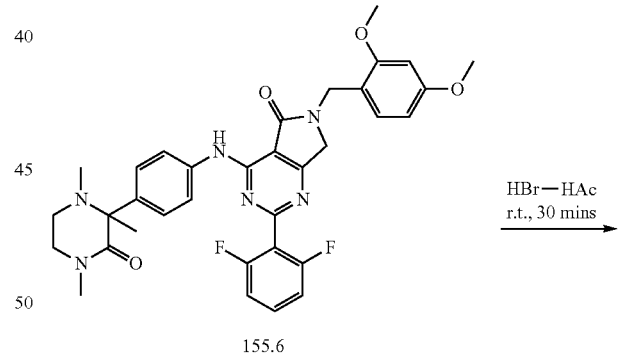

155.6

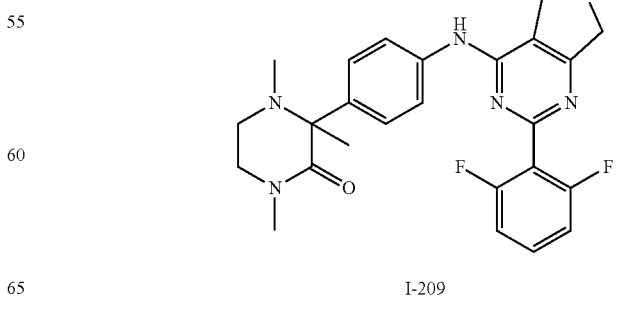

I-209

Synthesis of Compound 155.2.

To a solution of 155.1 (1.0 g, 4.72 mmol, 1.0 eq) in THF (15 ml) was added MeI (0.75 g, 5.25 mmol, 1.1 eq), 18-crown-6 (0.315 g, 1.19 mmol, 0.25 eq). Reaction mixture was cooled to −78° C. for 1 hour. To this solution was added Potassium tert-butoxide (0.590 g, 5.25 mmol, 1.1 eq). Reaction mixture was stirred at room temperature over night. After completion of the reaction, reaction mixture was cooled at −78° C. was added NH$_4$Cl solution and product was extracted with EtOAC. Organic layers were combined, dried over sodium sulphate and concentrated under reduced pressure to obtain the crude which was purified by column chromatography to get 155.2 (1.0 g, 93.72%). MS (ES): m/z 223.23 [M+H]$^+$.

Synthesis of Compound 178.3.

To a solution of 155.2 (0.9 g, 4.72 mmol, 1.0 eq) in CCl$_4$ (10 mL) were added NBS (0.571 g, 4.8 mmol, 1.2 eq), AIBN (0.066 g, 0.40 mmol, 0.1 eq). Reaction mixture was heated at 78° C. over night. To this reaction mixture was added NBS (0.571 g, 4.8 mmol, 1.2 eq), AIBN (0.066 g, 0.40 mmol, 0.1 eq). Reaction mixture was heated at 78° C. for 5-6 hours. Upon completion mixture was filtered and washed with hexane. Filtrate was purified by column chromatography to get 155.3 (0.5 g, 41.05%). MS (ES): m/z 302.23 [M+H]$^+$.

Synthesis of Compound 155.4.

To a solution of 155.3 (0.1 g, 0.33 mmol, 1.0 eq) in EtOH (2 mL) was added Dimethyl ethylamine (0.028 g, 0.40 mmol, 1.2 eq). The reaction was then stirred at room temperature for over night. After completion of the reaction, mixture was poured into water and product was extracted with EtOAC. Organic layers were combined and dried over sodium sulphate and concentrated under reduced pressure to obtain crude which was purified to get pure 155.4 (0.068 g, 78.03%). MS (ES): m/z 263.3 [M+H]$^+$.

Synthesis of Compound 155.5.

To a solution of 155.4 (0.068 g, 0.258 mmol, 1.0 eq) in MeOH (10 ml) was added 10% Pd/C (0.024 g) under nitrogen atmosphere. It was purged with hydrogen gas for 1.5 hours. Reaction mixture was filtered through celite and obtained filtrate was concentrated under reduced pressure to get crude 155.5 (0.059 g, 97.91%) which was used as such for the next step, MS (ES): m/z 233.23 [M+H]$^+$.

Synthesis of Compound 155.6.

To a solution of 57.4 (0.110 g, 0.25 mmol, 1.0 eq.) in t-Butanol (5 ml) was added 155.5 (0.059 g, 0.25 mmol, 1.0 eq.) and DIPEA (0.08 g, 0.62 mmol, 2.5 eq) at room temperature. Reaction was stirred at 85° C. for 2 h. After completion of the reaction, mixture was poured into water and extracted using EtOAc. Organic layer was washed with brine solution. Organic layer was dried over sodium sulfate and concentrated under reduced pressure. Crude was purified by column chromatography, to afford pure 155.6 (0.130 g, 81.18%). MS (ES): m/z 628.6 [M+H]$^+$.

Synthesis of Compound I-209.

A solution of 155.6 (0.130 g) in HBr in HOAc (6 mL) was stirred at room temperature for 30 min. After completion of the reaction, mixture was concentrated under reduced pressure at 45° C. Obtained residue was poured into cold water, neutralized with NaHCO$_3$ and product was extracted with EtOAC. Solvent was removed under reduced pressure and crude was purified by preparative TLC to afford pure I-209 (0.079 g, 79.84%). MS (ES): m/z 478.4 [M+H]$^+$, $^1$H NMR (400 MHz, DMSO-d6): δ 9.05 (s, 1H), 8.91 (s, 1H), 7.72-7.70 (d, 2H), 7.62-7.58 (m, 1H), 7.40-7.38 (d, 2H), 7.30-7.25 (m, 2H), 4.48 (s, 2H), 3.29-3.26 (m, 3H), 2.82 (s, 4H), 2.03 (s, 3H), 1.50 (s, 3H).

Example 156. Synthesis of (R)-2-(2,6-difluorophenyl)-4-((4-(1,2,4-trimethyl-3-oxopiperazin-2-yl)phenyl)amino)-6,7-dihydro-5H-pyrrolo[3,4-d]pyrimidin-5-one, I-210

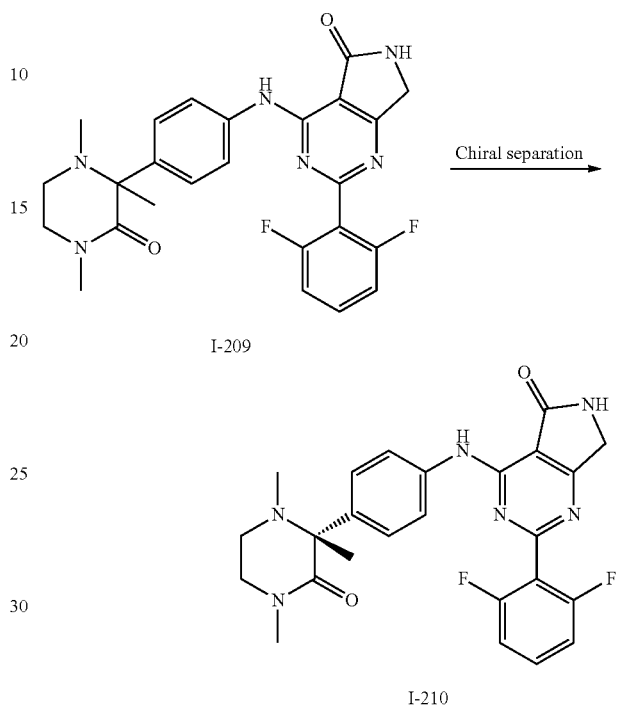

Compound I-210 was prepared by chiral separation of compound I-209. MS (ES): m/z 478.4 [M+H]$^+$, $^1$H NMR (400 MHz, DMSO-d$_6$): δ 9.05 (s, 1H), 8.91 (s, 1H), 7.72-7.70 (d, 2H), 7.63-7.58 (m, 1H), 7.40-7.38 (d, 2H), 7.30-7.26 (m, 2H), 4.48 (s, 2H), 3.51-3.47 (m, 2H), 3.30-3.24 (m, 2H), 2.28 (s, 3H), 2.03 (s, 3H), 1.50 (s, 3H).

Example 157. Synthesis of (S)-2-(2,6-difluorophenyl)-4-((4-(1,2,4-trimethyl-3-oxopiperazin-2-yl)phenyl)amino)-6,7-dihydro-5H-pyrrolo[3,4-d]pyrimidin-5-one, I-211

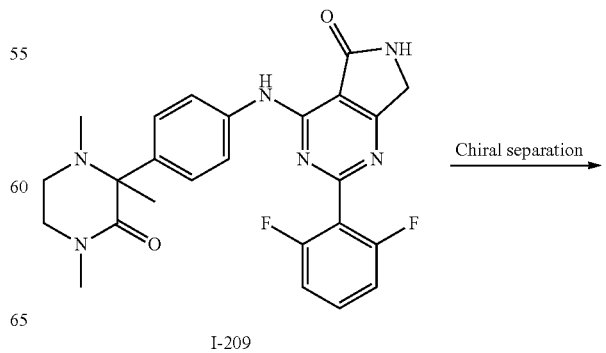

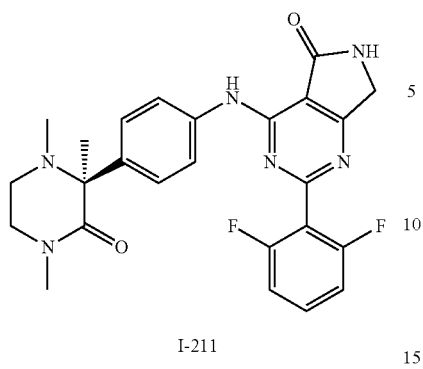

I-211

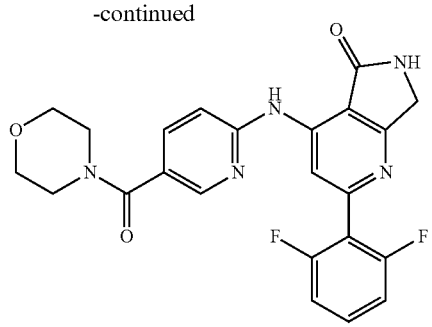

I-212

Compound I-209 was prepared by chiral separation of compound I-211. MS (ES): m/z 478.4 [M+H]⁺, ¹H NMR (400 MHz, DMSO-d₆): δ 9.05 (s, 1H), 8.91 (s, 1H), 7.72-7.70 (d, 2H), 7.64-7.57 (m, 1H), 7.40-7.38 (d, 2H), 7.30-7.26 (m, 2H), 4.48 (s, 2H), 3.53-3.47 (m, 2H), 3.30-3.24 (m, 2H), 2.86 (s, 3H), 2.03 (s, 3H), 1.50 (s, 3H).

Example 158. Synthesis of 2-(2,6-difluorophenyl)-4-((5-(morpholine-4-carbonyl)pyridin-2-yl)amino)-6,7-dihydro-5H-pyrrolo[3,4-b]pyridin-5-one, I-212

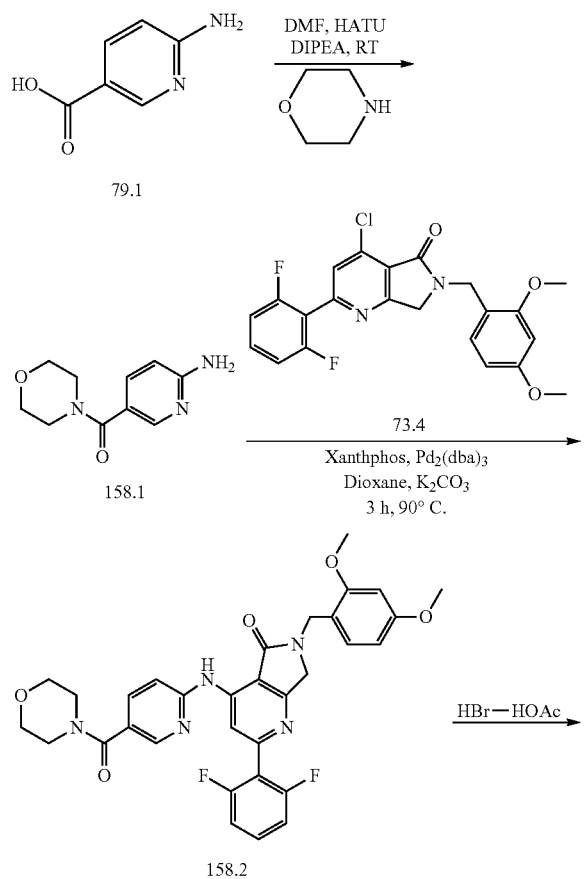

Synthesis of Compound 158.1.

To a solution of 79.1 (0.5 g, 3.62 mmol, 1.0 eq) in DMF (10 ml) was added morpholine (0.380 g, 4.34 mmol, 1.2 eq), HATU (2.0 g, 5.4 mmol, 1.5 eq). Reaction mixture was cooled to 0° C. DIPEA (1.8 ml, 10.8 mmol, 3.0 eq) was added at 0° C. Reaction was stirred at room temperature for 2 h. The reaction mixture was poured into water and product was extracted with EtOAc. Organic layers were combined, dried over sodium sulphate and concentrated under reduced pressure to obtain crude which was purified by column chromatography to get pure 158.1 (0.200 g, 26.66%). MS (ES): m/z 225.2 [M+H]⁺.

Synthesis of Compound 158.2.

To a solution of 73.4 (0.190 g, 0.44 mmol, 1.0 eq) in 1,4-dioxane (3 ml) was added 79.1 (0.1 g, 0.44 mmol, 1.0 eq) and K₂CO₃ (0.180 g, 1.32 mmol, 3.0 eq). The reaction mixture was degassed for 10 min. using argon, then Pd₂(dba)₃ (0.04 g, 0.044 mmol, 0.1 eq) and Xantphos (0.05 g, 0.088 mmol, 0.2 eq) were added, again degassed for 5 min. Reaction was heated at 110° C. for 4 h. After completion of the reaction, mixture was poured into water and product was extracted with EtOAc. Organic layers were combined and dried over sodium sulphate and concentrated under reduced pressure to obtain crude material which was purified using column chromatography to get pure 158.2 (0.100 g, 14.32%). MS (ES): m/z 601.6 [M+H]⁺.

Synthesis of Compound I-212.

Compound 158.2 (0.100 g, 0.166 mmol, 1.0 eq) was dissolved in HBr/HOAc (2 ml) and stirred at room temperature for 1 h. After completion of the reaction, mixture was poured into water and basified with saturated bicarbonate solution and extracted with EtOAc. Organic layers were combined and dried over sodium sulphate and concentrated under reduced pressure to obtain crude which was purified by column chromatography to furnish I-212 (0.040 g, 53.3%). MS (ES): m/z 451.5 [M+H]⁺, ¹H NMR (DMSO-d₆, 400 MHz): 9.93 (S, 1H), 8.95 (S, 1H), 8.60 (s, 1H), 8.42-8.41 (d, 1H), 7.84-7.81 (m, 1H), 7.62-7.55 (m, 1H), 7.29-7.23 (m, 3H), 4.46 (s, 2H), 3.60-3.52 (m, 8H).

Example 159. Synthesis of 2-(2,6-difluorophenyl)-4-((4-(5,5-dimethyl-2-oxopyrrolidin-3-yl)phenyl)amino)-6,7-dihydro-5H-pyrrolo[3,4-d]pyrimidin-5-one, I-213

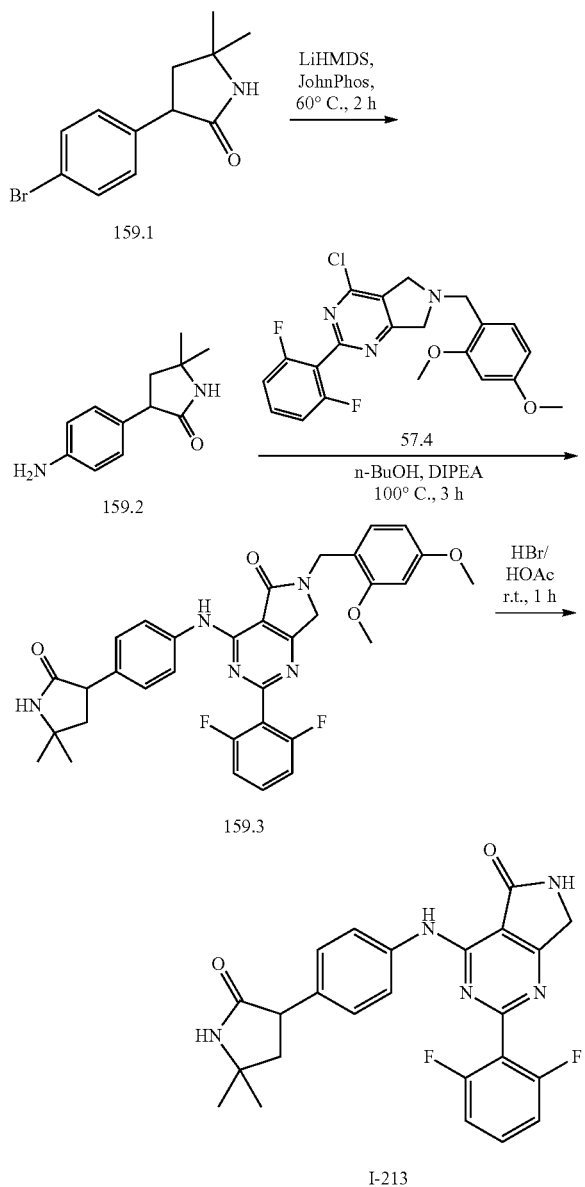

Synthesis of Compound 159.2.

To a solution of 182.1 (0.4 g, 1.44 mmol, 1.0 eq) in THF (10 ml) was degassed for 10 min. LHMDS (7.5 ml, 7.5 mmol, 5.0 eq), Pd$_2$(dba)$_3$ (0.013 g, 0.014 mmol, 0.1 eq), and JohnPhos (0.011 g, 0.03 mmol, 0.2 eq) were added. reaction mixture was heated at 60° C. for 2 h. After completion of reaction, mixture was quenched with ice cold water and product was extracted with EtOAc. Organic layers were combined, dried over sodium sulphate and concentrated under reduced pressure to get 159.2 (0.130 g, 42.66%). MS (ES): m/z 204.2 [M+H]$^+$.

Synthesis of Compound 159.3.

To a solution of 57.4 (0.05 g, 0.11 mmol, 1.0 eq) in 1-butanol (5 ml) was added 159.3 (0.023 g, 0.11 mmol, 1.0 eq) and DIPEA (0.05 ml, 0.33 mmol, 3 eq). The reaction was stirred at 100° C. for 3 h. After completion of the reaction, mixture was poured into water and product was extracted with EtOAc. Organic layers were combined, dried over sodium sulphate and concentrated under reduced pressure to obtain crude which was purified using column chromatography to get pure 159.3 (0.04 g, 57.61%). MS (ES): m/z 599.5 [M+H]$^+$.

Synthesis of Compound I-213.

Mixture of 159.3 (0.04 g, 0.06 mmol, 1.0 eq) and HBr/HOAc (5 mL) was stirred at room temperature for 1 hour. Reaction mixture was neutralized using satd. NaHCO$_3$ solution and extracted with ETOAc. Organic layers were combined, dried over sodium sulphate and concentrated under reduced pressure to obtain crude which was purified by column chromatography to furnish I-213 (0.015 g, 50.0%). MS (ES): m/z 449.7 [M+H]$^+$. $^1$H NMR (DMSO-d$_6$, 400 MHz): δ 9.06 (s, 1H), 8.89 (s, 1H), 7.92 (s, 1H), 7.69-7.67 (d, 2H), 7.62-7.58 (m, 1H), 7.28-7.20 (m, 4H), 4.47 (s, 2H), 3.79-3.74 (t, 1H), 2.33-2.27 (m, 1H), 1.91-1.85 (m, 1H), 1.29-1.18 (m, 6H).

Example 160. Synthesis of 2-(2,6-difluorophenyl)-4-((5-(3-hydroxyazetidin-1-yl)pyridin-2-yl)amino)-6,7-dihydro-5H-pyrrolo[3,4-b]pyridin-5-one, I-214

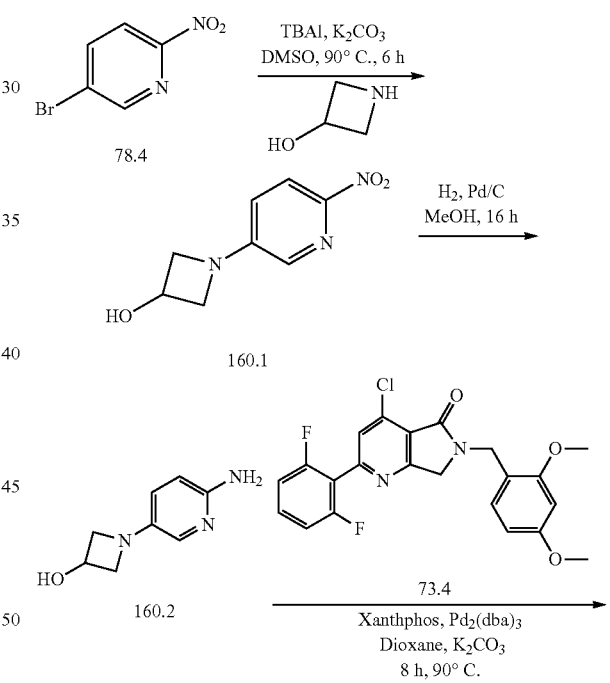

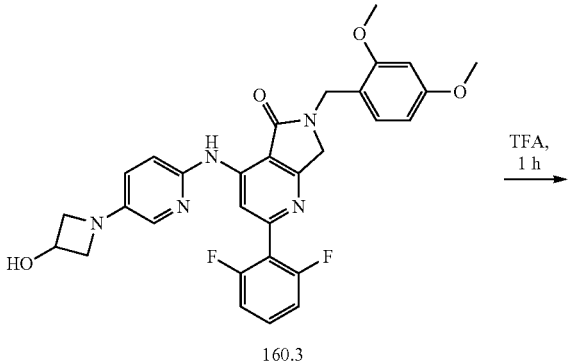

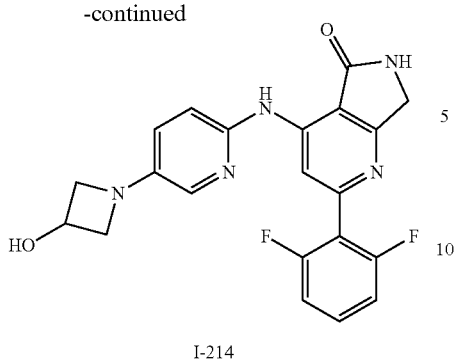

I-214

Synthesis of Compound 160.1.

To a solution of 78.4 (0.4 g, 1.97 mmol, 1.0 eq) in DMSO (3 ml) were added tetrabutyl ammonium iodide (0.072 g, 0.19 mmol, 1.2 eq), azetidin-3-ol (0.259 g, 2.36 mmol, 1.2 eq), and $K_2CO_3$ (0.81 g, 5.9 mmol, 3.0 eq). Reaction mixture was heated at 100° C. for 5 h. Reaction mixture was poured into water and product was extracted with EtOAc. Organic layers were combined, dried over sodium sulphate and concentrated under reduced pressure to obtain crude which was purified to get pure 160.1 (0.2 g, 52.0%). MS (ES): m/z 195.1 $[M+H]^+$.

Synthesis of Compound 160.2.

A solution of 160.1 (0.2 g, 1.02 mmol, 1.0 eq) in MeOH (5 mL) was added 10% Pd/C (0.1 g) under nitrogen atmosphere. It was purged with hydrogen gas for 1 h. Reaction mixture was filtered through celite and obtained filtrate was concentrated under reduced pressure to get crude 160.2 (0.140 g, 70.82%) which was used as such for the next step, MS (ES): m/z 165.23 $[M+H]^+$.

Synthesis of Compound 160.3.

To a solution of 73.4 (0.2 g, 0.60 mmol, 1.0 eq) in 1,4-dioxane (5 mL) were added 183.2 (0.1 g, 0.60 mmol, 1.0 eq) and $K_2CO_3$ (0.250 g, 1.80 mmol, 3.0 eq). The reaction mixture was degassed for 10 min. under argon atmosphere, then Pd2(dba)3 (0.055 g, 0.060 mmol, 0.1 eq) and Xantphos (0.070 g, 0.012 mmol, 0.2 eq) were added. The reaction was then heated at 110° C. for 6 h. After completion of the reaction, mixture was poured into water and product was extracted with EtOAC. Organic layer was dried over sodium sulphate and concentrated under reduced pressure to obtain crude which was purified to get pure 160.3 (0.1 g, 38.5%). MS (ES): m/z 559.6 $[M+H]^+$.

Synthesis of Compound I-214.

The compound 160.3 (0.1 g, 0.178 mmol, 1.0 eq) was dissolved in TFA (2 ml) and stirred at room temperature for 1 h. After completion of the reaction, mixture was poured into water and basified with saturated bicarbonate solution and extracted with EtOAc. Organic layers were combined, dried over sodium sulphate and concentrated under reduced pressure to obtain crude which was purified by column chromatography to get pure I-214 (0.005 g, 6.83%). MS (ES): m/z 409.4 $[M+H]^+$ $^1H$ NMR (DMSO-$d_6$, 400 MHZ): 9.40 (s, 1H), 8.75 (s, 1H), 8.27 (s, 1H), 7.58-7.53 (m, 2H), 7.25-7.21 (m, 2H), 7.06-7.04 (d, 1H), 6.97-6.95 (d, 1H), 4.54-4.53 (m, 1H), 4.38 (s, 2H), 4.09-4.05 (m, 2H), 3.68-3.69 (d, 1H), 3.51-3.48 (m, 2H).

Example 161. Synthesis of 2-(2,6-difluorophenyl)-4-((4-(2,4-dimethyl-3-oxopiperazin-2-yl)phenyl)amino)-6,7-dihydro-5H-pyrrolo[3,4-d]pyrimidin-5-one, I-215

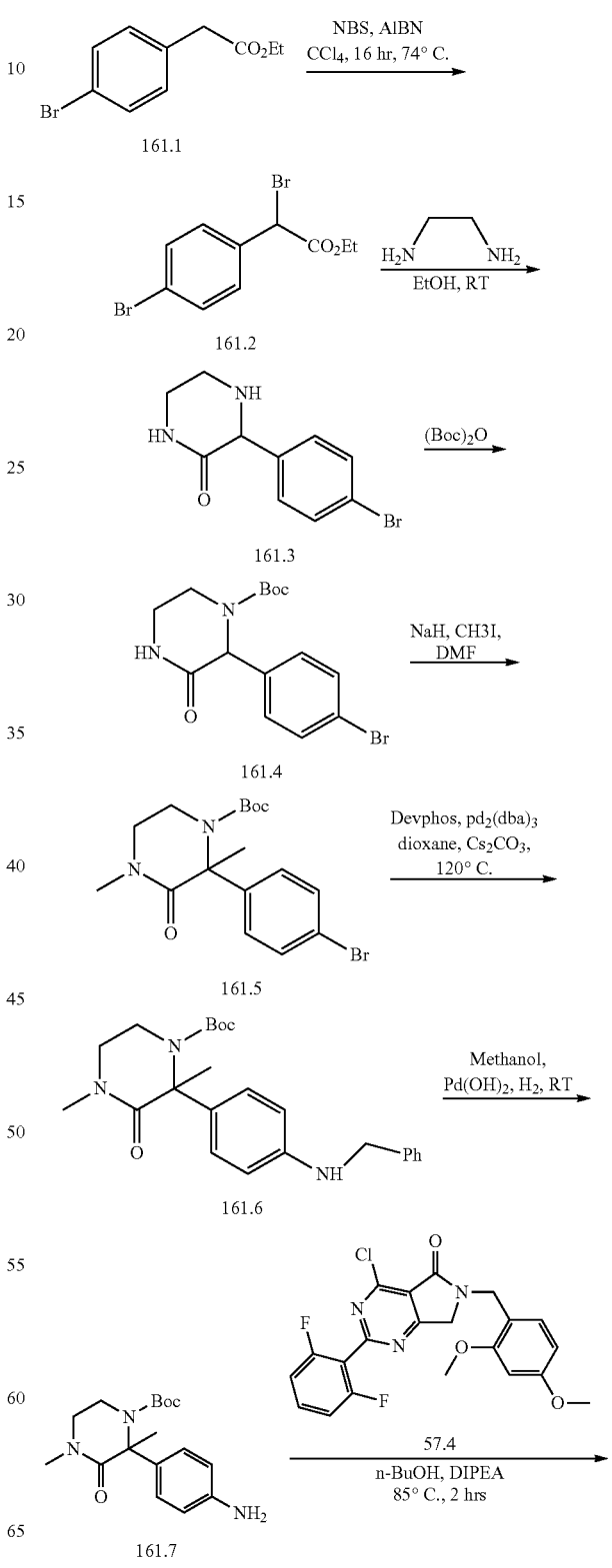

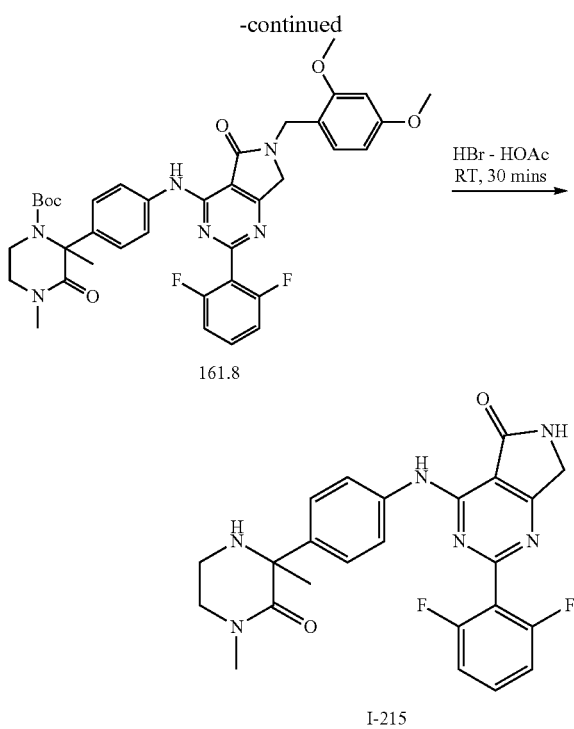

Synthesis of Compound 161.2.

To a solution of 161.1 (5 g, 20.57 mmol, 1.0 eq.) in CCl$_4$ (25 mL) were added NBS (2.91 g, 24.69 mmol, 1.2 eq.) and AIBN (0.1 g, 0.61 mmol, 0.03 eq.). Reaction mixture was stirred at 80° C. for 6 hours. Again add NBS (2.91 g, 24.69 mmol, 1.2 eq.) and AIBN (0.1 g, 0.61 mmol, 0.03 eq.) and reaction mixture was stirred at 80° C. for addition 6 hrs. After completion of the reaction, mixture was filtered and washed with CH$_2$C12 (50 ml×3). The filtrate was concentrated under reduced pressure to afford crude compound 161.2 (6 g, 90.63%), which was used for the next step without further purification.

Synthesis of Compound 161.3.

To a solution of 161.2 (6 g, 18.60 mmol, 1.0 eq.) in EtOH (50 ml) was added ethane-1,2-diamine (5.6 g, 93.1 mmol. 5.0 eq.) and stirred for 3 hrs at room temperature. After completion of the reaction, solvent was evaporated and reaction mixture was poured into water and extracted using EtOAc. Organic layer was washed with brine, and dried over sodium sulfate and concentrated under reduced pressure to get crude. The crude was purified by triturating in hexane to afford pure 161.3 (4.5 g, 95.74%), MS (ES): m/z 256.2 [M+H]$^+$ Synthesis of Compound 161.4.

To a solution of 161.3 (5.3 g, 20.7 mmol, 1.0 eq.) in CH$_2$Cl$_2$ (50.0 mL) was added boc anhydride (9 g, 41.5 mmol, 2.0 eq.). The reaction mixture was stirred at room temperature for 3 hrs. After completion of the reaction, mixture was poured into water and extracted using CH$_2$Cl$_2$ (50 ml×3). Organic layer was washed with brine, dried over sodium sulfate and concentrated under reduced pressure to get crude. The crude was purified by triturating in hexane to afford pure 161.4 (4.7 g, 64%), MS (ES): m/z 356.2 [M+H]$^+$ Synthesis of Compound 161.5.

To a suspension of NaH (60% dispersion in mineral oil (2.64 g, 66.1 mmol, 5.0 eq.) in DMF (50.0 mL) was added 161.4 (4.7 g, 13.2 mmol, 1.0 eq.). The reaction mixture was stirred at room temperature for 30 minutes and to it was added MeI (9.4 g, 66.1 mmol, 5.0 eq.). The reaction mixture was stirred for 3 hrs at room temperature. After completion of the reaction, mixture was poured in to ice water, stirred d for 30 minutes. Solids were filtered and washed with water. Crude was purified by trituration to furnish 161.5 (4 g, 80%), MS (ES): m/z 384.1 [M+H]$^+$.

Synthesis of Compound 161.6.

To a solution of 161.5 (2 g, 5.2 mmol, 1.0 eq.) in 1-4 Dioxane (20.0 mL) were added Cs$_2$CO$_3$ (3.4 g, 10.4 mmol, 2.0 eq.) and benzyl amine (0.84 g, 7.8 mmol, 1.5 eq.) and degassed for 30 minutes under argon. 2-Dicyclohexylphosphino-2'-(N,N-dimethylamino)biphenyl (0.41 g, 1.0 mmol, 0.2 eq.) and Pd$_2$(dba)$_3$ (0.47 g, 0.52 mmol, 0.1 eq.) were added. The reaction mixture was heated at 120° C. for 3 hours. After completion of the reaction, mixture was poured into water and extracted using EtOAc. Organic layer was washed with brine. Organic layer was dried over sodium sulfate and concentrated under reduced pressure to get crude. The crude was purified by column chromatography to afford pure 161.6 (1 g, 46.9%), MS (ES): m/z 409.9 [M+H]$^+$.

Synthesis of Compound 161.7.

To a suspension of Pd(OH)$_2$ (1.1 g) in MeOH (30.0 mL) was added 184.6 (1 g, 2.4 mmol, 1.0 eq.). Hydrogen gas was bubbled for 3 hrs at room temperature. After completion of the reaction, mixture was filtered through celite bed and washed with methanol. The filtrate was concentrated under reduced pressure to get crude. The crude was purified by column chromatography to afford pure 161.7 (0.5 g, 64.1%), MS (ES): m/z 319.9 [M+H]$^+$.

Synthesis of Compound 161.8.

To a solution of 57.4 (0.15 g, 0.348 mmol, 1.0 eq.) in n-butanol (1.0 mL) was added 161.7 (0.11 g, 0.35 mmol, 1.0 eq.). DIPEA (0.09 g, 0.69 mmol, 2.0 eq.) was added. The reaction mixture was stirred at 80° C. for 2 hours. After completion of the reaction, mixture was poured into water and extracted using EtOAc. Organic layer was washed by brine, dried over sodium sulfate and concentrated under reduced pressure to afford 161.8 (0.2 g, 80.64%), which was used for the next step without further purification. MS (ES): m/z 715.2 [M+H]$^+$.

Synthesis of Compound I-215.

A solution of 161.8 (0.2 g, 0.28 mmol, 1.0 eq.) in HBr/HOAc (33%) (1.5 ml) was stirred at room temperature for 45 minutes. After completion of the reaction, mixture was poured into cold water, neutralized with NaHCO$_3$ and extracted with EtOAc. Solvent was removed under reduced pressure. The crude was purified by triturating with hexane to afford I-215 (65 mg, 50.38%). MS (ES): m/z −465.17 [M+H]$^+$, $^1$H NMR (400 MHz, DMSO-d$_6$): δ 9.04 (s, 1H), 8.90 (s, 1H), 7.72-7.70 (d, 2H), 7.62-7.58 (m, 1H), 7.47-7.45 (d, 2H), 7.30-7.26 (t, 2H), 4.48 (s, 2H), 3.18-3.16 (d, 2H), 3.11-3.09 (d, 2H), 2.86 (s, 3H), 1.41 (s, 3H).

443

Example 162. Synthesis of (R)-2-(2,6-difluorophenyl)-4-((4-(2,4-dimethyl-3-oxopiperazin-2-yl)phenyl)amino)-6,7-dihydro-5H-pyrrolo[3,4-d]pyrimidin-5-one, I-216

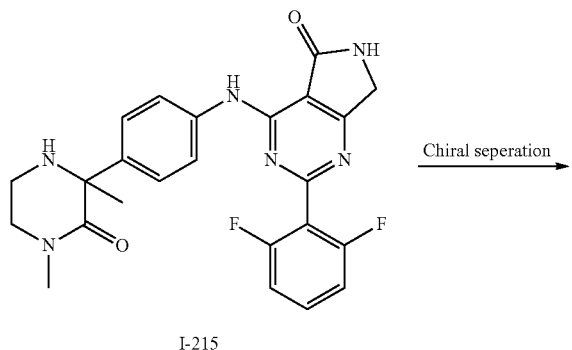

I-215

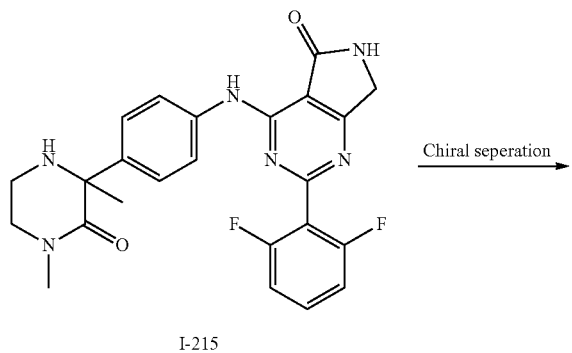

I-216

Compound I-216 was prepared by chiral separation of I-215. ¹H NMR (400 MHz, MeOD): δ 7.81-7.79 (d, 2H), 7.59-7.52 (m, 1H), 7.46-7.44 (d, 2H), 7.17-7.13 (t, 2H), 4.51 (s, 2H), 3.96-3.92 (m, 1H), 3.58-3.51 (m, 1H), 3.30-3.26 (m, 2H), 3.04 (s, 3H), 1.62 (s, 3H).

Example 163. Synthesis of (S)-2-(2,6-difluorophenyl)-4-((4-(2,4-dimethyl-3-oxopiperazin-2-yl)phenyl)amino)-6,7-dihydro-5H-pyrrolo[3,4-d]pyrimidin-5-one, I-217

444

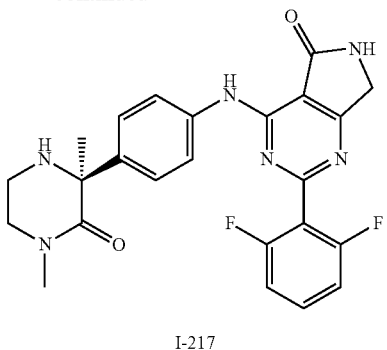

I-217

Compound I-217 was prepared by chiral separation of I-215. ¹H NMR (400 MHz, MeOD): δ 8.00-7.98 (d, 2H), 7.59-7.53 (m, 1H), 7.49-7.47 (d, 2H), 7.17-7.13 (t, 2H), 4.54 (s, 2H), 3.96-3.92 (m, 1H), 3.77-3.72 (m, 1H), 3.67-3.62 (m, 1H), 3.50-3.43 (m, 1H), 3.14 (s, 3H), 1.96 (s, 3H).

Example 164. Synthesis of (S)-2-(2,6-difluorophenyl)-4-((4-(5,5-dimethyl-2-oxopyrrolidin-3-yl)phenyl)amino)-6,7-dihydro-5H-pyrrolo[3,4-d]pyrimidin-5-one, I-218

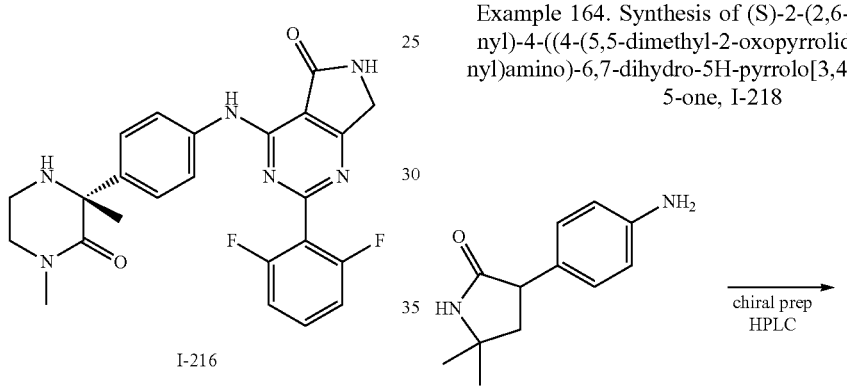

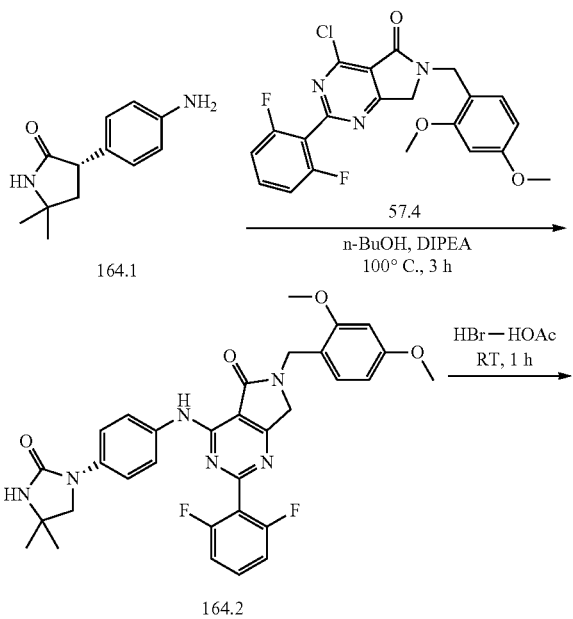

445
-continued

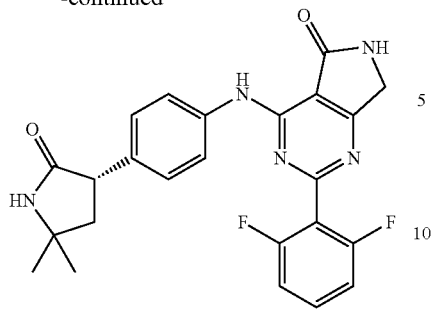

I-218

Synthesis of Compound 164.1.

Compound 164.1 was prepared by chiral separation of compound 159.2.

Synthesis of Compound 164.2.

To a solution of 57.4 (0.1 g, 0.23 mmol, 1.0 eq) in 1-butanol (2 mL) was added 187.1 (0.04 g, 0.23 mmol, 1.0 eq) and DIPEA (0.12 g, 0.69 mmol, 3 eq). The reaction mixture was then heated at 100° C. for 3 h. After completion of the reaction, mixture was poured in water and product was extracted with EtOAc. Organic layers were combined, dried over sodium sulphate and concentrated under reduced pressure to obtain crude which was purified by column chromatography to get pure 164.2 (0.05 g, 36.01%). MS (ES): m/z 599.5 [M+H]$^+$.

Synthesis of Compound I-218.

Mixture of 164.2 (0.05 g, 0.08 mmol, 1.0 eq) and HBr/HOAc (5 mL) was stirred at room temperature for 1 h. Reaction mixture was neutralized using satd. NaHCO$_3$ solution and extracted with ethyl acetate (25 mL×2). Organic layers were combined, dried over sodium sulphate and concentrated under reduced pressure to obtain crude which was purified using column chromatography to get pure I-218 (0.020 g, 53.37%). MS (ES): m/z 449.7 [M+H]$^+$; $^1$H NMR (CDCl$_3$, 400 MHz): δ 8.81 (s, 1H), 7.80-7.78 (d, 2H), 7.46-7.40 (m, 1H), 7.31-7.29 (d, 2H), 7.07-7.02 (m, 2H), 6.20 (s, 1H), 5.74 (s, 1H), 4.56 (s, 2H), 3.88-3.83 (t, 1H), 2.48-2.42 (t, 1H), 2.10-2.03 (t, 1H), 1.39-1.38 (d, 6H).

Example 165. Synthesis of (R)-2-(2,6-difluorophenyl)-4-((4-(5,5-dimethyl-2-oxopyrrolidin-3-yl)phenyl)amino)-6,7-dihydro-5H-pyrrolo[3,4-d]pyrimidin-5-one I-219

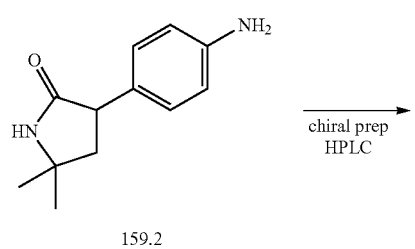

159.2

446
-continued

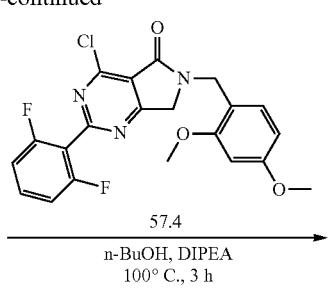

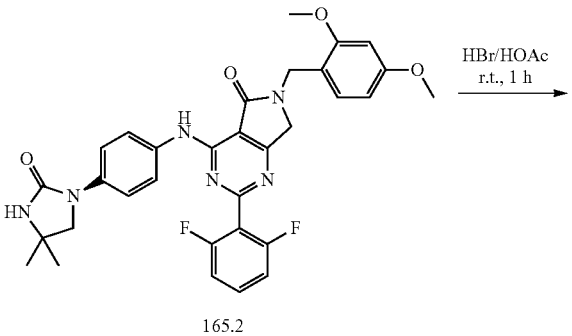

165.2

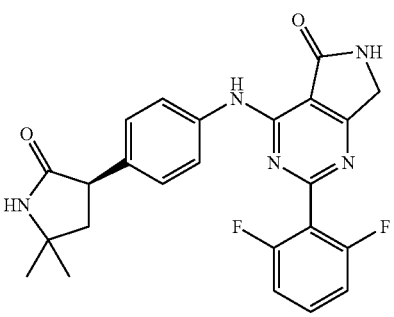

I-219

Synthesis of Compound 165.1.

Compound 165.1 was prepared by chiral separation of compound 159.2.

Synthesis of Compound 165.2

Compound 165.2 was prepared using equivalent protocol described for preparation of compound 164.2 (0.05 g, 36.0%). MS (ES): m/z 599.5 [M+H]$^+$.

Synthesis of Compound I-219.

Compound I-219 was prepared using procedure described for preparation of compound I-218 (0.02 g, 53.4%). MS (ES): m/z 449.7 [M+H]$^+$. $^1$H NMR (CDCl$_4$, 400 MHz): δ 8.79 (s, 1H), 7.80-7.78 (d, 2H), 7.45-7.41 (m, 1H), 7.31-7.29 (d, 2H), 7.06-7.02 (m, 2H), 6.27 (s, 1H), 5.79 (s, 1H), 4.54 (s, 2H), 3.88-3.83 (m, 1H), 2.48-2.42 (m, 1H), 2.10-2.04 (m, 1H), 1.39-1.38 (d, 6H).

Example 166. Synthesis of 2-(2,6-difluorophenyl)-4-((4-(1,3,5,5-tetramethyl-2-oxo-pyrrolidin-3-yl)phenyl)amino)-6,7-dihydro-5H-pyrrolo[3,4-d]pyrimidin-5-one, I-220
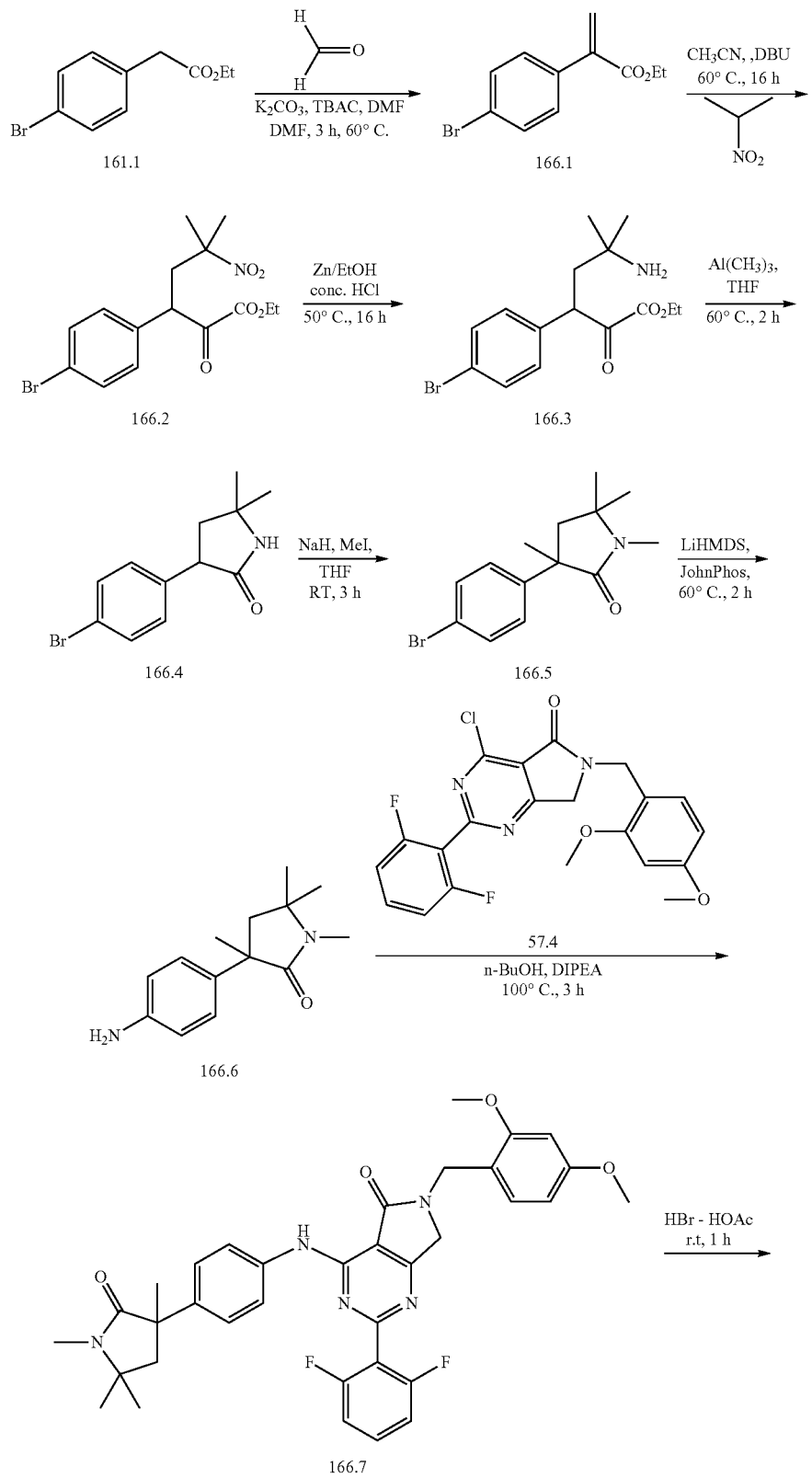

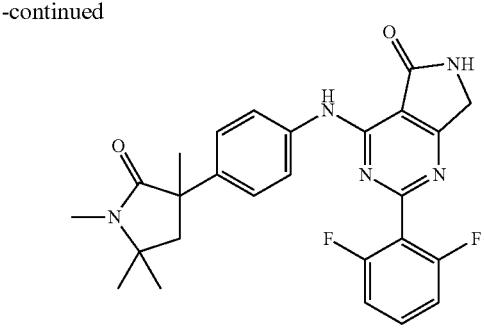

I-220

Synthesis of Compound 166.1.

To a solution of ethyl 161.1 (5.0 g, 20.6 mmol, 1.0 eq) in CH$_2$Cl$_2$ (50 mL) was added preraformaldehyde (0.938 g, 24.69 mmol, 1.2 eq) followed by tetrabutylammonium chloride (0.571 g, 2.05 mmol, 0.1 eq), and K$_2$CO$_3$ (6.2 g, 45.26 mmol, 2.2 eq). The reaction was stirred at 60° C. 3 h. The reaction mixture was quenched with ice cold water and product was extracted with CH$_2$Cl$_2$ (50 mL×2). Organic layer were combined and dried over sodium sulphate and concentrated under reduced pressure to obtain 166.1 (2.5 g, 47.65%). MS (ES): 256.4 m/z [M+H]$^+$.

Synthesis of Compound 166.2.

To a solution of 166.1 (2.5 g, 9.8 mmol, 1.0 eq) in CH3CN (20 mL) was added 2-nitro propane (1.0 g, 1.2 eq) and DBU (1.8 g, 1.17 mmol, 1.2 eq). Reaction mixture was heated at 60° C. over night. Reaction mixture was concentrated under reduced pressure. Residue was dissolved in EtOAc, washed with satd. NaHCO$_3$ solution. Organic layer was separated, dried over sodium sulaphate and concentrated under reduced pressure to obtain 166.2 (2.0 g, 54.83%) which was used as such for the next step, MS (ES): m/z 373.21 [M–H]$^+$ Synthesis of Compound 166.3.

To a solution of 166.2 (2.0 g, 6.0 mmol, 1.0 eq) in EtOH (30 mL) was added Zinc (0.69 g, 10.6 mmol, 5.0 eq), Conc HCl (5.2 ml). The reaction mixture was heated at 50° C. over night. Reaction mixture was diluted with ethyl EtOAc washed with satd. NaHCO$_3$ solution. Organic layer was dried over sodium sulphate and concentrated under reduced pressure to obtain 166.3 (1.8 g, 90.0%). MS (ES): m/z 342.3 [M+H]$^+$.

Synthesis of Compound 166.4.

To a solution 166.3 (1.8 g, 6.0 mmol, 1.0 eq) in THE (20 mL) was added Me$_3$Al (6 ml, 12.12 mmol, 2.0 eq) and DIPEA (2.0 ml, 12.12 mmol, 2.0 eq). Reaction mixture was heated at 60° C. for 2 h. After completion of reaction, mixture was quenched with ice cold water and product was extracted with ethyl EtOAc. Organic layers were combined and dried over sodium sulphate and concentrated under reduced pressure to get 166.4 (1.3 g, 92.2%). MS (ES): m/z 269.1 [M+H]$^+$.

Synthesis of Compound 166.5.

To a solution 166.4 (0.8 g, 2.9 mmol, 1.0 eq) in DMF (10 mL) was added NaH (60% in oil) (0.720 g, 14.9 mmol, 5.0 eq) at 0° C. Reaction mixture was stirred at 0° C. for 30 min. Methyl iodide (2.1 g, 14.9 mmol, 5.0 eq) was added dropwise at 0° C. Reaction mixture was stirred at room temperature for 3 h. After completion of the reaction, mixture was quenched with ice cold water and product was extracted with EtOAc. Organic layers were combined and dried over sodium sulphate and concentrated under reduced pressure to get 166.5 (0.6 g, 67.90%). MS (ES): m/z 297.2 [M+H]$^+$.

Synthesis of Compound 166.6.

A solution 166.5 (0.4 g, 1.44 mmol, 1.0 eq) in tTHF (10 ml) was degassed for 10 min. LHMDS (0.5 ml, 0.5 mmol, 3.0 eq), Pd$_2$(dba)$_3$ (0.015 g, 0.016 mmol, 0.1 eq), and (2-Biphenyl)di-tert-butylphosphine (0.011 g, 0.03 mmol, 0.2 eq) were added. Reaction mixture was heated at 60° C. for 2 h. After completion of the reaction, mixture was quenched with ice cold water and product was extracted with EtOAc. Organic layers were combined and dried over sodium sulphate and concentrated under reduced pressure to get 166.6 (0.2 g, 63.75%). MS (ES): m/z 232.2 [M+H]$^+$.

Synthesis of Compound 166.7.

To a solution of 57.4 (0.05 g, 0.11 mmol, 1.0 eq) in 1-butanol (2 mL) was added 189.6 (0.026 g, 0.11 mmol, 1.0 eq) and DIPEA (0.04 g, 0.33 mmol, 3 eq). The reaction mixture was then heated at 100° C. for 3 h. After completion of the reaction, mixture was poured into water and product was extracted with EtOAC. Organic layer was dried over sodium sulphate and concentrated under reduced pressure to obtain crude which was purified by column chromatography to get pure 166.7 (0.06 g, 82.55%). MS (ES): m/z 629.5 [M+H]$^+$.

Synthesis of Compound I-220.

Mixture of 166.7 (00.06 g, 0.09 mmol, 1.0 eq) and HBr/HOAc (5 mL) was stirred at room temperature for 1 h. Reaction mixture was neutralized using satd. NaHCO$_3$ and extracted with EtOAc. Organic layers were combined, dried over sodium sulphate and concentrated under reduced pressure to obtain crude which was purified by column chromatography to get pure I-220 (0.015 g, 32.86%). MS (ES): m/z 478.7 [M+H]$^+$. $^1$H NMR (DMSO-d$_6$, 400 MHz): δ 9.03 (s, 1H), 8.90 (s, 1H), 7.72-7.70 (d, 2H), 7.62-7.52 (m, 1H), 7.35-7.33 (d, 2H), 7.30-7.25 (m, 2H), 4.47 (s, 2H), 2.71 (s, 3H), 2.40-2.37 (d, 1H), 2.03-2.00 (d, 1H), 1.39 (s, 3H), 1.24 (s, 3H), 0.95 (s, 3H).

Example 167. Synthesis of (S)-2-(2,6-difluorophenyl)-4-((4-(1,3,5,5-tetramethyl-2-oxopyrrolidin-3-yl)phenyl)amino)-6,7-dihydro-5H-pyrrolo[3,4-d]pyrimidin-5-one, I-221

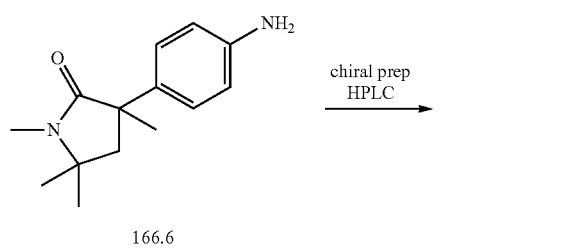

166.6

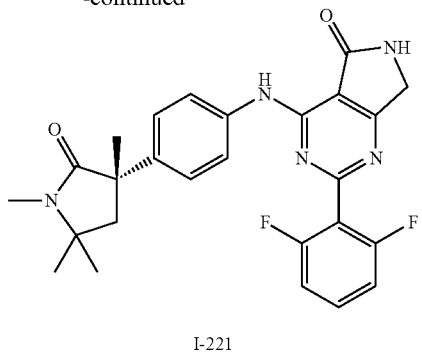

I-221

Synthesis of Compound 167.1.

Compound 167.1 was prepared by chiral separation of compound 166.6.

Synthesis of Compound 167.2.

To a solution of 57.4 (0.1 g, 0.23 mmol, 1.0 eq) in 1-butanol (2 mL) was added 167.1 (0.053 g, 0.23 mmol, 1.0 eq) and DIPEA (0.11 g, 0.92 mmol, 4 eq). The reaction mixture was then heated at 100° C. for 3 hours. After completion of the reaction, mixture was poured in water and product was extracted with EtOAc. Organic layers were combined, dried over sodium sulphate and concentrated under reduced pressure to obtain crude which was purified by column chromatography to get pure 167.2 (0.08 g, 55.04%). MS (ES): m/z 624.5 [M+H]$^+$.

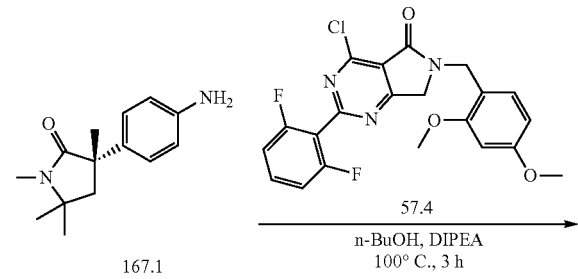

167.1

Synthesis of Compound I-221.

Mixture of 167.2 (0.08 g, 0.12 mmol, 1.0 eq) and HBr/HOAc (5 mL) was stirred at room temperature for 1 hour. Reaction mixture was neutralized using saturated NaHCO$_3$ solution and extracted with EtOAC. Organic layers were combined, dried over sodium sulphate and concentrated under reduced pressure to obtain crude which was purified by column chromatography to furnish I-221 (0.035 g, 57.51%). MS (ES): m/z 478.7 [M+H]$^+$. $^1$H NMR (DMSO-d$_6$, 400 MHz): δ 9.03 (s, 1H), 8.90 (1H), 7.72-7.70 (d, 2H), 7.64-7.57 (m, 1H), 7.35-7.33 (d, 2H), 7.30-7.25 (m, 2H), 4.47 (s, 2H), 2.82 (s, 3H), 2.40-2.37 (d, 1H), 2.03-1.99 (d, 1H), 1.39 (s, 3H), 1.31-1.27 (m, 3H), 0.95 (s, 3H).

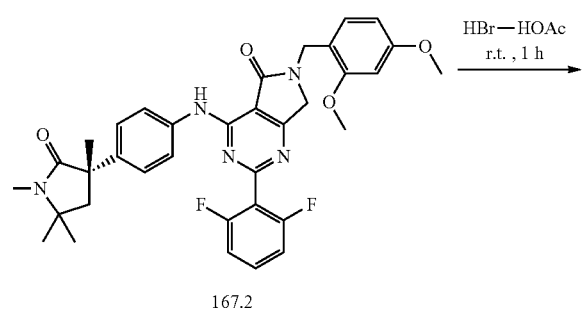

167.2

Example 168. Synthesis of (R)-2-(2,6-difluorophenyl)-4-((4-(1,3,5,5-tetramethyl-2-oxopyrrolidin-3-yl)phenyl)amino)-6,7-dihydro-5H-pyrrolo[3,4-d]pyrimidin-5-one, I-222

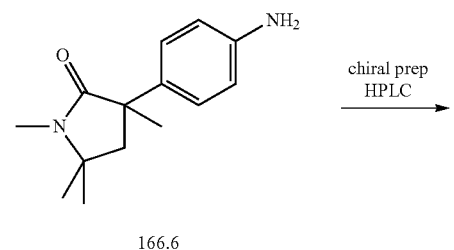

166.6

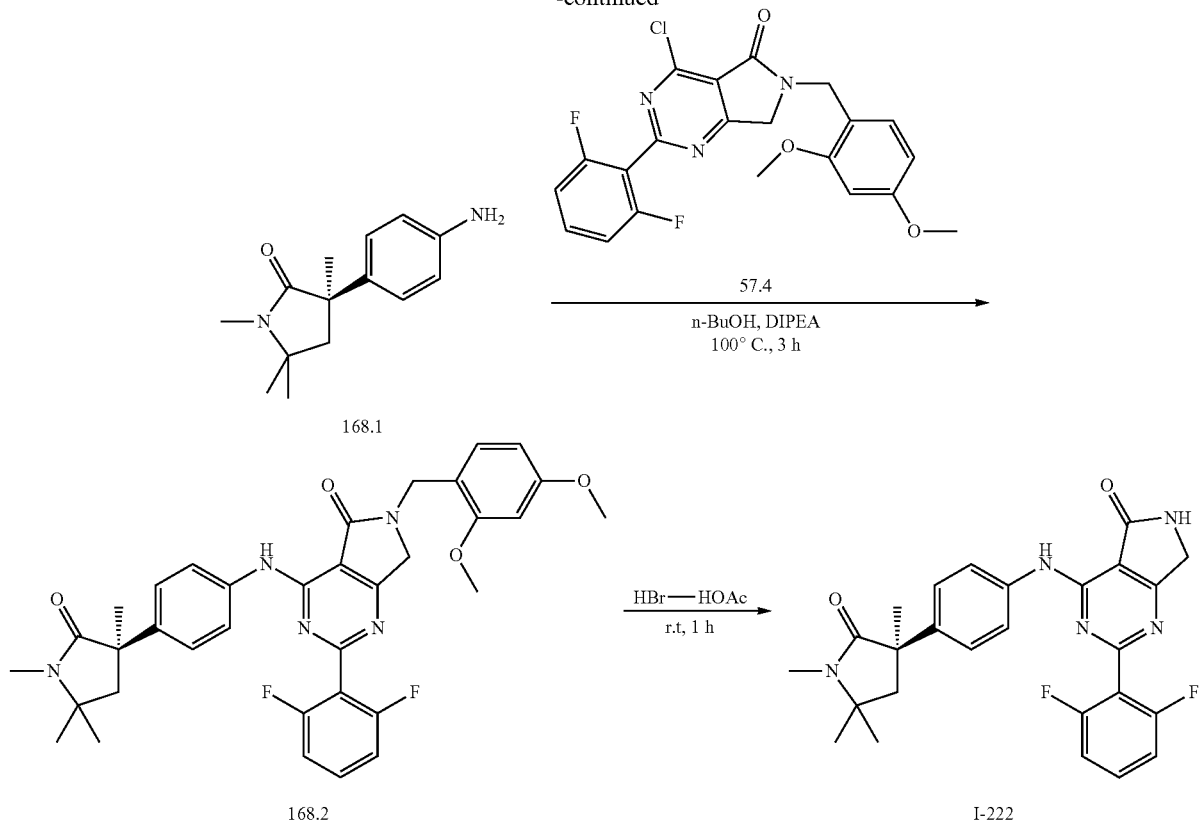

Synthesis of Compound 168.1.

Compound 168.1 was prepared by chiral separation of compound 166.6.

Synthesis of Compound 168.2.

Compound 168.2 was prepared using equivalent protocol described for preparation of compound 165.2 (0.05 g, 36.0%). MS (ES): m/z=624.5 [M+H]$^+$.

Synthesis of Compound I-222.

Compound I-222 was prepared using equivalent protocol described for preparation of compound I-221. MS (ES): m/z 478.7 [M+H]$^+$. $^1$H NMR (DMSO-d$_6$, 400 MHz): δ 9.03 (s, 1H), 8.90 (s, 1H), 7.72-7.70 (d, 2H), 7.64-7.57 (m, 1H), 7.35-7.33 (d, 2H), 7.30-7.25 (m, 2H), 4.47 (s, 2H), 2.71 (s, 3H), 2.40-2.37 (d, 1H), 2.03-1.99 (d, 1H), 1.39 (s, 3H), 0.95 (s, 3H).

Example 169. Synthesis of 2-(2,6-difluorophenyl)-4-((5-(2,4-dimethyl-3-oxopiperazin-2-yl)pyridin-2-yl)amino)-6,7-dihydro-5H-pyrrolo[3,4-b]pyridin-5-one, I-223

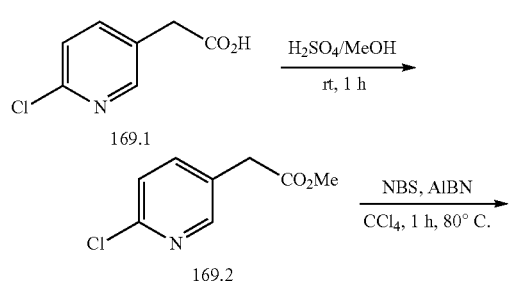

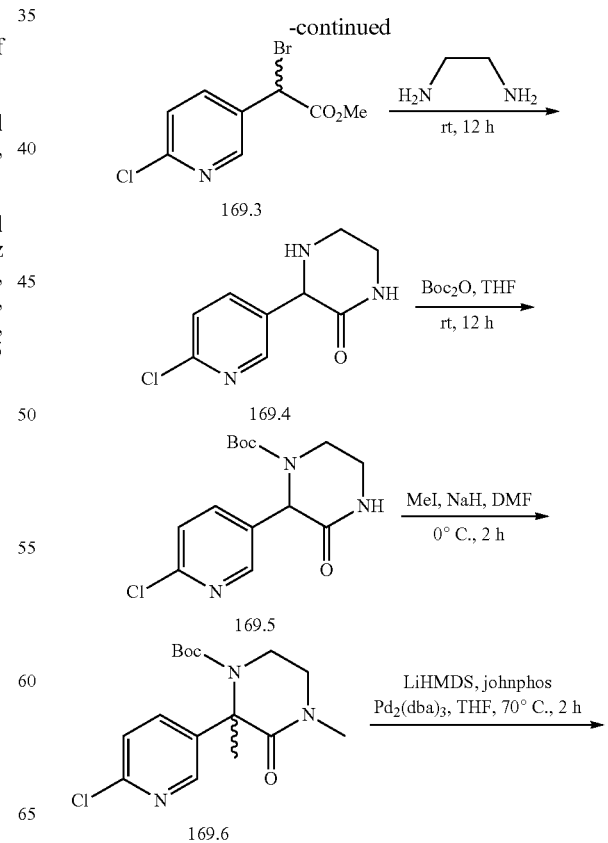

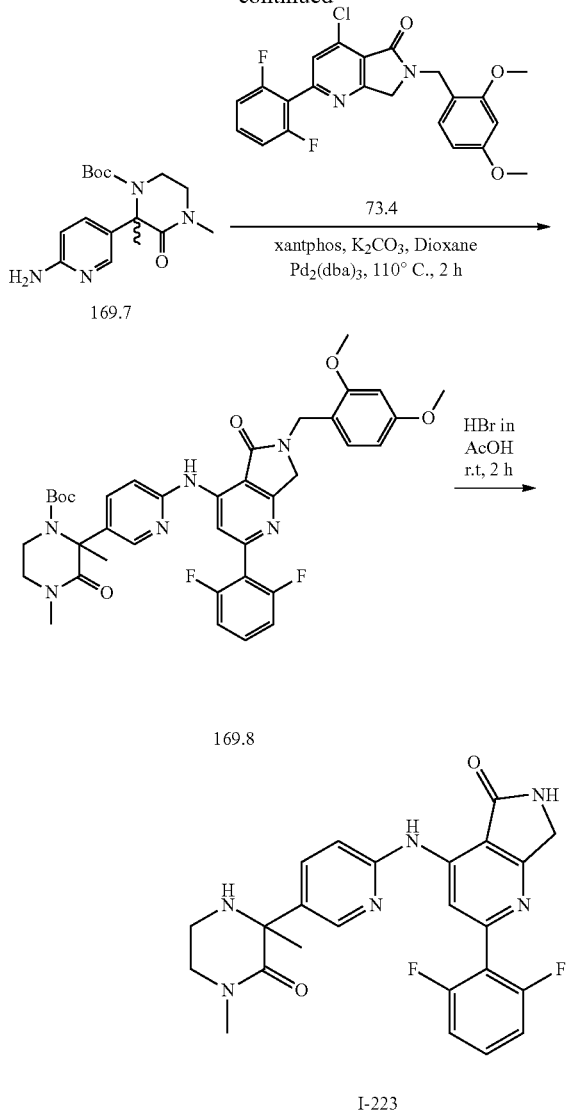

Synthesis of Compound 169.1.

To a solution of 169.1 (5.0 g, 29.23 mmol, 1.0 eq) in MeOH (50 mL), Sulfuric acid (1.9 ml) were added at room temperature. Reaction was stirred at room temperature for 1 hour. After completion of the reaction, mixture was poured into NaHCO$_3$ solution and extracted using EtOAC. Organic layer was dried over sodium sulfate and concentrate under reduced pressure. Crude was purified by column chromatography to afford 169.2 (5.0 g, 92.4%). MS (ES): m/z 185.4 [M+H]$^+$ Synthesis of Compound 169.3.

To a solution of 169.2 (5.0 g, 27.27 mmol, 1.0 eq) in CCl$_4$ (50 mL) were added AIBN (0.05 g), and NBS (4.85 g, 27.27 mmol, 1.0 eq). Reaction mixture was stirred at 80° C. for 1 h. After completion of the reaction, mixture was concentrated under reduced pressure. Crude was purified by column chromatography to afford 169.3 (5.5 g, 77.19%). MS (ES): m/z=264.4 [M+H]$^+$.

Synthesis of Compound 169.4.

To a solution of 169.3 (5.0 g, 18.93 mmol, 1.0 eq) in EtOH (45 ml), was added ethylinediamine (6.3 ml, 94.7 mmol, 5.0 eq) at room temperature. Reaction was stirred at room temperature for 12 h. After completion of the reaction, solvent was removed under reduced pressure, residue diluted with water and extracted in to EtOAc. Solvent was removed under reduced pressure. Crude was purified by column chromatography to afford 169.4 (2.5 g, 62.49%). MS (ES): m/z 212.5 [M+H]$^+$.

Synthesis of Compound 169.5.

To a solution of 169.4 (1.0 g, 4.72 mmol, 1.0 eq) in THF (18 mL), was added Boc-anhydride (1.0 g, 4.83 mmol, 1.0 eq) at 0 to 10° C. Reaction was stirred at room temperature for 12 hours. After completion of the reaction, solvent was removed under reduced pressure; residue was diluted with water and extracted into CH$_2$Cl$_2$. Solvent was removed under reduced pressure to afford 169.5 (1.0 g, 67.9%). MS (ES): m/z 312.5 [M+H]$^+$.

Synthesis of Compound 169.6.

A solution of NaH (0.384 g, 9.61 mmol, 2.5 eq) in DMF (12 ml) was cooled to 0° C. Compound 169.5 (1.0 g, 3.84 mmol, 1.0 eq) was added at 0° C. and reaction mixture was stirred for 30 min. Methyl iodide (0.8 ml, 11.5 mmol, 3.0 eq) was added drop wise at 0° C. and reaction mixture was stirred for 2 hours at 0° C. After completion of the reaction, mixture was poured into cold water, neutralized with NaHCO$_3$ and product was extracted with EtOAc. Solvent was removed under reduced pressure to afford 169.6 (0.68 g, 62.7%). MS (ES): m/z 312.5 [M+H]$^+$.

Synthesis of Compound 169.7.

To a degassed solution of 169.6 (0.572 g, 1.68 mmol, 1.0 eq) in THF (10 mL) were added Pd$_2$(dba)$_3$ (0.154 g, 0.17 mmol, 0.1 eq) and 2-(Dicyclohexylphosphino)biphenyl (0.118 g, 0.337 mmol, 0.2 eq) and LHMDS (0.845 g, 5.06 mmol, 3.0 eq) were added, again degassed for 5 min. The reaction was stirred at 70° C. for 2 hours. After completion of the reaction, mixture was poured into water and product was extracted with EtOAc. Organic layers were combined, dried over sodium sulphate and concentrated under reduced pressure to obtain crude which was purified by column chromatography get pure 169.7 (0.280 g, 51.9%). MS (ES): m/z 321.6 [M+H]$^+$.

Synthesis of Compound 169.8.

To a solution of 73.4 in 1,4-dioxane (3 ml) was added 169.7 (0.081 g, 0.25 mmol, 1.1 eq) and K$_2$CO$_3$ (0.080 g, 0.58 mmol, 2.5 eq). The reaction mixture was degassed for 10 min. using argon, then Pd$_2$(dba)$_3$ (0.021 g, 0.023 mmol, 0.1 eq) and Xantphos (0.026 g, 0.046 mmol, 0.2 eq) were added, again degassed for 5 min. The reaction was stirred at 110° C. for 2 h. After completion of the reaction, reaction mixture was poured into water and product was extracted with EtOAc. Organic layers were combined, dried over Na$_2$SO$_4$ and concentrated under reduced pressure to obtain crude which was purified by column chromatography to get pure 169.8 (0.120 g, 72.33%). MS (ES): m/z 715.6 [M+H]$^+$.

Synthesis of Compound I-223.

Compound 169.8 (0.120 g, 0.168 mmol, 1.0 eq) was dissolved in HBr/HOAc (3 mL) and stirred at room temperature for 2 hours. After completion of the reaction, mixture was poured into water and basified with NaHCO$_3$ solution and product was extracted with EtOAc. Organic layers were combined, dried over sodium sulphate and concentrated under reduced pressure to obtain crude which was purified by column chromatography to get pure I-223 (0.040 g, 51.03%). MS (ES): m/z 465.5 [M+H]$^+$, $^1$H NMR (DMSO-d$_6$, 400 MHz): 9.74 (s, 1H), 8.90 (s, 1H), 8.60 (s, 1H), 8.38 (s, 1H), 7.89-7.86 (m, 1H), 7.62-7.54 (m, 1H), 7.28-7.24 (m, 2H), 7.15-7.13 (d, 1H), 4.43 (s, 2H), 3.44-3.38 (m, 1H), 3.18-3.15 (m, 1H), 3.87 (s, 3H), 3.83 (s, 1H), 3.67-3.65 (m, 1H), 1.47 (s, 3H).

Example 170. Synthesis of (R)-2-(2,6-difluorophenyl)-4-((5-(2,4-dimethyl-3-oxopiperazin-2-yl)pyridin-2-yl)amino)-6,7-dihydro-5H-pyrrolo[3,4-b]pyridin-5-one, I-224

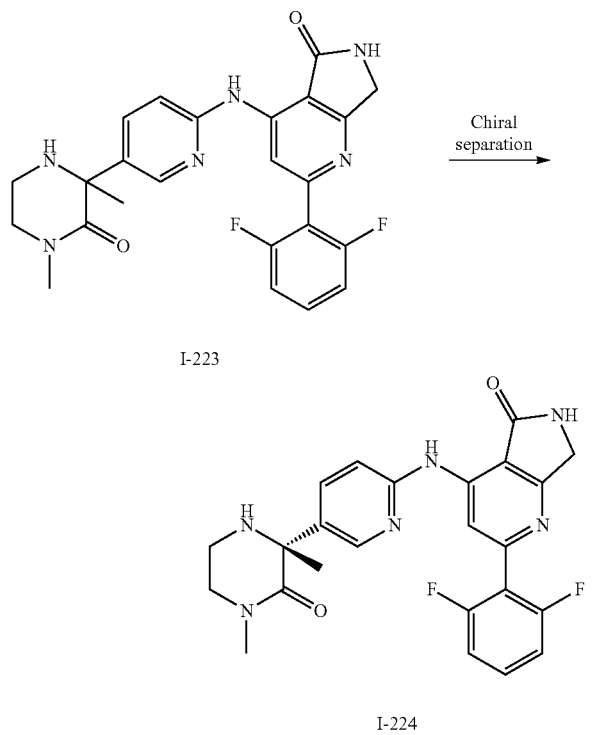

Compound I-224 was prepared by chiral separation of compound I-223. MS (ES): m/z 465.3 [M+H]$^+$, $^1$H NMR (400 MHz, DMSO-d$_6$): δ 9.73 (s, 1H), 8.90 (s, 1H), 8.60 (s, 1H), 8.38-8.37 (d, 1H), 7.89-7.86 (m, 2H), 7.62-7.56 (m, 2H), 7.28-7.24 (m, 2H), 7.15-7.13 (d, 1H), 4.43 (s, 2H), 3.44-3.34 (m, 1H), 3.29-3.14 (m, 1H), 2.87 (s, 3H), 2.82 (s, 1H), 2.67-2.60 (m, 1H), 1.46 (s, 3H).

Example 171. Synthesis of (S)-2-(2,6-difluorophenyl)-4-((5-(2,4-dimethyl-3-oxopiperazin-2-yl)pyridin-2-yl)amino)-6,7-dihydro-5H-pyrrolo[3,4-b]pyridin-5-one, I-225

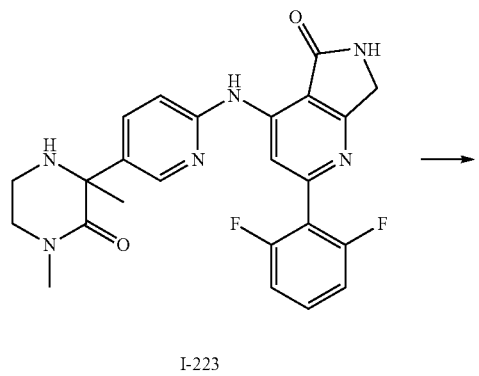

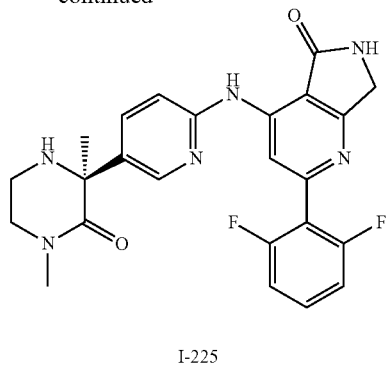

Compound I-225 was prepared by chiral separation of compound I-223. MS (ES): m/z 465.5 [M+H]$^+$, $^1$H NMR (400 MHz, DMSO-d$_6$): δ 9.73 (s, 1H), 8.90 (s, 1H), 8.60 (s, 1H), 8.38-8.37 (d, 1H), 7.89-7.86 (m, 1H), 7.62-7.56 (m, 1H), 7.28-7.24 (m, 2H), 7.15-7.13 (d, 1H), 4.43 (s, 2H), 3.44-3.34 (m, 1H), 3.29-3.14 (m, 1H), 2.87 (s, 3H), 2.82 (s, 1H), 2.67-2.60 (m, 1H), 1.46 (s, 3H).

Example 172. Synthesis of compound N-(cyclopropylmethyl)-6-((2-(2,6-difluorophenyl)-5-oxo-6,7-dihydro-5H-pyrrolo[3,4-b]pyridin-4-yl)amino)nicotinamide, I-226

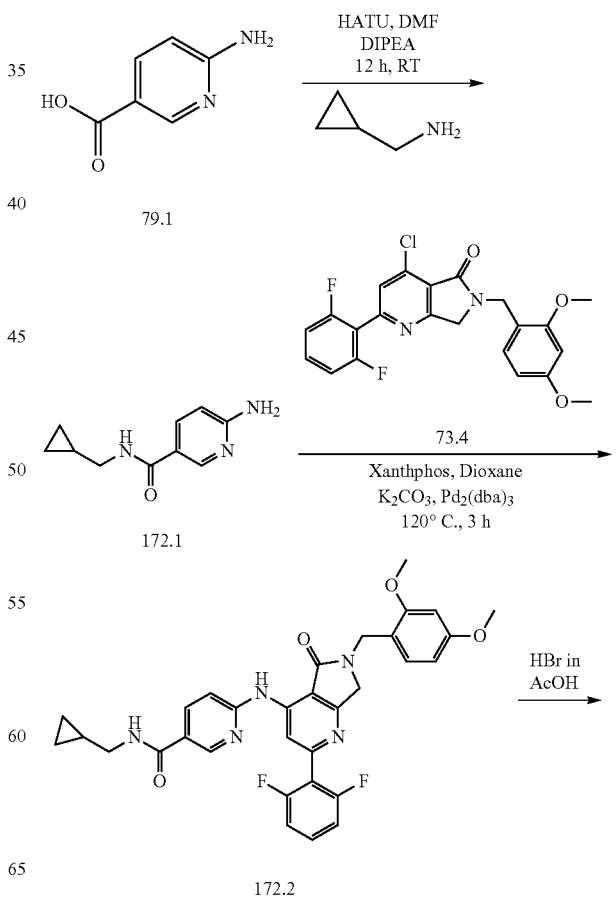

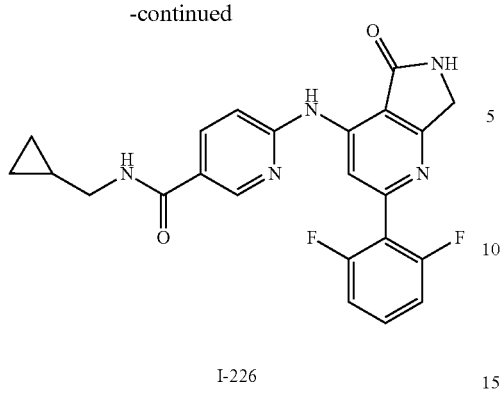

I-226

Synthesis of Compound 172.1.

To a solution of 79.1 (0.5 g, 3.62 mmol, 1.0 eq) in DMF (10 ml) were added cyclopropylmethanamine (0.31 g, 4.34 mmol, 1.2 eq) and HATU (2.8 g, 7.24 mmol, 2.0 eq). Reaction mixture was cooled at 0° C. DIPEA (1.8 ml, 10.86 mmol, 3.0 eq) was added at 0° C. The reaction mixture was stirred at room temperature for 12 h. The reaction mixture was poured into water and product was extracted with EtOAc. Organic layers were combined, dried over sodium sulphate and concentrated under reduced pressure to obtain crude which was purified by column chromatography to get pure 172.1 (0.220 g, 31.78%). MS (ES): m/z 192.2 [M+H]$^+$.

Synthesis of Compound 172.2.

To a solution of 73.4 (0.150 g, 0.35 mmol, 1.0 eq) in 1,4-dioxane (4 ml) were added 196.1 (0.07 g, 0.35 mmol, 1.0 eq) and $K_2CO_3$ (0.120 g, 0.87 mmol, 2.5 eq). The reaction mixture was degassed for 10 minutes using argon, then $Pd_2(dba)_3$ (0.031 g, 0.069 mmol, 0.1 eq) and Xantphos (0.04 g, 0.034 mmol, 0.2 eq) were added, again degassed for 5 minutes. The reaction was then heated at 110° C. for 3 h. After completion of the reaction, mixture was poured in water and product was extracted with EtOAC. Organic layers were combined, dried over sodium sulphate and concentrated under reduced pressure to obtain crude which was purified by column chromatography to get pure 172.2 (0.089 g, 43.65%). MS (ES): m/z 586.6 [M+H]$^+$.

Synthesis of Compound I-226.

The compound 172.2 (0.089 g, 0.152 mmol, 1.0 eq) was dissolved in HBr/HOAc (2 mL) and stirred at room temperature for 2 h. After completion of the reaction, reaction mixture was poured in water and basified with satd. $NaHCO_3$ solution and product was extracted with EtOAC. Organic layer was combined, dried over sodium sulphate and concentrated under reduced pressure to obtain crude which was purified by column chromatography to get pure I-226 (0.045 g, 68.00%). MS (ES): m/z 436.5 [M+H]$^+$, $^1$H NMR (DMSO-$d_6$, 400 MHz): 9.96 (s, 1H), 8.95 (s, 1H), 8.82 (s, 1H), 8.66 (s, 1H), 8.58-8.56 (m, 1H), 8.18-8.15 (m, 1H), 7.63-7.55 (m, 1H), 7.30-7.25 (m, 3H), 4.46 (s, 2H), 3.15-3.12 (t, 2H), 1.03-1.00 (m, 1H), 0.45-0.44 (m, 4H).

Example 173. Synthesis of 4-((5-(4-(tert-butyl)piperazin-1-yl)pyridin-2-yl)amino)-2-(2,6-difluorophenyl)-6,7-dihydro-5H-pyrrolo[3,4-b]pyridin-5-one, I-227

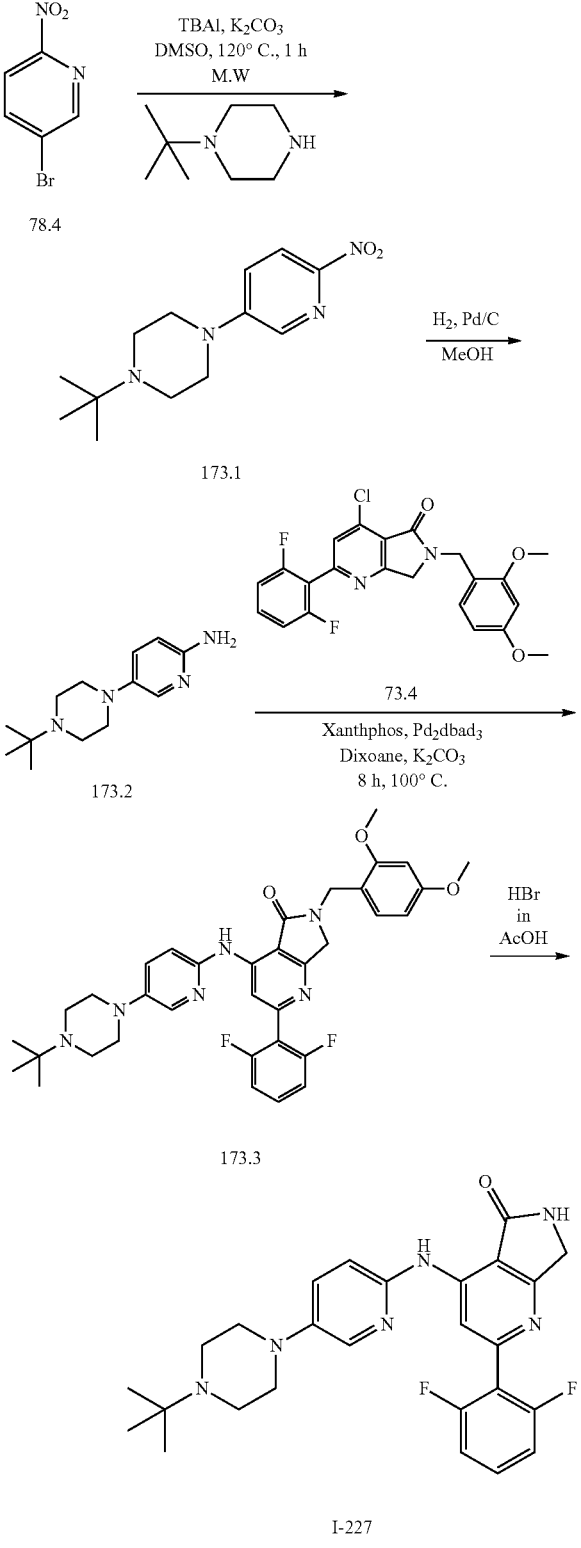

Synthesis of Compound 173.1.

To a solution of 78.4 (0.350 g, 1.72 mol, 1.0 eq) in DMSO (5 ml) was added TBAI (0.127 g, 0.34 mmol, 0.2 eq), 1-(tert-butyl) piperazine (0.293 sg, 2.06 mmol, 1.2 eq), and K₂CO₃ (0.713 g, 5.17 mmol, 3.0 eq). Reaction mixture was heated in microwave at 120° C. for 1 h. Reaction mixture was poured into water and product was extracted with EtOAC. Organic layers were combined, dried over sodium sulphate and concentrated under reduced pressure to obtain crude which was purified by column chromatography to furnish 173.1 (0.30 g, 65.8%). MS (ES): m/z 264.2 [M+H]⁺.

Synthesis of Compound 173.2.

To a solution of 173.1 (0.300 g, 1.13 mmol, 1.0 eq) in MeOH (15 mL) was added 10% Pd/C (0.060 g) under nitrogen atmosphere. It was purged with hydrogen for 1 h. Reaction mixture was filtered through celite and obtained filtrate was concentrated under reduced pressure to get crude 173.2 (0.263 g, 98.88%) which was used as such for the next step, MS (ES): m/z 235.3 [M+H]⁺.

Synthesis of Compound 173.3.

To a solution of 73.4 (0.120 g, 0.279 mmol, 1.0 eq) in 1,4-dioxane (3 ml) was added 173.2 (0.078 g, 0.33 mmol, 1.2 eq) and K₂CO₃ (0.08 g, 0.55 mmol, 2.0 eq). The reaction mixture was degassed for 10 min. under argon atmosphere, then Pd₂(dba)₃ (0.025 g, 0.027 mmol, 0.1 eq) and Xantphos (0.032 g, 0.055 mmol, 0.2 eq) were added, and again degassed for 5 min. The reaction was stirred at 100° C. for 8 h. After completion of the reaction, mixture was poured into water and product was extracted with EtOAc. Organic layers were combined, dried over sodium sulphate and concentrated under reduced pressure to obtain crude which was purified by column chromatography to furnish 173.3 (0.120 g, 68.5%). MS (ES): m/z 629.7 [M+H]⁺.

Synthesis of Compound I-227.

Compound 173.3 (0.12 g, 0.19 mmol, 1.0 eq) was dissolved in HBr/HOAc (5 ml) and stirred at room temperature for 1 h. After completion of the reaction, mixture was poured into water and basified with satd. NaHCO₃ and extracted with EtOAc. Organic layers were combined, dried over Na₂SO₄ and concentrated under reduced pressure to obtain crude which was purified by column chromatography to get pure I-227 (0.069 g, 75.5%). MS (ES): m/z 479.4 [M+H]⁺, ¹H NMR (DMSO-d₆, 400 MHz): 9.52 (s, 1H), 8.82 (s, 1H), 8.39 (s, 1H), 8.02 (s, 1H), 7.61-7.53 (m, 1H), 7.46-7.45 (d, 1H), 7.27-7.24 (m, 2H), 7.11-7.09 (d, 1H), 4.40 (s, 2H), 3.01-2.99 (m, 4H), 2.67 (m, 2H), 1.23-1.22 (m, 2H), 1.05 (s, 9H).

Example 174. Synthesis of 2-(2,6-difluorophenyl)-4-((5-(3-hydroxy-3-methylazetidin-1-yl)pyridin-2-yl)amino)-6,7-dihydro-5H-pyrrolo[3,4-b]pyridin-5-one, I-228

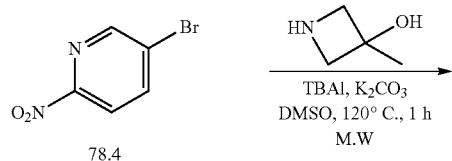

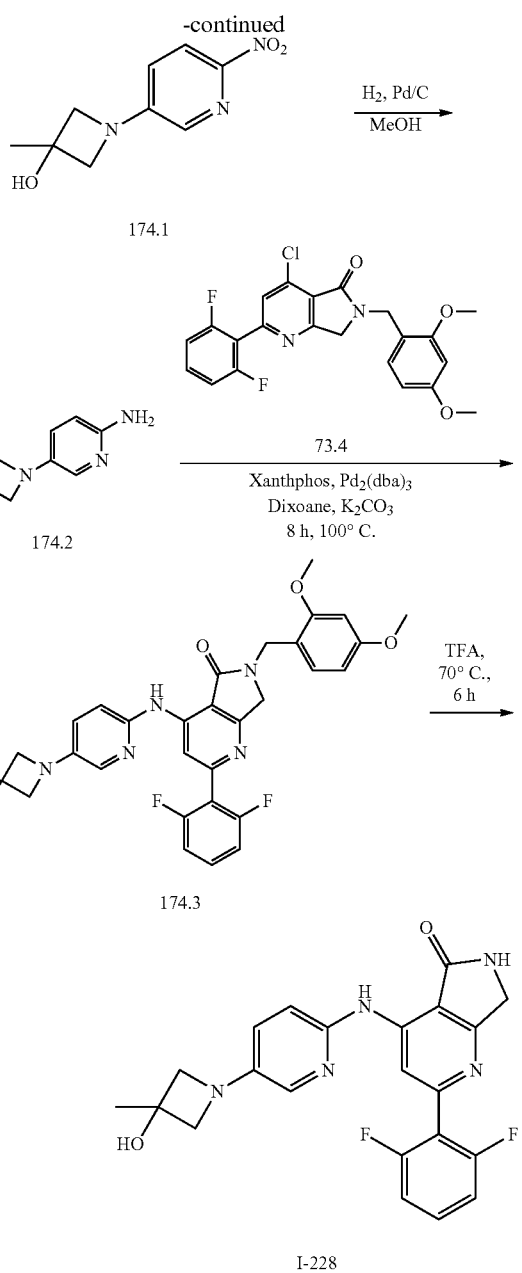

Synthesis of Compound 174.1.

To a solution of 78.4 (0.150 g, 0.73 mol, 1.0 eq) in DMSO (5 mL) was added TBAI (0.053 g, 0.14 mmol, 0.2 eq), 3-methylazetidin-3-ol (0.100 g, 0.80 mmol, 1.1 eq), and K₂CO₃ (0.302 g, 21.9 mmol, 3.0 eq). Reaction mixture was heated in microwave at 120° C. for 1 h. Reaction mixture was poured into water and product was extracted with ethyl acetate. Organic layers were combined, dried over Na₂SO₄ and concentrated under reduced pressure to obtain crude which was purified by column chromatography to get pure 174.1 (0.068 g, 43.99%). MS (ES): m/z 209.2 [M+H]⁺.

Synthesis of Compound 174.2.

To a solution of 174.1 (0.068 g, 0.32 mmol, 1.0 eq) in MeOH (10 ml) was added 10% Pd/C (0.020 g) under nitrogen atmosphere. It was purged with hydrogen for 1 h. Reaction mixture was filtered through celite and obtained filtrate was concentrated under reduced pressure to get crude 174.2 (0.040 g, 68.66%) which was used as such for the next step, MS (ES): m/z 180.3 [M+H]$^+$.

Synthesis of Compound 174.3.

To a solution of 73.4 (0.087 g, 0.20 mmol, 1.0 eq) in 1,4-dioxane (3 ml) was added 174.2 (0.040 g, 0.22 mmol, 1.1 eq) and K$_2$CO$_3$ (0.060 g, 0.44 mmol, 2.0 eq). The reaction mixture was degassed for 10 min. under argon atmosphere, then Pd$_2$(dba)$_3$ (0.020 g, 0.022 mmol, 0.1 eq) and Xantphos (0.025 g, 0.044 mmol, 0.2 eq) were added, and again degassed for 5 min. The reaction was then heated at 100° C. for 8 h. After completion of the reaction, mixture was poured in water and product was extracted with EtOAc. Organic layers were combined, dried over sodium sulphate and concentrated under reduced pressure to obtain crude which was purified by column chromatography to furnish 174.3 (0.089 g, 76.8%). MS (ES): m/z 573.7 [M+H]$^+$.

Synthesis of Compound I-228.

The compound 174.3 (0.120 g, 0.191 mmol, 1.0 eq) was dissolved in TFA (5 ml) and stirred at 70° C. for 6 hours. After completion of the reaction, mixture was poured into water and basified with satd. NaHCO$_3$ and extracted with EtOAc. Organic layers were combined, dried over sodium sulphate and concentrated under reduced pressure to obtain crude which was purified by column chromatography to furnish I-228 (0.019 g, 28.92%). MS (ES): m/z 423.4 [M+H]$^+$, $^1$H NMR (DMSO-d$_6$, 400 MHz): 9.45 (s, 1H), 8.78 (s, 1H), 8.29 (s, 1H), 7.61-7.54 (m, 2H), 7.27-7.23 (m, 2H), 7.07-7.05 (d, 1H), 6.98-6.95 (m, 1H), 5.52 (s, 1H), 4.40 (s, 2H), 3.77-3.75 (d, 2H), 3.61-3.59 (d, 2H), 1.44 (s, 3H).

Example 175. Synthesis of 4-((5-(3,3-difluoroazetidin-1-yl)pyridin-2-yl)amino)-2-(2,6-difluorophenyl)-6,7-dihydro-5H-pyrrolo[3,4-b]pyridin-5-one I-229

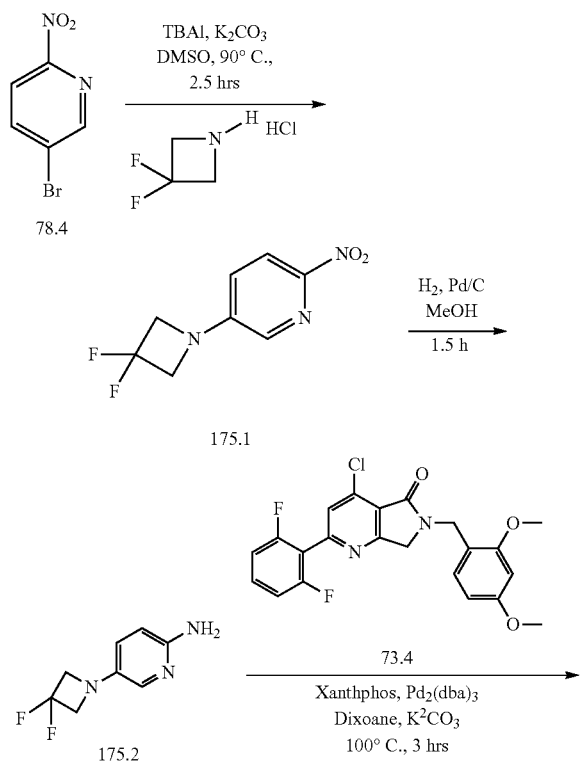

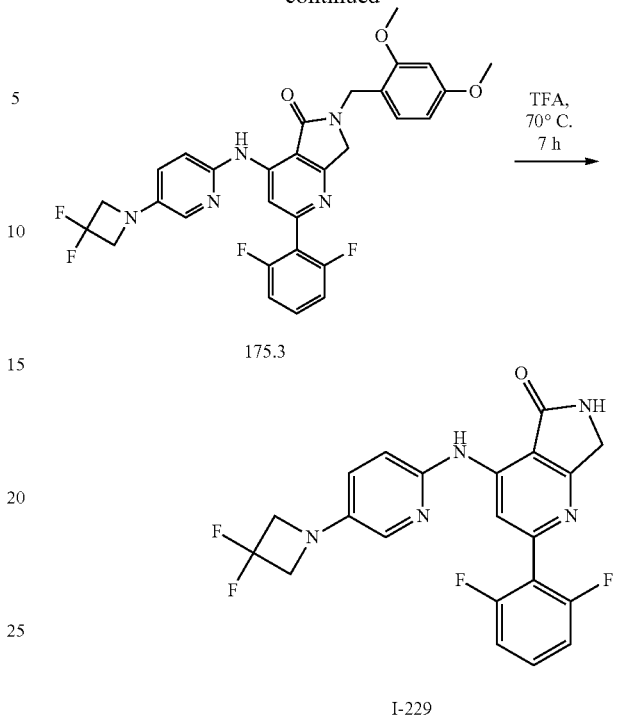

Synthesis of Compound 175.1.

To a solution of 78.4 (0.300 g, 1.477 mmol, 1.0 eq) in DMSO (5 ml) were added TBAI (0.109 g, 0.259 mmol, 0.2 eq), 3, 3-difluoroazetidine hydrochloride (0.209 g, 1.625 mmol, 1.1 eq), and K$_2$CO$_3$ (0.611 g, 4.433 mmol, 3.0 eq). Reaction mixture was heated at 110° C. for 2.5 h. After completion of the reaction, mixture was poured in water to give solid product. The solid product was filtered, washed with water and dried and purified by column chromatography and prep HPLC to get pure 175.1 (0.065 g, 20.44%). MS (ES): m/z 215.1 [M+H]$^+$.

Synthesis of Compound 175.2.

To a solution of 175.1 (0.065 g, 0.31 mmol, 1.0 eq) in MeOH (5 ml) was added 10% Pd/C (0.020 g) under nitrogen atmosphere. It was purged with hydrogen for 1.5 h. Reaction mixture was filtered through celite and obtained filtrate was concentrated under reduced pressure to get crude which was purified by column chromatography to give pure 175.2 (0.050 g, 89.38%), MS (ES): m/z 185.1 [M+H]$^+$.

Synthesis of Compound 175.3.

To a solution of 73.4 (0.100 g, 0.232 mmol, 1.0 eq) in 1,4-dioxane (2 mL) was added compound 175.2 (0.047 g, 0.255 mmol, 1.2 eq) and K$_2$CO$_3$ (0.080 g, 0.581 mmol, 2.5 eq). reaction mixture was degassed for 10 minutes using argon then Pd$_2$(dba)$_3$ (0.021 g, 0.0232 mmol, 0.1 eq) and Xantphos (0.026 g, 0.0465 mmol, 0.2 eq) were added, and again degassed for 5 min. The reaction was stirred at 100° C. for 3 h. After completion of the reaction, mixture was poured into water and product was extracted with EtOAc. Organic layers were combined, dried over sodium sulphate and concentrated under reduced pressure to obtain crude which was purified by column chromatography to get pure 175.3 (0.120 g, 89.21%). MS (ES): m/z 579.56 [M+H]$^+$.

Synthesis of Compound I-229.

Compound 175.3 (0.110 g, 0.189 mmol, 1.0 eq) was dissolved in TFA (1.5 ml) and stirred at 70° C. for 7 hours. After completion of the reaction, mixture was poured into water and basified with saturated bicarbonate solution and extracted with EtOAc. Organic layers were combined, dried over sodium sulphate and concentrated under reduced pressure to obtain crude which was purified by column chromatography to get pure I-229 (0.050 g, 61.35%). MS (ES): m/z 429.38 [M+H]+, 1H NMR (DMSO-d6, 400 MHz): 9.53 (s, 1H), 8.81 (s, 1H), 8.36 (s, 1H), 7.75-7.74 (d, 1H), 7.59-7.54 (m, 1H), 7.27-7.23 (m, 2H), 7.16-7.10 (m, 2H), 5.76 (s, 1H), 4.41 (s, 2H), 4.32-4.26 (t, 4H).

Example 176. Synthesis of 2-(2,6-difluorophenyl)-4-((4-methoxyphenyl)amino)-6,7-dihydro-5H-pyrrolo[3,4-b]pyridin-5-one, I-230

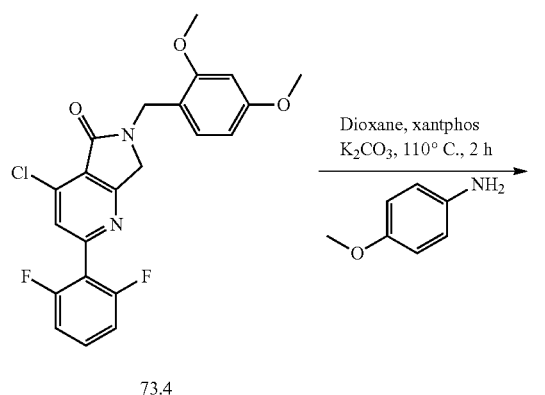

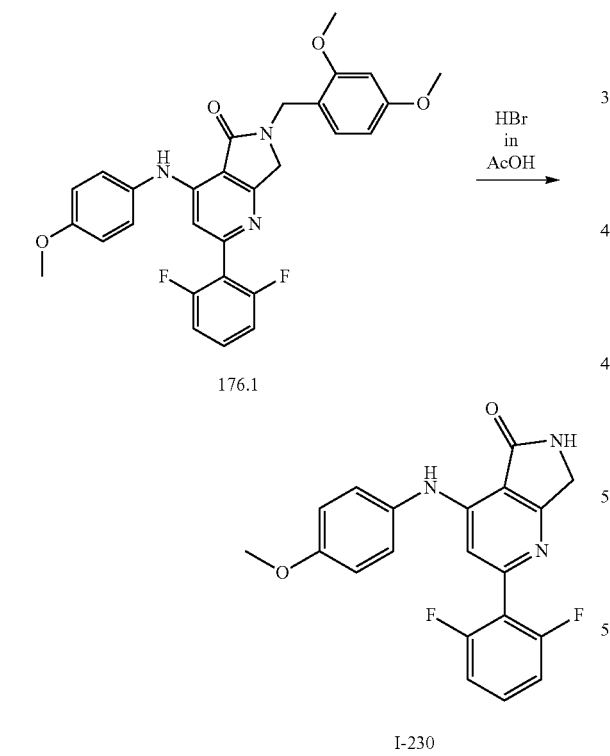

Synthesis of Compound 176.1.

To a solution of 73.4 (0.100 g, 0.23 mmol, 1.0 eq) in 1,4-dioxane (3 mL) was added 4-methoxyaniline (0.031 g, 0.25 mmol, 1.1 eq) and K2CO3 (0.063 g, 0.46 mmol, 2.0 eq). The reaction mixture was degassed for 10 min. under argon atmosphere, then Pd2(dba)3 (0.021 g, 0.023 mmol, 0.1 eq) and Xantphos (0.026 g, 0.046 mmol, 0.2 eq) were added, and again degassed for 5 min. The reaction was then heated at 110° C. for 2 h. After completion of the reaction, mixture was poured into water and product was extracted with EtOAc. Organic layers were combined, dried over sodium sulphate and concentrated under reduced pressure to obtain crude which was purified by column chromatography to get pure 176.1 (0.120 g, 99.09%). MS (ES): m/z 518.6 [M+H]+.

Synthesis of Compound I-220.

Compound 176.1 (0.120 g, 0.232 mmol, 1.0 eq) was dissolved in HBr/HOAc (2 mL) and stirred at room temperature for 1 h. After completion of the reaction, mixture was poured into water and basified with satd. NaHCO3 and extracted with EtOAc. Organic layers were combined, dried over Na2SO4 and concentrated under reduced pressure to obtain crude which was purified by column chromatography to get pure I-230 (0.055 g, 64.57%). MS (ES): m/z 368.4 [M+H]+, 1H NMR (DMSO-d6, 400 MHz): 8.76 (s, 1H), 8.65 (s, 1H), 7.53-7.49 (m, 1H), 7.29-7.27 (d, 2H), 7.20-7.16 (m, 2H), 6.99-6.97 (d, 2H), 6.74 (s, 1H), 4.37 (s, 2H), 3.75 (s, 3H).

Example 177. Synthesis of 2-(2,6-difluorophenyl)-4-((4-(morpholine-4-carbonyl)-phenyl)amino)-6,7-dihydro-5H-pyrrolo[3,4-b]pyridin-5-one, I-231

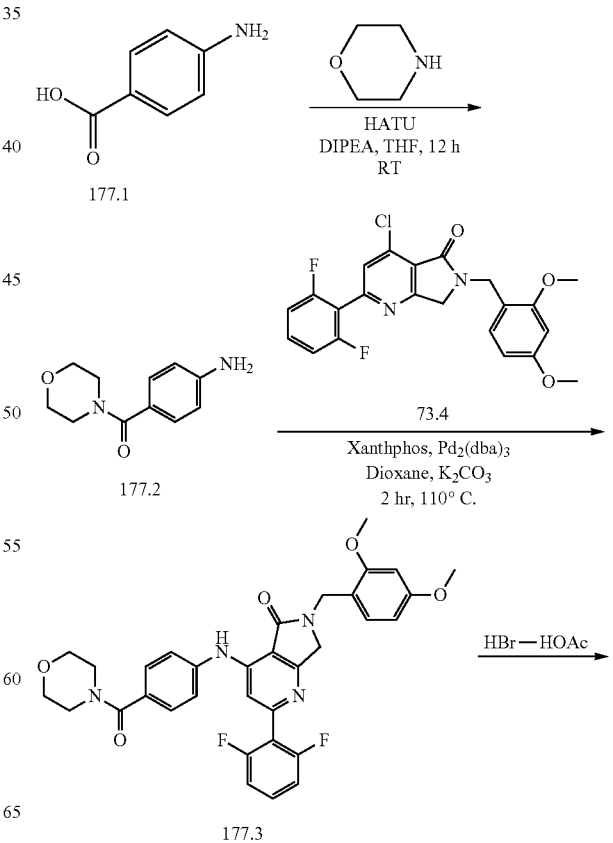

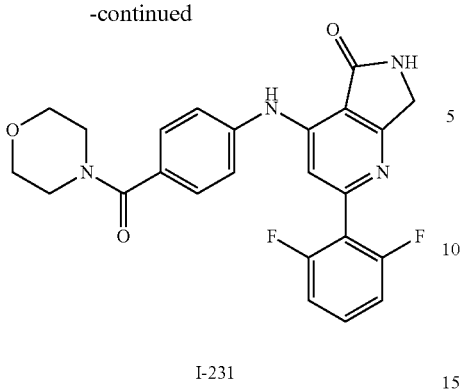

I-231

Synthesis of Compound 177.2.

To a solution of 177.1 (0.5 g, 3.72 mmol, 1.0 eq) in DMF (10 ml) were added morpholine (0.409 g, 4.74 mmol, 1.3 eq), and HATU (2.8 g, 7.29 mmol, 2.0 eq). Reaction mixture was cooled to 0° C. DIPEA (1.8 ml, 32.8 mmol, 3.0 eq) was added at 0° C. Reaction mixture was stirred at room temperature for 12 h. Upon completion mixture was poured into water and product was extracted with EtOAC. Organic layers were combined and dried over $Na_2SO_4$ and concentrated under reduced pressure to obtain crude which was purified using column chromatography to get pure 177.2 (0.350 g, 46.54%). MS (ES): m/z 206.2 $[M+H]^+$.

Synthesis of Compound 177.3.

To a solution of 73.4 (0.150 g, 0.35 mmol, 1.0 eq) in 1,4-dioxane (3 ml) was added 177.2 (0.072 g, 0.35 mmol, 1.0 eq) and $K_2CO_3$ (0.096 g, 0.70 mmol, 2.0 eq). Reaction mixture was degassed for 10 minutes using argon, then $Pd_2(dba)_3$ (0.032 g, 0.035 mmol, 0.1 eq) and Xantphos (0.04 g, 0.077 mmol, 0.2 eq) were added, and again degassed for 5 min. The reaction was then heated at 110° C. for 2 h. After completion of the reaction, mixture was poured in water and product was extracted with EtOAc. Organic layers were combined, dried over $Na_2SO_4$ and concentrated under reduced pressure to obtain crude which was purified purified by column chromatography to get pure 177.3 (0.110 g, 52.60%). MS (ES): m/z 601.6 $[M+H]^+$.

Synthesis of I-231. Compound 177.3 (0.110 g, 0.183 mmol, 1.0 eq) was dissolved in HBr/HOAc (2 ml) and stirred at room temperature for 2 hours. After completion of the reaction, mixture was poured into water, basified with satd. $NaHCO_3$ and extracted with EtOAc. Organic layers were combined, dried over $Na_2SO_4$ and concentrated under reduced pressure to obtain crude which was purified by column chromatography to get pure I-231 (0.075 g, 90.9%). MS (ES): m/z 451.5 $[M+H]^+$, $^1H$ NMR (DMSO-$d_6$, 400 MHz): 9.16 (s, 1H), 8.77 (s, 1H), 7.56-7.52 (m, 1H), 7.50-7.41 (m, 4H), 7.24-7.20 (m, 3H), 4.41 (s, 2H), 3.59-3.49 (m, 8H).

Example 178. Synthesis of 4-((2-(2,6-difluorophenyl)-5-oxo-6,7-dihydro-5H-pyrrolo[3,4-b]pyridin-4-yl)amino)-N-isopropylbenzamide, I-232

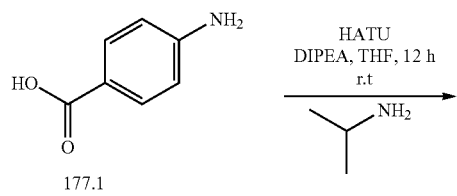

177.1

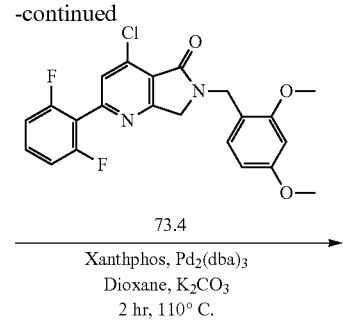

178.1

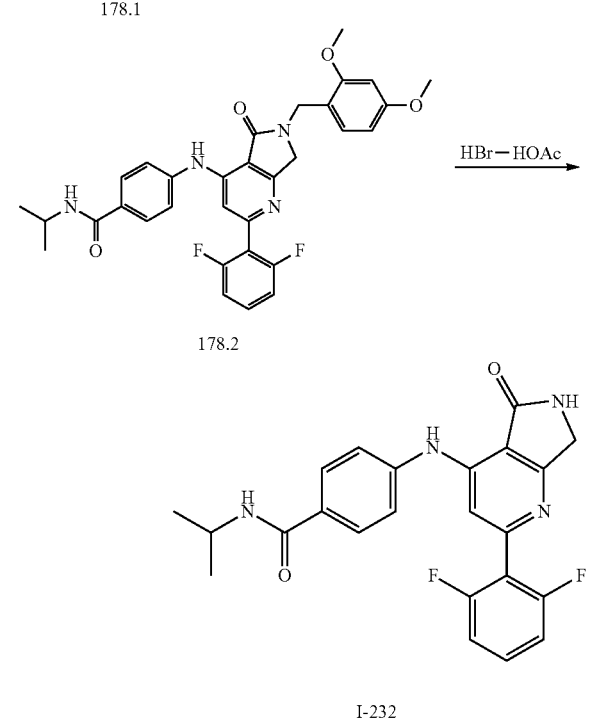

178.2

I-232

Synthesis of Compound 178.1.

To a solution of 177.1 (0.6 g, 4.37 mmol, 1.0 eq) in DMF (6 mL) were added isopropyl amine (0.73 mLl, 8.75 mmol, 2.0 eq), HATU (2.49 g, 6.55 mmol, 1.5 eq). Reaction mixture was cooled to 0° C. DIPEA (1.4 ml, 8.74 mmol, 2.0 eq) was added at 0° C. Reaction mixture was stirred at room temperature for 2 hours. Upon reaction completion, mixture was poured into water and product was extracted with EtOAC. Organic layers were combined, dried over sodium sulphate and concentrated under reduced pressure to obtain crude which was purified to get pure 178.1 (0.30 g, 38.5%). MS (ES): m/z 176.2 $[M+H]^+$.

Synthesis of Compound 178.2.

To a solution of 76.4 (0.150 g, 0.35 mmol, 1.0 eq) in 1,4-dioxane (3 mL) was added 178.1 (0.092 g, 0.52 mmol, 1.0 eq) and $K_2CO_3$ (0.110 g, 0.86 mmol, 2.5 eq). Reaction mixture was degassed for 10 minutes using argon gas, then $Pd_2(dba)_3$ (0.031 g, 0.034 mmol, 0.1 eq) and Xantphos (0.042 g, 0.069 mmol, 0.2 eq) were added, and again degassed for 5 minutes. Reaction was stirred at 110° C. for 2 hours. After completion of the reaction, mixture was poured into water and extracted with EtOAc. Organic layers were combined, dried over $Na_2SO_4$ and concentrated under reduced pressure to obtain crude which was purified by column chromatography to furnish 178.2 (0.110 g, 55.18%). MS (ES): m/z 573.6 $[M+H]^+$.

Synthesis of Compound I-232.

Compound 178.2 (0.110 g, 0.183 mmol, 1.0 eq) was dissolved in HBr/HOAc (2 ml) and stirred at room temperature for 2 hours. After completion of the reaction, mixture was poured into water and basified with satd. NaHCO$_3$ and extracted with EtOAc. Organic layers were combined, dried over Na$_2$SO$_4$ and concentrated under reduced pressure to obtain crude which was purified by column chromatography to furnish I-232 (0.025 g, 30.81%). MS (ES): m/z 423.5 [M+H]$^+$, $^1$H NMR (DMSO-d$_6$, 400 MHz): 9.18 (s, 1H), 8.77 (s, 1H), 8.17-8.15 (d, 1H), 7.88-7.86 (d, 2H), 7.56-7.52 (m, 1H), 7.44-7.42 (d, 2H), 7.25-7.19 (m, 3H), 4.41 (s, 2H), 4.11-4.06 (m, 1H), 1.16-1.14 (d 6H).

Example 179. Synthesis of 4-((5-(5-azaspiro[2.4]heptan-5-yl)pyridin-2-yl)amino)-2-(2,6-difluorophenyl)-6,7-dihydro-5H-pyrrolo[3,4-b]pyridin-5-one, I-233

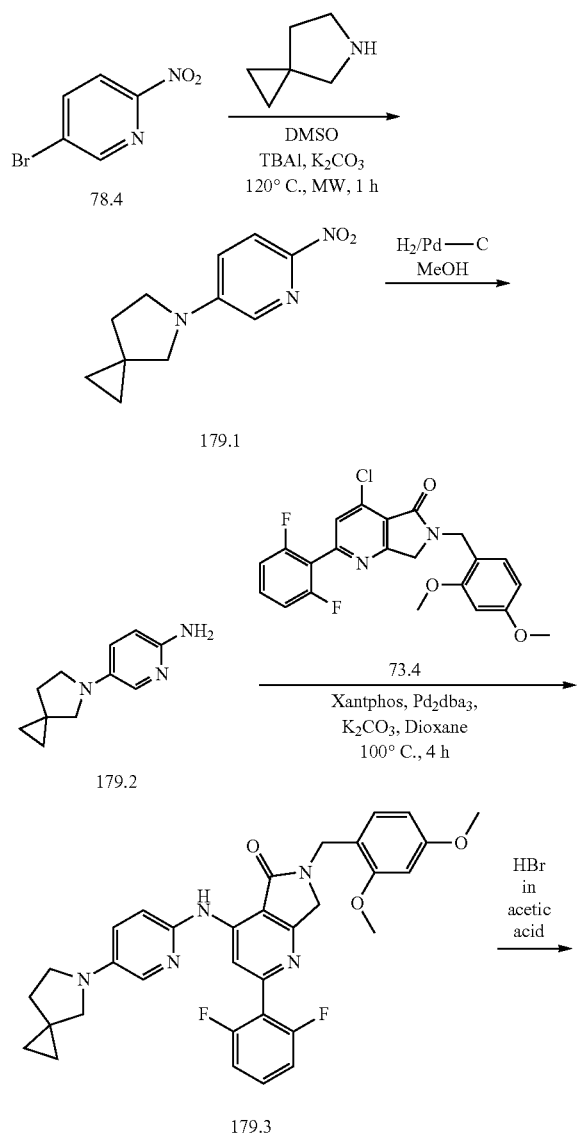

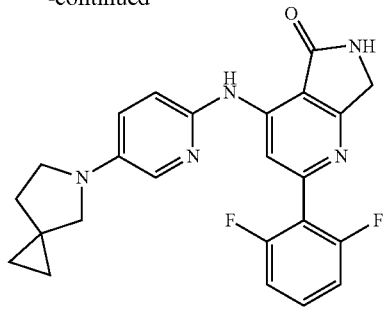

I-233

Synthesis of Compound 179.1.

To a solution of 78.4 (0.3 g, 1.47 mmol, 1.0 eq) in DMSO (3 ml) was added tetrabutyl ammonium iodide (0.109 g, 0.29 mmol, 0.2 eq), 5-azaspiro[2.4]heptane (0.196 g, 1.47 mmol, 1.0 eq), and K$_2$CO$_3$ (0.611 g, 4.43 mmol, 3.0 eq). Reaction mixture was heated in microwave at 120° C. for 1 hour. Reaction mixture was poured into water and product was extracted with EtOAc. Organic layers were combined, dried over Na$_2$SO$_4$ and concentrated under reduced pressure to obtain crude which was purified by column chromatography to get pure 179.1 (0.080 g, 24.69%). MS (ES): m/z 219.2 [M+H]$^+$.

Synthesis of Compound 179.2.

To a solution of 179.1 (0.080 g, 0.365 mmol, 1.0 eq) in MeOH (5 mL) was added 10% Pd/C (0.030 g) under nitrogen atmosphere. It was purged with hydrogen for 1 hour. Reaction mixture was filtered through celite and obtained filtrate was concentrated under reduced pressure to get crude 214.2 (0.053 g, 76.75%) which was used as such for the next step, MS (ES): m/z 190.23 [M+H]$^+$.

Synthesis of Compound 179.3.

To a solution of 73.4 (0.120 g, 0.278 mmol, 1.0 eq) in 1,4-dioxane (3 ml) was added 214.2 (0.053 g, 0.278 mmol, 1.0 eq) and K$_2$CO$_3$ (0.096 g, 0.695 mmol, 3.0 eq). The reaction mixture was degassed for 10 minutes using argon, then Pd$_2$(dba)$_3$ (0.025 g, 0.0278 mmol, 0.1 eq) and Xantphos (0.032 g, 0.055 mmol, 0.2 eq) were added, again degassed for 5 min. The reaction was then heated at 100° C. for 4 h. After completion of the reaction, mixture was poured into water and extracted with EtOAc. Organic layers were combined, dried over Na$_2$SO$_4$ and concentrated under reduced pressure to obtain crude which was purified by column chromatography to get pure 179.3 (0.120 g, 73.82%). MS (ES): m/z 584.6 [M+H]$^+$.

Synthesis of Compound I-233.

Compound 179.3 (0.120 g, 0.205 mmol, 1.0 eq) was dissolved in HBr/HOAc (5 ml) and stirred at room temperature for 1 hour. After completion of reaction, mixture was poured into water and basified with satd. NaHCO$_3$ solution and extracted with EtOAc. Organic layers were combined, dried over Na$_2$SO$_4$ and concentrated under reduced pressure to obtain crude which was purified by column chromatography to get pure I-233 (0.038 g, 72.11%). MS (ES): m/z 458.4 [M+H]$^+$, $^1$H NMR (DMSO-d$_6$, 400 MHz): 9.54 (s, 1H), 8.82 (s, 1H), 8.41 (s, 1H), 8.10 (s, 1H), 7.59-7.53 (m, H), 7.28-7.24 (t, H), 7.13-7.11 (d, 2H), 4.41 (s, 2H), 2.05-1.99 (m, 4H), 1.23-1.16 (m, 4H).

Example 180. Synthesis of 2-(2,6-difluorophenyl)-4-((5-fluoropyridin-2-yl)amino)-6,7-dihydro-5H-pyrrolo[3,4-b]pyridin-5-one, I-234

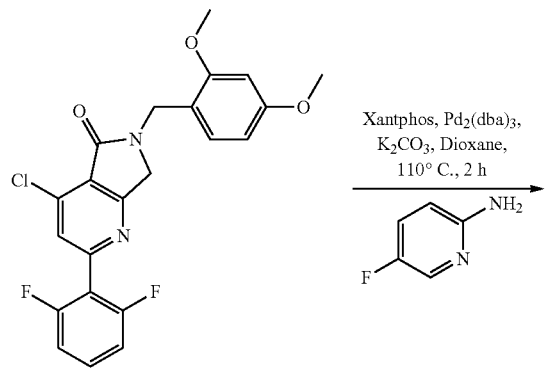

73.4

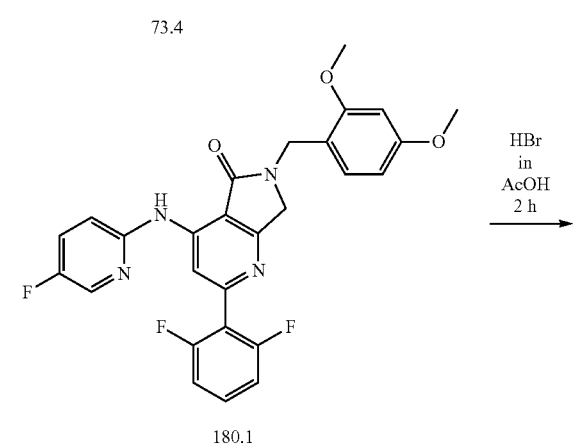

180.1

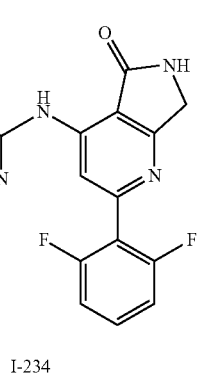

I-234

Synthesis of Compound 180.1.

To a solution of 76.4 (0.100 g, 0.231 mmol, 1.0 eq) in 1,4-dioxane (2 mL) was added 5-fluoropyridin-2-amine (e was 0.031 g, 0.278 mmol, 1.2 eq) and $K_2CO_3$ (0.079 g, 0.0577 mmol, 2.5 eq). The reaction mixture degassed for 10 min. using argon, then Pd2(dba)3 (0.021 g, 0.0231 mmol, 0.1 eq) and Xantphos (0.026 g, 0.0462 mmol, 0.2 eq) were added, and again degassed for 5 min. Reaction was was stirred at 110° C. for 2 hours. After completion of the reaction, mixture was poured into water and extracted with EtOAc. Organic layers were combined, dried over $Na_2SO_4$ and concentrated under reduced pressure to obtain crude which was purified by column chromatography to give 180.1 (0.090 g, 76.92%). MS (ES): m/z 506.49 [M+H]$^+$.

Synthesis of Compound I-234.

Solution of 180.1 (0.090 g, 0.177 mmol, 1.0 eq) in HBr/HOAc (2 ml) was stirred at room temperature for 2 h. After completion of the reaction pH was adjusted to 7 by addition of $NaHCO_3$ solution. The product was extracted with EtOAc. Combined organic layers were washed with brine, dried over sodium sulphate and concentrated under reduced pressure at 45° C. to afford crude, which was purified by column chromatography to furnish I-234 (0.030 g, 47.4%). MS (ES): m/z 356.31 [M+H]$^+$. $^1$H NMR (DMSO-$d_6$, 400 MHz): 9.79 (s, 1H), 8.90 (s, 1H), 8.46 (s, 1H), 8.35-8.34 (d, 1H), 7.77-7.72 (td, 1H), 7.60-7.56 (m, 1H), 7.31-7.24 (m, 3H), 4.44 (s, 2H).

Example 181. Synthesis of 2-(2,6-difluorophenyl)-4-((4-fluorophenyl)amino)-6,7-dihydro-5H-pyrrolo[3,4-b]pyridin-5-one, I-235

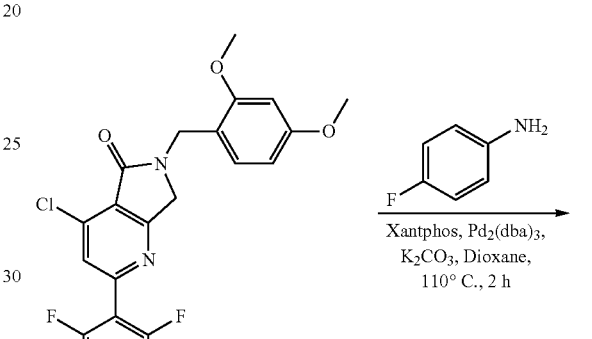

73.4

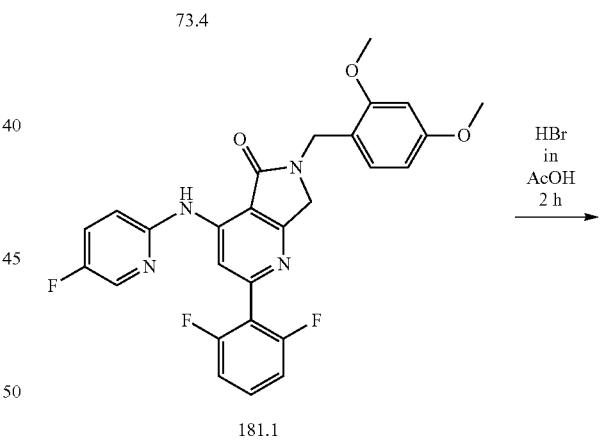

181.1

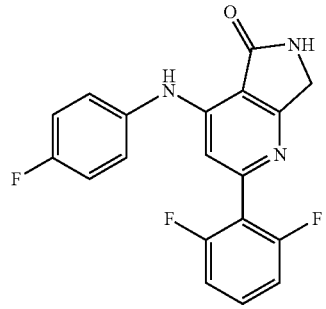

I-235

Synthesis of Compound 181.1.

To a solution of 73.4 (0.100 g, 0.23 mmol, 1.0 eq) in 1,4-dioxane (2 ml) was added 4-fluoroaniline (0.028 g, 0.25 mmol, 1.1 eq) and K$_2$CO$_3$ (0.063 g, 0.46 mmol, 2 eq). Reaction mixture was degassed for 10 min. using argon, then Pd$_2$(dba)$_3$ (0.021 g, 0.023 mmol, 0.1 eq) and Xantphos (0.027 g, 0.0464 mmol, 0.2 eq) were added, and again degassed for 5 min. Reaction was stirred at 110° C. for 2 h. After completion of the reaction, mixture was poured into water and product was extracted with EtOAc. Organic layers were combined, dried over Na$_2$SO$_4$ and concentrated under reduced pressure to obtain crude which was purified by column chromatography to furnish 181.1 (0.091 g, 77.77%). MS (ES): m/z 505.50 [M+H]$^+$.

Synthesis of Compound I-235.

A solution of 181.1 (0.091 g, 0.18 mmol, 1.0 eq) in HBr/HOAc (2 ml) was stirred at room temperature for 1 hour. After completion of the reaction pH was adjusted to 7 by addition of NaHCO$_3$ solution. Product was extracted with EtOAc. Combined organic layers were washed with brine, dried over sodium sulphate and concentrated under reduced pressure to afford crude, which was purified by column chromatography to furnish I-235 (0.042 g, 66.45%). MS (ES): m/z 355.32 [M+H]$^+$. $^1$H NMR (DMSO-d$_6$, 400 MHz): 8.95 (s, 1H), 8.71 (s, 1H), 7.56-7.49 (m, 1H), 7.42-7.38 (m, 2H), 7.27-7.18 (m, 4H), 6.88 (s, 1H), 4.38 (s, 2H).

Example 182. Synthesis of 2-(2,6-difluorophenyl)-4-((4-((trifluoromethyl)sulfonyl)phenyl)-amino)-6,7-dihydro-5H-pyrrolo[3,4-d]pyrimidin-5-one, I-236

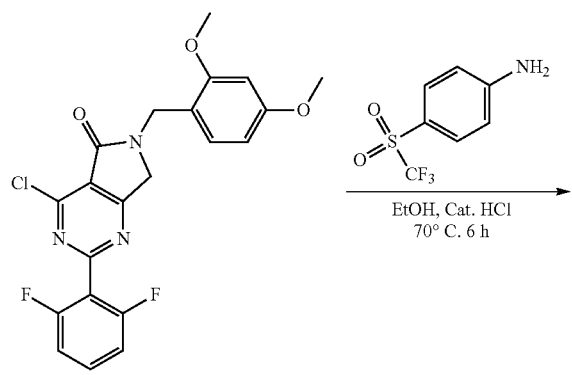

57.4

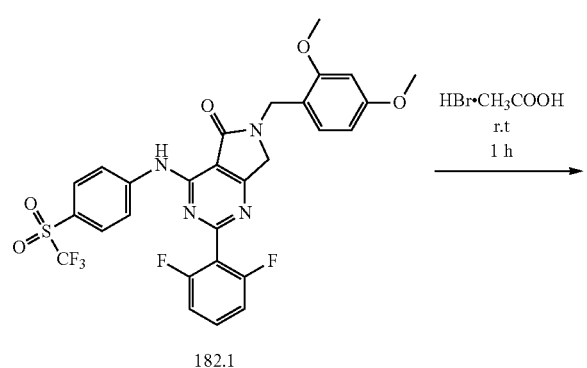

182.1

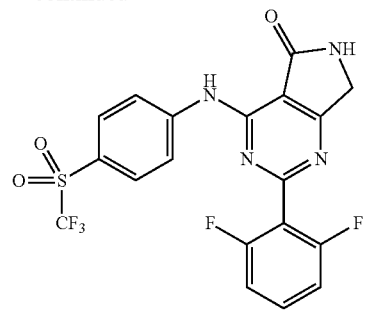

I-236

Synthesis of Compound 182.1.

To a solution of 57.4 (0.100 g, 0.232 mmol, 1.0 eq) in EtOH (2 ml) was added 4-((trifluoromethyl)sulfonyl)aniline (0.052 g, 0.232 mmol, 1.0 eq) and conc. HCl (catalytic amount). The reaction was then heated at 70° C. for 6 h. After completion of the reaction, mixture was poured into water and product was extracted with EtOAc. Organic layers were combined, dried over Na$_2$SO$_4$ and concentrated under reduced pressure to obtain crude which was purified by column chromatography to get pure 182.1 (0.100 g, 69.59%). MS (ES): m/z 620.55 [M+H]$^+$.

Synthesis of Compound I-236.

Solution of 182.1 (0.100 g, 0.161 mmol, 1.0 eq) in HBr/HOAc (2 ml) was stirred at room temperature for 1 h. After completion of reaction pH was adjusted to 7 by addition of NaHCO$_3$ solution. Product was extracted with EtOAc. Combined organic layers were washed with brine, dried over Na$_2$SO$_4$ and concentrated under reduced pressure to afford crude, which was purified by column chromatography to furnish I-236 (0.035 g, 46.17%). MS (ES): m/z 470.37 [M+H]$^+$. $^1$H NMR (DMSO-d$_6$, 400 MHz): 9.72 (s, 1H), 9.06 (s, 1H), 8.28-8.26 (d, 2H), 8.10-8.07 (d, 2H), 7.68-7.61 (m, 1H), 7.32-7.28 (t, 2H), 4.56 (s, 2H).

Example 183. Synthesis of N-(6-((2-(2,6-difluoro-phenyl)-5-oxo-6,7-dihydro-5H-pyrrolo[3,4-b]pyridin-4-yl)amino)pyridin-3-yl)acetamide, I-237

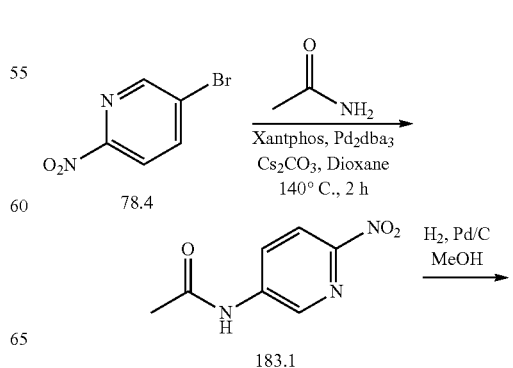

78.4

183.1

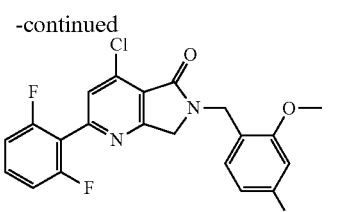

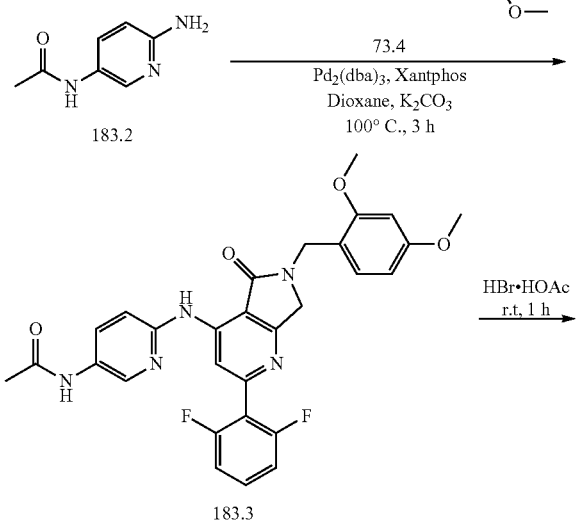

Synthesis of Compound 183.1.

To a solution of 78.4 (0.500 g, 2.46 mmol, 1.0 eq) in 1,4-dioxane (10 ml) were added Acetamide (0.174 g, 2.95 mmol, 1.0 eq) and Cs$_2$CO$_3$ (1.6 g, 7.38 mmol, 3.0 eq). Reaction mixture was degassed for 10 min. under argon atmosphere, then Pd$_2$(dba)$_3$ (0.225 g, 0.246 mmol, 0.1 eq) and Xantphos (0.284 g, 0.492 mmol, 0.2 eq) were added, and again degassed for 5 minutes. Reaction was stirred at 140° C. in microwave for 2 hours. After completion of the reaction, mixture was poured into water and product was extracted with EtOAc. Organic layers were combined, dried over Na$_2$SO$_4$ and concentrated under reduced pressure to obtain crude which was purified by column chromatography to get pure 183.1 (0.210 g, 47.06%). MS (ES): m/z 181.6 [M+H]$^+$.

Synthesis of Compound 183.2.

A solution of 183.1 (0.210 g, 1.160 mmol, 1.0 eq) in MeOH (5 mL) was added 10% Pd/C (0.040 g) under nitrogen atmosphere. It was purged with hydrogen for 1 hour. Reaction mixture was filtered through celite and obtained filtrate was concentrated under reduced pressure to get crude 183.2 (0.18 g, 99.86%) which was used as such for the next step, MS (ES): m/z 151.23 [M+H]$^+$.

Synthesis of Compound 184.3.

To a solution of 73.4 (0.100 g, 0.231 mmol, 1.0 eq) in 1,4-dioxane (3 ml) was added 224.2 (0.038 g, 0.255 mmol, 1.1 eq) and K$_2$CO$_3$ (0.079 g, 0.577 mmol, 2.5 eq). Reaction mixture was degassed for 10 min. using argon then Pd$_2$(dba)$_3$ (0.021 g, 0.0231 mmol, 0.1 eq) and Xantphos (0.026 g, 0.0462 mmol, 0.2 eq) were added, again degassed for 5 min. Reaction was stirred at 110° C. for 4 hours. After completion of the reaction. mixture was poured into water and extracted with EtOAc. Organic layers were combined, dried over Na$_2$SO$_4$ and concentrated under reduced pressure to obtain crude which was purified by column chromatography to furnish 184.3 (0.090 g, 71.08%). MS (ES): m/z 546.5 [M+H]$^+$.

Synthesis of Compound I-237.

Compound 183.3 (0.090 g, 0.165 mmol, 1.0 eq) was dissolved in HBr/HOAc (2 mL) and stirred at room temperature for 1 hour. After completion of the reaction, mixture were poured in water and basified with satd. NaHCO$_3$ and extracted with EtOAc. Organic layers was combined, dried over Na$_2$SO$_4$ and concentrated under reduced pressure to obtain crude which was purified by column chromatography to furnish I-237 (0.015 g, 23.07%). MS (ES): m/z 396.5 [M+H]$^+$; $^1$H NMR (DMSO-d$_6$, 400 MHz): 10.08 (s, 1H), 9.68 (s, 1H), 8.87 (s, 1H), 8.49-8.48 (d, 1H), 8.42 (s, 1H), 7.99-7.96 (m, 1H), 7.61-7.54 (m, 1H), 7.28-7.23 (m, 2H), 7.18-7.16 (d, 1H), 4.42 (s, 2H), 2.05 (s. 3H).

Example 184. Synthesis of 2-(2,6-difluorophenyl)-4-((6-morpholinopyridin-3-yl)amino)-6,7-dihydro-5H-pyrrolo[3,4-b]pyridin-5-one, I-238

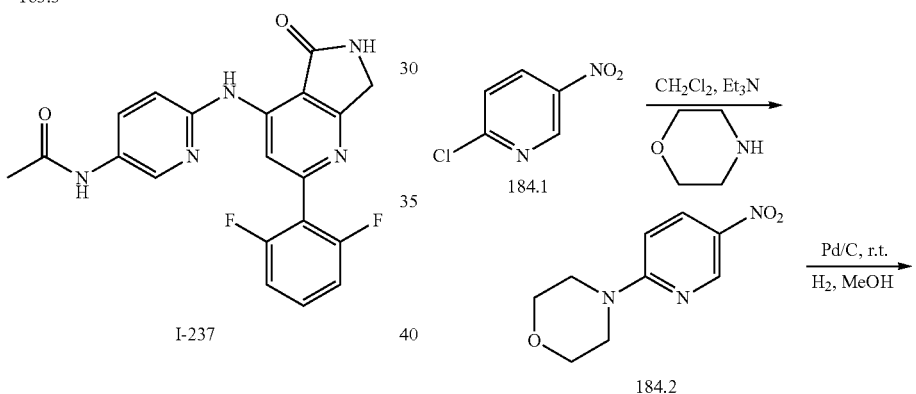

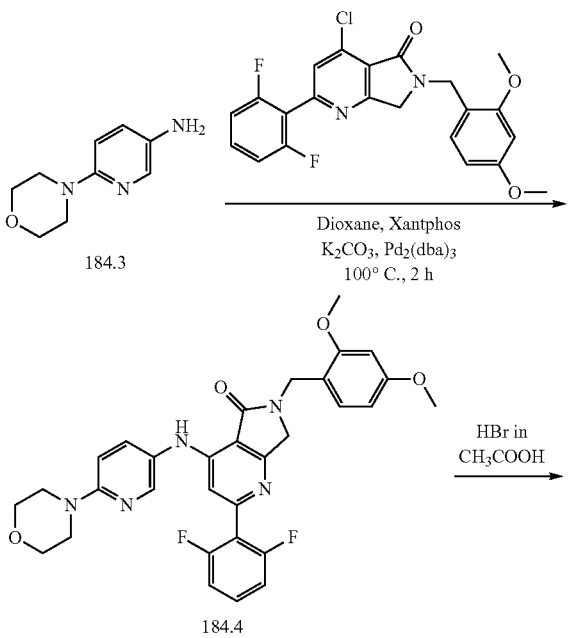

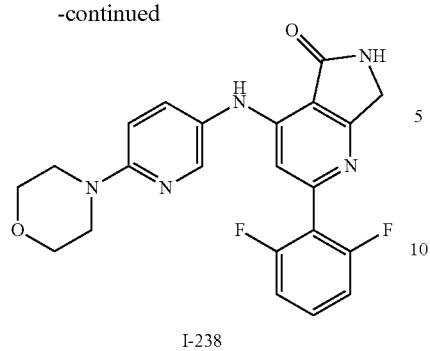

I-238

Synthesis of Compound 184.2.

To a solution of 184.1 (0.5 g, 3.16 mmol, 1.0 eq) in CH$_2$Cl$_2$ (3 ml) were added morpholine (0.33 g, 3.79 mmol, 1.2 eq), and Et$_3$N (0.96 g, 9.49 mmol, 3.0 eq). Reaction mixture was stirred at room temperature for 1 hour. The reaction mixture was poured in water and extracted with EtOAc. Organic layers were combined and dried over Na$_2$SO$_4$ and concentrated under reduced pressure to obtain crude which was purified by column chromatography to furnish 184.2 (0.65 g, 98.2%). MS (ES): m/z 209.2 [M+H]$^+$.

Synthesis of Compound 184.3.

A solution of 184.2 (0.650 g, 0.365 mmol, 1.0 eq) in MeOH (20 mL) was added 10% Pd/C (0.200 g) under nitrogen. It was purged with H$_2$ for 1 hour. Reaction mixture was filtered through celite and obtained filtrate was concentrated under reduced pressure to get crude 184.3 (0.50 g, 89.8%) which was used as such for the next step, MS (ES): m/z 179.23 [M+H]$^+$.

Synthesis of Compound 184.4.

To a solution of 73.4 (0.11 g, 0.25 mmol, 1.0 eq) in 1,4-dioxane (3 mL) was added 184.3 (0.045 g, 0.250 mmol, 1.0 eq) and K$_2$CO$_3$ (0.070 g, 0.500 mmol, 2.0 eq). The reaction mixture was degassed for 10 minutes using argon then Pd$_2$(dba)$_3$ (0.046 g, 0.05 mmol, 0.1 eq) and Xantphos (0.028 g, 0.05 mmol, 0.2 eq) were added, again degassed for 5 minutes. The reaction was stirred at 100° C. for 4 hours. After completion of the reaction, mixture was poured into water and product was extracted with EtOAc. Organic layers were combined, dried over Na$_2$SO$_4$ and concentrated under reduced pressure to obtain crude which was purified by column chromatography to get pure 184.4 (0.095 g, 64.87%). MS (ES): m/z 572.6 [M+H]$^+$.

Synthesis of Compound I-238.

Compound 184.4 (0.095 g, 0.165 mmol, 1.0 eq) was dissolved in HBr/HOAc (5 ml) and stirred at room temperature for 1 hour. After completion of the reaction, mixture was poured in water and basified with satd. NaHCO$_3$ and product was extracted with EtOAc. Organic layers were combined, dried over sodium sulphate and concentrated under reduced pressure to obtain crude which was purified by column chromatography to get pure I-238 (0.043 g, 61.32%). MS(ES): m/z 422.4 [M+H]$^+$, $^1$H NMR (DMSO-d6, 400 MHz): 8.66-8.62 (d, 2H), 8.13 (s, 1H), 7.58-7.48 (m, 2H), 7.19-7.15 (t, 2H), 6.90-6.88 (d, 1H), 6.59 (s, 1H), 4.36 (s, 2H), 3.70-3.68 (m, 2H), 3.44-3.41 (m, 2H).

Example 185. Synthesis of 2-(2,6-difluorophenyl)-4-((5-methoxypyridin-2-yl)amino)-7-methyl-6,7-dihydro-5H-pyrrolo[3,4-b]pyridin-5-one I-239

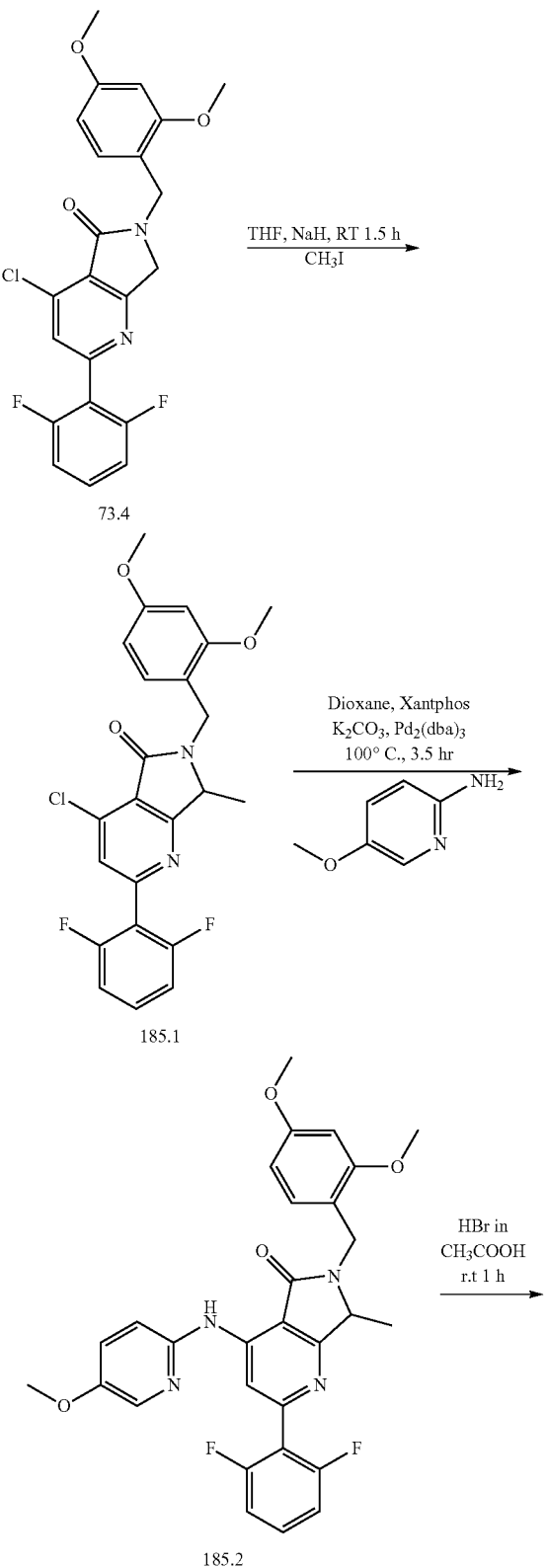

-continued

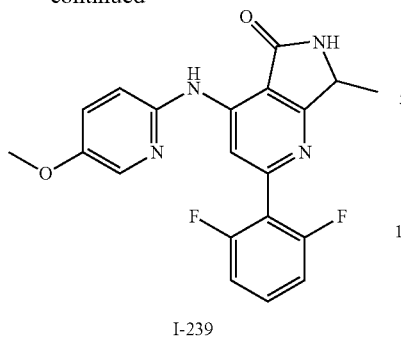

I-239

Synthesis of Compound 185.1.

To a solution of 73.4 (0.200 g, 0.465 mmol, 1.0 eq) in THF (6 mL) was added NaH (0.0170 g, 0.697 mmol, 1.5 eq) at 0° C. reaction was stirred for 30 minutes. Methyl iodide (0.0726 g, 0.511 mmol, 1.1 eq) was added to the reaction mixture and it was allowed to stir for 1.5 hours. After completion of the reaction, mixture was poured into chilled water. The product was extracted with EtOAc. Organic layers were combined, dried over $Na_2SO_4$ and concentrated under reduced pressure to obtain crude which was purified by column chromatography to furnish 185.1 (0.080 g, 38.74%). MS (ES): m/z 444.86 $[M+H]^+$.

Synthesis of Compound 185.2.

To a solution of 185.1 (0.080 g, 0.180 mmol, 1.0 eq) in 1,4-dioxane (2 ml) was added 5-methoxypyridin-2-amine (0.026 g, 0.216 mmol, 1.2 eq) and $K_2CO_3$ (0.049 g, 0.36 mmol, 2 eq). The reaction mixture was degassed for 10 min. using argon, then $Pd_2(dba)_3$ (0.0164 g, 0.018 mmol, 0.1 eq) and Xantphos (0.0208 g, 0.0360 mmol, 0.2 eq) were added, and again degassed for 5 minutes. Reaction was stirred at 100° C. for 3.5 hours. After completion of the reaction, mixture was poured into water and product was extracted with EtOAc. Organic layers were combined, dried over $Na_2SO_4$ and concentrated under reduced pressure to obtain crude which was purified by column chromatography to furnish 185.2 (0.064 g, 66.83%). MS (ES): m/z 532.55 $[M+H]^+$.

Synthesis of Compound I-239.

A solution of 185.2 (0.064 g, 0.120 mmol, 1.0 eq) in HBr/HOAc (2 mL) was stirred at room temperature for 1 h. After completion of the reaction pH was adjusted to 7 by addition of $NaHCO_3$ solution. The product was extracted with EtOAc. Combined organic layers were washed with brine, dried over $Na_2SO_4$ and concentrated under reduced pressure to afford crude, which was purified by column chromatography to furnish I-239 (0.038 g, 82.7%). MS (ES): m/z 382.37 $[M+H]^+$. $^1H$ NMR (DMSO-$d_6$, 400 MHz): 9.58 (s, 1H), 8.92 (s, 1H), 8.38 (s, 1H), 8.08-8.07 (d, 1H), 7.59-7.55 (m, 1H), 7.46-7.43 (dd, 1H), 7.28-7.23 (m, 2H), 7.19-7.17 (d, 1H), 4.65-4.60 (q, 1H), 3.88 (s, 3H), 1.40 (s, 3H).

Example 186. Synthesis of (R)-2-(2,6-difluorophenyl)-4-((5-methoxypyridin-2-yl)amino)-7-methyl-6,7-dihydro-5H-pyrrolo[3,4-b]pyridin-5-one, I-240

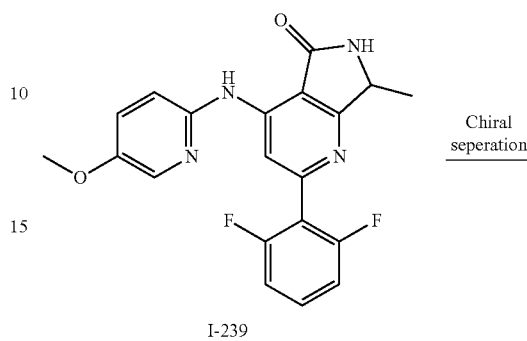

I-239

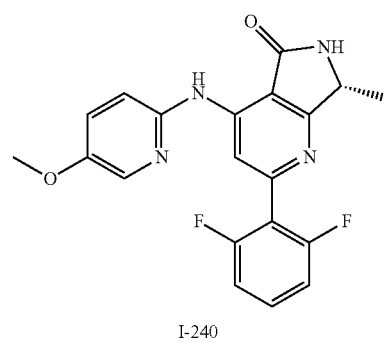

I-240

Compound I-240 was prepared by chiral separation of compound I-239. MS (ES): m/z 382.37 $[M+H]^+$, $^1H$ NMR (400 MHz, MeOD): δ 8.65 (s, 1H), 8.12-8.11 (d, 1H), 7.67-7.61 (m, 1H), 7.49-7.46 (m, 1H), 7.25-7.18 (m, 3H), 4.85-4.79 (q, 1H), 3.88 (s, 3H), 1.32 (s, 3H)

Example 187. Synthesis of (S)-2-(2,6-difluorophenyl)-4-((5-methoxypyridin-2-yl)amino)-7-methyl-6,7-dihydro-5H-pyrrolo[3,4-b]pyridin-5-one, I-241

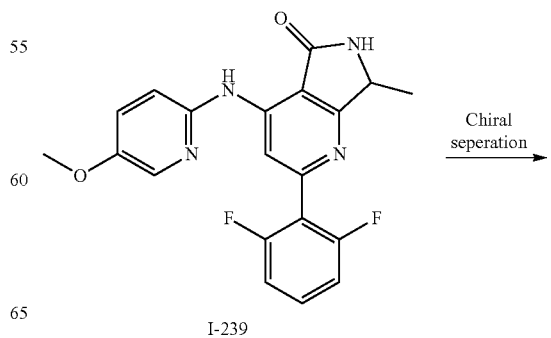

I-239

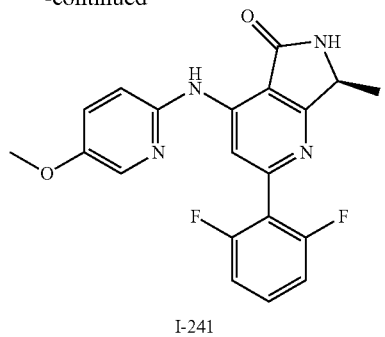
I-241
Compound I-241 was prepared by chiral separation of I-239. MS (ES): m/z 382.37 [M+H]$^+$, $^1$H NMR (400 MHz, MeOD): δ 8.67 (s, 1H), 8.12 (d, 1H), 7.67-7.63 (m, 1H), 7.50-7.47 (m, 1H), 7.26-7.19 (m, 3H), 4.87-4.82 (q, 1H), 3.87 (s, 3H), 1.32 (s, 3H).
Example 188. Synthesis of 2-(2,6-difluorophenyl)-4-((5-(4-isopropyl-2-oxopiperazin-1-yl)pyridin-2-yl)amino)-6,7-dihydro-5H-pyrrolo[3,4-b]pyridin-5-one, I-242
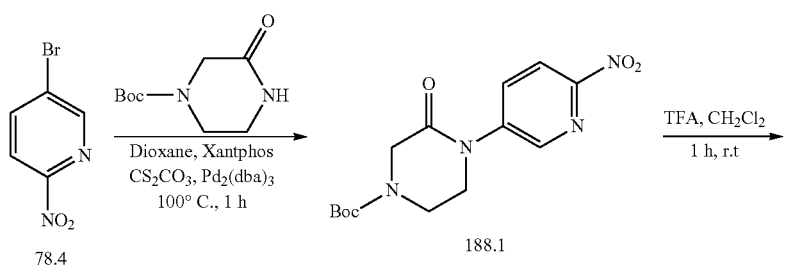
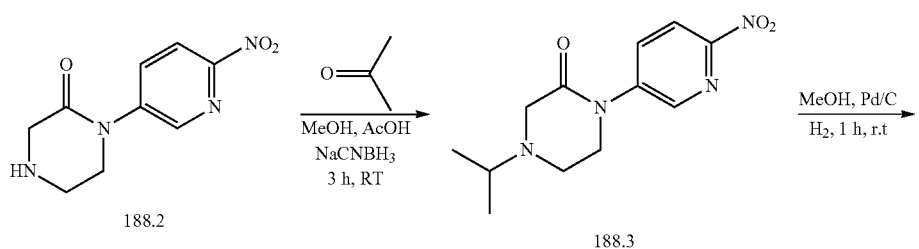
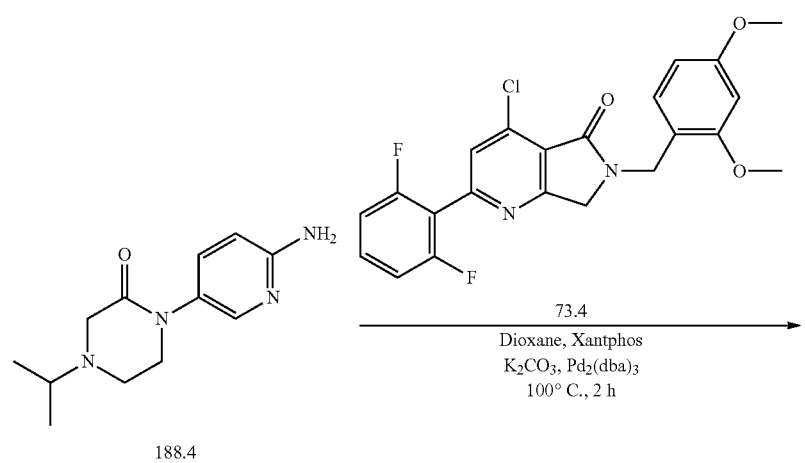

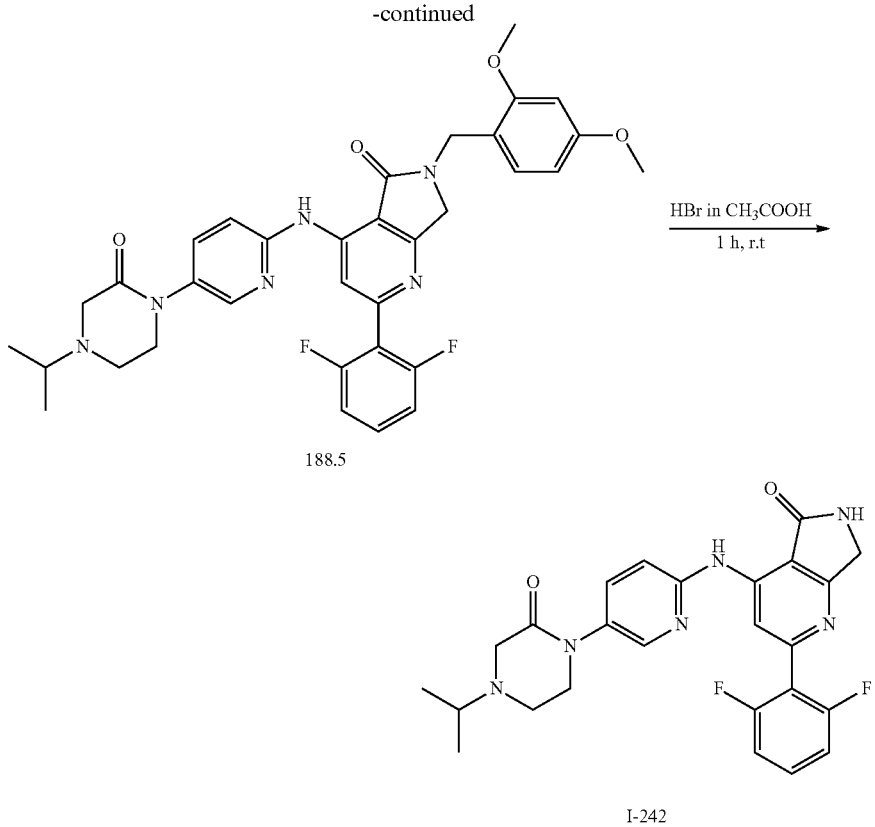

Synthesis of Compound 188.1.

To a solution of 78.4 (1.0 g, 4.92 mmol, 1.0 eq) in 1,4-dioxane (15 ml) was added tert-butyl 3-oxopiperazine-1-carboxylate (1.18 g, 5.91 mmol, 1.2 eq) and $Cs_2CO_3$ (3.2 g, 9.85 mmol, 2.0 eq). Reaction mixture was degassed for 10 minutes using argon, then $Pd_2(dba)_3$ (0.450 g, 0.492 mmol, 0.1 eq) and xantphos (0.560 g, 0.985 mmol, 0.2 eq) were added, and again degassed for 5 minutes. The reaction was stirred at 100° C. in for 1 h. After completion of the reaction, mixture was poured into water and product was extracted with EtOAc. Organic layers were combined and dried over $Na_2SO_4$ and concentrated under reduced pressure to obtain crude which was purified by column chromatography to furnish pure 188.1 (0.760 g, 47.86%). MS (ES): m/z 323.6 [M+H]⁺.

Synthesis of Compound 188.2.

A solution of 188.1 (0.760 g, 2.32 mmol, 1.0 eq) in HCl acid in dioxane (5 mL) was stirred at room temperature for 1 hour. After completion of the reaction, mixture was poured into water, neutralized with $NaHCO_3$ product was extracted with EtOAc. Organic layer was dried over sodium sulphate and concentrated under reduced pressure to obtain crude 188.2 (0.51 g, 98.6%) which was used as such for the next step, MS (ES): m/z 223.23 [M+H]⁺.

Synthesis of Compound 188.3.

To a solution of 188.3 (0.210 g, 0.945 mmol, 1.0 eq) in Acetone (2 mL) and MeOH (4 mL) was added Acetic acid (0.1 mL). Reaction was stirred for 15 min at room temperature. $NaCNBH_3$ (0.119 g, 1.89 mmol, 2.0 eq) was added. Reaction was stirred at room temperature for 3 hours. After completion of the reaction, mixture was poured into water and product was extracted with EtAOc. Organic layers were combined, dried over $Na_2SO_4$ and concentrated under reduced pressure to obtain crude which was purified by column chromatography to furnish 188.3 (0.105 g, 42.0%). MS (ES): m/z 265.5 [M+H]⁺.

Synthesis of Compound 188.4.

To a solution of 188.4 (0.105 g, 0.378 mmol, 1.0 eq) in MeOH (6 mL) was added 10% Pd/C (0.025 g) under nitrogen atmosphere. It was purged with hydrogen for 1 h. Reaction mixture was filtered through celite and obtained filtrate was concentrated under reduced pressure to get crude 188.4 (0.08 g, 85.94%) which was used as such for the next step, MS (ES): m/z 235.23 [M+H]⁺.

Synthesis of Compound 188.5.

To a solution of 73.4 (0.100 g, 0.231 mmol, 1.0 eq) in 1,4-dioxane (5 ml) was added 188.4. (0.059 g, 0.255 mmol, 1.1 eq) and $K_2CO_3$ (0.064 g, 0.464 mmol, 2.0 eq). The reaction mixture was degassed for 10 min. under argon atmosphere, then $Pd_2(dba)_3$ (0.021 g, 0.0231 mmol, 0.1 eq) and Xantphos (0.026 g, 0.0462 mmol, 0.2 eq) were added, and again degassed for 5 minutes. Reaction was stirred at 110° C. for 2 h. After completion of the reaction, mixture was poured into water and product was extracted with EtOAc. Organic layers were combined and dried over $Na_2SO_4$ and concentrated under reduced pressure to obtain crude which was purified by column chromatography to furnish 188.5 (0.090 g, 61.68%). MS(ES): m/z 629.6 [M+H]⁺.

Synthesis of Compound I-242.

Compound 188.5 (0.090 g, 0.111 mmol, 1.0 eq) was dissolved in Hbr/HOAc (5 ml) and stirred at room temperature for 1 hour. After completion of the reaction, mixture was poured in water and basified with satd. NaHCO$_3$ and extracted with EtOAc. Organic layers were combined, dried over Na$_2$SO$_4$ and concentrated under reduced pressure to obtain crude which was purified by column chromatography to furnish I-242 (0.038 g, 55.5%). MS (ES): m/z 480.5 [M+H]$^+$, $^1$H NMR (DMSO-d$_6$, 400 MHz): 9.81 (s, 1H), 8.91 (s, 1H), 8.54 (s, 1H), 8.33-8.32 (d, 1H), 7.79-7.77 (m, 1H), 7.60-7.56 (m, 1H), 7.28-7.22 (m, 3H), 4.44 (s, 2H), 3.65-3.63 (m, 2H), 3.24 (s, 2H), 2.81-2.74 (m, 2H), 1.23-1.14 (m, 1H), 1.03-1.01 (d, 6H).

Example 189. Synthesis of 2-(2,6-difluorophenyl)-4-((4-(4-isopropylpiperazine-1-carbo-nyl)phenyl)amino)-6,7-dihydro-5H-pyrrolo[3,4-b]pyridin-5-one, I-243

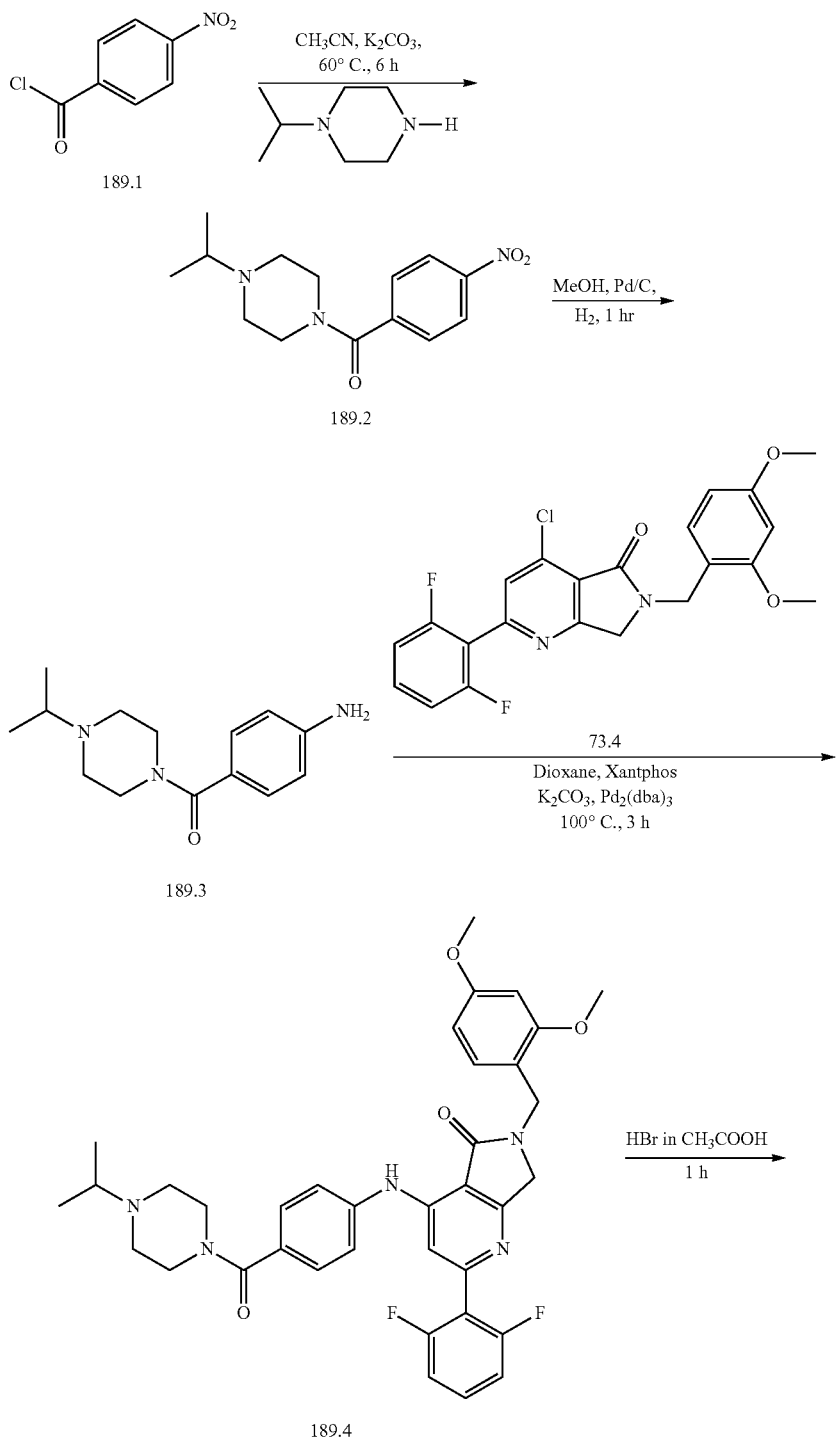

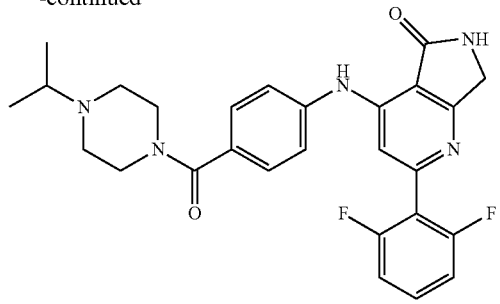

I-243

Synthesis of Compound 189.2.

To a solution of 1-isopropylpiperazine (0.35 g, 2.7 mmol, 1.0 eq) in CH₃CN (5 ml) was added potassium carbonate (1.12 g, 8.1 mmol, 3.0 eq). Compound 189.1 (0.5 g, 2.7 mmol, 1.0 eq) in CH₃CN (5 ml) was added dropwise to the reaction mixture. Reaction mixture was then stirred at 60° C. for 6 hours. After completion of the reaction, mixture was poured into water and product was extracted with EtOAc. Organic layers were combined, washed with brine, dried over Na₂SO₄ and concentrated under reduced pressure to obtain crude which was purified by column chromatography to furnish 189.2 (0.460 g, 61.56%). MS (ES): m/z 277.32 [M+H]⁺.

Synthesis of Compound 189.3.

To a solution of 189.2 (0.460 g, 1.66 mmol, 1.0 eq) in methanol (10 ml) was added 10% Pd/C (0.18 g) under nitrogen. It was purged with H₂ gas for 1 hour. Reaction mixture was filtered through celite and obtained filtrate was concentrated under reduced pressure to furnish crude 189.3 (0.35 g, 85.3%) which was used as such for the next step, MS (ES): m/z 247.34 [M+H]⁺.

Synthesis of Compound 189.4.

To a solution of 73.4 (0.100 g, 0.232 mmol, 1.0 eq) in 1,4-dioxane (4 mL) was added 189.3 (0.063 g, 0.255 mmol, 1.1 eq) and K₂CO₃ (0.080 g, 0.58 mmol, 2.5 eq). Reaction was degassed for 10 minutes using argon then Pd2(dba)3 (0.021 g, 0.0231 mmol, 0.1 eq) and xantphos (0.026 g, 0.046 mmol, 0.2 eq) were added, and again degassed for 5 minutes. Reaction was stirred at 100° C. for 3 hours. After completion of the reaction, mixture was poured into water and extracted with EtOAc. Organic layers were combined, washed with brine, dried over Na₂SO₄ and concentrated under reduced pressure to obtain crude which was purified by column chromatography to furnish 189.4 (0.09 g, 60.4%). MS (ES): m/z 641.72 [M+H]⁺.

Synthesis of Compound I-243.

The compound 189.4 (0.09 g, 0.14 mmol, 1.0 eq) was dissolved in HBr/HOAc (3 ml) and stirred at room temperature for 1 h. After completion of the reaction, mixture was poured into water, washed with saturated NaHCO₃ and extracted with EtOAc. Organic layers were combined, dried over Na₂SO₄ and concentrated under reduced pressure to obtain crude which was purified by column chromatography to furnish I-243 (0.055 g, 79.8%). MS (ES): m/z 491.5 [M+H]⁺, ¹H NMR (DMSO-d₆, 400 MHz): 9.16 (s, 1H), 8.77 (s, 1H), 7.56-7.50 (m, 1H), 7.42 (s, 4H), 7.24-7.20 (m, 3H), 4.41 (s, 2H), 3.52-3.44 (m, 4H), 2.69-2.60 (m, 1H), 2.51-2.50 (m, 4H), 0.97-0.95 (d, 6H).

Example 190. Synthesis of 2-(2,6-difluorophenyl)-4-((5-(3-methylmorpholino)pyridin-2-yl)amino)-6,7-dihydro-5H-pyrrolo[3,4-b]pyridin-5-one, I-244

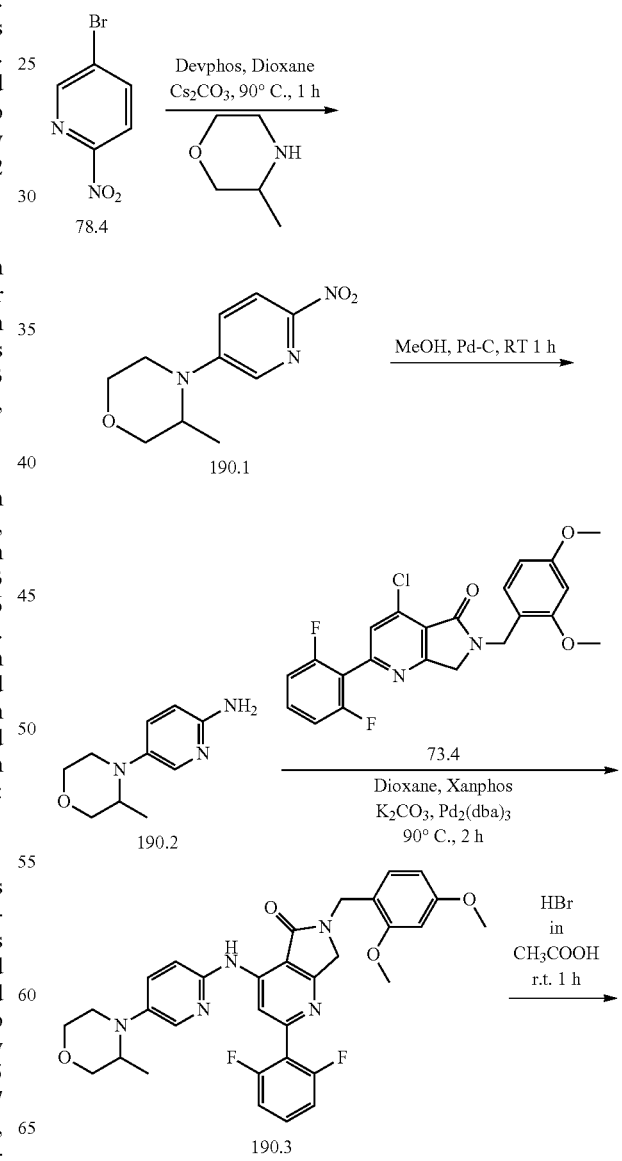

489

-continued

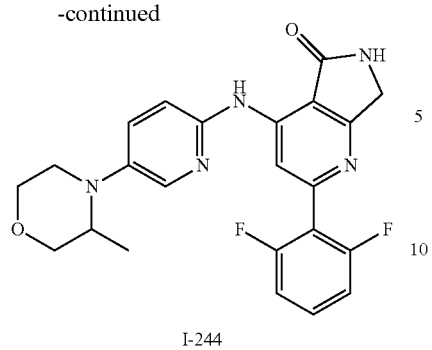

I-244

Synthesis of Compound 190.1.

To a solution of 78.4 (0.2 g, 0.985 mmol, 1.0 eq) in 1,4-dioxane (3 ml) was added 3-methylmorpholine (0.119 g, 1.182 mmol, 1.2 eq) and $Cs_2CO_3$ (0.960 g, 2.955 mmol, 3.0 eq). The reaction mixture was degassed for 10 min. under argon atmosphere, then $Pd_2(dba)_3$ (0.090 g, 0.098 mmol, 0.1 eq) and 2-Dicylcohexylphosphino-2'-(N,N-dimethylamino)-biphenyl (0.113 g, 0.197 mmol, 0.2 eq) were added, and again degassed for 5 min. The reaction was stirred at 90° C. for 1 hour. After completion of the reaction, mixture was poured into water and extracted with EtOAc. Organic layers were combined, dried over $Na_2SO_4$ and concentrated under reduced pressure to obtain crude which was purified by column chromatography to furnish 190.1 (0.127 g, 57.74%). MS (ES): m/z 223.23 $[M+H]^+$.

Synthesis of Compound 190.2.

To a solution of 190.1 (0.127 g, 0.569 mmol, 1.0 eq) in MeOH (10 mL) was added 10% Pd/C (0.100 g) under nitrogen atmosphere. Suspension was purged with $H_2$ gas for 1 hour. Reaction mixture was filtered through celite and obtained filtrate was concentrated under reduced pressure to get crude 190.2 (0.08 g, 72.8%) which was used as such in the next step, MS (ES): m/z 193.25 $[M+H]^+$.

Synthesis of Compound 190.3.

To a solution of 73.4 (0.150 g, 0.348 mmol, 1.0 eq) in 1,4-dioxane (5 mL) was added 190.2 (0.067 g, 0.348 mmol, 1.0 eq) and $K_2CO_3$ (0.144 g, 1.046 mmol, 3.0 eq). Reaction mixture was degassed for 10 min. using argon, then $Pd_2(dba)_3$ (0.031 g, 0.034 mmol, 0.1 eq) and Xantphos (0.04 g, 0.069 mmol, 0.2 eq) were added, and again degassed for 5 min. Reaction was stirred at 90° C. for 2 hours. After completion of the reaction, mixture was poured into water and product was extracted with EtOAc. Organic layers were combined, dried over $Na_2SO_4$ and concentrated under reduced pressure to obtain crude which was purified by column chromatography to furnish get pure 190.3 (0.12 g, 58.7%). MS(ES): m/z 587.63 $[M+H]^+$.

Synthesis of Compound I-244.

Compound 190.3 (0.120 g, 0.204 mmol, 1.0 eq) was dissolved in HBr/HOAc (5 ml) and stirred at room temperature for 1 hour. After completion of the reaction, mixture was poured into water and basified with satd. $NaHCO_3$ and extracted with EtOAc. Organic layers were combined, dried over sodium sulphate and concentrated under reduced pressure. Crude was purified by column chromatography to furnish compound I-244 (0.066 g, 73.9%). MS (ES): m/z 437.35 $[M+H]^+$, $^1H$ NMR (DMSO-$d_6$, 400 MHz): δ 9.53 (s, 1H), 8.81 (s, 1H), 8.39 (s, 1H), 8.33-8.32 (d, 1H), 7.60-7.55 (m, 1H), 7.44-7.41 (m, 1H), 7.27-7.23 (t, 2H), 7.13-7.10 (d, 1H), 4.41 (s, 2H), 3.78-3.70 (m, 2H), 3.63-3.55 (m, 2H), 3.18-2.99 (m, 2H), 0.96-0.95 (d, 3H).

490

Example 191. Synthesis of (S)-2-(2,6-difluorophenyl)-4-((5-(3-methylmorpholino)pyridin-2-yl)amino)-6,7-dihydro-5H-pyrrolo[3,4-b]pyridin-5-one, I-245

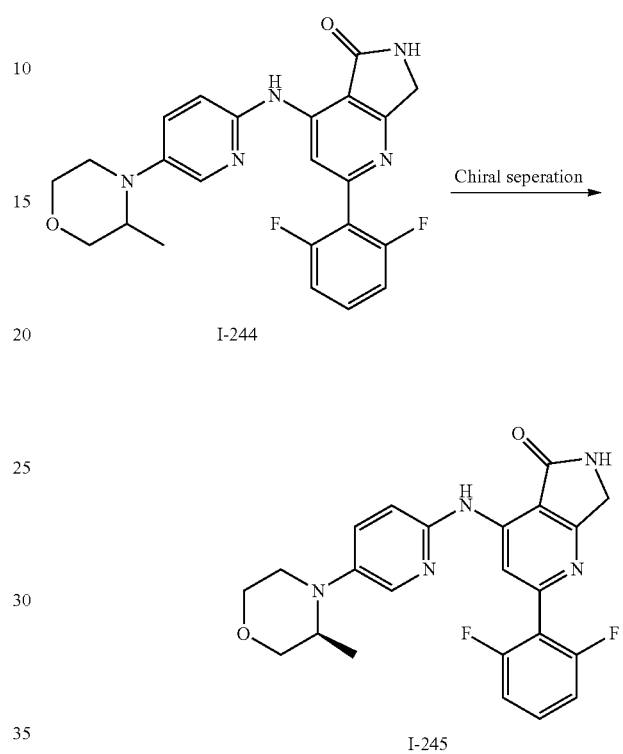

Compound I-245 was prepared by chiral separation of compound I-244. MS (ES): m/z 437.35 $[M+H]^+$, $^1H$ NMR (DMSO-$d_6$, 400 MHz): δ 9.53 (s, 1H), 8.82 (s, 1H), 8.39 (s, 1H), 7.99-7.98 (d, 1H), 7.59-7.55 (m, 1H), 7.44-7.42 (m, 1H), 7.28-7.23 (t, 2H), 7.13-7.10 (d, 1H), 4.41 (s, 2H), 3.78-3.73 (m, 2H), 3.70-3.55 (m, 2H), 3.15-2.96 (m, 2H), 0.96-0.94 (d, 3H)

Example 192. Synthesis of (R)-2-(2,6-difluorophenyl)-4-((5-(3-methylmorpholino)pyridin-2-yl)amino)-6,7-dihydro-5H-pyrrolo[3,4-b]pyridin-5-one, I-246

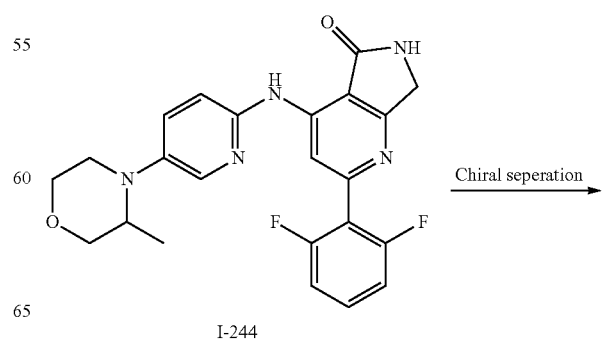

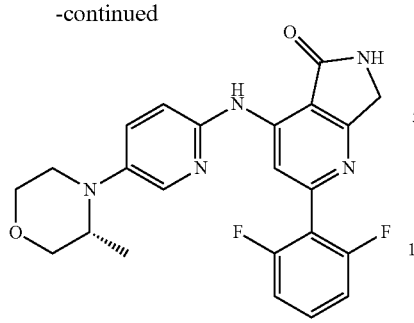
I-246
Compound I-246 was prepared by chiral separation of compound I-244. MS (ES): m/z 437.35 [M+H]$^+$, $^1$H NMR (DMSO-d$_6$, 400 MHz): δ 9.53 (s, 1H), 8.81 (s, 1H), 8.39 (s, 1H), 7.99-7.98 (d, 1H), 7.59-7.55 (m, 1H), 7.45-7.42 (m, 1H), 7.27-7.23 (t, 2H), 7.13-7.10 (d, 1H), 4.41 (s, 2H), 3.78-3.73 (m, 2H), 3.71-3.55 (m, 2H), 3.18-2.97 (m, 2H), 0.96-0.95 (d, 3H).
Example 193. Synthesis of 4-((5-(4-(2,2-difluoro-ethyl)piperazin-1-yl)pyridin-2-yl)amino)-2-(2,6-difluorophenyl)-6,7-dihydro-5H-pyrrolo[3,4-b]pyridin-5-one, I-247
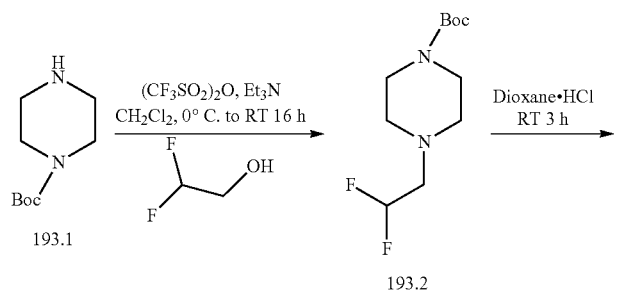
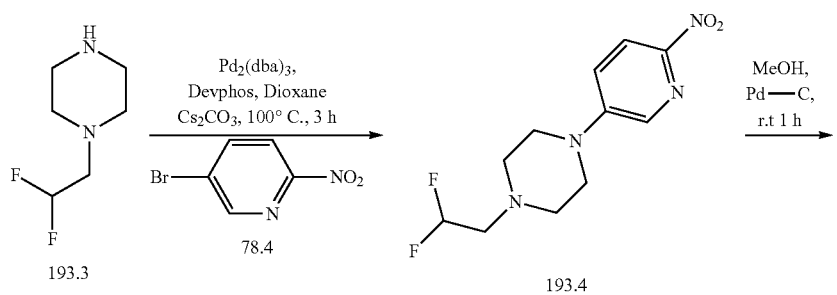
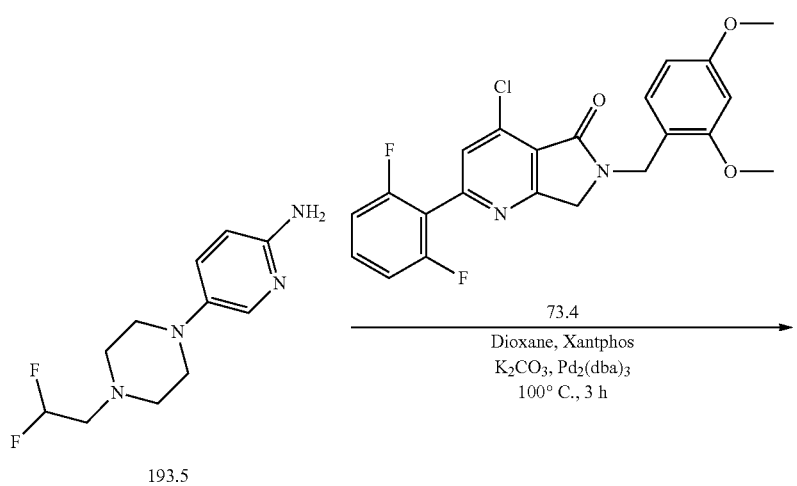

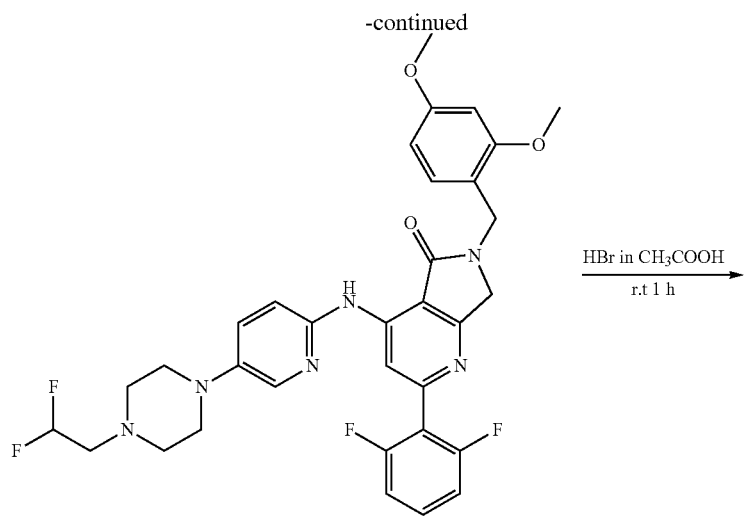

193.6

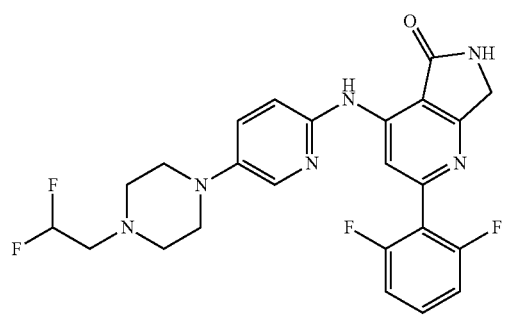

I-247

Synthesis of Compound 193.2.

To a solution of 2,2-difluoroethanol (0.407 ml, 6.437 mmol, 1.19 eq.) in $CH_2Cl_2$ (10 mL) was added anhydrous $Et_3N$ (1.33 ml, 9.610 mmol, 1.79 eq.) and trifluoromethane sulphonic acid anhydride (1.26 ml, 7.516 mmol, 1.40 eq.) at 0° C. Reaction was stirred at 0° C. for 30 minutes. A solution of 193.1 (1.0 g, 5.37 mmol, 1.0 eq.) in $CH_2Cl_2$ (10 ml) was added to the reaction mixture. The reaction mixture was stirred at room temperature for 16 h. After completion of the reaction, mixture was poured into water and product was extracted with EtOAc. Organic layers were combined, dried over $Na_2SO_4$ and concentrated under reduced pressure to obtain crude which was purified by column chromatography to furnish 193.2 (0.39 g, 29.02%). MS (ES): m/z 250.29 $[M+H]^+$.

Synthesis of Compound 193.3.

Solution of 193.2 (0.39 g, 1.558 mmol, 1.0 eq) in 1,4-dioxane in HCl (5 ml, 4M) was stirred at room temperature for 3 h. After completion of the reaction, solvent was removed under reduced pressure and the product was collected as HCl salt. Product was triturated with diethyl ether to get pure 193.3 (0.208 g, 88.89%) which was used as such for the next step, MS (ES): m/z 150.17 $[M+H]^+$.

Synthesis of Compound 193.4.

To a solution of 78.4 (0.25 g, 1.231 mmol, 1.0 eq) in 1,4-dioxane (5 ml) was added 193.3 (0.203 g, 1.354 mol, 1.1 eq) and $Cs_2CO_3$ (0.8 g, 2.463 mmol, 2.0 eq). The mixture was degassed for 10 min. using argon, then $Pd_2(dba)_3$ (0.112 g, 0.123 mmol, 0.1 eq) and dicylcohexylphosphino-2'-(N,N-dimethylamino)-biphenyl (0.096 g, 0.246 mmol, 0.2 eq) were added, and again degassed for 5 minutes. Reaction was stirred at 100° C. for 3 h. After completion of reaction, mixture was poured into water and product was extracted with EtOAc. Organic layers were combined, dried over $Na_2SO_4$ and concentrated under reduced pressure to obtain crude which was purified by column chromatography to furnish 193.4 (0.198 g, 59.05%). MS(ES): m/z 272.26 $[M+H]^+$.

Synthesis of Compound 193.5.

To a solution of 193.4 (0.198 g, 0.727 mmol, 1.0 eq) in MeOH (5 ml) was added 10% Pd/C (0.08 g) under nitrogen atmosphere. It was purged with hydrogen for 1 h. Reaction mixture was filtered through celite and obtained filtrate was concentrated under reduced pressure to get crude 193.5 (0.144 g, 81.73%) which was used as such for the next step, MS (ES): m/z 242.27 $[M+H]^+$.

Synthesis of Compound 193.6.

To a solution of 73.4 (0.125 g, 0.290 mmol, 1.0 eq) in 1,4-dioxane (4 ml) was added 193.5 (0.077 g, 0.319 mmol, 1.1 eq) and $K_2CO_3$ (0.1 g, 0.726 mmol, 2.5 eq). Mixture was degassed for 10 minutes using argon then $Pd_2(dba)_3$ (0.026 g, 0.029 mmol, 0.1 eq) and Xantphos (0.033 g, 0.058 mmol, 0.2 eq) were added, and again degassed for 5 min. The reaction was stirred at 100° C. for 3 h. After completion of reaction, mixture was poured into water and product was extracted with EtOAc. Organic layers were combined, dried over $Na_2SO_4$ and concentrated under reduced pressure to obtain crude which was purified by column chromatography to furnish 193.6 (0.120 g, 64.97%). MS(ES): m/z 635.65 $[M+H]^+$.

Synthesis of Compound I-247.

Compound 193.6 (0.120 g, 0.188 mmol, 1.0 eq) was dissolved in HBr/HOAc (5 mL) and stirred at room temperature for 1 hour. After completion of the reaction, water was added to the mixture and basified with satd. NaHCO$_3$ and extracted with EtOAc. Organic layers were combined, dried over Na$_2$SO$_4$ and concentrated under reduced pressure to obtain crude which was purified by column chromatography to furnish I-247 (0.070 g, 76.3%). MS (ES): m/z 486.47 [M+H]$^+$, $^1$H NMR (DMSO-d$_6$, 400 MHz): δ 9.52 (s, 1H), 8.82 (s, 1H), 8.39 (s, 1H), 8.02 (d, 1H), 7.60-7.53 (m, 1H), 7.49-7.44 (dd, 1H), 7.28-7.23 (m, 2H), 7.11-7.09 (d, 1H), 6.33-6.04 (dt, 1H), 4.39 (s, 2H), 3.15-3.11 (t, 4H), 2.82-2.73 (td, 2H), 2.67-2.65 (t, 3H).

Example 194. Synthesis of 4-(6-((2-(2,6-difluorophenyl)-5-oxo-6,7-dihydro-5H-pyrrolo[3,4-b]pyridin-4-yl)amino)pyridin-3-yl)morpholin-3-one, I-248

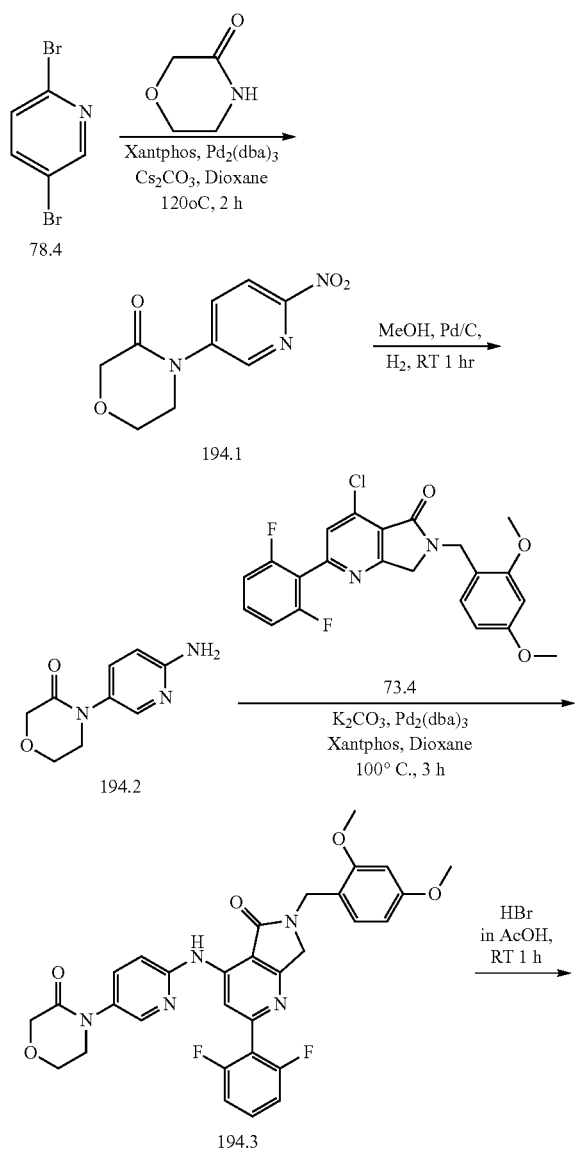

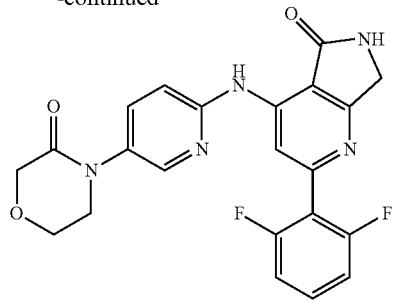

I-248

Synthesis of Compound 194.1.

To a solution of 78.4 (0.6 g, 2.955 mmol, 1.0 eq) in 1,4-dioxane (5 ml) was added morpholin-3-one (0.298 g, 2.955 mmol, 1.0 eq) and Cs$_2$CO$_3$ (1.921 g, 5.911 mmol, 2.0 eq). Mixture was degassed for 10 min. under argon atmosphere, then Pd$_2$(dba)$_3$ (0.270 g, 0.295 mmol, 0.1 eq) and xantphos (0.341 g, 0.591 mmol, 0.2 eq) were added, and again degassed for 5 min. The reaction was stirred at 120° C. in for 2 h. After completion of the reaction, mixture was poured into water and product was extracted with EtOAc. Organic layers were combined and dried over Na$_2$SO$_4$ and concentrated under reduced pressure to obtain crude which was purified by column chromatography to yield 194.1 (0.550 g, 83.37%). MS (ES): m/z 223.19 [M+H]$^+$.

Synthesis of Compound 194.2.

To a solution of 194.1 (0.4 g, 1.792 mmol, 1.0 eq) in MeOH (4 mL) was added 10% Pd/C (0.100 g) under N$_2$. Reaction was purged with hydrogen for 1 h. Reaction mixture was filtered through celite and obtained filtrate was concentrated under reduced pressure to get crude 194.2 (0.295 g, 85.2%) which was used as such for the next step, MS (ES): m/z 193.21 [M+H]$^+$.

Synthesis of Compound 194.3.

To a solution of 73.4 (0.100 g, 0.232 mmol, 1.0 eq) in 1,4-dioxane (2 mL) was added 194.2 (0.044 g, 0.23 mmol, 1.0 eq) and K$_2$CO$_3$ (0.064 g, 0.464 mmol, 2.0 eq). The reaction mixture was degassed for 10 min. under argon atmosphere, then Pd$_2$(dba)$_3$ (0.02 g, 0.02 mmol, 0.1 eq) and Xantphos (0.026 g, 0.046 mmol, 0.2 eq) were added, and again degassed for 5 min. The reaction was stirred at 100° C. for 3 hours. After completion of the reaction, mixture was poured into water and product was extracted with EtOAc. Organic layers were combined, dried over Na$_2$SO$_4$ and concentrated under reduced pressure to obtain crude which was purified to furnish 194.3 (0.085 g, 62.3%). MS(ES): m/z 587.58 [M+H]$^+$.

Synthesis of Compound I-248.

Compound 194.3 (0.085 g, 0.141 mmol, 1.0 eq) was dissolved in Hbr/HOAc (5 mL) and stirred at room temperature for 1 h. After completion of the reaction, water was added to the mixture, basified with satd. NaHCO$_3$ and extracted with EtOAc. Organic layers were combined, dried over Na$_2$SO$_4$ and concentrated under reduced pressure to obtain crude which was purified by column chromatography to yield I-248 (0.035 g, 55.3%). MS (ES): m/z 437.41 [M+H]$^+$, $^1$H NMR (DMSO-d$_6$, 400 MHz): δ 9.82 (s, 1H), 8.91 (s, 1H), 8.55 (s, 1H), 8.39 (d, 1H), 7.86-7.83 (dd, 1H), 7.60-7.54 (m, 1H), 7.28-7.25 (t, 3H), 4.45 (s, 2H), 4.22 (s, 2H), 3.99-3.96 (t, 3H), 3.77-3.74 (t, 2H).

497

Example 195. Synthesis of 2-(2,6-difluorophenyl)-4-((5-(3,6-dihydro-2H-pyran-4-yl)pyridin-2-yl)amino)-6,7-dihydro-5H-pyrrolo[3,4-b]pyridin-5-one, I-249

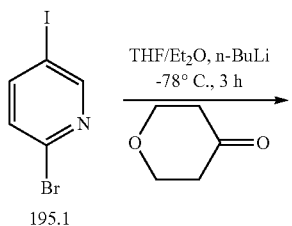

195.1

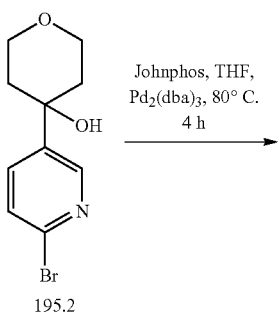

195.2

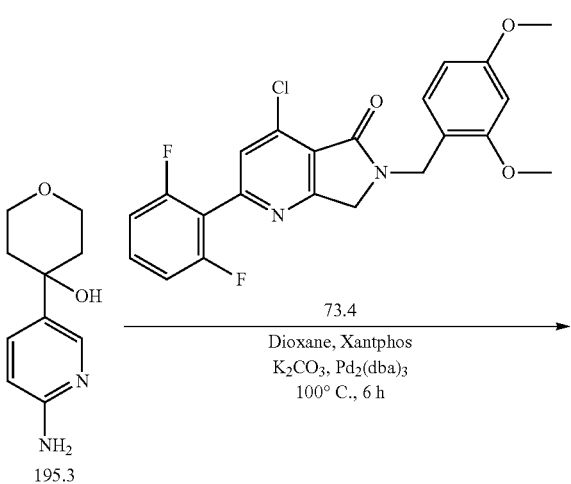

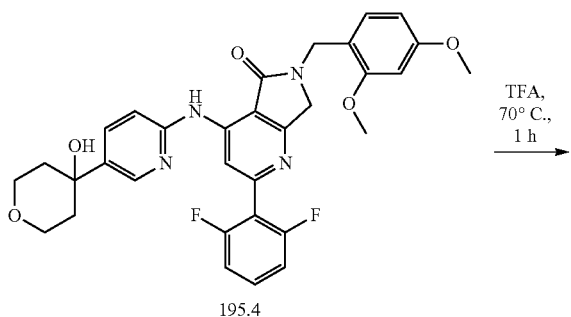

195.4

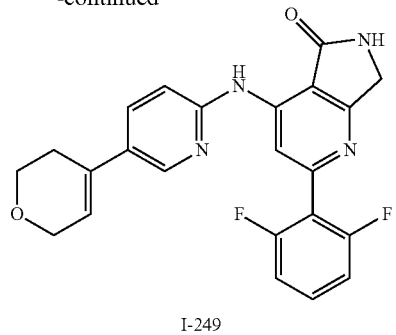

I-249

Synthesis of Compound 195.2.

To a solution of 195.1 (1.0 g, 3.522 mmol, 1.0 eq) in THF (7 ml) and Et$_2$O (9 ml) was added n-butyl lithium (0.225 g, 3.52 mmol, 1.0 eq.) at −78° C. Reaction was stirred at −78° C. for 1 h. Tetrahydro-4H-pyran-4-one was added to the reaction mixture at −78° C. and the reaction mixture was stirred at the same temperature for 2 h. After completion of the reaction, mixture was poured into water, quenched with NH$_4$Cl and extracted with EtOAc. Organic layers were combined, dried over Na$_2$SO$_4$ and concentrated under reduced pressure to obtain crude which was purified by column chromatography and preparative HPLC to furnish compound 195.2 (0.21 g, 23.1%). MS (ES): m/z 258.12 [M+H]$^+$.

Synthesis of Compound 195.3.

Compound 195.2 (0.210 g, 0.813 mmol, 1.0 eq) was dissolved in THF (2 mL). Mixture was degassed under argon atmosphere for 10 minutes. Pd$_2$(dba)$_3$ (0.074 g, 0.081 mmol, 0.1 eq) and 2-Biphenylyl[bis(2-methyl-2-propanyl)]phosphine (0.056 g, 0.162 mmol, 0.2 eq) were added. Reaction was degassed for 15 minutes and then LHMDS (2.5 ml) was added. The reaction was stirred at 80° C. for 4 h. After completion of the reaction, mixture was poured into water, quenched with NH$_4$Cl solution and extracted with EtOAc. Organic layers were combined, dried over Na$_2$SO$_4$ and concentrated under reduced pressure to obtain crude which was purified by column chromatography to yield 195.3 (0.095 g, 60.12%), MS (ES): m/z 194.23 [M+H]$^+$.

Synthesis of Compound 195.4.

To a solution of 73.4 (0.100 g, 0.232 mmol, 1.0 eq) in 1,4-dioxane (2 mL) was added 195.3 (0.04 g, 0.23 mmol, 1.0 eq) and K$_2$CO$_3$ (0.096 g, 0.69 mmol, 3.0 eq). Reaction was degassed for 10 minutes using argon, then Pd$_2$(dba)$_3$ (0.021 g, 0.023 mmol, 0.1 eq) and xantphos (0.026 g, 0.046 mmol, 0.2 eq) were added, and again degassed for 5 min. The reaction was stirred at 100° C. for 6 hours. After completion of the reaction, mixture was poured into water and product was extracted with EtAOc. Organic layers were combined, dried over Na$_2$SO$_4$ and concentrated under reduced pressure to obtain crude which was purified by column chromatography to furnish 195.4 (0.05 g, 36.6%). MS(ES): m/z 588.61 [M+H]$^+$.

Synthesis of Compound I-249.

Compound 195.4 (0.05 g, 0.084 mmol, 1.0 eq) was dissolved in TFA and heated at 70° C. for 1 hours. After completion of the reaction, water was added, basified with saturated satd. NaHCO$_3$ and product was extracted with EtOAc. Organic layers were combined, dried over sodium sulphate and concentrated under reduced pressure resulting crude was purified by column chromatography and preparative TLC to yield I-249 (0.006 g, 16.8%). MS (ES): m/z 420.42 [M+H]⁺; ¹H NMR (DMSO-d₆, 400 MHz): δ 9.79 (s, 1H), 8.91 (s, 1H), 8.60 (s, 1H), 8.44-8.43 (d, 1H), 7.90-7.87 (dd, 1H), 7.60-7.56 (m, 1H), 7.29-7.25 (t, 3H), 7.19-7.17 (d, 1H), 6.31 (s, 1H), 4.44 (s, 2H), 4.22-4.21 (d, 2H), 3.82-3.80 (t, 2H), 2.45 (s, 2H).

Example 196. Synthesis of 3,5-difluoro-4-(4-((5-morpholinopyridin-2-yl)amino)-5-oxo-6,7-dihydro-5H-pyrrolo[3,4-b]pyridin-2-yl)benzamide, I-250

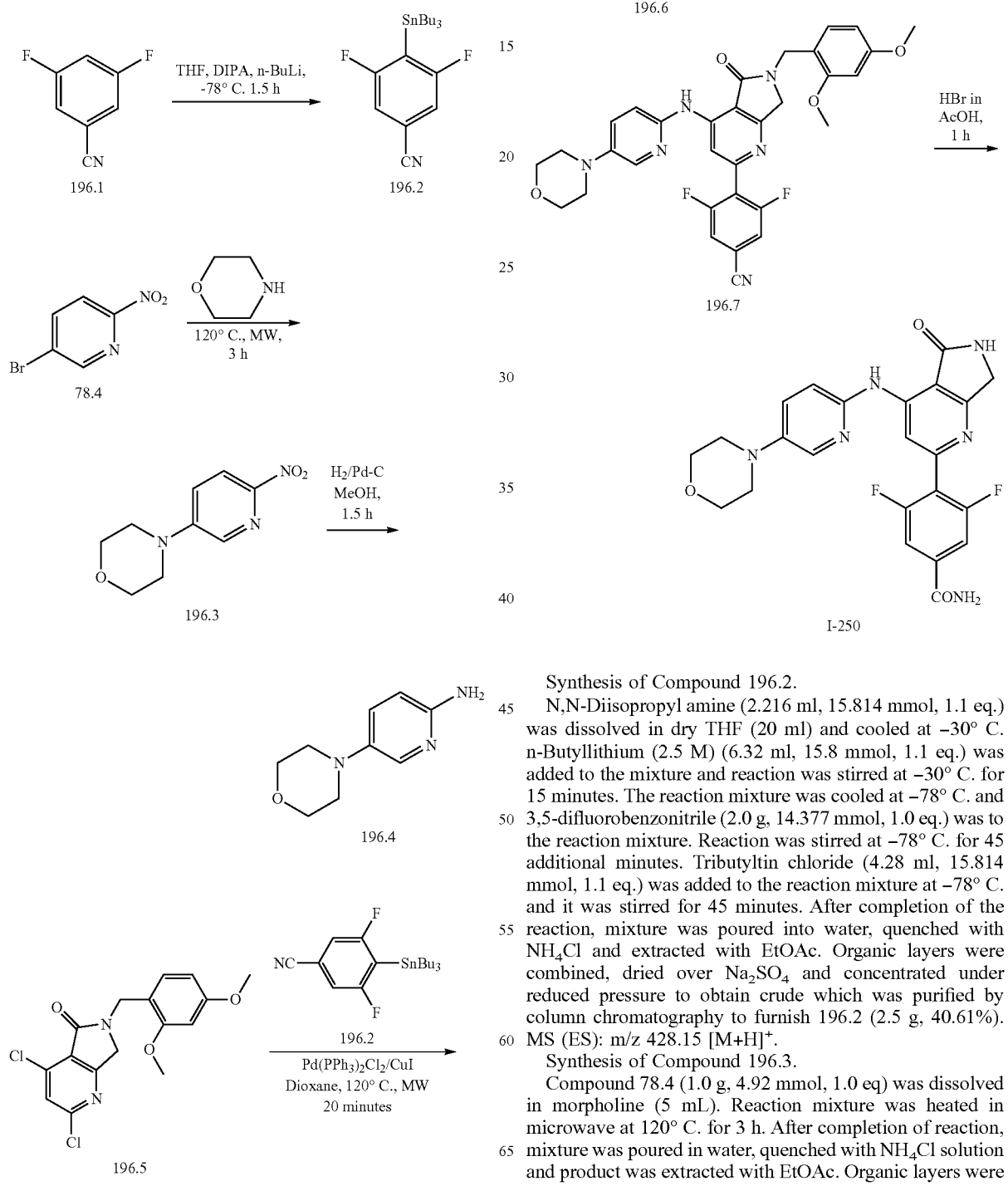

Synthesis of Compound 196.2.

N,N-Diisopropyl amine (2.216 ml, 15.814 mmol, 1.1 eq.) was dissolved in dry THF (20 ml) and cooled at −30° C. n-Butyllithium (2.5 M) (6.32 ml, 15.8 mmol, 1.1 eq.) was added to the mixture and reaction was stirred at −30° C. for 15 minutes. The reaction mixture was cooled at −78° C. and 3,5-difluorobenzonitrile (2.0 g, 14.377 mmol, 1.0 eq.) was to the reaction mixture. Reaction was stirred at −78° C. for 45 additional minutes. Tributyltin chloride (4.28 ml, 15.814 mmol, 1.1 eq.) was added to the reaction mixture at −78° C. and it was stirred for 45 minutes. After completion of the reaction, mixture was poured into water, quenched with NH₄Cl and extracted with EtOAc. Organic layers were combined, dried over Na₂SO₄ and concentrated under reduced pressure to obtain crude which was purified by column chromatography to furnish 196.2 (2.5 g, 40.61%). MS (ES): m/z 428.15 [M+H]⁺.

Synthesis of Compound 196.3.

Compound 78.4 (1.0 g, 4.92 mmol, 1.0 eq) was dissolved in morpholine (5 mL). Reaction mixture was heated in microwave at 120° C. for 3 h. After completion of reaction, mixture was poured in water, quenched with NH₄Cl solution and product was extracted with EtOAc. Organic layers were combined, dried over Na₂SO₄ and concentrated under reduced pressure to obtain crude which was purified by column chromatography to furnish 196.3 (0.6 g, 58.2%). MS (ES): m/z 209.20 [M+H]$^+$.

Synthesis of Compound 196.4.

To a solution of 196.3 (0.6 g, 2.87 mmol, 1.0 eq) in methanol (15 mL) was added 10% Pd/C (0.10 g) under nitrogen. It was purged with H$_2$ gas for 1.5 hours. Reaction mixture was filtered through celite and obtained filtrate was concentrated under reduced pressure to get crude 196.4 (0.47 g, 91.4%) which was used as such for the next step, MS (ES): m/z 179.22 [M+H]$^+$.

Synthesis of Compound 196.6.

To a solution of compound 196.5 (0.330 g, 0.937 mmol, 1.0 eq) in 1,4-dioxane (4 mL) was added 196.2 (0.60 g, 1.40 mmol, 1.5 eq) and CuI (0.035 g, 0.187 mmol, 0.2 eq). Reaction mixture was degassed for 10 minutes using argon, then Pd(PPh$_3$)$_2$Cl$_2$ (0.037 g, 0.09 mmol, 0.1 eq) was added. Reaction was stirred at 120° C. for 20 minutes in microwave. After completion of the reaction, mixture was poured into water and product was extracted with EtOAc. Organic layers were combined, dried over Na$_2$SO$_4$ and concentrated under reduced pressure to obtain crude which was purified by column chromatography to furnish 196.6 (0.1 g, 23.5%). MS(ES): m/z 455.85 [M+H]$^+$.

Synthesis of Compound 196.7.

To a solution of compound 196.6 (0.075 g, 0.164 mmol, 1.0 eq) in 1,4-dioxane (2 ml) was added 196.4 (0.032 g, 0.181 mmol, 1.1 eq) and K$_2$CO$_3$ (0.134 g, 0.41 mmol, 2.5 eq). The reaction mixture was degassed for 10 minutes using argon then Pd$_2$(dba)$_3$ (0.015 g, 0.01 mmol, 0.1 eq) and Xantphos (0.019 g, 0.03 mmol, 0.2 eq) were added, and suspension was again degassed for 5 minutes. The reaction was stirred at 100° C. for 1.5 h. After completion of the reaction, mixture was poured into water and product was extracted with EtOAc. Organic layers was combined, dried over Na$_2$SO$_4$ and concentrated under reduced pressure to obtain crude which was purified by column chromatography to furnish 196.7 (0.045 g, 45.69%). MS(ES): m/z 598.61 [M+H]$^+$.

Synthesis of Compound I-250.

Compound 196.7 (0.045 g, 0.075 mmol, 1.0 eq) was dissolved in HBr/HOAc (0.5 mL) and the reaction was stirred at room temperature for 1 hour. After completion of the reaction, water was added to mixture, basified with satd. NaHCO$_3$ and and mixture extracted with EtAOc. Organic layers were combined, dried over Na$_2$SO$_4$ and concentrated under reduced pressure to obtain crude which was purified by preparative TLC and by column chromatography to provide I-250 (0.006 g, 17.1%). MS (ES): m/z 466.45 [M+H]$^+$, $^1$H NMR (DMSO-d$_6$, 400 MHz): δ 9.55 (s, 1H), 8.84 (s, 1H), 8.41 (s, 1H), 8.23 (s, 1H), 8.03 (d, 1H), 7.78 (s, 1H), 7.73-7.71 (d, 2H), 7.49-7.46 (dd, 2H), 7.14-7.12 (d, 1H), 4.42 (s, 2H), 3.73-3.72 (d, 4H), 3.11-3.08 (t, 4H).

Example 197. Synthesis of 2-(2,6-difluorophenyl)-4-((5-(4-hydroxytetrahydro-2H-pyran-4-yl)pyridin-2-yl)amino)-6,7-dihydro-5H-pyrrolo[3,4-b]pyridin-5-one, I-251

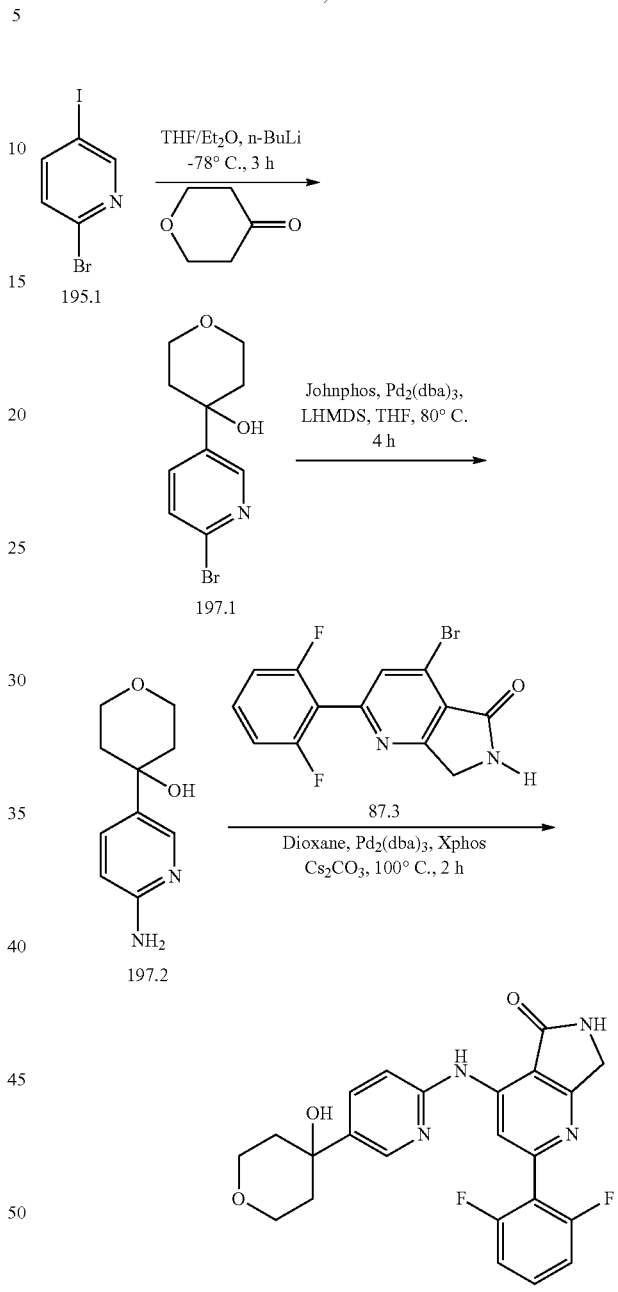

Synthesis of Compound 197.1.

To a solution of 195.1 (1.0 g, 3.52 mmol, 1.0 eq) in THF (5 mL) and Et$_2$O (6 mL) was added n-BuLi (0.225 g, 3.522 mmol, 1.0 eq.) at −78° C. Reaction mixture was stirred at −78° C. for 1 hour. Tetrahydro-4H-pyran-4-one (0.35 g, 3.52 mmol, 1.0 eq.) was added to the reaction mixture at −78° C. and the reaction was stirred for 2 hours. After completion of the reaction, mixture was poured into water, quenched with NH$_4$Cl solution and extracted with EtOAc. Organic layers were combined and dried over Na$_2$SO$_4$ concentrated under reduced pressure to obtain crude which was purified by combi flash and preparative HPLC to furnish 197.1 (0.21 g, 23.1%). MS (ES): m/z 258.12 [M+H]$^+$.

Synthesis of Compound 197.2.

The compound 197.1 (0.210 g, 0.813 mmol, 1.0 eq) was dissolved in THF (2 mL). The reaction mixture was degassed under argon atmosphere for 10 minutes. Pd$_2$(dba)$_3$ (0.074 g, 0.081 mmol, 0.1 eq) and Xphos (0.056 g, 0.162 mmol, 0.2 eq) were added. The reaction mixture was degassed for 15 minutes and then LHMDS (2.5 ml) was added. The reaction mixture was heated at 80° C. for 4 h. After completion of the reaction, mixture was poured into water, quenched with NH$_4$Cl solution and product was extracted with EtOAc. Organic layers were combined, dried over Na$_2$SO$_4$ and concentrated under reduced pressure to obtain crude which was purified by column chromatography to furnish 197.2 (0.095 g, 60.1%), MS (ES): m/z 194.23 [M+H]$^+$.

Synthesis of Compound I-251.

To a solution of 87.3 (0.200 g, 0.615 mmol, 1.0 eq) in 1,4-dioxane (2 mL) was added 197.2 (0.12 g, 0.615 mmol, 1.0 eq) and Cs$_2$CO$_3$ (0.6 g, 1.846 mmol, 3.0 eq). The reaction mixture was degassed for 10 min. under argon atmosphere, then Pd$_2$(dba)$_3$ (0.112 g, 0.123 mmol, 0.2 eq) and X-Phos (0.029 g, 0.061 mmol, 0.1 eq) were added, and again degassed for 5 min. The reaction was then heated at 100° C. for 2 h. After completion of the reaction, mixture was concentrated under reduced pressure to obtain crude which was purified by column chromatography to furnish I-251 (0.007 g, 2.6%). MS(ES): m/z 438.43 [M+H]$^+$. $^1$H NMR (DMSO-d$_6$, 400 MHz): δ 9.73 (s, 1H), 8.89 (s, 1H), 8.58 (s, 1H), 8.43-8.42 (d, 1H), 7.88-7.85 (dd, 1H), 7.60-7.58 (m, 1H), 7.29-7.25 (t, 2H), 7.16-7.14 (d, 1H), 5.15 (s, 1H), 4.43 (s, 2H), 3.81-3.67 (m, 4H), 2.00-1.93 (m, 2H), 1.58-1.55 (d, 2H).

Example 198. Synthesis of 2-(2,6-difluorophenyl)-4-((5-(4,4-dimethylpiperidin-1-yl)pyridin-2-yl)amino)-6,7-dihydro-5H-pyrrolo[3,4-b]pyridin-5-one, I-252

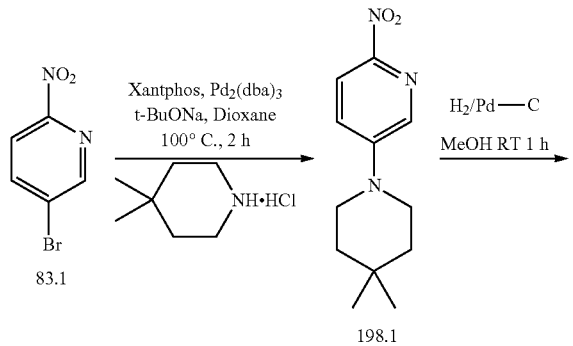

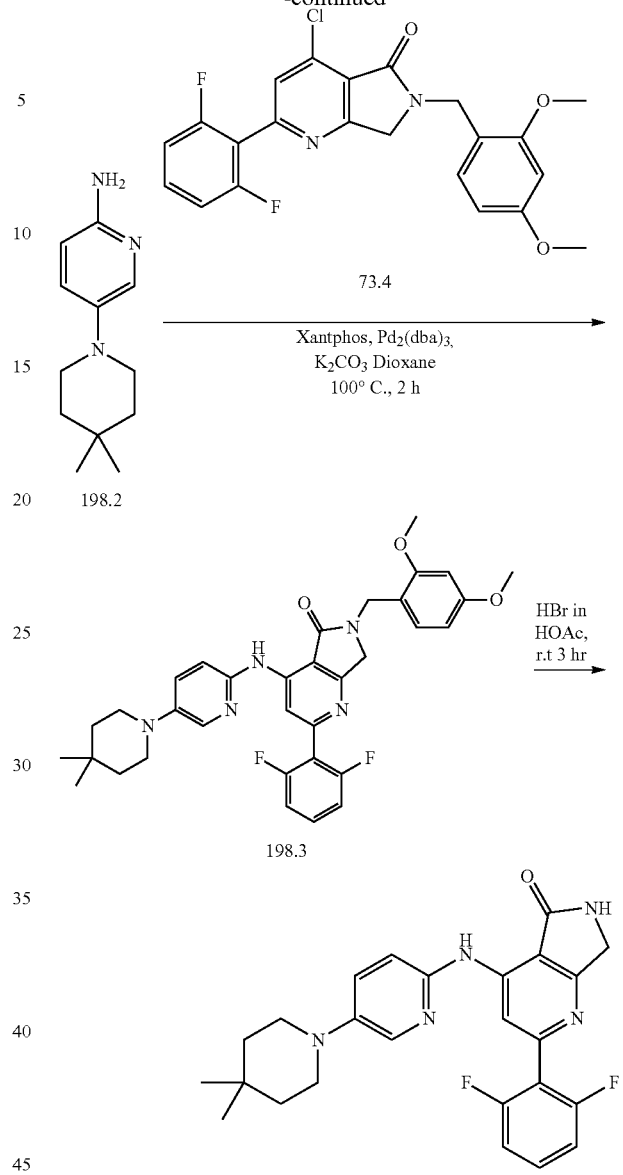

Synthesis of Compound 198.1.

To a solution of 83.1 (0.250 g, 1.231 mmol, 1.0 eq) in 1,4-dioxane (2 mL) was added 4,4-dimethylpiperidine hydrochloride (0.184 g, 1.231 mmol, 1.0 eq) and sodium tert-butoxide (0.236 g, 2.46 mmol, 2.0 eq.). Reaction mixture was degassed for 10 min under argon atmosphere, then Pd$_2$(dba)$_3$ (0.112 g, 0.123 mmol, 0.1 eq) and Xantphos (0.096 g, 0.246 mmol, 0.2 eq) were added, then again degassed for 5 min. The reaction was then heated at 100° C. for 2 hours. After completion of the reaction, mixture was poured into water and extracted with EtOAc. Organic layers were combined, dried over Na$_2$SO$_4$ and concentrated under reduced pressure to obtain crude which was purified by column chromatography to furnish 198.1 (0.160 g, 55.22%). MS (ES): m/z 235.29 [M+H]$^+$.

Synthesis of Compound 198.2.

To a solution of 198.1 (0.16 g, 0.68 mmol, 1.0 eq) in MeOH (10 mL) was added 10% Pd/C (0.01 g) under nitrogen atmosphere. It was purged with H₂ gas for 1 h. Reaction mixture was filtered through celite and obtained filtrate was concentrated under reduced pressure and purified by chromatography to get pure 198.2 (0.090 g, 64.46%) MS (ES): m/z 205.31 [M+H]⁺.

Synthesis of Compound 198.3.

To a solution of 73.4 (0.100 g, 0.231 mmol, 1.0 eq) in 1,4-dioxane (2 mL) was added 198.2 (0.057 g, 0.278 mmol, 1.2 eq) and K₂CO₃ (0.080 g, 0.579 mmol, 2.5 eq). The reaction mixture was degassed for 10 min. under argon atmosphere, then Pd₂(dba)₃ (0.021 g, 0.023 mmol, 0.1 eq) and Xantphos (0.026 g, 0.046 mmol, 0.2 eq) were added, again degassed for 5 min. The reaction was then heated at 100° C. for 2 h. After completion, reaction, was concentrated under reduced pressure to obtain crude which was purified by chromatography to get pure 198.3 (0.09 g, 64.7%). MS(ES): m/z 599.68 [M+H]⁺.

Synthesis of Compound I-252.

Compound 198.3 (0.09 g, 0.15 mmol, 1.0 eq) was dissolved in HBr/HOAc (3 mL) and stirred at room temperature for 3 hours. After completion of the reaction, mixture was poured into water and basified with satd. NaHCO₃ and product was extracted with EtOAc. Organic layers were combined and dried over Na₂SO₄ and concentrated under reduced pressure to obtain crude which was purified by column chromatography to furnish I-252 (0.03 g, 44.5%). MS(ES): m/z 449.51 [M+H]⁺, ¹H NMR (DMSO-d₆, 400 MHz): 9.49 (s, 1H), 8.81 (s, 1H), 8.35 (s, 1H), 8.03-8.02 (d, 1H), 7.57-7.55 (m, 1H), 7.46-7.43 (dd, 1H), 7.27-7.23 (t, 2H), 7.08-7.06 (d, 1H), 4.40 (s, 2H), 3.17-3.10 (m, 4H), 1.44-1.41 (t, 4H), 0.94 (s, 6H).

Example 199. Synthesis of 4-((5-(1,4-oxazepan-4-yl)pyridin-2-yl)amino)-2-(2,6-difluoro-phenyl)-6,7-dihydro-5H-pyrrolo[3,4-b]pyridin-5-one, I-253

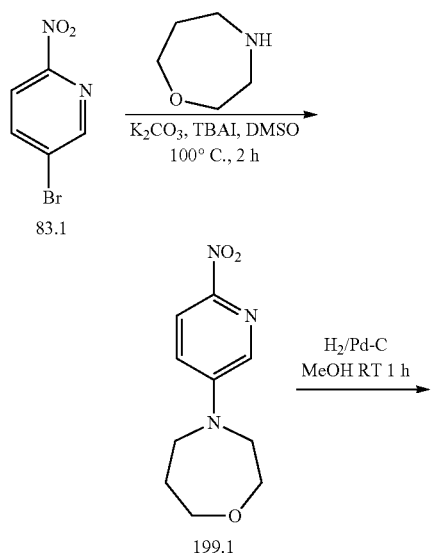

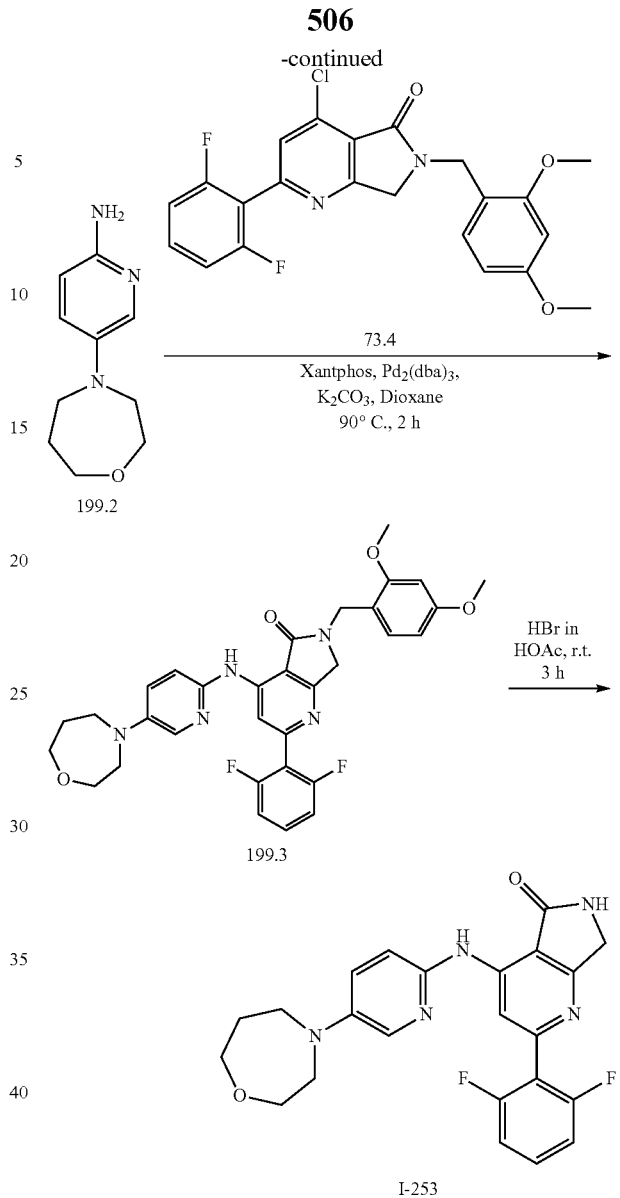

Synthesis of Compound 199.1.

To a solution of 83.1 (0.30 g, 1.477 mmol, 1.0 eq) in DMSO (3 mL) was added 1,4-oxazepane (0.149 g, 1.48 mmol, 1.0 eq), K₂CO₃ (0.408 g, 2.955 mmol, 2.0 eq.) and tetra n-butyl ammonium iodide (0.054 g, 0.15 mmol, 0.1 eq.). The reaction was then stirred at 100° C. for 2 h. After completion of the reaction, mixture was poured into water and product was extracted with EtOAc. Organic layers were combined, dried over Na₂SO₄ and concentrated under reduced pressure to obtain crude which was purified by column chromatography get pure 199.1 (0.135 g, 40.92%). MS (ES): m/z 223.23 [M+H]⁺.

Synthesis of Compound 199.2.

To a solution of 199.1 (0.135 g, 0.60 mmol, 1.0 eq) in MeOH (10 mL) was added 10% Pd/C (0.010 g) under nitrogen atmosphere. It was purged with hydrogen for 1 hour. Reaction mixture was filtered through celite and obtained filtrate was concentrated under reduced pressure and purified by flash chromatography, to get pure 199.2 (0.105 g, 89.8%) MS (ES): m/z 193.25 [M+H]⁺.

Synthesis of Compound 199.3.

To a solution of 73.4 (0.10 g, 0.231 mmol, 1.0 eq) in 1,4-dioxane (2 ml) was added 199.2 (0.053 g, 0.278 mmol, 1.2 eq) and $K_2CO_3$ (0.08 g, 0.58 mmol, 2.5 eq). The reaction mixture was degassed for 10 minutes under argon, then $Pd_2(dba)_3$ (0.021 g, 0.023 mmol, 0.1 eq) and Xantphos (0.026 g, 0.046 mmol, 0.2 eq) were added, and again degassed for 5 min. The reaction was then heated at 100° C. for 2 hours. After completion, reaction was concentrated under reduced pressure to obtain crude which was purified by column chromatography to get pure 199.3 (0.07 g, 51.3%). MS(ES): m/z 587.63 [M+H]$^+$.

Synthesis of Compound I-253.

Compound 199.3 (0.070 g, 0.119 mmol, 1.0 eq) was dissolved in HBr/HOAc (3 ml) and stirred at room temperature for 3 h. After completion of the reaction, mixture was poured into water and basified with satd. $NaHCO_3$ solution and extracted with EtOAc. Organic layers were combined, dried over $Na_2SO_4$ and concentrated under reduced pressure to obtain crude which was purified by column chromatography to get pure I-253 (0.020 g, 38.4%). MS(ES): m/z 437.45 [M+H]$^+$, $^1$H NMR (DMSO-d$_6$, 400 MHz): 9.41 (s, 1H), 8.77 (s, 1H), 8.30 (s, 1H), 7.90-7.89 (d, 1H), 7.58-7.54 (m, 1H), 7.28-7.23 (dd, 3H), 7.06-7.04 (d, 1H), 4.39 (s, 2H), 3.71-3.68 (m, 2H), 3.58-3.54 (m, 6H), 1.89-1.84 (m, 2H).

Example 200. Synthesis of 2-(2,6-difluorophenyl)-3-fluoro-4-((5-morpholinopyridin-2-yl)amino)-6,7-dihydro-5H-pyrrolo[3,4-b]pyridin-5-one, I-254

Synthesis of Compound I-254.

The compound I-171 (0.02 g, 0.046 mmol, 1.0 eq.) was dissolved in $CH_2Cl_2$ and the reaction was cooled at 0° C. Selectrofluor (0.033 g, 0.093 mmol, 2.0 eq.) was added and reaction was stirred at room temperature for 24 h. After completion of the reaction, mixture was poured into water, quenched with satd. $NaHCO_3$ and extracted with EtOAc. Organic layers were combined, dried over $Na_2SO_4$ and concentrated under reduced pressure to obtain crude which was purified by column chromatography to get pure I-254 (0.015 g, 71.9%). MS (ES): m/z 441.41 [M+H]$^+$; $^1$H NMR (DMSO-d$_6$, 400 MHz): 9.67 (s, 1H), 8.89 (s, 1H), 8.23 (s, 1H), 7.62-7.57 (m, 2H), 7.29-7.25 (t, 2H), 7.15-7.13 (d, 1H), 4.43 (s, 2H), 3.74-3.71 (t, 4H), 2.99-2.96 (t, 4H).

Example 201. Synthesis of 2-(2,6-difluorophenyl)-4-((4-(3-methyloxetan-3-yl)phenyl)-amino)-6,7-dihydro-5H-pyrrolo[3,4-d]pyrimidin-5-one, I-255

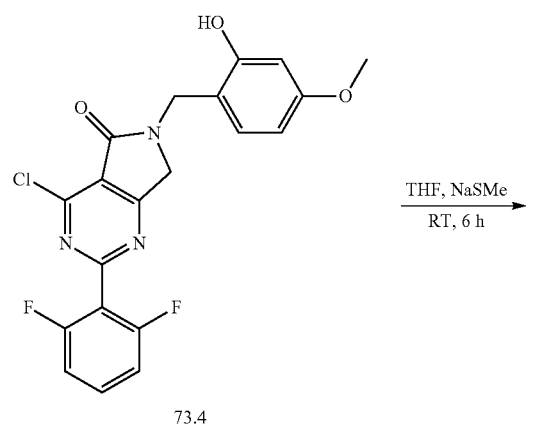

73.4

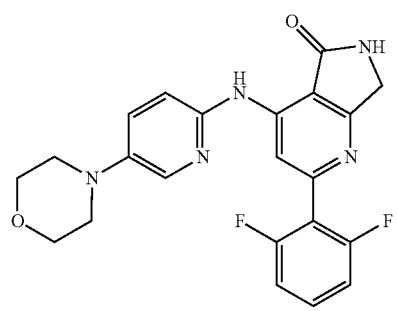

I-171

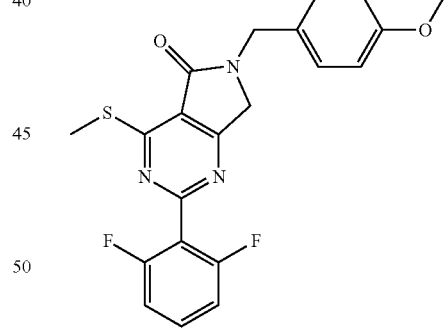

201.1

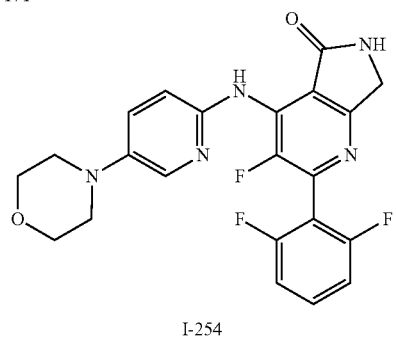

I-254

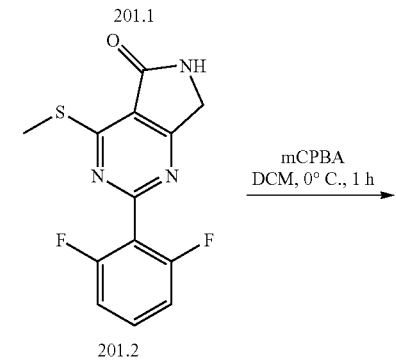

201.2

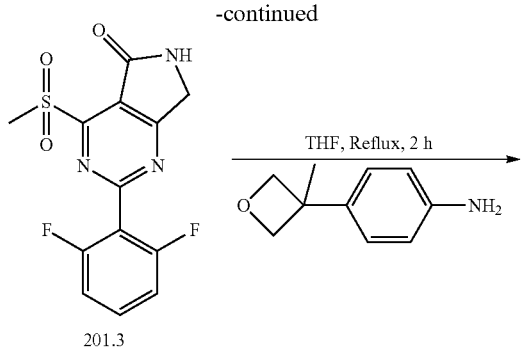

201.3

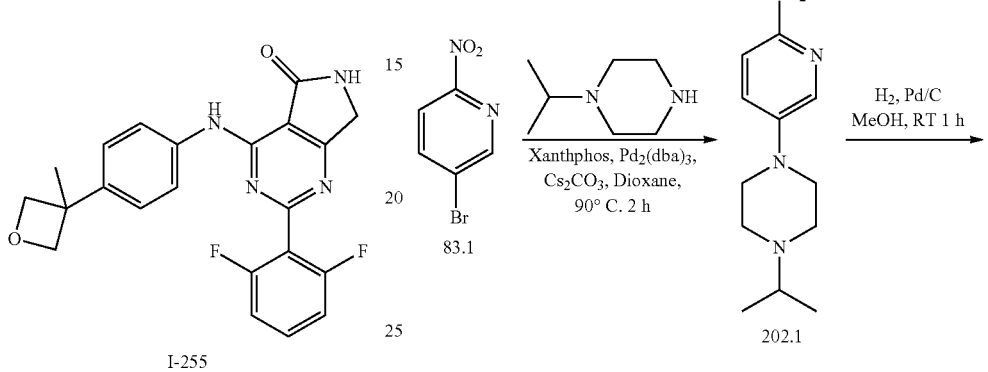

I-255

Synthesis of Compound 201.1.

To a solution of 73.4 (1.0 g, 2.32 mmol, 1.0 eq) in THF (10 ml) was added sodium methanethiolate (0.324 g, 4.64 mmol, 2 eq). The reaction was stirred at room temperature for 6 hours. After completion of the reaction, mixture was poured into water and product was extracted with EtOAc. Organic layers were combined, dried over $Na_2SO_4$ and concentrated under reduced pressure to obtain crude which was purified by column chromatography to furnish 201.1 (0.70 g, 68.2%). MS (ES): m/z 443.47 $[M+H]^+$.

Synthesis of Compound 201.2.

Compound 201.1 (0.70 g, 1.58 mmol, 1.0 eq) was dissolved in HBr/HOAc (3 mL) and stirred at room temperature for 1 h. After completion of the reaction, mixture was poured into water, basified with satd. $NaHCO_3$ solution and extracted with EtOAc. Organic layers were combined, dried over $Na_2SO_4$ and concentrated under reduced pressure to obtain crude which was purified by column chromatography to furnish 201.2 (0.31 g, 67.0%) MS (ES): m/z 293.29 $[M+H]^+$.

Synthesis of Compound 201.3.

The compound 201.2 (0.125 g, 0.426 mmol, 1.0 eq.) was dissolved in $CH_2Cl_2$ (4 mL) and cooled at 0° C. m-Chloroperoxybenzoic acid (0.367 g, 2.133 mmol, 5.0 eq.) was added to the reaction mixture. Reaction was stirred at 0° C. for 1 h. After completion of reaction, solvent was removed under reduced pressure. The crude was triturated with diethyl ether to get pure 201.3 (0.070 g, 6.31%). MS(ES): m/z 325.29 $[M+H]^+$.

Synthesis of Compound I-255.

Compound 201.3 (0.07 g, 0.215 mmol, 1.0 eq) was dissolved in THF (3 mL) and 4-(3-methyloxetan-3-yl)aniline (0.035 g, 0.215 mmol, 1.0 eq.) was added to the reaction mixture. Reaction was refluxed for 2 hours. After completion of the reaction, solvent was removed under reduced pressure to get crude which was purified by column chromatography to furnish I-255 (0.035 g, 39.8%). MS(ES): m/z 408.41 $[M+H]^+$; $^1H$ NMR (DMSO-$d_6$, 400 MHz): 9.07 (s, 1H), 8.91 (s, 1H), 7.76-7.73 (d, 2H), 7.60-7.58 (m, 1H), 7.29-7.23 (m, 4H), 4.79-4.77 (d, 2H), 4.51-4.48 (m, 4H), 1.61 (s, 3H).

Example 202. Synthesis of 2-(2,6-difluorophenyl)-4-((5-(4-isopropylpiperazin-1-yl)pyridin-2-yl)amino)-6,7-dihydro-5H-pyrrolo[3,4-b]pyridin-5-one I-256

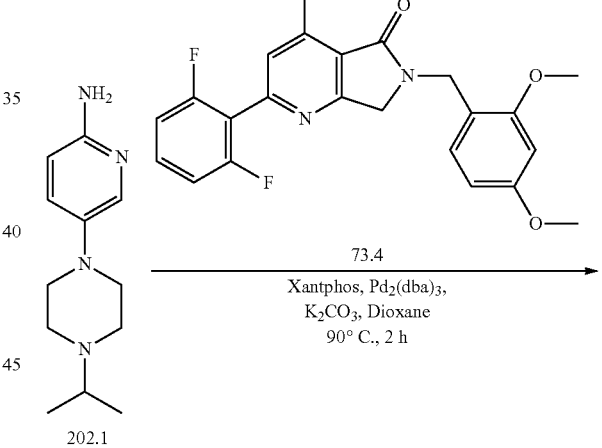

202.1

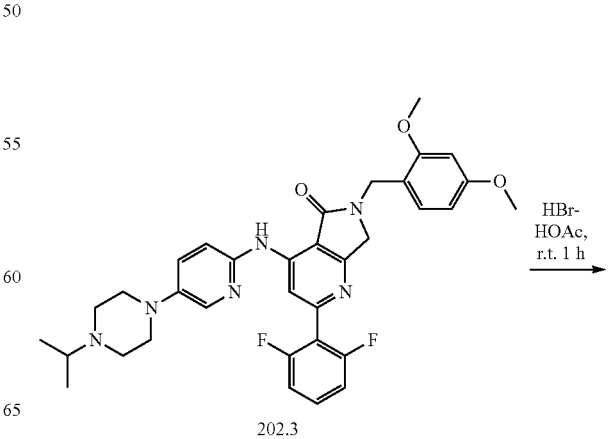

202.3

-continued

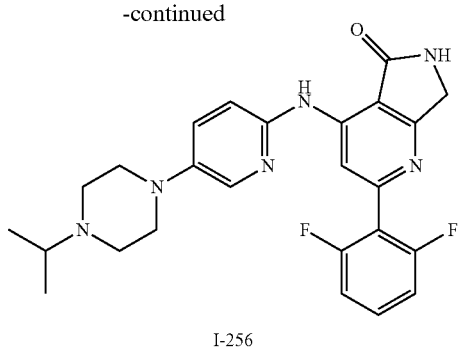

I-256

Synthesis of Compound 202.1.

To a solution of 83.1 (0.20 g, 0.99 mmol, 1.0 eq) in 1,4-dioxane (5 ml) was added 1-isopropylpiperazine (0.151 g, 1.182 mmol, 1.2 eq) and cesium carbonate (0.94 g, 2.96 mmol, 3.0 eq.). The reaction mixture was degassed for 10 min. under argon atmosphere, then Pd$_2$(dba)$_3$ (0.09 g, 0.098 mmol, 0.1 eq) and Xantphos (0.077 g, 0.197 mmol, 0.2 eq) were added, and again degassed for 5 min. The reaction was then heated at 90° C. for 2 h. After completion of the reaction, mixture was poured in water and extracted with EtOAc. Organic layers were combined, dried over Na$_2$SO$_4$ and concentrated under reduced pressure to obtain crude which was purified by column chromatography to get pure 202.1 (0.083 g, 33.66%). MS (ES): m/z 250.30 [M+H]$^+$.

Synthesis of Compound 202.2.

To a solution of 202.1 (0.083 g, 0.331 mmol, 1.0 eq) in MeOH (8 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to furnish 202.2 (0.052 g, 71.2%) MS (ES): m/z 220.32 [M+H]$^+$.

Synthesis of Compound 202.3.

To a solution of 73.4 (0.090 g, 0.209 mmol, 1.0 eq) in 1,4-dioxane (3 ml) was added 202.2 (0.039 g, 0.209 mmol, 1.2 eq) and K$_2$CO$_3$ (0.086 g, 0.627 mmol, 3.0 eq). The reaction mixture was degassed for 10 min. under argon atmosphere, then Pd$_2$(dba)$_3$ (0.019 g, 0.020 mmol, 0.1 eq) and Xantphos (0.024 g, 0.041 mmol, 0.2 eq) were added, and again degassed for 5 min. The reaction was then heated at 90° C. for 2 h. After completion of the reaction, mixture was poured in water and product was extracted with EtOAc. Organic layers were combined, dried over Na$_2$SO$_4$ and concentrated under reduced pressure to obtain crude material which was purified by chromatography get pure 202.3 (0.089 g, 69.31%). MS(ES): m/z 614.70 [M+H]$^+$.

Synthesis of Compound I-256.

The compound 202.3 (0.089 g, 0.144 mmol, 1.0 eq) was dissolved in HBr/HOAc (3 mL) and stirred at room temperature for 1 hour. After completion of the reaction, mixture was poured into water and basified with satd. NaHCO$_3$ and extracted with EtOAc. Organic layers were combined, dried over Na$_2$SO$_4$ and concentrated under reduced pressure to obtain crude which was purified by column chromatography to get pure I-256 (0.044 g, 65.4%). MS(ES): m/z 464.52 [M+H]$^+$; $^1$H NMR (DMSO-d$_6$, 400 MHz): 9.51 (s, 1H), 8.82 (s, 1H), 8.38 (s, 1H), 8.01 (d, 1H), 7.60-7.53 (m, 1H), 7.46-7.43 (dd, 1H), 7.27-7.22 (t, 2H), 7.10-7.08 (d, 1H), 4.41 (s, 2H), 3.10 (m, 4H), 2.51 (t, 4H), 1.09-1.07 (d, 6H).

Example 203. Synthesis of 2-(2,6-difluorophenyl)-4-((4-(piperidine-1-carbonyl)phenyl)-amino)-6,7-dihydro-5H-pyrrolo[3,4-b]pyridin-5-one, I-257

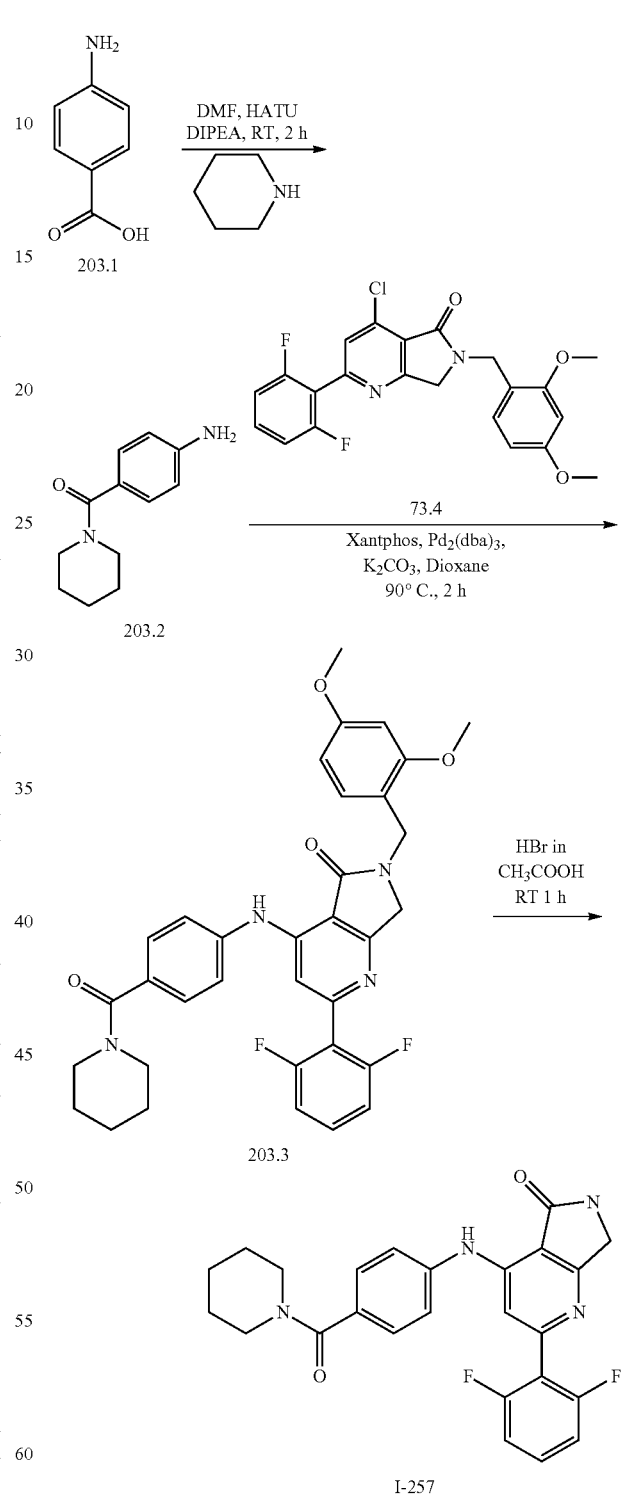

Synthesis of Compound 203.2.

To a solution of 203.1 (1.0 g, 7.28 mmol, 1.0 eq) in DMF (10 mL) was added HATU (4.14 g, 10.9 mmol, 1.5 eq.). The reaction was allowed to stir at room temperature for 15 minutes. Further piperidine (0.743 g, 8.73 mmol, 1.2 eq.) and DIPEA (2.820 g, 2.183 mmol, 3.0 eq.) were added to the reaction and the reaction was allowed to stir at same temperature for 2 hours. After completion of the reaction, mixture was poured into water and extracted with EtOAc. Organic layers were combined, dried over Na$_2$SO$_4$ and concentrated under reduced pressure to obtain crude which was purified by column chromatography to get pure 203.2 (1.0 g, 67.13%). MS (ES): m/z 204.27 [M+H]$^+$.

Synthesis of Compound 203.3.

To a solution of 73.4 (0.100 g, 0.232 mmol, 1.0 eq) in 1,4-dioxane (3 ml) was added 203.2 (0.047 g, 0.232 mmol, 1.0 eq) and K$_2$CO$_3$ (0.10 g, 0.697 mmol, 3.0 eq). The reaction mixture was degassed for 10 min. under argon atmosphere, then Pd$_2$(dba)$_3$ (0.021 g, 0.023 mmol, 0.1 eq) and Xantphos (0.026 g, 0.046 mmol, 0.2 eq) were added, and again degassed for 5 minutes. The reaction was then heated at 90° C. for 2 h. After completion of reaction, mixture was poured into water and product was extracted with EtOAc. Organic layers were combined, dried over Na$_2$SO$_4$ and concentrated under reduced pressure to obtain crude which was purified by column chromatography to furnish 203.3 (0.080 g, 57.57%). MS(ES): m/z 598.65 [M+H]$^+$.

Synthesis of Compound I-257.

The compound 203.3 (0.080 g, 0.133 mmol, 1.0 eq) was dissolved in HBr/HOAc (3 mL) and stirred at room temperature for 1 h. After completion of the reaction, mixture was poured into water, basified with satd. NaHCO$_3$ and extracted with EtOAc. Organic layers were combined, dried over Na$_2$SO$_4$ and concentrated under reduced pressure to obtain crude which was purified by column chromatography to furnish I-257 (0.042 g, 70.1%). MS (ES): m/z 448.47 [M+H]$^+$; $^1$H NMR (DMSO-d$_6$, 400 MHz): 9.15 (s, 1H), 8.77 (s, 1H), 7.55-7.52 (m, 1H), 7.41 (s, 4H), 7.23-7.19 (m, 3H), 4.41 (s, 2H), 3.51-3.35 (s, 2H), 1.60 (s, 2H), 1.50 (s, 4H).

Example 204. Synthesis of 3-fluoro-2-(4-((5-methoxypyridin-2-yl)amino)-5-oxo-6,7-dihydro-5H-pyrrolo[3,4-b]pyridin-2-yl)benzonitrile, I-258

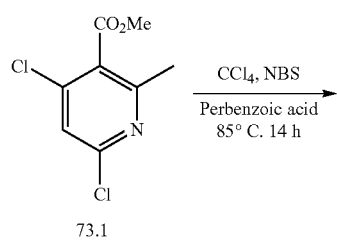

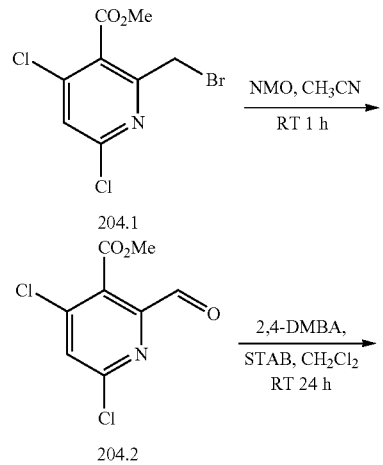

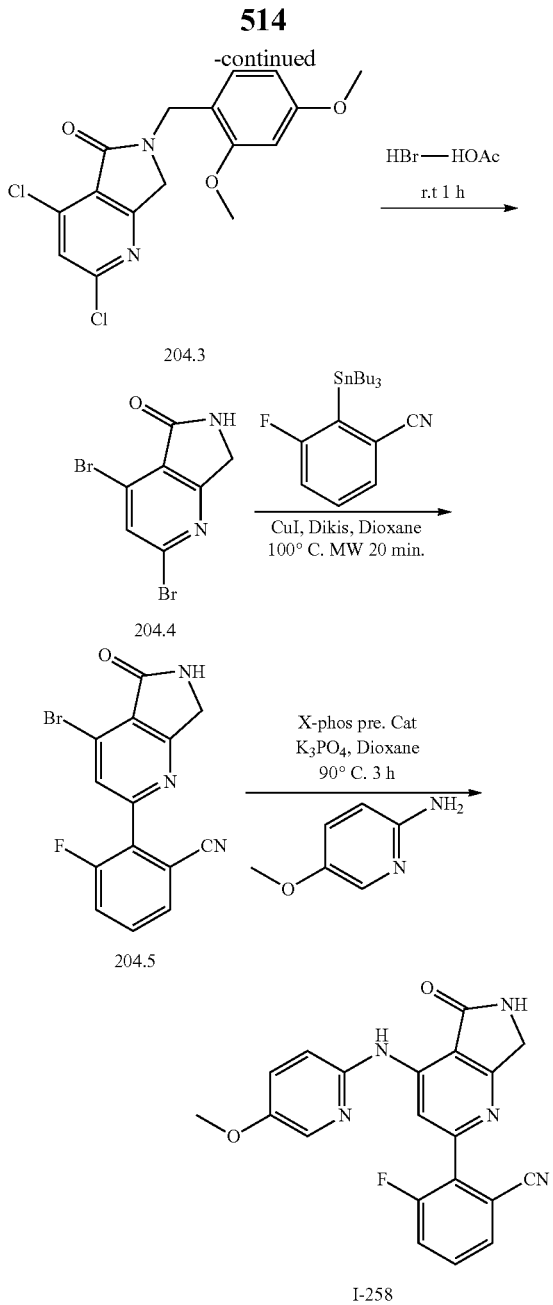

Synthesis of Compound 204.1.

To a solution of 73.1 (4.0 g, 18.181 mmol, 1.0 eq) in CCl$_4$ (40 ml) was added NBS (9.71 g, 54.5 mmol, 3.0 eq.) and perbenzoic acid (0.88 g, 3.64 mmol, 0.1 eq.). The reaction mixture was stirred at 85° C. for 14 h. After completion of the reaction, mixture was poured into water and product was extracted with EtOAc. Organic layer was dried over Na$_2$SO$_4$ and concentrated under reduced pressure to obtain crude which was purified by column chromatography to get pure 204.1 (1.3 g, 23.9%). MS (ES): m/z 298.94 [M+H]$^+$.

Synthesis of Compound 204.2.

To a solution of 204.1 (1.3 g, 3.661 mmol, 1.0 eq) in acetonitrile (10 ml) was added N-methyl morpholine N-oxide (0.86 g, 7.32 mmol, 2.0 eq.). The reaction was then stirred at room temperature for 1 hr. After completion of reaction, mixture was filtered through celite and washed with EtOAc. Organic layers were combined, dried over $Na_2SO_4$ and concentrated under reduced pressure to obtain crude which was purified by column chromatography to get pure 204.2 (0.85 g, 100%). MS (ES): m/z 234.3 [M+H]$^+$.

Synthesis of Compound 204.3.

To a solution of 204.2 (0.85 g, 2.920 mmol, 1.0 eq) in $CH_2Cl_2$ (10 ml) was added 2,4-dimethoxy benzyl amine (0.487 g, 2.92 mmol, 1.0 eq.) and $NaBH(OAc)_3$ (1.86 g, 8.76 mmol, 3.0 eq.). The reaction was then stirred at room temperature for 16 hr. After completion of the reaction, water was added to the reaction mixture and it was quenched with satd. $NaHCO_3$. The compound was extracted with ethyl acetate. Organic layers were combined, dried over $Na_2SO_4$ and concentrated under reduced pressure to obtain crude which was purified by column chromatography to furnish 204.3 (0.7 g, 54.6%). MS(ES): m/z 353.20[M+H]$^+$.

Synthesis of Compound 204.4.

Compound 204.3 (0.7 g, 1.98 mmol, 1.0 eq) was dissolved in HBr/HOAc (3 mL) and stirred at room temperature for 1 h. After completion of reaction, mixture was poured into water and basified with satd. $NaHCO_3$ and product was extracted with EtOAC. Organic layers were combined, dried over $Na_2SO_4$ and concentrated under reduced pressure to obtain crude which was purified by column chromatography to get pure 204.4 (0.45 g, 77.78%). MS(ES): m/z 291.93 [M+H]$^+$.

Synthesis of Compound 204.5.

To a solution of 204.4 (0.230 g, 0.784 mmol, 1.0 eq) in 1,4-dioxane (4 ml) was added 3-fluoro-2-(tributylstannyl) benzonitrile (0.354 g, 0.863 mmol, 1.1 eq) and copper iodide (0.029 g, 0.156 mmol, 0.2 eq). The reaction mixture was degassed for 20 min. under argon atmosphere, then $PdCl_2(PPh_3)_2$ (0.055 g, 0.078 mmol, 0.1 eq) was added, and again degassed for 5 minutes. The reaction was then heated in microwave for 20 minutes. After completion of the reaction, solvent was removed under reduced pressure to get crude which was purified by prep HPLC to get pure 204.5 (0.05 g, 19.1%). MS(ES): m/z 332.13 [M+H]$^+$.

Synthesis of Compound I-258.

To a solution of 204.5 (0.050 g, 0.151 mmol, 1.0 eq) in 1,4-dioxane (3 ml) was added 5-methoxypyridin-2-amine (0.022 g, 0.181 mmol, 1.2 eq) and potassium phosphate (0.096 g, 0.453 mmol, 3.0 eq). The reaction mixture was degassed for 10 min under argon atmosphere, then precatalyst (0.022 g, 0.030 mmol, 0.2 eq) was added, again degassed for 5 min. The reaction was then heated at 90° C. for 3 h. After completion of the reaction, mixture was poured into water and product was extracted with EtOAc. Organic layers were combined, dried over $Na_2SO_4$ and concentrated under reduced pressure to obtain crude which was purified by column chromatography and preparative HPLC to furnish I-258 (0.006, 10.6%). MS(ES): m/z 375.36 [M+H]$^+$; $^1$H NMR (DMSO-d$_6$, 400 MHz): 9.65 (s, 1H), 9.90 (s, 1H), 8.51 (s, 1H), 8.08-8.07 (d, 1H), 7.89-7.87 (dd, 1H), 7.81-7.72 (m, 2H), 7.47-7.44 (dd, 1H), 7.23-7.21 (d, 1H), 4.43 (s, 2H), 3.80 (s, 3H), 1.60 (s, 2H), 1.50 (s, 4H).

Example 205. Synthesis of 4-((2-(2,6-difluorophenyl)-5-oxo-6,7-dihydro-5H-pyrrolo[3,4-b]pyridin-4-yl)amino)-N,N-diethylbenzamide, I-259

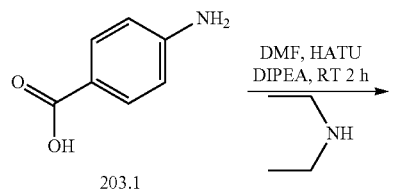

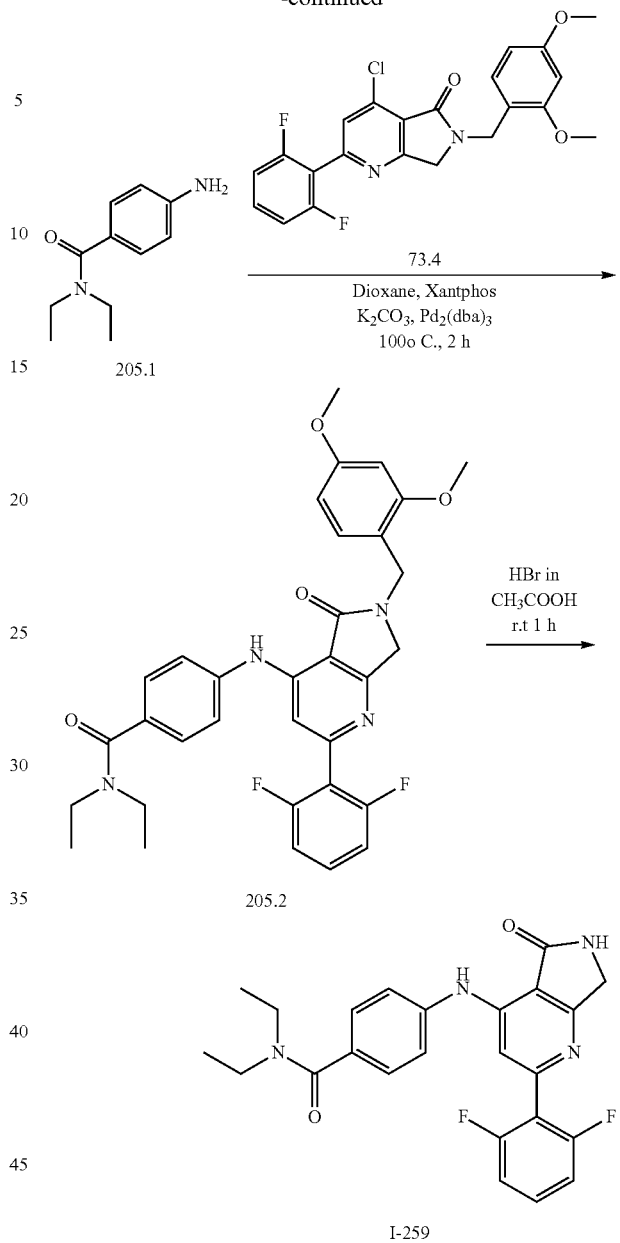

Synthesis of Compound 205.1.

To a solution of 203.1 (1.0 g, 7.246 mmol, 1.0 eq) in DMF (10 ml) was added HATU (4.13 g, 10.86 mmol, 1.5 eq.). The reaction was allowed to stir at room temperature for 15 minutes. Further diethyl amine (0.795 g, 10.86 mmol, 1.5 eq.) and DIPEA (2.804 g, 21.73 mmol, 3.0 eq.) were added to the reaction mixture at room temperature and the reaction was stirred for 2 hours. After completion of the reaction, mixture was poured into water and product was extracted with EtOAc. Organic layers were combined, dried over $Na_2SO_4$ and concentrated under reduced pressure to obtain crude which was purified by column chromatography to get pure 1.1 (1.0 g, 71.33%). MS (ES): m/z 192.26 [M+H]$^+$.

Synthesis of Compound 205.2.

To a solution of 73.4 (0.100 g, 0.232 mmol, 1.0 eq) in 1,4-dioxane (3 mL) was added 205.1 (0.053 g, 0.28 mmol, 1.2 eq) and $K_2CO_3$ (0.096 g, 0.697 mmol, 3.0 eq). Reaction mixture was degassed for 10 min. using argon, then Pd₂(dba)₃ (0.021 g, 0.023 mmol, 0.1 eq) and Xantphos (0.026 g, 0.046 mmol, 0.2 eq) were added, and again degassed for 5 minutes. The reaction was stirred at 100° C. for 2 h. After completion of the reaction, mixture was poured into water and product was extracted with EtOAc. Organic layers were combined, dried over Na₂SO₄ and concentrated under reduced pressure to obtain crude which was purified by column chromatography to furnish 205.2 (0.072 g, 52.9%). MS(ES): m/z 586.64 [M+H]⁺.

Synthesis of Compound I-259.

Compound 205.2 (0.072 g, 0.122 mmol, 1.0 eq) was dissolved in HBr/HOAc (3 ml) and stirred at room temperature for 1 h. After completion of the reaction, mixture was poured into water, basified with saturated bicarbonate solution and product was extracted with EtOAc. Organic layers were combined, dried over Na₂SO₄ and concentrated under reduced pressure to obtain crude which was purified by column chromatography to furnish I-259 (0.025 g, 46.7%). MS(ES): m/z 436.46 [M+H]⁺; ¹H NMR (DMSO-d₆, 400 MHz): 9.14 (s, 1H), 8.76 (s, 1H), 7.56-7.51 (m, 1H), 7.42-7.36 (dd, 4H), 7.23-7.19 (t, 3H), 7.17 (s, 1H), 4.41 (s, 2H), 1.10 (s, 6H).

Example 206. Synthesis of 5-((2-(2,6-difluorophenyl)-5-oxo-6,7-dihydro-5H-pyrrolo[3,4-b]pyridin-4-yl)amino)-N-ethylpicolinamide, I-260

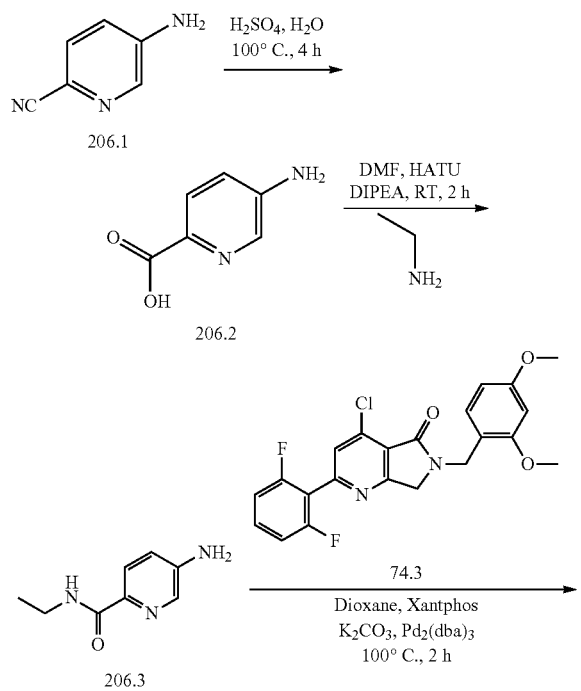

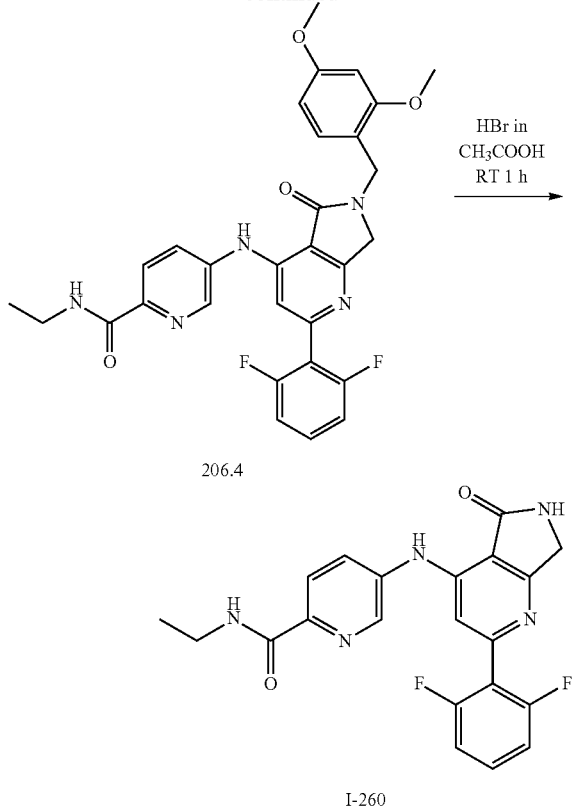

Synthesis of Compound 206.2.

The solution of 206.1 (4.0 g, 33.61 mmol, 1.0 eq) in concentrated H₂SO₄ (20 ml) was heated at 100° C. for 2 h. Further water (20 ml) was added to the reaction mixture and it was heated at 100° C. for 2 h. After completion of reaction, reaction mixture was poured in ice cold water and product was filtered to get pure 206.2 (3.0 g, 64.68%). MS (ES): m/z 138.13 [M+H]⁺.

Synthesis of Compound 206.3.

To a solution of 5-aminopicolinic acid (1.0 g, 7.246 mmol, 1.0 eq) in DMF 10 ml) was added HATU (4.13 g, 10.86 mmol, 1.5 eq.). The reaction was allowed to stir at room temperature for 15 minutes. Further ethyl amine (0.391 g, 8.69 mmol, 1.2 eq.) and DIPEA (2.804 g, 21.73 mmol, 3.0 eq.) were added to the reaction mixture at room temperature and the reaction was stirred for 2 h. After completion of the reaction, reaction mixture was poured in water and product was extracted with EtOAc. Organic layers were combined, dried over sodium sulphate and concentrated under reduced pressure to obtain crude which was purified by column chromatography to furnish 206.3 (0.650 g, 54.35%). MS (ES): m/z 165.20 [M+H]⁺.

Synthesis of Compound 206.4.

To a solution of 73.4 (0.100 g, 0.232 mmol, 1.0 eq) in 1,4-dioxane (3 ml) was added 206.3 (0.042 g, 0.255 mmol, 1.1 eq) and K₂CO₃ (0.080 g, 0.581 mmol, 2.5 eq). The reaction mixture was degassed for 10 min. under argon atmosphere, then Pd₂(dba)₃ (0.021 g, 0.023 mmol, 0.1 eq) and Xantphos (0.026 g, 0.046 mmol, 0.2 eq) were added, again degassed for 5 min. The reaction was then heated at 100° C. for 2 h. After completion of reaction, reaction mixture was poured in water and product was extracted with EtOAc. Organic layers were combined, dried over Na₂SO₄ and concentrated under reduced pressure to obtain crude which was purified by column chromatography to furnish 206.4 (0.091 g, 70.1%). MS(ES): m/z 559.57 [M+H]⁺.

Synthesis of Compound I-260.

Compound 206.4 (0.091 g, 0.211 mmol, 1.0 eq) was dissolved in HBr/HOAc (3 ml) and stirred at room temperature for 1 hour. After completion of the reaction, mixture was poured into water, basified with saturated bicarbonate solution and product was extracted with EtOAc. Organic layers were combined and dried over Na₂SO₄ and concentrated under reduced pressure to obtain crude which was purified by column chromatography to furnish I-260 (0.05 g, 75.1%). MS(ES): m/z 409.40 [M+H]⁺; ¹H NMR (DMSO-d6, 400 MHz): 9.31 (s, 1H), 8.80 (s, 1H), 8.75-8.72 (t, 1H), 8.66-8.65 (d, 1H), 8.01-7.95 (m, 2H), 7.58-7.50 (m, 1H), 7.23-7.18 (m, 3H), 4.43 (s, 2H), 3.32-3.27 (dd, 2H), 1.13-1.09 (t, 3H).

Example 207. Synthesis of 2-(2,6-difluorophenyl)-4-((5-((2R,6S)-2,6-dimethylpiperidin-1-yl)pyridin-2-yl)amino)-6,7-dihydro-5H-pyrrolo[3,4-b]pyridin-5-one, I-261

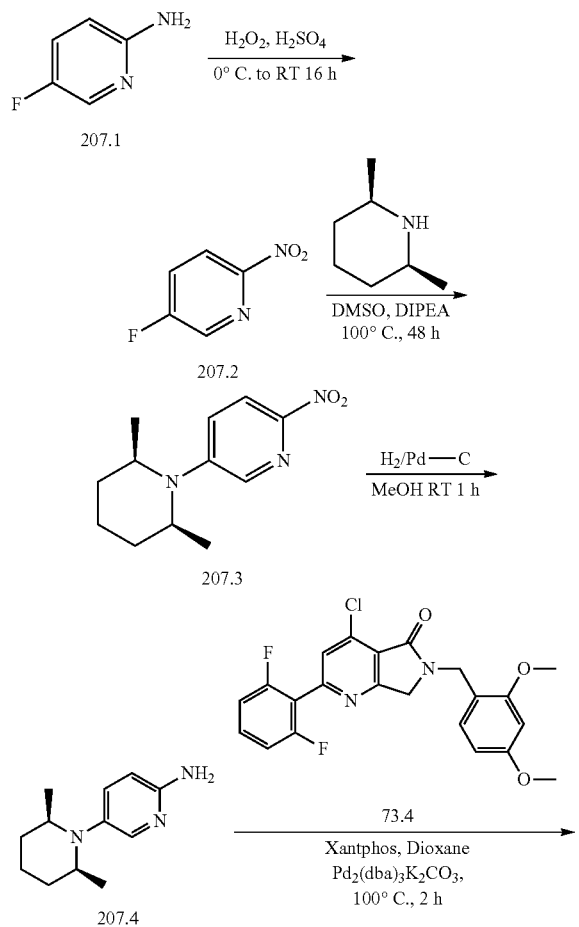

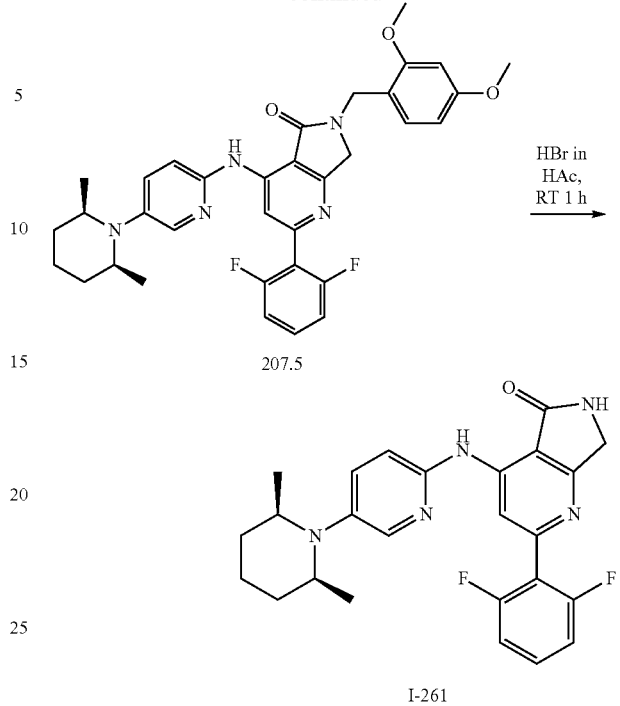

Synthesis of Compound 207.2.

A solution of 207.1 (6.0 g, 53.51 mmol, 1.0 eq) in concentrated H₂SO₄ (60 ml) was cooled at 0° C. (A). Further in another flask hydrogen peroxide (13 ml) was added to concentrated sulphuric acid at 0° C. (B). Further solution (A) was added dropwise to solution (B) at 0° C. The reaction was stirred at room temperature for 16 h. After completion of reaction, reaction mixture was poured in ice cold water and product was extracted with EtOAc. Organic layers were combined, dried over sodium sulphate and evaporated to obtain pure compound 207.2 (3.0 g, 39.45%). MS (ES): m/z 142.09 [M+H]⁺.

Synthesis of Compound 207.3.

To a solution of compound 207.2 (3.0 g, 21.12 mmol, 1.0 eq) in DMSO (50 ml) was added (2R,6S)-2,6-dimethylpiperidine (4.77 g, 42.25 mmol, 2.0 eq.) and DIPEA (27.2 g, 0.21 mmol, 10.0 eq.). The reaction was heated at 100° C. for 48 h. After completion of the reaction, mixture was poured in water and product was extracted with EtOAC. Organic layers were combined and dried over Na₂SO₄ and concentrated under reduced pressure to obtain crude which was purified by column chromatography to get pure 207.3 (0.400 g, 8.05%). MS (ES): m/z 235.29 [M+H]⁺.

Synthesis of Compound 207.4.

To a solution of 207.3 (0.4 g, 1.700 mmol, 1.0 eq) in MeOH (8 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to get pure 207.4 (0.172 g, 49.28%) MS (ES): m/z 205.31 [M+H]⁺.

Synthesis of Compound 207.5.

To a solution of 73.4 (0.100 g, 0.232 mmol, 1.0 eq) in 1,4-dioxane (3 ml) was added 207.4 (0.057 g, 0.279 mmol, 1.2 eq) and K₂CO₃ (0.096 g, 0.697 mmol, 3.0 eq). The reaction mixture was degassed for 10 min. under argon atmosphere, then Pd₂(dba)₃ (0.021 g, 0.023 mmol, 0.1 eq)

and Xantphos (0.026 g, 0.046 mmol, 0.2 eq) were added, and again degassed for 5 min. The reaction was then heated at 100° C. for 2 h. After completion of the reaction, reaction mixture was poured into water and product was extracted with EtOAc. Organic layer was dried over Na$_2$SO$_4$ and concentrated under reduced pressure to obtain crude which was purified by column chromatography to get pure 207.5 (0.090 g, 64.66%). MS(ES): m/z 599.68 [M+H]$^+$.

Synthesis of Compound I-261.

The compound 207.5 (0.090 g, 0.150 mmol, 1.0 eq) was dissolved in HBr/HOAc (3 ml) and stirred at room temperature for 1 h. After completion of the reaction, mixture was poured in water and basified with saturated bicarbonate solution and product was extracted with EtOAc. Organic layers were combined, dried over Na$_2$SO$_4$ and concentrated under reduced pressure to obtain crude which was purified by column chromatography to furnish get pure I-261 (0.045 g, 66.7%). MS(ES): m/z 449.51 [M+H]$^+$; $^1$H NMR (DMSO-d$_6$, 400 MHz): 9.70 (s, 1H), 8.87 (s, 1H), 8.50 (s, 1H), 8.02 (d, 1H), 7.62-7.56 (m, 2H), 7.28-7.24 (t, 2H), Example 208, Synthesis of 2-(2,6-difluorophenyl)-4-((5-(4-(3,3,3-trifluoropropyl)piperazin-1-yl)pyridin-2-yl)amino)-6,7-dihydro-5H-pyrrolo[3,4-b]pyridin-5-one, I-262

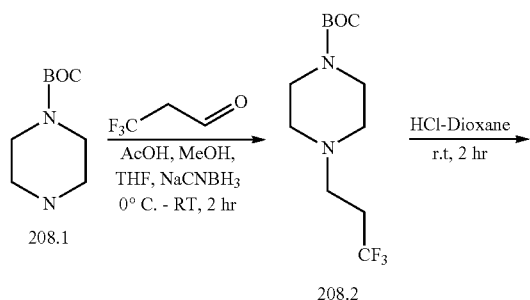

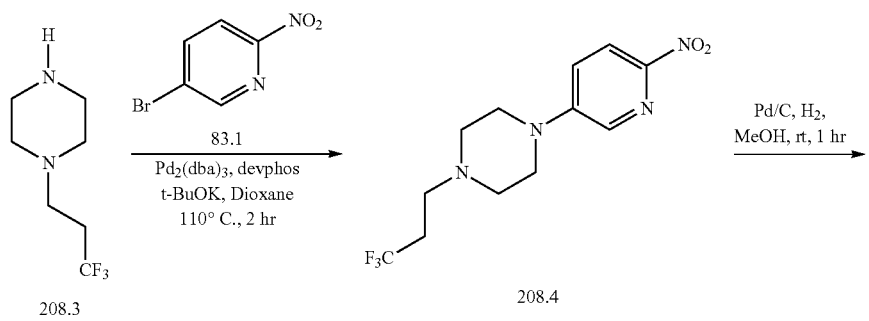

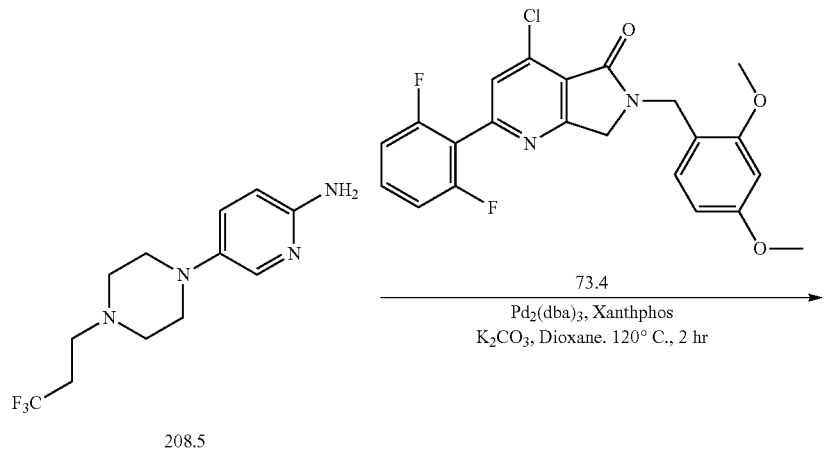

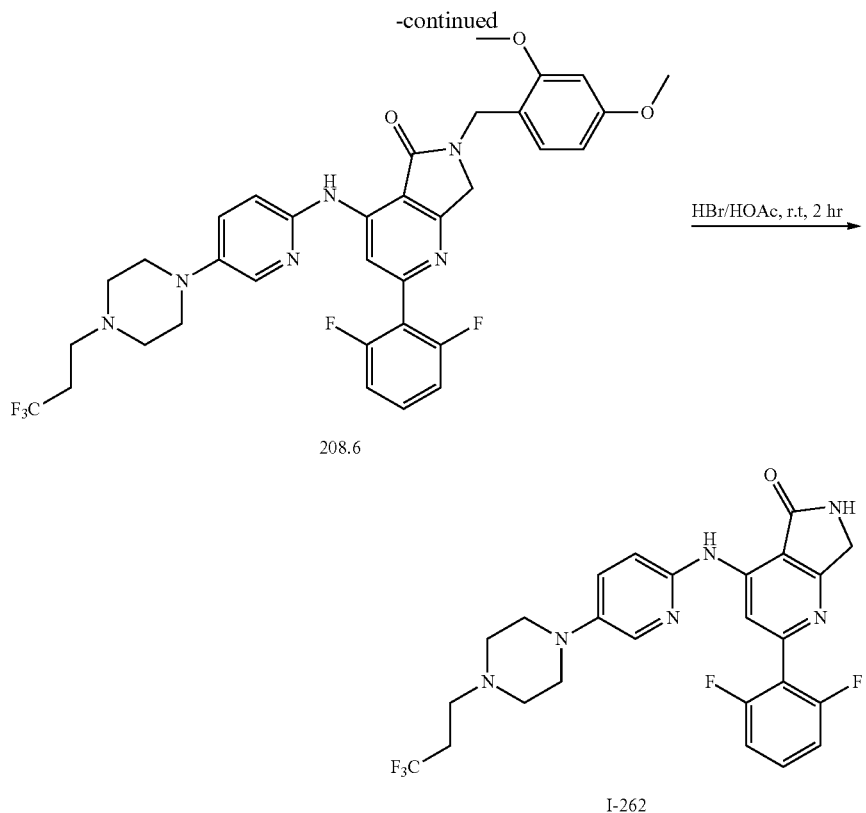

Synthesis of Compound 208.2.

The solution of N-boc piperazine (1.0 g, 5.375 mmol, 2.0 eq) in THF (5 ml) and methanol (3 ml) was cooled to 0° C. A solution of 3,3,3-trifluoropropanal (0.301 g, 2.687 mmol, 1.0 eq.) in THF (2 ml) was added to the reaction mixture at 0° C. To the reaction mixture, acetic acid (0.16 ml, 2.687 mmol, 1.0 eq.) and NaCNBH$_3$ (0.17 g, 2.687 mmol, 1.0 eq.) was added at 0° C. and the reaction mixture was stirred at room temperature for 2 h. After completion of the reaction, mixture was poured into water and product was extracted with EtOAc. Organic layers were combined, washed with NaHCO$_3$ and brine solution, dried over sodium sulphate and concentrated under reduced pressure to obtain crude which was purified by flash chromatography to furnish 208.2 (0.4 g, 26.39%). MS (ES): m/z 282.31 [M+H]$^+$.

Synthesis of Compound 208.3.

A solution of compound 208.2 (0.4 g, 1.418 mmol, 1.0 eq.) in Dioxane HCl (13 ml) was stirred at room temperature for 2 h. After completion of the reaction, mixture was poured in water and product was extracted with EtOAc. Organic layers were combined, washed with NaHCO$_3$ and brine solution, dried over Na$_2$SO$_4$ and concentrated under reduced pressure to obtain crude which was purified by flash chromatography to get pure 208.3 (0.306 g, 100%). MS (ES): m/z 218.59 [M+H]$^+$.

Synthesis of Compound 208.4.

To a solution of 5-bromo-2-nitropyridine (0.3 g, 1.477 mmol, 1.0 eq) in 1,4-dioxane (3 ml) was added 208.3 (0.320 g, 1.477 mmol, 1.0 eq.) and potassium tertiary butoxide (0.354 g, 3.694 mmol, 2.5 eq.). The reaction mixture was degassed under argon atmosphere for 10 minutes. Pd$_2$(dba)$_3$ (0.135 g, 0.147 mmol, 0.1 eq) and Xantphos (0.116 g, 0.295 mmol, 0.2 eq) were added. The reaction mixture was degassed for 15 minutes and further was heated at 110° C. for 2 h. After completion of reaction, mixture was poured in water and product was extracted with EtOAc. Organic layers were combined, dried over sodium sulphate and concentrated under reduced pressure to obtain crude which was purified by column chromatography to furnish 208.4 (0.2 g, 44.48%), MS (ES): m/z 304.27 [M+H]$^+$.

Synthesis of Compound 208.5.

To a solution of 208.4 (0.2 g, 0.657 mmol, 1.0 eq) in MeOH (10 mL) was added 10% Pd/C (0.020 g) under nitrogen atmosphere. It was purged with hydrogen for 1 h. Reaction mixture was filtered through celite and obtained filtrate was concentrated under reduced pressure and purified by flash chromatography to furnish 208.5 (0.162 g, 100%) MS (ES): m/z 247.27 [M+H]$^+$.

Synthesis of Compound 208.6.

To a solution of 73.4 (0.12 g, 0.279 mmol, 1.0 eq) in 1,4-dioxane (4 ml) was added 208.5 (0.084 g, 0.306 mmol, 1.1 eq) and K$_2$CO$_3$ (0.096 g, 0.697 mmol, 2.5 eq). The reaction mixture was degassed for 10 min. under argon atmosphere, then Pd$_2$(dba)$_3$ (0.025 g, 0.027 mmol, 0.1 eq) and Xantphos (0.032 g, 0.055 mmol, 0.2 eq) were added, again degassed for 5 min. The reaction was stirred at 120° C. for 2 h. After completion of the reaction, mixture was poured into water and product was extracted with EtOAc. Organic layers were combined, dried over sodium sulphate and concentrated under reduced pressure to obtain crude which was purified by flash chromatography to furnish 208.6 (0.120 g, 64.43%), MS (ES): m/z 668.67 [M+H]$^+$.

Synthesis of Compound I-262.

Compound 108.6 (0.120 g, 0.179 mmol, 1.0 eq) was dissolved in HBr/HOAc (3 ml) and stirred at room temperature for 2 h. After completion of reaction, mixture was poured in water, basified with saturated bicarbonate solution and product was extracted with EtOAc. Organic layers were combined, dried over Na$_2$SO$_4$ and concentrated under reduced pressure to obtain crude which was purified by column chromatography to furnish I-262 (0.075 g, 80.6%). MS(ES): m/z 518.49 [M+H]$^+$; $^1$H NMR (DMSO-d6, 400 MHz): 9.51 (s, 1H), 8.81 (s, 1H), 8.38 (s, 1H), 8.03-8.02 (d, 1H), 7.60-7.53 (m, 1H), 7.48-7.45 (dd, 1H), 7.27-7.23 (t, 2H), 7.11-7.08 (d, 1H), 4.41 (s, 2H), 3.12-3.10 (m, 4H), 3.54-3.51 (m, 6H).

Example 209. Synthesis of compound 2-(2,6-difluorophenyl)-4-((5-((3R,5R)-3,5-dimethylmorpholino)pyridin-2-yl)amino)-6,7-dihydro-5H-pyrrolo[3,4-b]pyridin-5-one I-263

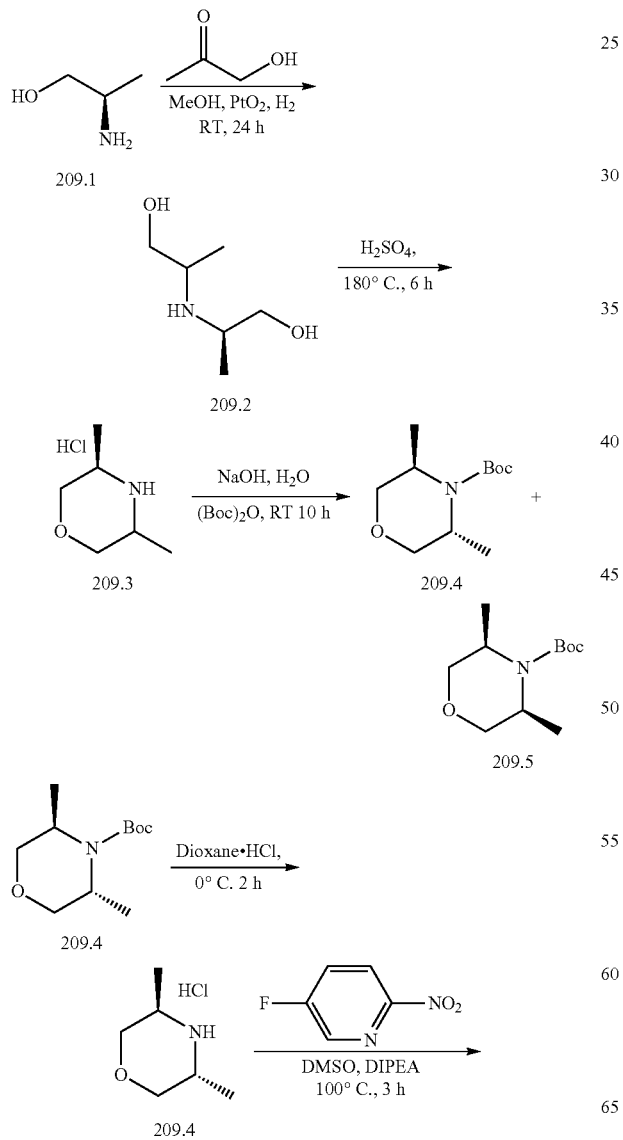

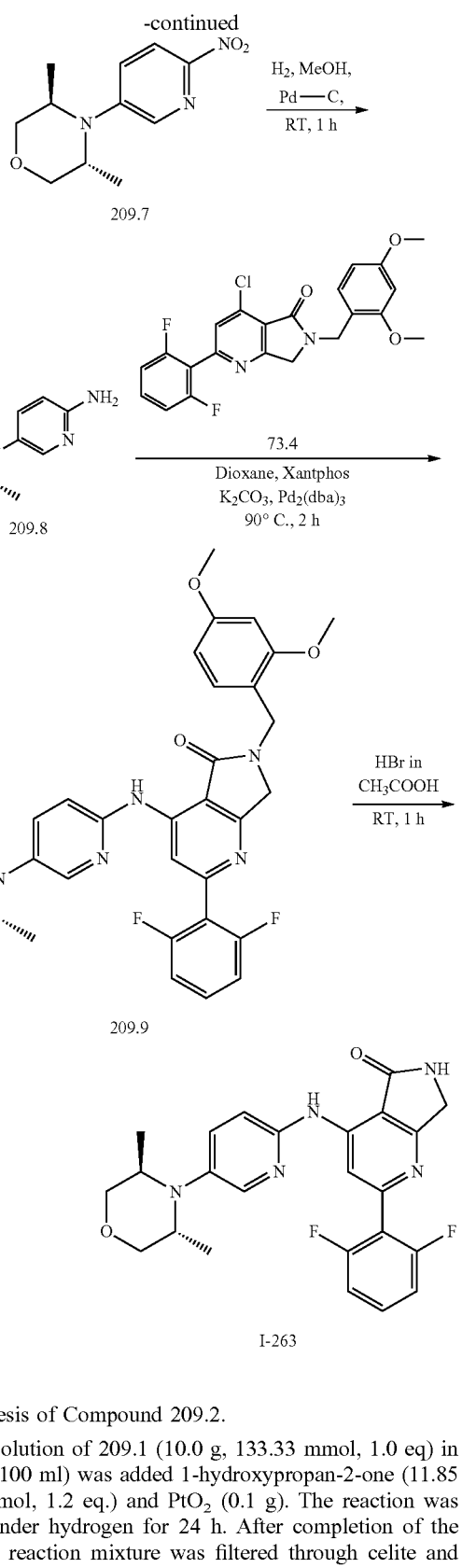

Synthesis of Compound 209.2.

To a solution of 209.1 (10.0 g, 133.33 mmol, 1.0 eq) in MeOH (100 ml) was added 1-hydroxypropan-2-one (11.85 g, 16 mmol, 1.2 eq.) and PtO$_2$ (0.1 g). The reaction was stirred under hydrogen for 24 h. After completion of the reaction, reaction mixture was filtered through celite and washed with EtOAc. Organic layers were combined, dried over sodium sulphate and concentrated under reduced pressure to obtain crude which was to get pure 209.2 (7.0 g, 39.48%), MS (ES): m/z 133.19 [M+H]$^+$.

Synthesis of Compound 209.3.

The solution of 209.2 (7.0 g, 52.556 mmol, 1.0 eq) in concentrated $H_2SO_4$ (75 mL) was heated at 180° C. for 6 h. After completion of reaction, mixture was poured into water, quenched with KOH and filtered on celite and washed with water. Combined filtrate was distilled, distillate was acidified with 6 N HCl and water was removed under reduced pressure to obtain 209.3 (1.8 g, 29.74%) MS (ES): m/z 151.15 $[M+H]^+$.

Synthesis of Compound 209.4.

To a solution of 209.3 (1.8 g, 15.65 mmol, 1.0 eq) in water was added NaOH (1.37 g, 34.4 mmol, 2.2 eq.) and BOC anhydride (3.75 g, 17.21 mmol, 1.1 eq.) dropwise. The reaction was stirred at room temperature for 10 h. After completion of the reaction, mixture was poured into water and extracted with EtOAc. Organic layers was combined, dried over sodium sulphate and concentrated under reduced pressure to obtain which was purified by flash chromatography to get pure 209.4 (0.81 g, 31.6%) MS (ES): m/z 215.29 $[M+H]^+$.

Synthesis of Compound 209.6

A solution of 209.4 (0.81 g, 3.7 mmol, 1.0 eq) in 1,4-dioxane HCl (2 ml) was stirred at 0° C. for 2 h. After completion of the reaction, solvent was removed under reduced pressure to get 209.6 (0.600 g, 95%) MS (ES): m/z 151.68 $[M+H]^+$.

Synthesis of Compound 209.7.

To a solution of 209.6 (0.600 g, 3.95 mmol, 1.0 eq) in DMSO (2 mL) was added 5-fluoro-2-nitropyridine (0.561 g, 3.95 mmol, 1.0 eq.) and DIPEA (5.10 g, 39.55 mmol, 10.0 eq.). Reaction was heated at 100° C. for 3 h. After completion of the reaction, mixture was poured into water and extracted with EtOAc. Organic layers were combined, dried over $Na_2SO_4$ and concentrated under reduced pressure to obtain crude which was purified by flash chromatography to furnish 209.7 (0.055 g, 10%) MS (ES): m/z 237.26 $[M+H]^+$.

Synthesis of Compound 209.8.

To a solution of 209.7 (0.055 g, 0.231 mmol, 1.0 eq) in MeOH (5 mL) was added 10% Pd/C (0.010 g) under nitrogen atmosphere. It was purged with hydrogen for 1 h. Reaction mixture was filtered through celite and washed methanol filtrate was concentrated under reduced pressure to get pure 209.7 (0.04 g, 83.2%) MS (ES): m/z 207.28 $[M+H]^+$.

Synthesis of Compound 209.9.

To a solution of 73.4 (0.075 g, 0.174 mmol, 1.0 eq) in 1,4-dioxane (3 ml) was added 1.6 (0.036 g, 0.174 mmol, 1.0 eq) and $K_2CO_3$ (0.072 g, 0.522 mmol, 3.0 eq). Reaction mixture was degassed for 10 min. under argon then $Pd_2(dba)_3$ (0.015 g, 0.017 mmol, 0.1 eq) and Xantphos (0.020 g, 0.034 mmol, 0.2 eq) were added, again degassed for 5 min. Reaction was then stirred at 90° C. for 2 h. After completion of the reaction, mixture was poured into water and product was extracted with EtOAc. Organic layers were combined and dried over $Na_2SO_4$ and concentrated under reduced pressure to obtain crude which was purified by flash chromatography to get pure 209.9 (0.060 g, 57.29%). MS(ES): m/z 601.65 $[M+H]^+$.

Synthesis of Compound I-263.

The compound 209.9 (0.060 g, 0.099 mmol, 1.0 eq) was dissolved in HBr/HOAc (3 mL) and stirred at room temperature for 1 hour. After completion of the reaction, mixture was poured into water, basified with saturated bicarbonate solution and extracted with EtOAc. Organic layer were combined, dried over $Na_2SO_4$ and concentrated under reduced pressure to obtain crude which was purified by flash chromatography get pure I-263 (0.030 g, 66.6%). MS(ES): m/z 451.48 $[M+H]^+$; $^1H$ NMR (DMSO-$d_6$, 400 MHZ): 9.65 (s, 1H), 8.85 (s, 1H), 8.49 (s, 1H), 8.06-8.05 (d, 1H), 7.61-7.54 (m, 1H), 7.50-7.47 (dd, 1H), 7.28-7.14 (t, 2H), 7.14-7.12 (d, 1H), 4.42 (s, 2H), 3.82-3.79 (dd, 2H), 3.48-3.44 (m, 2H), 3.43-3.34 (m, 2H), 1.30-1.21 (m, 2H), 0.83-0.82 (d, 6H).

Example 210. Synthesis of 2-(2,6-difluorophenyl)-4-((5-((3S,5S)-3,5-dimethyl-morpholino)pyridin-2-yl)amino)-6,7-dihydro-5H-pyrrolo[3,4-b]pyridin-5-one, I-264

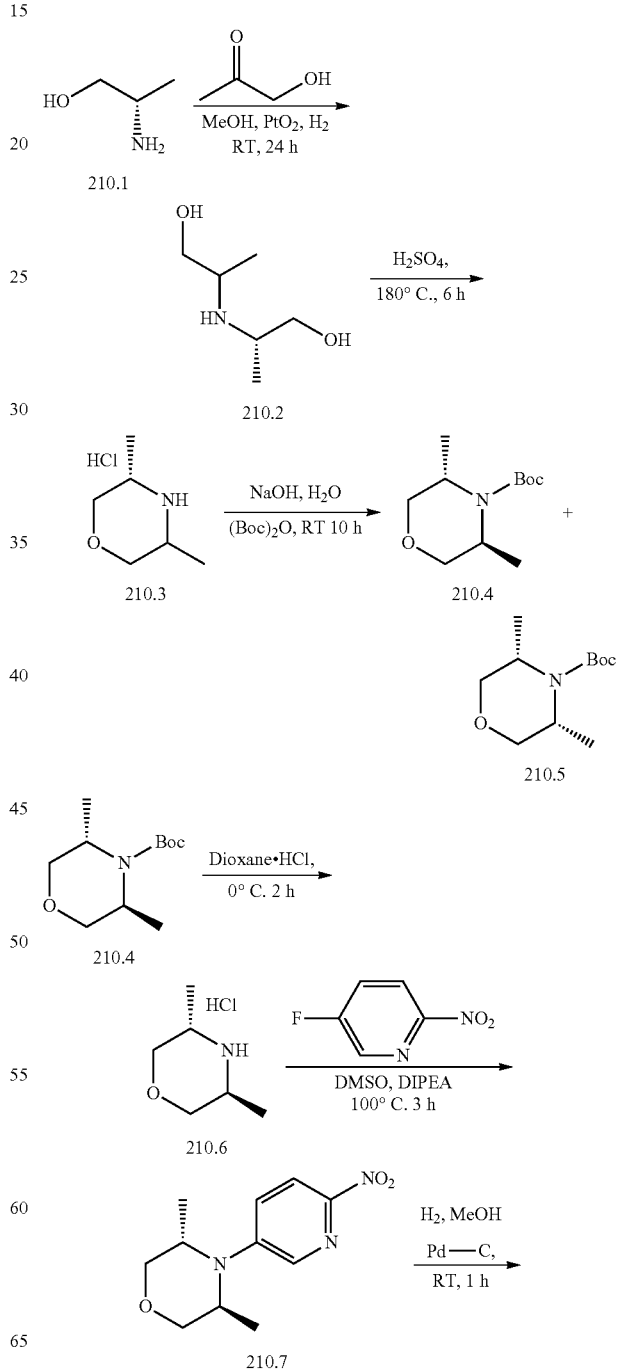

529

-continued

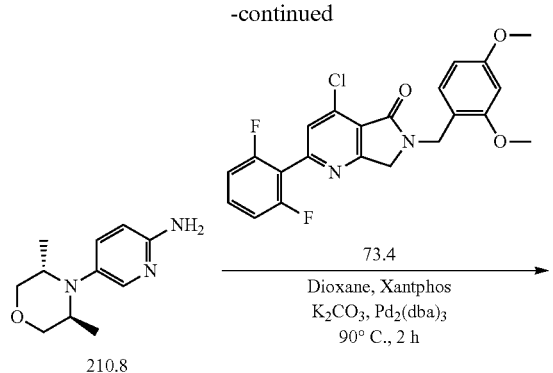

210.8

73.4
Dioxane, Xantphos
K₂CO₃, Pd₂(dba)₃
90° C., 2 h
→

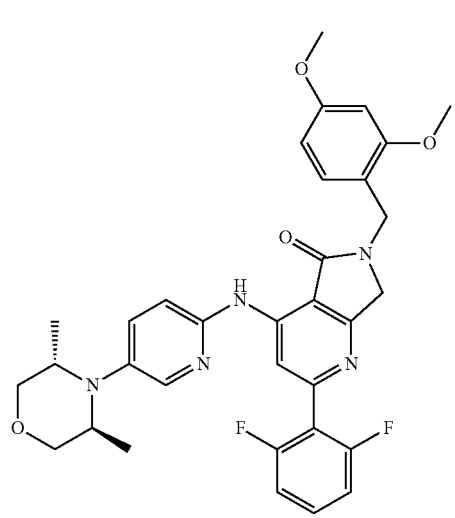

210.9

HBr in
CH₃COOH
RT, 1 h
→

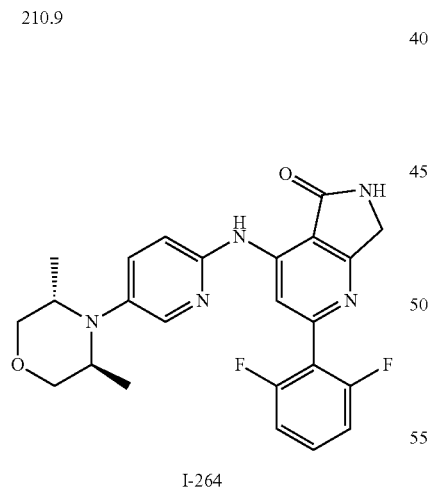

I-264

Compound I-264 was prepared from compound 210.1 using the exact synthetic sequence as described in Example 209. (0.02 g, 76.2%). MS(ES): m/z 451.48 [M+H]⁺; ¹H NMR (DMSO-d₆, 400 MHz): 9.68 (s, 1H), 8.88 (s, 1H), 8.50 (s, 1H), 8.07 (s, 1H), 7.60-7.56 (m, 1H), 7.52-7.50 (m, 1H), 7.29-7.25 (t, 2H), 7.16-7.14 (d, 1H), 4.43 (s, 2H), 3.82-3.80 (m, 2H), 3.47-3.42 (m, 2H), 3.41-3.33 (m, 2H), 1.57-1.50 (m, 2H), 0.84-0.83 (d, 6H).

530

Example 211. Synthesis of 2-(2,6-difluorophenyl)-4-((5-((2R,6R)-2,6-dimethylpiperidin-1-yl)pyridin-2-yl)amino)-6,7-dihydro-5H-pyrrolo[3,4-b]pyridin-5-one, I-265

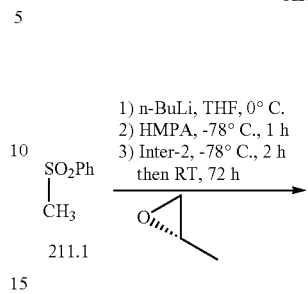

211.1

1) n-BuLi, THF, 0° C.
2) HMPA, -78° C., 1 h
3) Inter-2, -78° C., 2 h
   then RT, 72 h
→

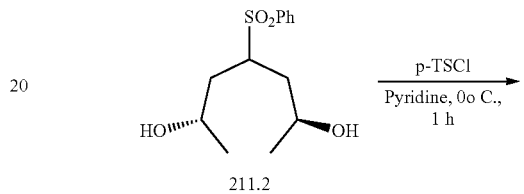

211.2 p-TSCl
Pyridine, 0o C.,
1 h
→

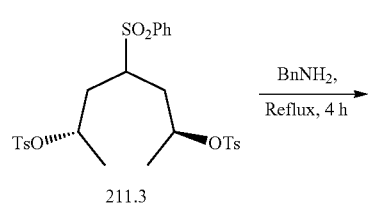

211.3

BnNH₂,
Reflux, 4 h
→

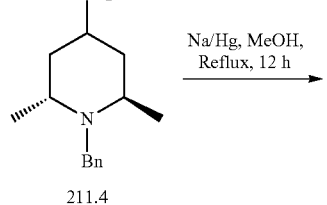

211.4

Na/Hg, MeOH,
Reflux, 12 h
→

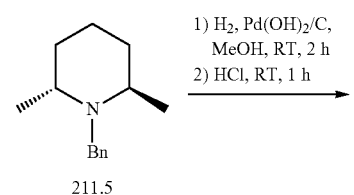

211.5

1) H₂, Pd(OH)₂/C,
   MeOH, RT, 2 h
2) HCl, RT, 1 h
→

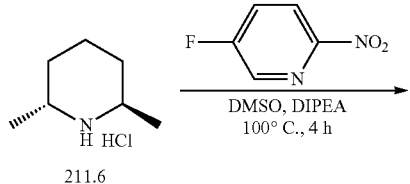

211.6

DMSO, DIPEA
100° C., 4 h
→

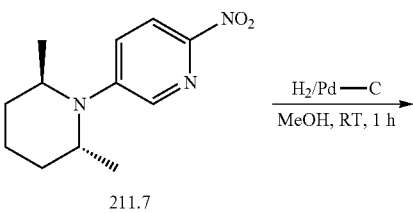

211.7

H₂/Pd—C
MeOH, RT, 1 h
→

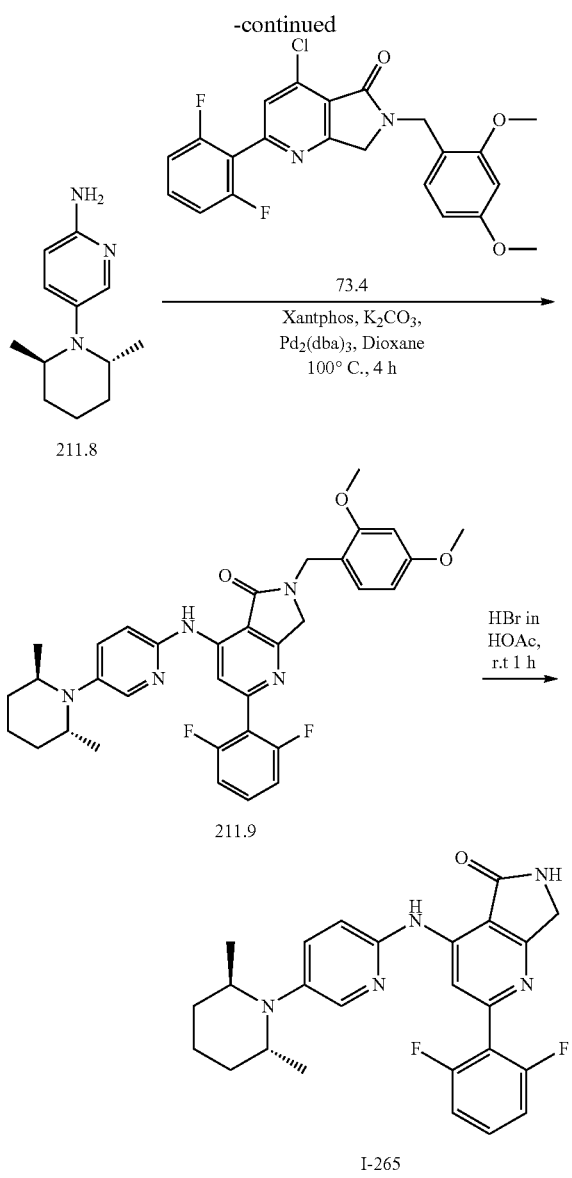

Synthesis of Compound 211.2.

To a solution of 211.1 (20.0 g, 128.04 mmol, 1.0 eq) in THF (250 mL) was added n-butyl lithium (18.04 g, 0.281 mmol, 2.2 eq) at 0° C. Reaction was stirred at 0° C. for 1 h. HMPT (50.47 g, 0.281 mmol, 2.2 eq) was added to the reaction mixture at −78° C. and the reaction was allowed to stir at −78° C. for 1 h. Further S-(−)-propylene oxide (15.24 g, 0.262 mmol, 2.05 eq) dissolved in THF (50 mL) was added to the reaction mixture at −78° C. and the reaction was allowed to stir at room temperature for 72 h. After completion of the reaction, mixture was quenched with $NH_4Cl$ solution and extracted with EtOAc. Organic layers were combined, dried over sodium sulphate and concentrated under reduced pressure to give crude which was purified by column chromatography to furnish 211.2 (15.2 g, 43.59%), MS (ES): m/z 272.36 [M+H]$^+$.

Synthesis of Compound 211.3.

The solution of 211.2 (15.2 g, 55.80 mmol, 1.0 eq) in pyridine (95 mL) was cooled at 0° C. p-toluene sulphonyl chloride (23.4 g, 0.122 mmol, 2.2 eq) dissolved in pyridine (95 mL) at 0° C. was added to the reaction mixture at same temperature. Reaction was stirred at 0° C. for 1 h. After completion of the reaction, mixture was poured into diethyl ether, solid precipitates were filtered through celite and filtrate was evaporated under reduced pressure to give crude which was purified by flash chromatography to furnish pure 211.3 (18.2 g, 56.16%), MS (ES): m/z 580.73 [M+H]$^+$.

Synthesis of Compound 211.4.

A solution of 211.3 (18.2 g, 31.33 mmol, 1.0 eq) in benzyl amine (150 mL) was refluxed for 4 h. After completion of the reaction, benzyl amine was removed under reduced pressure and reaction mixture was poured into water and extracted with EtOAc. Organic layers were combined, dried over sodium sulphate and concentrated under reduced pressure to give crude which was purified by column chromatography to furnish 211.4 (8.0 g, 74.3%), MS (ES): m/z 343.48 [M+H]$^+$.

Synthesis of Compound 211.5.

Solution of 211.4 (8.0 g, 23.3 mmol, 1.0 eq) in methanol was refluxed for 15 minutes. Sodium mercury amalgam (10.0 g) was added portion wise to the reaction mixture over 2 hours and the reaction mixture was allowed to reflux for 12 h. After completion of the reaction, mixture was filtered through celite and concentrated under reduced pressure to give crude which was purified by flash chromatography to furnish 211.5 (3.9 g, 82.35%) MS (ES): m/z 203.33 [M+H]$^+$.

Synthesis of Compound 211.6.

A solution of 211.5 (3.9 g, 19.18 mmol, 1.0 eq) in methanol was added to PdOH (1.2 g) (suspended in methanol). Reaction was purged with hydrogen for 2 h. After completion of the reaction, mixture was filtered through celite and HCl in methanol (20 mL) was added. Reaction was stirred for 1 h. Solvent was removed under reduced pressure and crude was purified via trituration to furnish 211.6 (2.12 g, 73.85%), MS (ES): m/z 149.7 [M+H]$^+$.

Synthesis of Compound 211.7.

To a solution of compound 5-fluoro-2-nitropyridine (0.600 g, 4.008 mmol, 1.0 eq) in dimethyl sulphoxide (10 mL) was added 211.6 (0.569 g, 4.008 mmol, 1.0 eq) and DIPEA (0.52 g, 4.0 mmol, 10.0 eq). The reaction was heated at 100° C. for 4 h. After completion of the reaction, mixture was poured into water and product was extracted with EtOAc. Organic layers were combined, dried over sodium sulphate and concentrated under reduced pressure to obtain crude material which was purified via flash chromatography to furnish 211.7. (0.140 g, 14.09%), MS (ES): m/z 235.29 [M+H]$^+$.

Synthesis of Compound 211.8.

A solution of 211.7 (0.140 g, 0.595 mmol, 1.0 eq) in methanol (5 mL) was added to 10% Pd/C 0.010 g, suspended in Methanol) under nitrogen atmosphere. Reaction was purged with $H_2$ for 1 hr. Reaction mixture was filtered through celite and obtained filtrate was concentrated under reduced pressure and purified by flash chromatography to get pure 211.8 (0.100 g, 81.86%), MS (ES): m/z 205.31 [M+H]$^+$.

Synthesis of Compound 211.9.

To a solution of 73.4 (0.100 g, 0.232 mmol, 1.0 eq) in 1,4-dioxane (3 mL) was added 211.8 (0.047 g, 0.232 mmol, 1.0 eq) and $K_2CO_3$ (0.064 g, 0.464 mmol, 2.0 eq). The reaction mixture was degassed for 10 minutes under argon atmosphere, then $Pd_2(dba)_3$ (0.021 g, 0.023 mmol, 0.1 eq) and Xantphos (0.026 g, 0.046 mmol, 0.2 eq) were added, again degassed for 5 minutes. The reaction was stirred at 100° C. for 4 h. After completion of the reaction, mixture was poured into water and product was extracted with EtOAc. Organic layers were combined, dried over sodium sulphate and concentrated under reduced pressure to obtain crude which was purified by combi flash, to furnish 211.9 (0.090 g, 64.66%). MS(ES): m/z 599.68 [M+H]+.

Synthesis of Compound I-265.

The compound 211.9 (0.090 g, 0.150 mmol, 1.0 eq) was dissolved in HBr/HOAc (33%, 3 mL) and stirred at room temperature for 1 h. After completion of the reaction, mixture was poured into water and basified with saturated bicarbonate solution and extracted with EtOAc. Organic layers were combined, dried over Na$_2$SO$_4$ and concentrated under reduced pressure to obtain crude which was purified via flash chromatography to furnish I-265 (0.019 g, 28.16%). MS(ES): m/z 449.51 [M+H]+; $^1$H NMR (DMSO-d$_6$, 400 MHz): 8.62 (s, 1H), 8.08 (s, 1H), 7.56-7.50 (m, 2H), 7.17-7.13 (t, 2H), 7.07-7.04 (d, 1H), 7.28-7.24 (t, 2H), 4.48 (s, 2H), 3.52-3.48 (m, 2H), 1.96-1.89 (m, 2H), 1.70-1.64 (m, 2H), 1.55-1.47 (m, 1H), 0.96-0.90 (d, 6H).

Example 212. Synthesis of 2-(2,6-difluorophenyl)-4-((5-(4-hydroxy-3,3-dimethylpiperidin-1-yl)pyridin-2-yl)amino)-6,7-dihydro-5H-pyrrolo[3,4-b]pyridin-5-one, I-266

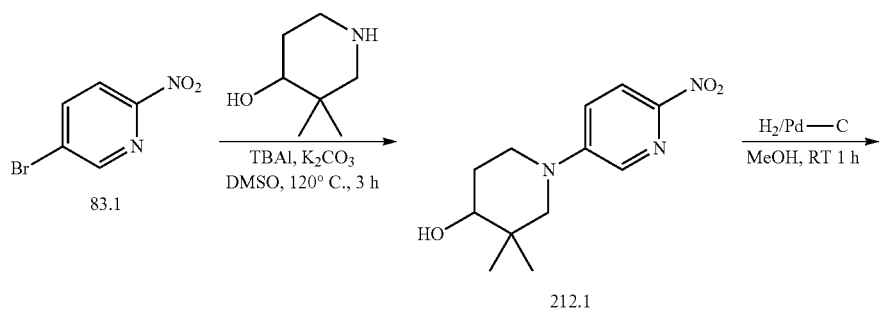

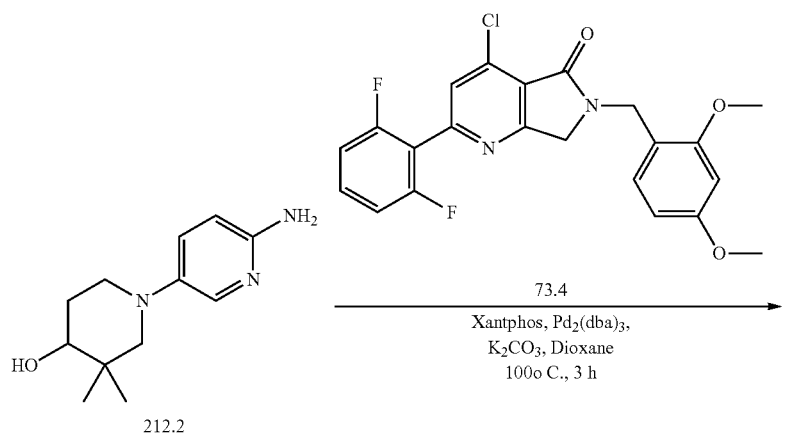

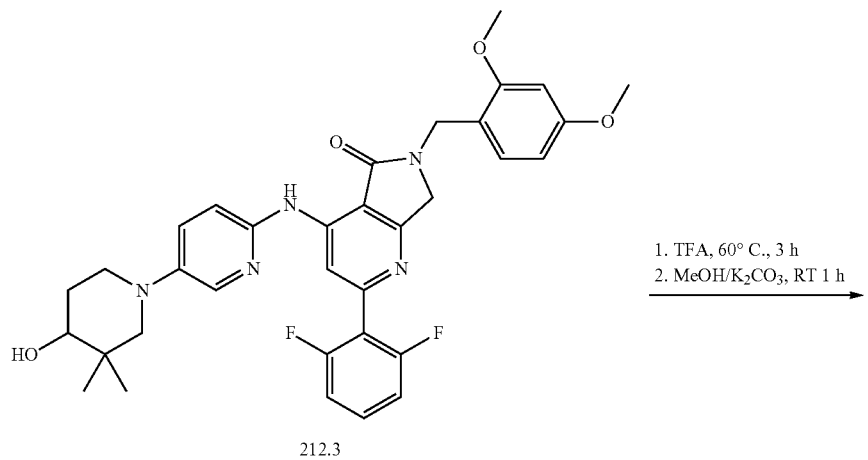

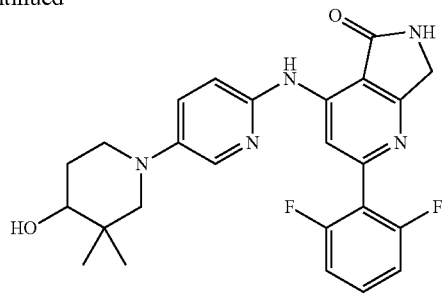

I-266

Synthesis of Compound 212.1.

To a solution of 83.1 (0.3 g, 1.477 mmol, 1.0 eq) in DMSO (5 ml) was added 3,3-dimethylpiperidin-4-ol (0.190 g, 1.477 mmol, 1.0 eq.), $K_2CO_3$ (0.611 g, 4.433 mmol, 3.0 eq.) and tetra n-butyl ammonium iodide (0.054 g, 0.147 mmol, 0.1 eq.). Reaction was stirred at 120° C. for 3 h. After completion of the reaction, mixture was poured in water and product was extracted with EtOAc. Organic layers were combined, dried over sodium sulphate and concentrated under reduced pressure to obtain crude which was purified by flash chromatography to furnish 212.1 (0.220 g, 59.24%), MS (ES): m/z 251.29 $[M+H]^+$.

Synthesis of Compound 212.2.

To a solution of 212.1 (0.220 g, 0.875 mmol, 1.0 eq) in methanol (5 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to get pure 212.2 (0.180 g, 92.90%) MS (ES): m/z 221.30 $[M+H]^+$.

Synthesis of Compound 212.3.

To a solution of 73.4 (0.100 g, 0.232 mmol, 1.0 eq) in 1,4-dioxane (3 ml) was added 212.2 (0.051 g, 0.232 mmol, 1.0 eq) and $K_2CO_3$ (0.096 g, 0.697 mmol, 3.0 eq). The reaction mixture was degassed for 10 min. under argon atmosphere, then $Pd_2(dba)_3$ (0.021 g, 0.023 mmol, 0.1 eq) and Xantphos (0.026 g, 0.046 mmol, 0.2 eq) were added, again degassed for 5 min. The reaction was then heated at 100° C. for 3 h. After completion of the reaction, mixture was poured into water and product was extracted with ethyl acetate. Organic layer were combined and dried over $Na_2SO_4$ and concentrated under reduced pressure to obtain crude which was purified by column chromatography to furnish 212.3 (0.090 g, 62.98%). MS(ES): m/z 615.68 $[M+H]^+$.

Synthesis of Compound I-266.

The compound 212.3 (0.080 g, 0.129 mmol, 1.0 eq) was dissolved in trifluoro acetic acid (3 mL) and stirred at 60° C. for 3 h. After completion of the reaction, trifluoro acetic acid was removed under reduced pressure and further MeOH (8 mL) and potassium carbonate (0.1 g) were added. The reaction mixture was stirred at room temperature for 1 h. Methanol was removed under reduced pressure and water was added to the reaction mixture. The product was extracted with EtOAc. Organic layers were, dried over sodium sulphate and concentrated under reduced pressure to obtain crude which was purified via flash chromatography to furnish I-266 (0.035 g, 57.86%). MS(ES): m/z 465.50 $[M+H]^+$; $^1H$ NMR (DMSO-$d_6$, 400 MHz): δ 9.48 (s, 1H), 8.80 (s, 1H), 8.36 (s, 1H), 8.00-7.99 (d, 1H), 7.60-7.53 (m, 1H), 7.43-7.40 (dd, 1H), 7.27-7.23 (t, 2H), 7.07-7.04 (d, 1H), 4.61-4.60 (d, 1H), 4.40 (s, 2H), 3.44-3.31 (m, 1H), 3.24-3.20 (m, 1H), 3.18-3.15 (m, 1H), 2.79-2.72 (m, 1H), 1.74-1.69 (m, 1H), 1.64-1.59 (m, 1H).

Example 213. Synthesis of (S)-2-(2,6-difluorophenyl)-4-((5-(4-hydroxy-3,3-dimethylpiperidin-1-yl)pyridin-2-yl)amino)-6,7-dihydro-5H-pyrrolo[3,4-b]pyridin-5-one, I-267

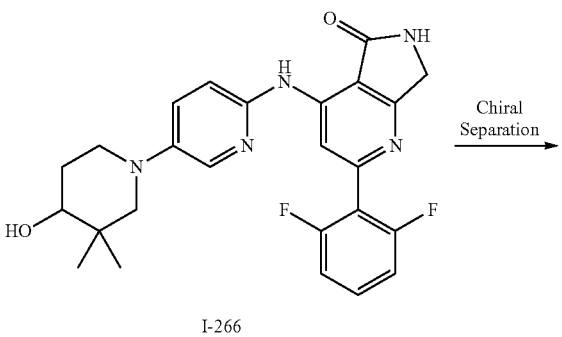

I-266

Chiral Separation →

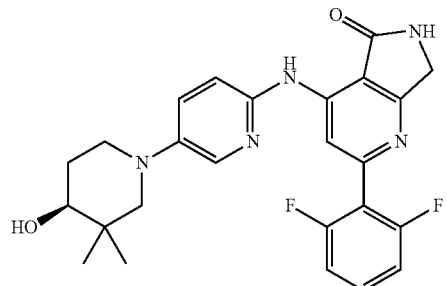

I-267

Compound I-267 was prepared by chiral separation of compound I-266. MS (ES): m/z 465.50 $[M+H]^+$; $^1H$ NMR (DMSO-$d_6$, 400 MHz): δ 9.48 (s, 1H), 8.79 (s, 1H), 8.35 (s, 1H), 8.00-7.99 (d, 1H), 7.59-7.55 (m, 1H), 7.43-7.40 (dd, 1H), 7.27-7.23 (t, 2H), 7.06-7.04 (d, 1H), 4.60-4.59 (d, 1H), 4.40 (s, 2H), 3.44-3.15 (m, 3H), 2.78-2.73 (m, 1H), 1.74-1.59 (m, 2H), 1.25 (m 1H), 0.92 and 0.90 (s, 6H).

Example 214. Synthesis of (R)-2-(2,6-difluorophenyl)-4-((5-(4-hydroxy-3,3-dimethyl-piperidin-1-yl)pyridin-2-yl)amino)-6,7-dihydro-5H-pyrrolo[3,4-b]pyridin-5-one, I-268

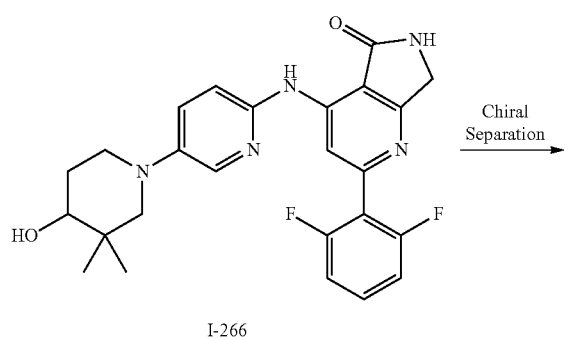

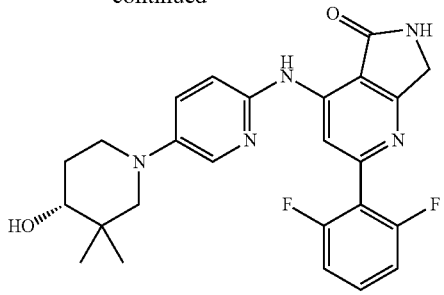

Compound I-268 was prepared by chiral separation of compound I-266. MS (ES): m/z 465.50 [M+H]$^+$; $^1$H NMR (DMSO-d$_6$, 400 MHZ): δ 9.48 (s, 1H), 8.80 (s, 1H), 8.36 (s, 1H), 8.00-7.99 (d, 1H), 7.57 (m, 1H), 7.43-7.40 (dd, 1H), 7.27-7.23 (t, 2H), 7.07-7.04 (d, 1H), 4.61-4.60 (d, 1H), 4.40 (s, 2H), 3.44-3.15 (m, 3H), 2.76-2.75 (m, 1H), 1.70-1.69 (m, 2H), 1.24 (m, 1H), 0.92 and 0.90 (s, 6H).

Example 215. Synthesis of 2-(2,6-difluorophenyl)-4-((5-(3-hydroxypiperidin-1-yl)pyridin-2-yl)amino)-6,7-dihydro-5H-pyrrolo[3,4-b]pyridin-5-one, I-269

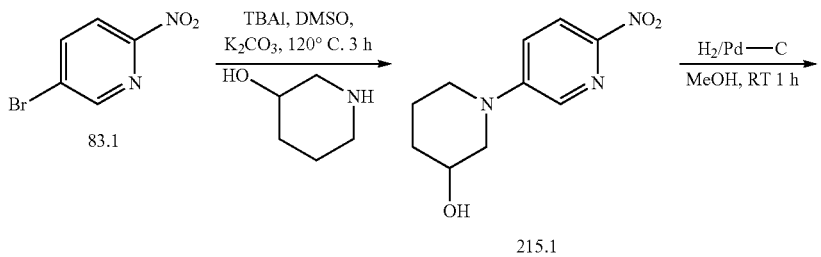

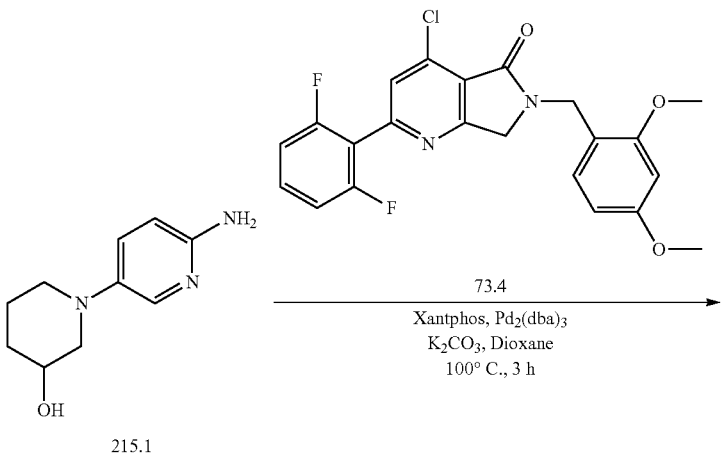

-continued

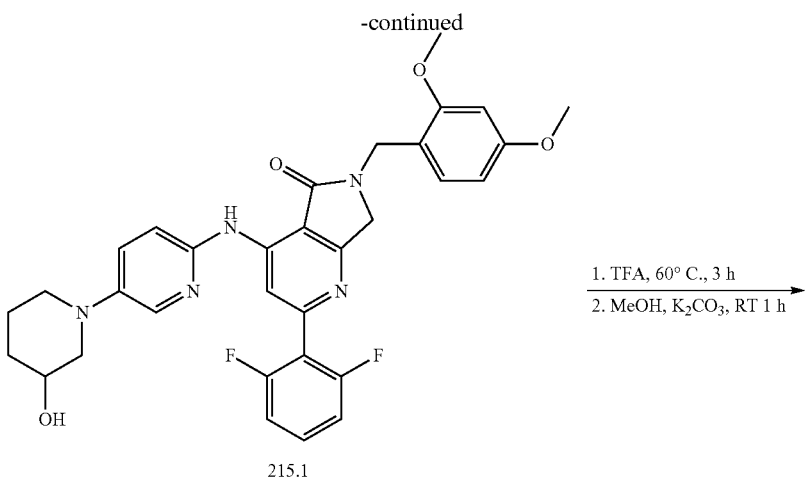

215.1

1. TFA, 60° C., 3 h
2. MeOH, K₂CO₃, RT 1 h

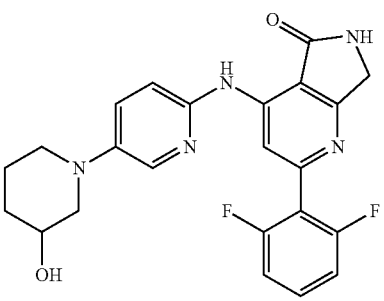

I-269

Synthesis of Compound 215.1.

To a solution of 83.1 (0.3 g, 1.477 mmol, 1.0 eq) in DMSO (5 ml) was added piperidin-3-ol (0.149 g, 1.477 mmol, 1.0 eq.), K$_2$CO$_3$ (0.509 g, 3.694 mmol, 2.5 eq.) and tetra n-butyl ammonium iodide (0.054 g, 0.147 mmol, 0.1 eq.). Reaction mixture was heated at 120° C. for 3 hours. After completion of the reaction, mixture was poured in water and product was extracted with EtOAc. Organic layers were combined, dried over sodium sulphate and concentrated under reduced pressure to obtain crude which was purified via flash chromatography to furnish 215.1 (0.23 g, 69.7%), MS (ES): m/z 223.23 [M+H]$^+$.

Synthesis of Compound 215.2.

To a solution of 215.1 (0.230 g, 1.030 mmol, 1.0 eq) in methanol (5 mL) was added 10% Pd/C (0.010 g) under nitrogen atmosphere. It was purged with hydrogen for 1 h. Reaction mixture was filtered through celite and obtained filtrate was concentrated under reduced pressure to get pure 215.2 (0.190 g, 95.43%) MS (ES): m/z 193.25 [M+H]$^+$.

Synthesis of Compound 215.3.

To a solution of 73.4 (0.250 g, 0.581 mmol, 1.0 eq) in 1,4-dioxane (3 ml) was added 215.2 (0.112 g, 0.581 mmol, 1.0 eq) and K$_2$CO$_3$ (0.240 g, 1.744 mmol, 3.0 eq). The reaction mixture was degassed for 10 min. under argon atmosphere, then Pd$_2$(dba)$_3$ (0.053 g, 0.058 mmol, 0.1 eq) and Xantphos (0.067 g, 0.116 mmol, 0.2 eq) were added, again degassed for 5 min. The reaction was stirred at 100° C. for 3 h. After completion of the reaction, reaction mixture was poured into water and product was extracted with EtOAc. Organic layers were combined dried over sodium sulphate and concentrated under reduced pressure to obtain crude which was purified using flash chromatography to furnish 215.3 (0.180 g, 52.79%). MS(ES): m/z 587.63[M+H]$^+$.

Synthesis of Compound I-269.

Compound 215.3 (0.160 g, 0.272 mmol, 1.0 eq) was dissolved in trifluoro acetic acid (3 ml) and stirred at 60° C. for 3 h. After completion of the reaction, trifluoro acetic acid was removed under reduced pressure and sodium bicarbonate solution was added to the reaction mixture. Product was extracted with EtOAc. Organic layers were combined, dried over Na$_2$SO$_4$ and concentrated under reduced pressure. Methanol (8 mL) and potassium carbonate (0.1 g) were added. The reaction mixture was stirred at room temperature for 1 h. Methanol was removed under reduced pressure and water was added to the reaction mixture. Product was extracted with EtOAc. Organic layer were combined, dried over Na$_2$SO$_4$ and concentrated under reduced pressure to obtain crude which was purified using column chromatography to furnish I-269 (0.070 g, 58.77%). MS(ES): m/z 437.45 [M+H]$^+$; $^1$H NMR (DMSO-d$_6$, 400 MHz): 9.50 (s, 1H), 8.81 (s, 1H), 8.35 (s, 1H), 7.99-7.98 (d, 1H), 7.59-7.53 (m, 1H), 7.43-7.40 (dd, 1H), 7.27-7.23 (t, 2H), 7.09-7.06 (d, 1H), 4.83-4.82 (d, 1H), 4.40 (s, 2H), 3.61-3.33 (m, 3H), 2.69-2.54 (m, 1H), 1.87-1.84 (m, 1H), 1.76-1.72 (m, 1H), 1.53-1.50 (m, 1H), 1.30-1.22 (m, 1H).

Example 216. Synthesis of (S)-2-(2,6-difluorophenyl)-4-((5-(3-hydroxypiperidin-1-yl)pyridin-2-yl)amino)-6,7-dihydro-5H-pyrrolo[3,4-b]pyridin-5-one, I-270

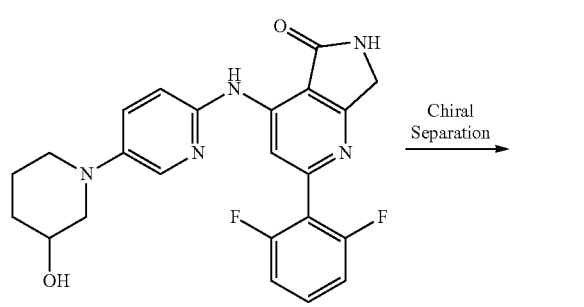

I-269

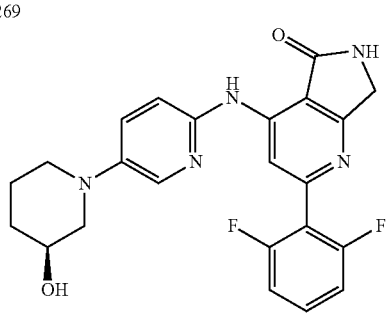

I-270

Compound I-270 was prepared by chiral separation of compound I-269. MS (ES): m/z 437.45 [M+H]$^+$; $^1$H NMR (DMSO-d6, 400 MHz): δ 9.50 (s, 1H), 8.84 (s, 1H), 8.36 (s, 1H), 8.03 (d, 1H), 7.60-7.56 (m, 1H), 7.48-7.45 (dd, 1H), 7.28-7.24 (t, 2H), 7.12-7.10 (d, 1H), 4.42 (s, 3H), 3.63-3.59 (s, 1H), 3.55-3.47 (m, 1H), 3.45-3.42 (s, 1H), 2.74-2.69 (m, 1H), 1.87-1.84 (m, 1H), 1.77-1.74 (m, 1H), 1.54-1.51 (m, 1H), 1.32-1.23 (m, 1H).

Example 217. Synthesis of (R)-2-(2,6-difluorophenyl)-4-((5-(3-hydroxypiperidin-1-yl)pyridin-2-yl)amino)-6,7-dihydro-5H-pyrrolo[3,4-b]pyridin-5-one, I-271

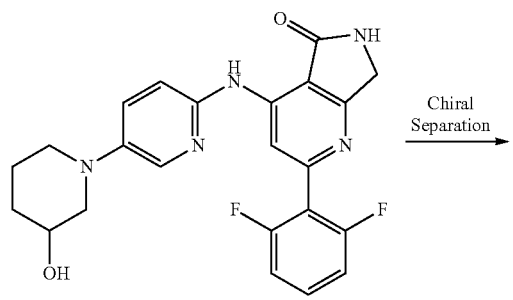

I-269

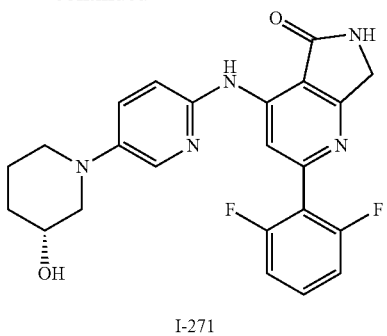

I-271

Compound I-271 was prepared by chiral separation of compound I-269. MS (ES): m/z 437.45 [M+H]$^+$; $^1$H NMR (DMSO-d$_6$, 400 MHz): δ 9.49 (s, 1H), 8.80 (s, 1H), 8.34 (s, 1H), 7.99-7.98 (d, 1H), 7.59-7.53 (m, 1H), 7.43-7.40 (dd, 1H), 7.27-7.23 (t, 2H), 7.08-7.06 (d, 1H), 4.81-4.80 (d, 1H), 4.40 (s, 2H), 3.60-3.30 (m, 3H), 2.69-2.64 (m, 1H), 1.85-1.84 (m, 1H), 1.76-1.72 (m, 1H), 1.53-1.50 (m, 1H), 1.28-1.23 (m, 1H).

Example 218. Synthesis of 2-(2,6-difluorophenyl)-4-((5-(2,2-dimethyl-5-oxopyrrolidin-1-yl)pyridin-2-yl)amino)-6,7-dihydro-5H-pyrrolo[3,4-b]pyridin-5-one, I-272

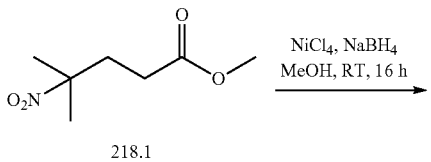

218.1

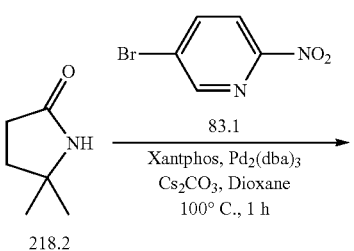

218.2

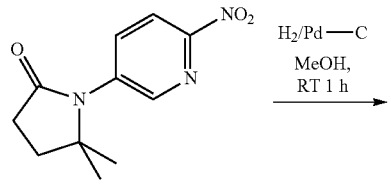

218.3

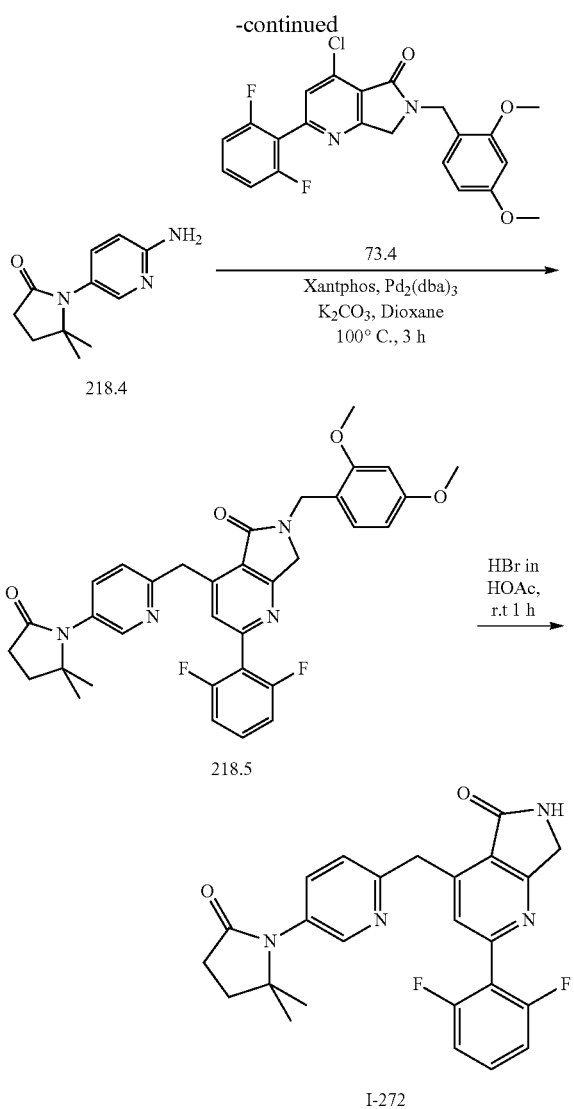

Synthesis of Compound 218.2.

To a solution of nickel chloride (2.291 g, 11.428 mmol, 2.0 eq.) in MeOH (10 mL) was added NaBH$_4$ (0.717 g, 11.428 mmol, 2.0 eq.) and the reaction was stirred at room temperature for 30 minutes. Methyl 4-methyl-4-nitropentanoate (1.0 g, 5.714 mmol, 1.0 eq.) was added dropwise to the above reaction mixture and the reaction was stirred at room temperature for 16 h. After completion of reaction, solvent was removed under reduced pressure and water was added to the reaction mixture. The product was extracted with EtOAc, organic layers were combined, dried over sodium sulphate and concentrated under reduced pressure to obtain crude which was purified by flash chromatography to give 218.2 (0.250 g, 38.70%), MS (ES): m/z 113.16 [M+H]$^+$.

Synthesis of Compound 218.3.

To a solution of 83.1 (0.3 g, 1.477 mmol, 1.0 eq) in 1,4-dioxane (5 mL) was added 218.2 (0.17, 1.48 mmol, 1.0 eq.) and Cs$_2$CO$_3$ (1.445 g, 4.433 mmol, 3.0 eq.). Reaction mixture was degassed for 10 min. under argon atmosphere, then Pd$_2$(dba)$_3$ (0.135 g, 0.147 mmol, 0.1 eq) and Xantphos (0.170 g, 0.295 mmol, 0.2 eq) were added, and again degassed for 5 min. The reaction was stirred at 100° C. for 1 h. After completion of the reaction, mixture was poured into water and product was extracted with EtOAc. Organic layers were combined, dried over sodium sulphate and concentrated under reduced pressure to obtain crude which was purified by column chromatography to furnish 218.3 (0.200 g, 57.53%). MS(ES): m/z 235.24 [M+H]$^+$.

Synthesis of Compound 218.4.

To a solution of 218.3 (0.200 g, 0.850 mmol, 1.0 eq) in methanol (5 mL) was added 10% Pd/C (0.010 g) under nitrogen atmosphere. It was purged with hydrogen gas for 1 h. Reaction mixture was filtered through celite and obtained filtrate was concentrated under reduced pressure and purified by flash chromatography to get pure 218.4 (0.150 g, 85.9%) MS (ES): m/z 205.26 [M+H]$^+$.

Synthesis of Compound 218.5.

To a solution of 73.4 (0.100 g, 0.232 mmol, 1.0 eq) in 1,4-dioxane (3 ml) was added 218.4 (0.047 g, 0.232 mmol, 1.0 eq) and K$_2$CO$_3$ (0.096 g, 0.697 mmol, 3.0 eq). The reaction mixture was degassed for 10 min. under argon atmosphere, then Pd2(dba)3 (0.021 g, 0.023 mmol, 0.1 eq) and Xantphos (0.026 g, 0.046 mmol, 0.2 eq) were added, again degassed for 5 min. The reaction was stirred at 100° C. for 3 h. After completion of the reaction, mixture was poured into water and product was extracted with EtOAc. Organic layers were combined, dried over Na$_2$SO$_4$ and concentrated under reduced pressure to obtain crude which was purified by flash chromatography to furnish 218.5 (0.055 g, 32.39%). MS(ES): m/z 598.65 [M+H]$^+$.

Synthesis of Compound I-272.

Compound 218.5 (0.055 g, 0.091 mmol, 1.0 eq) was dissolved in HBr/HOAc (3 mL) and stirred at room temperature for 1 hour. After completion of the reaction, mixture was poured into water, basified with satd. NaHCO$_3$ and extracted with EtOAC. Organic layers were combined, dried over Na$_2$SO$_4$ and concentrated under reduced pressure to obtain crude which was purified by column chromatography to get pure I-272 (0.020 g, 48.43%). MS(ES): m/z 449.46 [M+H]$^+$; $^1$H NMR (DMSO-d$_6$, 400 MHz): 9.87 (s, 1H), 8.93 (s, 1H), 8.58 (s, 1H), 8.11 (s, 1H), 7.57 (s, 2H), 7.27 (s, 3H), 4.45 (s, 2H), 1.99 (s, 2H), 1.19 (s 6H).

Example 219. Synthesis of 4-(6-((2-(2,6-difluorophenyl)-5-oxo-6,7-dihydro-5H-pyrrolo[3,4-b]pyridin-4-yl)amino)pyridin-3-yl)-2,2-dimethylmorpholin-3-one, I-273

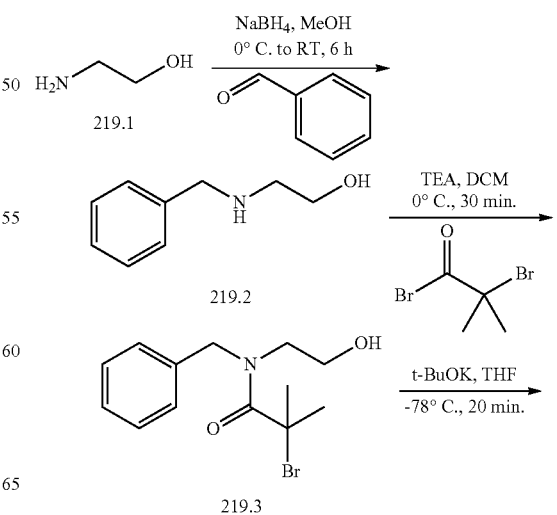

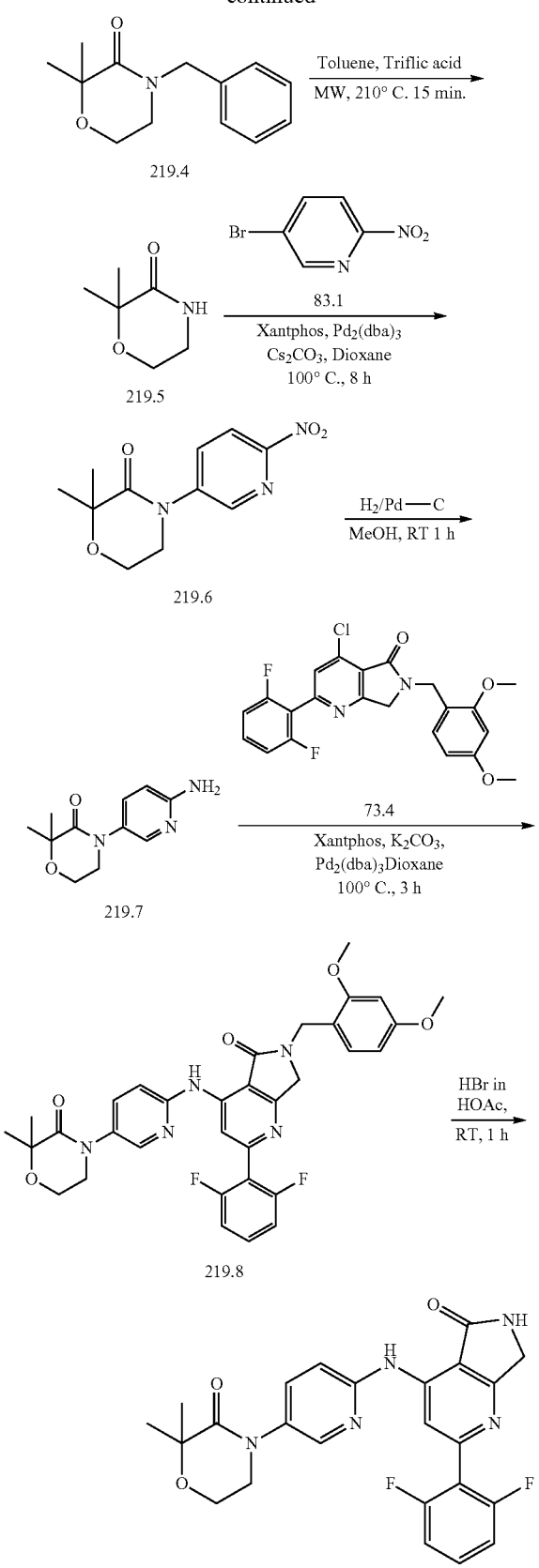

Synthesis of Compound 219.2.

To a solution of 219.1 (25.0 g, 409 mmol, 1.0 eq) in MeOH (250 mL) was added benzaldehyde (43.43 g, 409 mmol, 1.0 eq) and NaBH$_4$ (7.77 g, 204 mmol, 0.5 eq) at 0° C. Reaction mixture was stirred at room temperature for 6 h. After completion of the reaction, solvent was removed under reduced pressure, mixture was poured into water extracted with EtOAc. Organic layers were combined, dried over sodium sulphate and concentrated under reduced pressure to obtain crude which was purified by column chromatography to furnish 219.2 (49.0 g, 79.2%). MS (ES): m/z 151.21 [M+H]$^+$.

Synthesis of Compound 219.3.

To a solution of 219.2 (49.0 g, 324 mmol, 1.0 eq) in dichloromethane (100 mL) was added Et$_3$N (49.1 g, 486 mmol, 1.5 eq.) at 0° C. The reaction was allowed to stir at 0° C. for 15 minutes. 2-bromo-2-methylpropanoyl bromide (74.50 g, 324 mmol, 1.0 eq) was added and the reaction mixture was allowed to stir at 0° C. for 20 minutes. After completion of reaction, reaction mixture was poured in water and product was extracted with CH$_2$Cl$_2$. Organic layer was dried over sodium sulphate and concentrated under reduced pressure to obtain crude which was purified by column chromatography to get pure 219.3 (9.0 g, 9.25%). MS (ES): m/z 300.20 [M+H]$^+$.

Synthesis of Compound 219.4.

To a solution of 219.3 (4.0 g, 13.33 mmol, 1.0 eq) in THF (90 mL) was added potassium tertiary butoxide (1.492 g, 13.33 mmol, 1.0 eq) at −78° C. The reaction was allowed to stir at −78° C. for 20 minutes. After completion of the reaction, mixture was poured in water at −78° C. and product was extracted with EtOAc. Organic layers were combined, dried over Na$_2$SO$_4$ and concentrated under reduced pressure to obtain crude which was purified by preparative HPLC to furnish 219.4 (0.810 g, 27.72%). MS(ES): m/z 219.28 [M+H]$^+$.

Synthesis of Compound 219.5.

To a solution of 219.4 (0.450 g, 2.052 mmol, 1.0 eq) in toluene (5 mL) was added trifluoromethanesulfonic acid (1.231 g, 8.020 mmol, 4.0 eq) and the reaction mixture was heated in microwave at 210° C. for 15 minutes. After completion of reaction, the reaction mixture was diluted with MeOH and polymer supported ammonium carbonate was added till neutral pH. Further the reaction mixture was diluted with MeOH/CH$_2$Cl$_2$. Organic layer was decanted and evaporated under reduced pressure to give crude product, which was further purified by combiflash chromatography to get pure 219.5 (0.172 g, 64.89%). MS (ES): m/z 129.16 [M+H]$^+$.

Synthesis of Compound 219.6.

To a solution of 5-bromo-2-nitropyridine (0.200 g, 9.900 mmol, 1.0 eq) in 1,4-dioxane (4 mL) was added 219.5 (0.127 g, 9.990 mmol, 1.0 eq.) and cesium carbonate (0.643 g, 1.980 mmol, 2.0 eq). The reaction mixture was degassed for 10 min. under argon atmosphere, then Pd$_2$(dba)$_3$ (0.090 g, 0.099 mmol, 0.1 eq) and Xantphos (0.114 g, 0.198 mmol, 0.2 eq) were added, again degassed for 5 minutes. The reaction was then heated at 100° C. for 8 h. After completion of reaction, mixture was poured into water and product was extracted with EtOAc. Organic layers were combined, dried over sodium sulphate and concentrated under reduced pressure to obtain crude which was purified by column chromatography to get pure 219.6 (0.190 g, 76.76%). MS(ES): m/z 251.24 [M+H]$^+$.

Synthesis of Compound 219.7.

To a solution of 219.6 (0.190 g, 0.756 mmol, 1.0 eq) in methanol (5 mL) was added to 10% Pd/C (0.010 g, suspended in methanol) under nitrogen atmosphere. It was purged with hydrogen for 1 h. Reaction mixture was filtered through celite and obtained filtrate was concentrated under reduced pressure and purified by flash chromatography to furnish 219.7 (0.140 g, 83.67%) MS (ES): m/z 221.26 [M+H]⁺.

Synthesis of Compound 219.8.

To a solution of 73.4 (0.100 g, 0.232 mmol, 1.0 eq) in 1,4-dioxane (3 mL) was added 219.7 (0.051 g, 0.232 mmol, 1.1 eq) and potassium carbonate (0.064 g, 0.465 mmol, 2.0 eq). The reaction mixture was degassed for 10 minutes. under argon atmosphere, then Pd2(dba)3 (0.021 g, 0.023 mmol, 0.1 eq) and Xantphos (0.026 g, 0.046 mmol, 0.2 eq) were added, again degassed for 5 minutes. The reaction was then heated at 100° C. for 3 h. After completion of reaction, mixture was poured in water and product was extracted with ethyl acetate. Organic layers were combined, dried over sodium sulphate and concentrated under reduced pressure to obtain crude which was purified by column chromatography to get pure 219.8 (0.109 g, 76.28%). MS(ES): m/z 615.64 [M+H]⁺.

Synthesis of Compound I-273.

The compound 219.8 (0.109 g, 0.177 mmol, 1.0 eq) was dissolved in HBr/HOAc (3 ml) and stirred at room temperature for 1 h. After completion of reaction, mixture was poured in water, basified with saturated bicarbonate solution and product was extracted with EtOAc. Organic layers were combined, dried over sodium sulphate and concentrated under reduced pressure to obtain crude which was purified by column chromatography to get pure I-273 (0.051 g, 61.9%). MS(ES): m/z 465.46 [M+H]⁺; ¹H NMR (DMSO-d6, 400 MHz): 9.81 (s, 1H), 8.93 (s, 1H), 8.56 (s, 1H), 8.35 (d, 1H), 7.81-7.78 (dd, 1H), 7.60-7.56 (m, 1H), 7.29-7.23 (m, 3H), 4.45 (s, 2H), 3.96-3.94 (t, 2H), 3.75-3.73 (t, 2H), 1.41 (s, 6H).

Example 220. Synthesis of 4-((5-(tert-butyl(methyl)amino)pyridin-2-yl)amino)-2-(2,6-difluorophenyl)-6,7-dihydro-5H-pyrrolo[3,4-b]pyridin-5-one, I-274

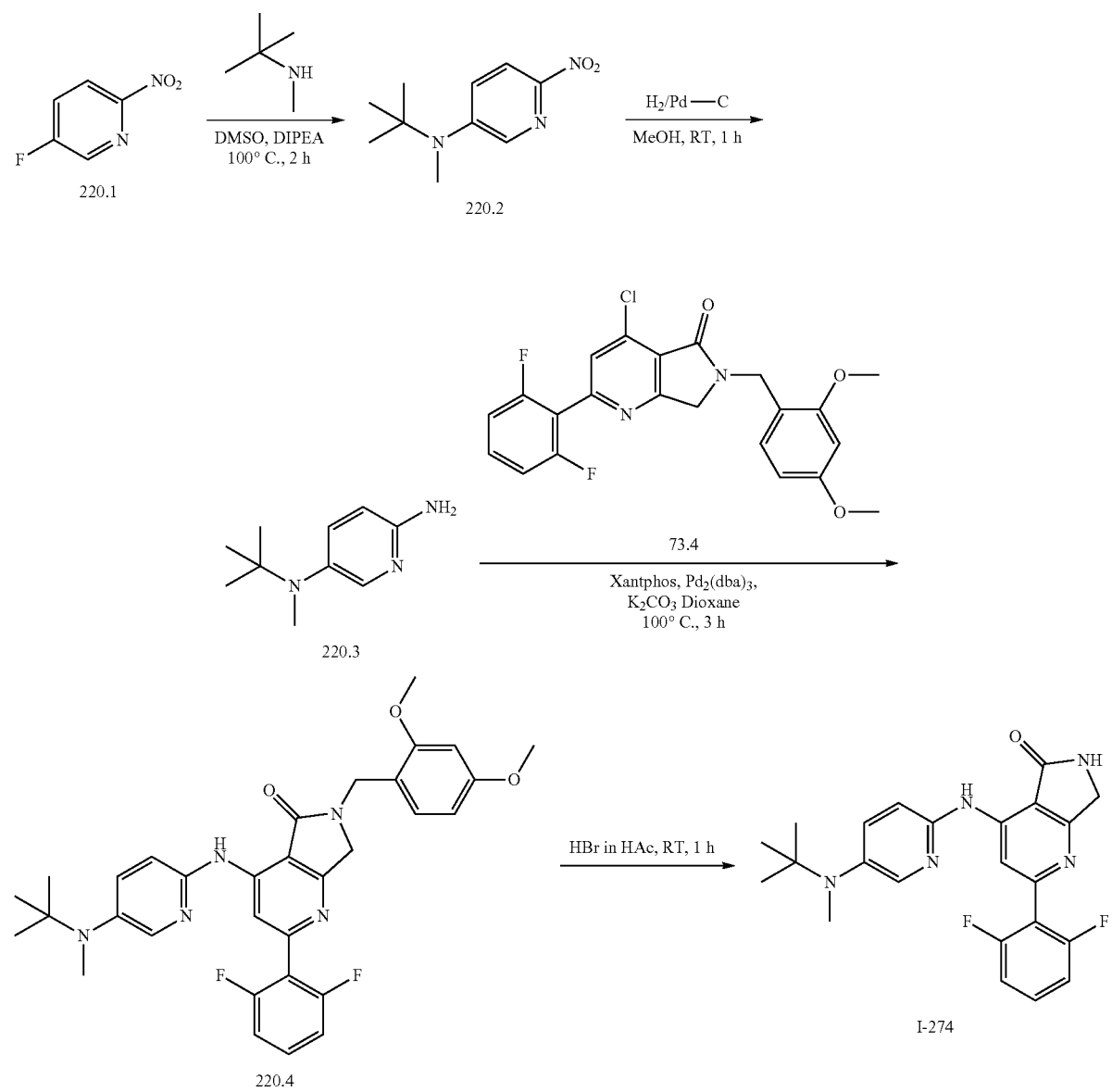

Synthesis of Compound 220.2.

To a solution of 220.1 (0.375 g, 2.64 mmol, 1.0 eq) in DMSO (5 mL) was added N,2-dimethylpropan-2-amine (0.23, 2.64 mmol, 1.0 eq.) and DIPEA (3.413 g, 26.108 mmol, 10.0 eq.). The reaction was then heated at 100° C. for 2 h. After completion of reaction, mixture was poured in water and product was extracted with EtOAC. Organic layers were combined, dried over sodium sulphate and concentrated under reduced pressure to obtain crude which was purified by column chromatography to get pure 220.2 (0.080 g, 14.49%). MS(ES): m/z 209.25 [M+H]$^+$.

Synthesis of Compound 220.2.

To a solution of 220.1 (0.080 g, 0.382 mmol, 1.0 eq) in methanol (5 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to get pure 220.2 (0.060 g, 87.54%) MS (ES): m/z 179.27 [M+H]$^+$.

Synthesis of Compound 220.3.

To a solution of 73.4 (0.100 g, 0.232 mmol, 1.0 eq) in 1,4-dioxane (3 mL) was added 220.2 (0.045 g, 0.255 mmol, 1.1 eq) and K$_2$CO$_3$ (0.080 g, 0.580 mmol, 2.5 eq). The reaction mixture was degassed for 10 min. under argon atmosphere, then Pd$_2$(dba)$_3$ (0.021 g, 0.023 mmol, 0.1 eq) and Xantphos (0.026 g, 0.046 mmol, 0.2 eq) were added, and again degassed for 5 min. The reaction was heated at 100° C. for 3 h. After completion of reaction, mixture was poured in water and product was extracted with ethyl acetate. Organic layers were combined, dried over sodium sulphate and concentrated under reduced pressure to obtain crude which was purified by column chromatography to get pure 220.3 (0.070 g, 52.57%). MS(ES): m/z 573.64 [M+H]$^+$.

Synthesis of Compound I-274.

Compound 120.3 (0.070 g, 0.122 mmol, 1.0 eq) was dissolved in HBr/HOAc (3 ml) and stirred at room temperature for 1 h. After completion of reaction, mixture was poured into water, basified with saturated bicarbonate solution and product was extracted with ethyl acetate. Organic layers were combined, dried over Na$_2$SO$_4$ and concentrated under reduced pressure to obtain crude which was purified by combi flash to furnish I-274 (0.022 g, 42.6%). MS(ES): m/z 423.47 [M+H]$^+$; $^1$H NMR (DMSO-d$_6$, 400 MHz): 9.69 (s, 1H), 8.87 (s, 1H), 8.51 (s, 1H), 8.10 (d, 1H), 7.60-7.55 (m, 2H), 7.28-7.24 (t, 3H), 7.10-7.08 (d, 1H), 4.43 (s, 2H), 2.66 (s, 3H), 1.06 (s, 9H).

Example 221. Synthesis of 2-(2,6-difluorophenyl)-4-((4-(4-hydroxy-4-methylpiperidine-1-carbonyl)phenyl)amino)-6,7-dihydro-5H-pyrrolo[3,4-b]pyridin-5-one, I-275

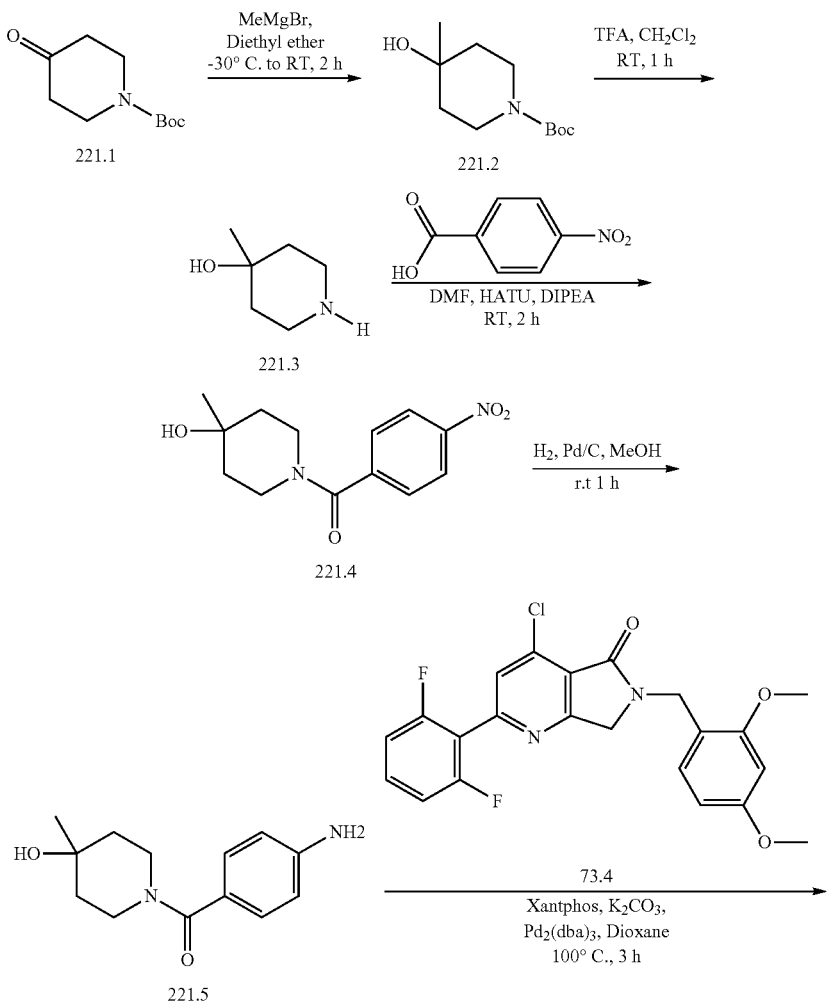

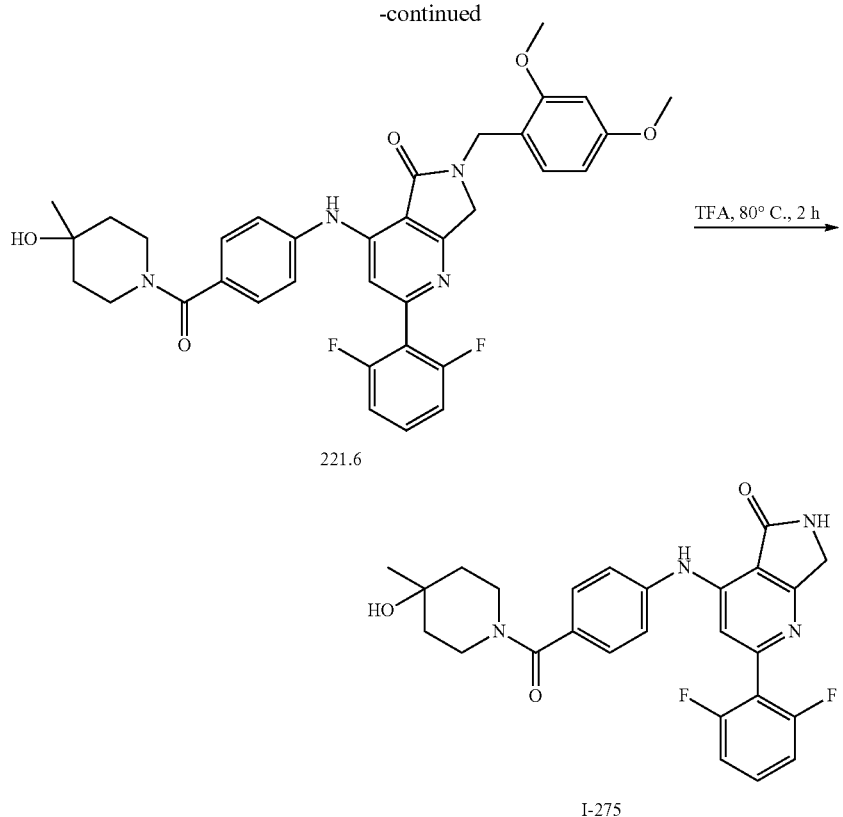

Synthesis of Compound 221.2.

To a solution of tert-butyl 221.1 (2.0 g, 10.03 mmol, 1.0 eq) in Et₂O (20 ml) was added 1M MeMgBr in Et₂O (1.196 g, 10.03 mmol, 1.0 eq.) at −20° C. under argon atmosphere. The reaction mixture was allowed to stir at room temperature for 2 hrs. After completion of reaction, mixture was poured in to satd. NH₄Cl solution and product was extracted with EtOAc. Organic layers were combined, dried over sodium sulphate and concentrated under reduced pressure to obtain crude which was purified by column chromatography to get pure 221.2 (1.3 g, 60.2%). MS(ES): m/z 215.29 [M+H]⁺.

Synthesis of Compound 221.3.

To a solution of 221.2 (1.3 g, 6.04 mmol, 1.0 eq) in CH₂Cl₂ (10 mL) was added trifluoroacetic acid (5 mL). The reaction was allowed to stir at room temperature for 1 h. After completion of reaction, solvent was evaporated under reduced pressure to obtain pure TFA salt of 221.3 (0.650 g, 93.46%). MS(ES): m/z 115.18 [M+H]⁺.

Synthesis of Compound 221.4.

To a solution of p-nitro benzoic acid (0.500 g, 3.62 mmol, 1.0 eq) in DMF (10 mL) was added HATU (2.06 g, 5.43 mmol, 1.5 eq.). The reaction was allowed to stir at room temperature for 15 minutes. Further 4-methylpiperidin-4-ol (0.500 g, 4.34 mmol, 1.2 eq.) and DIPEA (1.402 g, 10.86 mmol, 3.0 eq.) were added to the reaction mixture at room temperature and the reaction was allowed to stir for 2 h. After completion of the reaction, reaction mixture was poured in water and product was extracted with EtOAc. Organic layer was combined, dried over sodium sulphate and concentrated under reduced pressure to obtain crude which was purified by flash chromatography to furnish 221.4 (0.270 g, 34.15%). MS (ES): m/z 264.28 [M+H]⁺.

Synthesis of Compound 221.5.

To a suspension of 10% Pd/C (0.020 g) in methanol (5 mL) was added 221.4 (0.270 g, 1.021 mmol, 1.0 eq) in MeOH (5 ml) under nitrogen atmosphere. Hydrogen gas was purged for 1 h. Reaction mixture was filtered through celite and washed with methanol, obtained filtrate was concentrated under reduced pressure and purified by flash chromatography to get pure 221.5 (0.150 g, 62.66%) MS (ES): m/z 234.30 [M+H]⁺.

Synthesis of Compound 221.6.

To a solution of 73.4 (0.150 g, 0.348 mmol, 1.0 eq) in 1,4-dioxane (7 ml) was added 221.5 (0.098 g, 0.418 mmol, 1.2 eq) and K₂CO₃ (0.144 g, 1.046 mmol, 3.0 eq). The reaction mixture was degassed for 10 min. under argon atmosphere, then Pd2(dba)3 (0.031 g, 0.034 mmol, 0.1 eq) and Xantphos (0.040 g, 0.069 mmol, 0.2 eq) were added, again degassed for 5 min. Reaction was heated at 100° C. for 4 hrs. After completion of the reaction, mixture was poured in water and product was extracted with EtOAc. Organic layers were combined, dried over sodium sulphate and concentrated under reduced pressure to obtain crude which was purified by column chromatography to get pure 221.6 (0.120 g, 54.82%). MS(ES): m/z 628.68 [M+H]⁺.

Synthesis of Compound I-275.

The compound 221.6 (0.120 g, 0.190 mmol, 1.0 eq) was dissolved in TFA (3 mL) and heated at 80° C. for 2 hrs. After completion of the reaction, trifluoro acetic acid was evaporated under reduced pressure, reaction mixture was poured into water, basified with saturated bicarbonate solution and extracted with EtOAc. Organic layers were combined, dried over Na₂SO₄ and concentrated under reduced pressure to obtain crude which was purified by column chromatography to get pure I-275 (0.010 g, 10.95%). MS(ES): m/z 478.50

[M+H]+; 1H NMR (DMSO-d6, 400 MHz): 9.15 (s, 1H), 8.77 (s, 1H), 7.54-7.52 (m, 2H), 7.41 (s, 4H), 7.24-7.19 (m, 3H), 4.43-4.41 (d, 3H), 1.48-1.45 (m, 3H), 1.23 (d, 2H), 1.14 (s, 2H).

Example 222. Synthesis of 4-((5-(cyclobutylamino)pyridin-2-yl)amino)-2-(2,6-difluoro-phenyl)-6,7-dihydro-5H-pyrrolo[3,4-b]pyridin-5-one I-276

Synthesis of Compound 222.1.

To a solution of 220.1 (0.275 g, 1.936 mmol, 1.0 eq) in DMSO (5 ml) was added cyclobutyl amine (0.165 g, 2.323 mmol, 1.2 eq.) and DIPEA (2.5 g, 19.4 mmol, 10 eq.). Reaction mixture was heated at 100° C. for 1 h. After completion of reaction, mixture was poured in water, quenched with ammonium chloride solution and product was extracted with EtOAc. Organic layers were combined,

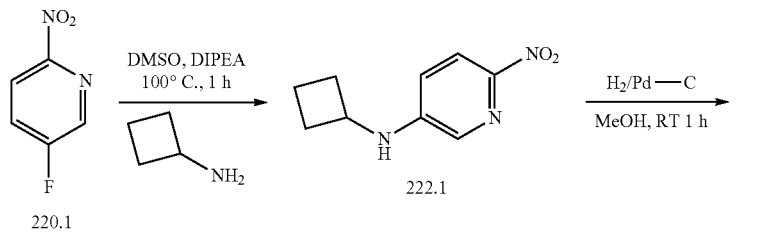

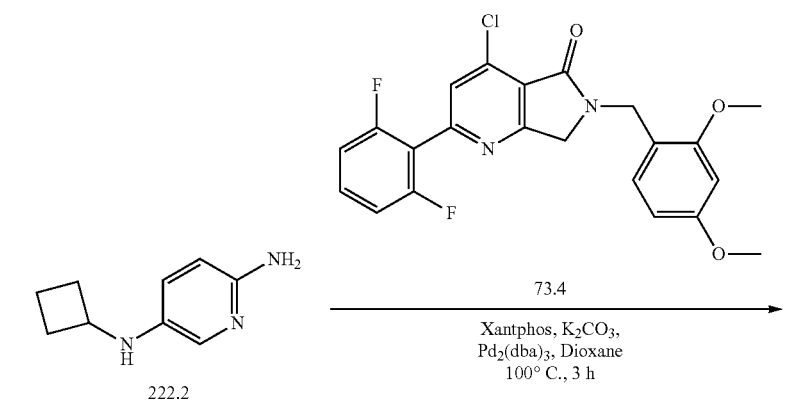

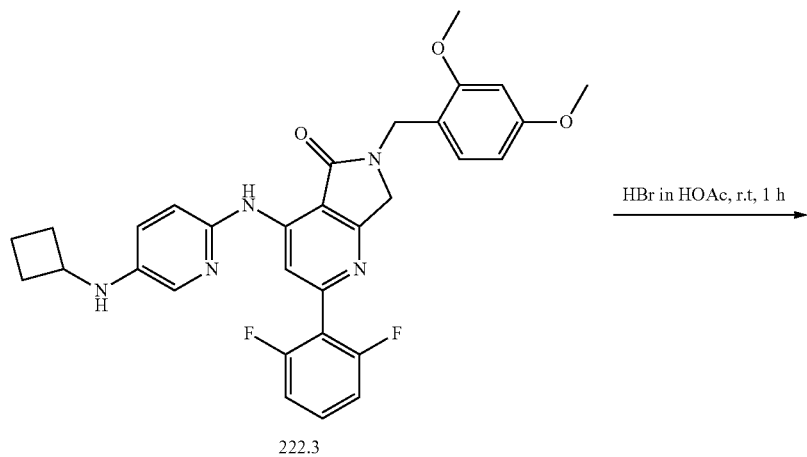

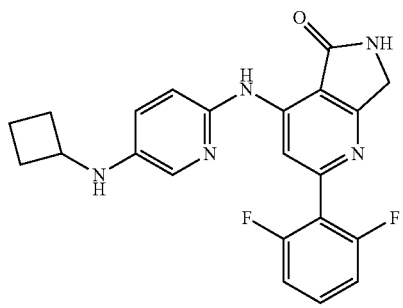

dried over sodium sulphate and concentrated under reduced pressure to obtain crude which was purified by column chromatography to get pure 222.1 (0.3 g, 80.2%). MS(ES): m/z 193.21 [M+H]⁺.

Synthesis of Compound 222.2.

To a solution of 222.1 (0.300 g, 1.552 mmol, 1.0 eq) in methanol (5 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to get pure 222.2 (0.250 g, 98.64%) MS (ES): m/z 163.22 [M+H]⁺.

Synthesis of Compound 222.3.

To a mixture of 73.4 (0.100 g, 0.232 mmol, 1.0 eq) in 1,4-dioxane (3 ml) was added 222.2 (0.041 g, 0.255 mmol, 1.1 eq) and potassium carbonate (0.080 g, 0.579 mmol, 2.5 eq). The reaction mixture was degassed for 10 min. under argon atmosphere, then Pd₂(dba)₃ (0.021 g, 0.023 mmol, 0.1 eq) and Xantphos (0.026 g, 0.046 mmol, 0.2 eq) were added, again degassed for 5 min. The reaction was then heated at 100° C. for 3 h. After completion of reaction, mixture was poured into water and product was extracted with EtOAc. Organic layers was combined, dried over sodium sulphate and concentrated under reduced pressure to obtain crude which was purified by column chromatography to get pure 222.3 (0.095 g, 73.4%). MS(ES): m/z 557.60 [M+H]⁺.

Synthesis of compound I-276 The compound 222.3 (0.095 g, 0.170 mmol, 1.0 eq) was dissolved in HBr/HOAc (3 ml) and reaction was stirred at room temperature for 2 h. After completion of the reaction, mixture was poured into water, basified with saturated bicarbonate solution and extracted with EtOAc. Organic layers were combined, dried over sodium sulphate and concentrated under reduced pressure to obtain crude which was purified by column chromatography to get pure I-276 (0.038 g, 54.7%). MS(ES): m/z 407.42 [M+H]⁺; ¹H NMR (DMSO-d₆, 400 MHz): 9.35 (s, 1H), 8.76 (s, 1H), 8.18 (s, 1H), 7.61-7.52 (m, 2H), 7.26-7.21 (t, 2H), 7.01-6.96 (m, 2H), 5.95-5.93 (d, 1H), 4.38 (s, 2H), 3.85-3.79 (m, 1H), 2.35-2.30 (m 2H), 1.84-1.64 (m, 4H).

Example 223. Synthesis of N-(6-((2-(2,6-difluorophenyl)-5-oxo-6,7-dihydro-5H-pyrrolo[3,4-b]pyridin-4-yl)amino)pyridin-3-yl)-1,1-difluoromethanesulfonamide, I-277

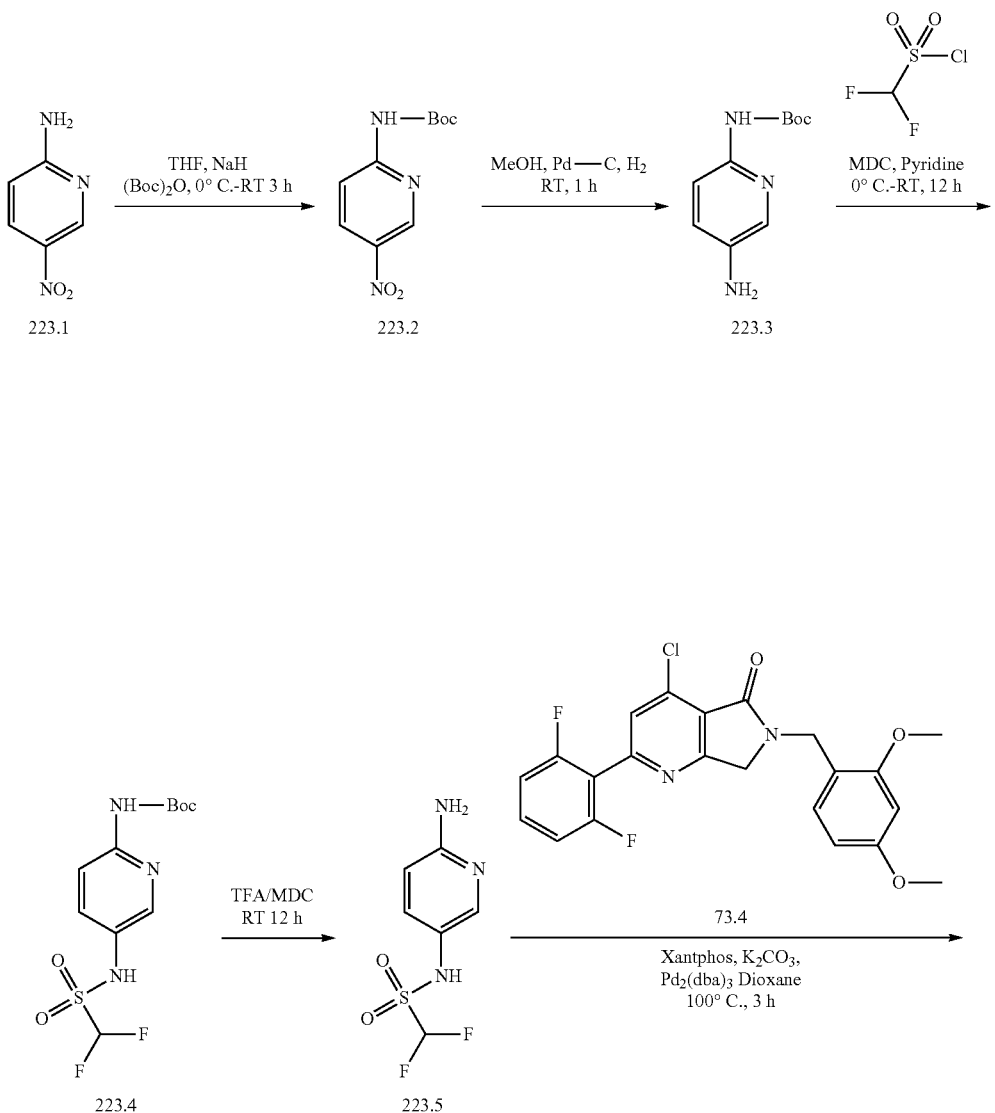

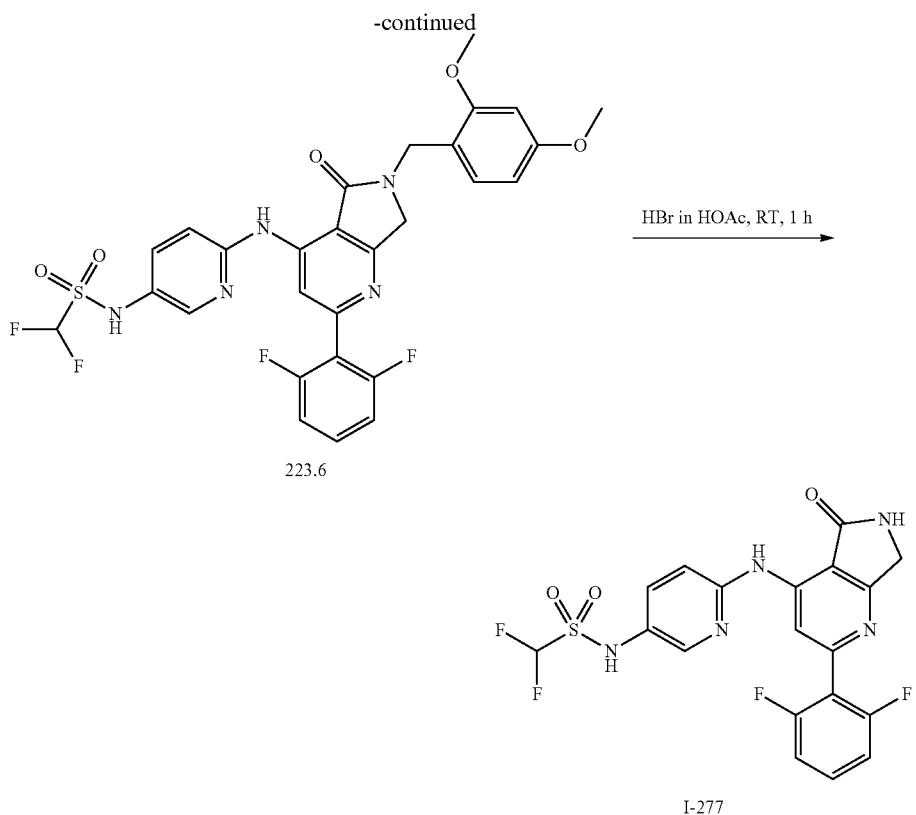

Synthesis of Compound 223.2.

To a solution of NaH (1.15 g, 28.75 mmol, 1.0 eq.) in THF (20 ml) was added 223.1 (4.0 g, 28.75 mmol, 1.0 eq) at 0° C. the reaction mixture was stirred at room temperature for 30 minutes. Boc anhydride (6.26 g, 28.75 mmol, 1.0 eq.) in THF (10 mL) was added to the reaction mixture at room temperature and reaction was allowed to stir for 3 hours. After completion of the reaction, mixture was poured in water and solid product was filtered, dried to get pure 223.2 (4.4 g, 63.9%). MS(ES): m/z 239.23 [M+H]$^+$.

Synthesis of Compound 223.3.

To a suspension of 10% Pd/C (0.010 g) in methanol (5 ml) was added 223.2 (0.500 g, 2.1 mmol, 1.0 eq) in MeOH (5 mL). Suspension was purged with hydrogen gas for 1 h at room temperature. Reaction mixture was filtered through celite washed with methanol and obtained filtrate was concentrated under reduced pressure and purified by flash chromatography to get pure 223.3 (0.28 g, 64.0%) MS (ES): m/z 209.25 [M+H]$^+$.

Synthesis of Compound 223.4.

To a solution of 223.3 (0.180 g, 0.865 mmol, 1.0 eq) in CH$_2$Cl$_2$ (5 mL) was added pyridine (0.2 mL) and the reaction mixture was cooled to 0° C. Difluoromethanesulfonyl chloride (0.207 g, 1.384 mmol, 1.6 eq.) was added drop wise to the reaction mixture and the reaction was stirred at room temperature for 12 hrs. After completion of the reaction, solvent was evaporated under reduced pressure to get crude which was purified via flash chromatography to furnish 223.4 (0.150 g, 53.93%) MS (ES): m/z 323.31 [M+H]$^+$.

Synthesis of Compound 223.5.

To a solution of 223.4 (0.150 g, 0.463 mmol, 1.0 eq) in CH$_2$Cl$_2$ was added trifluoroacetic acid (2 mL). The reaction mixture was stirred at room temperature for 12 hrs. After completion of reaction, solvent was evaporated under reduced pressure to get pure 223.5 (0.050 g, 48.29%) MS (ES): m/z 223.30 [M+H]$^+$.

Synthesis of Compound 223.6.

To a solution of 73.4 (0.200 g, 0.465 mmol, 1.0 eq) in 1,4-dioxane (3 ml) was added 223.5 (0.102 g, 0.4695 mmol, 1.0 eq) and potassium carbonate (0.192 g, 1.395 mmol, 3.0 eq). The reaction mixture was degassed for 10 min. under argon atmosphere, then Pd$_2$(dba)$_3$ (0.042 g, 0.046 mmol, 0.1 eq) and Xantphos (0.053 g, 0.093 mmol, 0.2 eq) were added, and again degassed for 5 min. The reaction was then heated at 100° C. for 3 hours. After completion of the reaction, reaction mixture was poured in water and product was extracted with ethyl acetate. Organic layers were combined, dried over sodium sulphate and concentrated under reduced pressure to obtain crude which was purified by column chromatography to get pure 223.6 (0.078 g, 27.21%). MS(ES): m/z 617.58 [M+H].

Synthesis of Compound I-277.

The compound 223.6 (0.078 g, 0.126 mmol, 1.0 eq) was dissolved in HBr/HOAc (3 mL) and reaction was stirred at room temperature for 1 h. After completion of the reaction, mixture was poured into ice water and basified with saturated sodium bicarbonate solution and extracted with EtOAc. Organic layers were combined, dried over Na$_2$SO$_4$ and concentrated under reduced pressure to obtain crude which was purified by flash chromatography to furnish I-277 (0.023 g, 38.96%). MS(ES): m/z 467.40 [M+H]$^+$; $^1$H NMR (DMSO-d$_6$, 400 MHz): 11.06 (s, 1H), 9.80 (s, 1H), 8.90 (s, 1H), 8.50 (s, H), 8.19-8.18 (d, 1H), 7.63-7.54 (m, 2H), 7.28-7.22 (m, 3H), 7.16-7.03 (s, 1H) 4.44 (s, 2H).

Example 224. Synthesis of 4-((5-(tert-butylamino)pyridin-2-yl)amino)-2-(2,6-difluoro-phenyl)-6,7-dihydro-5H-pyrrolo[3,4-b]pyridin-5-one, I-278

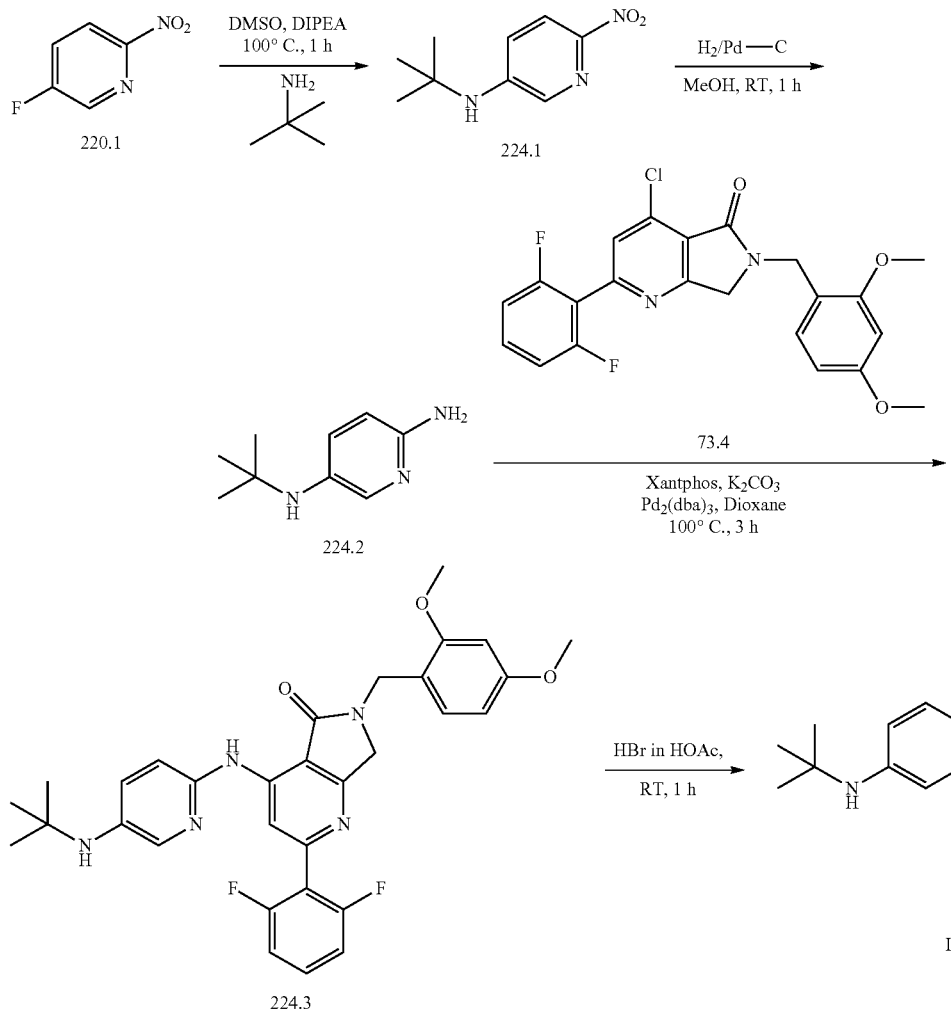

Synthesis of Compound 224.1.

To a solution of 220.1 (0.300 g, 2.11 mmol, 1.0 eq) in DMSO (5 ml) was added 2-methylpropan-2-amine (0.185 g, 2.533 mmol, 1.2 eq.) and DIPEA (2.72 g, 21.11 mmol, 10.0 eq.). The reaction mixture was heated at 100° C. for 1 h. After completion of reaction, mixture was poured in water, quenched with NH$_4$Cl solution and extracted with EtOAc. Organic layers were combined, dried over sodium sulphate and concentrated under reduced pressure to obtain crude which was purified by chromatography to get pure 224.1 (0.225 g, 54.59%). MS(ES): m/z 195.22 [M+H]$^+$.

Synthesis of Compound 224.2.

To a solution of 224.1 (0.225 g, 1.152 mmol, 1.0 eq) in methanol (5 mL) was added 10% Pd/C (0.010 g) under nitrogen atmosphere. It was purged with hydrogen for 1 h. Reaction mixture was filtered through celite and obtained filtrate was concentrated under reduced pressure and purified by flash chromatography to furnish 224.2 (0.190 g, 99.77%) MS (ES): m/z 165.24 [M+H]$^+$.

Synthesis of Compound 224.3.

To a mixture of 74.3 (0.100 g, 0.232 mmol, 1.0 eq) in 1,4-dioxane (3 mL) was added 224.2 (0.042 g, 0.255 mmol, 1.1 eq) and potassium carbonate (0.080 g, 0.579 mmol, 2.5 eq). The reaction mixture was degassed for 10 min. under argon atmosphere, then Pd$_2$(dba)$_3$ (0.021 g, 0.023 mmol, 0.1 eq) and Xantphos (0.026 g, 0.046 mmol, 0.2 eq) were added, and again degassed for 5 min. The reaction was then heated at 100° C. for 3 h. After completion of the reaction, mixture was poured into water and product was extracted with ethyl acetate. Organic layers were combined, dried over sodium sulphate and concentrated under reduced pressure to obtain crude which was purified by column chromatography to furnish 224.3 (0.070 g, 53.89%). MS(ES): m/z 559.62 [M+H]$^+$.

Synthesis of Compound I-278.

The compound 224.3 (0.070 g, 0.125 mmol, 1.0 eq) was dissolved in HBr/HOAc (3 ml) and reaction was stirred at room temperature for 1 h. After completion of reaction, mixture was poured in water, basified with saturated bicarbonate solution and product was extracted with EtOAc. Organic layers were combined, dried over sodium sulphate and concentrated under reduced pressure to obtain crude which was purified by flash column chromatography to furnish I-278 (0.025 g, 48.8%). MS(ES): m/z 409.44 [M+H]$^+$; $^1$H NMR (DMSO-d$_6$, 400 MHz): 9.39 (s, 1H), 8.77

(s, 1H), 8.21 (s, 1H), 7.84 (d, 1H), 7.58-7.54 (m, 1H), 7.26-7.20 (m, 3H), 6.98-6.96 (d, 1H), 5.09 (s, 1H), 4.39 (s, 2H), 1.25 (s, 9H).

Example 225. Synthesis of 4-((5-(3-oxa-6-azabicyclo[3.1.1]heptan-6-yl)pyridin-2-yl)amino)-2-(2,6-difluorophenyl)-6,7-dihydro-5H-pyrrolo[3,4-b]pyridin-5-one, I-279

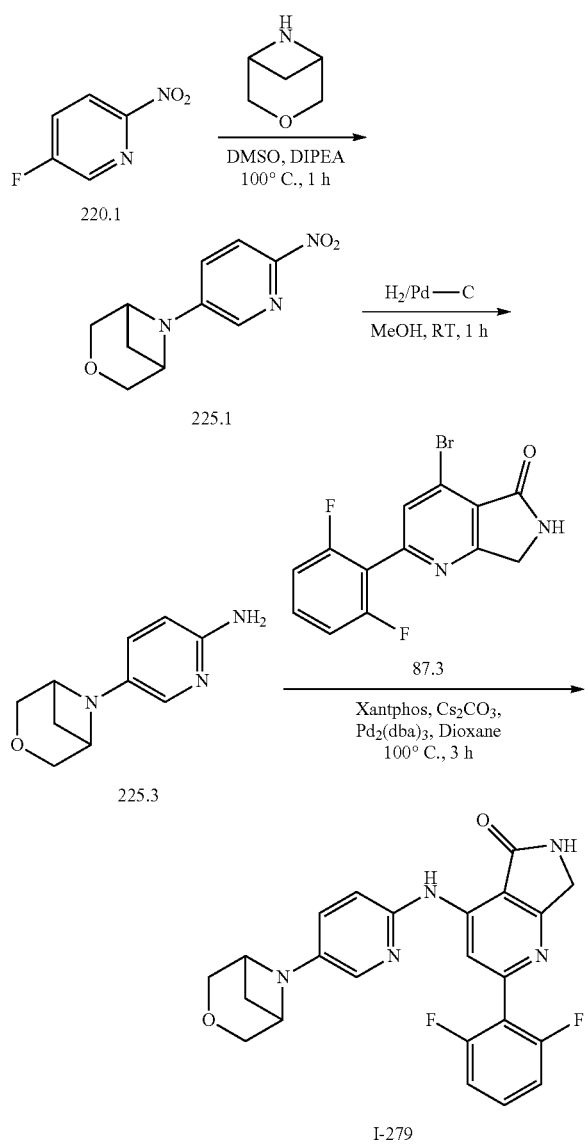

Synthesis of Compound 225.1.

To a solution of 220.1 (0.150 g, 1.056 mmol, 1.0 eq) in DMSO (3 mL) was added 3-oxa-6-azabicyclo[3.1.1]heptane (0.104 g, 1.056 mmol, 1.0 eq) and DIPEA (1.36 g, 10.56 mmol, 10.0 eq). Reaction mixture was heated at 100° C. for 1 h. After completion of reaction, mixture was quenched with NH₄Cl solution and product was extracted with EtOAc. Organic layers were combined, dried over sodium sulphate and concentrated under reduced pressure to obtain crude which was purified by column chromatography to get pure 225.1 (0.15 g, 65.1%). MS (ES): m/z 221.22 [M+H]$^+$.

Synthesis of Compound 225.2.

A solution of 225.1 (0.152 g, 0.687 mmol, 1.0 eq) in methanol (5 mL) was added to 10% Pd/C (0.010 g, suspended in methanol) under nitrogen atmosphere. It was purged with hydrogen for 1 h. Reaction mixture was filtered through celite and obtained filtrate was concentrated under reduced pressure and purified by flash chromatography to furnish 225.2 (0.110 g, 84.83%). MS (ES): m/z 191.23 [M+H]$^+$.

Synthesis of Compound I-279.

To a solution of 87.3 (0.225 g, 0.692 mmol, 1.0 eq) in 1,4-dioxane (3 mL) was added 225.2 (0.132 g, 0.692 mmol, 1.0 eq) and cesium carbonate (0.674 g, 2.076 mmol, 3.0 eq). The reaction mixture was degassed for 10 minutes under argon atmosphere, then Pd$_2$(dba)$_3$ (0.063 g, 0.069 mmol, 0.1 eq) and X-phos precatalyst (0.065 g, 0.138 mmol, 0.2 eq) were added, and again degassed for 5 minutes. The reaction was then heated at 100° C. for 3 h. After completion of reaction, mixture was poured in water and product was extracted with ethyl acetate. Organic layers were combined, dried over Na$_2$SO$_4$ and concentrated under reduced pressure to obtain crude which was purified by column chromatography to get pure I-279 (0.012 g, 3.9%). MS(ES): m/z 435.43 [M+H]$^+$; $^1$H NMR (DMSO-d$_6$, 400 MHz): 9.48 (s, 1H), 8.80 (s, 1H), 8.37 (s, 1H), 7.75 (d, 1H), 7.58-7.54 (m, 1H), 7.28-7.23 (t, 2H), 7.13-7.07 (s, 2H), 4.40 (s, 2H), 4.27-4.25 (s, 2H), 4.14-4.12 (s, 2H), 3.63-3.60 (d, 2H), 2.69-2.67 (m, 1H), 1.82-1.80 (d, 1H).

Example 226. Synthesis of 2-(2,6-difluorophenyl)-4-((6-(morpholine-4-carbonyl)pyridin-3-yl)amino)-6,7-dihydro-5H-pyrrolo[3,4-b]pyridin-5-one, I-280

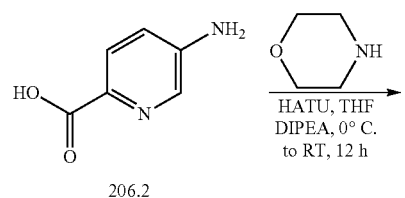

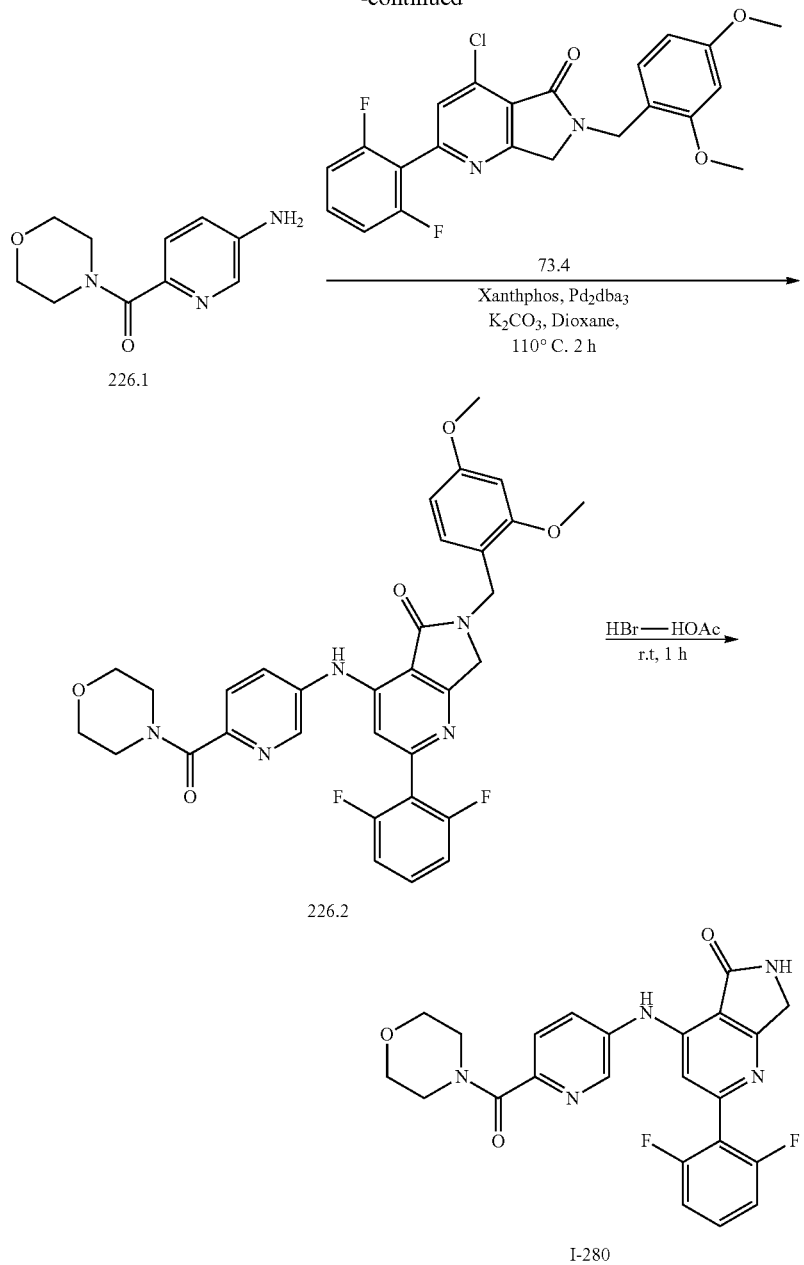

Synthesis of Compound 226.1.

To a solution of 206.2 (1.0 g, 7.246 mmol, 1.0 eq) in THF (12 ml) was added HATU (4.13 g, 10.86 mmol, 1.5 eq) at 0° C. The reaction was stirred at 0° C. for 45 minutes. Morpholine (0.756 g, 8.695 mmol, 1.2 eq.) and DIPEA (2.804 g, 21.73 mmol, 3.0 eq.) were added to the reaction mixture at 0° C. and the reaction was allowed to stir at room temperature for 12 h. After completion of the reaction, mixture was poured into water and product was extracted with EtOAc. Organic layers were combined, washed with brine, dried over sodium sulphate and concentrated under reduced pressure to obtain crude which was purified by column chromatography to get pure 226.1 (0.40 g, 26.7%). MS (ES): m/z 207.23 [M+H]$^+$.

Synthesis of Compound 226.2.

To a solution of 73.4 (0.100 g, 0.232 mmol, 1.0 eq) in 1,4-dioxane (3 ml) was added 226.1 (0.052 g, 0.255 mmol, 1.1 eq) and K$_2$CO$_3$ (0.080 g, 0.581 mmol, 2.5 eq). The reaction mixture was degassed for 10 minutes under argon atmosphere, then Pd$_2$(dba)$_3$ (0.021 g, 0.023 mmol, 0.1 eq) and Xantphos (0.026 g, 0.046 mmol, 0.2 eq) were added, and again degassed for 5 min. The reaction was then heated at 110° C. for 2 h. After completion of the reaction, mixture was poured into water and product was extracted with EtOAc. Organic layers were combined, washed with brine, dried over sodium sulphate and concentrated under reduced pressure to obtain crude which was purified by column chromatography to get pure 226.2 (0.07 g, 50.1%). MS(ES): m/z 601.61 [M+H]$^+$.

Synthesis of Compound I-280.

Compound 226.2 (0.070 g, 0.116 mmol, 1.0 eq) was dissolved in HBr/HOAc (3 ml) and stirred at room temperature for 1 h. After completion of the reaction, mixture was poured in ice-water, basified with saturated bicarbonate solution and extracted with EtOAc. Organic layers were combined, washed with brine solution, dried over $Na_2SO_4$ and concentrated under reduced pressure to obtain crude material. The crude was purified by column chromatography to furnish I-280 (0.044 g, 83.8%). MS(ES): m/z 451.43 [M+H]$^+$; $^1$H NMR (DMSO-d$_6$, 400 MHz): 9.25 (s, 1H), 8.78 (s, 1H), 8.62-8.61 (d, 1H), 7.95-7.92 (dd, 1H), 7.66-7.63 (d, 1H), 7.56-7.50 (m, 1H), 7.23-7.19 (m, 3H), 4.42 (s, 2H), 3.65-3.56 (m, 8H).

Example 227. Synthesis of 3-fluoro-2-(4-((5-morpholinopyridin-2-yl)amino)-5-oxo-6,7-dihydro-5H-pyrrolo[3,4-b]pyridin-2-yl)benzonitrile, I-281

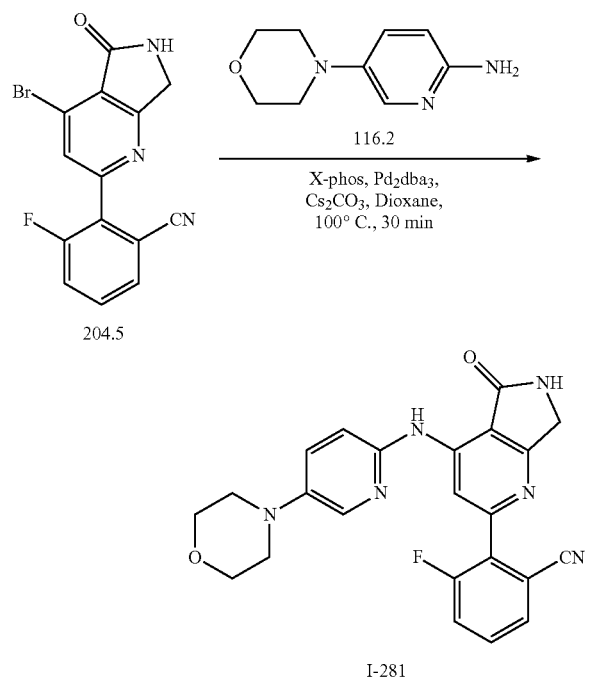

I-281

Synthesis of Compound I-281.

To a mixture of 204.5 (0.065 g, 0.195 mmol, 1.0 eq) in 1,4-dioxane (3 mL) was added 116.2 (0.035 g, 0.195 mmol, 1.0 eq) and $Cs_2CO_3$ (0.127 g, 0.391 mmol, 2.0 eq). The reaction mixture was degassed for 10 minutes under argon atmosphere, then Pd$_2$(dba)$_3$ (0.017 g, 0.019 mmol, 0.1 eq) and X-Phos (0.018 g, 0.039 mmol, 0.2 eq) were added, and again degassed for 5 minutes. The reaction was stirred at 100° C. for 30 minutes. After completion of reaction, mixture was poured in water and product was extracted with EtOAc. Organic layers were combined, washed with brine solution, dried over sodium sulphate and concentrated under reduced pressure to obtain crude material. The crude was purified by flash chromatography to furnish I-281 (0.009 g, 10.7%). MS(ES): m/z 430.44 [M+H]$^+$; $^1$H NMR (DMSO-d$_6$, 400 MHZ): 9.58 (s, 1H), 8.86 (s, 1H), 8.49 (s, 1H), 8.04-8.03 (d, 1H), 7.89-7.87 (dd, 1H), 7.80-7.71 (m, 2H), 7.49-7.46 (dd, 1H), 7.16-7.14 (d, 1H), 4.43 (s, 2H), 3.74-3.72 (t, 4H), 3.11-3.09 (t, 4H).

Example 228. Synthesis of 6-((2-(2-cyano-6-fluorophenyl)-5-oxo-6,7-dihydro-5H-pyrrolo[3,4-b]pyridin-4-yl)amino)-N-ethylnicotinamide, I-282

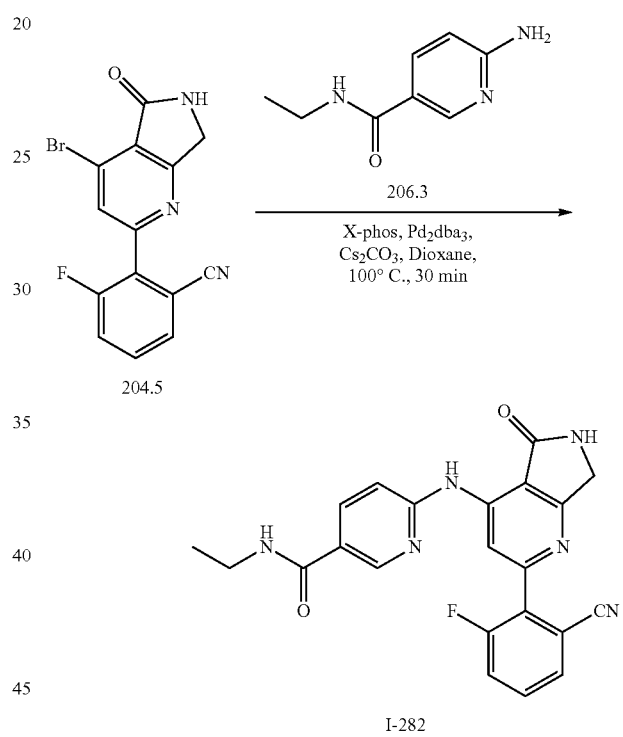

I-282

Synthesis of Compound I-282.

To a mixture of 204.5 (0.065 g, 0.195 mmol, 1.0 eq) in 1,4-dioxane (3 mL) were added 206.3 (0.032 g, 0.195 mmol, 1.0 eq) and $Cs_2CO_3$ (0.127 g, 0.39 mmol, 2.0 eq). The reaction mixture was degassed for 10 minutes under argon atmosphere, then Pd$_2$(dba)$_3$ (0.017 g, 0.019 mmol, 0.1 eq) and X-Phos (0.018 g, 0.039 mmol, 0.2 eq) were added, and again degassed for 5 minutes. The reaction was stirred at 100° C. for 30 minutes. After completion of the reaction, mixture was poured into water and product was extracted with EtOAc. Organic layers were combined, washed with brine, dried over $Na_2SO_4$ and concentrated under reduced pressure to obtain crude which was purified by column and preparative HPLC to furnish I-282 (0.01 g, 12.3%). MS(ES): m/z 416.42 [M+H]$^+$; $^1$NMR (DMSO-d$_6$, 400 MHz): 10.02 (s, 1H), 9.02 (s, 1H), 8.81-8.78 (m, 2H), 8.51-8.49 (t, 1H), 8.18-8.15 (dd, 1H), 7.91-7.89 (d, 1H), 7.83-7.75 (m, 2H), 7.30-7.28 (d, 1H), 4.48 (s, 2H), 3.28-3.25 (q, 2H), 1.14-1.10 (t, 3H).

Example 229. Synthesis of 2-(2,6-difluorophenyl)-4-((4-(4,4-difluoropiperidine-1-carbonyl)phenyl)amino)-6,7-dihydro-5H-pyrrolo[3,4-b]pyridin-5-one, I-283

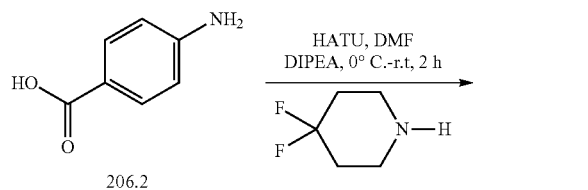

206.2

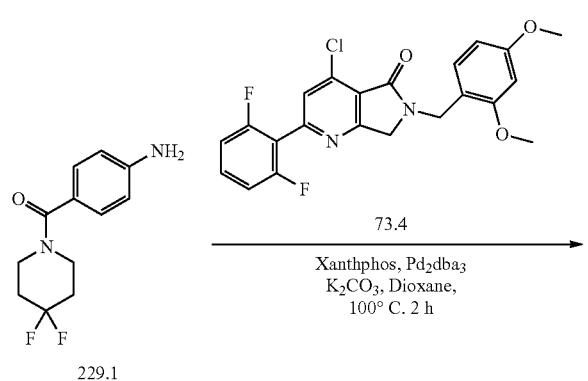

229.1

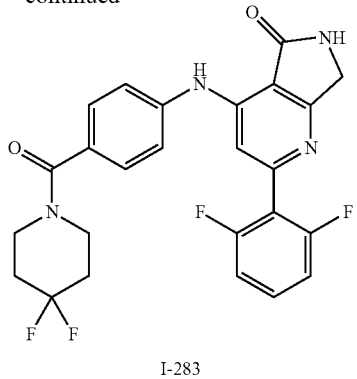

I-283

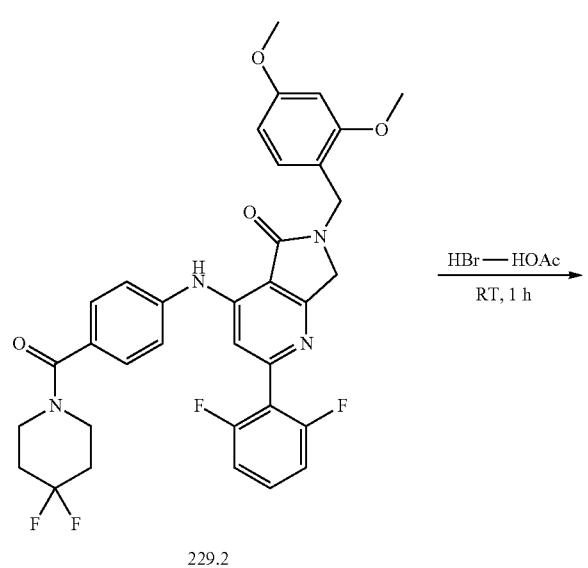

229.2

Synthesis of Compound 229.1.

To a solution of 206.2 (0.1 g, 0.729 mmol, 1.0 eq) in DMF (2 ml) was added HATU (0.33 g, 0.88 mmol, 1.2 eq.) at 0° C. The reaction was allowed to stir at 0° C. for 30 minutes. The reaction was stirred at room temperature for 10 minutes. Further 4,4-difluoropiperidine (0.172 g, 1.094 mmol, 1.5 eq.) and DIPEA (0.188 g, 1.459 mmol, 2.0 eq.) were added to the reaction mixture at 0° C. Reaction was stirred at room temperature for 2 h. After completion of the reaction, mixture was poured into water and product was extracted with EtOAc. Organic layers were combined, washed with brine, dried over $Na_2SO_4$ and concentrated under reduced pressure to obtain crude which was purified by column chromatography to get pure 229.1 (0.13 g, 74.2%). MS (ES): m/z 240.25 [M+H]$^+$.

Synthesis of Compound 229.2.

To a solution of 73.4 (0.100 g, 0.232 mmol, 1.0 eq) in 1,4-dioxane (3 ml) was added 229.1 (0.06 g, 0.255 mmol, 1.1 eq) and potassium carbonate (0.080 g, 0.581 mmol, 2.5 eq). The reaction mixture was degassed for 10 min. under argon atmosphere, then $Pd_2(dba)_3$ (0.021 g, 0.023 mmol, 0.1 eq) and Xantphos (0.026 g, 0.046 mmol, 0.2 eq) were added, again degassed for 5 min. The reaction was stirred at 100° C. for 2 h. After completion of the reaction, mixture was poured into water and extracted with EtOAc. Organic layers were combined, washed with brine, dried over $Na_2SO_4$ and concentrated under reduced pressure to obtain crude which was purified by flash chromatography to furnish 229.2 (0.103, 69.9%). MS(ES): m/z 634.63 [M+H]$^+$.

Synthesis of Compound I-283.

The compound 229.2 (0.103 g, 0.162 mmol, 1.0 eq) was dissolved in HBr/HOAc (3 mL) and stirred at room temperature for 1 h. After completion of the reaction, reaction mixture was poured in ice-water, basified with satd. $NaHCO_3$ and product was extracted with EtOAc. Organic layers were combined, washed with brine solution, dried over sodium sulphate and concentrated under reduced pressure to obtain crude material. The crude was purified by column chromatography to furnish I-283 (0.05 g, 63.6%). MS(ES): m/z 484.45 [M+H]$^+$; $^1$H NMR (DMSO-d$_6$, 400 MHz): 9.17 (s, 1H), 8.76 (s, 1H), 7.56-7.42 (m, 5H), 7.23-7.19 (m, 3H), 4.41 (s, 2H), 3.60 (m, 4H), 2.07-2.00 (m, 4H).

Example 230. Synthesis of 2-(2,6-difluorophenyl)-4-((5-(2,2-dimethyl-6-oxopiperidin-1-yl)pyridin-2-yl)amino)-6,7-dihydro-5H-pyrrolo[3,4-b]pyridin-5-one, I-284
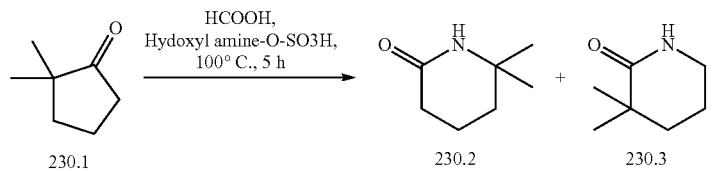
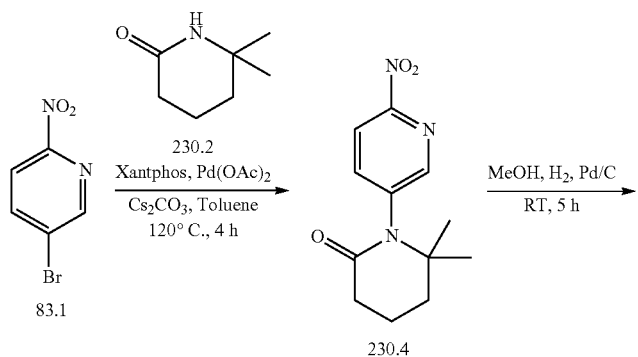
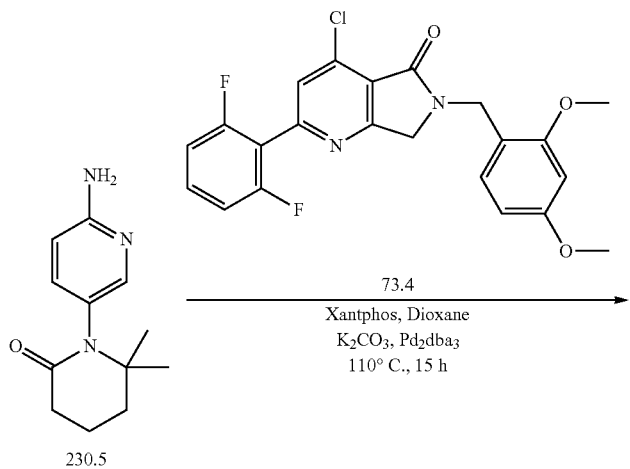
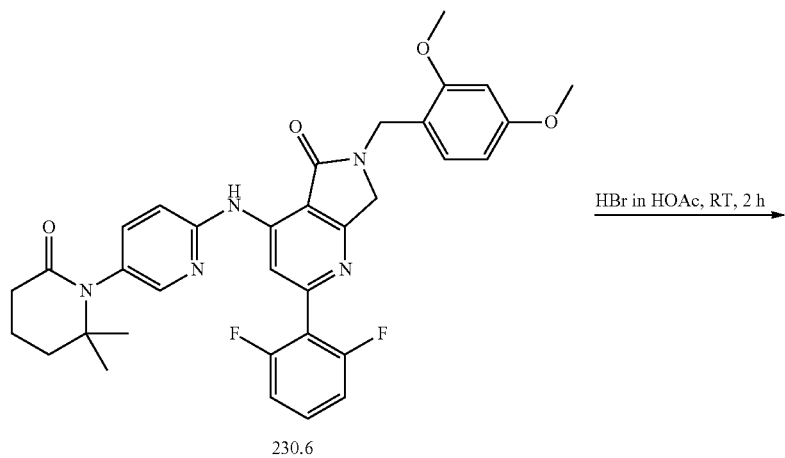

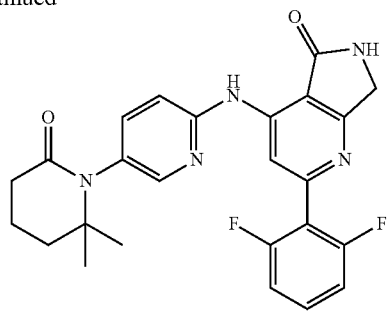

I-284

Synthesis of Compound 230.2.

To a solution of 230.1 (4.0 g, 35.71 mmol, 1.0 eq) in formic acid (30 mL) was added hydroxyl amine-O-sulphonic acid (6.05 g, 53.57 mmol, 1.5 eq) over a period of 10 minutes. The reaction mixture was heated at 100° C. for 5 h. After completion of reaction, mixture was concentrated under reduced pressure at 45° C. to remove excess formic acid and residue was poured in crushed ice, neutralized by 4M NaOH solution and then product was extracted with $CH_2Cl_2$ (100 mL×5). Organic layers were combined, washed with brine solution, dried over sodium sulphate and concentrated under reduced pressure to obtain crude material. Crude was purified by column chromatography to furnish 230.2 (0.65 g, 14.3%). MS(ES): m/z 127.19 [M+H]$^+$.

Synthesis of Compound 230.4.

To a mixture of 83.1 (0.240 g, 1.182 mmol, 1.0 eq) in toluene (5 mL) was added 230.2 (0.165 g, 1.3 mmol, 1.1 eq) and $Cs_2CO_3$ (0.768 g, 2.364 mmol, 2.0 eq). The reaction mixture was degassed for 10 minutes under argon atmosphere, then Pd(OAc)$_2$ (0.026 g, 0.118 mmol, 0.1 eq) and Xantphos (0.136 g, 0.236 mmol, 0.2 eq) were added, and again degassed for 5 min. The reaction was then heated at 120° C. for 4 h. After completion of the reaction, the reaction mixture was poured in water and product was extracted with EtOAc. Organic layers were combined, washed with brine solution, dried over $Na_2SO_4$ and concentrated under reduced pressure to obtain crude which was purified by column chromatography to furnish 230.4 (0.04 g, 13.6%). MS(ES): m/z 249.27 [M+H]$^+$.

Synthesis of Compound 230.5.

To a suspension of Pd/C (0.02 g) in MeOH (3 mL) was added 230.4 (0.04 g, 0.16 mmol, 1.0 eq) in methanol (2 mL). Reaction was purged with $H_2$ gas for 5 h. After completion of the reaction, mixture was filtered through celite, washed with MeOH and filtrate was concentrated under reduced pressure to get pure 230.5 (0.017 g, 48.31%). MS(ES): m/z 219.29 [M+H]$^+$.

Synthesis of Compound 230.6.

To a mixture of 73.4 (0.030 g, 0.069 mmol, 1.0 eq) in 1,4-dioxane (1 mL) was added 230.5 (0.015 g, 0.07 mmol, 1.0 eq) and $K_2CO_3$ (0.019 g, 0.14 mmol, 2.0 eq). The reaction mixture was degassed for 10 minutes under argon atmosphere, then Pd$_2$(dba)3 (0.006 g, 0.006 mmol, 0.1 eq) and Xantphos (0.008 g, 0.013 mmol, 0.2 eq) were added, and again degassed for 5 min. The reaction was then heated at 110° C. for 15 h. After completion of the reaction, mixture was poured into water and product was extracted with EtOAc. Organic layers were combined, washed with brine, dried over sodium sulphate and concentrated under reduced pressure to obtain crude. The crude was purified by column chromatography to get pure 230.6 (0.033 g, 77.23%). MS(ES): m/z 613.67 [M+H]$^+$.

Synthesis of Compound I-284.

Compound 230.6 (0.033 g, 0.053 mmol, 1.0 eq) was dissolved in HBr/HOAc (2 mL) and reaction was stirred at room temperature for 2 h. After completion of the reaction, mixture was poured into water, basified with satd. NaHCO$_3$ and product was extracted with EtOAc. Organic layers were combined, dried over sodium sulphate and concentrated under reduced pressure to obtain crude which was purified by column chromatography to get pure I-284 (0.012 g, 48.2%). MS(ES): m/z 463.49 [M+H]$^+$; $^1$H NMR (DMSO-d$_6$, 400 MHz): 9.84 (s, 1H), 8.92 (s, 1H), 8.57 (s, 1H), 8.04-8.03 (d, 1H), 7.60-7.56 (m, 1H), 7.52-7.49 (dd, 1H), 7.28-7.21 (m, 3H), 4.45 (s, 2H), 2.37 (s, 2H), 1.84 (d, 4H), 1.15 (s, 6H).

Example 231. Synthesis of 2-(2,6-difluorophenyl)-4-((4-((3R,5R)-3,5-dimethylmorpholine-4-carbonyl)phenyl)amino)-6,7-dihydro-5H-pyrrolo[3,4-b]pyridin-5-one, I-285

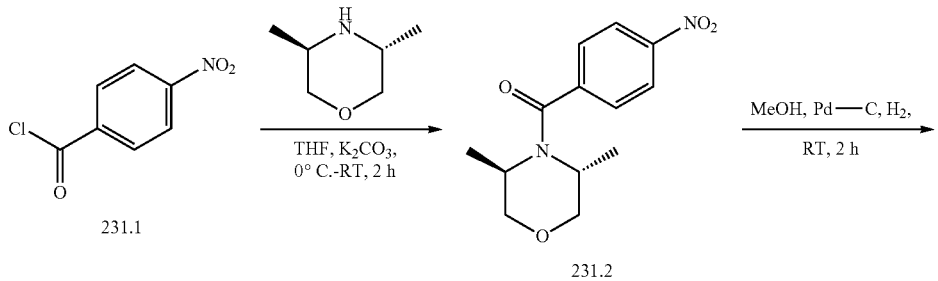

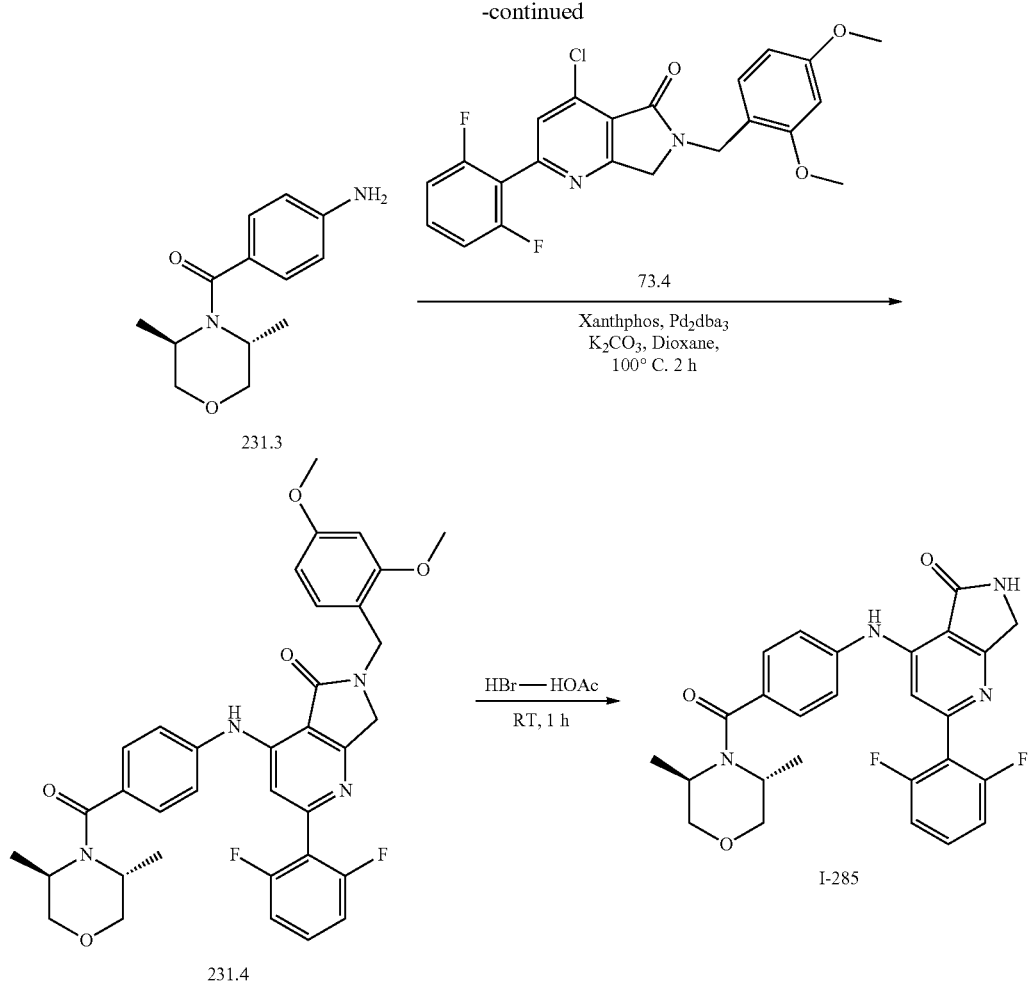

Synthesis of Compound 231.2.

To a solution of (3R,5R)-3,5-dimethylmorpholine (0.098 g, 0.648 mmol, 1.0 eq) in dry THF were added $K_2CO_3$ (0.179 g, 1.29 mmol, 2.0 eq) and 231.1 (0.120 g, 0.648 mmol, 1.0 eq) at 0° C. Reaction was stirred at room temperature for 2 h. After completion of the reaction, mixture was poured in crushed ice, neutralized by $NaHCO_3$ solution and extracted with EtOAC. Organic layers were combined, washed with brine, dried over $Na_2SO_4$ and concentrated under reduced pressure to obtain crude that was purified by trituration with n-hexane to get pure 231.2 (0.130 g, 76.07%). MS(ES): m/z 264.28 $[M+H]^+$.

Synthesis of Compound 231.3.

To a suspension of Pd/C (0.025 g) in methanol (3 mL) was added 231.2 (0.130 g, 0.491 mmol, 1.0 eq) in MeOH (2 mL). Suspension was purged with $H_2$ gas for 2 hours. After completion of the reaction, mixture was filtered through celite, and washed with MeOH. Filtrate was concentrated under reduced pressure to obtain crude which was purified by column chromatography to get 231.3 (0.09 g, 78.1%). MS(ES): m/z 234.3 $[M+H]^+$.

Synthesis of Compound 231.4.

To a mixture of 73.4 (0.100 g, 0.232 mmol, 1.0 eq) in 1,4-dioxane (3 mL) was added 231.3 (0.054 g, 0.232 mmol, 1.0 eq) and $K_2CO_3$ (0.064 g, 0.465 mmol, 2.0 eq). The reaction mixture was degassed for 10 minutes under argon, then $Pd_2(dba)_3$ (0.021 g, 0.023 mmol, 0.1 eq) and Xantphos (0.026 g, 0.046 mmol, 0.2 eq) were added, and again degassed for 5 min. Reaction was stirred at 100° C. for 2 h. After completion of the reaction, mixture was poured into water and product was extracted with EtOAc. Organic layers were combined, washed with brine, dried over $Na_2SO_4$ and concentrated under reduced pressure to obtain crude which was purified by column chromatography to get pure 231.4 (0.092 g, 63.05%). MS(ES): m/z 628.68 $[M+H]^+$.

Synthesis of Compound I-285.

Compound 231.2 (0.092 g, 0.146 mmol, 1.0 eq) was dissolved in HBr/HOAc (2 mL) and reaction was stirred at room temperature for 1 h. After completion of the reaction, mixture was poured into water, basified with satd. $NaHCO_3$ and extracted with EtOAC. Organic layers were combined, dried over $Na_2SO_4$ and concentrated under reduced pressure to obtain crude which was purified by column chromatography to furnish I-285 (0.040 g, 57.1%). MS(ES): m/z 478.50 $[M+H]^+$; $^1H$ NMR (DMSO-$d_6$, 400 MHz): 9.21 (s, 1H), 8.79 (s, 1H), 7.58-7.50 (m, 3H), 7.44-7.42 (d, 2H), 7.24-7.20 (t, 3H), 4.41 (s, 2H), 3.81-3.72 (m, 4H), 3.40-3.36 (m, 2H), 1.13-1.11 (s, 6H).

575

Example 232. Synthesis of 6-((2-(2,6-difluorophenyl)-5-oxo-6,7-dihydro-5H-pyrrolo[3,4-b]pyridin-4-yl)amino)-N-ethyl-4-fluoronicotinamide, I-286

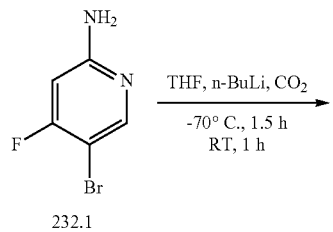

232.1

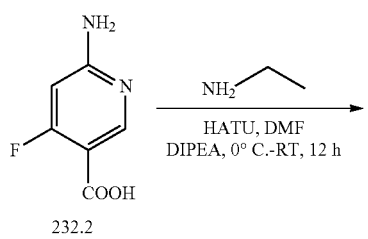

232.2

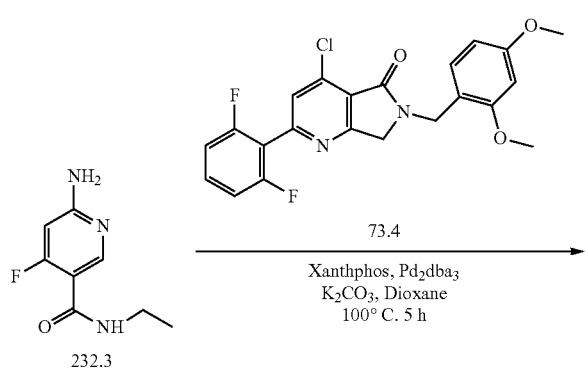

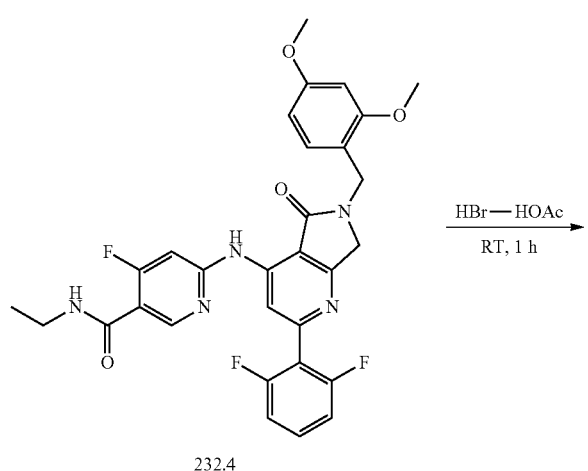

232.4

576

-continued

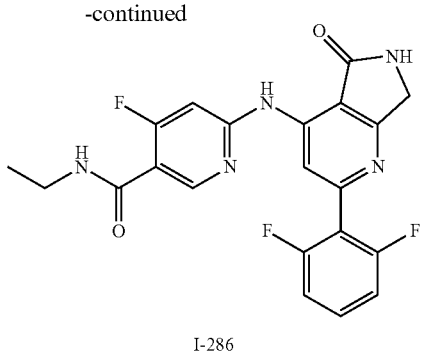

I-286

Synthesis of Compound 232.2.

To a solution of 232.1 (0.1 g, 0.523 mmol, 1.0 eq) in dry THF (5 mL) under nitrogen atmosphere at −70° C. was added n-butyl lithium (0.1 g, 1.570 mmol, 3.0 eq) portionwise. The reaction mixture was stirred at −70° C. for 30 minutes. Dry carbon dioxide was added at −70° C. and the reaction mixture was stirred at −70° C. for 1 h. Then the reaction mixture was stirred at room temperature for 1 h. After completion of the reaction, mixture was poured in water, quenched by 2N HCl solution and then organic impurities were extracted with EtOAc. Aqueous layers were combined and concentrated under reduced pressure to obtain crude 232.2 (0.080 g, 97.9%). MS(ES): m/z 156.12 [M+H]$^+$. The crude material was directly used for next step without any purification.

Synthesis of Compound 232.3.

To a solution of 232.2 (0.08 g, 0.512 mmol, 1.0 eq) in DMF (1 mL) was added HATU (0.389 g, 1.025 mmol, 2.0 eq.) at 0° C. The reaction was stirred at 0° C. for 15 minutes. Further ethanamine (2M in THF) (0.034 g, 0.769 mmol, 1.5 eq.) and DIPEA (0.330 g, 2.564 mmol, 5.0 eq.) were added to the reaction mixture at room temperature. Reaction was stirred at room temperature for 12 hours. After completion of the reaction, mixture was poured in water and product was extracted with EtOAc. Organic layers were combined, washed with brine solution, dried over Na$_2$SO$_4$ and concentrated under reduced pressure to obtain crude material. Crude was purified by column chromatography to furnish 232.3 (0.02 g, 21.31%). MS (ES): m/z 183.19 [M+H]$^+$.

Synthesis of Compound 232.4.

To a mixture of 73.4 (0.045 g, 0.104 mmol, 1.0 eq) in 1,4-dioxane (1 mL) was added 232.3 (0.019 g, 0.104 mmol, 1.0 eq) and K$_2$CO$_3$ (0.028 g, 0.209 mmol, 2.0 eq). The reaction mixture was degassed for 10 minutes under argon atmosphere, then Pd$_2$(dba)$_3$ (0.009 g, 0.010 mmol, 0.1 eq) and Xantphos (0.012 g, 0.020 mmol, 0.2 eq) were added, and again degassed for 5 min. The reaction was then heated at 100° C. for 5 h. After completion of the reaction, mixture was poured into water and product was extracted with EtOAc. Organic layers were combined, washed with brine, dried over sodium sulphate and concentrated under reduced pressure to obtain crude material. The crude was purified by column chromatography, to get pure 232.4 (0.044 g, 72.94%). MS(ES): m/z 577.56 [M+H]$^+$.

Synthesis of Compound I-286.

The compound 232.4 (0.044 g, 0.076 mmol, 1.0 eq) was dissolved in HBr/HOAc (2 mL) and reaction was stirred at room temperature for 1 hour. After completion of the reaction, mixture was poured into water, basified with satd NaHCO$_3$ and product was extracted with EtOAC. Organic layers were combined, dried over sodium sulphate and concentrated under reduced pressure to obtain crude which was purified by triturating with Et₂O to get pure I-286 (0.022 g, 67.6%). MS(ES): m/z 427.39 [M+H]⁺; ¹H NMR (MeOD, 400 MHz): 8.84 (s, 1H), 8.69-8.65 (dd, 1H), 7.58-7.54 (m, 1H), 7.19-7.15 (m, 2H), 7.04-7.00 (dd, 1H), 4.52 (s, 2H), 3.45-3.40 (q, 2H), 1.26-1.22 (m, 3H).

Example 233. Synthesis of 3-fluoro-2-(4-((4-(morpholine-4-carbonyl)phenyl)amino)-5-oxo-6,7-dihydro-5H-pyrrolo[3,4-b]pyridin-2-yl)benzonitrile, I-287

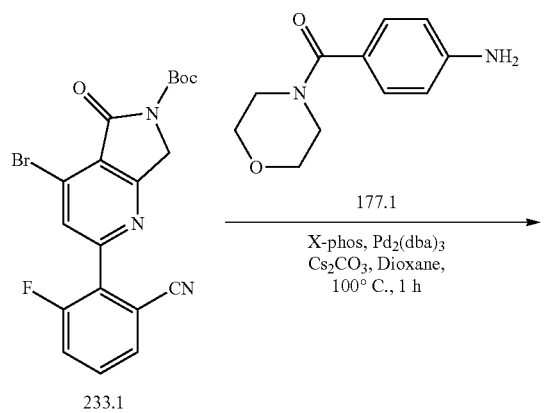

233.1

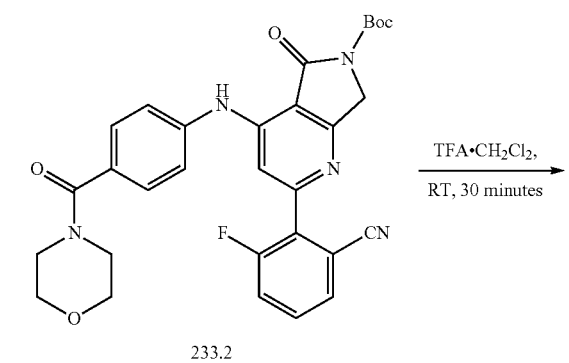

233.2

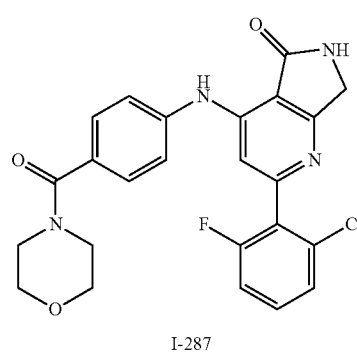

I-287

Synthesis of Compound 233.2.
To a mixture of 233.1 (0.011 g, 0.025 mmol, 1.0 eq) in 1,4-dioxane (0.5 mL) was added 177.1 (0.005 g, 0.025 mmol, 1.0 eq) and K₂CO₃ (0.007 g, 0.051 mmol, 2.0 eq). The reaction mixture was degassed for 10 minutes under argon atmosphere, then Pd₂(dba)₃ (0.002 g, 0.002 mmol, 0.1 eq) and X-Phos (0.003 g, 0.005 mmol, 0.2 eq) were added, and again degassed for 5 minutes. The reaction was stirred at 100° C. for 1 h. After completion of the reaction, mixture was poured into water and product was extracted with EtOAc. Organic layers were combined, washed with brine, dried over Na₂SO₄ and concentrated under reduced pressure to obtain crude which was purified by column chromatography to furnish 233.2 (0.010 g, 70.47%). MS(ES): m/z 557.58 [M+H]⁺.

Synthesis of Compound I-287.
The compound 233.2 (0.010 g, 0.017 mmol, 1.0 eq) was dissolved in CH₂Cl₂ (0.5 mL) and TFA (0.5 mL) was added to the reaction mixture. Reaction was stirred at room temperature for 30 minutes. After completion, reaction mixture was poured into water, neutralized with saturated NaHCO₃ solution and extracted with EtAOc. Organic layers were combined, dried over Na₂SO₄ and concentrated under reduced pressure to obtain crude material. Crude was purified by trituration with hexane to get pure I-287 (0.004 g, 48.8%). MS(ES): m/z 457.47 [M+H]⁺; ¹H NMR (MeOD, 400 MHz): 7.76-7.74 (m, 1H), 7.70-7.60 (m, 2H), 7.58-7.50 (m, 4H), 7.32 (s, 1H), 4.64 (s, 4H), 4.51 (s, 2H), 3.73-3.69 (m, 4H).

Example 234. Synthesis of 2-(2,6-difluorophenyl)-4-((5-(4-hydroxy-2,6-dimethylpiperidin-1-yl)pyridin-2-yl)amino)-6,7-dihydro-5H-pyrrolo[3,4-b]pyridin-5-one, I-288

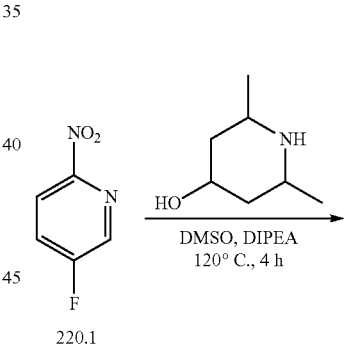

220.1

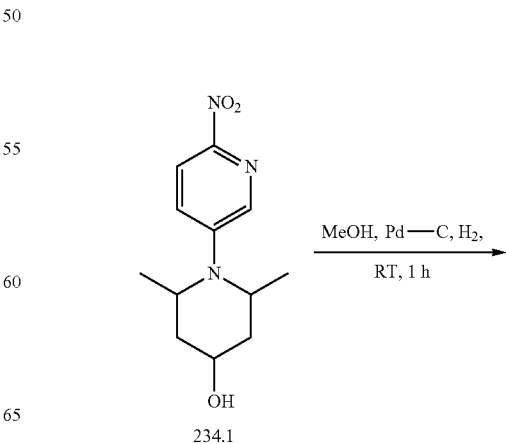

234.1

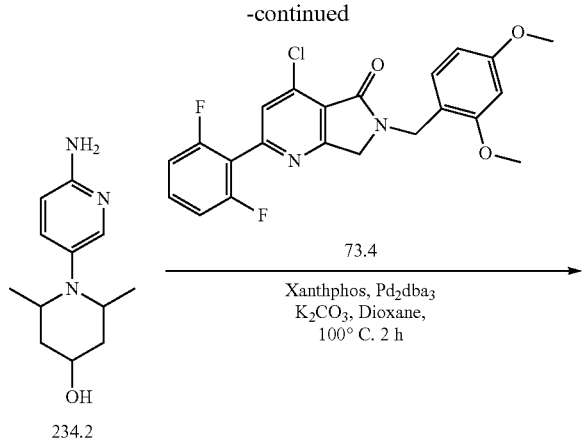

234.2

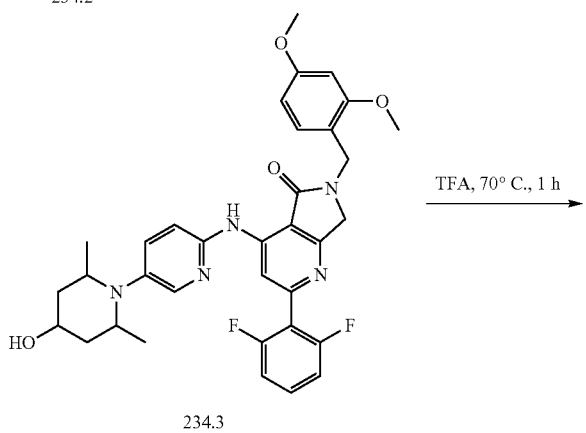

234.3

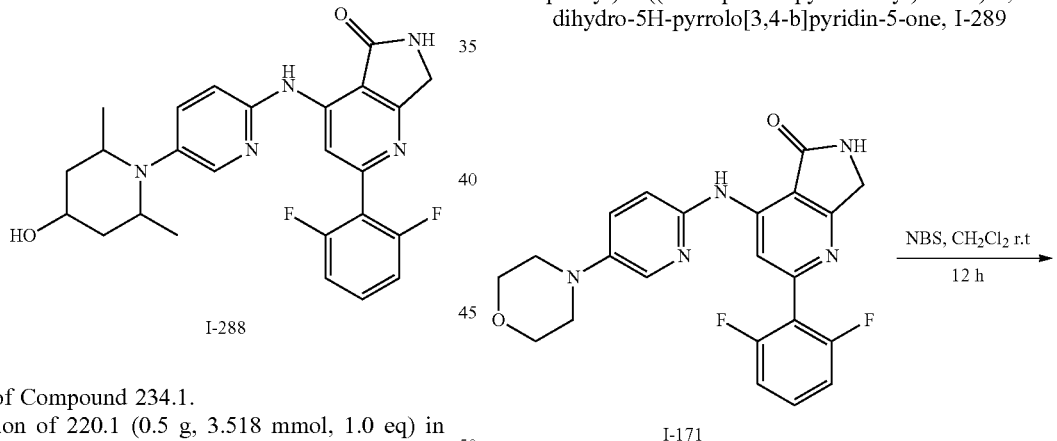

I-288

Synthesis of Compound 234.1.

To a solution of 220.1 (0.5 g, 3.518 mmol, 1.0 eq) in DMSO (5 mL) was added 2,6-dimethylpiperidin-4-ol (0.5 g, 3.870 mmol, 1.1 eq.) and DIPEA (4.54 g, 35.18 mmol, 10.0 eq.). The reaction mixture was heated at 120° C. for 4 h. After completion of the reaction, mixture was poured into water and product was extracted with EtOAc. Organic layers were combined, washed with brine s, dried over Na$_2$SO$_4$ and concentrated under reduced pressure to obtain crude material. The crude was purified by combi flash to get pure 234.1 (0.05 g, 5.65%). MS(ES): m/z 251.29 [M+H]$^+$.

Synthesis of Compound 234.2.

To a suspension of 10% Pd/C (0.010 g) in methanol (1.5 mL) was added a solution of 234.1 (0.05 g, 0.198 mmol, 1.0 eq) in MeOH (1 mL) under nitrogen. Reaction was purged with H$_2$ gas for 1 h. After completion of the reaction, mixture was filtered through celite, washed with MeOH and obtained filtrate was concentrated under reduced pressure to get pure 234.2 (0.033 g, 74.9%) MS (ES): m/z 221.30 [M+H]$^+$.

Synthesis of Compound 234.3.

To a solution of 73.4 (0.058 g, 0.134 mmol, 1.0 eq) in 1,4-dioxane (3 ml) was added 234.2 (0.029 g, 0.134 mmol, 1.0 eq), Xantphos (0.015 g, 0.026 mmol, 0.2 eq) and K$_2$CO$_3$ (0.046 g, 0.337 mmol, 2.5 eq). The reaction mixture was degassed for 10 min. under argon atmosphere, then Pd$_2$(dba)$_3$ (0.012 g, 0.013 mmol, 0.1 eq) and were added, and again degassed for 5 min. The reaction was stirred at 100° C. for 2 h. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to provide 234.3 (0.043 g, 51.88%). MS(ES): m/z 615.68 [M+H]$^+$.

Synthesis of Compound I-288.

Compound 234.3 (0.043 g, 0.069 mmol, 1.0 eq) was dissolved in TFA (2 mL) and reaction was heated at 70° C. for 1 h. After completion of the reaction, mixture was concentrated. To mixture was added 10% MeOH/CH$_2$Cl$_2$. Organic layer was washed with satd. NaHCO$_3$ solution, brine, then dried over Na$_2$SO$_4$ and concentrated under reduced pressure to obtain crude which was purified by column chromatography to furnish I-288 (0.02 g, 61.52%). MS(ES): m/z 465.50 [M+H]$^+$; $^1$H NMR (DMSO-d$_6$, 400 MHz): 9.64 (s, 1H), 8.84 (s, 1H), 8.46 (s, 1H), 8.02-8.01 (d, 1H), 7.61-7.55 (dd, 1H), 7.47-7.44 (d, 1H), 7.28-7.24 (t, 2H), 7.13-7.08 (t, 1H), 4.59-4.56 (d, 1H), 4.42 (s, 2H), 3.80 (s, 1H), 3.56 (m, 1H), 3.43 (m, 1H), 1.95-1.50 (m, 4H), 0.90-0.82 (d, 6H).

Example 235. Synthesis of 3-bromo-2-(2,6-difluorophenyl)-4-((5-morpholinopyridin-2-yl)amino)-6,7-dihydro-5H-pyrrolo[3,4-b]pyridin-5-one, I-289

I-171

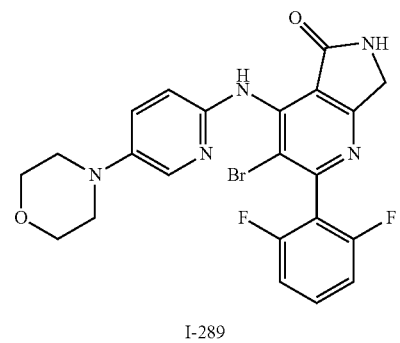

I-289

Synthesis of Compound I-289.

To a solution of I-171 (0.250 g, 0.709 mmol, 1.0 eq) in CH$_2$Cl$_2$ (10 mL) was added N-bromosuccinimide (0.13 g, 0.71 mmol, 1.0 eq) and the reaction was allowed to stir at room temperature for 12 h. After completion of the reaction, mixture was poured into water and product was extracted with CH₂Cl₂. Organic layers were combined, washed with NaHCO₃ solution and brine solution, dried over Na₂SO₄ and concentrated under reduced pressure to obtain crude material which was purified by preparative HPLC to furnish I-289 (0.050 g, 14.05%). MS(ES): m/z 502.32 [M+H]$^+$; $^1$H NMR (DMSO-d₆, 400 MHz): 9.75 (s, 1H), 8.91 (s, 1H), 8.37 (s, 1H), 7.65-7.54 (m, 2H), 7.29-7.25 (m, 3H), 4.44 (s, 2H), 3.74-3.72 (t, 4H), 2.95-2.93 (t, 1H).

Example 236. Synthesis of 2-(2,6-difluorophenyl)-4-((5-morpholinopyridin-2-yl)amino)-5-oxo-6,7-dihydro-5H-pyrrolo[3,4-b]pyridine-3-carbonitrile, I-290

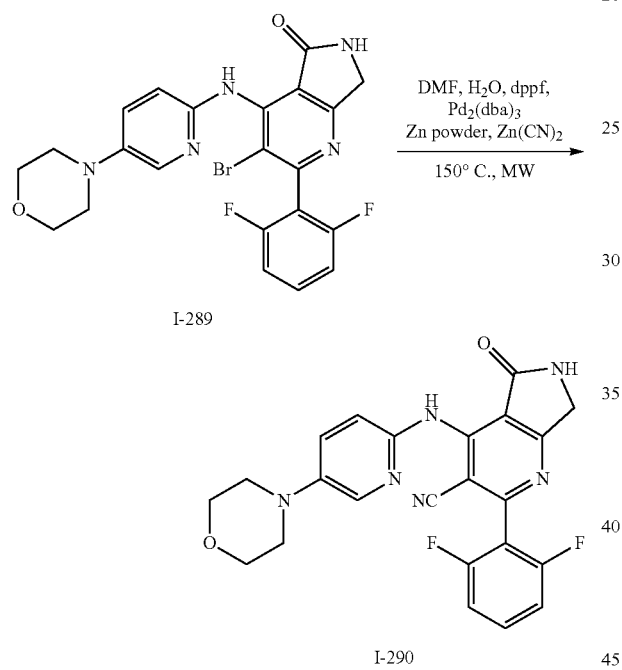

Synthesis of Compound I-290.

To a solution of I-289 (0.045 g, 0.089 mmol, 1.0 eq) in DMF (1 mL) and water (0.2 mL) were added zinc cyanide (0.006 g, 0.053 mmol, 0.6 eq) and zinc powder (0.0005 g, 0.008 mmol, 0.1 eq). The reaction mixture was degassed under argon for 30 minutes. 1,1'-Bis(diphenylphosphino)ferrocene (0.009 g, 0.017 mmol, 0.2 eq) and Pd₂(dba)₃ (0.008 g, 0.008 mmol, 0.1 eq) were added to the mixture and the reaction was heated at 150° C. for 1 h in microwave. After completion of the reaction, mixture was poured into water and the product was extracted with EtOAc. Organic layers were separated, washed with brine, dried over sodium sulphate and evaporated under reduce pressure to get crude material. The crude was purified by column chromatography to furnish I-290 (0.030 g, 74.69%). MS(ES): m/z 448.32 [M+H]$^+$; $^1$H NMR (DMSO-d₆, 400 MHz): 9.82 (s, 1H), 8.93 (s, 1H), 8.40 (s, 1H), 7.77-7.74 (m, 1H), 7.60-7.54 (m, 2H), 7.30-7.26 (m, 2H), 4.45 (s, 2H), 3.76-3.74 (t, 4H), 3.14-3.12 (t, 4H).

Example 237. Synthesis of 2-(2-fluorophenyl)-4-((5-morpholinopyridin-2-yl)amino)-6,7-dihydro-5H-pyrrolo[3,4-b]pyridin-5-one I-291

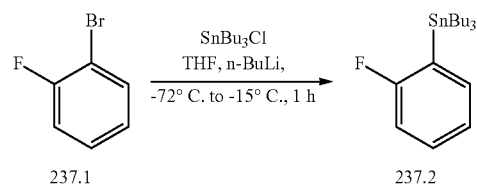

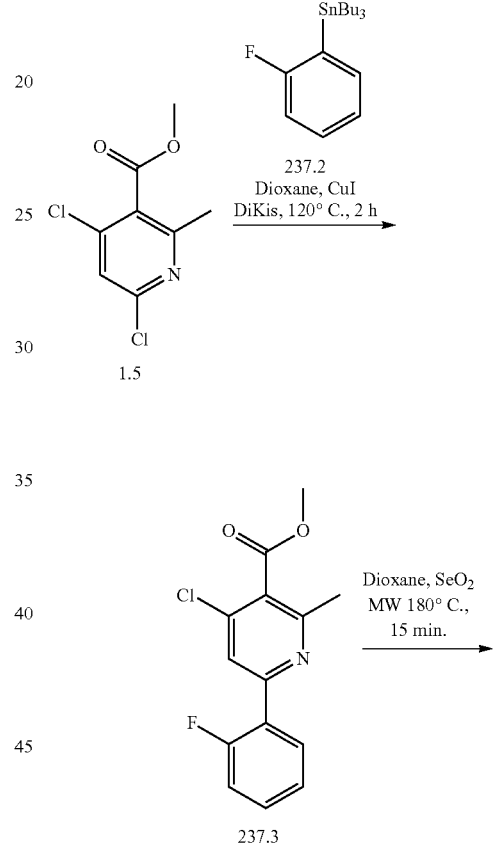

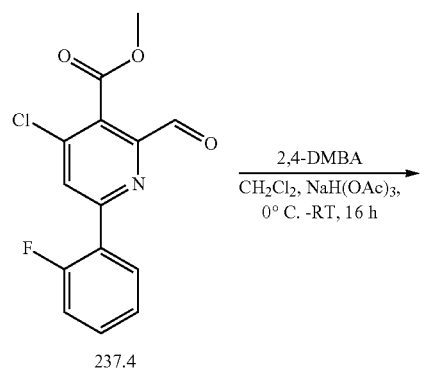

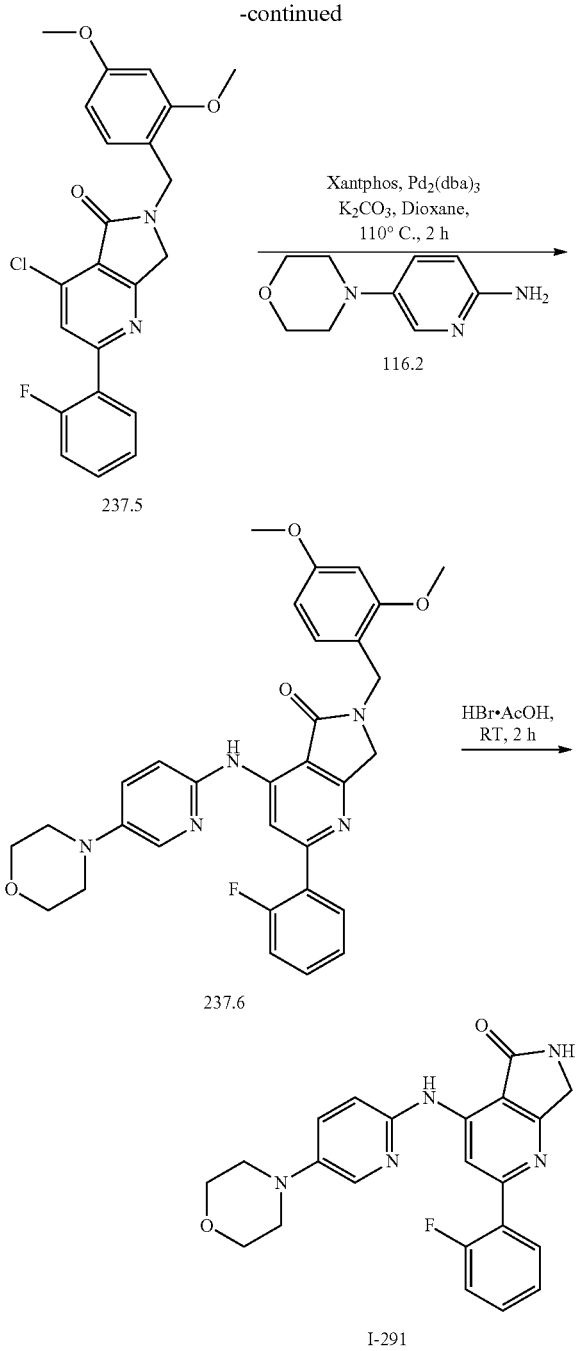

Synthesis of Compound 237.2.

To a solution of 237.1 (5.0 g, 28.57 mmol, 1.0 eq) in THF (25 mL) was added n-BuLi (12 mL, 29.99 mmol, 1.05 eq) dropwise at −72° C. under nitrogen. The reaction was allowed to stir at same temperature for 40 minutes. Tributyl tin chloride (9.7 g, 29.99 mmol, 1.05 eq) dissolved in THF (25 mL) was added dropwise to the reaction mixture at −72° C. under nitrogen and the reaction mixture was stirred at same temperature for 15 minutes. The reaction mixture was allowed to warm to −15° C. in 30 minutes. The reaction mixture was quenched with NH$_4$Cl solution and was extracted with Et$_2$O. Organic layers were combined, washed with brine, dried over Na$_2$SO$_4$, filtered and concentrated under reduced pressure to obtain crude 237.2 (10 g, 90.9%) which was used for next step without any purification. $^1$H NMR (CDCl$_3$, 400 MHz): 7.45-7.39 (m, 1H), 7.39-7.31 (m 1H), 7.18-7.10 (m, 1H), 7.10-6.96 (m, 1H), 1.55-1.45 (m, 4H), 1.4-1.29 (m, 8H), 1.18-1.10 (m, 3H), 0.98-0.89 (m, 12H).

Synthesis of Compound 237.3.

To a solution of 1.5 (3.0 g, 13.6 mmol, 1.0 eq) in 1,4-dioxane (30 mL) was added compound 237.2 (7.8 g, 20.45 mmol, 1.5 eq) and argon gas was purged for 15 minutes. 1,1'-Bis(triphenyl phosphino) palladium (II) chloride (0.95 g, 1.363 mmol, 0.1 eq) was added to the reaction mixture and the reaction mixture was purged with argon gas for 5 minutes. Cuprous iodide (0.51 g, 2.727 mmol, 0.2 eq) was added to the mixture and the reaction was further purged with argon gas for 5 minutes. The reaction mixture was heated at 120° C. for 2 h. After completion of the reaction, the reaction mixture was cooled to room temperature and then filtered through celite. Filtrate was concentrated under reduced pressure to get crude material. The crude product was purified by flash chromatography to furnish 237.3 (2.0 g, 52.6%). $^1$HNMR (DMSO-d$_6$, 400 MHz): 7.95 (dt, 1H), 7.85 (s, 1H), 7.59-7.53 (m, 1H), 7.40-7.35 (m, 2H), 3.96 (s, 3H), 2.56 (s, 3H).

Synthesis of Compound 237.4.

To a solution of 237.3 (2.0 g, 6.72 mmol, 1.0 eq) in 1,4-dioxane (20 mL) was added SeO$_2$ (1.49 g, 13.43 mmol, 2.0 eq). The reaction was irradiated in microwave at 180° C. for 25 minutes. After completion of the reaction, mixture was cooled to room temperature and then filtered through celite. The celite bed was washed with EtOAc and the filtrate obtained was concentrated under reduced pressure to get crude 237.4 (2.0 g, 95.24%) LCMS (ES): m/z 294.09 [M+H]$^+$.

Synthesis of Compound 237.5.

To a solution of 237.4 (2.0 g, 6.809 mmol, 1.0 eq) in CH$_2$Cl$_2$ (30 mL) was added 2,4-dimethoxy benzyl amine (0.91 g, 5.44 mmol, 0.8 eq). The reaction mixture was stirred at room temperature for 45 minutes under nitrogen atmosphere. Sodium triacetoxy borohydride (2.16 g, 10.2 mmol, 1.5 eq) was added in portions to the reaction mixture over 45 minutes under nitrogen atmosphere at 0-5° C. The reaction mixture was stirred at room temperature for 16 h. The reaction mixture was quenched with saturated bicarbonate solution and was extracted with CH$_2$Cl$_2$. The organic layer was washed with water. The organic extracts were combined, washed with brine solution, dried over Na$_2$SO$_4$ and concentrated under reduced pressure to get crude. The crude product was purified by flash chromatography to furnish 237.5 (0.6 g, 21.3%) LCMS (ES): m/z 413.27 [M+H]$^+$.

Synthesis of Compound 237.6.

To a solution of 240.5 (0.110 g, 0.266 mmol, 1.0 eq) in 1,4-dioxane (3 mL) was added 116.2 (0.047 g, 0.266 mmol, 1.0 eq) and K$_2$CO$_3$ (0.11 g, 0.799 mmol, 3.0 eq). Reaction mixture was degassed for 10 min. under argon atmosphere, then Pd$_2$(dba)$_3$ (0.024 g, 0.026 mmol, 0.1 eq) and Xantphos (0.03 g, 0.05 mmol, 0.2 eq) were added, and again degassed for 5 min. The reaction was stirred at 110° C. for 2 h. The reaction mixture was poured into water and product was extracted with EtOAc. Organic extracts were combined, washed with brine solution, dried over Na$_2$SO$_4$ and concentrated under reduced pressure to obtain crude material. Crude was purified by combiflash to provide 237.6 (0.09 g, 60.8%). LCMS (ES): m/z 556.49 [M+H]$^+$.

Synthesis of Compound I-291.

Compound 237.6 (0.09 g, 0.16 mmol, 1.0 eq) was dissolved in HBr/HOAc (4 mL, 33% solution of HBr in acetic acid) and reaction was stirred at room temperature for 2.5 h.

The reaction mixture was poured over ice cold water, neutralized with NaHCO$_3$ and extracted with EtOAc. Organic extracts were combined, dried over Na$_2$SO$_4$ and concentrated under reduced pressure to obtain crude which was purified by column chromatography to furnish I-291 (0.035 g, 53.4%). MS(ES): m/z 406.40 [M+H]$^+$; $^1$H NMR (CDCl$_3$, 400 MHz): 9.32 (s, 1H), 8.77 (d, 1H), 8.07 (d, 1H), 7.90 (dt, 1H), 7.43-7.39 (m, 1H), 7.32-7.27 (m, 1H), 7.23-7.17 (m, 1H), 6.96 (d, 1H), 6.17 (s, 1H), 4.52 (s, 2H), 3.90 (t, 4H), 3.16 (t, 4H).

Example 238. Synthesis of 2-(2,6-difluorophenyl)-4-((3-fluoro-4-methylphenyl)amino)-6,7-dihydro-5H-pyrrolo[3,4-d]pyrimidin-5-one I-292

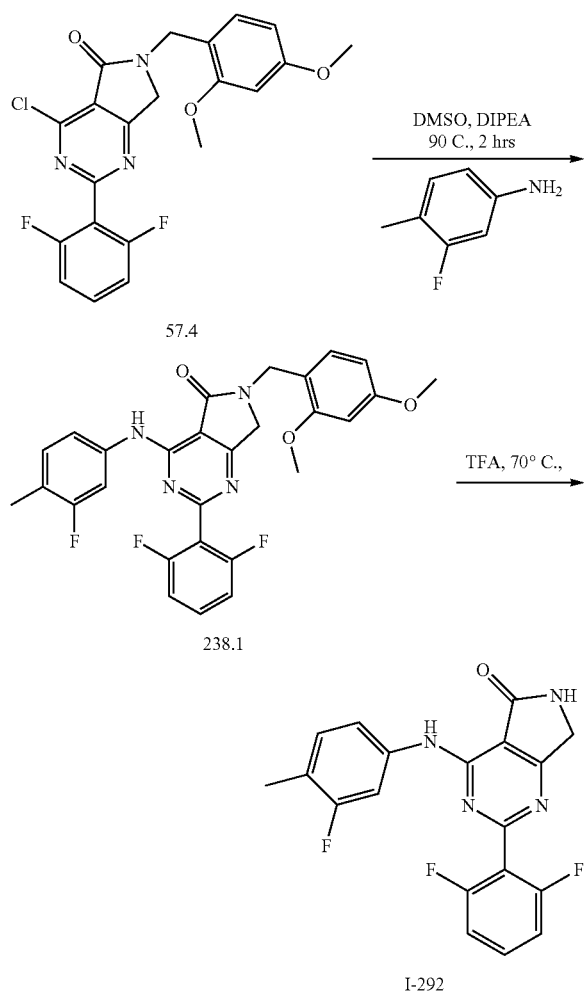

Synthesis of Compound 238.1.

To a solution of 57.4 (0.125 g, 0.290 mmol, 1.0 eq.) in DMSO (2 mL), 3-fluoro-4-methylaniline (0.036 g, 0.290 mmol, 1.0 eq) and DIPEA (0.14 mL, 0.870 mmol, 3.0 eq) were added at room temperature. Reaction mixture was heated at 90° C. for 2 hours. After completion of the reaction, mixture was poured into cold water and extracted using ethyl acetate (20 mL×2). Organic layer was dried over sodium sulfate and concentrated under reduced pressure. Crude was purified by column chromatography to afford 238.1 (0.063 g, 41.81%). MS (ES): m/z 520.5 [M+H]$^+$.

Synthesis of Compound I-292.

A solution of 238.1 (0.063 g, 0.121 mmol, 1 eq) in trifluoroacetic acid (6 ml) was heated at 70° C. for 8 hours. After completion of the reaction, mixture was poured into cold water, neutralized with saturated sodium bicarbonate solution and extracted with ethyl acetate (10 mL×2). Solvent was removed under reduced pressure and resulting crude was purified to afford I-292 (0.023 g, 51.3%). MS (ES): m/z 370.4 [M+H]$^+$ $^1$H NMR (400 MHz, DMSO-d$^6$): δ 9.13 (s, 1H), 8.91 (s, 1H), 7.77-7.73 (dd, 1H), 7.64-7.59 (m, 1H), 7.41-7.39 (d, 1H), 7.30-7.22 (m, 3H), 4.48 (s, 2H), 2.18 (s, 3H).

Example 239: Tyk2 & JAK2 Radioactive Kinase Assay

Peptide substrate, [KKSRGDYMTMQIG], (20 µM) is prepared in reaction buffer (20 mM Hepes pH 7.5, 10 mM MgCl$_2$, 1 mM EGTA, 0.02% Brij35, 0.02 mg/mL BSA, 0.1 mM Na$_3$PO$_4$, 2 mM DTT, 1% DMSO. TYK2 (Invitrogen) kinase is added, followed by compounds in DMSO. 33PATP is added to initiate the reaction in ATP at 10 µM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr](4:1), 0.2 mg/ml is used, in the reaction carried out the same as for TYK2.

Example 240: Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM MgCl$_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Table 2 shows the activity of selected compounds of this invention in the Tyk2 and JAK2 activity inhibition assay. The compound numbers correspond to the compound numbers in Table 1. Compounds having an activity designated as "A" provided an Ki≤0.01 µM; compounds having an activity designated as "B" provided an Ki of 0.01-0.1 µM; compounds having an activity designated as "C" provided an Ki of 0.1-1.0 µM; and compounds having an activity designated as "D" provided an Ki≥1.0 µM.

TABLE 2

| Tyk2 & JAK2 Activity Inhibition Data | | |
|---|---|---|
| Cmpd # | Tyk2 Ki | JAK2 Ki |
| I-1 | A | C |
| I-2 | A | D |
| I-3 | A | C |

TABLE 2-continued

Tyk2 & JAK2 Activity Inhibition Data

| Cmpd # | Tyk2 Ki | JAK2 Ki |
|---|---|---|
| I-4 | A | C |
| I-5 | A | C |
| I-6 | A | C |
| I-7 | B | D |
| I-8 | B | D |
| I-9 | A | C |
| I-10 | A | C |
| I-11 | A | C |
| I-12 | A | C |
| I-13 | A | C |
| I-14 | A | C |
| I-15 | A | C |
| I-16 | A | C |
| I-17 | C | D |
| I-18 | C | D |
| I-19 | C | D |
| I-20 | B | C |
| I-21 | A | D |
| I-22 | A | B |
| I-23 | B | D |
| I-61 | A | C |
| I-62 | A | C |
| I-63 | A | C |
| I-64 | A | C |
| I-65 | A | C |
| I-66 | A | C |
| I-67 | A | B |
| I-68 | B | D |
| I-69 | B | D |
| I-70 | B | D |
| I-71 | B | D |
| I-72 | A | C |
| I-73 | A | C |
| I-74 | A | C |
| I-75 | A | C |
| I-76 | A | B |
| I-77 | A | C |
| I-78 | A | B |
| I-79 | A | C |
| I-80 | A | C |
| I-81 | A | C |
| I-82 | B | D |
| I-83 | B | C |
| I-84 | A | B |
| I-85 | B | D |
| I-86 | A | B |
| I-87 | A | B |
| I-88 | B | C |
| I-91 | A | B |
| I-92 | A | B |
| I-109 | A | C |
| I-110 | A | D |
| I-111 | B | C |
| I-112 | A | C |
| I-113 | A | C |
| I-114 | A | C |
| I-115 | B | C |
| I-116 | A | B |
| I-117 | A | C |
| I-118 | A | C |
| I-119 | A | C |
| I-120 | A | C |
| I-121 | A | C |
| I-122 | A | C |
| I-123 | A | C |
| I-124 | A | B |
| I-125 | A | B |
| I-126 | A | B |
| I-127 | A | B |
| I-128 | A | C |
| I-129 | D | D |
| I-130 | D | D |
| I-131 | D | D |
| I-132 | A | B |
| I-133 | A | B |
| I-134 | A | B |
| I-135 | A | B |
| I-136 | A | B |
| I-137 | A | B |
| I-138 | A | B |
| I-139 | A | B |
| I-140 | A | B |
| I-141 | A | B |
| I-142 | A | B |
| I-143 | A | B |
| I-144 | A | A |
| I-145 | A | B |
| I-146 | A | B |
| I-147 | A | B |
| I-148 | A | B |
| I-149 | A | C |
| I-150 | A | B |
| I-151 | A | C |
| I-152 | A | C |
| I-153 | A | C |
| I-154 | A | C |
| I-155 | A | C |
| I-156 | A | C |
| I-157 | B | C |
| I-158 | B | C |
| I-159 | A | A |
| I-160 | B | D |
| I-161 | A | C |
| I-162 | A | B |
| I-163 | A | B |
| I-164 | A | B |
| I-165 | A | B |
| I-166 | C | D |
| I-167 | A | C |
| I-168 | A | C |
| I-169 | D | D |
| I-170 | A | B |
| I-171 | A | B |
| I-172 | A | B |
| I-173 | A | B |
| I-174 | A | B |
| I-175 | A | B |
| I-176 | A | B |
| I-177 | A | B |
| I-178 | A | C |
| I-179 | B | C |
| I-180 | B | D |
| I-181 | A | C |
| I-182 | A | B |
| I-183 | A | B |
| I-184 | B | D |
| I-185 | A | C |
| I-186 | A | C |
| I-187 | A | B |
| I-188 | A | B |
| I-189 | A | C |
| I-190 | A | C |
| I-191 | A | C |
| I-192 | A | C |
| I-193 | A | C |
| I-194 | B | C |
| I-195 | A | C |
| I-196 | A | C |
| I-197 | C | D |
| I-198 | A | C |
| I-199 | A | B |
| I-200 | A | B |
| I-201 | A | C |
| I-202 | A | C |
| I-203 | B | C |
| I-204 | A | D |
| I-205 | A | D |
| I-206 | A | C |
| I-207 | A | C |
| I-208 | C | D |

TABLE 2-continued

Tyk2 & JAK2 Activity Inhibition Data

| Cmpd # | Tyk2 Ki | JAK2 Ki |
|---|---|---|
| I-209 | A | B |
| I-210 | A | B |
| I-211 | A | B |
| I-212 | A | B |
| I-213 | A | C |
| I-214 | A | B |
| I-215 | A | B |
| I-216 | A | C |
| I-217 | A | B |
| I-218 | A | C |
| I-219 | A | B |
| I-220 | A | B |
| I-221 | A | B |
| I-222 | A | B |
| I-223 | A | A |
| I-224 | A | A |
| I-225 | A | A |
| I-226 | A | B |
| I-227 | A | A |
| I-228 | A | B |
| I-229 | A | B |
| I-230 | A | C |
| I-231 | A | B |
| I-232 | A | B |
| I-233 | A | D |
| I-234 | A | A |
| I-235 | A | C |
| I-236 | B | D |
| I-237 | A | B |
| I-238 | A | C |
| I-239 | A | C |
| I-240 | A | NA |
| I-241 | C | NA |
| I-242 | A | B |
| I-243 | A | B |
| I-244 | A | B |
| I-245 | A | A |
| I-246 | A | A |
| I-247 | A | B |
| I-248 | A | B |
| I-249 | A | B |
| I-250 | B | C |
| I-251 | A | B |
| I-252 | A | C |
| I-253 | A | B |
| I-254 | A | B |
| I-255 | A | B |
| I-256 | A | A |
| I-257 | A | B |
| I-258 | A | A |
| I-259 | A | A |
| I-260 | A | C |
| I-261 | A | B |
| I-262 | A | B |
| I-263 | A | A |
| I-264 | A | A |
| I-265 | A | B |
| I-266 | A | A |
| I-267 | A | B |
| I-268 | A | B |
| I-269 | A | B |
| I-270 | A | A |
| I-271 | A | A |
| I-272 | A | A |
| I-273 | A | B |
| I-274 | A | A |
| I-275 | A | B |
| I-276 | A | B |
| I-277 | A | A |
| I-278 | A | A |
| I-279 | A | B |
| I-280 | B | C |
| I-281 | A | A |
| I-282 | A | A |
| I-283 | A | A |
| I-284 | A | B |
| I-285 | A | A |
| I-286 | A | C |
| I-287 | A | A |
| I-288 | A | A |
| I-292 | B | D |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Example 241. IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 µl per well is 200,000 cells. 15 µl of compound or DMSO is added to the well at the desired concentrations and incubated at 1 hr at 37 C. 15 µl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

Example 242. GM-CSF Induced pSTAT5 in Human PBMC

Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Table 3 shows the activity of selected compounds of this invention in the IL-12 induced pSTAT4 and GM-CSF induced pSTAT5 inhibition assays in human PBMC. The compound numbers correspond to the compound numbers in Table 1. Compounds having an activity designated as "A" provided an $EC_{50} \leq 2$ µM; compounds having an activity designated as "B" provided a $EC_{50}$ of 2-20 µM; and compounds having an activity designated as "C" provided an $EC_{50} > 20$ µM.

TABLE 3

Cell activity data

| Compound | Tyk2-pSTAT4 $EC_{50}$ | JAK2-pSTAT5 $EC_{50}$ |
|---|---|---|
| I-20 | A | C |
| I-80 | A | C |
| I-67 | A | C |
| I-16 | A | C |
| I-65 | A | C |
| I-66 | A | C |

TABLE 3-continued

Cell activity data

| Compound | Tyk2-pSTAT4 $EC_{50}$ | JAK2-pSTAT5 $EC_{50}$ |
|---|---|---|
| I-64 | A | C |
| I-21 | A | C |
| I-78 | A | C |
| I-86 | A | C |
| I-87 | A | C |
| I-109 | B | C |
| I-110 | A | C |
| I-88 | A | A |
| I-114 | A | B |
| I-115 | A | B |
| I-117 | A | C |
| I-128 | A | C |
| I-135 | A | A |
| I-136 | A | A |
| I-137 | A | A |
| I-138 | A | B |
| I-140 | A | B |
| I-142 | A | C |
| I-144 | A | D |
| I-147 | A | A |
| I-148 | A | B |
| I-150 | A | B |
| I-154 | A | C |
| I-161 | A | B |
| I-163 | A | B |
| I-165 | A | B |
| I-167 | A | C |
| I-170 | A | B |
| I-171 | A | B |
| I-176 | A | B |
| I-181 | A | C |
| I-182 | A | B |
| I-195 | A | C |
| I-196 | A | C |
| I-205 | A | B |
| I-206 | A | C |
| I-207 | A | B |
| I-214 | A | B |
| I-227 | A | A |
| I-228 | A | B |
| I-229 | A | B |
| I-231 | A | B |
| I-232 | A | B |
| I-237 | A | C |
| I-238 | A | C |
| I-242 | A | B |
| I-243 | A | B |
| I-247 | A | A |
| I-248 | A | A |
| I-253 | A | C |
| I-256 | A | A |
| I-257 | A | B |
| I-260 | A | C |
| I-262 | A | A |
| I-263 | A | A |
| I-265 | A | B |
| I-272 | A | A |
| I-273 | A | A |
| I-276 | A | A |

Example 243. Acute Mouse Model for IL-12/IL-18 Induced IFNγ in Serum

C57BL/6 mice mice are dosed PO or SC with test compound at various doses or vehicle (n=9 or 10 per group) and then, 30 minutes later, injected IP with 10 ng IL-12 and 1 μg IL-18. Three hours after IL-12/IL-18 injection, mice were bled and serum isolated. Concentration of cytokines in serum were determined using CBA analysis.

Certain compounds of the invention inhibit ~50% of the IL-12/IL-18 induced IFNγ production in vivo. Compound I-80 inhibited IL-12/IL-18 induced IFNγ production in vivo in rats at an efficacious dose of 30 mg/kg SC.

Example 244. Ex Vivo Mouse IL-12 Induced IFNγ Studies

C57/BL6 mice were given a single oral dose of either vehicle or different doses of compound at a volume of 10 mL/kg. 30 minutes to 1 hour after dosing, animals were euthanized and blood was collected via vena cava into sodium heparin blood collection tubes and inverted several times. Blood was then plated on anti-CD3 coated plates and stimulated with 2 ng/ml of mouse IL-12 in RPMI media for 24 hours at 37° C. in humidified incubator with 5% $CO_2$. At the end of the incubation, blood was centrifuged at 260 g for 5 minutes to collect supernatant. IFNγ concentration in the supernatant was determined with mouse IFNγ MSD kit per manufacture's instruction (Meso Scale Discovery). At the time of the blood collection, plasma was collected for drug level analysis by LC-MS/MS.

Certain compounds of the invention inhibit IL-12 induced IFNγ production in the ex-vivo mouse model. Compounds I-136, I-165, and I-195 significantly inhibit IL-12 induced IFNγ production at doses of ≤10 mg/kg.

Example 245. T-ALL Cell Proliferation Assay

Figure 2:
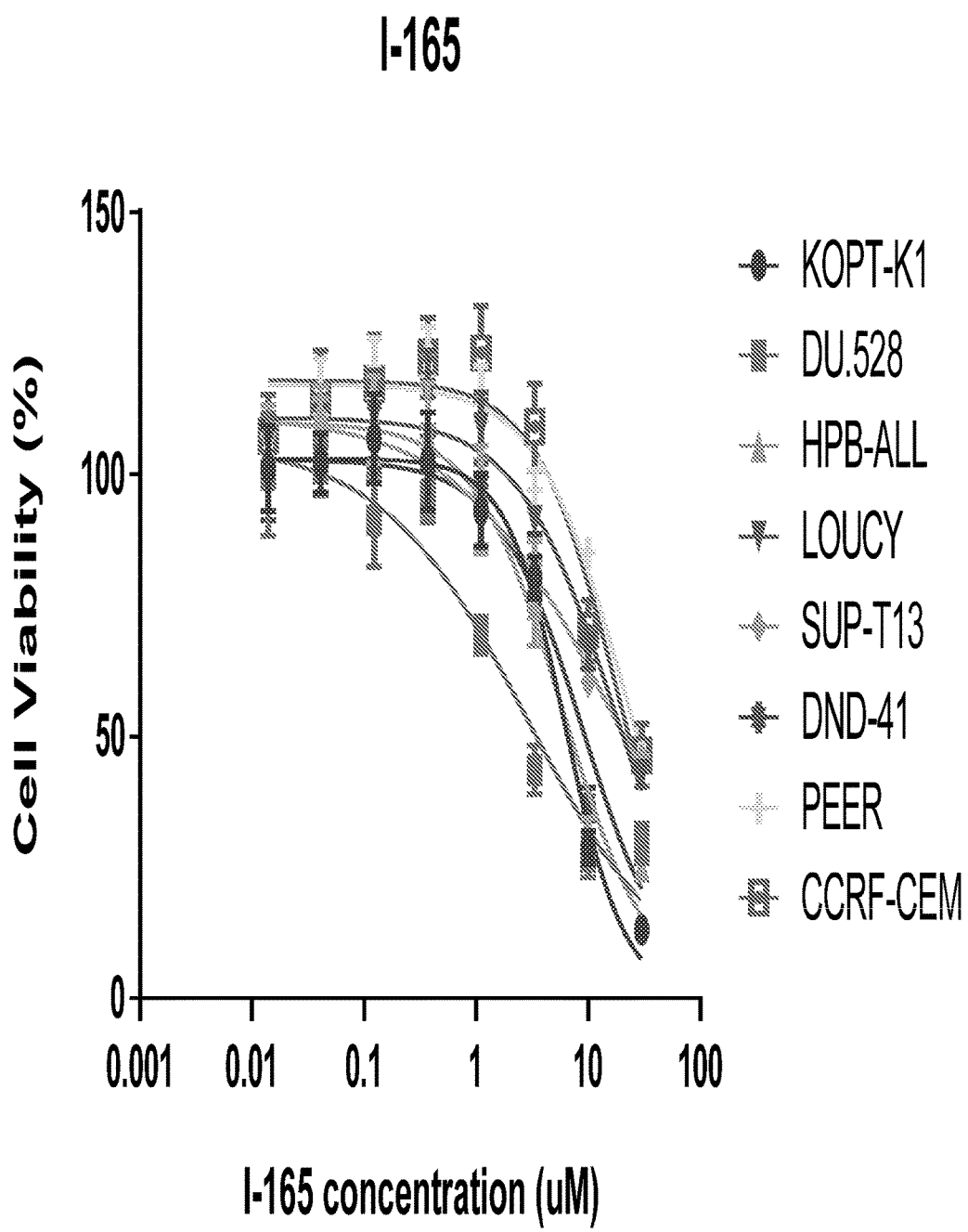
FIG. 2 depicts results of a T-ALL cell proliferation inhibition assay using compound I-165

T-ALL cell lines KOPT-K1, HPB-ALL, DND-41, PEER, and CCRF-CEM were cultured in RPMI-1640 medium with 10% fetal bovine serum and penicillin/streptomycin. Cells were plated in triplicate at $1 \times 10^4$ cells per well in 96-well plates. T-ALL cell lines DU.528, LOUCY, and SUP-T13 were cultured in the same medium and plated at a density of $1.5 \times 10^4$ cells per well. The cells were treated with DMSO or different concentrations of each compound of the invention. Cell viability at 72 hour exposure to the drug was assessed by CellTiter-Glo Luminescent Cell Viability Assay (Promega). CellTiter-Glo Reagent was added into the well and incubated for 10 minutes. Luminescence was measured subsequently using a 96-well plate luminescence reader. Cell viability was calculated by using the DMSO treated samples as 100%. $IC_{50}$ value was calculated by nonlinear regression using GraphPad Prism software. Results of a T-ALL cell proliferation assay are shown in FIG. 1 and FIG. 2.

We claim:
1. A method comprising the step of:
deprotecting a compound of formula A-5:

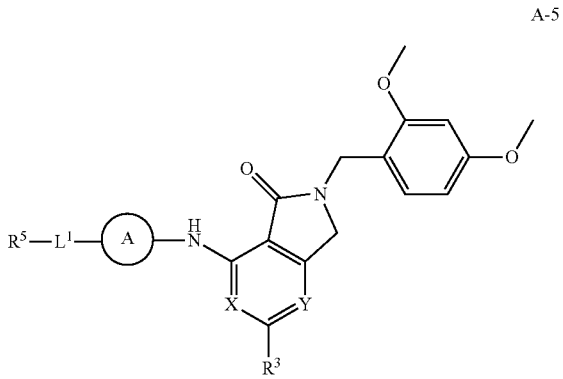

A-5 wherein:
each of X and Y is independently =C(R⁶)— or =N—, provided that X and Y are not simultaneously =C(R⁶)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;
$R^5$ is a group selected from hydrogen, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;
provided that when $R^3$ is other than phenyl, $R^5$ is not hydrogen or unsubstituted alkyl when $L^1$ is a covalent bond;
each instance of $R^6$, $R^7$, and $R^8$ is independently —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
each instance of $R^9$ is independently oxo, $C_{1-6}$ hydroxyaliphatic, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;
m is 0-4;
n is 0-4;
p is 0-6; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
to form a compound of formula II:

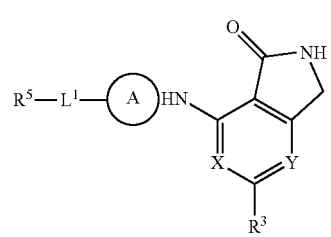

II wherein:
each of X and Y is independently =C(R⁶)— or =N—, provided that X and Y are not simultaneously =C(R⁶)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;
$R^5$ is a group selected from hydrogen, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;
provided that when $R^3$ is other than phenyl, $R^5$ is not hydrogen or unsubstituted alkyl when $L^1$ is a covalent bond;
each instance of $R^6$, $R^7$, and $R^8$ is independently —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
each instance of $R^9$ is independently oxo, $C_{1-6}$ hydroxyaliphatic, —$R^2$, halogen, —CN, —NO₂, —OR, —SR, —NR₂, —S(O)₂R, —S(O)₂NR₂, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

L$^1$ is a covalent bond or a C$_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4;
n is 0-4;
p is 0-6; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. The method of claim 1, wherein deprotecting is effected by trifluoroacetic acid.

3. The method of claim 1, further comprising the step of treating a compound of formula A-4:

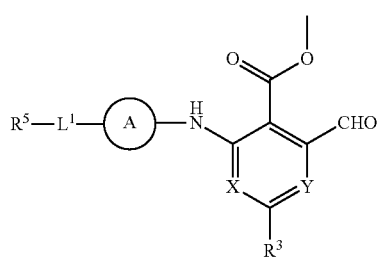

A-4 with 2,4-dimethoxybenzylamine under conditions to effect reductive amination to form the compound of formula A-5.

4. The method of claim 3, wherein the reductive amination is effected by sodium cyanoborohydride.

5. The method of claim 3, further comprising the step of treating a compound of formula A-3:

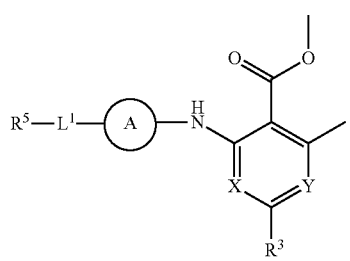

A-3 with an oxidizing agent to form the compound of formula A-4.

6. The method of claim 5, wherein the oxidizing agent is selenium dioxide.

7. The method of claim 5, further comprising the step of treating a compound of formula A-2:

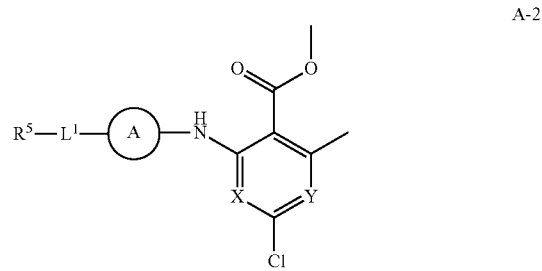

A-2 with a boronic acid of the formula R$^3$—B(OH)$_2$ under Suzuki conditions to form the compound of formula A-3.

8. The method of claim 7, further comprising the step of treating a compound of formula A-1:

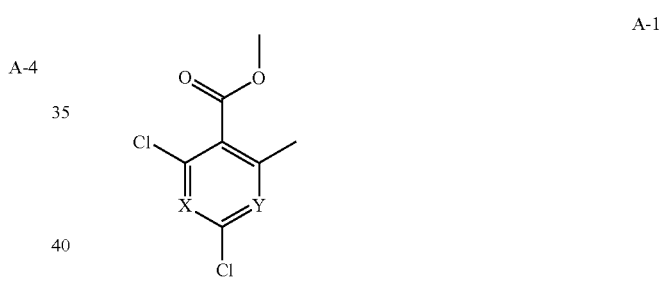

A-1 with an amine of the formula A-1':

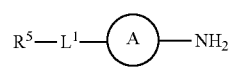

A-1' in the presence of base to form the compound of formula A-2.

9. The method of claim 8, wherein the base is an amine base.

10. The method of claim 9, wherein the amine is diisopropylethylamine.

11. The method of claim 1, wherein the compound of formula II is selected from those depicted below:

| Compound | Structure |
|---|---|
| I-1 | 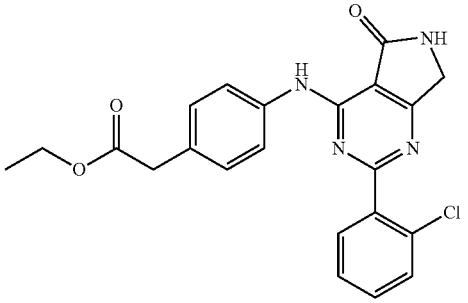 [SMILES: CCOC(=O)Cc1ccc(Nc2nc(-c3ccccc3Cl)nc3c2C(=O)NC3)cc1] |
| I-2 | 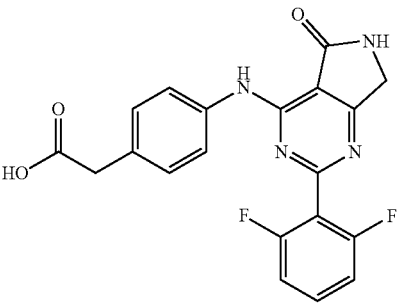 [SMILES: O=C(O)Cc1ccc(Nc2nc(-c3c(F)cccc3F)nc3c2C(=O)NC3)cc1] |
| I-3 | 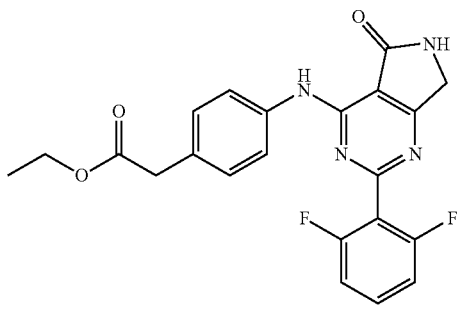 [SMILES: CCOC(=O)Cc1ccc(Nc2nc(-c3c(F)cccc3F)nc3c2C(=O)NC3)cc1] |
| I-4 | 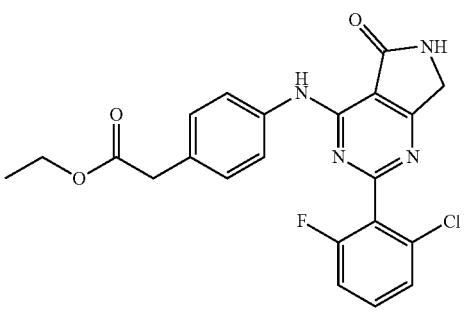 [SMILES: CCOC(=O)Cc1ccc(Nc2nc(-c3c(F)cccc3Cl)nc3c2C(=O)NC3)cc1] |
| I-5 | 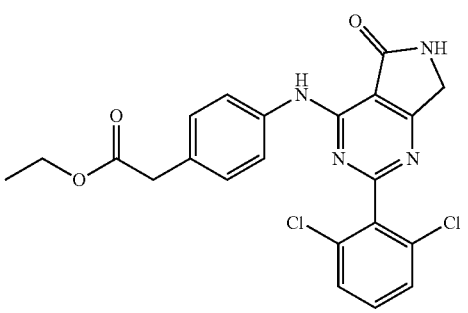 [SMILES: CCOC(=O)Cc1ccc(Nc2nc(-c3c(Cl)cccc3Cl)nc3c2C(=O)NC3)cc1] |
| I-6 | 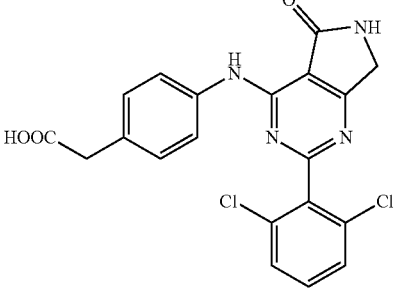 |
| I-7 | 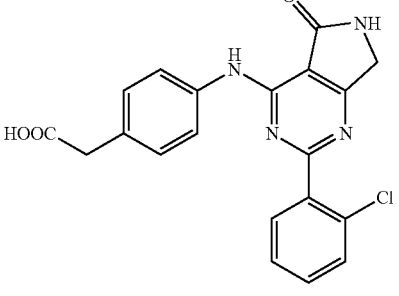 |
| I-8 | 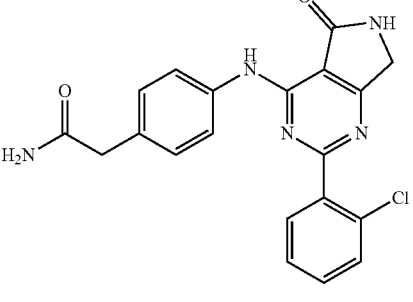 |
| I-9 | 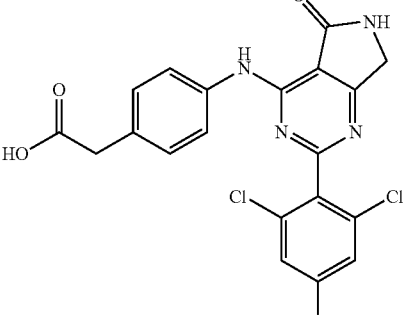 |
| I-10 | 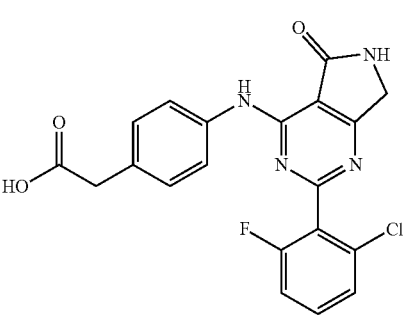 [SMILES: O=C(O)Cc1ccc(Nc2nc(-c3c(F)cccc3Cl)nc3c2C(=O)NC3)cc1] |

| Compound | Structure |
|---|---|
| I-11 | 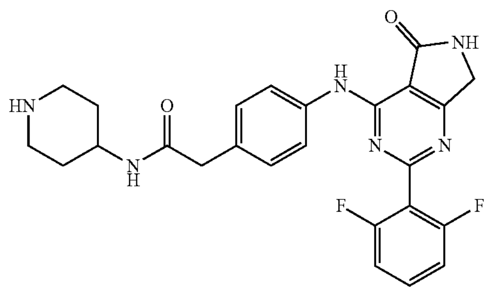 [SMILES: O=C(Cc1ccc(Nc2nc(-c3c(F)cccc3F)nc3c2C(=O)NC3)cc1)NC1CCNCC1] |
| I-12 | 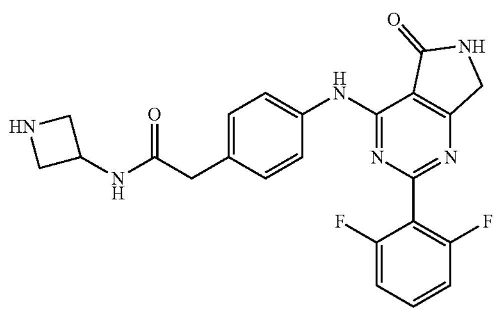 [SMILES: O=C(Cc1ccc(Nc2nc(-c3c(F)cccc3F)nc3c2C(=O)NC3)cc1)NC1CNC1] |
| I-13 | 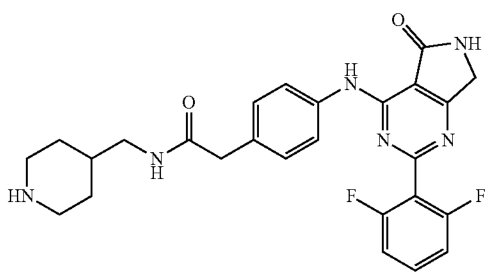 [SMILES: O=C(Cc1ccc(Nc2nc(-c3c(F)cccc3F)nc3c2C(=O)NC3)cc1)NCC1CCNCC1] |
| I-14 | 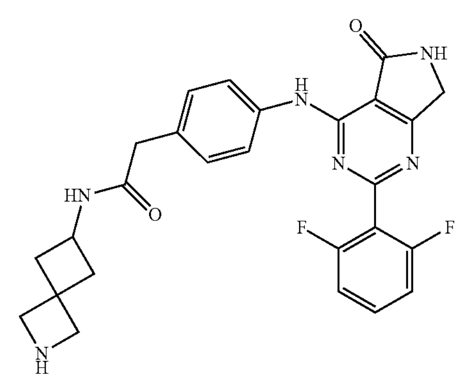 [SMILES: O=C(Cc1ccc(Nc2nc(-c3c(F)cccc3F)nc3c2C(=O)NC3)cc1)NC1CC2(CNC2)C1] |
| I-15 | 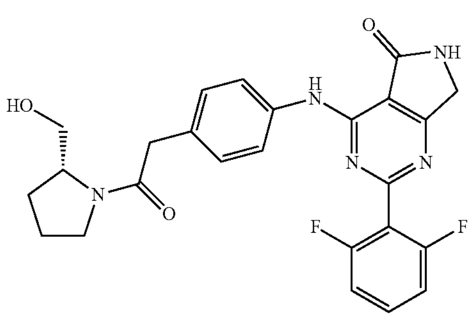 [SMILES: O=C1NCc2nc(-c3c(F)cccc3F)nc(Nc3ccc(CC(=O)N4CCC[C@@H]4CO)cc3)c21] |
| I-16 | 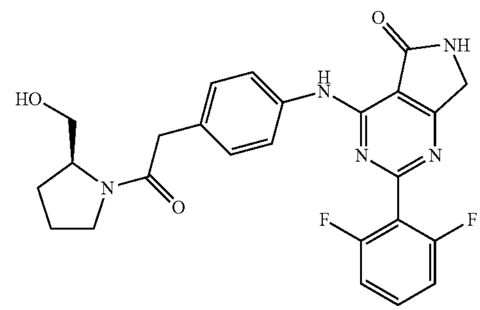 [SMILES: O=C1NCc2nc(-c3c(F)cccc3F)nc(Nc3ccc(CC(=O)N4CCC[C@H]4CO)cc3)c21] |
| I-17 | 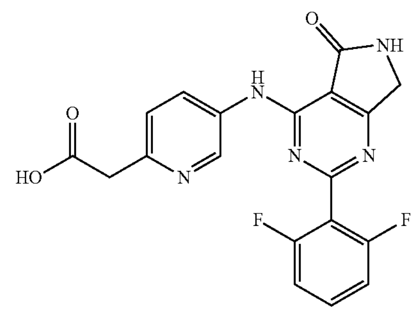 [SMILES: O=C(O)Cc1ccc(Nc2nc(-c3c(F)cccc3F)nc3c2C(=O)NC3)cn1] |
| I-18 | 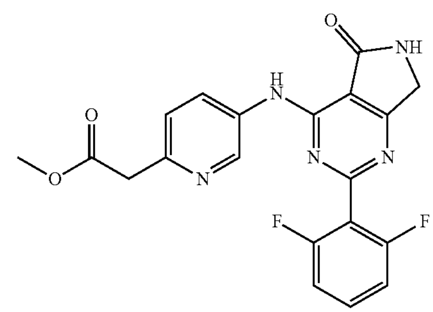 [SMILES: COC(=O)Cc1ccc(Nc2nc(-c3c(F)cccc3F)nc3c2C(=O)NC3)cn1] |
| I-19 | 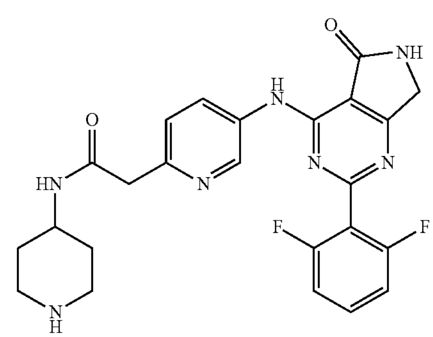 [SMILES: O=C(Cc1ccc(Nc2nc(-c3c(F)cccc3F)nc3c2C(=O)NC3)cn1)NC1CCNCC1] |
| I-20 | 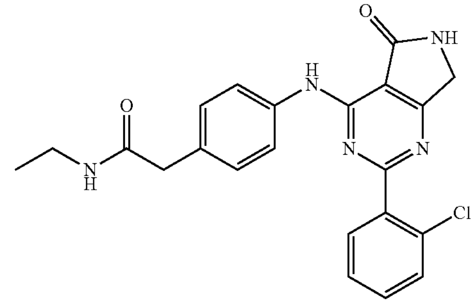 [SMILES: CCNC(=O)Cc1ccc(Nc2nc(-c3ccccc3Cl)nc3c2C(=O)NC3)cc1] |

| Compound | Structure |
|---|---|
| I-21 | 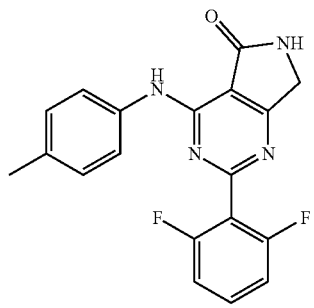 [SMILES: Cc1ccc(Nc2nc(-c3c(F)cccc3F)nc3c2C(=O)NC3)cc1] |
| I-22 | 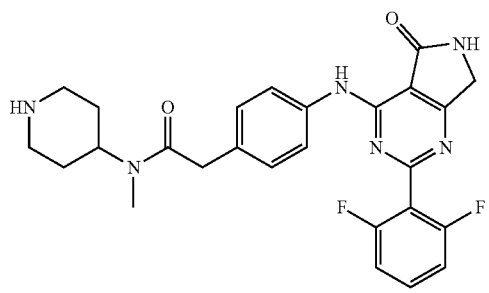 [SMILES: CN(C(=O)Cc1ccc(Nc2nc(-c3c(F)cccc3F)nc3c2C(=O)NC3)cc1)C1CCNCC1] |
| I-23 | 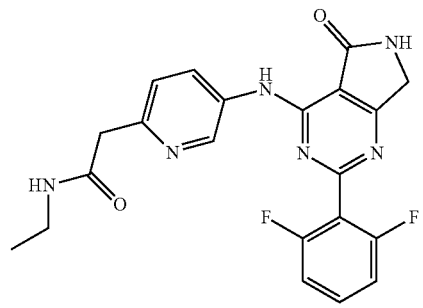 [SMILES: CCNC(=O)Cc1ccc(Nc2nc(-c3c(F)cccc3F)nc3c2C(=O)NC3)cn1] |
| I-24 | 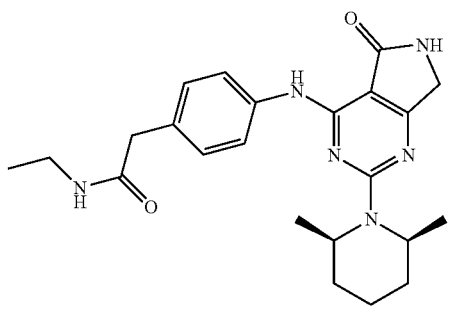 [SMILES: CCNC(=O)Cc1ccc(Nc2nc(N3[C@H](C)CCC[C@@H]3C)nc3c2C(=O)NC3)cc1] |
| I-25 | 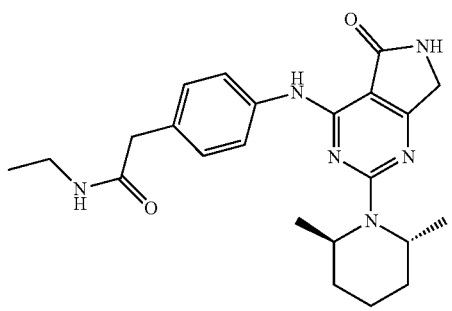 [SMILES: CCNC(=O)Cc1ccc(Nc2nc(N3[C@H](C)CCC[C@H]3C)nc3c2C(=O)NC3)cc1] |
| Compound | Structure |
|---|---|
| I-26 | 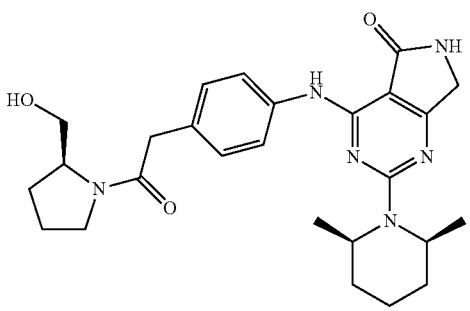 [SMILES: C[C@@H]1CCC[C@H](C)N1c1nc2c(c(Nc3ccc(CC(=O)N4CCC[C@H]4CO)cc3)n1)C(=O)NC2] |
| I-27 | 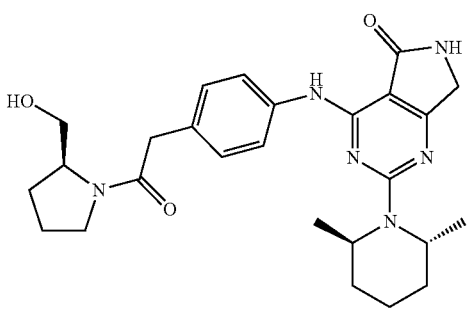 [SMILES: C[C@@H]1CCC[C@@H](C)N1c1nc2c(c(Nc3ccc(CC(=O)N4CCC[C@H]4CO)cc3)n1)C(=O)NC2] |
| I-28 | 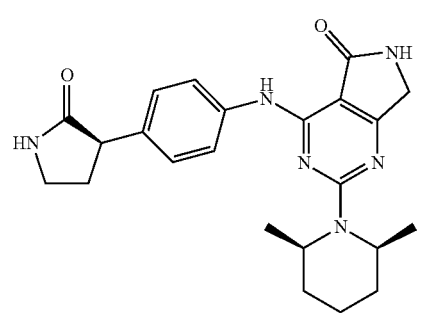 [SMILES: C[C@@H]1CCC[C@H](C)N1c1nc2c(c(Nc3ccc([C@H]4CCNC4=O)cc3)n1)C(=O)NC2] |
| I-29 | 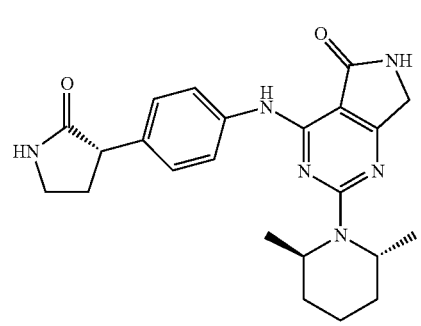 [SMILES: C[C@@H]1CCC[C@@H](C)N1c1nc2c(c(Nc3ccc([C@@H]4CCNC4=O)cc3)n1)C(=O)NC2] |
| I-30 | 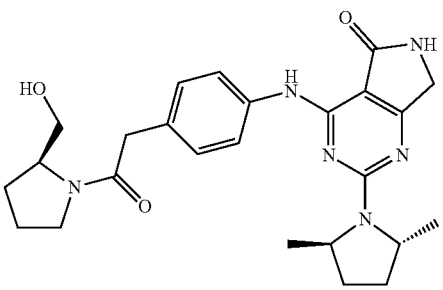 [SMILES: C[C@@H]1CC[C@@H](C)N1c1nc2c(c(Nc3ccc(CC(=O)N4CCC[C@H]4CO)cc3)n1)C(=O)NC2] |

| Compound | Structure |
|---|---|
| I-31 | 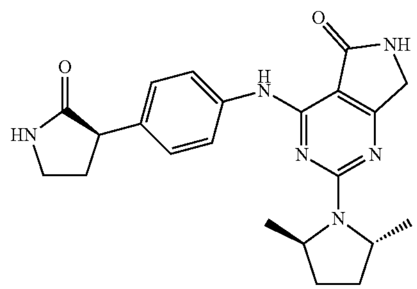 [SMILES: C[C@@H]1CC[C@@H](C)N1c1nc2c(c(Nc3ccc([C@H]4CCNC4=O)cc3)n1)C(=O)NC2] |
| I-32 | 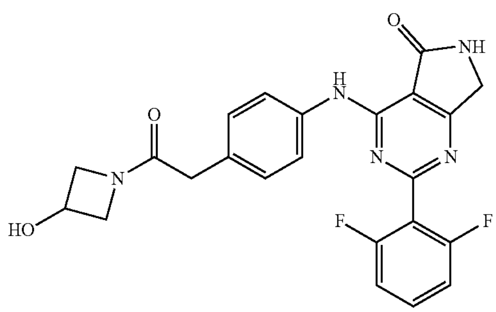 [SMILES: O=C1NCc2nc(-c3c(F)cccc3F)nc(Nc3ccc(CC(=O)N4CC(O)C4)cc3)c21] |
| I-33 | 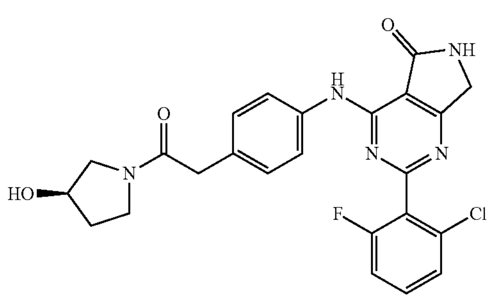 [SMILES: O=C1NCc2nc(-c3c(F)cccc3Cl)nc(Nc3ccc(CC(=O)N4CC[C@@H](O)C4)cc3)c21] |
| I-34 | 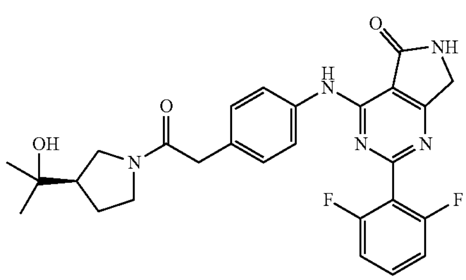 [SMILES: CC(C)(O)[C@@H]1CCN(C(=O)Cc2ccc(Nc3nc(-c4c(F)cccc4F)nc4c3C(=O)NC4)cc2)C1] |
| I-35 | 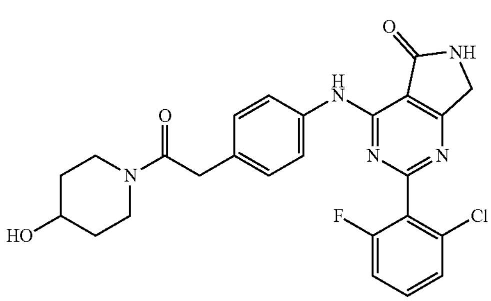 [SMILES: O=C1NCc2nc(-c3c(F)cccc3Cl)nc(Nc3ccc(CC(=O)N4CCC(O)CC4)cc3)c21] |
| I-36 | |
| I-37 | |
| I-38 | |
| I-39 | |
| I-40 | |

| Compound | Structure |
|---|---|
| I-41 | 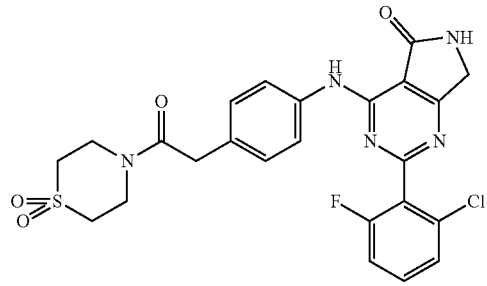 [SMILES: O=C1NCc2nc(-c3c(F)cccc3Cl)nc(Nc3ccc(CC(=O)N4CCS(=O)(=O)CC4)cc3)c21] |
| I-42 | 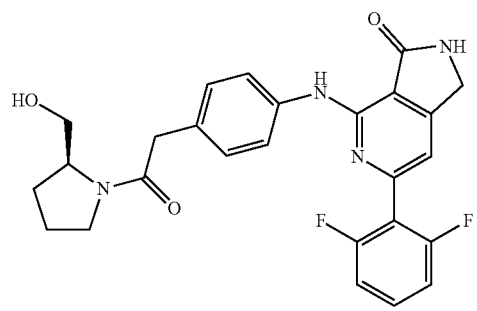 |
| I-43 | 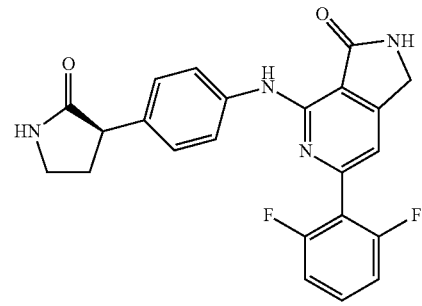 [SMILES: O=C1NCc2cc(-c3c(F)cccc3F)nc(Nc3ccc([C@H]4CCNC4=O)cc3)c21] |
| I-44 | 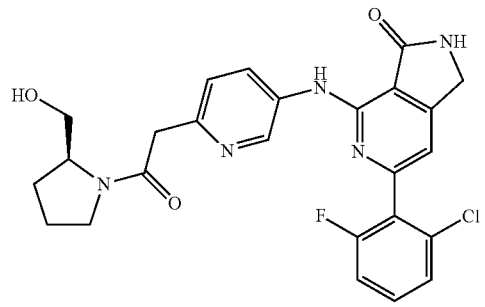 [SMILES: O=C1NCc2cc(-c3c(F)cccc3Cl)nc(Nc3ccc(CC(=O)N4CCC[C@H]4CO)nc3)c21] |
| I-45 | 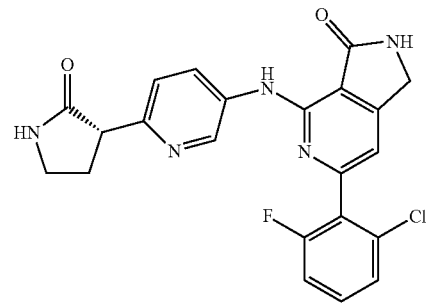 [SMILES: O=C1NCc2cc(-c3c(F)cccc3Cl)nc(Nc3ccc([C@@H]4CCNC4=O)nc3)c21] |
| Compound | Structure |
|---|---|
| I-46 | 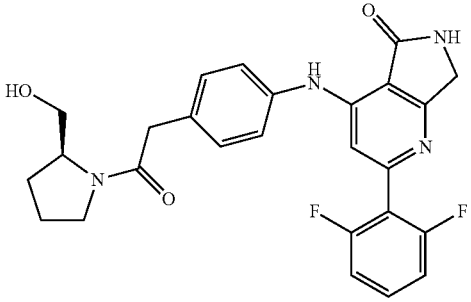 |
| I-47 | 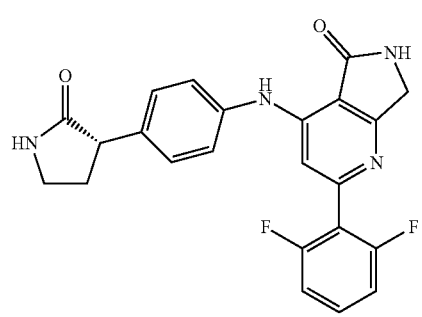 [SMILES: O=C1NCc2nc(-c3c(F)cccc3F)cc(Nc3ccc([C@@H]4CCNC4=O)cc3)c21] |
| I-48 | 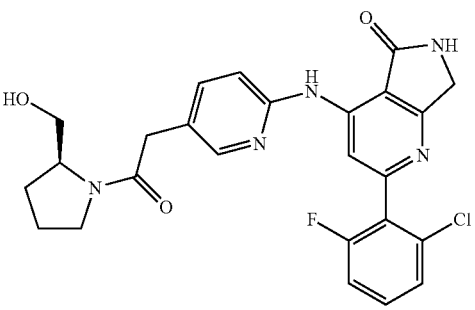 [SMILES: O=C1NCc2nc(-c3c(F)cccc3Cl)cc(Nc3ccc(CC(=O)N4CCC[C@H]4CO)cn3)c21] |
| I-49 | 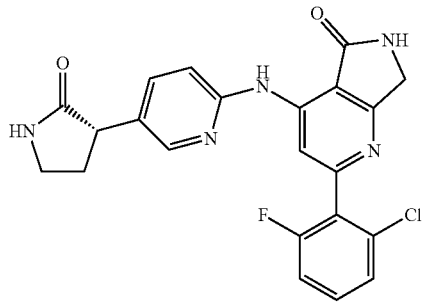 [SMILES: O=C1NCc2nc(-c3c(F)cccc3Cl)cc(Nc3ccc([C@@H]4CCNC4=O)cn3)c21] |
| I-50 | 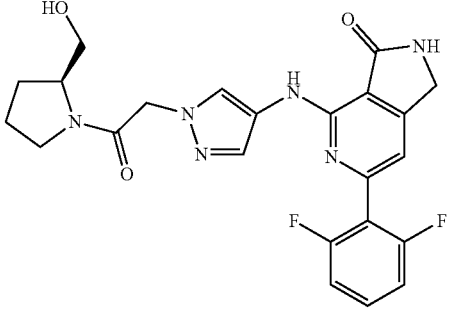 [SMILES: O=C1NCc2cc(-c3c(F)cccc3F)nc(Nc3cnn(CC(=O)N4CCC[C@H]4CO)c3)c21] |

607
-continued
| Compound | Structure |
|---|---|
| I-51 | 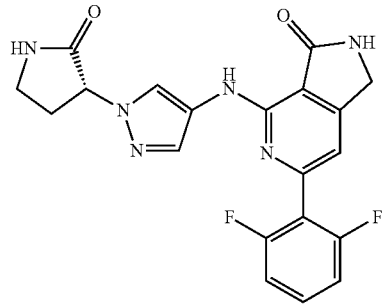 [SMILES: O=C1NCc2cc(-c3c(F)cccc3F)nc(Nc3cnn([C@@H]4CCNC4=O)c3)c21] |
| I-52 | 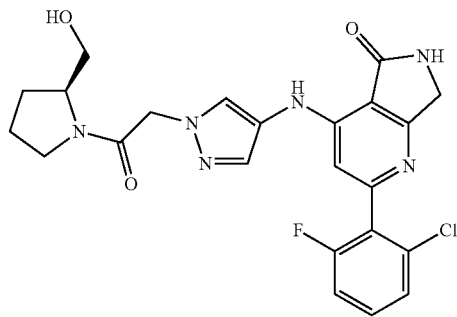 [SMILES: O=C1NCc2nc(-c3c(F)cccc3Cl)cc(Nc3cnn(CC(=O)N4CCC[C@H]4CO)c3)c21] |
| I-53 | 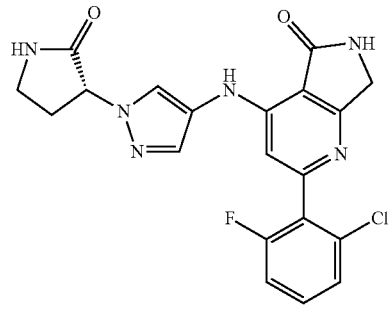 [SMILES: O=C1NCc2nc(-c3c(F)cccc3Cl)cc(Nc3cnn([C@@H]4CCNC4=O)c3)c21] |
| I-54 | 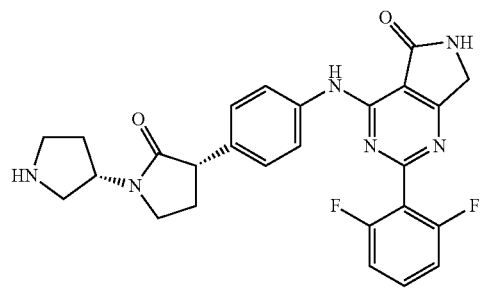 [SMILES: O=C1NCc2nc(-c3c(F)cccc3F)nc(Nc3ccc([C@@H]4CCN([C@H]5CCNC5)C4=O)cc3)c21] |
| I-55 | 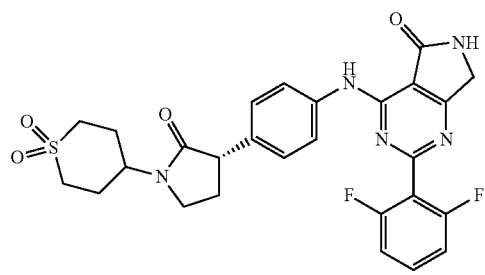 [SMILES: O=C1NCc2nc(-c3c(F)cccc3F)nc(Nc3ccc([C@@H]4CCN(C5CCS(=O)(=O)CC5)C4=O)cc3)c21] |
608
-continued
| Compound | Structure |
|---|---|
| I-56 | 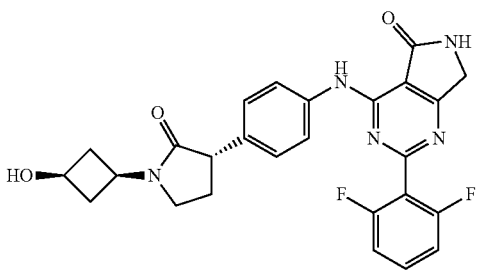 [SMILES: O=C1NCc2nc(-c3c(F)cccc3F)nc(Nc3ccc([C@@H]4CCN([C@H]5C[C@@H](O)C5)C4=O)cc3)c21] |
| I-57 | 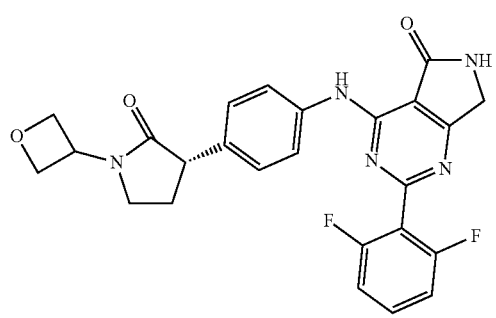 [SMILES: O=C1NCc2nc(-c3c(F)cccc3F)nc(Nc3ccc([C@@H]4CCN(C5COC5)C4=O)cc3)c21] |
| I-58 | 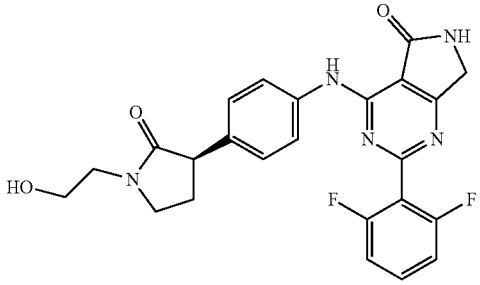 [SMILES: O=C1NCc2nc(-c3c(F)cccc3F)nc(Nc3ccc([C@H]4CCN(CCO)C4=O)cc3)c21] |
| I-59 | 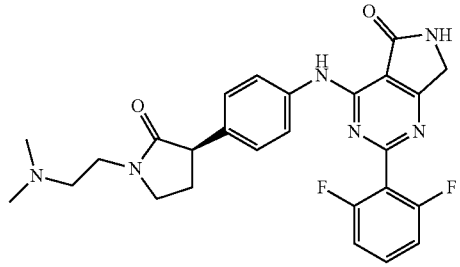 [SMILES: CN(C)CCN1CC[C@H](c2ccc(Nc3nc(-c4c(F)cccc4F)nc4c3C(=O)NC4)cc2)C1=O] |
| I-61 | 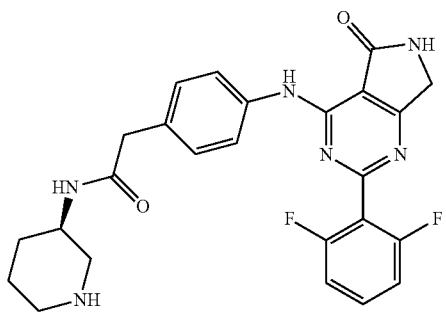 [SMILES: O=C(Cc1ccc(Nc2nc(-c3c(F)cccc3F)nc3c2C(=O)NC3)cc1)N[C@@H]1CCCNC1] |

609
-continued
| Compound | Structure |
|---|---|
| I-62 | 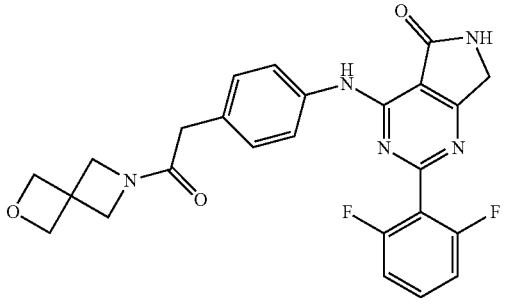 [SMILES: O=C1NCc2nc(-c3c(F)cccc3F)nc(Nc3ccc(CC(=O)N4CC5(COC5)C4)cc3)c21] |
| I-63 | 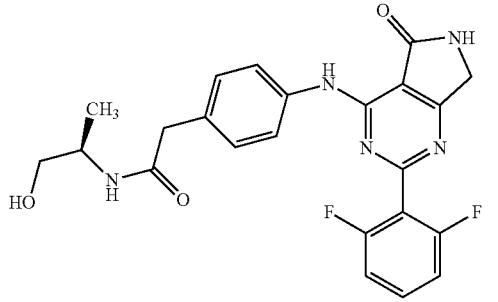 [SMILES: C[C@H](CO)NC(=O)Cc1ccc(Nc2nc(-c3c(F)cccc3F)nc3c2C(=O)NC3)cc1] |
| I-64 | 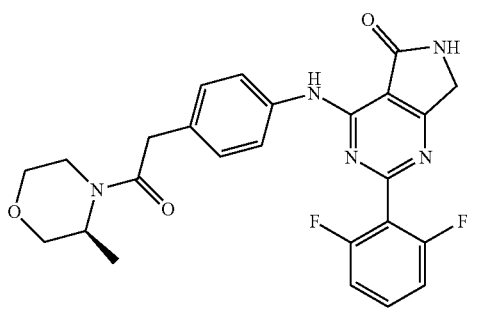 [SMILES: C[C@H]1COCCN1C(=O)Cc1ccc(Nc2nc(-c3c(F)cccc3F)nc3c2C(=O)NC3)cc1] |
| I-65 | 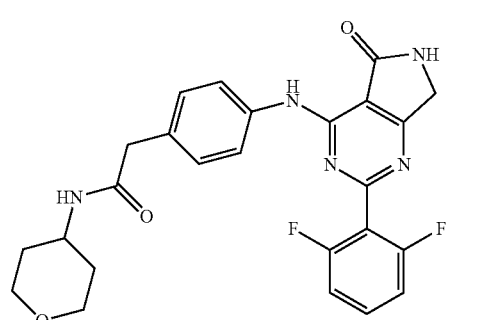 |
| I-66 | 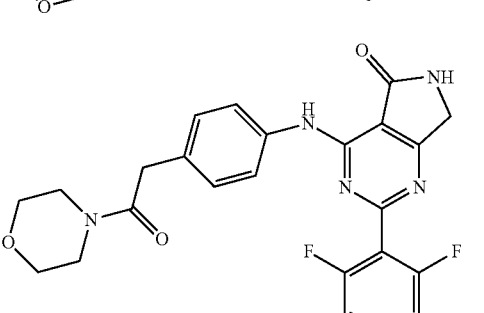 |
610
-continued
| Compound | Structure |
|---|---|
| I-67 | 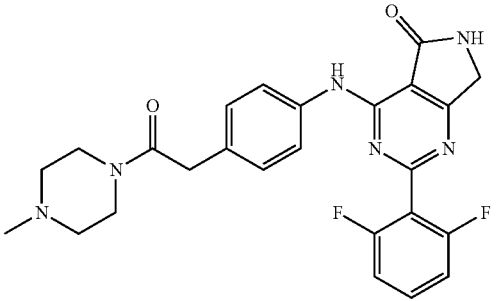 [SMILES: CN1CCN(C(=O)Cc2ccc(Nc3nc(-c4c(F)cccc4F)nc4c3C(=O)NC4)cc2)CC1] |
| I-68 | 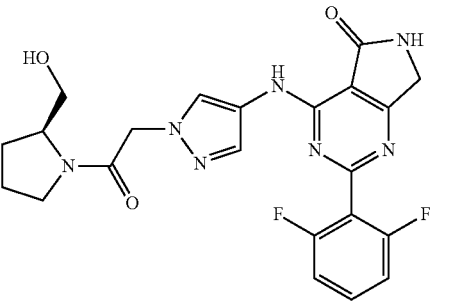 [SMILES: O=C1NCc2nc(-c3c(F)cccc3F)nc(Nc3cnn(CC(=O)N4CCC[C@H]4CO)c3)c21] |
| I-69 | 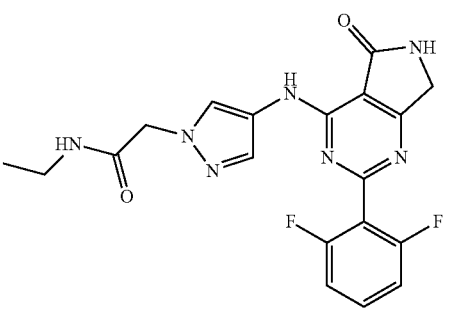 [SMILES: CCNC(=O)Cn1cc(Nc2nc(-c3c(F)cccc3F)nc3c2C(=O)NC3)cn1] |
| I-70 | 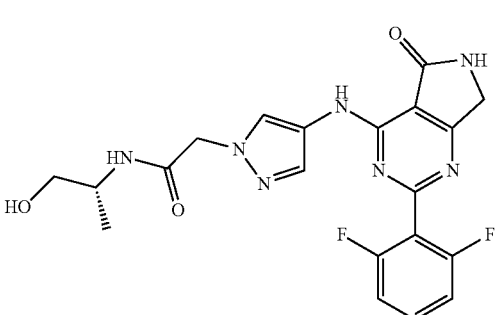 |
| I-71 | 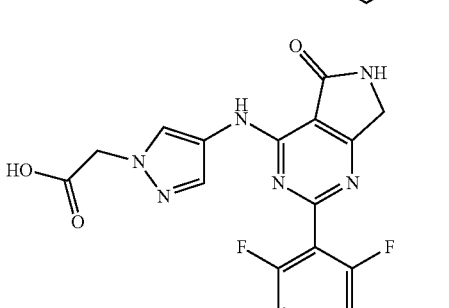 |

| Compound | Structure |
|---|---|
| I-72 | 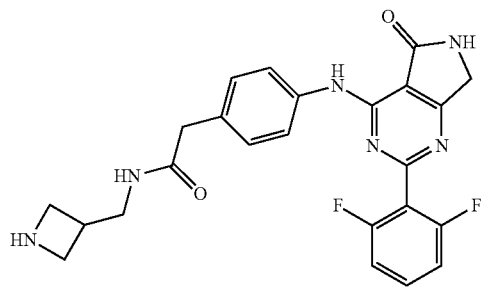 [SMILES: O=C(Cc1ccc(Nc2nc(-c3c(F)cccc3F)nc3c2C(=O)NC3)cc1)NCC1CNC1] |
| I-73 | 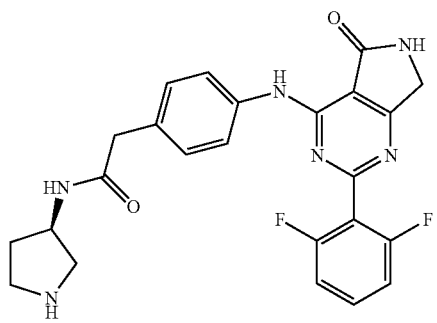 [SMILES: O=C(Cc1ccc(Nc2nc(-c3c(F)cccc3F)nc3c2C(=O)NC3)cc1)N[C@@H]1CCNC1] |
| I-74 | 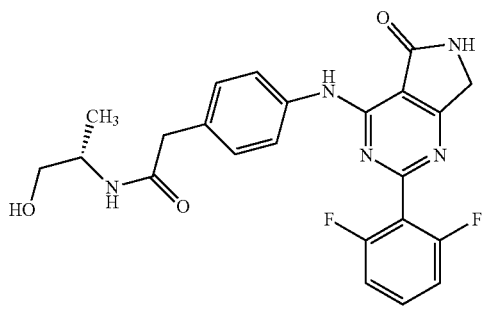 [SMILES: C[C@@H](CO)NC(=O)Cc1ccc(Nc2nc(-c3c(F)cccc3F)nc3c2C(=O)NC3)cc1] |
| I-75 | 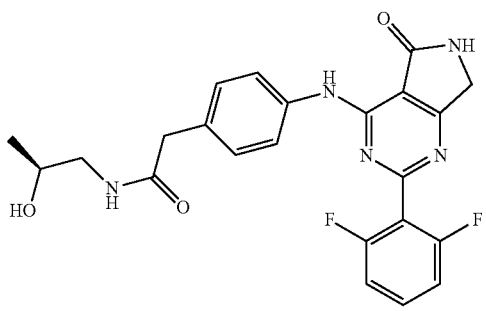 [SMILES: C[C@H](O)CNC(=O)Cc1ccc(Nc2nc(-c3c(F)cccc3F)nc3c2C(=O)NC3)cc1] |
| I-76 | 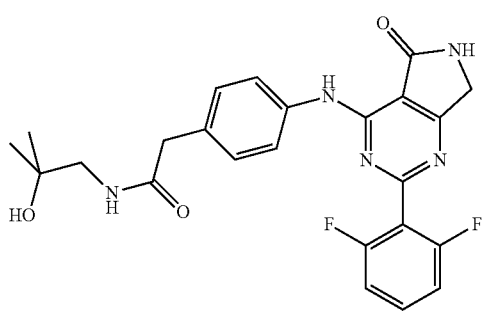 [SMILES: CC(C)(O)CNC(=O)Cc1ccc(Nc2nc(-c3c(F)cccc3F)nc3c2C(=O)NC3)cc1] |
| Compound | Structure |
|---|---|
| I-77 | 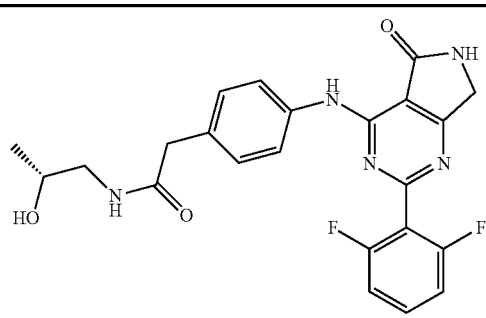 |
| I-78 | 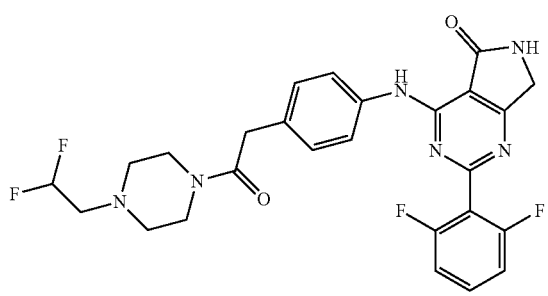 [SMILES: O=C1NCc2nc(-c3c(F)cccc3F)nc(Nc3ccc(CC(=O)N4CCN(CC(F)F)CC4)cc3)c21] |
| I-79 | 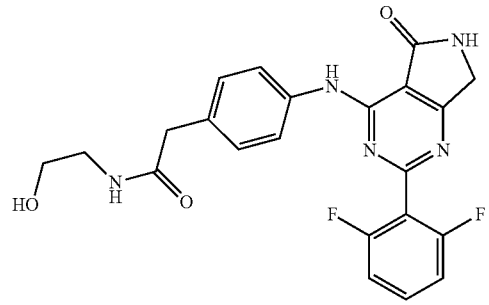 [SMILES: O=C(Cc1ccc(Nc2nc(-c3c(F)cccc3F)nc3c2C(=O)NC3)cc1)NCCO] |
| I-80 | 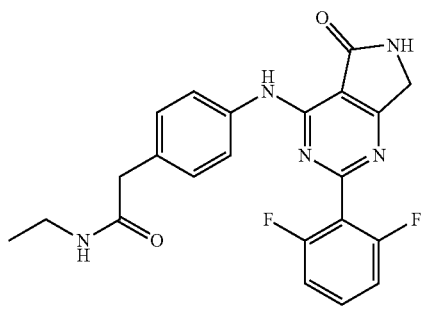 [SMILES: CCNC(=O)Cc1ccc(Nc2nc(-c3c(F)cccc3F)nc3c2C(=O)NC3)cc1] |
| I-81 | 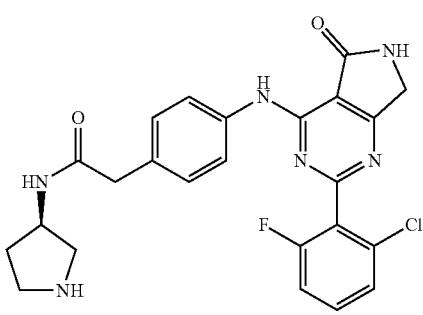 [SMILES: O=C(Cc1ccc(Nc2nc(-c3c(F)cccc3Cl)nc3c2C(=O)NC3)cc1)N[C@@H]1CCNC1] |

| Compound | Structure |
|---|---|
| I-82 | |
| I-83 | |
| I-84 | |
| I-85 | |
| I-86 | |

| Compound | Structure |
|---|---|
| I-87 | |
| I-88 | |
| I-89 | |
| I-90 | |
| I-91 | |

| Compound | Structure |
|---|---|
| I-92 | 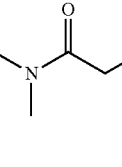 |
| I-93 | 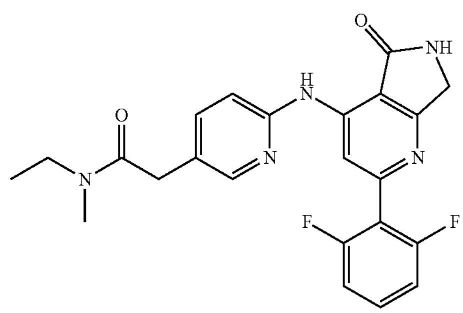 [SMILES: CCN(C)C(=O)Cc1ccc(Nc2cc(-c3c(F)cccc3F)nc3c2C(=O)NC3)nc1] |
| I-94 | 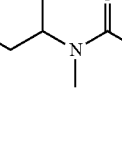 |
| I-95 | 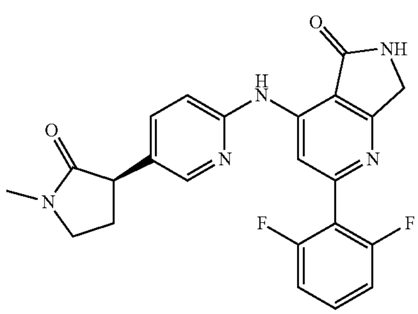 [SMILES: CN1CC[C@H](c2ccc(Nc3cc(-c4c(F)cccc4F)nc4c3C(=O)NC4)nc2)C1=O] |
| I-96 | 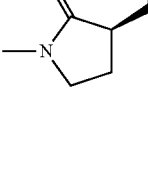 |
| I-97 | |
| I-98 | |
| I-99 | |
| I-100 | |
| I-101 |  |

| Compound | Structure |
|---|---|
| I-102 | 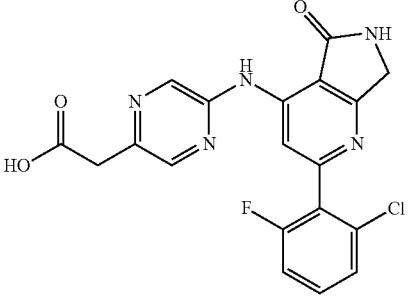 [SMILES: O=C(O)Cc1cnc(Nc2cc(-c3c(F)cccc3Cl)nc3c2C(=O)NC3)cn1] |
| I-103 | 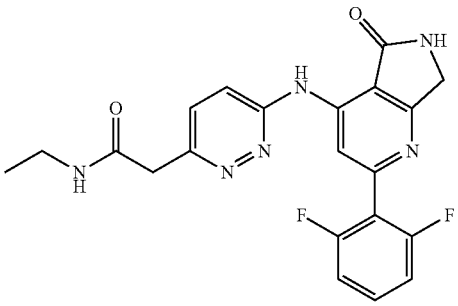 [SMILES: CCNC(=O)Cc1ccc(Nc2cc(-c3c(F)cccc3F)nc3c2C(=O)NC3)nn1] |
| I-104 | 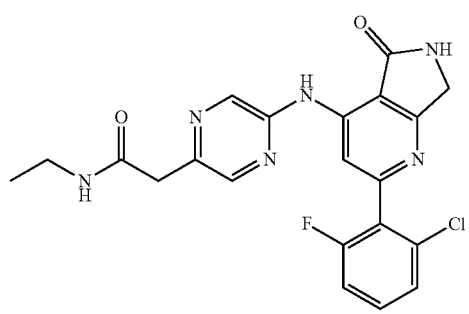 [SMILES: CCNC(=O)Cc1cnc(Nc2cc(-c3c(F)cccc3Cl)nc3c2C(=O)NC3)cn1] |
| I-105 | 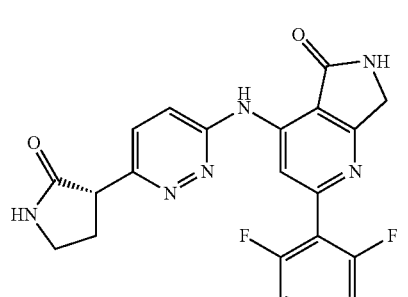 |
| I-106 | 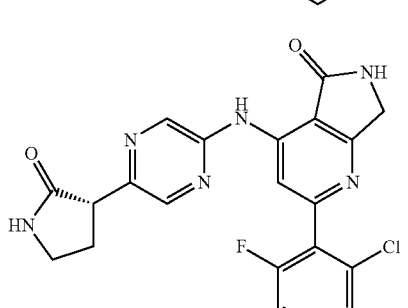 |
| I-107 | 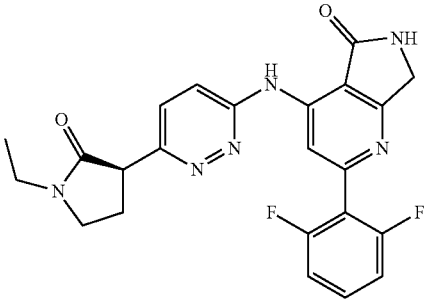 [SMILES: CCN1CC[C@H](c2ccc(Nc3cc(-c4c(F)cccc4F)nc4c3C(=O)NC4)nn2)C1=O] |
| I-108 | 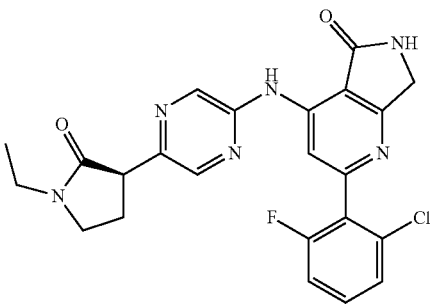 [SMILES: CCN1CC[C@H](c2cnc(Nc3cc(-c4c(F)cccc4Cl)nc4c3C(=O)NC4)cn2)C1=O] |
| I-109 | 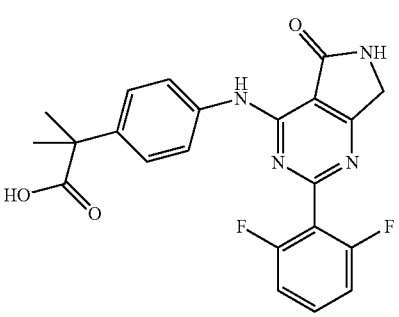 [SMILES: CC(C)(C(=O)O)c1ccc(Nc2nc(-c3c(F)cccc3F)nc3c2C(=O)NC3)cc1] |
| I-110 | 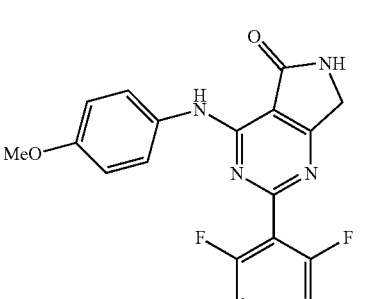 |
| I-111 | 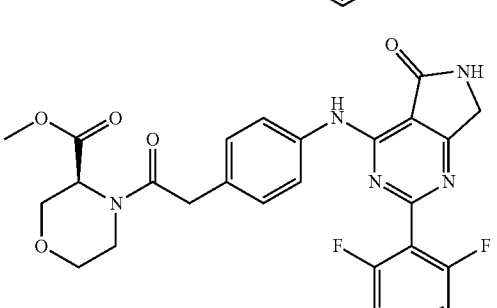 |

-continued

| Compound | Structure |
|---|---|
| I-112 | |
| I-113 | |
| I-114 | |
| I-115 | |
| I-116 | |

-continued

| Compound | Structure |
|---|---|
| I-117 | |
| I-118 | |
| I-119 | |
| I-120 | |
| I-121 | |

| Compound | Structure |
|---|---|
| I-122 | 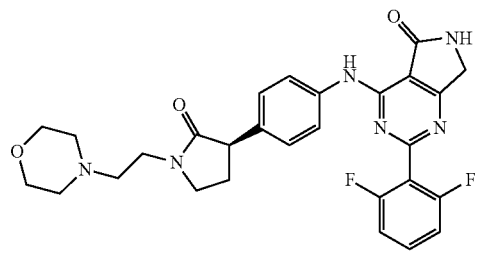 [SMILES: O=C1NCc2nc(-c3c(F)cccc3F)nc(Nc3ccc([C@H]4CCN(CCN5CCOCC5)C4=O)cc3)c21] |
| I-123 | 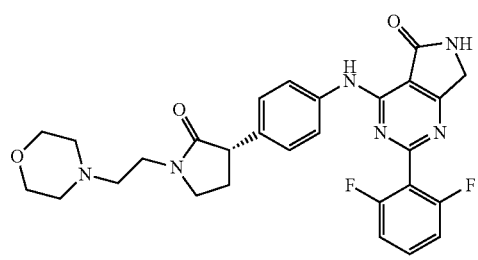 [SMILES: O=C1NCc2nc(-c3c(F)cccc3F)nc(Nc3ccc([C@@H]4CCN(CCN5CCOCC5)C4=O)cc3)c21] |
| I-124 | 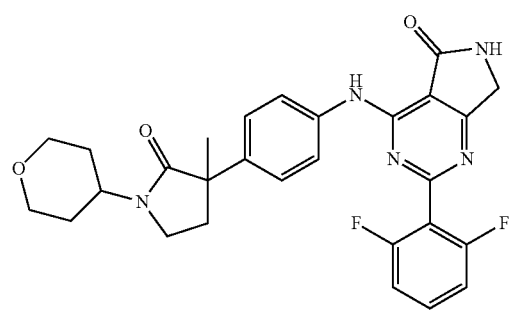 [SMILES: CC1(c2ccc(Nc3nc(-c4c(F)cccc4F)nc4c3C(=O)NC4)cc2)CCN(C2CCOCC2)C1=O] |
| I-125 | 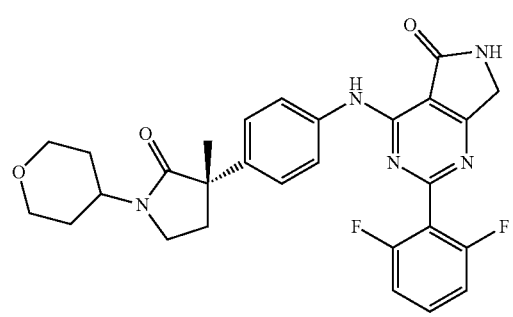 [SMILES: C[C@@]1(c2ccc(Nc3nc(-c4c(F)cccc4F)nc4c3C(=O)NC4)cc2)CCN(C2CCOCC2)C1=O] |
| I-126 | 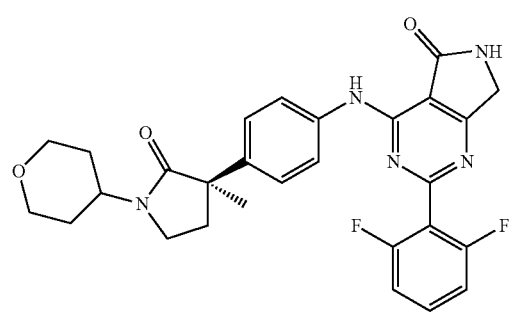 [SMILES: C[C@]1(c2ccc(Nc3nc(-c4c(F)cccc4F)nc4c3C(=O)NC4)cc2)CCN(C2CCOCC2)C1=O] |
| Compound | Structure |
|---|---|
| I-127 | 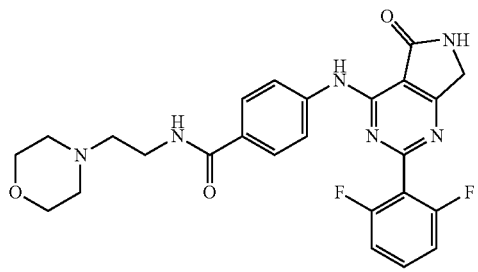 [SMILES: O=C(NCCN1CCOCC1)c1ccc(Nc2nc(-c3c(F)cccc3F)nc3c2C(=O)NC3)cc1] |
| I-128 | 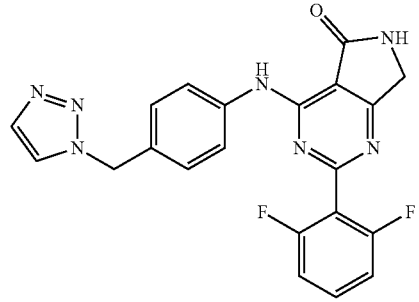 [SMILES: O=C1NCc2nc(-c3c(F)cccc3F)nc(Nc3ccc(Cn4ccnn4)cc3)c21] |
| I-129 | 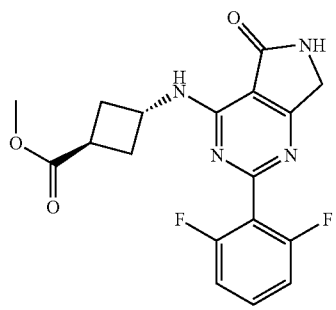 [SMILES: COC(=O)[C@H]1C[C@H](Nc2nc(-c3c(F)cccc3F)nc3c2C(=O)NC3)C1] |
| I-130 | 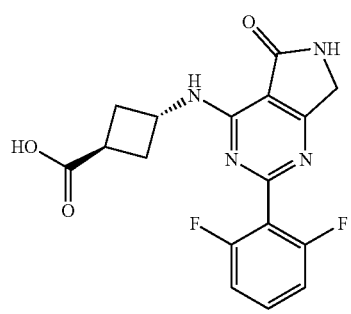 [SMILES: O=C1NCc2nc(-c3c(F)cccc3F)nc(N[C@H]3C[C@H](C(=O)O)C3)c21] |
| I-131 | 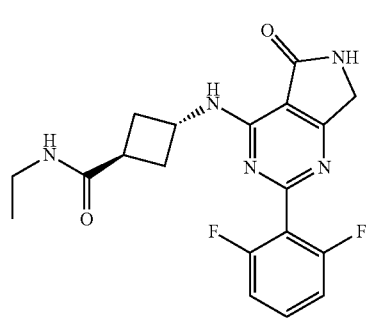 [SMILES: CCNC(=O)[C@H]1C[C@H](Nc2nc(-c3c(F)cccc3F)nc3c2C(=O)NC3)C1] |

-continued
| Compound | Structure |
|---|---|
| I-132 | 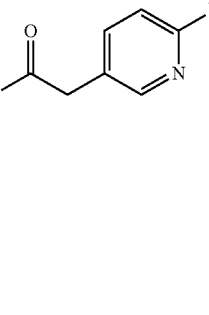 |
| I-133 | |
| I-134 | |
| I-135 | |
-continued
| Compound | Structure |
|---|---|
| I-136 | 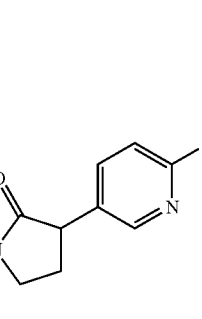 |
| I-137 | |
| I-138 | |
| I-139 | |
| I-140 | |

625
-continued
| Compound | Structure |
|---|---|
| I-141 | 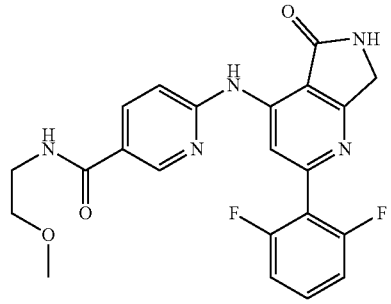 [SMILES: COCCNC(=O)c1ccc(Nc2cc(-c3c(F)cccc3F)nc3c2C(=O)NC3)nc1] |
| I-142 | 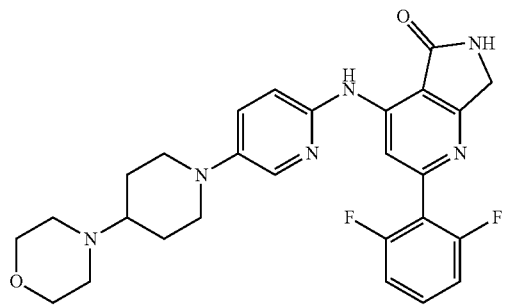 [SMILES: O=C1NCc2nc(-c3c(F)cccc3F)cc(Nc3ccc(N4CCC(N5CCOCC5)CC4)cn3)c21] |
| I-143 | 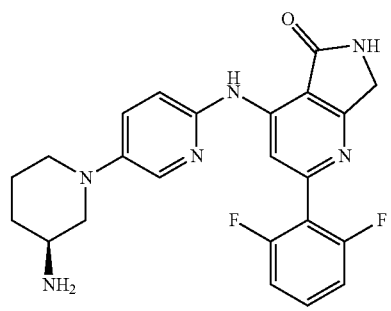 [SMILES: N[C@H]1CCCN(c2ccc(Nc3cc(-c4c(F)cccc4F)nc4c3C(=O)NC4)nc2)C1] |
| I-144 | 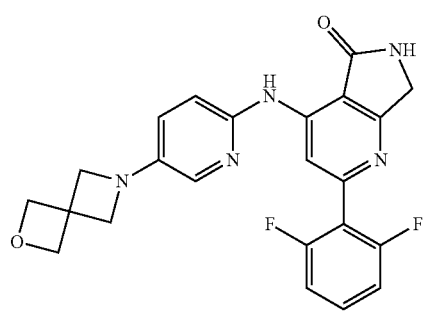 [SMILES: O=C1NCc2nc(-c3c(F)cccc3F)cc(Nc3ccc(N4CC5(COC5)C4)cn3)c21] |
| I-145 | 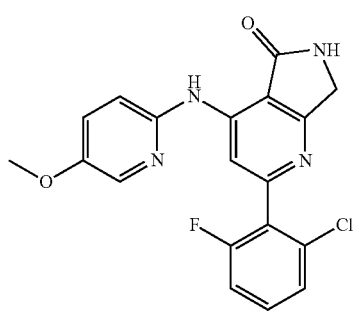 [SMILES: COc1ccc(Nc2cc(-c3c(F)cccc3Cl)nc3c2C(=O)NC3)nc1] |
626
-continued
| Compound | Structure |
|---|---|
| I-146 | 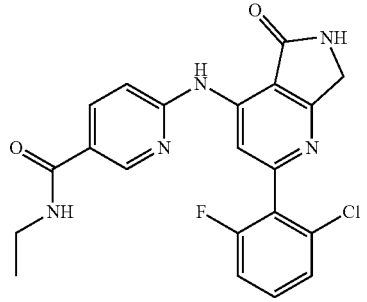 [SMILES: CCNC(=O)c1ccc(Nc2cc(-c3c(F)cccc3Cl)nc3c2C(=O)NC3)nc1] |
| I-147 | 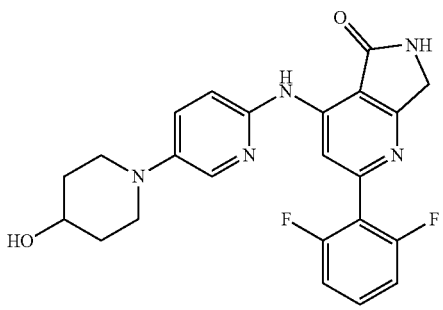 [SMILES: O=C1NCc2nc(-c3c(F)cccc3F)cc(Nc3ccc(N4CCC(O)CC4)cn3)c21] |
| I-148 | 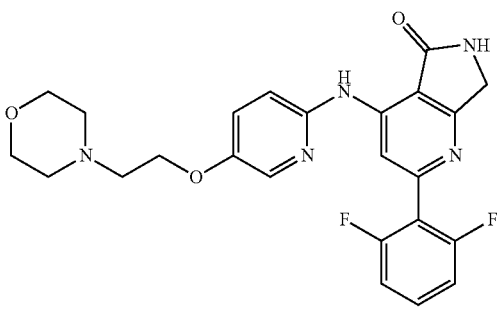 [SMILES: O=C1NCc2nc(-c3c(F)cccc3F)cc(Nc3ccc(OCCN4CCOCC4)cn3)c21] |
| I-149 | 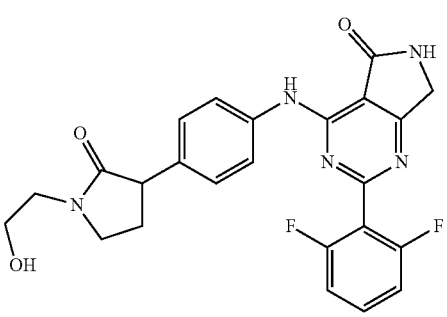 [SMILES: O=C1NCc2nc(-c3c(F)cccc3F)nc(Nc3ccc(C4CCN(CCO)C4=O)cc3)c21] |
| I-150 | 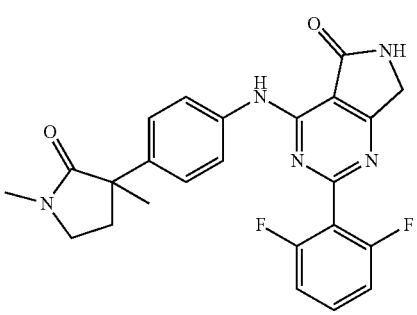 [SMILES: CN1CCC(C)(c2ccc(Nc3nc(-c4c(F)cccc4F)nc4c3C(=O)NC4)cc2)C1=O] |

US 10,196,390 B2
627
-continued
| Compound | Structure |
|---|---|
| I-151 | 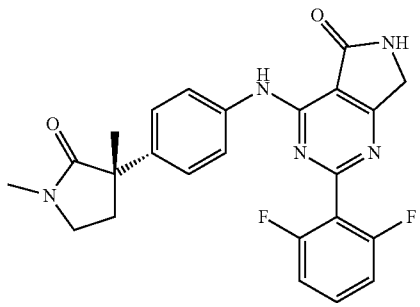 |
| I-152 | 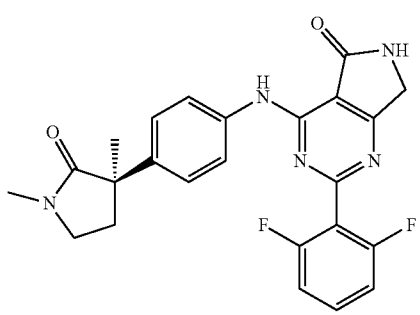 [SMILES: CN1CC[C@](C)(c2ccc(Nc3nc(-c4c(F)cccc4F)nc4c3C(=O)NC4)cc2)C1=O] |
| I-153 | 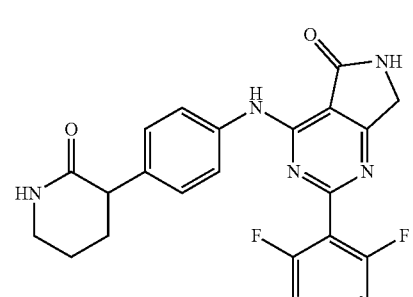 |
| I-154 | 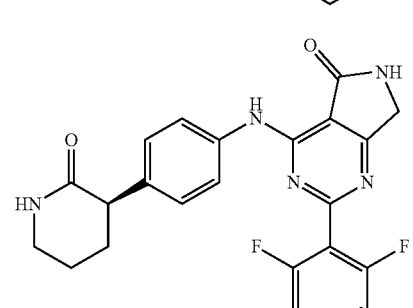 |
| I-155 | 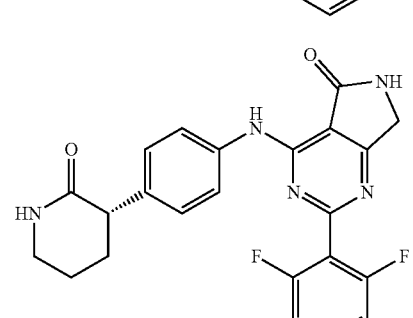 |
628
-continued
| Compound | Structure |
|---|---|
| I-156 | 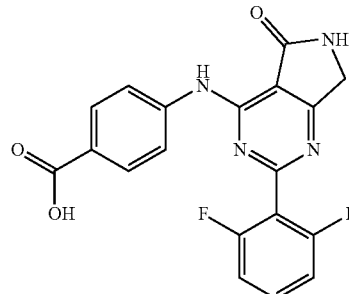 |
| I-157 | 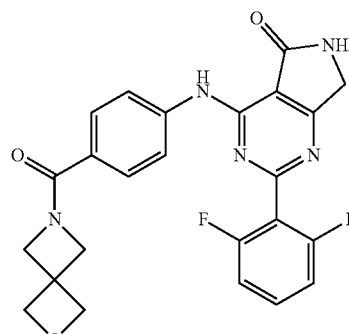 |
| I-158 | 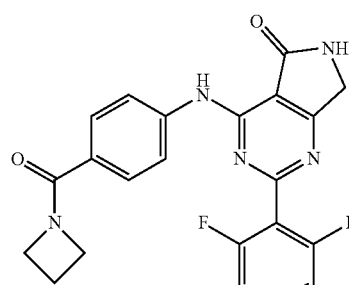 |
| I-159 | 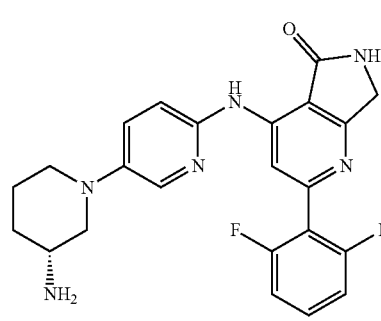 |
| I-160 | 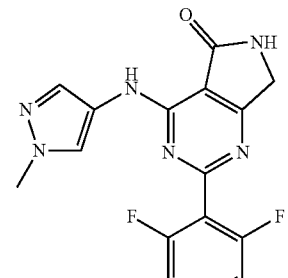 |

| Compound | Structure |
|---|---|
| I-161 | 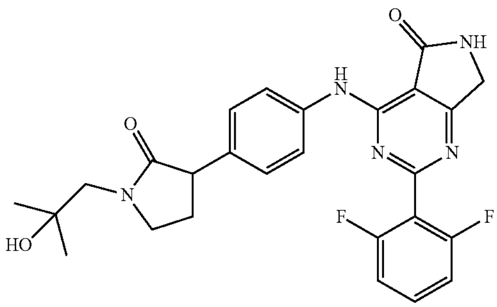 [SMILES: CC(C)(O)CN1CCC(c2ccc(Nc3nc(-c4c(F)cccc4F)nc4c3C(=O)NC4)cc2)C1=O] |
| I-162 | 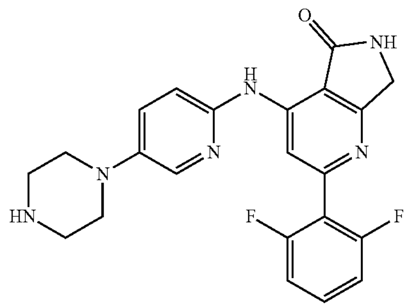 [SMILES: O=C1NCc2nc(-c3c(F)cccc3F)cc(Nc3ccc(N4CCNCC4)cn3)c21] |
| I-163 | 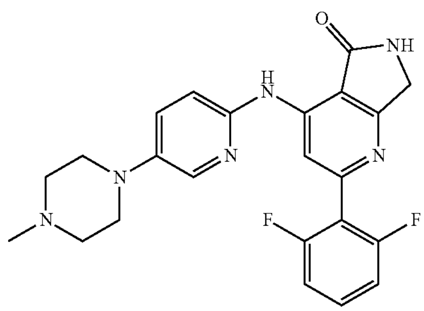 [SMILES: CN1CCN(c2ccc(Nc3cc(-c4c(F)cccc4F)nc4c3C(=O)NC4)nc2)CC1] |
| I-164 | 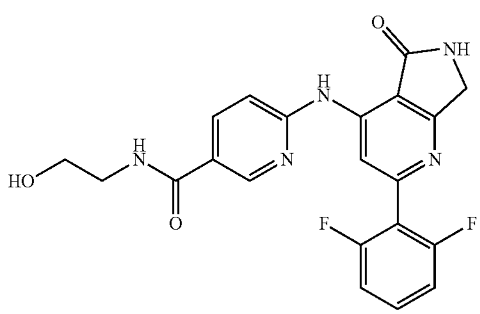 [SMILES: O=C(NCCO)c1ccc(Nc2cc(-c3c(F)cccc3F)nc3c2C(=O)NC3)nc1] |
| I-165 | 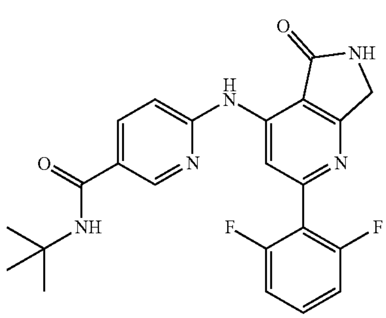 [SMILES: CC(C)(C)NC(=O)c1ccc(Nc2cc(-c3c(F)cccc3F)nc3c2C(=O)NC3)nc1] |
| I-166 | |
| I-167 | |
| I-168 | |
| I-169 | |
| I-170 | |

| Compound | Structure |
|---|---|
| I-171 | 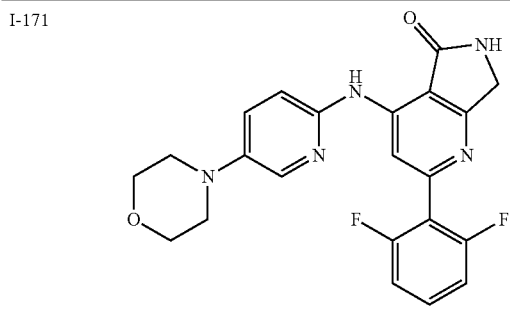 |
| I-172 | 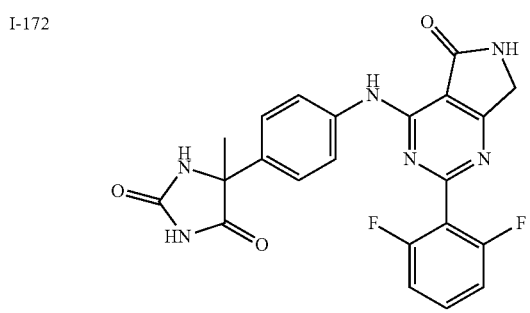 |
| I-173 | 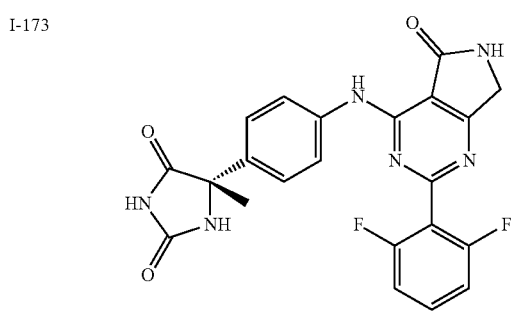 |
| I-174 | 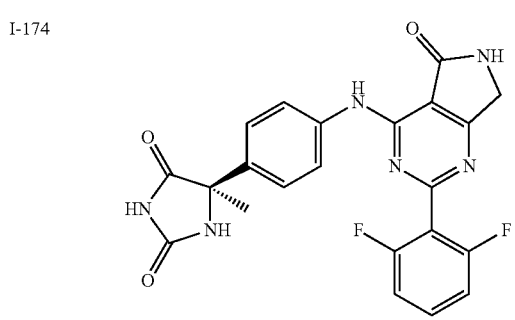 |
| I-175 | 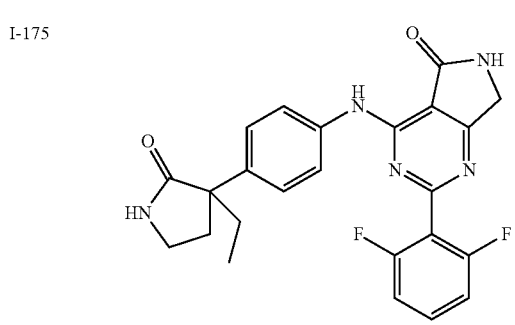 |
| I-176 | 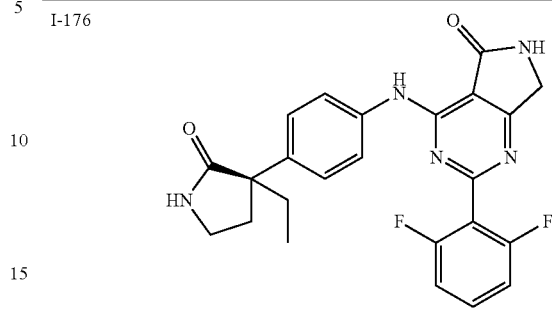 |
| I-177 | 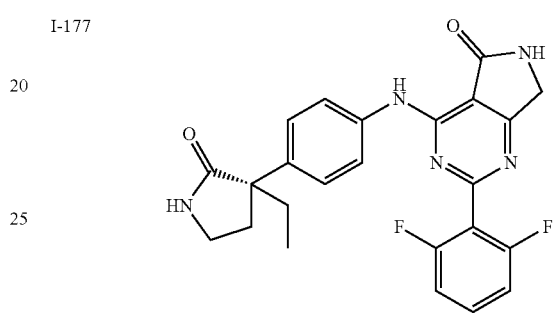 |
| I-178 | 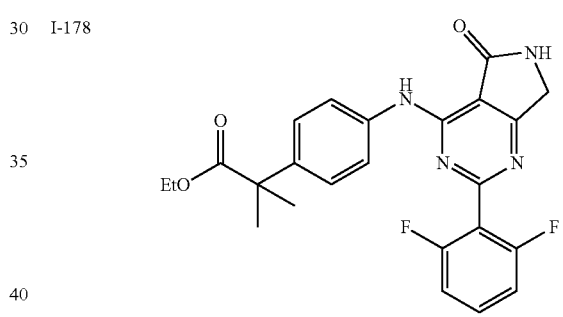 |
| I-179 | 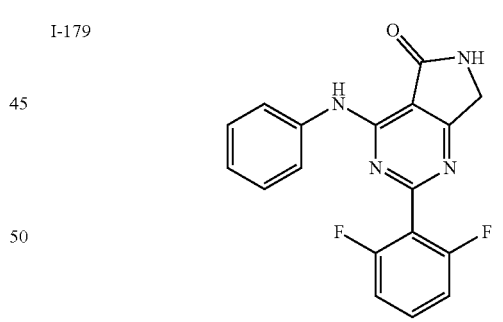 |
| I-180 | 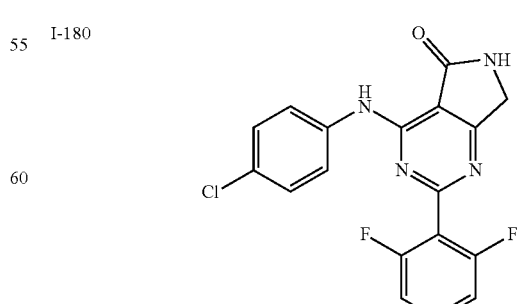 |

| Compound | Structure |
|---|---|
| I-181 | 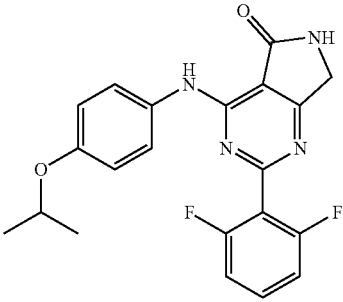 [SMILES: CC(C)Oc1ccc(Nc2nc(-c3c(F)cccc3F)nc3c2C(=O)NC3)cc1] |
| I-182 | 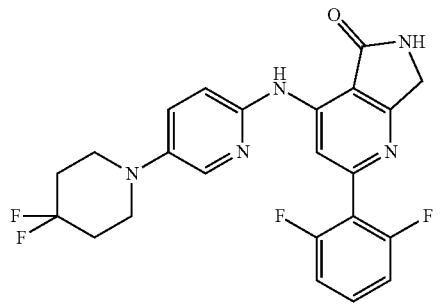 [SMILES: O=C1NCc2nc(-c3c(F)cccc3F)cc(Nc3ccc(N4CCC(F)(F)CC4)cn3)c21] |
| I-183 | 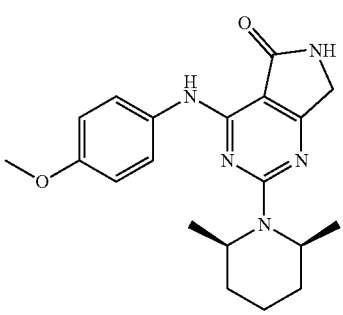 |
| I-184 | 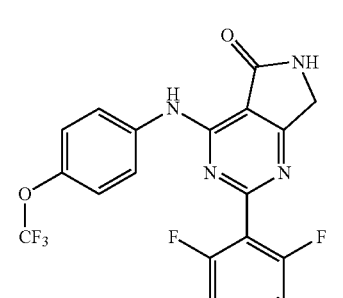 |
| I-185 | 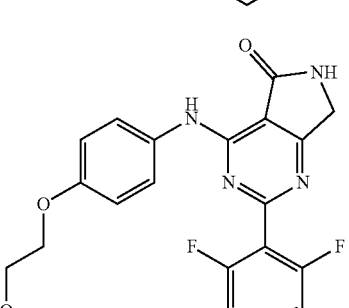 |
| I-186 | 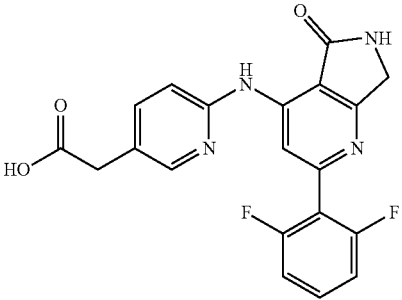 [SMILES: O=C(O)Cc1ccc(Nc2cc(-c3c(F)cccc3F)nc3c2C(=O)NC3)nc1] |
| I-187 | 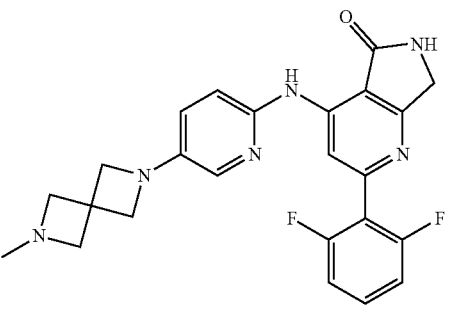 [SMILES: CN1CC2(C1)CN(c1ccc(Nc3cc(-c4c(F)cccc4F)nc4c3C(=O)NC4)nc1)C2] |
| I-188 | 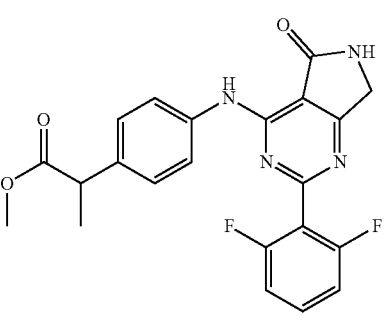 [SMILES: COC(=O)C(C)c1ccc(Nc2nc(-c3c(F)cccc3F)nc3c2C(=O)NC3)cc1] |
| I-189 | 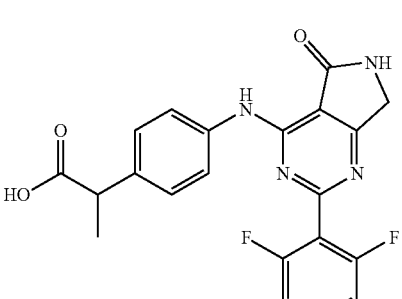 |
| I-190 | 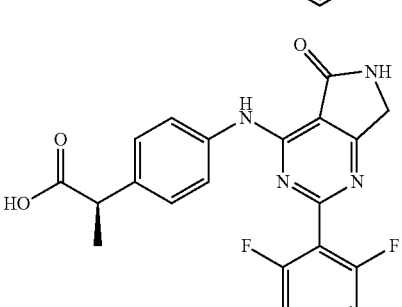 |

| Compound | Structure |
|---|---|
| I-191 | 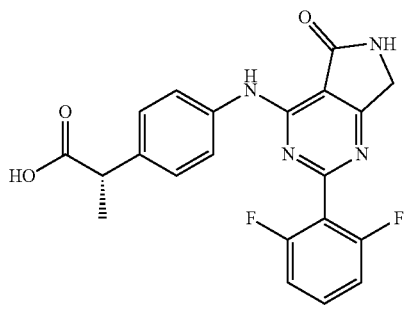 [SMILES: C[C@H](C(=O)O)c1ccc(Nc2nc(-c3c(F)cccc3F)nc3c2C(=O)NC3)cc1] |
| I-192 | 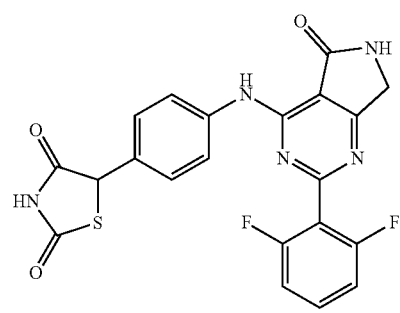 [SMILES: O=C1NC(=O)C(c2ccc(Nc3nc(-c4c(F)cccc4F)nc4c3C(=O)NC4)cc2)S1] |
| I-193 | 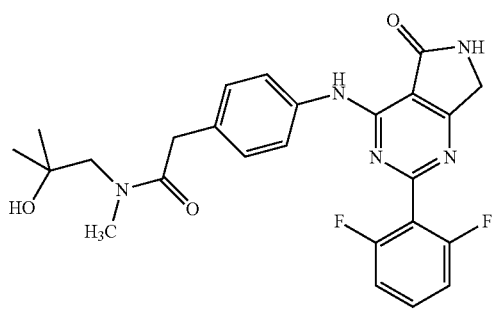 [SMILES: CN(CC(C)(C)O)C(=O)Cc1ccc(Nc2nc(-c3c(F)cccc3F)nc3c2C(=O)NC3)cc1] |
| I-194 | 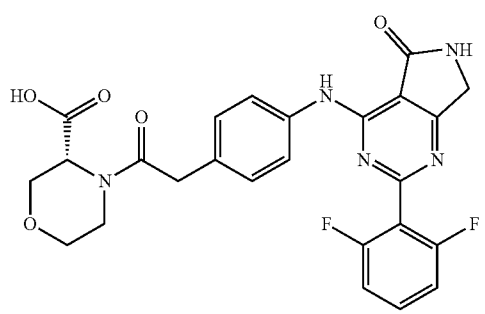 [SMILES: O=C1NCc2nc(-c3c(F)cccc3F)nc(Nc3ccc(CC(=O)N4CCOC[C@@H]4C(=O)O)cc3)c21] |
| I-195 | 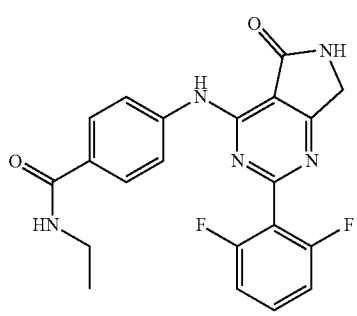 [SMILES: CCNC(=O)c1ccc(Nc2nc(-c3c(F)cccc3F)nc3c2C(=O)NC3)cc1] |
| Compound | Structure |
|---|---|
| I-196 | 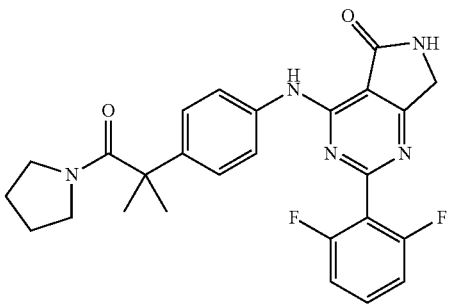 [SMILES: CC(C)(C(=O)N1CCCC1)c1ccc(Nc2nc(-c3c(F)cccc3F)nc3c2C(=O)NC3)cc1] |
| I-197 | 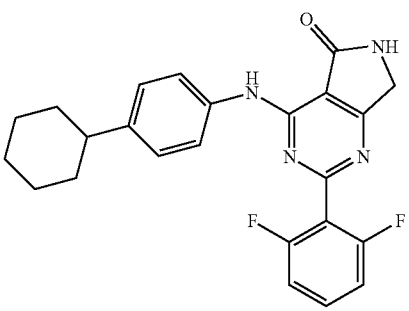 [SMILES: O=C1NCc2nc(-c3c(F)cccc3F)nc(Nc3ccc(C4CCCCC4)cc3)c21] |
| I-198 | 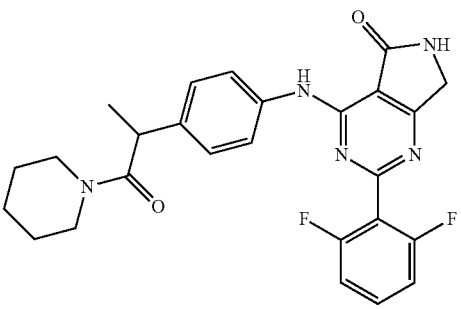 [SMILES: CC(C(=O)N1CCCCC1)c1ccc(Nc2nc(-c3c(F)cccc3F)nc3c2C(=O)NC3)cc1] |
| I-199 | 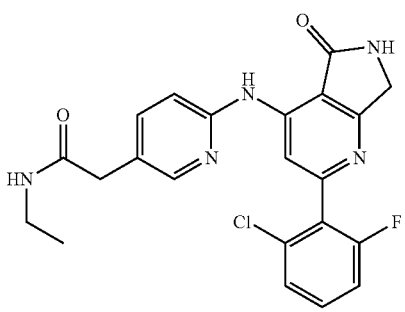 [SMILES: CCNC(=O)Cc1ccc(Nc2cc(-c3c(F)cccc3Cl)nc3c2C(=O)NC3)nc1] |
| I-200 | 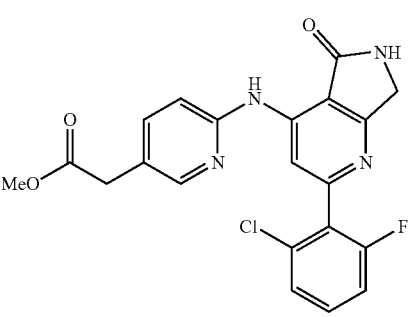 [SMILES: COC(=O)Cc1ccc(Nc2cc(-c3c(F)cccc3Cl)nc3c2C(=O)NC3)nc1] |

-continued

| Compound | Structure |
|---|---|
| I-201 | 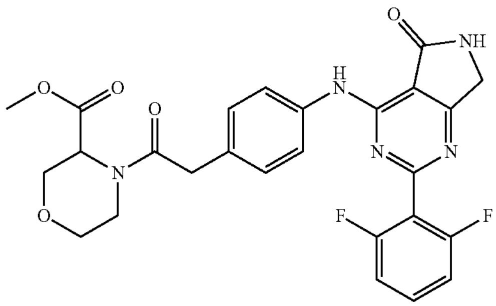 [SMILES: COC(=O)C1COCCN1C(=O)Cc1ccc(Nc2nc(-c3c(F)cccc3F)nc3c2C(=O)NC3)cc1] |
| I-202 | 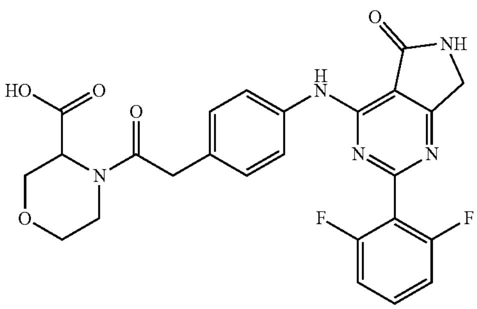 [SMILES: O=C1NCc2nc(-c3c(F)cccc3F)nc(Nc3ccc(CC(=O)N4CCOCC4C(=O)O)cc3)c21] |
| I-203 | 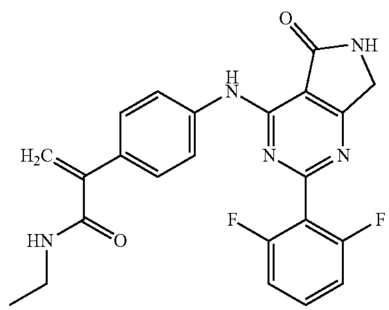 [SMILES: C=C(C(=O)NCC)c1ccc(Nc2nc(-c3c(F)cccc3F)nc3c2C(=O)NC3)cc1] |
| I-204 | 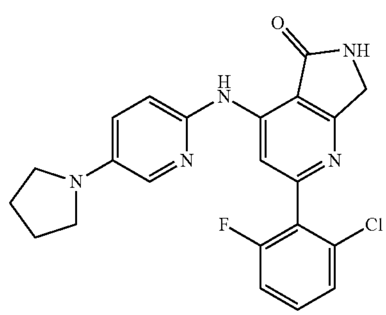 [SMILES: O=C1NCc2nc(-c3c(F)cccc3Cl)cc(Nc3ccc(N4CCCC4)cn3)c21] |
| I-205 | 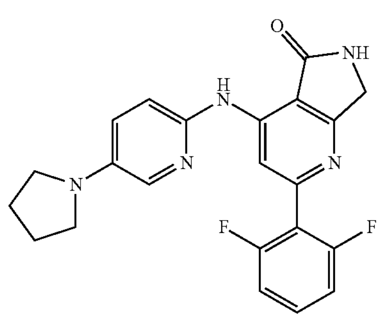 [SMILES: O=C1NCc2nc(-c3c(F)cccc3F)cc(Nc3ccc(N4CCCC4)cn3)c21] |

-continued

| Compound | Structure |
|---|---|
| I-206 | 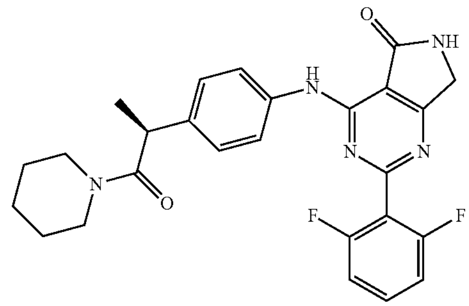 [SMILES: C[C@H](C(=O)N1CCCCC1)c1ccc(Nc2nc(-c3c(F)cccc3F)nc3c2C(=O)NC3)cc1] |
| I-207 | 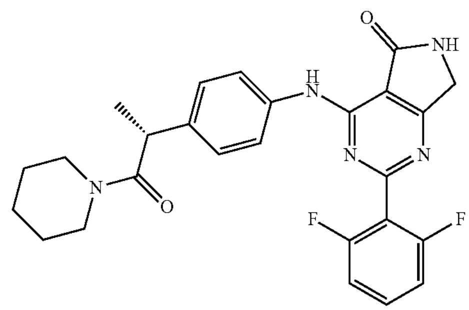 |
| I-208 | 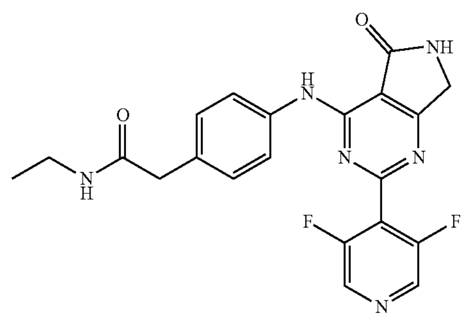 [SMILES: CCNC(=O)Cc1ccc(Nc2nc(-c3c(F)cncc3F)nc3c2C(=O)NC3)cc1] |
| I-209 | 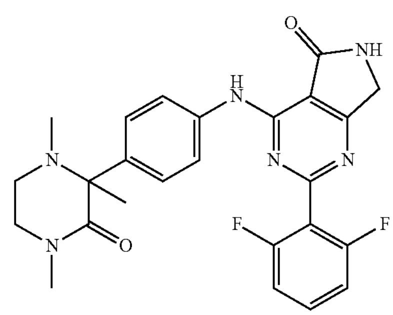 [SMILES: CN1CCN(C)C(C)(c2ccc(Nc3nc(-c4c(F)cccc4F)nc4c3C(=O)NC4)cc2)C1=O] |
| I-210 | 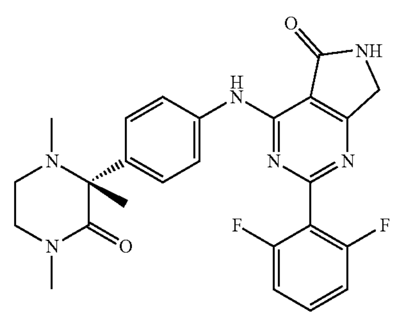 [SMILES: CN1CCN(C)[C@](C)(c2ccc(Nc3nc(-c4c(F)cccc4F)nc4c3C(=O)NC4)cc2)C1=O] |

639
-continued

| Compound | Structure |
|---|---|
| I-211 | 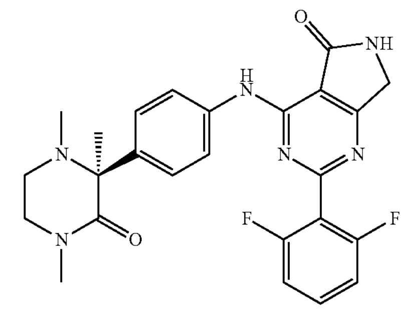 [SMILES: CN1CCN(C)[C@@](C)(c2ccc(Nc3nc(-c4c(F)cccc4F)nc4c3C(=O)NC4)cc2)C1=O] |
| I-212 | 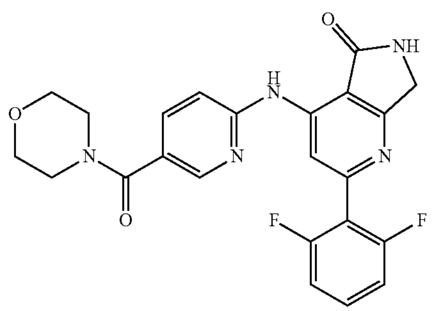 |
| I-213 | 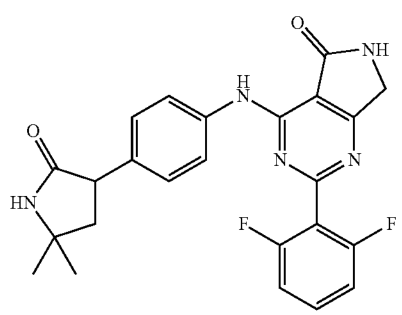 |
| I-214 | 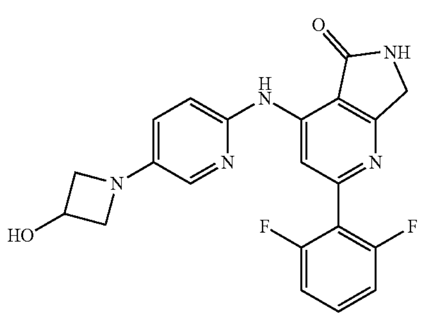 [SMILES: O=C1NCc2nc(-c3c(F)cccc3F)cc(Nc3ccc(N4CC(O)C4)cn3)c21] |
| I-215 | 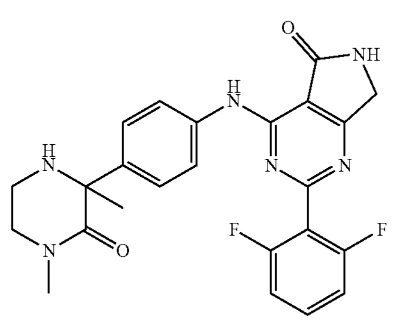 [SMILES: CN1CCNC(C)(c2ccc(Nc3nc(-c4c(F)cccc4F)nc4c3C(=O)NC4)cc2)C1=O] |

640
-continued

| Compound | Structure |
|---|---|
| I-216 | |
| I-217 | |
| I-218 | |
| I-219 | |
| I-220 | |

| Compound | Structure |
|---|---|
| I-221 | 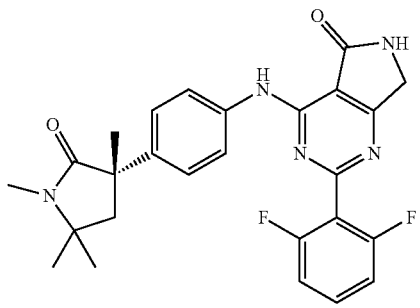 [SMILES: CN1C(=O)[C@](C)(c2ccc(Nc3nc(-c4c(F)cccc4F)nc4c3C(=O)NC4)cc2)CC1(C)C] |
| I-222 | 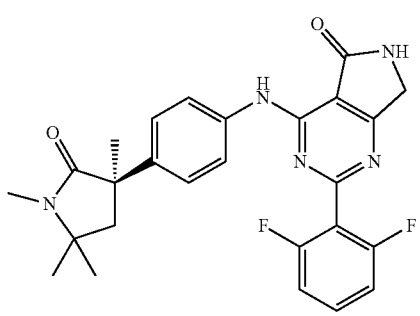 [SMILES: CN1C(=O)[C@@](C)(c2ccc(Nc3nc(-c4c(F)cccc4F)nc4c3C(=O)NC4)cc2)CC1(C)C] |
| I-223 | 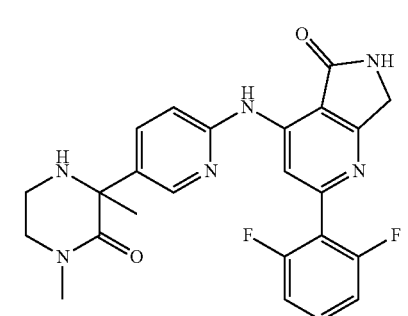 |
| I-224 | 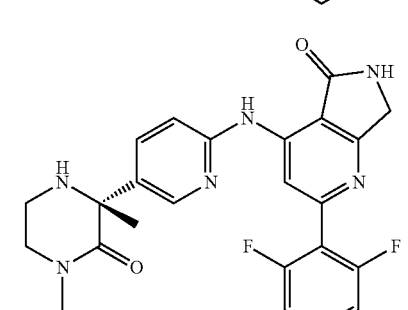 |
| I-225 | 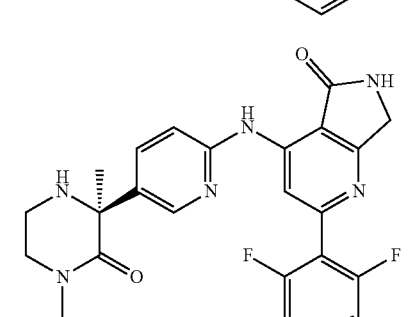 |
| I-226 | 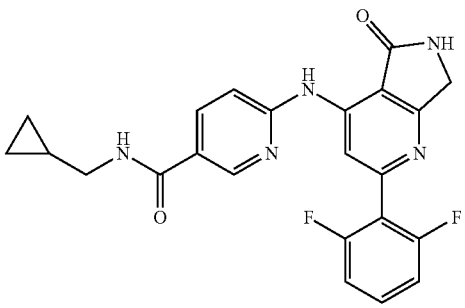 [SMILES: O=C(NCC1CC1)c1ccc(Nc2cc(-c3c(F)cccc3F)nc3c2C(=O)NC3)nc1] |
| I-227 | 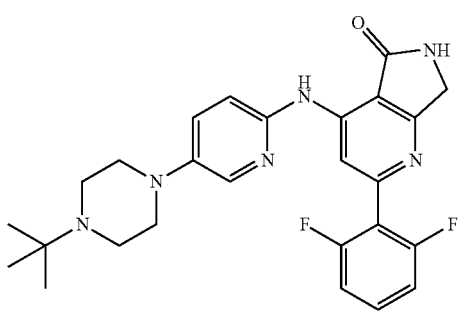 [SMILES: CC(C)(C)N1CCN(c2ccc(Nc3cc(-c4c(F)cccc4F)nc4c3C(=O)NC4)nc2)CC1] |
| I-228 | 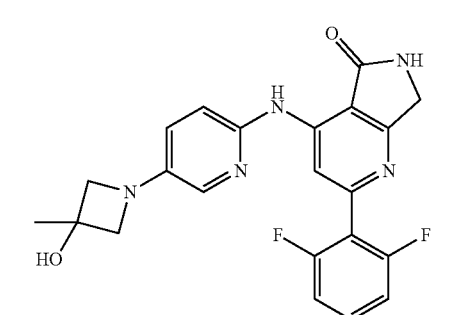 |
| I-229 | 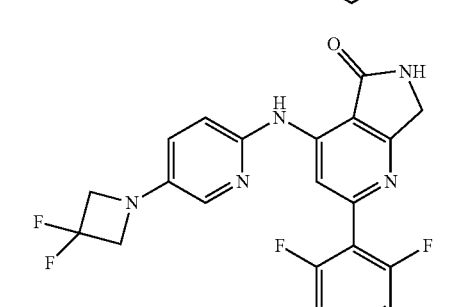 |
| I-230 | 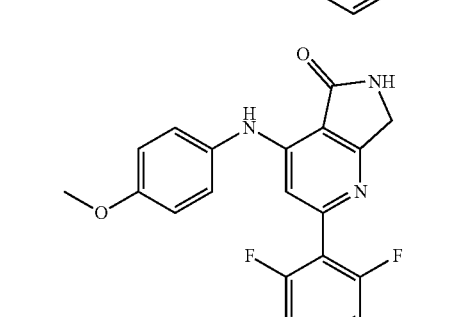 |

643
-continued
| Compound | Structure |
|---|---|
| I-231 | 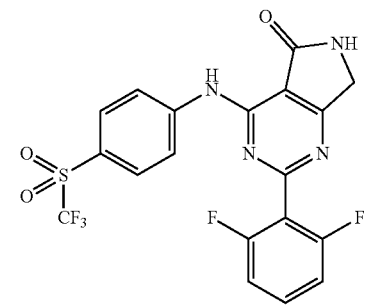 |
| I-232 | 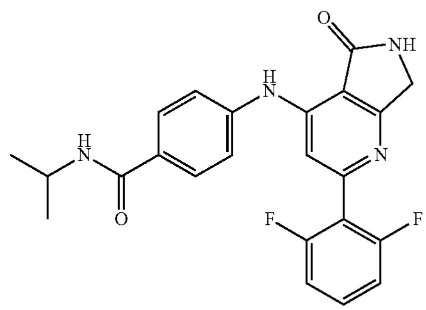 [SMILES: CC(C)NC(=O)c1ccc(Nc2cc(-c3c(F)cccc3F)nc3c2C(=O)NC3)cc1] |
| I-233 | 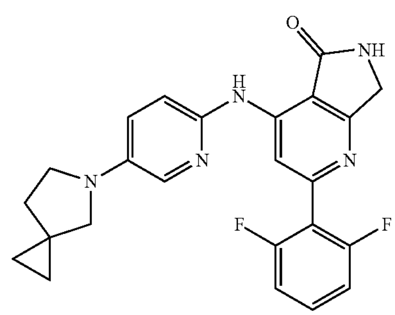 [SMILES: O=C1NCc2nc(-c3c(F)cccc3F)cc(Nc3ccc(N4CCC5(CC5)C4)cn3)c21] |
| I-234 | 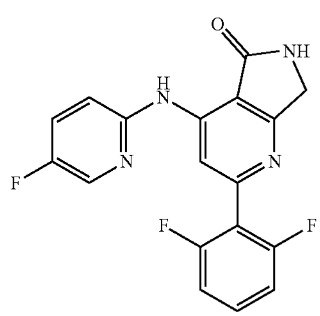 [SMILES: O=C1NCc2nc(-c3c(F)cccc3F)cc(Nc3ccc(F)cn3)c21] |
| I-235 | 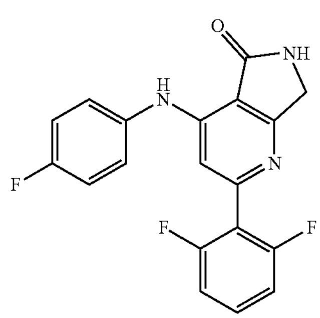 [SMILES: O=C1NCc2nc(-c3c(F)cccc3F)cc(Nc3ccc(F)cc3)c21] |
644
-continued
| Compound | Structure |
|---|---|
| I-236 | 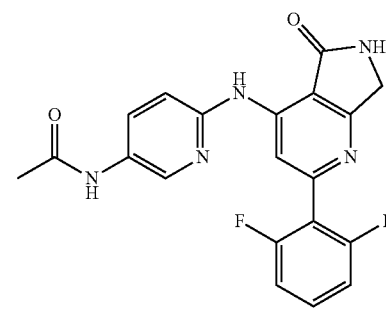 |
| I-237 | 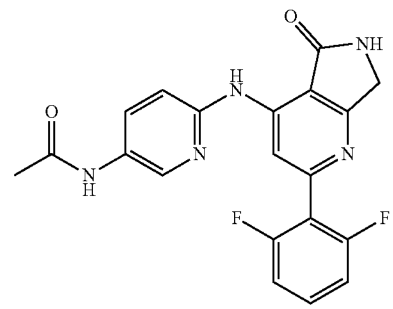 [SMILES: CC(=O)Nc1ccc(Nc2cc(-c3c(F)cccc3F)nc3c2C(=O)NC3)nc1] |
| I-238 | 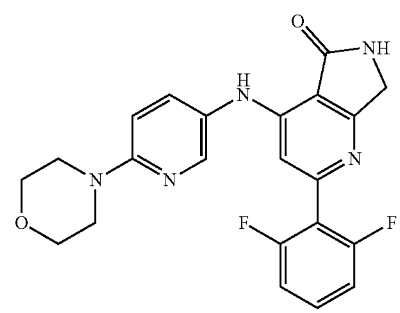 [SMILES: O=C1NCc2nc(-c3c(F)cccc3F)cc(Nc3ccc(N4CCOCC4)nc3)c21] |
| I-242 | 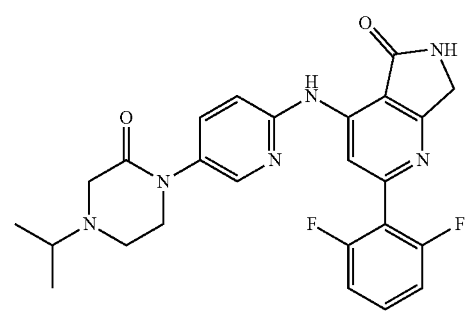 [SMILES: CC(C)N1CCN(c2ccc(Nc3cc(-c4c(F)cccc4F)nc4c3C(=O)NC4)nc2)C(=O)C1] |
| I-243 | 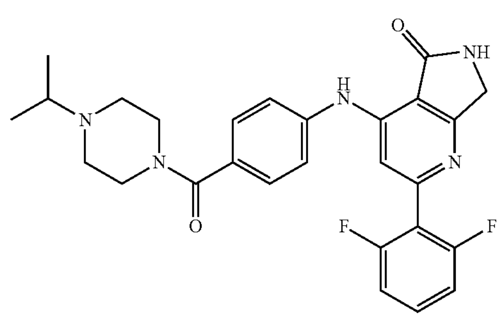 [SMILES: CC(C)N1CCN(C(=O)c2ccc(Nc3cc(-c4c(F)cccc4F)nc4c3C(=O)NC4)cc2)CC1] |

| Compound | Structure |
|---|---|
| I-244 | 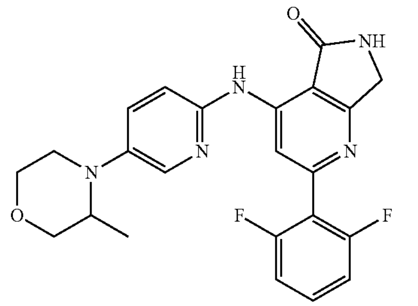 [SMILES: CC1COCCN1c1ccc(Nc2cc(-c3c(F)cccc3F)nc3c2C(=O)NC3)nc1] |
| I-245 | 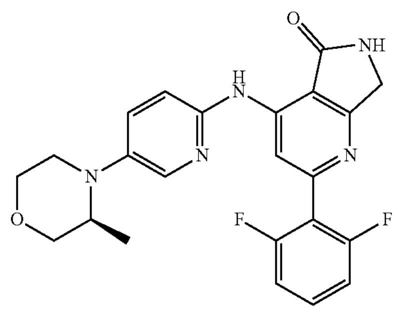 [SMILES: C[C@H]1COCCN1c1ccc(Nc2cc(-c3c(F)cccc3F)nc3c2C(=O)NC3)nc1] |
| I-246 | 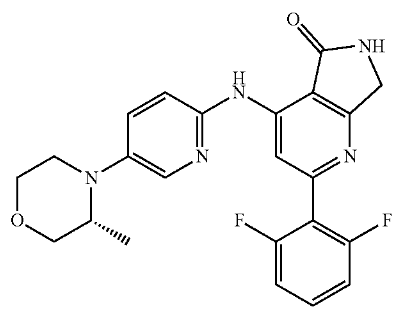 [SMILES: C[C@@H]1COCCN1c1ccc(Nc2cc(-c3c(F)cccc3F)nc3c2C(=O)NC3)nc1] |
| I-247 | 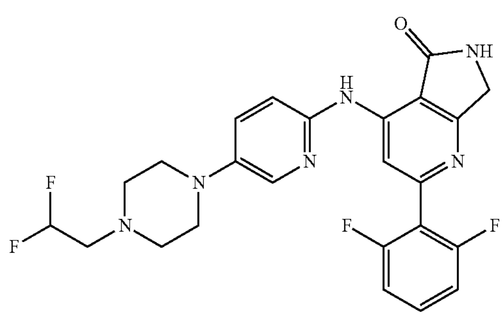 [SMILES: O=C1NCc2nc(-c3c(F)cccc3F)cc(Nc3ccc(N4CCN(CC(F)F)CC4)cn3)c21] |
| I-248 | 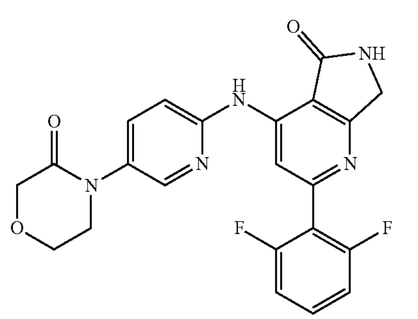 [SMILES: O=C1NCc2nc(-c3c(F)cccc3F)cc(Nc3ccc(N4CCOCC4=O)cn3)c21] |
| I-249 | |
| I-250 | |
| I-251 | |
| I-252 | |

-continued

| Compound | Structure |
|---|---|
| I-253 | 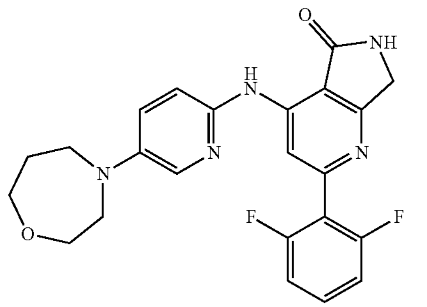 [SMILES: O=C1NCc2nc(-c3c(F)cccc3F)cc(Nc3ccc(N4CCCOCC4)cn3)c21] |
| I-254 | 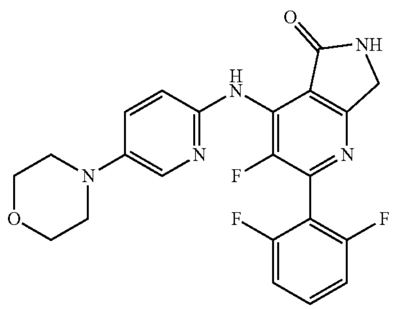 [SMILES: O=C1NCc2nc(-c3c(F)cccc3F)c(F)c(Nc3ccc(N4CCOCC4)cn3)c21] |
| I-255 | 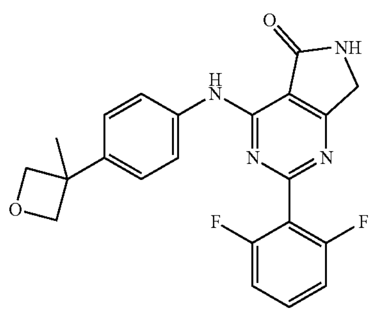 [SMILES: CC1(c2ccc(Nc3nc(-c4c(F)cccc4F)nc4c3C(=O)NC4)cc2)COC1] |
| I-256 | 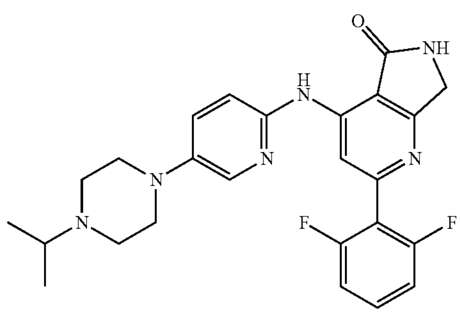 [SMILES: CC(C)N1CCN(c2ccc(Nc3cc(-c4c(F)cccc4F)nc4c3C(=O)NC4)nc2)CC1] |
| I-257 | 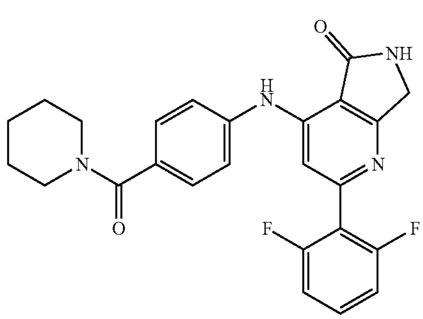 [SMILES: O=C1NCc2nc(-c3c(F)cccc3F)cc(Nc3ccc(C(=O)N4CCCCC4)cc3)c21] |

-continued

| Compound | Structure |
|---|---|
| I-258 | 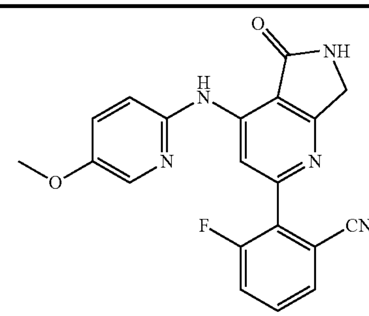 |
| I-259 | 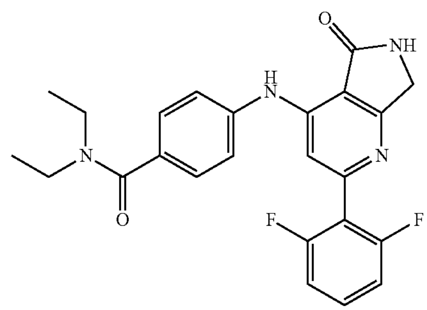 [SMILES: CCN(CC)C(=O)c1ccc(Nc2cc(-c3c(F)cccc3F)nc3c2C(=O)NC3)cc1] |
| I-260 | 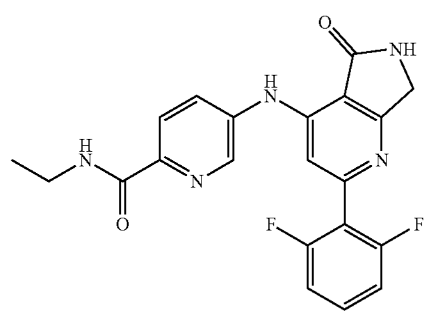 [SMILES: CCNC(=O)c1ccc(Nc2cc(-c3c(F)cccc3F)nc3c2C(=O)NC3)cn1] |
| I-261 | 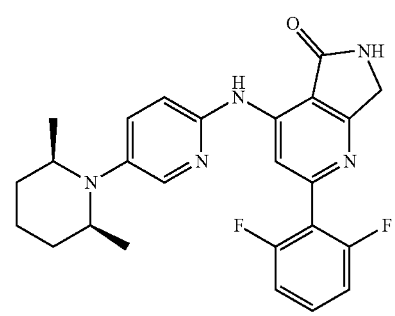 [SMILES: C[C@@H]1CCC[C@H](C)N1c1ccc(Nc2cc(-c3c(F)cccc3F)nc3c2C(=O)NC3)nc1] |
| I-262 | 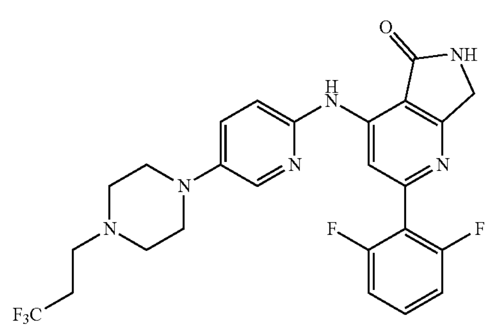 [SMILES: O=C1NCc2nc(-c3c(F)cccc3F)cc(Nc3ccc(N4CCN(CCC(F)(F)F)CC4)cn3)c21] |

| Compound | Structure |
|---|---|
| I-263 | 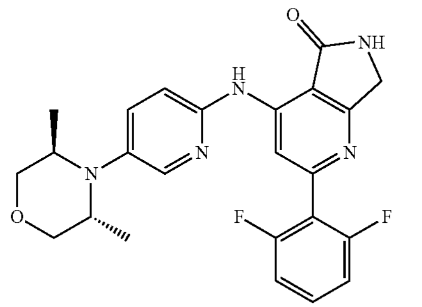 [SMILES: C[C@@H]1COC[C@@H](C)N1c1ccc(Nc2cc(-c3c(F)cccc3F)nc3c2C(=O)NC3)nc1] |
| I-264 | 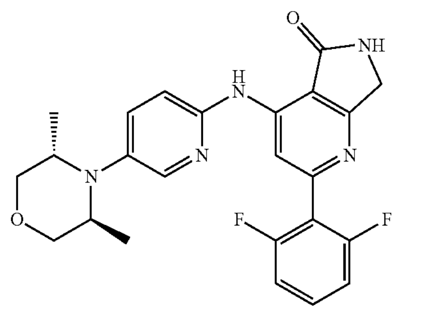 [SMILES: C[C@H]1COC[C@H](C)N1c1ccc(Nc2cc(-c3c(F)cccc3F)nc3c2C(=O)NC3)nc1] |
| I-265 | 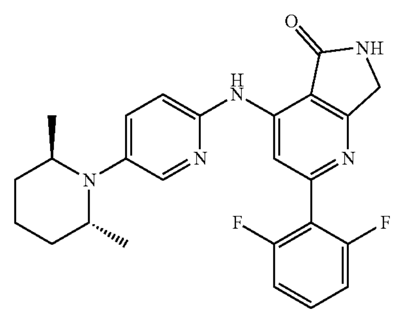 [SMILES: C[C@@H]1CCC[C@@H](C)N1c1ccc(Nc2cc(-c3c(F)cccc3F)nc3c2C(=O)NC3)nc1] |
| I-266 | 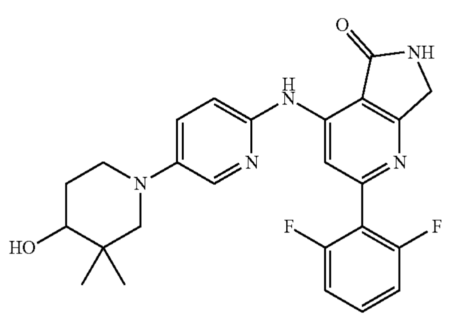 [SMILES: CC1(C)CN(c2ccc(Nc3cc(-c4c(F)cccc4F)nc4c3C(=O)NC4)nc2)CCC1O] |
| I-267 | 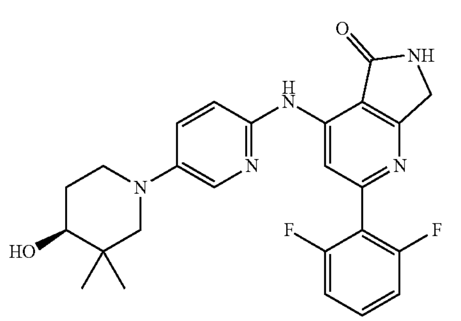 [SMILES: CC1(C)CN(c2ccc(Nc3cc(-c4c(F)cccc4F)nc4c3C(=O)NC4)nc2)CC[C@@H]1O] |
| I-268 | |
| I-269 | |
| I-270 | |
| I-271 | |
| I-272 | |

| Compound | Structure |
|---|---|
| I-273 | 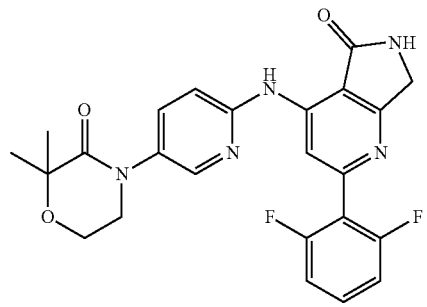 [SMILES: CC1(C)OCCN(c2ccc(Nc3cc(-c4c(F)cccc4F)nc4c3C(=O)NC4)nc2)C1=O] |
| I-274 | 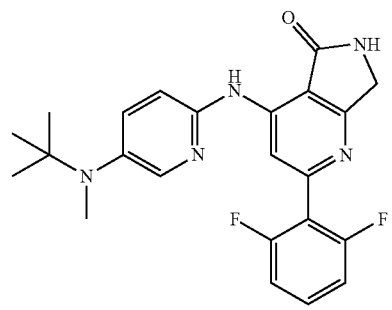 [SMILES: CN(c1ccc(Nc2cc(-c3c(F)cccc3F)nc3c2C(=O)NC3)nc1)C(C)(C)C] |
| I-275 | 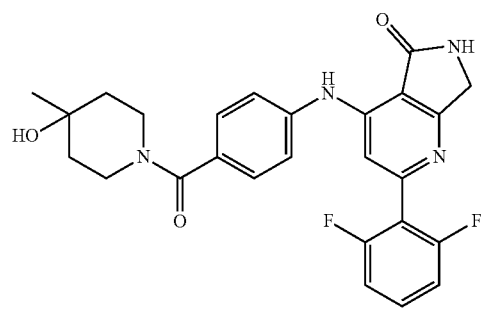 [SMILES: CC1(O)CCN(C(=O)c2ccc(Nc3cc(-c4c(F)cccc4F)nc4c3C(=O)NC4)cc2)CC1] |
| I-276 | 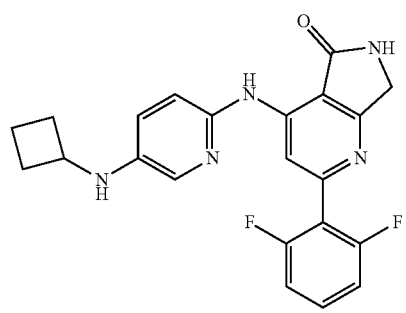 [SMILES: O=C1NCc2nc(-c3c(F)cccc3F)cc(Nc3ccc(NC4CCC4)cn3)c21] |
| I-277 | 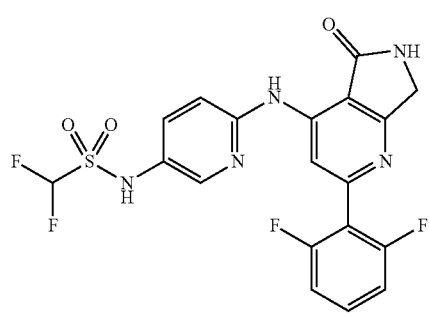 |
| Compound | Structure |
|---|---|
| I-278 | 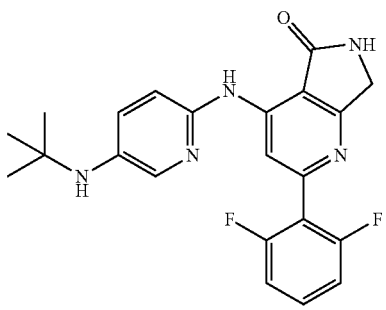 [SMILES: CC(C)(C)Nc1ccc(Nc2cc(-c3c(F)cccc3F)nc3c2C(=O)NC3)nc1] |
| I-279 | 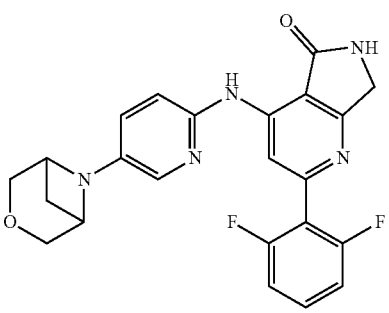 [SMILES: O=C1NCc2nc(-c3c(F)cccc3F)cc(Nc3ccc(N4C5COCC4C5)cn3)c21] |
| I-280 | 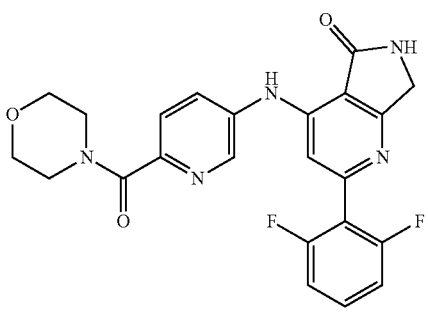 [SMILES: O=C1NCc2nc(-c3c(F)cccc3F)cc(Nc3ccc(C(=O)N4CCOCC4)nc3)c21] |
| I-281 | 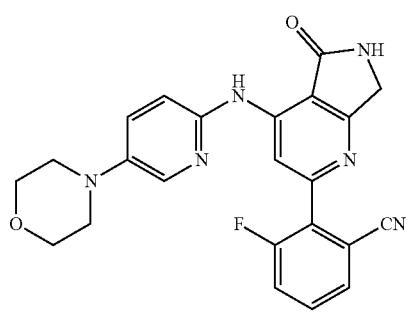 [SMILES: N#Cc1cccc(F)c1-c1cc(Nc2ccc(N3CCOCC3)cn2)c2c(n1)CNC2=O] |
| I-282 | 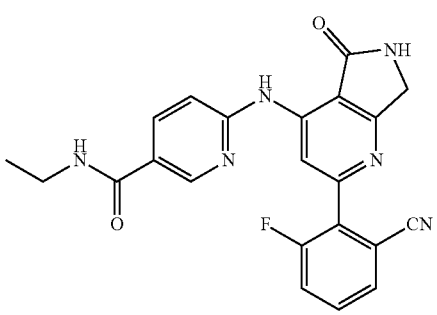 [SMILES: CCNC(=O)c1ccc(Nc2cc(-c3c(F)cccc3C#N)nc3c2C(=O)NC3)nc1] |

653
-continued
| Compound | Structure |
|---|---|
| I-283 | 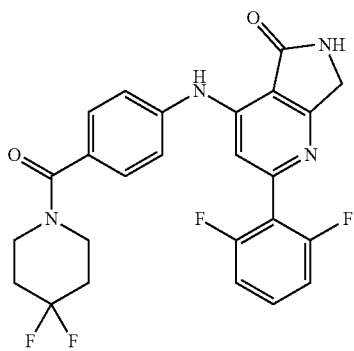 [SMILES: O=C1NCc2nc(-c3c(F)cccc3F)cc(Nc3ccc(C(=O)N4CCC(F)(F)CC4)cc3)c21] |
| I-284 | 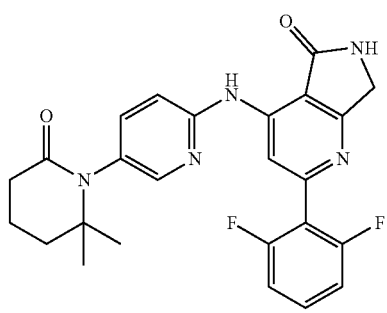 [SMILES: CC1(C)CCCC(=O)N1c1ccc(Nc2cc(-c3c(F)cccc3F)nc3c2C(=O)NC3)nc1] |
| I-285 | 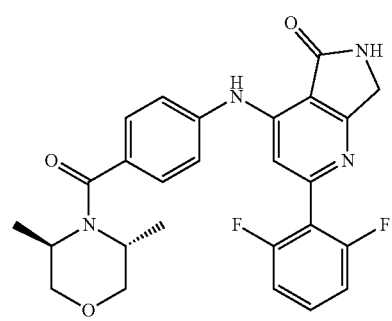 [SMILES: C[C@@H]1COC[C@@H](C)N1C(=O)c1ccc(Nc2cc(-c3c(F)cccc3F)nc3c2C(=O)NC3)cc1] |
| I-286 | 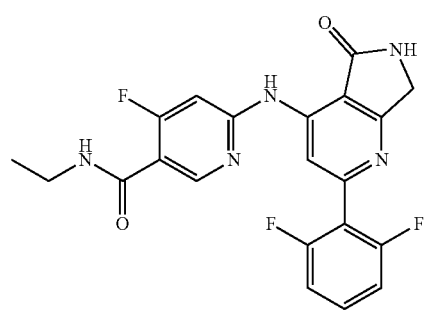 [SMILES: CCNC(=O)c1cnc(Nc2cc(-c3c(F)cccc3F)nc3c2C(=O)NC3)cc1F] |
654
-continued
| Compound | Structure |
|---|---|
| I-287 | 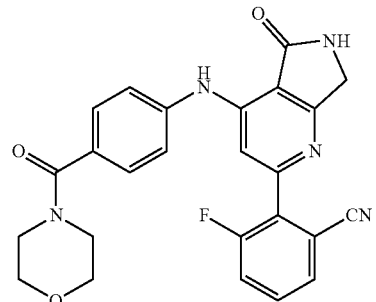 |
| I-288 | 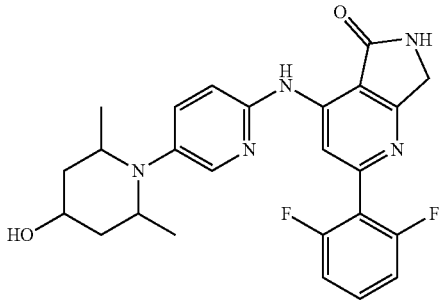 [SMILES: CC1CC(O)CC(C)N1c1ccc(Nc2cc(-c3c(F)cccc3F)nc3c2C(=O)NC3)nc1] |
| I-289 | 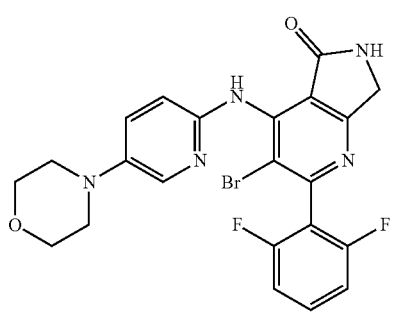 [SMILES: O=C1NCc2nc(-c3c(F)cccc3F)c(Br)c(Nc3ccc(N4CCOCC4)cn3)c21] |
| I-290 | 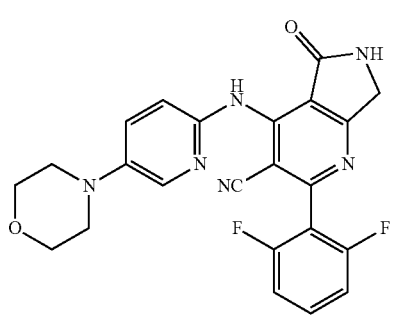 [SMILES: N#Cc1c(-c2c(F)cccc2F)nc2c(c1Nc1ccc(N3CCOCC3)cn1)C(=O)NC2] |
| I-291 | 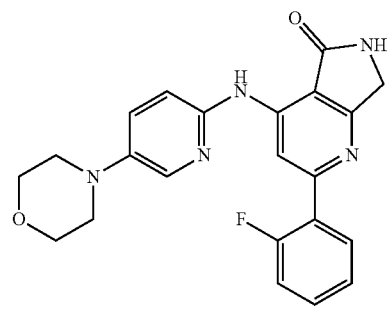 [SMILES: O=C1NCc2nc(-c3ccccc3F)cc(Nc3ccc(N4CCOCC4)cn3)c21] |

| Compound | Structure |
|---|---|
| I-292 | 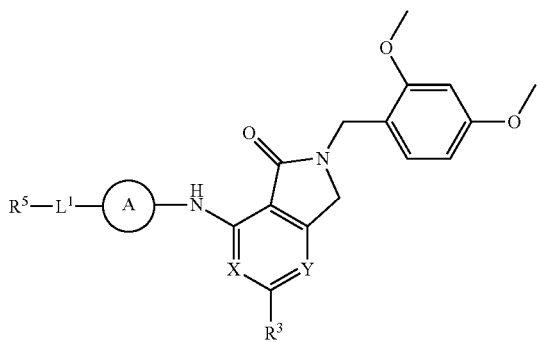 |

12. A compound of formula A-5:

A-5

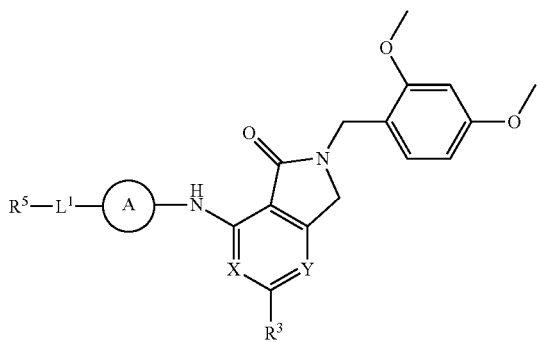

wherein:
each of X and Y is independently =C(R⁶)— or =N—, provided that X and Y are not simultaneously =C(R⁶)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;
$R^5$ is a group selected from hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S(O)$_2$R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;
provided that when $R^3$ is other than phenyl, $R^5$ is not hydrogen or unsubstituted alkyl when $L^1$ is a covalent bond;
each instance of $R^6$, $R^7$, and $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
m is 0-4;
n is 0-4;
p is 0-6; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

13. A method of treating a TYK2-mediated disorder, disease or condition in a patient wherein the disorder, disease or condition is associated with transplantation, comprising administering to said patient a compound of formula I, or a pharmaceutical composition thereof:

I

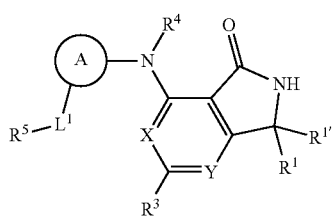

or a pharmaceutically acceptable salt thereof, wherein:
each of X and Y is independently =C(R⁶)— or =N—, provided that X and Y are not simultaneously =C(R⁶)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;

each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R; or
 $R^1$ and $R^{1'}$ are taken together with their intervening atoms to form an optionally substituted 3-7 membered spiro-fused ring having 0-2 heteroatoms independently selected from nitrogen, oxygen, and sulfur;

each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic;

$R^5$ is a group selected from hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S(O)$_2$R, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;

provided that when $R^3$ is other than phenyl, $R^5$ is not hydrogen or unsubstituted alkyl when $L^1$ is a covalent bond;

each instance of $R^6$, $R^7$, and $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

m is 0-4;

n is 0-4;

p is 0-6; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
 two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

14. The method of claim 13 wherein the disorder is transplant rejection or graft versus host disease.

* * * * *